(12) United States Patent
Nikiforov et al.

(10) Patent No.: US 9,365,838 B2
(45) Date of Patent: Jun. 14, 2016

(54) CONJUGATES OF BIOMOLECULES TO NANOPARTICLES

(71) Applicant: LIFE TECHNOLOGIES CORPORATION, Carlsbad, CA (US)

(72) Inventors: Theo Nikiforov, Carlsbad, CA (US); Daniel Mazur, San Diego, CA (US); Xinzhan Peng, Carlsbad, CA (US); Tommie Lloyd Lincecum, Houston, TX (US); Yuri Belosludtsev, The Woodlands, TX (US); Howard Reese, Poway, CA (US); Dmitriy Gremyachinskiy, San Francisco, CA (US); Roman Rozhkov, Redwood City, CA (US); John Mauro, Burlingame (CA); Joseph Beechem, Eugene, OR (US); Eric Tulsky, Berkeley, CA (US); Imad Naasani, Manchester (GB); Kari Haley, Eugene, OR (US); Joseph Treadway, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 271 days.

(21) Appl. No.: 14/087,307

(22) Filed: Nov. 22, 2013

(65) Prior Publication Data

US 2014/0308730 A1 Oct. 16, 2014

Related U.S. Application Data

(62) Division of application No. 12/748,355, filed on Mar. 26, 2010, now Pat. No. 8,603,792.

(60) Provisional application No. 61/164,324, filed on Mar. 27, 2009, provisional application No. 61/184,770, filed on Jun. 5, 2009, provisional application No. 61/242,771, filed on Sep. 15, 2009, provisional application No. 61/245,457, filed on Sep. 24, 2009, provisional application No. 61/263,974, filed on Nov. 24, 2009, provisional application No. 61/289,388, filed on Dec. 22, 2009, provisional application No. 61/293,618, filed on Jan. 8, 2010, provisional application No. 61/293,616, filed on Jan. 8, 2010, provisional application No. 61/299,919, filed on Jan. 29, 2010, provisional application No. 61/299,917, filed on Jan. 29, 2010, provisional application No. 61/307,356, filed on Feb. 23, 2010.

(51) Int. Cl.
*C12N 9/12* (2006.01)
*C07H 19/20* (2006.01)
*C12Q 1/68* (2006.01)

(52) U.S. Cl.
CPC .............. *C12N 9/1241* (2013.01); *C07H 19/20* (2013.01); *C12N 9/1252* (2013.01); *C12Q 1/6869* (2013.01)

(58) Field of Classification Search
None
See application file for complete search history.

(56) References Cited

U.S. PATENT DOCUMENTS

| | | |
|---|---|---|
| 4,658,649 A | 4/1987 | Brook |
| 5,001,050 A | 3/1991 | Blanco et al. |
| 5,151,507 A | 9/1992 | Hobbs et al. |
| 5,188,934 A | 2/1993 | Menchen et al. |
| 5,198,543 A | 3/1993 | Blanco et al. |
| 5,322,785 A | 6/1994 | Comb et al. |
| 5,473,060 A | 12/1995 | Gryaznov et al. |
| 5,510,270 A | 4/1996 | Fodor et al. |
| 5,558,991 A | 9/1996 | Trainor |
| 5,576,204 A | 11/1996 | Blanco et al. |
| 5,599,695 A | 2/1997 | Pease et al. |
| 5,707,804 A | 1/1998 | Mathies et al. |
| 5,723,584 A | 3/1998 | Schatz |
| 5,831,070 A | 11/1998 | Pease et al. |
| 5,874,239 A | 2/1999 | Schatz |
| 5,932,433 A | 8/1999 | Schatz |
| 6,087,095 A | 7/2000 | Rosenthal et al. |
| 6,207,229 B1 | 3/2001 | Bawendi et al. |
| 6,221,592 B1 | 4/2001 | Schwartz et al. |
| 6,255,083 B1 | 7/2001 | Williams |
| 6,294,136 B1 | 9/2001 | Schwartz |
| 6,322,901 B1 | 11/2001 | Bawendi et al. |
| 6,399,304 B1 | 6/2002 | Kilger et al. |

(Continued)

FOREIGN PATENT DOCUMENTS

| | | |
|---|---|---|
| EP | 0272007 B1 | 3/1992 |
| EP | 1681356 | 7/2006 |

(Continued)

OTHER PUBLICATIONS

Motre et al., "Enhancing helicase-dependent amplification by fusing the helicase with the DNA polymerase", Gene 420: 17-22 (2008).*
Agard, N et al., "A Strain-Promoted [3+2]Azide-Alkyne Cycloaddition for Covalent Modification of Biomolecules in Living Systems", *J. Am. Chem Soc*, vol. 126(46), 2004, pp. 15046-15047.
Ahn, Jinwoo et al., "DNA Polymerase Beta: Structure-Fidelity Relationship from Pre-Steady-State Kinetic Analyses of All Possible Correct and Incorrect Base Pairs for Wild Type and R283A Mutant", *Biochemistry* 36, 1997, 1100-1107.

(Continued)

*Primary Examiner* — Anand Desai

(57) ABSTRACT

Disclosed herein are conjugates comprising a biomolecule linked to a label that have biological activity and are useful in a wide variety of biological applications. For example, provided herein are polymerase-nanoparticle conjugates including a polymerase linked to a nanoparticle, wherein the conjugate has polymerase activity. Such conjugates can exhibit reduced aggregation and improved stochiometries wherein the average biomolecule:nanoparticle ratio approaches or equals 1:1. Also disclosed herein are improved methods for preparing such conjugates, and methods and systems for using such conjugates in biological applications such as nucleotide incorporation, primer extension and single molecule sequencing.

20 Claims, 66 Drawing Sheets

(56) References Cited

U.S. PATENT DOCUMENTS

| | | |
|---|---|---|
| 6,399,335 B1 | 6/2002 | Kao et al. |
| 6,423,551 B1 | 7/2002 | Weiss et al. |
| 6,524,829 B1 | 2/2003 | Seeger |
| 6,627,424 B1 | 9/2003 | Wang |
| 6,635,163 B1 | 10/2003 | Han et al. |
| 6,664,079 B2 | 12/2003 | Ju et al. |
| 6,815,064 B2 | 11/2004 | Treadway et al. |
| 6,818,395 B1 | 11/2004 | Quake et al. |
| 6,849,411 B2 | 2/2005 | Knapp et al. |
| 6,864,626 B1 | 3/2005 | Weiss et al. |
| 6,911,345 B2 | 6/2005 | Quake et al. |
| 6,955,855 B2 | 10/2005 | Naasani |
| 6,960,437 B2 | 11/2005 | Enzelberger et al. |
| 6,982,146 B1 | 1/2006 | Schneider et al. |
| 7,033,762 B2 | 4/2006 | Nelson et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,078,499 B2 | 7/2006 | Odedra et al. |
| 7,125,671 B2 | 10/2006 | Sood et al. |
| 7,198,847 B2 | 4/2007 | Naasani |
| 7,205,048 B2 | 4/2007 | Naasani |
| 7,211,414 B2 | 5/2007 | Hardin et |
| 7,214,428 B2 | 5/2007 | Naasani |
| 7,217,562 B2 | 5/2007 | Cao et al. |
| 7,223,541 B2 | 5/2007 | Fuller et al. |
| 7,223,568 B2 | 5/2007 | Kondow et al. |
| 7,229,799 B2 | 6/2007 | Williams |
| 7,244,566 B2 | 7/2007 | Sood et al. |
| 7,244,602 B2 | 7/2007 | Frey et al. |
| 7,256,019 B2 | 8/2007 | Sood et al. |
| 7,264,934 B2 | 9/2007 | Fuller |
| 7,270,951 B1 | 9/2007 | Stemple et al. |
| 7,276,720 B2 | 10/2007 | Ulmer |
| 7,329,492 B2 | 2/2008 | Hardin et al. |
| 7,345,159 B2 | 3/2008 | Ju et al. |
| 7,361,466 B2 | 4/2008 | Korlach et al. |
| 7,368,086 B2 | 5/2008 | Naasani |
| 7,393,640 B2 | 7/2008 | Kumar et al. |
| 7,405,281 B2 | 7/2008 | Xu et al. |
| 7,416,844 B2 | 8/2008 | Korlach et al. |
| 7,427,673 B2 | 9/2008 | Balasubramanian et al. |
| 7,452,698 B2 | 11/2008 | Sood et al. |
| 7,456,954 B2 | 11/2008 | Weiss et al. |
| 7,485,424 B2 | 2/2009 | Korlach et al. |
| 7,501,245 B2 | 3/2009 | Quake et al. |
| 7,521,541 B2 | 4/2009 | Eigenbrot et al. |
| 7,541,444 B2 | 6/2009 | Milton et al. |
| 7,553,949 B2 | 6/2009 | Lee et al. |
| 7,599,059 B2 | 10/2009 | Laurence et al. |
| 7,611,907 B2 | 11/2009 | Dickson et al. |
| 7,668,697 B2 | 2/2010 | Volkov et al. |
| 7,670,770 B2 | 3/2010 | Chou et al. |
| 7,745,116 B2 | 6/2010 | Williams |
| 7,928,038 B2 | 4/2011 | Menchen et al. |
| 8,058,414 B2 | 11/2011 | Menchen et al. |
| 8,603,792 B2 * | 12/2013 | Nikiforov .............. C07H 19/20 435/194 |
| 2002/0115092 A1 | 8/2002 | Rebek, Jr. |
| 2002/0132259 A1 | 9/2002 | Wagner, Jr. et al. |
| 2002/0197611 A1 | 12/2002 | Chagovetz |
| 2003/0044781 A1 | 3/2003 | Korlach et al. |
| 2003/0064366 A1 | 4/2003 | Hardin et al. |
| 2003/0087300 A1 | 5/2003 | Knapp et al. |
| 2003/0092005 A1 | 5/2003 | Levene et al. |
| 2004/0048300 A1 | 3/2004 | Sood et al. |
| 2004/0152119 A1 | 8/2004 | Sood et al. |
| 2004/0197800 A1 | 10/2004 | Borns |
| 2004/0197843 A1 | 10/2004 | Chou et al. |
| 2004/0244827 A1 | 12/2004 | Hatsukaiwa et al. |
| 2005/0003464 A1 | 1/2005 | Tibbe et al. |
| 2005/0042633 A1 | 2/2005 | Williams |
| 2005/0164255 A1 | 7/2005 | Korlach et al. |
| 2005/0244827 A1 | 11/2005 | Olsson et al. |
| 2005/0266424 A1 | 12/2005 | Hardin et al. |
| 2006/0003383 A1 | 1/2006 | Graham |
| 2006/0057565 A1 | 3/2006 | Ju et al. |
| 2006/0063264 A1 | 3/2006 | Turner et al. |
| 2006/0078937 A1 | 4/2006 | Korlach |
| 2006/0176479 A1 | 8/2006 | Laurence et al. |
| 2006/0177495 A1 | 8/2006 | Allen et al. |
| 2006/0275806 A1 | 12/2006 | Schwartz et al. |
| 2007/0009980 A1 | 1/2007 | Graham |
| 2007/0020772 A1 | 1/2007 | Cao et al. |
| 2007/0072196 A1 | 3/2007 | Xu et al. |
| 2007/0109536 A1 | 5/2007 | Weiss et al. |
| 2007/0111350 A1 | 5/2007 | Weiss et al. |
| 2007/0116868 A1 | 5/2007 | Weiss et al. |
| 2007/0128133 A1 | 6/2007 | Eid et al. |
| 2007/0161028 A1 | 7/2007 | Schwartz et al. |
| 2007/0172819 A1 | 7/2007 | Hardin et al. |
| 2007/0172858 A1 | 7/2007 | Hardin et al. |
| 2007/0172859 A1 | 7/2007 | Hardin et al. |
| 2007/0172860 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0172869 A1 | 7/2007 | Hardin et al. |
| 2007/0184475 A1 | 8/2007 | Hardin et al. |
| 2007/0196846 A1 | 8/2007 | Hanzel et al. |
| 2007/0250274 A1 | 10/2007 | Volkov et al. |
| 2007/0275395 A1 | 11/2007 | Hardin et al. |
| 2007/0292679 A1 | 12/2007 | Pellerite et al. |
| 2007/0292867 A1 | 12/2007 | Hardin et al. |
| 2008/0009100 A1 | 1/2008 | Davison |
| 2008/0091005 A1 | 4/2008 | Wang et al. |
| 2008/0108082 A1 | 5/2008 | Rank et al. |
| 2008/0131952 A1 | 6/2008 | Wu et al. |
| 2008/0132692 A1 | 6/2008 | Wu et al. |
| 2008/0176316 A1 | 7/2008 | Eid et al. |
| 2008/0176761 A1 | 7/2008 | Menchen et al. |
| 2008/0213910 A1 | 9/2008 | Jogikalmath |
| 2008/0219888 A1 | 9/2008 | Lawson et al. |
| 2008/0219890 A1 | 9/2008 | Lawson et al. |
| 2008/0261833 A1 | 10/2008 | Stemmer et al. |
| 2008/0274905 A1 | 11/2008 | Greene |
| 2008/0293071 A1 | 11/2008 | Gelfand et al. |
| 2009/0024331 A1 | 1/2009 | Tomaney et al. |
| 2009/0029385 A1 | 1/2009 | Christians et al. |
| 2009/0047699 A1 | 2/2009 | Graham |
| 2009/0061447 A1 | 3/2009 | Schneider |
| 2009/0081686 A1 | 3/2009 | Wu et al. |
| 2009/0176233 A1 | 7/2009 | Clark et al. |
| 2009/0275036 A1 | 11/2009 | Hardin et al. |
| 2009/0286245 A1 | 11/2009 | Bjornson et al. |
| 2009/0298075 A1 | 12/2009 | Travers et al. |
| 2009/0305248 A1 | 12/2009 | Lander et al. |
| 2009/0305278 A1 | 12/2009 | Hardin et al. |
| 2010/0216122 A1 | 8/2010 | Hardin et al. |
| 2010/0255463 A1 | 10/2010 | Harsin et al. |
| 2010/0255464 A1 | 10/2010 | Hardin et al. |
| 2010/0255487 A1 | 10/2010 | Beechem et al. |
| 2010/0261185 A1 | 10/2010 | Nikiforov |
| 2010/0304367 A1 | 12/2010 | Hardin et al. |
| 2010/0317005 A1 | 12/2010 | Hardin et al. |
| 2010/0330570 A1 | 12/2010 | Vander Horn et al. |
| 2011/0003343 A1 | 1/2011 | Nikiforov et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0184163 A1 | 7/2011 | Hardin et al. |
| 2011/0220844 A1 | 9/2011 | Tulsky et al. |
| 2011/0226995 A1 | 9/2011 | Tulsky et al. |
| 2011/0281740 A1 | 11/2011 | Beechem et al. |
| 2011/0306079 A1 | 12/2011 | Tulsky et al. |

(56) References Cited

U.S. PATENT DOCUMENTS

| | | |
|---|---|---|
| 2012/0322057 A1 | 12/2012 | Hendricks et al. |
| 2012/0329042 A1 | 12/2012 | Beechem et al. |
| 2013/0005020 A1 | 1/2013 | Peris et al. |
| 2013/0040363 A1 | 2/2013 | Nikiforov |
| 2013/0102050 A1 | 4/2013 | Hardin et al. |

FOREIGN PATENT DOCUMENTS

| | | |
|---|---|---|
| WO | WO-90/07576 | 7/1990 |
| WO | WO-91/01087 | 2/1991 |
| WO | WO-91/05060 | 4/1991 |
| WO | WO-91/06678 | 5/1991 |
| WO | WO-98/022615 | 5/1998 |
| WO | WO-98/31834 | 7/1998 |
| WO | WO-99/053034 | 12/1999 |
| WO | WO-00/17330 | 3/2000 |
| WO | WO-00/36151 | 6/2000 |
| WO | WO-00/36152 | 6/2000 |
| WO | WO-00/67698 | 11/2000 |
| WO | WO-00/70073 | 11/2000 |
| WO | WO-02/04680 | 1/2002 |
| WO | WO-02/44425 | 6/2002 |
| WO | WO-2007/070642 | 6/2007 |
| WO | WO-2008/030115 | 3/2008 |
| WO | WO-2008/154317 | 12/2008 |
| WO | WO-2009/017678 | 2/2009 |
| WO | WO-2009/091847 | 7/2009 |
| WO | WO-2010/002939 | 1/2010 |
| WO | WO-2010/039897 | 4/2010 |
| WO | WO-2010/040111 | 4/2010 |
| WO | WO-2010/048580 | 4/2010 |
| WO | WO-2010/048581 | 4/2010 |
| WO | WO-2010/096084 | 8/2010 |
| WO | WO-2010/111674 | 9/2010 |
| WO | WO-2010/111686 | 9/2010 |
| WO | WO-2010/111690 | 9/2010 |
| WO | WO-2010/111691 | 9/2010 |
| WO | WO-2010/111691 A3 | 9/2010 |
| WO | WO-2010/111691 A9 | 9/2010 |
| WO | WO-2010111686 | 9/2010 |
| WO | WO-2010/151714 | 12/2010 |
| WO | WO-2010/111690 A3 | 3/2011 |
| WO | WO-2011/038158 | 3/2011 |
| WO | WO-2010/111686 A3 | 5/2011 |
| WO | WO-2011/078897 | 6/2011 |

OTHER PUBLICATIONS

Akerman, Maria E. et al., "Nanocrystal targeting in vivo", *Proceedings of the National Academy of Sciences (PNAS)*, vol. 99, No. 20, Oct. 1, 2002, 12617-12621.

Arenkov, Pavel et al., "Protein Microchips: Use for Immunoassay and Enzymatic Reactions", *Analytical Biochemistry*, vol. 278, 2000, 123-131.

Arion, Dominique et al., "HIV resistance to zidovudine: the role of pyrophosphorolysis", *Drug Resistance Updates*, vol. 2, No. 2, Apr. 1999, 91-95.

Arkin, A. P. et al., "An algorithm for protein engineering: Simulations of recursive ensemble mutagenesis", *PNAS USA*; vol. 89, 1992, pp. 7811-7815.

Arzumanov, Andrey A. et al., "γ-Phosphate-substituted 2'-Deoxynucleoside 5'-Triphosphates as Substrates for DNA Polymerases", *J. Biol. Chem.*, vol. 271(40), 1996, pp. 24389-24394.

Bakhtina, Marina et al., "Contribution of the Reverse Rate of the Conformational Step to Polymerase B Fidelity", *Biochem.*, vol. 48, 2009, 3197-3208.

Barone, A. D. et al., "Novel Nucleoside Triphosphate Analogs for the Enzymatic Labeling of Nucleic Acids", *Nucleosides, Nucleotides & Nucleic Acids*, 20(4-7), 2001, 1141-1145.

Barone, Anthony D. et al., "Photolithographic Synthesis of High-Density Oligonucleotide Probe Arrays", *Nucleosides, Nucleotides & Nucleic Acids*, vol. 20, Nos. 4-7, 2001, 525-531.

Beattie, W. G. et al., "Hybridization of DNA targets to glass-tethered oligonucleotide probes", *Mol. Biotechnology*, vol. 4(3), 1995, pp. 213-225.

Berman, Andrea J. et al., "Structures of phi29 DNA polymerase complexed with substrate: the mechanism of translocation in B-family polymerases", *The EMBO Journal*, vol. 26, 2007, 3494-3505.

Bernad, Antonio et al., "Structural and functional relationships between prokaryotic and eukaryotic DNA polymerases", *The EMBO Journal*, vol. 6 No. 13, 1987, 4219-4225.

Blanco, L. et al., "A general structure for DNA-dependent DNA polymerases", *Gene*, vol. 100, Elsevier Science Publishers B.V., 1991, 27-38.

Blasco, M. A. et al., "Phi29 D A polymerase active site. Residue ASP249 of co nserved amino acid motif "Dx2SLYP" is critical for synthetic activities", *The Journal of Biological Chemistry*, vol. 268, No. 32, Nov. 15, 1993, pp. 241-24113.

Blasco, M. A., "Phi29 DNA polymerase active site. Mutants in conserved residues Tyr254 and Tyr390 are affected in dNTP binding", *The Journal of Biological Chemistry*, vol. 267 No. 27, Sep. 25, 1992, pp. 19427-19434.

Blasco, M. A. et al., "Primer terminus stabi l izat ion at the phi29 DNA polymer ase active site. Mutational anaylsis of conserved motif KXY", *The Journal of Biological Chemistry*. vol. 270 No. 6, Feb. 10, 1995, pp. 2735-2740.

Blasco, Maria et al., "Phi29 DNA Polymerase Active Site", *The Journal of Biological Chemistry*, vol. 268, No. 22,, 1993, 16763-16770.

Bouizar, et al., "Purification and Characterization of Calcitonin Receptors in Rat Kidney Membranes by Covalent Cross-Linking Techniques.", *European Journal of Biochemistry*, vol. 155, No. 1, 1986, 141-147.

Bowers, Jayson et al., "Virtual terminator nucleotides for next-generation DNA sequencing", *Nature Methods*, vol. 6, No. 8, 2009, 593-595.

Braslavsky, Ido et al., "Sequence information can be obtained from single DNA molecules", *Proc. Natl. Acad. Sci.*, vol. 100(7), 2003, pp. 3960-3964.

Brinkley, "A Brief Survey of Methods for Preparing Protein Conjugates with Dyes, Haptens, and Cross-Linking Reagents", *Bioconjugate Chemistry*, vol. 3, No. 1, 1992, 2-13.

Browning, et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Brustad, Eric et al., "A General and Efficient Method for the Site-Specific Dual-Labeling of Proteins for Single Molecule Fluorescence Resonance Energy Transfer"*J. Am. Chem. Soc.*, 130, 2008, 17664-17665.

Calogero, S. et al., "In vivo recombination and the production of hybrid genes", *FEMS Microbiology Letters*, vol. 97, 1992, pp. 41-44.

Campbell, A. K. et al., "A homogeneous immunoassay for cyclic nucleotides based on chemiluminescence energy transfer", *Biochem. J.*, vol. 216, 1983, pp. 185-194.

Caren, R. et al., "Efficient Sampling of Protein Sequence Space for Multiple Mutants", *Bio/Technology*, vol. 12, 1994, pp. 517-520.

Caspar, J. et al., "Photochemistry of Ru(bpy)3 2+. Solvent Effects", *J. Am. Chem. Soc.*, 105, 1983, 5583.

Caspar, Jonathan V. et al., "Application of the Energy Gap Law to Nonradiative, Excited-State Decay", *J. Phys. Chem.*, vol. 87, No. 6, 1983, pp. 952-957.

Castro, Christian et al., "Nucleic acid polymerases use a general acid for nucleotidyl transfer", *Nature Structural & Molecular Biology*, vol. 16 No. 2, 2009, 212-218.

Cha, Taewoon et al., "Enzymatic activity on a chip: The critical role of protein orientation", *Proteomics*, vol. 5, 2005, 416-419.

Cha, Taewoon et al., "Immobilization of oriented protein molecules on poly(ethylene glycol)-coated Si(111)", *Proteomics*, vol. 4, 2004, 1965-1976.

Choi, H. S. et al., "Nature Biotechnology", vol. 25, No. 10, Oct. 2007, pp. 1165-1170.

Chrisey, Linda A. et al., "Covalent attachment of synthetic DNA to self-assembled monolayer films", *Nucleic Acid Research*, vol. 24, No. 15, 1996, pp. 3031-3039.

(56) References Cited

OTHER PUBLICATIONS

Clapp, A.R. et al., "Fluorescence Resonance Energy Transfer Between Quantum Dot Donars and Dye-Labeled Protein Acceptors", *J. Am. Chem. Soc.*, 126, 2004, 301-310.

Clapp, Aaron et al., "Capping of CdSe—ZnS quantum dots with DHLA and subsequent conjugation with proteins", *Nature Protocols*, vol. 1 No. 3, 2006, 1258-1266.

Cull, Millard G. et al., "Screening for receptor ligands using large libraries of peptides linked to the C terminus of the lac repressor", *Proc. Natl. Acad. Sci. USA*, vol. 89, 1992, pp. 1865-1869.

Cwirla, Steven E. et al., "Peptides on phage: A vast library of peptides for identifying ligands", *PNAS*, vol. 87, 1990, pp. 6378-6382.

Dafni, H. et al., "Overexpression of Vascular Endothelial Growth Factor 165 Drives Peritumor Interstitial Convection and Induces Lymphatic Drain: Magnetic Resonance Imaging, Confocal Microscopy, and Histological Tracking of Triple-labeled Albumin", *Cancer Research*. vol. 62, No. 15, Nov. 15, 2002, pp. 6731-6739.

Dawson, Philip et al., "Synthesis of Native Proteins by Chemical Ligation", *Annu. Rev. Biochem.*, 69:, 2000, 923-960.

Dawson, Philip E. et al., "Synthesis of Proteins by Native Chemical Ligation", *Science*, vol. 266, 1994, pp. 776-779.

De Graaf, Albert et al., "Nonnatural Amino Acids for Site-Specific Protein Conjugation", *Bioconjugate Chem.*, vol. 20, No. 7, 2009, 1281-1295.

De Vega, Miguel et al., "Primer-terminus stabilization at the 3'-5' exonuclease active site of Phi29 DNA polymerase. Involvement of two amino acid residues highly conserved in proofreading DNA polymerases", *The EMBO Journal*, vol. 15 No. 5, 1996, 1182-1192.

Decher, G. et al., "Buildup of ultrathin multilayer films by a self-assembly process: III. Consecutively alternating adsorption of anionic and cationic polyelectrolytes on charged surfaces", *Thin Solid Films*, vol. 210-211, Part 2, 1992, pp. 831-835.

Delagrave, Simon et al., "Recursive ensemble mutagenesis", *Protein Engineering*, vol. 6, No. 3, 1993, 327-331.

Delagrave, Simon et al., "Searching Sequence Space to Engineer Proteins: Expoential Ensemble Mutagenesis", *Bio/Technology*, vol. 11, 1993, pp. 1548-1552.

Derfus, A. M. et al., "Nano Letters.", vol. 4, No. 1, Dec. 10, 2003, pp. 11-18.

Deuschle, Karen et al., "Construction and optimization of a family of genetically encoded metabolite sensors by semirational protein engineering", *Protein Science*, vol. 14, Iss. 9, 14, 2005, 2304-2314.

Dilgimen, Aydan Salman et al., "Water-soluble covalent conjugates of bovine serum albumin with anionic poly(N-isopropyl-acrylamide) and their immunogenicity", *Biomaterials*, 22, 2001, 2383-2392.

Dos Remedios, Cristobal G. et al., "Fluorescence Resonance Energy Transfer Spectroscopy is a Reliable "Ruler" for Measuring Structural Changes in Proteins", *Journal of Structural Biology*, vol. 115, pp. 175-185.

Drosopoulos, W. et al., "Virtues of being faithful: Can we limit the genetic variation in Human Immunodeficiency Virus", *J. Molecular Medicine*, vol. 76 (9), Aug. 1998, pp. 604-612.

Dryden, D.T.F. et al., "Nucleoside triphosphate-dependent restriction enzymes", *Nucleic Acids Research*, vol. 29, No. 18, 2001, 3728-3741.

Eigen, Manfred et al., "The fifth Paul Ehrlich lecture virus strains as models of molecular evolution", *Medicinal Research Reviews*, vol. 13, No. 4 (XP000430626), Jul. 1993, 385-398.

Eschenmoser, Albert , "Chemical Etiology of Nucleic Acid Structure", *Science*, vol. 284, 1999, 2118-2124.

Fasman, Gerald D., "UV Spectral Characteristics and Acidic Dissociation Constants of 280 Alkyl Bases. Nucleosides and Nucleotides", *Practical Handbook of Biochemistry and Molecular Biology*, CRC Press, Boca Raton, FL, 1989, pp. 385-394.

Fazio, Teresa et al., "DNA Curtains and Nanoscale Curtain Rods: High-Throughput Tools for Single Molecule Imaging", *Langmuir*, vol. 24, 2008, 10524-10531.

Ferrero, Miguel et al., "Biocatalytic Selective Modifications of Conventional Nucleosides, Carbocyclic Nucleosides, and C-Nucleosides", *Chem. Rev.*, vol. 100, No. 12, 2000, 4319-4348.

Flemer, Stevenson et al., "Strategies for the Solid-Phase Diversification of Poly-L-proline-Type II Peptide Mimic Scaffolds and Peptide Scaffolds Through Guanidinylation", *J. Org. Chem.*, vol. 73. 2008, 7593-7602.

Forster, T., "Intermolecular energy migration and fluorescence", *Annalen der Physik*, vol. 437(1-2), 1948, 55-75.

Fu, Dong-Jing et al., "Sequencing double-stranded DNA by strand displacement", *Nucleic Acids Research*, vol. 25 (3), Feb. 1997, pp. 677-679.

Furey, W. S. et al., "Use of Fluorescence Resonance Energy Transfer to Investigate the Conformation of DNA Substrates Bound to the Klenow Fragment", *Biochemistry*, vol. 37, No. 9, 1998, 2979-2990.

Ge, Hui, "UPA, a universal protein array system for quantitative detection of protein-protein, protein-DNA, protein-RNA and protein-ligand interaction", *Nucleic Acids Research*, vol. 28(2), 2000, pp. i-vii.

Ghadessy, Farid J. et al., "Generic expansion of the substrate spectrum of a DNA polymerase by directed evolution", *Nature Biotech.*, vol. 22, No. 6, 2004, 755-759.

Gheorghe, Alexandru et al., "Combination of Perfluoroalkyl and Triazole Moieties: A New Recovery Strategy for TEMPT", *Organic Letters*, vol. 10, No. 19, 2008, 4171-4174.

Givens, R. et al., "New Photoactivated Protecting Groups", *J. Am. Chem. Soc.*, vol. 119, 1997, pp. 8369-8370.

Goldman, E. et al., "An Algorithmically Optimized Combinatorial Library Screened by Digital Imaging Spectroscopy", *Bio/Technology*, vol. 10, 1992, pp. 1557-1561.

Goldman, E. R. et al., "Luminescent Quantum Dot-Adaptor Protein-Antibody Conjugates for Use in Fluoroimmunoassays", *Phys. stat. sol.* (b), 229, No. 1, 2002, 407-414.

Goldman, Ellen et al., "Avidin: A Natural Bridge for Quantum Dot-Antibody Conjugates", *J. Am. Chem. Soc.*, 124, 2002, 6378-6382.

Goldman, Ellen et al., "Conjugation of Luminescent Quantum Dots with Antibodies Using an Engineered Adaptor Protein to Provide New Reagents for Fluoroimmunoassays", *Anal. Chem.*, 74, 2002, 841-847.

Goldman, Ellen et al., "Self-assembled luminescent CdSe—ZnS quantum dot bioconjugates prepared using engineered poly-histidine terminated proteins", *Analytica Chimica Acta*, 534, 2005, 63-67.

Gram, Hermann et al., "In vitro selection and affinity maturation of antibodies from a naive combinatorial immunoglobulin library", *PNAS*, vol. 89, 1992, pp. 3576-3580.

Guo, Zhen et al., "Direct fluorescence analysis of genetic polymorphisms by hybridization with oligonucleotide arrays on glass supports", *Nucleic Acids Research*, vol. 22, No. 24, 1994, 5456-5465.

Ha, Taekjip et al., "Initiation and re-initiation of DNA unwinding by the *Escherichia coli* Rep helicase", *Nature*, vol. 419, 2002, 638-641.

Haab, Brian B. et al., "Protein microarrays for highly parallel detection and quantitation of specific proteins and antibodies in complex solutions", *Genome Biology*, vol. 2, No. 2, 2001, 1-13.

Hainfeld, James F. et al., "Ni-NTA—Gold Clusters Target His-Tagged Proteins", *Journal of Structural Biology*, 127, 1999, 185-198.

Han, et al., "Quantum-dot-tagged Microbeads for Multiplexed Optical Coding of Biomolecules,", *Nature Biotech*, vol. 19, Jul. 2001, 631-635.

Harris, Timothy D. et al., "Single-Molecule DNA Sequencing of a Viral Genome", *Science*, vol. 320 2008, 106-109.

Hermes, J, et al., "Searching sequence space by definably random mutagenesis: Improving the catalytic potency of an enzyme", *PNAS*, vol. 87, 1990, pp. 696-700.

Howarth, Mark et al., "Targeting quantum dots to surface proteins in living cells with biotin ligase", *PNAS*, vol. 102, No. 21, 2005, 7583-7588.

Jaiswal, Jyoti et al., "Use of quantum dots for live cell imaging", *Nature Methods*, vol. 1, No. 1, 2004, 71-78.

Jares-Erijman, Elizabeth A. et al., "FRET imaging", *Nature Biotechnology*, vol. 21, No. 11, 2003, 1387-1395.

Jauffred, Liselotte et al., "Three-Dimensional Optical Control of Individual Quantum Dots", *Nano Letter*, vol. 8, No. 10, 2008, 3376-3380.

(56) References Cited

OTHER PUBLICATIONS

Jeong, Lak S. et al., "Structure-activity relationships of .beta.-D-(2S,5R)- and .alpha.-D(2S,5S)-1,3-oxathiolanyl nucleosides as potential anti-HIV agents", *J. Med. Chem.*, vol. 36,.1993, pp. 2627-2638.
Jewett, John et al., "Rapid Cu-Free Click Chemistry with Readily Synthesized Biarylazacyclooctynones", *J. Am. Chem. Soc.*, 132, 2010, 3688-3690.
Johnson, Erik et al., "Insights into the Mechanism and Catalysis of the Native Chemical Ligation Reaction", *J. Am. Chem. Soc.*, 128, 2006, 6640-6646.
Johnson, K., "Rapid kinetic analysis of mechanochemical adenosinetriphosphatases", *Methods Enzymol.*, vol. 134, 1986, pp. 677-705.
Joos, Beda et al., "Covalent Attachment of Hybridizable Oligonucleotides to Glass Supports", *Analytical Biochem.*, vol. 247(1), 1997, pp. 96-101.
Joshi, et al., "ATP Synthase Complex from Bovine Heart Mitochondria", *Journal of Biological Chemistry*, vol. 265, No. 24, 1990, 14518-14525.
Jung, et al., "Crosslinking of platelet glycoprotein lb by N-succinimidyl(4-azidophenyldithio)propionate and 3,3'-dithiobis-(sulfosuccinimidyl propionate)",*Biochimica et Biophysica Acta*, vol. 761, No. 2, 1983, 152-162.
Kamiya, Mako et al., "Extension of the Applicable Range of Fluorescein: A Fluorescein-Based Probe for Western Blot Analysis", *Angew. Chem. Int. Ed.*, vol. 44, 2005, 5439-5441.
Kamtekar, Satwik et al., "The phi29 DNA polymerase:protein-primer structure suggests a model for the initiation to elongation transition", *EMBO Journal*, vol. 25, No. 6, 2006, 1335-1343.
Kim, Hea O. et al., "1,3-Dioxalanylpurine nucleosides (2R,4R) and (2R,4S) with selective anti-HIV-1 activity in human lymphocytes", *J. Med. Chem.*, vol. 36, No. 1, 1993, 30-37.
Kiyonaka, Shigeki et al., "Semi-wet peptide/protein array using supramolecular hydrogel", *Nature Materials*, vol. 3, 2004, 58-64.
Kumar, Amarendra et al., "Inhibition of T7 RNA Polymerase: Transcription Initiation and Transition from Initiation to Elongation Are Inhibited by T7 Lysozyme via a Ternary Complex with RNA Polymerase and Promoter DNA", *Biochemistry*, vol. 36, No. 45, 1997, pp. 13954-13962.
Kumar, Shiv et al., "Terminal Phosphate Labeled Nucleotides: Synthesis, Applications, and Linker Effect on Incorporation by DNA Polymerases", *Nucleosides, Nucleotides and Nucleic Acids*, vol. 24, Nos. 5-7, 2005, 401-408.
Kunkel, Thomas A., "DNA replication fidelity", *Journal of Biological Chemistry*, vol. 267, No. 26, Sep. 15, 1992, 18251-18254.
Laitala, Ville et al., "Homogeneous Assay Based on Anti-Stokes' Shift Time-Resolved Fluorescence Resonance Energy-Transfer Measurement", *Analytical Chem.*, vol. 77, 2005, 1483-1487.
Lakowicz, J. R., "Energy Transfer", *Principles of Fluorescence Spectroscopy*, 2nd Ed. Plenum Publishing Corp., New York, NY, 1999, 367-394.
Lamture, J. et al., "Direct detection of nucleic acid hybridization on the surface of a charge coupled device", *Nucleic Acids Research*, vol. 22(11), 1994, pp. 2121-2125.
Liu, Wenshe et al., "Genetic incorporation of unnatural amino acids into proteins in mammalian cells", *Nature Methods*, vol. 4, No. 3, 2007, 239-244.
Lundberg, Kelly S. et al., "High-fidelity amplification using a thermostabile DNA polymerase isolated from Pyrococcus furiosus", *Gene*, vol. 108, Elsevier Science Publishers B.V.,, 1991, 1-6.
Mac Beath, Gavin et al., "Printing Proteins as Microarrays for High-Throughput Function Determination", *Science*, vol. 289, 2000, 1760-1763.
Marshall, P. N., "Rules for the visible absorption spectra of halogenated Fluorescein dyes", *Histochemical Journal*, vol. 7, 1975, pp. 299-303.
Martinez, Carlos I. et al., "Acyclic nucleoside triphosphate analogs as terminators in biocatalytic DNA replication", *Bioorganic & Medicinal Chemistry Letters*, vol. 7(23), 1997, pp. 3013-3016.
Martinez, Carlos I. et al., "An allylic/acyclic adenosine nucleoside triphosphate for termination of DNA synthesis by DNA template-dependent polymerases", *Nucleic Acids Research*, vol. 27, No. 5, 1999, 1271-1274.
Matayoshi, et al., "Novel Fluoregenic Substrates for Assaying Retroviral Proteases by Resonance Energy Transfer", *Science*, vol. 247, Feb. 23, 1990, pp. 954-958.
Mathis, G., "Probing molecular interactions with homogeneous techniques based on rare earth cryptates and fluorescence energy transfer", *Clin. Chem.*, vol. 41, No. 9, 1995, pp. 1391-1397.
Matsumoto, et al., "Genbank Accession No. M33144", 1993.
Mattoussi, H. et al., "Bioconjugation of Highly Luminescent Colloidal CdSe—ZnS Quantum Dots with an Engineered Two-Domain Recombinant Protein", *Phys. Status Solido B-Basic Res.*, 224, No. 1, 2001, 277-283.283.
Mattoussi, H. et al., "Self-Assembly of CdSe—ZnS Quantum Dot Bioconjugates Using an Engineered Recombinant Protein", *J Am Chem Soc*, vol. 122, No. 49, Nov. 22, 2000, 12142-12150.
Mc Cafferty, J. et al., "Phage Antibodies: Filamentous Phage Displaying Antibody Variable Domains", *Nature*, vol. 348, 1990, pp. 552-554.
Medintz, et al., "A fluorescence resonance energy transfer-derived structure of a quantum dot-protein bioconjugate nanoassembly", *Proceedings of the National Academy of Sciences (PNAS)*, 101(26), 2004, 9612-9617.
Medintz, Igor L. et al., "Self-assembled nanoscale biosensors based on quantum dot FRET donors", *Nature Materials*, vol. 2, 2003, 630-638.
Megiatto, Jackson D. et al., "General Method for Synthesis of Functionalized Macrocycles and Catenanes Utilizing "Click" Chemistry", *J. Am. Chem. Soc.*, vol. 130, 2008, 12872-12873.
Meijer, Wilfried et al., "Phi29 Family of Phages", *Microbiology and Molecular Biology Reviews*, vol. 65, No. 2, 2001, 261-287.
Meisel, Andreas et al., "Type III restriction enzymes need two inversely oriented recognition sites for DNA cleavage", *Nature*, vol. 335, 1992, 467-469.
Moll, Jonathan R. et al., "Designed heterodimerizing leucine zippers with a ranger of pIs and stabilities up to 10-15 M", *Protein Science*, vol. 10, 2001, 649-655.
Murray, Noreen E., "Type I Restriction Systems: Sophisticated Molecular Machines (a Legacy of Bertani and Weigle)", *Microbiology and Molecular Biology Reviews*, vol. 64, No. 2, 2000, 412-434.
Nakaji-Hirabayashi, Tadashi et al., "Oriented immobilization of epidermal growth factor onto culture substrates for the selective expansion of neural stem cells", *Biomaterials*, vol. 28, No. 24, 2007, 3517-3529.
Nakanishi, Kazuhiro et al., "Recent Advances in Controlled Immobilization of Proteins onto the Surface of the Solid Substrate and Its Possible Application to Proteomics", *Current Proteomics*, vol. 5, 2008, 161-175.
Ngo, et al., "The Protein Folding Problem and Tertiary Structure Predict ion", Merz et al. (ed .), Birkhauser, Boston, MA, 1994, pp. 433 and 492-495.
Oliphant, Arnold R. et al., "Cloning of random-sequence oligodeoxynucleotides", *Gene*, vol. 44, Iss. 2-3, 1986, 177-183.
Park, et al., "Characterization of the Cell Surface Receptor for a Multi-Lineage Colony-Stimulating Factor (CSF-2alpha)*", *Journal of Biological Chemistry*, vol. 261, No. 1, 1986, 205-207.
Park, Chan-Ho et al., "New Photoactivated Protecting Groups. 6. p-Hydroxyphenacyl: A Phototrigger for Chemical and Biochemical Probes1,2", *J. Am. Chem. Soc.*, vol. 119, No. 10, 1997, 2453-2463.
Patel, Smita et al., "Pre-Steady-State Kinetic Analysis of Processive DNA Replication Including Complete Characterization of an Exonuclease-Deficient Mutant", *Biochemistry*, 30, 1991, 511-525.
PCT/US01/21811, International Search Report mailed May 12, 2003.
PCT/US01/45819, International Search Report mailed Jun. 2, 2003.
PCTUS1028974, International Search Report and Written Opinion Received mailed on Jan. 26, 2011, 13 pgs.
PCTUS1050406, International Search Report and Written Opinion Received mailed on Feb. 21, 2011, 14pgs.
PCTUS2010028952, International Search Report and Written Opinion Received mailed on Mar. 29, 2011, 11 pgs.

(56) References Cited

OTHER PUBLICATIONS

PCTUS2010028967, International Search Report and Written Opinion Received mailed on Mar. 18, 2011, 10 pgs.

PCTUS2010028972, International Search Report and Written Opinion Received mailed on Jan. 21, 2011, 13 pgs.

Pease, Ann C. et al., "Light-Generated Oligonucleotide Arrays for Rapid DNA Sequence Analysis", *Proc. Natl. Acad. Sci.*, vol. 91, May 1994, 5022-5026.

Pecenkova, et al., "DNA Polymerase (Early Protein GP2)", *UniProt Accession Q37882*, Dec. 1998, 1-2.

Pecenkova, Tamara et al., "Bacteriophage B103: complete DNA sequence of its genome and relationship to other Bacillus phages", *Gene*, 199, 1997, 157-163.

Pingoud, Alfred et al., "Structure and function of type II restriction endonucleases", *Nucleic Acids Research*, vol. 29, No. 18, 2001, 3705-3727.

Piston, David W. et al., "Fluorescent protein FRET: the good, the bad and the ugly", *Trends Biochem. Sci.*, vol. 32, No. 9, 2007, 407-414.

Qu, Lianhua et al., "Alternative Routes Toward High Quality CdSe Nanocrystals", *Nano Letters*, vol. 1, No. 6, 2001, 333-337.

Rao, et al., "Oriented Immobilization of Proteins", *Mikrochim. Acta*, vol. 128, 1998, 127-143.

Richard, Jean-Alexandre et al., "7-Hydroxycoumarin-Hemicyanine Hybrids: A New Class of Far-Red Emitting Flurogenic Dyes", *Organic Letters*, vol. 10, 2008, 4175-4178.

Rienitz, Axel et al., "On the fidelity of DNA polymerase alpha: the influence of alpha-thio dNTPs, Mn2+ and mismatch repair", *Nucleic Acids Research*, vol. 13, No. 15, 1985, 5685-5695.

Roettger, Michelle P. et al., "Mismatched and Matched dNTP Incorporation by DNA Polymerase # Proceed via Analogous Kinetic Pathways", *Biochemistry*, vol. 47, No. 37, 2008, 9718-9727.

Rogers, Yu-Hui et al., "Immobilization of Oligonucleotides onto a Glass Support via Disulfide Bonds: A Method for Preparatin of DNA Microarrays", *Analytical Biochemistry*, vol. 266, 1999, 23-30.

Ronaghi, M et al., "Real-time DNA Sequencing Using Detection of Pyrophosphate Release", *Anal Biochem*, vol. 242(1), 1996, pp. 84-89.

Rothwell, Paul J. et al., "Structure and Mechanism of DNA Polymerases", *Advances in Protein Chemistry*, vol. 71, 2005, 401-440.

Sapsford, Kim E. et al., "Materials for Fluorescence Resonance Energy Transfer Analysis: Beyond Traditional Donor-Acceptor Combinations", *Angew. Chem. Int. Ed.*, vol. 45, 2006, 4562-4588.

Sarkez, A. et al., "A Fluorescence-based Assay for Analysis of Biotinylated Proteins and Nucleic Acids", *Biophysical Society 48th Annual Meeting*, Feb. 14, 2004, 1-6.

Schlageck, Joseph G. et al., "Spectroscopic techniques for study of phosphodiester bond formation by *Escherichia coli* RNA polymerase", *Journal of Biological Chemistry*, vol. 254, No. 23, Dec. 10, 1979, 12074-12077.

Schmitt, Christophe et al., "Kinetics of Formation and Functional Properties of Conjugates Prepared by Dry-State Incubation of Beta-Lactoglobulin/Acacia Gum Electrostatic Complexes", *J. Agric. Food Chem.*, 53, 2005, 9089-9099.

Schwartz, David C. et al., "Separation of Yeast Chromosome-Sized DNAs by Pulsed Field Gradient Gel Electrophoreis", *Cell*, vol. 37, 1984, 67-75.

Scott, Jamie K. et al., "Searching for Peptide Ligands with an Epitope Library", *Science*, vol. 249, 1990, 386-390.

Selvin, "Fluorescence Resonance Energy Transfer", *Methods in Enzymology*, vol. 246, 1995, 300-334.

Shao, Jun et al., "Unprotected Peptides as Building Blocks for the Synthesis of Peptide Dendrimers with Oxime, Hydrazone, and Thiazolidine Linkages", *J. Am. Chem. Soc.*, vol. 117, No. 14, 1995, 3893-3899.

Smith, J. J. et al., "Orthogonal Site-Specific Protein Modification by Engineering Reversible Thiol Protection Mechanisms", *Protein Science*, vol. 14, 2005, 64-73.

Soengas, Maria et al., "Site-directed mutagenesis at the Exo III motif of Phi29 DNA polymerase; overlapping structural domains for the 3'-5' exonuclease and strand-displacement activities", *The EMBO Journal*, vol. 1 1 No. 1 1, 1992, 4227-4237.

Sood, Anup et al., "Terminal Phosphate-Labeled Nucleotides with Improved Substrate Properties for Homogeneous Nucleic Acid Assays", *J. Am. Chem. Soc.*, vol. 127, No. 8, 2005, 2394-2395.

Steitz, Thomas, "DNA Polymerases: Structural Diversity and Common Mechanisms", *The Journal of Bilogical Chemistry*, vol. 274, No. 25, 1999, 17395-17398.

Stryer, "Fluorescence Energy Transfer as a Spectroscopic Ruler", *Annual Review of Biochemistry*, vol. 47, Jul. 1978, 819-846.

Sun, Lan et al., "Surface-Enhanced Raman Scattering Based Nonfluorescent Probe for Multiplex Detection", *Analytical Chemistry*, vol. 79, No. 11, 2007, 3981-3988.

Tolbert, Thomas et al., "Conjugation of Glycopeptide Thioesters to Expressed Protein Fragments", *Methods in Molecular Biology, Bioconjugation Protocols: Strategies and Methods*, 283, 2004, 255-266.

Tominaga, Jo et al., "An enzymatic strategy for site-specific immobilization of functional proteins using microbial transglutaminase", *Enzyme and Microbial Technology*, vol. 35, Iss. 6-7, 2004, 613-618.

Truniger, V. et al., "Phi29 DNA polymerase residue Leu384 , highly conserved in motif B of eukaryotic type DNA replicases, is involved in nucleotide insert ion fidelity", *The Journal of Biological Chemistry*, vol. 278 No. 35, Jun. 12, 2003, pp. 33482-33491.

Truniger, V. et al., "Two positively charged residues of phi29 DNA polymerase conserved in protein-primed DNA polymerases, are invlved in stabil isation of the incoming nucleotide", *Journal of Molecular Biology*. vol. 335 No. 2, Jan. 9, 2004, pp. 481-494.

Tsai, Yu-Chih et al., "A New Paradigm for DNA Polymerase Specificity", *Biochemistry*, vol. 45, No. 32, 2006, 9675-9687.

Tsang, Shui Y. et al., "Copper-1,10-phenanthroline induces internucleosomal DNA fragmentation in HepG2 cells, resulting from direct oxidation by the hydroxyl radical", *Biochem. J.*, vol. 317, 1996, 13-16.

Tyagi, Sanjay et al., "Multicolor molecular beacons for allele discrimination", *Nature Biotechnology*, vol. 16, 1998, 49-53.

Tyagi, Sanjay, "Taking DNA probes into a protein world", *Nature Biotechnology*, vol. 14, 1996, 947-948.

Vallina-Garcia, Romina et al., "Oriented immobilisation of anti-pneumolysin Fab through a histidine tag for electrochemical immunosensors", *Biosensors and Bioelectronics*, vol. 23, Iss. 2, 2007, 210-217.

Watkins, Lucas P. et al., "Detection of Intensity Change Points in Time-Resolved Single-Molecule Measurements", *J. Phys. Chem. B.*, vol. 109(1), 2005, 617-628.

Werts, Michel P., "Mechanically Linked Polyrotaxanes: A Stepwise Approach", *Macromolecules*, vol. 36, Iss. 19, 2003, 7004-7013.

Wetmur, J. G., "DNA probes: applications of the principles of nucleic acid hybridization", *Crit. Rev. Biochem. Mol. Biol.*, vol. 26, Nos. 3-4, 1991, 227-259.

Williams, J. G. et al., "An artificial processivity clamp made with streptavidin facilitates oriented attachment of polymerase—DNA complexes to surfaces", *Nucleic Acid Research*. vol. 36, No. 18., Aug. 22, 2008, pp. e21.

Wong, Isaac et al., "An induced-fit kinetic mechanism for DNA replication fidelity: direct measurement by single-turnover kinetics", *Biochemistry*, vol. 30, No. 2, Jan. 1991, 526-537.

Wu, Felicia et al., "Synthesis and Properties of Adenosine-5'-triphosphoro-gamma-1-(5-sulfonic acid)naphthyl Ethylamidate: A Fluorescent Nucleotide Substrate for DNA-Dependent RNA Polymerase from *Escherichia coli*", *Archives of Biochemistry and Biophysics*, vol. 246, No. 2, 1986, 564-571.

Wu, P. et al., "Resonance Energy Transfer: Methods and Applications", *Anal. Biochem.*, vol. 218(1), 1994, pp. 1-13.

Xia, Jie et al., "Photolabile 'Caged' Fatty Acids Containing a 1-(2'-Nitrophenyl)-1,2-Ethanediol Moiety", *Bioorganic & Medicinal Chemistry Letters*, vol. 7, Iss. 10, 1997, 1243-1248.

(56) References Cited

OTHER PUBLICATIONS

Xu, Yao et al., "Imaging protein interactions with bioluminescence resonance energy transfer (BRET) in plant and mammalian cells and tissues", *Proc. Natl. Acad. Sci.*, vol. 96, 1999, 151-156.

Yarbrough, L. R. et al., "Synthesis and properties of fluorescent nucleotide substrates for DNA-dependent RNA polymerases", *Journal of Biological Chemistry*, vol. 254, No. 23, Dec. 10, 1979, 12069-12073.

Yarbrough, Lynwood R., "Synthesis and Properties of a New Fluorescent Analog of ATP: Adenosine-5'-Triphosphoro-y-1-(5-SUlfonic Acid) Napthylamidate", *Biochemical and Biophysical Research Communications*, vol. 81, No. 1, Mar. 15, 1978, 35-41.

Yeo, Sanghak et al., "The patterned hydrophilic surfaces of glass slides to be applicable for the construction of protein chips", *Current Applied Physics*, vol. 6, 2006, 267-270.

Zarling, et al., "Mapping of Lymphocyte Surface Polypeptide Antigens by Chemical Cross-Linking with BSOCOES", *Journal of Immunology*, vol. 124, No. 2, 1980, 913-920.

Zhang, Kechun et al., "Artificial Polypeptide Scaffold for Protein Immobilization", *J. Am. Chem. Soc.*, vol. 127, No. 29, 2005, 10136-10137.

Zhu, Heng et al., "Analysis of Yeast Protein Kinases Using Protein Chips", *Nature Genetics*, vol. 26, 2000, 283-289.

Zhu, Heng et al., "Protein Chip Technology", *Curr. Opin. Chem. Biol.*, vol. 7, No. 1, 2003, 55-63.

\* cited by examiner

HP1 binding curve

$$Y = b + \frac{a-b}{1+10^{(\log EC50-X)*c}}$$

Y: mP
X: log[Fphi29(nM)]
logEC50: 1.931
a (top): 387.2
b (bottom): 133.6
c (slope): 2.272

Active phi29 per conjugate

| oligo221 conc 150nM, 1x extension buffer pH7.5 | | | | |
|---|---|---|---|---|
| C8-GST-HP1_5x (XP065) Conc. (nM) | 30 | 30 | 60 | 60 |
| FP(mP) | 207.127505 | 209.177046 | 251.4517 | 265.8863 |
| log(HP1) conc.,nM)= | 1.759786288 | 1.767229714 | 1.903976 | 1.947551 |
| HP1 conc.(nM)= | 57.51568393 | 58.50994823 | 80.16338 | 88.62401 |
| Number of active HP1 per conjugate= | 1.9 | 2.0 | 1.3 | 1.5 |
| average= | 1.7 | | | |

HP1 binding curve

$$Y = b + \frac{a-b}{1+10^{(\log EC50-X)*c}}$$

Y:        mP
X:        log[Fphi29(nM)]
logEC50:  1.931
a (top):  387.2
b (bottom): 133.6
c (slope): 2.272

Active phi29 per conjugate

| | | | | |
|---|---|---|---|---|
| oligo221 conc 150nM, 1x extension buffer pH7.5 | | | | |
| C8-MBP-HP1_5x (XP064) Conc. (nM) | 30 | 30 | 60 | 60 |
| FP(mP) | 210.73466 | 219.579263 | 323.2496 | 314.5863 |
| log(HP1) conc.,nM)= | 1.772809046 | 1.803388192 | 2.138794 | 2.105572 |
| HP1 conc.(nM)= | 59.26646797 | 63.58990732 | 137.6557 | 127.518 |
| Number of active HP1 per conjugate= | 2.0 | 2.1 | 2.3 | 2.1 |
| average= | 2.1 | | | |

$$Y = b + \frac{a-b}{1+10^{(\log EC50-X)*c}}$$

Y:        mP
X:        log[Fphi29(nM)]
logEC50:  1.931
a (top):  387.2
b (bottom): 133.6
c (slope): 2.272

Active phi29 per conjugate
oligo221 conc 150nM, 1x extension buffer pH7.5

| | | |
|---|---:|---:|
| C8-CAT-HP1_5x (XP066) Conc. (nM) | 60 | 60 |
| FP(mP) | 155.437334 | 164.804971 |
| log(HP1) conc.,nM)= | 1.479484216 | 1.555603304 |
| HP1 conc.(nM)= | 30.16367244 | 35.94208811 |
| Number of active HP1 per conjugate= | 0.5 | 0.6 |
| average= | 0.6 | |

- 100X brighter than single organic dyes
- Provide "clonally-amplified-like" signal levels with no amplification
- Stable for long periods of time, allowing long read lengths with continuous illumination Conjugation with Nonnatural Amino Acid, Acetylphenyl Alanine (ketone)

dN6P-C6-Dye

CONJUGATES OF BIOMOLECULES TO NANOPARTICLES

This application is a continuation of U.S. Nonprovisional application Ser. No. 12/748,355, filed on Mar. 26, 2010, which claims the filing date benefit of U.S. Provisional Application Nos. 61/164,324, filed on Mar. 27, 2009; 61/184,770, filed on Jun. 5, 2009; 61/242,771, filed on Sep. 15, 2009; 61/245,457, filed on Sep. 24, 2009; 61/263,974, filed on Nov. 24, 2009; 61/289,388; filed on Dec. 22, 2009; 61/293,618, filed on Jan. 8, 2010; 61/293,616, filed on Jan. 8, 2010; 61/299,919, filed on Jan. 29, 2010; 61/299,917, filed on Jan. 29, 2010; 61/307,356, filed on Feb. 23, 2010. The contents of each of the foregoing patent applications are incorporated by reference in their entirety.

FIELD

The present disclosure relates generally to conjugates comprising a biomolecule linked to a label, for use in a variety of biological applications. More particularly, disclosed herein are labeled polymerase conjugates comprising a polymerase linked to a label, wherein the conjugate has polymerase activity.

BACKGROUND

Labeling of biomolecules is frequently performed in biological assays. Such labeling studies have been widely used to elucidate structural and/or functional properties of various biomolecules, including carbohydrates, lipids, nucleic acids, nucleotides and proteins. Enzymes are of particular interest because they catalyze fundamental biochemical reactions within living organisms. For example, DNA and RNA polymerases assist in genomic replication and transcription by catalyzing the polymerization of nucleotides into nucleic acids.

Conventional labeling techniques generally involve the attachment of one or few organic labels comprising fluorescent small molecules, e.g., dyes, to the biomolecule of interest. However, such labeled conjugates are generally not suitable for use in single molecule assays due the toxicity effect of the label on the biomolecule, and/or the poor detectability (as characterized, for example, by low signal/noise ratio, brightness, e.g., quantum yield, signal lifetime, etc) and photostability of such conjugates. There is therefore a need in the art for labeled biomolecule conjugates that emit stronger and more stable signals than is feasible with conjugates produced by conventional labeling methods, and that retain sufficient biological activity for use in single molecule assays.

Disclosed herein are improved labeled biomolecule conjugates, as well as novel methods of making and using such conjugates. Such conjugates comprise labeled biomolecules exhibiting improved biological activity, detectability and/or photostability and that are suitable for use in single molecule assays. In some embodiments, the conjugates comprise biomolecules linked to nanoparticles, which exhibit superior detection qualities as compared to conventional organic dyes. In other embodiments, the conjugates comprise a biomolecule linked to multiple dye labels that retain sufficient biological activity for use in single molecule assays.

The superior detectability of the conjugates of the present disclosure permits a wide range of powerful new approaches not hitherto feasible using conventional labeling methods, including, for example, extended imaging of biological samples over an extended period of time, real time in situ visualization of biomolecules or biomolecular activity in vivo or in vitro, optical coding of biomolecules, physical manipulation of biomolecules and/or biomolecular sorting, all of which can optionally be performed in high-throughput format.

For example, disclosed herein are labeled polymerase conjugates comprising a polymerase linked to a label that emit signals of superior intensities and durations, thus improving their performance in single molecule sequencing applications. In some embodiments, the labeled polymerase conjugates include multiple dyes (typically three or more) linked in tandem to a single polymerase without significant loss of polymerase activity. In other embodiments, the labeled polymerase conjugates comprise a nanoparticle label that typically emits stronger and more stable signals relative to conventional organic dyes.

The labeled polymerase conjugates provided herein can undergo FRET with an acceptor-labeled nucleotide bound to the active site in such a manner that the resulting FRET-based signal is readily detectable in a single molecule system, and also emit signals of sufficient duration to permit longer "reads" from a single nucleic acid molecule, thus permitting single molecule reads of increased length and accuracy. Such conjugates also retain high levels of polymerase activity, thus increasing the efficiency of single molecule sequencing systems using such conjugates.

The production of such improved conjugates is associated with several technical challenges. For example, biomolecules labeled with nanoparticles frequently exhibit a high degree of aggregation; it can also be difficult to precisely control the ratios at which the biomolecule will attach to the nanoparticle, a problem compounded by the difficulty of determining the stoichiometric composition (i.e., ratio of biomolecule to nanoparticle) of the resulting conjugates. Similarly, while the detectability of conjugates comprising organic dye labels can be improved by increasing the number of dye labels linked to the biomolecule, such increased dye loading is typically accompanied by a reduction or loss in activity of the biomolecule. There remains a need in the art for labeled biomolecule conjugates exhibiting reduced aggregation and increased biomolecular activity along with superior detectability. There is also a need for improved methods for conjugating biomolecules, e.g., proteins, to labels wherein the stochiometry of the conjugated components can be reliably controlled and the activity of the biomolecule preserved.

SUMMARY

Disclosed herein are labeled biomolecule conjugates useful in a wide range of biological applications, methods of making and using such conjugates, as well as systems, apparatuses and kits comprising such conjugates. The compositions, methods, systems, apparatuses and kits described herein represent significant advances over the current methods. For example, disclosed herein is a composition comprising a labeled biomolecule conjugate including a biomolecule linked to a label, wherein the conjugate has a biological activity that is characteristic of the biomolecule. Typically, the label of the conjugate emits, or is capable of emitting, a signal. In some embodiments; the label induces emission, or is capable of inducing emission (e.g., via FRET) of the signal. Optionally, the signal can indicate various aspects of the biological activity of the conjugate.

In some embodiments, the conjugate can be visualized and tracked in real time, optionally in single molecule format.

Also provided herein is a polymerase-nanoparticle conjugate including a polymerase linked to a nanoparticle, wherein the conjugate has polymerase activity. In some embodiments, the polymerase activity of the conjugate is at least about 1%, 5%, 10%, 20%, 30%, 40%, 40%, 50%, 60%, 70%, 80%, 90%, 95%, 97% or 99% relative to the polymerase activity of the unconjugated polymerase. Optionally the polymerase activity is in the range of about 50% to 90% relative to the polymerase activity of the unconjugated polymerase.

In some embodiments, the polymerase of the conjugate includes, or is modified to include, a metal chelating group. Optionally, the metal chelating group can include one or more naturally occurring or engineered histidine residues of the enzyme.

In some embodiments, the polymerase comprises a His tag. Optionally, the His tag chelates with one or more metal atoms of the nanoparticle.

In some embodiments, the polymerase of the polymerase-nanoparticle conjugate comprises one member of a binding pair and the nanoparticle comprises a complementary member of the binding pair.

Optionally, the polymerase of the conjugate is a DNA polymerase. In some embodiments, the DNA polymerase is at least 95% identical to a DNA polymerase selected from the group consisting of: Phi-29 DNA polymerase, B103 DNA polymerase, the Klenow fragment of $E.$ $coli$ DNA polymerase and HIV reverse transcriptase.

In some embodiments, the linkage between the polymerase and the nanoparticle of the polymerase-nanoparticle conjugate comprises a bond selected from one of a group consisting of: covalent bonding, affinity bonding and electrostatic bonding. Optionally, the bond can be through a functional group selected from the group consisting of: a hydroxyl, a carboxyl, a carbonyl, a sulfhydryl, an amine, an amide, a nitrile, a nitrogen with a free lone pair of electrons, an amino acid, a thiol, a sulfonic acid, a sulfonyl halide, and an acyl halide.

Optionally, the bond can be an amide bond formed through reaction of a carboxyl group of the nanoparticle and an amine group of the enzyme.

Optionally, the polymerase and the nanoparticle of the conjugate are linked through a covalent bond formed through a reaction involving a thiol group of a natural or engineered cysteine residue of the polymerase. In some embodiments, the cysteine residue is an N-terminal cysteine residue located at the N-terminus of the polymerase. In some embodiments, the reaction involves the amino and/or thiol group of the N-terminal cysteine. In some embodiments, the bond can be a peptide bond formed through a reaction between a thioester group of the nanoparticle and the thiol group of the cysteine residue. In some embodiments, the bond can be a covalent bond formed through a reaction between an aldehyde group of the nanoparticle and the thiol group of the cysteine residue.

In some embodiments, the nanoparticle of the polymerase-nanoparticle conjugate includes a monodentate thiol ligand. In some embodiments, the monodentate thiol ligand can be mercaptoacetic acid.

In some embodiments, the nanoparticle of the polymerase-nanoparticle conjugate includes a bidentate thiol-based ligand coating.

In some embodiments, the nanoparticle of the polymerase-nanoparticle conjugate includes a dipeptide-based coating.

In some embodiments, the nanoparticle of the polymerase-nanoparticle conjugate includes a polycyclic acid-based ligand coating.

In some embodiments, the nanoparticle of the polymerase-nanoparticle conjugate includes a dihydrolipoic acid (DHLA)-based ligand coating.

In some embodiments, the nanoparticle of the polymerase-nanoparticle conjugate includes a tridentate thiol-based ligand coating. In some embodiments, the tridentate thiol-based ligand can include a compound of Formula II-VII as provided herein.

In some embodiments, the nanoparticle of the polymerase-nanoparticle conjugate comprises a surface coating including a tridentate thiol ligand. In some embodiments, the tridentate thiol ligand can include a compound of Formula II-VII as provided herein.

In some embodiments, the nanoparticle of the polymerase-nanoparticle conjugate comprises a surface coating including bipeptides.

Optionally, the nanoparticle of the polymerase-nanoparticle conjugate can be about 1 nm to about 100 nm in its largest dimension, about 1 nm to about 20 nm, about 1 nm to about 15 nm, about 1 nm to about 10 nm or preferably about 5 nm to about 10 nm in its largest dimension.

Optionally, the nanoparticle of the polymerase-nanoparticle conjugate is positioned relative to the polymerase to perform an energy transfer reaction. In some embodiments, the nanoparticle is positioned to perform FRET with a labeled nucleotide bound to an active site of the polymerase. Optionally, the label of the labeled conjugate is positioned to perform RET with a label linked to the terminal phosphate of a polyphosphate-comprising nucleotide. Optionally, the nanoparticle of the conjugate undergoes FRET with the nucleotide label with a FRET efficiency of at least about 20%.

In other embodiments, the polymerase is a mutant Phi-29 DNA polymerase comprising an N-terminal polyhistidine tag (His-tag) fused to an amino acid sequence at least 85% identical to a Phi-29 DNA polymerase comprising the amino acid sequence of SEQ ID NO: 3, or any biologically active fragment thereof.

In other embodiments, the polymerase is a mutant Phi-29 DNA polymerase comprising an N-terminal polyhistidine tag (His-tag) fused to an amino acid sequence at least 85% identical to a Phi-29 DNA polymerase comprising the amino acid sequence of SEQ ID NO: 3, or any biologically active fragment thereof. In some embodiments, the mutant Phi-29 DNA polymerase further includes an amino acid substitution at position 372 of the amino acid sequence of SEQ ID NO: 3.

In other embodiments, the polymerase is a mutant B103 DNA polymerase including an amino acid sequence at least 85% identical the amino acid sequence of SEQ ID NO: 33 or 34, or any biologically active fragment thereof. In some embodiments, the polymerase further comprises an amino acid substitution at position 370, wherein the numbering is relative to the amino acid sequence of SEQ ID NO: 33. In some embodiments, the polymerase further comprises an amino acid substitution at position 380 of the amino acid sequence of SEQ ID NO: 3.

Also disclosed herein is the polymerase-nanoparticle conjugate as used in a primer extension reaction.

Also provided herein are methods for performing a primer extension reaction using the polymerase-nanoparticle conjugates of the present disclosure. In some embodiments, the method for performing a primer extension reaction comprises contacting the polymerase-nanoparticle conjugate with a nucleic acid molecule and a nucleotide under conditions where the polymerase of the conjugate extends the nucleic acid molecule by a nucleotide. Optionally, the nucleotide further comprises a label linked to the terminal phosphate group of the nucleotide. In some embodiments, the method further comprises detecting a signal resulting from FRET between the nanoparticle and the label of the nucleotide.

Also provided herein are methods for making a population of the polymerase-nanoparticle conjugates of the present disclosure. In some embodiments, the method for making a population of polymerase-nanoparticle conjugates comprises contacting a plurality of nanoparticles with a plurality of polymerases and a quantity of an accessory compound to form a population of polymerase-nanoparticle conjugates with an average of about 0.5 to 1.5 polymerases per nanoparticle. In some embodiments, the method comprises contacting a plurality of nanoparticles with a plurality of polymerases and a quantity of an accessory compound to form a population of polymerase-nanoparticle conjugates with an average of about 2 to 8 polymerases per nanoparticle. Optionally, the accessory compound is selected from a group consisting of horseradish peroxidase, mucin, albumin, avidin, chloramphenicol acetyl-transferase, maltose binding protein and uracil DNA glycosylase. In some embodiments, the accessory compound further comprises a His-tag. In some embodiments, the contacting is performed by mixing the plurality of polymerases and plurality of nanoparticles in a molar ratio ranging from about 3:1 to about 2:1. In some embodiments, the contacting is performed by mixing the plurality of polymerases and plurality of nanoparticles in a molar ratio ranging from about 3:1 to about 15:1.

Also provided herein is a population of nanoparticles, wherein at least about 20% of nanoparticles are conjugated to an average of one polymerase.

In some embodiments, the polymerase-nanoparticle conjugate comprises a polymerase linked to a nanoparticle, where the polymerase includes a his-tag at the N-terminal end, and where the polymerase is linked to the nanoparticle via a His-tag mediated attachment, thereby forming a polymerase-nanoparticle conjugate.

Also disclosed herein are methods of making such a polymerase-nanoparticle conjugate, comprising: producing a polymerase including a His tag, and contacting the polymerase with a nanoparticle under conditions where the polymerase becomes linked to the nanoparticle via a His tag mediated attachment, thereby forming a polymerase-nanoparticle conjugate.

Also disclosed herein are methods for making a polymerase-nanoparticle conjugate, comprising: obtaining a nanoparticle including a surface thioester group; and contacting the nanoparticle with a biomolecule including an N-terminal cysteine residue under conditions where the polymerase becomes linked to the nanoparticle to form a polymerase-nanoparticle conjugate having polymerase activity.

Also disclosed herein are methods for making a polymerase-nanoparticle conjugate, comprising: obtaining a nanoparticle including a surface aldehyde; and contacting the nanoparticle with a biomolecule including an N-terminal cysteine residue under conditions where the polymerase becomes linked to the nanoparticle to form a polymerase-nanoparticle conjugate having polymerase activity.

DETAILED DESCRIPTION OF THE DRAWINGS

The following figures form part of the present specification and are included to further demonstrate certain aspects of subject matter disclosed herein by way of non-limiting embodiments and examples. This subject matter may be better understood by reference to one or more of these figures in combination with the detailed description of specific embodiments presented herein.

FIG. 1 depicts the results of an assay for DNA binding of an acceptor-labeled oligonucleotide by various conjugates comprising different forms of Klenow DNA polymerase linked to a nanoparticle.

FIGS. 2A-C depicts the results of an assay for DNA binding of an acceptor-labeled oligonucleotide by a conjugate comprising Klenow DNA polymerase linked to a nanoparticle using the linking agent SMCC. FIG. 2A shows the donor fluorescence intensity observed at 605 nm. FIG. 2B shows the acceptor fluorescence intensity observed at 670 nm. FIG. 2C shows the ratio of the donor to acceptor signal.

FIG. 3 depicts the results of nucleotide incorporation by various conjugates comprising Klenow DNA polymerase linked to a nanoparticle, showing an increase in the ratio of donor and acceptor fluorescence in the presence of nucleotides as compared to a control lacking nucleotides.

FIGS. 4A-B depicts the products obtained from a primer extension reaction wherein conjugates comprising either Klenow DNA polymerase, panel (A), or Phi-29 DNA polymerase, panel (B), linked to nanoparticles were contacted with a primed template in the presence of unlabeled nucleotides, unlabeled nucleoside tetraphosphates, and omega-labeled nucleoside tetraphosphates. FIG. 4A shows the results of primer extension reactions of Klenow, Klenow-nanoparticle conjugates, or Phi polymerase. FIG. 4B shows the results of primer extension reactions of unconjugated and Phi29 conjugates.

FIG. 5 depicts the results of nucleotide incorporation by conjugates comprising His-tagged Phi-29 polymerase linked to nanoparticles.

FIGS. 6A-C depicts the observed fluorescence intensities, in donor and acceptor channels, from reactions containing fluorescently labeled nucleic acid templates and polymerase-nanoparticle conjugates comprising His-tagged Phi-29 polymerase linked to nanoparticles. FIG. 6A shows an increase in FRET acceptor signal with an increase in the template concentration; FIG. 6B shows a decrease in FRET donor signal with an increase in the template concentration; FIG. 6C shows a decrease in the ratio of FRET donor/acceptor signal with an increase in the template concentration.

FIG. 7 depicts the results of nucleotide incorporation by conjugates comprising His-tagged Phi-29 polymerase linked to glutathione S-transferase (GST) treated nanoparticles.

FIGS. 8A-C depicts the observed fluorescence intensities from reactions containing of fluorescently labeled nucleic acid templates and polymerase-nanoparticle conjugates comprising His-tagged Phi-29 polymerase linked to nanoparticles treated with GST. FIG. 8A shows an increase in FRET acceptor signal with an increase in the template concentration; FIG. 8B shows a decrease in FRET donor signal with an increase in the template concentration; FIG. 8C shows a decrease in the ratio of FRET donor/acceptor signal with an increase in the template concentration.

FIGS. 9A-D depicts the results of various assays performed on polymerase-nanoparticle conjugates comprising Phi-29 polymerase linked to nanoparticles treated with glutathione S-transferase (GST). FIG. 9A depicts the results of size exclusion HPLC chromatography, showing the appearance of a single major peak around 12 minutes retention time; FIG. 9B depicts the results of a DNA binding assay wherein the conjugate was contacted with an acceptor-labeled nucleotide, showing observed fluorescence in the acceptor channel (top panel) and donor channel (bottom panel); FIG. 9C depicts the results of nucleotide incorporation by the conjugate, plotted as observed fluorescence over time; and FIG. 9D depicts the results of fluorescence polarization measurements for the conjugate, which measurements were used to calculate the average number of active Phi-29 polymerases per conjugate using regression analysis.

FIG. 10 depicts the results of nucleotide incorporation by conjugates comprising protein kinase A recognition sequence-tagged Phi-29 polymerase linked to nanoparticles.

FIGS. 11A-C depicts the results of binding of fluorescently-labeled templates to conjugates comprising PKA-Phi-29 polymerase linked to a nanoparticle.

FIG. 11A shows an increase in FRET acceptor signal with an increase in the template concentration; FIG. 11B shows a decrease in FRET donor signal with an increase in the template concentration; FIG. 11C shows a decrease in the ratio of FRET donor/acceptor signal with an increase in the template concentration.

FIG. 12 depicts the results of nucleotide incorporation by conjugates comprising His-tagged Phi-29 polymerase linked to nanoparticles treated with uracil DNA glycosylase (UDG) and uracil DNA glycosylase inhibitor (UGI).

FIGS. 13A-C depicts the observed fluorescence intensities from reactions containing of fluorescently labeled nucleic acid templates and polymerase-nanoparticle conjugates comprising His-tagged Phi-29 polymerase linked to nanoparticles treated with UDG and UGI. FIG. 13A shows an increase in FRET acceptor signal with an increase in the template concentration; FIG. 13B shows a decrease in FRET donor signal with an increase in the template concentration; FIG. 13C shows a decrease in the ratio of FRET donor/acceptor signal with an increase in the template concentration.

FIG. 14 depicts the results of nucleotide incorporation by conjugates comprising His-tagged Phi-29 polymerase linked to BSA-treated nanoparticles.

FIGS. 15A-C depicts the observed fluorescence intensities from reactions containing of fluorescently labeled nucleic acid templates and polymerase-nanoparticle conjugates comprising His-tagged Phi-29 polymerase linked to nanoparticles treated with BSA. FIG. 15A shows an increase in FRET acceptor signal with an increase in the template concentration; FIG. 15B shows a decrease in FRET donor signal with an increase in the template concentration; FIG. 15C shows a decrease in the ratio of FRET donor/acceptor signal with an increase in the template concentration.

FIGS. 16A-E depicts the results of various assays performed on conjugates comprising Phi-29 polymerase linked to nanoparticles treated with UDG and UGI. FIG. 16A depicts the results of size exclusion HPLC chromatography, showing the appearance of a single major peak around 12 minutes retention time; FIG. 16B depicts the results of a DNA binding assay wherein the conjugate was contacted with an acceptor-labeled nucleotide, showing observed fluorescence in the acceptor channel (top panel) and donor channel (bottom panel); FIG. 16C depicts the results of nucleotide incorporation by the conjugate, plotted as observed fluorescence over time; and FIG. 16D depicts the results of fluorescence polarization measurements for the conjugate, which measurements were used to calculate the average number of active Phi-29 polymerases per conjugate using regression analysis. FIG. 16E depicts the effect of different conjugate preparation methods upon the degree of aggregation (or conversely, the yield of monodisperse conjugates) observed in the four different conjugates populations prepared according to the methods described herein.

FIGS. 17A-D depicts the results of various assays performed on three different conjugates comprising Phi-29 polymerase linked to nanoparticles treated with UDG and UGI using different ratios of polymerase to nanoparticle in the conjugate reaction. FIG. 17A depicts the results of a DNA binding assay wherein the conjugate was contacted with an acceptor-labeled nucleotide, showing observed fluorescence in the acceptor channel (top panel) and donor channel (bottom panel); FIG. 17B depicts the results of nucleotide incorporation by the conjugate, plotted as observed fluorescence over time; FIG. 17C depicts the results of fluorescence polarization measurements for the conjugate, which measurements were used to calculate the average number of active Phi-29 polymerases per conjugate using regression analysis, and FIG. 17D depicts a graph showing the correlation between the conjugate activity, as measured in the nucleotide incorporation assay, and the number of active Phi-29 polymerases per conjugate (as calculated from results of the fluorescence polarization assay).

FIGS. 18A-D depicts the results of various assays performed on conjugates comprising Phi-29 polymerase linked to nanoparticles treated with maltose binding protein (MBP). FIG. 18A depicts the results of size exclusion HPLC chromatography, showing the appearance of a single major peak around 12 minutes retention time; FIG. 18B depicts the results of a DNA binding assay wherein the conjugate was contacted with an acceptor-labeled nucleotide, showing observed fluorescence in the acceptor channel (top panel) and donor channel (bottom panel); FIG. 18C depicts the results of nucleotide incorporation by the conjugate, plotted as observed fluorescence over time; and FIG. 18D depicts the results of fluorescence polarization measurements for the conjugate, which measurements were used to calculate the average number of active Phi-29 polymerases per conjugate using regression analysis.

FIGS. 19A-D depicts the results of various assays performed on conjugates comprising Phi-29 polymerase linked to nanoparticles treated with chloramphenicol acetyltransferase (CAT). FIG. 19A depicts the results of size exclusion HPLC chromatography, showing the appearance of a single major peak around 12 minutes retention time; FIG. 19B depicts the results of a DNA binding assay wherein the conjugate was contacted with an acceptor-labeled nucleotide, showing observed fluorescence in the acceptor channel (top panel) and donor channel (bottom panel); FIG. 19C depicts the results of nucleotide incorporation by the conjugate, plotted as observed fluorescence over time; and FIG. 19D depicts the results of fluorescence polarization measurements for the conjugate, which measurements were used to calculate the average number of active Phi-29 polymerases per conjugate using regression analysis.

FIGS. 20A-D depicts the results of various assays performed on conjugates comprising a His-tagged mutant Phi-29 polymerase, HP1, linked to nanoparticles. FIG. 20A depicts the results of size exclusion HPLC chromatography, showing the appearance of a single major peak around 12 minutes retention time; FIG. 20B depicts the results of a DNA binding assay wherein the conjugate was contacted with an acceptor-labeled nucleotide, showing observed fluorescence in the acceptor channel (top panel) and donor channel (bottom panel); FIG. 20C depicts the results of nucleotide incorporation by the conjugate, plotted as observed fluorescence over time; and FIG. 20D depicts the results of fluorescence polarization measurements for the conjugate, which measurements were used to calculate the average number of active Phi-29 polymerases per conjugate using regression analysis.

Figure 32A:
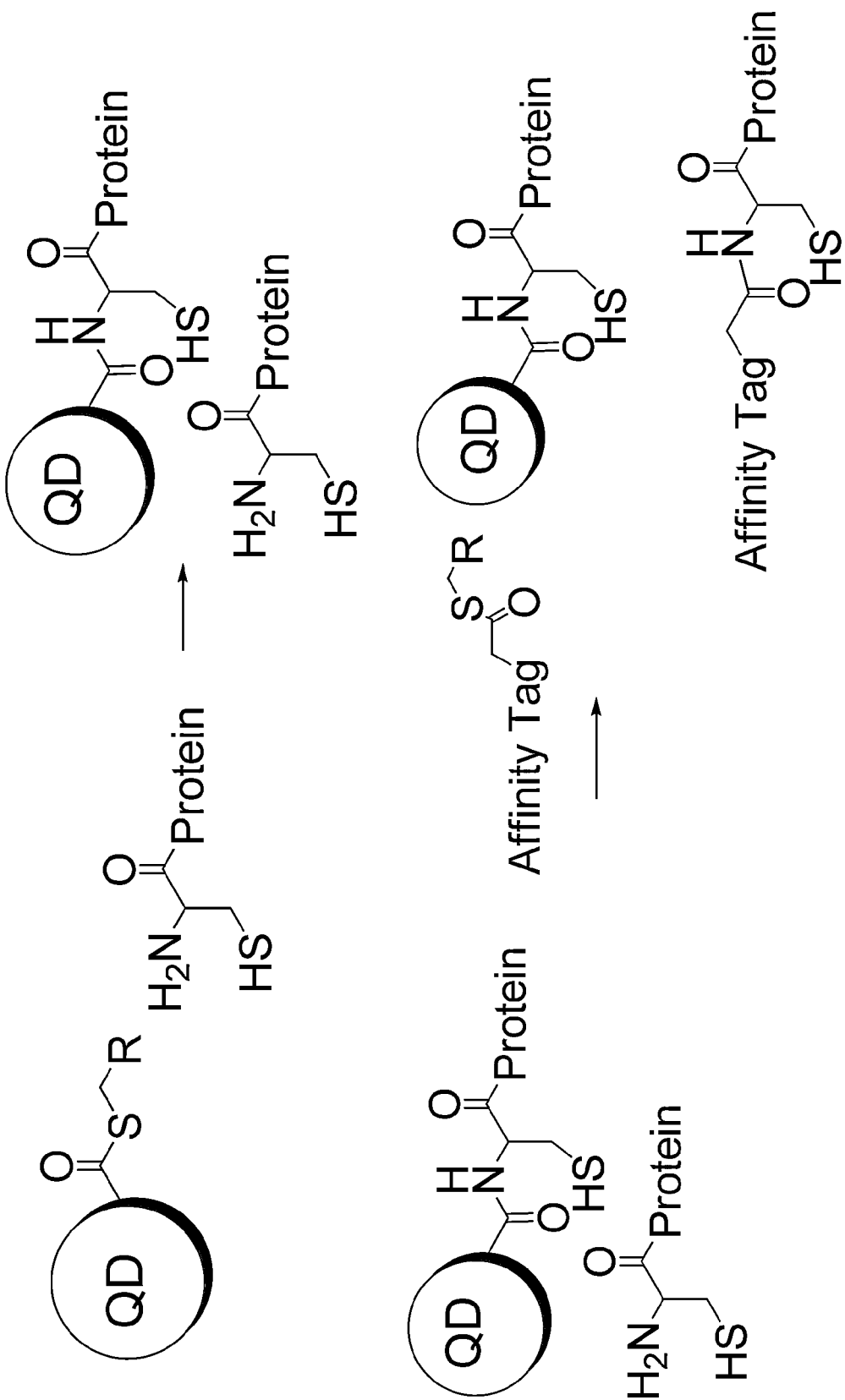
Figure 32B:
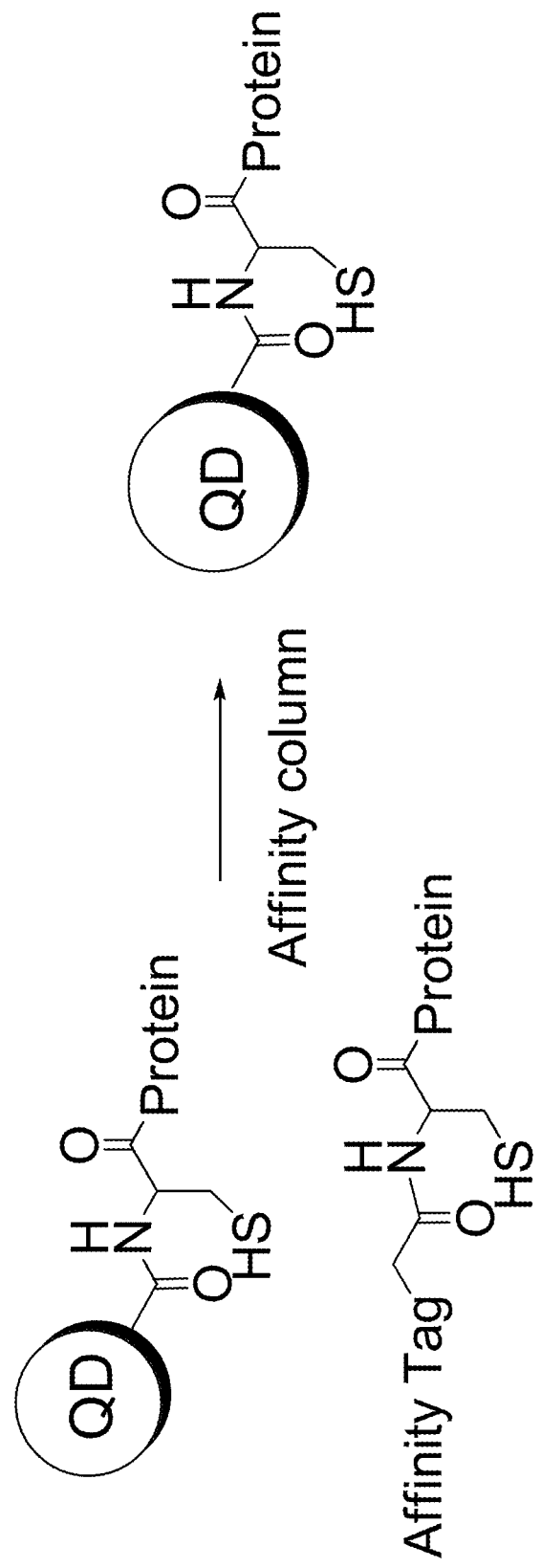

FIGS. 32A-B depicts an exemplary reaction pathway for forming a labeled polymerase conjugate according to the present disclosure. FIG. 32A shows a reaction between a biomolecule having a terminal cysteine and a quantum dot having a surface thioester. FIG. 32B shows a reaction between a biomolecule having a terminal cysteine and a quantum dot having a surface thioester.

Figure 33:
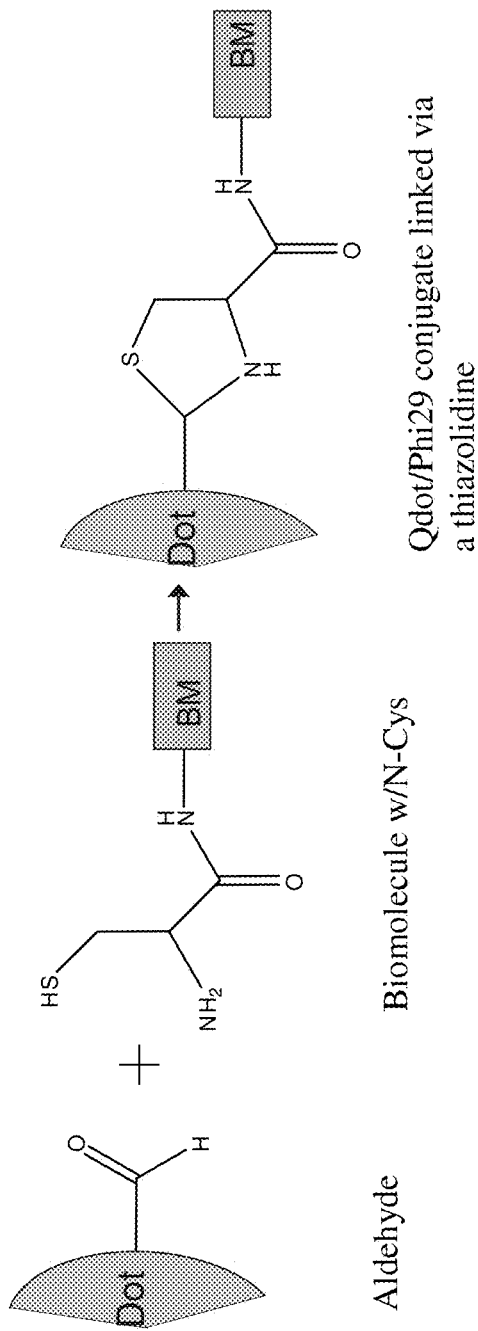

FIG. 33 depicts a second exemplary reaction pathway for forming a labeled polymerase conjugate according to the present disclosure.

Figure 34:
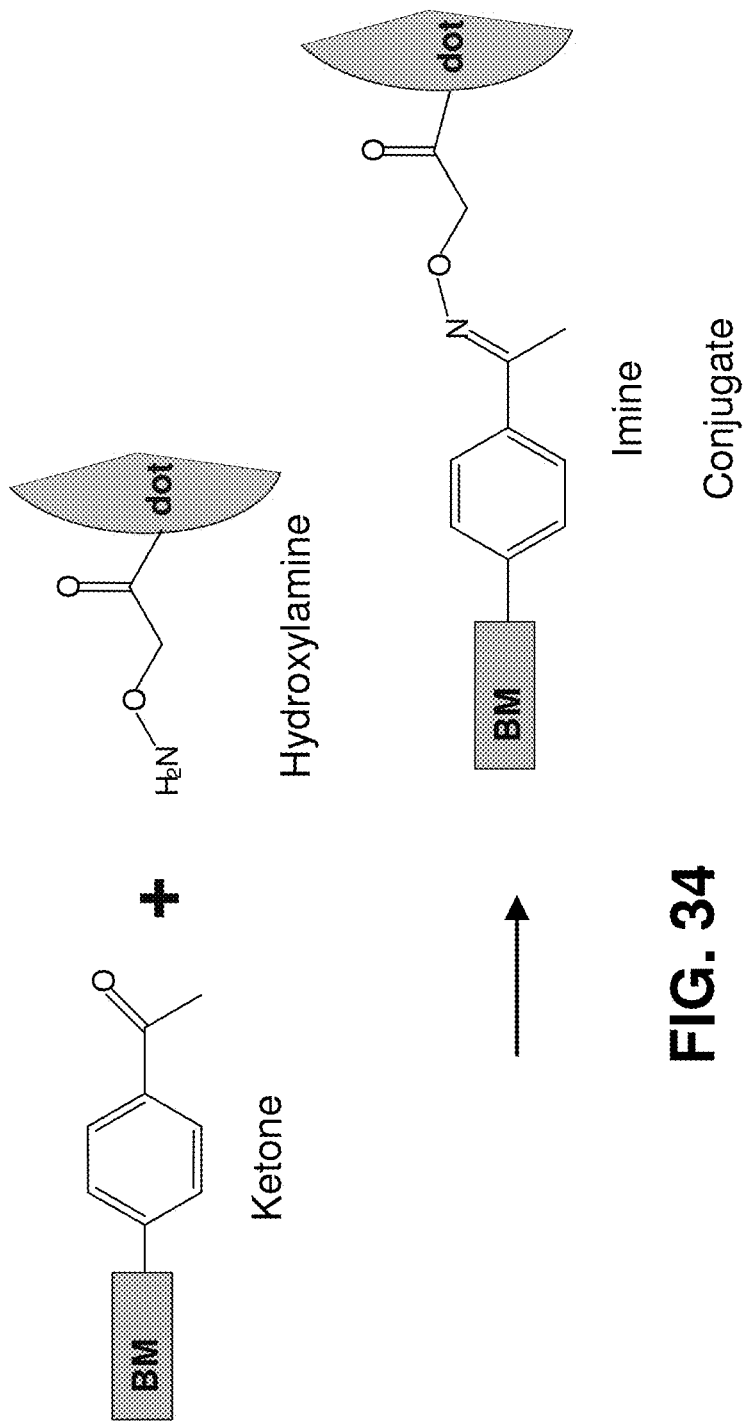

FIG. 34 depicts a third exemplary reaction pathway for forming a labeled polymerase conjugate according to the present disclosure.

Figure 35:
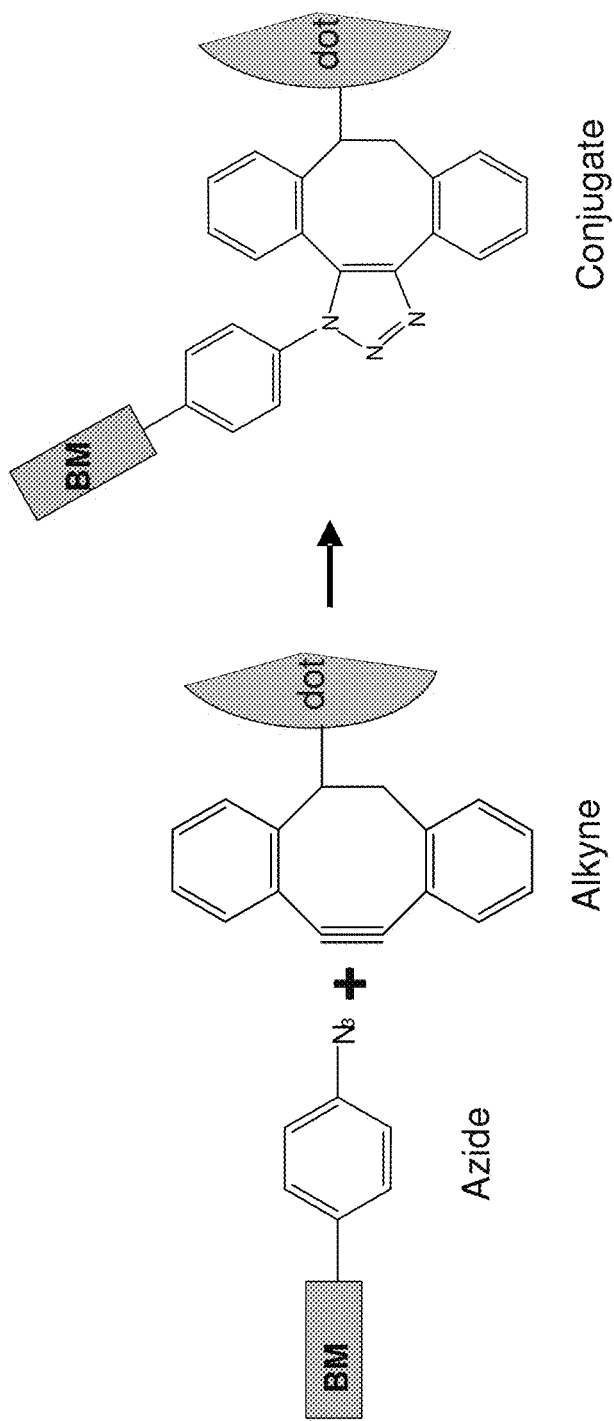

FIG. 35 depicts a fourth exemplary reaction pathway for forming a labeled polymerase conjugate according to the present disclosure.

Figure 36:
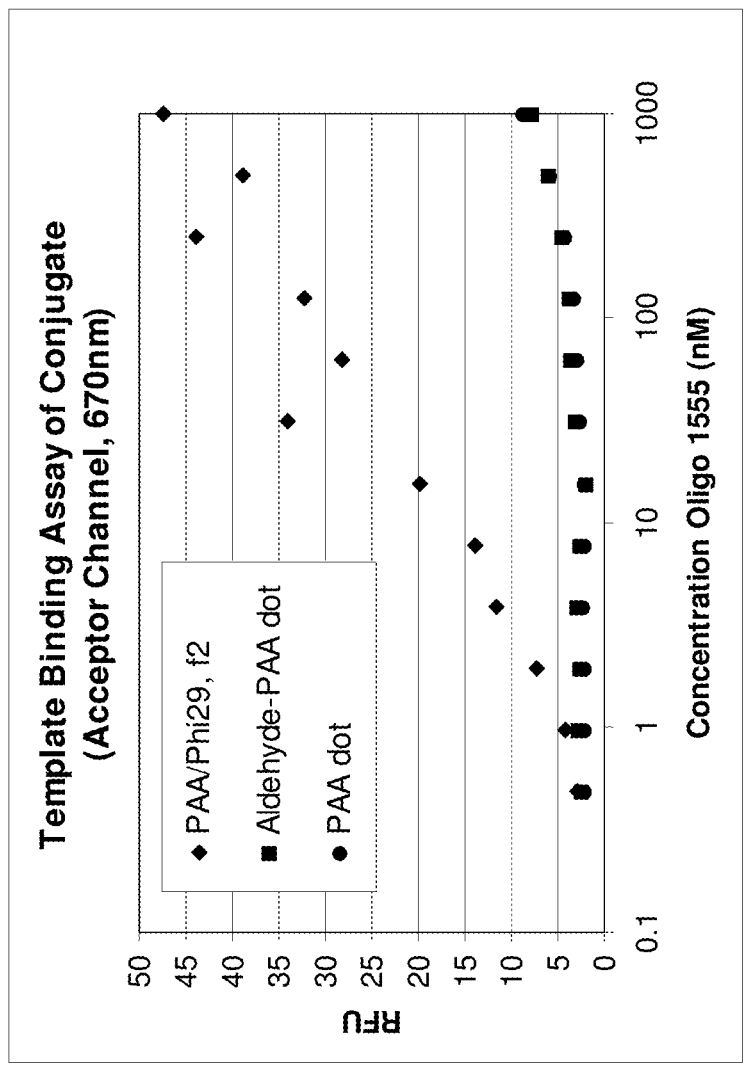

FIG. 36 depicts the results of a nucleic acid binding assay using a labeled polymerase conjugate of the present disclosure.

Figure 37:
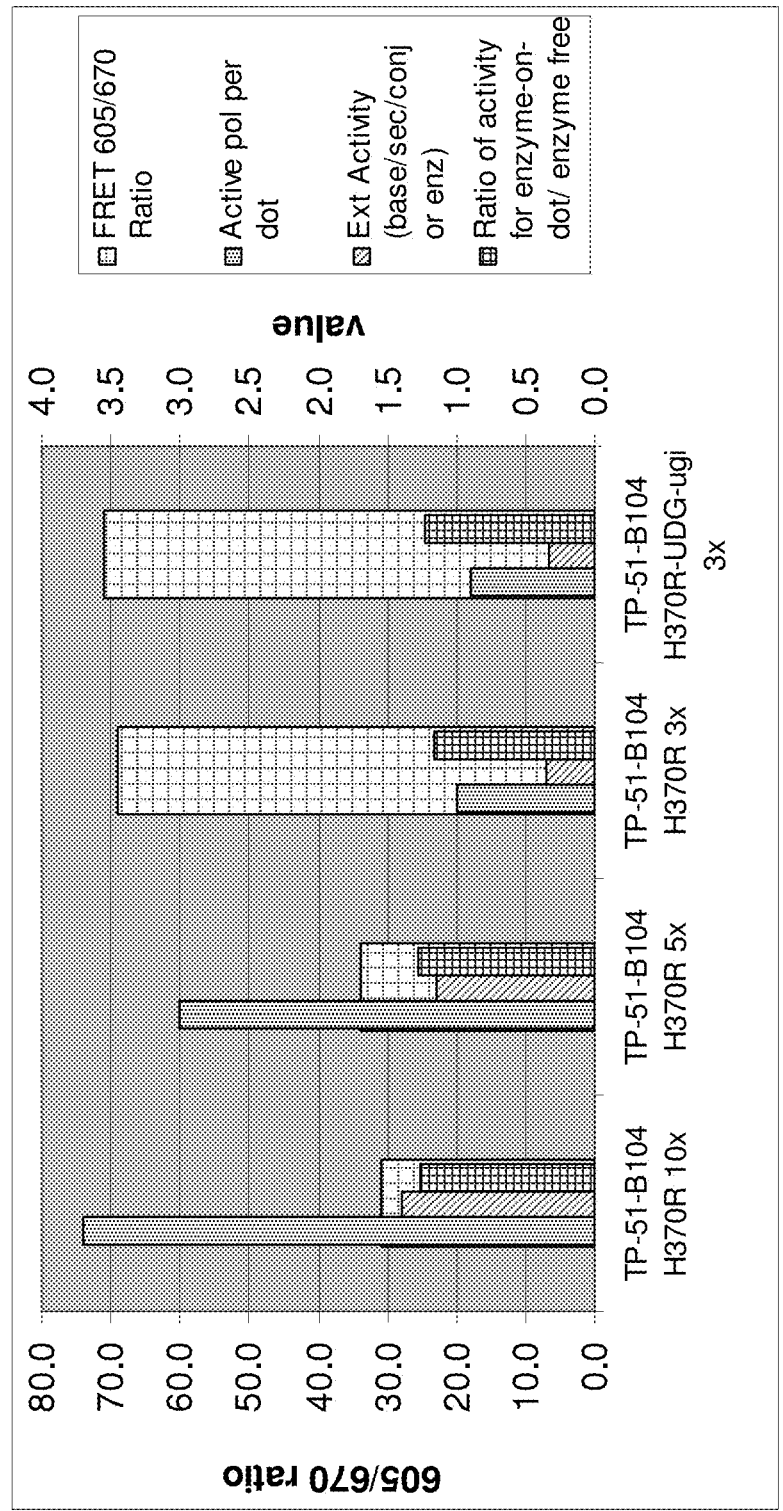

FIG. 37 depicts the results of assays to measure primer extension activity, stochiometry (i.e., active number of polymerase per conjugate), and DNA binding of exemplary labeled polymerase conjugates according to the present disclosure.

Figure 38:
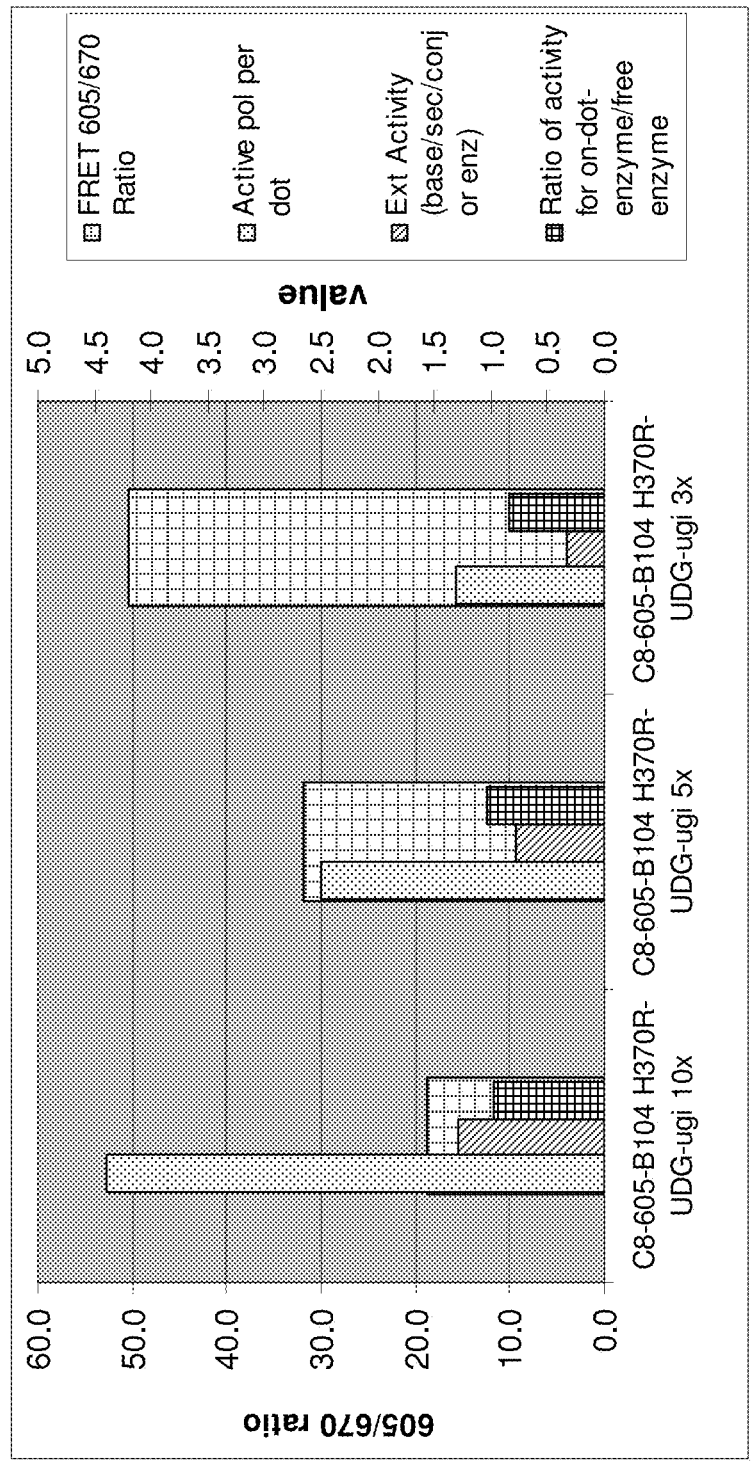

FIG. 38 depicts the results of assays to measure primer extension activity, stochiometry (i.e., active number of polymerase per conjugate), and DNA binding of exemplary labeled polymerase conjugates according to the present disclosure.

Figure 39:
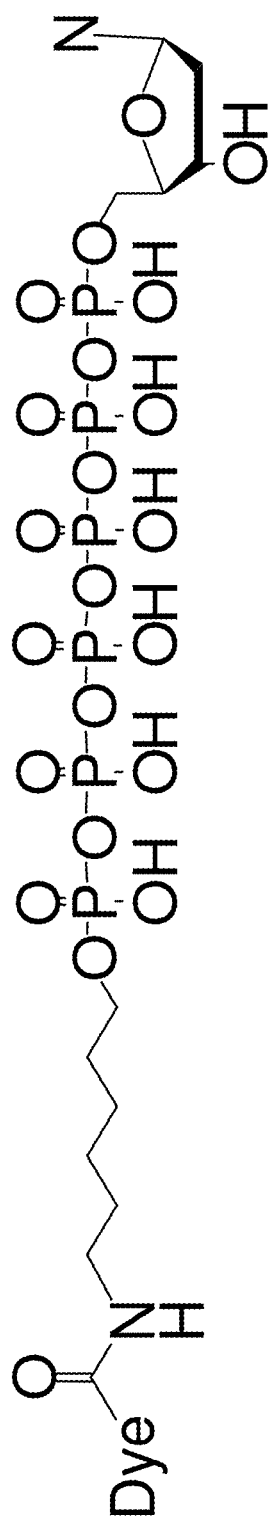

FIG. 39 depicts the structure of an exemplary nucleotide that can be used in conjunction with the labeled polymerase conjugates of the present disclosure in the methods, systems and kits provided herein.

DETAILED DESCRIPTION OF THE SEQUENCE LISTINGS

SEQ ID NO: 1 comprises the amino acid sequence of an *E. coli* K12 DNA polymerase.

SEQ ID NO: 2 comprises the amino acid sequence of the Klenow form of an *E. coli* K12 DNA polymerase.

SEQ ID NO: 3 comprises the amino acid sequence of a DNA polymerase of the bacteriophage Phi-29.

SEQ ID NO: 4 comprises the amino acid sequence of a peptide linker, herein referred to as "H-linker".

SEQ ID NO: 5 comprises the amino acid sequence of a peptide linker, herein referred to as "F-linker".

SEQ ID NO: 6 comprises the amino acid sequence of a Phi-29 polymerase peptide comprising a polycysteine tag and the F-linker sequence at its N-terminus.

SEQ ID NO: 7 comprises the amino acid sequence of a Phi-29 polymerase peptide comprising a polylysine tag and the F-linker sequence at its N-terminus.

SEQ ID NO: 8 comprises the amino acid sequence of a Phi-29 polymerase peptide comprising a His-tag, an F-linker peptide and a transglutaminase tag at its N-terminus.

SEQ ID NO: 9 comprises the amino acid sequence of a Phi-29 polymerase peptide comprising a protein kinase A (PKA) tag and the F-linker at its N-terminus.

SEQ ID NO: 10 comprises the amino acid sequence of a biotin acceptor peptide in an exemplary biotin ligase recognition sequence.

SEQ ID NO: 11 comprises the amino acid sequence of HBP1, a Phi-29 polymerase peptide comprising a His-tag and biotin acceptor peptide sequence at its N-terminus.

SEQ ID NO: 12 comprises the amino acid sequence of a Phi-29 polymerase peptide comprising a His-tag and the H-linker at its N-terminus.

SEQ ID NO: 13 comprises the amino acid sequence of a Phi-29 polymerase peptide comprising a His-tag and the F-linker at its N-terminus.

SEQ ID NO: 14 comprises the amino acid sequence of HP1, a Phi-29 polymerase peptide that lacks exonuclease activity and comprises an N-terminal His-tag, an intervening linker sequence, and the D12A and D66A mutations.

SEQ ID NO: 15 comprises the amino acid sequence of a Cyanophage S-CBP1 DNA polymerase.

SEQ ID NO: 16 comprises the amino acid sequence of a Cyanophage S-CBP2 DNA polymerase.

SEQ ID NO: 17 comprises the amino acid sequence of a Cyanophage S-CBP3 DNA polymerase.

SEQ ID NO: 18 comprises the amino acid sequence of a Cyanophage Syn-5 DNA polymerase.

SEQ ID NO: 19 comprises the amino acid sequence of a Cyanophage S-CBP42 DNA polymerase.

SEQ ID NO: 20 comprises the amino acid sequence of be a *Synechococcus* phage P60 DNA polymerase.

SEQ ID NO: 21 comprises the amino acid sequence of a *Roseobacter* phage SIO1 DNA polymerase.

SEQ ID NO: 22 comprises the amino acid sequence of a *Oedogonium cardiacum* chloroplast DNA Polymerase.

SEQ ID NO: 23 comprises the amino acid sequence of a Salterprovirus His1 polymerase.

SEQ ID NO: 24 comprises the amino acid sequence of a Salterprovirus His2 polymerase.

SEQ ID NO: 25 comprises the amino acid sequence of an *Ostreococcus tauri* V5 DNA polymerase.

SEQ ID NO: 26 comprises the amino acid sequence of an *Ectocarpus siliculosus* virus 1 DNA polymerases.

SEQ ID NO: 27 comprises the amino acid sequence of HP1 Q380A, a mutant form of HP1 comprising the mutation Q380A.

SEQ ID NO: 28 comprises the amino acid sequence of HP1 S388G, a mutant form of HP1 comprising the mutation S388G.

SEQ ID NO: 29 comprises the amino acid sequence of an RB69 polymerase comprising a His-tag at its N-terminus.

SEQ ID NO: 30 comprises the amino acid sequence of a GA-1 polymerase comprising a His-tag at its N-terminus.

SEQ ID NO: 31 comprises the amino acid sequence of a B103 polymerase comprising a His-tag at its N-terminus.

SEQ ID NO: 32 comprises the amino acid sequence of B103 polymerase.

SEQ ID NO: 33 comprises the amino acid sequence of a mutant B103 polymerase.

SEQ ID NO: 34 comprises the amino acid sequence of a second mutant B103 polymerase.

SEQ ID NO: 35 comprises the amino acid sequence of an M2Y DNA polymerase.

SEQ ID NO: 36 comprises the amino acid sequence of an Nf DNA polymerase.

SEQ ID NO: 37 comprises the amino acid sequence of an exemplary recognition sequence for the Tobacco Etch Virus (TEV) protease.

SEQ ID NO: 38 comprises the amino acid sequence of a Phi-29 polymerase fused to a TEV protease cleavage site.

SEQ ID NO: 39 comprises the amino acid sequence of a B103 polymerase fused to a TEV protease cleavage site.

SEQ ID NO: 40 comprises the amino acid sequence of a mutant B103 polymerase fused to a His-tag and biotin acceptor peptide sequence at its N-terminus.

SEQ ID NO: 41 comprises the nucleotide sequence of an oligonucleotide template used in a nucleotide incorporation assay as described, for example, in Example 19.

SEQ ID NO: 42 comprises the nucleotide sequence of an oligonucleotide primer used in a nucleotide incorporation assay as described, for example, in Example 19.

SEQ ID NO: 43 comprises the nucleotide sequence of a fluorescein-labeled oligonucleotide primer used to measure primer extension activity of a polymerase sample according to an exemplary assay, as described in, inter alia, Examples 3, 5 and 23.

SEQ ID NO: 44 comprises the nucleotide sequence of an exemplary polynucleotide template used in a stopped-flow assay for nucleotide incorporation kinetics as described, for example, in Example 30.

SEQ ID NO: 45 comprises the nucleotide sequence of an exemplary oligonucleotide primer used in a stopped-flow assay for nucleotide incorporation kinetics as described, for example, in Example 30.

SEQ ID NO: 46 comprises the nucleotide sequence of an exemplary polynucleotide template used in a stopped-flow assay for nucleotide incorporation kinetics as described, for example, in Example 30.

SEQ ID NO: 47 comprises the nucleotide sequence of an exemplary oligonucleotide primer used in a stopped-flow assay for nucleotide incorporation kinetics as described, for example, in Example 30.

SEQ ID NOS: 48-73 comprise the nucleotide sequences of various oligonucleotide templates and primers used in the assays of various Examples provided herein.

DETAILED DESCRIPTION

The present disclosure provides for compositions, methods and systems comprising labeled biomolecule conjugates comprising a biomolecule linked to a label, wherein the conjugate has biological activity (hereinafter "labeled biomolecule conjugates"). Also disclosed herein are improved methods for preparing such conjugates, as well as methods and systems for using such conjugates in biological applications.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, *Molecular Cloning: A Laboratory Manual*, Third Edition; Ausubel, F. M., et al., eds., 2002, *Short Protocols In Molecular Biology*, Fifth Edition.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; and the like. Some examples of linkages can be found, for example, in Hermanson, G., *Bioconjugate Techniques*, Second Edition (2008); Aslam, M., Dent, A., *Bioconjugation: Protein Coupling Techniques for the Biomedical Sciences*, London: Macmillan (1998); Aslam, M., Dent, A., *Bioconjugation: Protein Coupling Techniques for the Biomedical Sciences*, London: Macmillan (1998).

As used herein, the term "linker" and its variants comprises any composition, including any molecular complex or molecular assembly, that serves to link two or more compounds.

As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and *E. coli* DNA polymerase) and RNA polymerases. The term "polymerase"

and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. One exemplary embodiment of such a polymerase is Phusion® DNA polymerase (New England Biolabs), which comprises a *Pyrococcus*-like polymerase fused to a processivity-enhancing domain as described, for example, in U.S. Pat. No. 6,627,424.

As used herein, the term "polymerase activity" and its variants, when used in reference to a given polymerase, comprises any in vivo or in vitro enzymatic activity characteristic of a given polymerase that relates to catalyzing the polymerization of nucleotides into a nucleic acid strand, e.g., primer extension activity, and the like. Typically, but not necessarily such nucleotide polymerization occurs in a template-dependent fashion. In addition to such polymerase activity, the polymerase can typically possess other enzymatic activities, for example, 3' to 5' exonuclease activity.

As used herein, the term "nucleotide" and its variants comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprises polymerization of one or more nucleotides into a nucleic acid strand.

As used herein, the term "biomolecule" and its variants comprises any compound isolated from a living organism, as well as analogs (including engineered and/or synthetic analogs), derivatives, mutants or variants and/or biologically active fragments of the same. For example, the biomolecule can be a protein (e.g., enzyme), nucleic acid, nucleotide, carbohydrate or lipid. In some embodiments, the biomolecule can be an engineered or synthetic analog of a compound isolated from a living cell that is structurally different from the compound but retains a biological activity characteristic of that compound. As used herein, the term "target" and its variants comprises any compound that is capable of binding specifically to a particular biomolecule. In one exemplary embodiment, the target of an enzyme can be, for example, a substrate of the enzyme.

As used herein, the term "biological activity" and its variants, when used in reference to a biomolecule (such as, for example, an enzyme) refers to any in vivo or in vitro activity that is characteristic of the biomolecule itself, including the interaction of the biomolecule with one or more targets. For example, biological activity can optionally include the selective binding of an antibody to an antigen, the enzymatic activity of an enzyme, and the like. Such activity can also include, without limitation, binding, fusion, bond formation, association, approach, catalysis or chemical reaction, optionally with another biomolecule or with a target molecule.

As used herein, the term "biologically active fragment" and its variants refers to any fragment, derivative or analog of a biomolecule that possesses an in vivo or in vitro activity that is characteristic of the biomolecule itself. For example, the biomolecule can be an antibody that is characterized by antigen-binding activity, or an enzyme characterized by the ability to catalyze a particular biochemical reaction, etc. Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells. Because biomolecules often exhibit a range of physiological properties and because such properties can be attributable to different portions of the biomolecule, a useful biologically active fragment can be a fragment of a biomolecule that exhibits a biological activity in any biological assay. In some embodiments, the fragment or analog possesses 10%, 40%, 60%, 70%, 80% or 90% or greater of the activity of the biomolecule in any in vivo or in vitro assay of interest.

The term "modification" or "modified" and their variants, as used herein with reference to a protein, comprise any change in the structural, biological and/or chemical properties of the protein, particularly a change in the amino acid sequence of the protein. In some embodiments, the modification can comprise one or more amino acid mutations, including without limitation amino acid additions, deletions and substitutions (including both conservative and non-conservative substitutions).

As used herein, the terms "identical" or "percent identity," and their variants, when used in the context of two or more nucleic acid or polypeptide sequences, refer to two or more sequences or subsequences that are the same or have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "*A general method applicable to the search for similarities in the amino acid sequence of two proteins*" *Journal of Molecular Biology* 48 (3):443-53); Smith-Waterman (see, e.g., Smith, Temple F.; and Waterman, Michael S., "*Identification of Common Molecular Subsequences*" (1981) *Journal of Molecular Biology* 147:195-197); or BLAST (Basic Local Alignment Search Tool; see, e.g., Altschul S F, Gish W, Miller W, Myers E W, Lipman D J, "*Basic local alignment search tool*" (1990) *J Mol Biol* 215 (3):403-410).

The terms "resonance energy transfer" and "RET" and their variants, as used herein, refer to a radiationless transmission of excitation energy from a first moiety, termed a donor moiety, to a second moiety termed an acceptor moiety. One type of RET includes Forster Resonance Energy Transfer (FRET), in which a fluorophore (the donor) in an excited state transfers its energy to a proximal molecule (the acceptor) by nonradiative dipole-dipole interaction. See, e.g., Forster, T. "Intermolecular Energy Migration and Fluorescence", *Ann. Phys.*, 2:55-75, 1948; Lakowicz, J. R., Principles of Fluorescence Spectroscopy, 2nd ed. Plenum, N.Y. 367-394., 1999. RET also comprises luminescence resonance energy transfer, bioluminescence resonance energy transfer, chemiluminescence resonance energy transfer, and similar types of energy transfer not strictly following the Forster's theory, such as nonoverlapping energy transfer occurring when nonoverlapping acceptors are utilized. See, for example, Anal. Chem. 2005, 77: 1483-1487.

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, isoleucine or proline) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

The term "primer extension activity" and its variants, as used herein, when used in reference to a given polymerase, comprises any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. The primer extension activity is typically quantified as the total number of nucleotides incorporated (as measured by, e.g, radiometric or other suitable assay) by a unit amount of polymerase (in moles) per unit time (seconds) under a particular set of reaction conditions.

The terms "His tag" or "His-tag" and their variants as used herein refers to a stretch of amino acids comprising multiple histidine residues. Typically, the His tag can bind to metal ions, for example, $Zn^{2+}$, $Ni^{2+}$, $Co^{2+}$, or $Cu^{2+}$ ions. Optionally, the His tag comprises 2, 3, 4, 5, 6, 7, 8 or more histidine residues. In some embodiments, the His tag is fused to the N- or C-terminus of a protein; alternatively, it can be fused at any suitable location within the protein.

As used herein, the term "binding pair" and its variants refers to two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions. The two members of a binding pair are referred to herein as the "first member" and the "second member" respectively.

The following may be mentioned as non-limiting examples of molecules that can function as a member of a specific binding pair, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, receptors, carbohydrates, complementary nucleic acid sequences, and the like. Examples of specific binding pairs include without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; and an oligonucleotide or polynucleotide and its corresponding complement.

As used herein, the term "biotin moiety" and its variants comprises biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-e-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like. "Biotin moiety" also comprises biotin variants that can specifically bind to an avidin moiety.

The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

The terms "avidin" and "avidin moiety" and their variants, as used herein, comprises the native egg-white glycoprotein avidin, as well as any derivatives, analogs and other non-native forms of avidin, that can specifically bind to biotin moieties. In some embodiments, the avidin moiety can comprise deglycosylated forms of avidin, bacterial streptavidins produced by selected strains of Streptomyces, e.g., Streptomyces avidinii, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety.

As used herein, the term "biotin-avidin bond" and its variants refers to a specific linkage formed between a biotin moiety and an avidin moiety. Typically, a biotin moiety can bind with high affinity to an avidin moiety, with a dissociation constant $K_d$ typically in the order of $10^{-14}$ to $10^{-15}$ mol/L. Typically, such binding occurs via non-covalent interactions.

As used herein, the term "accessory compound" and its variants refers to any non-polymerase compound capable of attaching to a nanoparticle through one or more attachment sites. Optionally, the accessory compound can comprise a His tag.

As used herein, the term "modification enzyme recognition site" refers to an amino acid recognition sequence that is chemically modified in an enzyme-catalyzed reaction, wherein the enzyme catalyzing the reaction exhibits specificity for the amino acid recognition sequence. The amino acid recognition sequence may be inserted into a protein of interest, for example by conventional recombinant DNA techniques. Examples of modification enzyme recognition sites include, but are not limited to a biotin ligase modification site, for example a site comprising the amino acid sequence GLN-DIFEAQKIEWHE, for introducing a biotin moiety; a protein kinase modification site, for example a site comprising the amino acid sequence LRRASLG, for introducing a phosphorothioate moiety; and a transglutaminase modification site, for example a site comprising the amino acid sequence PKPQQF, for introducing an amine moiety.

The terms "reporter" and "reporter moiety" and their variants, as used herein, refer to any moiety that generates, or causes to be generated, a detectable signal. Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. The reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. The appropriate procedures for detecting a signal, or change in the signal, generated by the reporter moiety are well known in the art. The reporter moieties can be linked to a solid surface, polymerase, nucleotide (or analog thereof), target nucleic acid molecule, or primer. In one embodiment, a nucleotide can be linked to a reporter moiety. The reporter moiety can generate a signal, or a change in a signal, upon excitation from an appropriated energy source (e.g., electromagnetic source). In another embodiment, the polymerase can be linked to a reporter moiety (e.g., energy transfer donor moiety), and the nucleotide (or analog thereof) can be linked to a reporter moiety (e.g., energy transfer acceptor moiety). The reporter moieties (energy transfer donor and acceptor moieties) can generate a signal, or a change in a signal, upon excitation from an appropriated energy source (e.g., electromagnetic source) and when the nucleotide is proximal to the polymerase. The nucleotide can be proximal to the polymerase when the nucleotide binds the polymerase or when the polymerase incorporates the nucleotide. Some energy transfer reporter moieties can be optically or spectrally detectable.

The term "label" and its variants, as used herein, comprises any optically detectable moiety and includes any moiety that can be detected using, for example, fluorescence, luminescence and/or phosphoresecence spectroscopy, Raman scattering, or diffraction. Exemplary labels according to the present disclosure include fluorescent and luminescent moieties as well as quenchers thereof. Some typical labels include without limitation nanoparticles and organic dyes.

The term "attachment site" and its variants, as used herein, refer to any location or region on the biomolecule or the label that is capable of supporting attachment to another moiety. For example, the biomolecule can comprise one or more attachment sites for a label; alternatively the label (e.g., nanoparticle or organic dye moiety) can comprise one or more attachment sites for the biomolecule. The attachment site can variously comprise one or more functional groups (e.g., carboxyl, amine, thiol groups, etc), a surface ligand, one or more amino acid side chains, an exposed region of the metal surface, a bound metal ion, or any other suitable moiety capable of supporting attachment to, e.g., a biomolecule or label.

As used herein, the term "interaction" and its variants comprise any selective or specific interaction between a biomolecule and a target, including but not limited to approach of the biomolecule to the target, transmission of an electrical, optical, chemical or other impulse between a biomolecule and a target, and/or binding of the biomolecule with the target. Optionally, the interaction can involve the formation of a bond between the biomolecule and a target including, without limitation covalent, ionic, hydrogen, hydrophilic, hydrophobic, or affinity bonding as well as bonding or associations involving van der Waals forces and mechanical bonding. Some exemplary biomolecule-target interactions can include, for example, approach of the biomolecule and target to each other, movement of the biomolecule and target away from each other, association or dissociation of the biomolecule and target with each other, formation of a linkage between the biomolecule and target, transmission of a signal between the biomolecule and the target, independent binding of the biomolecule and target to a common entity or surface, activation of either the biomolecule or target by the other; etc.

Disclosed herein is a labeled biomolecule conjugate comprising: a biomolecule linked to a label to form a labeled biomolecule conjugate, wherein the conjugate has biological activity. Typically, the biological activity is an activity that is characteristic of the biomolecule.

In some embodiments, the label of the labeled biomolecule conjugate emits, or is capable of emitting, a signal. In some embodiments, the label of the labeled biomolecule conjugate induces, or is capable of inducing, the emission of a signal by another label. In some embodiments, the label of the conjugate is positioned to emit a signal during interaction of the biomolecule with a target. Optionally, the signal indicates occurrence of the interaction. In some embodiments, the signal can indicate the identity of the target. Optionally, the signal can be detected to visualize and/or track the conjugate in real time.

In some embodiments, the biomolecule of the conjugate is capable of undergoing one or more transient interactions with a target, and the label of the conjugate is capable of emitting, or causing to be emitted, a signal during each of the one or more transient interactions. The one or more interactions can occur successively or simultaneously, and can involve one or multiple targets.

In some embodiments, the label of the conjugate is capable of emitting or inducing the emission of a series of signals, each signal corresponding to a transient interaction between the biomolecule and a target. The transient interactions can occur successively or simultaneously, and can involve one or multiple targets.

In some embodiments, the biomolecule can be selected from the group consisting of: a protein, a carbohydrate, a lipid, a nucleotide and a nucleic acid. In a typical embodiment, the biomolecule is an enzyme, even more typically a polymerase.

In some embodiments, the label of the conjugate can be selected from the group consisting of a nanoparticle and an organic dye. In some embodiments, the label is a fluorescent label. Optionally, the label is a fluorescent dye. The dye can be selected from the group consisting of: Cy3, ALEXA FLUOR, and fluorescein. In some embodiments, the nanoparticle can be a nanocrystal, typically a quantum dot.

In some embodiments, the biomolecule comprises an enzyme or a biologically active fragment thereof, the target is an enzyme substrate, the one or more transient interactions include one or more enzyme-mediated reactions. Such conjugates are referred to herein as labeled enzyme conjugate.

In some embodiments, the label of the labeled enzyme conjugate is a RET moiety positioned to undergo RET with a labeled substrate bound to the active site of the enzyme. In some embodiments, the enzyme is capable of undergoing transient interactions with one or more substrates, which can occur simultaneously or successively. In some embodiments, the enzyme of the labeled enzyme conjugate is capable of undergoing transient interactions with a plurality of substrates either simultaneously or in succession, and the label of the conjugate is capable of generating a signal upon each such interaction. Optionally, the signal can be detected and analyzed to determine the identity of the substrate. In some embodiments, the enzyme of the conjugate is capable of undergoing transient interaction with a series of substrates in succession and the nanoparticle of the conjugate is capable of producing a series of signals that can be detected and analyzed to determine a time series of enzyme-substrate interactions.

In some embodiments, an attachment moiety serves to link the enzyme to the label. In one exemplary embodiment, the labeled enzyme conjugate comprises an enzyme linked to a label through an attachment moiety. Typically, the polymerase is linked to the attachment moiety, and the attachment moiety is linked to the label to form a labeled polymerase conjugate. In some embodiments, the attachment moiety of is an avidin moiety, and the enzyme comprises a biotin moiety, and the enzyme and the attachment moiety are linked to each other through a further biotin-avidin bond. In some embodiments, the attachment moiety is covalently attached to the label. In some embodiments, the label comprises a biotin moiety, and the attachment moiety is linked to the label through a second biotin-avidin bond. In some embodiments, the attachment moiety is linked to two, three, four, five, six, seven, eight, nine, ten or more labels. In some embodiments, at least two of the labels are different from each other. In some embodiments, at least two of the labels are the same. In some embodiments, at least two of the labels are positioned to undergo FRET with each other.

Also provided herein is a labeled enzyme conjugate, comprising: a first member of a binding pair linked to an enzyme; and a second member of the binding pair linked to a label; wherein the first member and the second member of the binding pair are linked to each other to form a labeled enzyme conjugate.

Also disclosed herein is a method of making a labeled enzyme conjugate, comprising: (a) linking a first member of a binding pair to an enzyme; (b) linking the second member of the binding pair to a label, and (c) contacting the products of steps (a) and (b) with each other under conditions where the first member and second members of the binding pair become linked to each other to a labeled enzyme conjugate comprising an enzyme linked to the label, where the conjugate has enzymatic activity.

In some embodiments, the first member of the binding pair is a biotin moiety and the second member of the binding pair comprises a streptavidin moiety.

Also disclosed herein is a labeled enzyme conjugate for use in single molecule reactions prepared by the above methods.

Disclosed herein are compositions providing for a conjugate comprising one or more biomolecules or biologically active fragments thereof operably linked to one or more nanoparticles, wherein the conjugate has a biological activity and the at least one nanoparticle is capable of emitting, or causing to be emitted, at least one detectable signal.

In some embodiments, the one or more biomolecules of the conjugate can be visualized and tracked in real time, optionally in single molecule format.

In some embodiments, at least one nanoparticle of the conjugate is capable of reporting one or more interactions of one or more biomolecules or fragments with at least one target. Such conjugates can permit the monitoring of biomolecular activity in real time and in single molecule format.

Also disclosed herein is a conjugate comprising one or more biomolecules or biologically active fragments thereof operably linked to at least one nanoparticle, wherein the one or more biomolecules are capable of undergoing one or more interactions with at least one target and the at least one nanoparticle is capable of emitting, or causing to be emitted, a detectable signal during each of the one or more interactions. The one or more interactions can occur successively or simultaneously, and can involve single or multiple targets.

In some embodiments, the conjugate comprises one or more biomolecules or biologically active fragments thereof operably linked to at least one nanoparticle, wherein the one or more biomolecules or biologically active fragments are capable of undergoing one or more transient interactions with at least one target, and the at least one nanoparticle is capable of emitting, or causing to be emitted, a detectable signal during each of the one or more transient interactions.

In some embodiments, the at least one nanoparticle of the conjugate is capable of emitting, or causing to be emitted, a series of detectable signals, at least one detectable signal corresponding to each of the transient interactions.

In some embodiments, the one or more biomolecules or biologically active fragments can be selected from the group consisting of: a protein, a carbohydrate, a lipid, a nucleotide and a nucleic acid.

The nanoparticle can be a nanocrystal. In some embodiments, the nanoparticle can be a quantum dot.

In some embodiments, the one or more biomolecules or biologically active fragments comprise an enzyme or a biologically active fragment thereof, the targets include one or more labeled enzyme substrates, the one or more transient interactions include one or more enzyme-mediated reactions, and the one or more detectable signals are FRET signals resulting from FRET between the at least one nanoparticle and the label of a labeled enzyme substrate during an enzyme-mediated reaction. As used herein, the term "enzyme-mediated reaction" and its variants refer to the selective binding of a substrate to the active site of an enzyme. In some embodiments, the enzyme-mediated reaction can optionally include any one or more steps selected from the group consisting of: approach of the substrate to the enzyme active site; catalysis, alteration, cleavage, conversion or breakdown of the substrate or alternatively dissociation of the substrate from the enzyme active site without catalysis, alteration, cleavage, conversion or breakdown; liberation of an enzymatic product (or alternatively the original substrate) from the enzyme active site and/or subsequent diffusion of the product (or original substrate) away from the enzyme.

In some embodiments, the enzyme is a nucleotide polymerase, the labeled enzyme substrate is a labeled nucleotide comprising a detectable nucleotide label bonded to a portion of the nucleotide that is released during nucleotide incorporation; and the enzyme-mediated reaction includes a nucleotide incorporation mediated by the nucleotide polymerase. Optionally, the detectable nucleotide label is bonded to the beta, gamma or other terminal phosphate of the labeled nucleotide.

In some embodiments, the nucleotide polymerase is a mutant or variant Klenow form of DNA polymerase comprising amino acid sequence at least 85% identical to the amino acid sequence of SEQ ID NO: 2 or any biologically active fragment thereof. Optionally, the nucleotide polymerase lacks 3' to 5' exonuclease activity.

In other embodiments, the nucleotide polymerase is a mutant or variant Phi-29 DNA polymerase comprising an N-terminal polyhistidine tag (His-tag) fused to an amino acid sequence at least 85% identical to a Phi-29 DNA polymerase comprising the amino acid sequence of SEQ ID NO: 3, or any biologically active fragment thereof.

In some embodiments, the one or more biomolecules or biologically active fragments are operably linked to the at least one nanoparticle through a linker or chemical linkage comprising at least one bond selected from the group consisting of: a covalent bond, an electrostatic bond and a chelation bond.

In some embodiments, the bond is a covalent bond, which can be a bond through a functional group selected from the group consisting of: a hydroxyl, a carboxyl, a carbonyl, a sulfhydryl, an amine, an amide, a nitrile, a nitrogen with a free lone pair of electrons, an amino acid, a thiol, a polyethylene glycol, a sulfonic acid, a sulfonyl halide, and an acyl halide. In some embodiments, the bond is an amide bond formed through reaction of a carboxyl group of the at least one nanoparticle and an amine group of the enzyme or biologically active fragment.

In some embodiments, the bond is a thioether bond formed through a reaction involving the thiol group of a natural or engineered cysteine residue of the enzyme or biologically active fragment.

In some embodiments, the enzyme is a Klenow DNA polymerase having the amino acid sequence of SEQ ID NO: 2 and further comprising an engineered cysteine introduced at amino acid positions 730, 748, 750, 751, 778, 922, 926, 927 and 928, or any combination thereof. In some embodiments, the enzyme is Phi-29 DNA polymerase having the amino acid sequence of SEQ ID NO: 3, and the cysteine at amino acid position 473 serves as an attachment site for the nanoparticle.

In some embodiments, the one or more biomolecules or biologically active fragments are operably linked to at least one nanoparticle through a linker or chemical linkage comprising at least one chelation bond. The chelation bond can be formed between a metal of the nanoparticle and a metal-chelating ligand attached to or otherwise associated with the enzyme or biologically active fragment. The metal-chelating ligand can comprise one or more naturally occurring or engineered histidine residues of the enzyme or biologically active fragment. In some embodiments, the metal-chelating ligand comprises a histidine tag fused to the N-terminus or the C-terminus of the enzyme or biologically active fragment.

In some embodiments, the conjugate comprises one or more biomolecules or biologically active fragments thereof operably linked to at least one nanoparticle through a linker or chemical linkage comprising at least one electrostatic bond.

In some embodiments, the conjugate comprises one or more biomolecules or biologically active fragments thereof operably linked to at least one nanoparticle through a linker or chemical linkage comprising at least one bond formed between a biotin moiety and an avidin moiety. In some embodiments, the one or more biomolecules or biologically active fragments can be a nucleotide polymerase or a biologically active fragment thereof, and the bond can be formed between a biotin moiety operably linked to the nucleotide polymerase or biologically active fragment and an avidin moiety attached to or otherwise associated with the at least one nanoparticle.

Also disclosed herein is a conjugate comprising one or more polymerases or biologically active fragments thereof operably linked to at least one nanoparticle, wherein the conjugate has polymerase activity. In some embodiments, the nanoparticle of the conjugate is capable of generating a detectable signal such that the conjugate can be visualized and tracked in real time.

In some embodiments, the at least one nanoparticle comprises a nanocrystal, typically a quantum dot. Optionally, the nanoparticle is capable of undergoing FRET with a labeled moiety located within or close to the active site of at least one polymerase or biologically active fragment of the conjugate.

In some embodiments, the conjugate is capable of binding one or more nucleotides in a template-dependent fashion, wherein at least one nucleotide is detectably labeled with a nucleotide label, and the at least one nanoparticle of the conjugate is capable of undergoing FRET with the nucleotide label.

In some embodiments, the nucleotide label comprises a detectable label bonded to a portion of the nucleotide that is released during nucleotide incorporation. Optionally, the nucleotide label is bonded to the beta, gamma or other terminal phosphate of the labeled nucleotide.

In some embodiments, the one or more polymerases or biologically active fragments of the conjugate are selected from the group consisting of: a RNA polymerase, a DNA polymerase or a reverse transcriptase. Optionally, the one or more polymerases or biologically active fragments are derived from a DNA polymerase selected from the group consisting of: the Klenow fragment of DNA polymerase I, *E. coli* DNA polymerase I, Phi-29 DNA polymerase, T7 DNA polymerase, T7 DNA polymerase or *Thermus acquaticus* DNA polymerase.

In some embodiments, the nucleotide polymerase or biologically active fragment of the conjugate is a mutant or variant Klenow form of DNA polymerase comprising amino acid sequence at least about 85% identical to the amino acid sequence of SEQ ID NO: 2, or a biologically active fragment thereof. Optionally, the nucleotide polymerase lacks 3' to 5' exonuclease activity.

In other embodiments, the nucleotide polymerase or biologically active fragment of the conjugate is a mutant or variant Phi-29 DNA polymerase comprising an N-terminal polyhistidine tag (His-tag) fused to an amino acid sequence at least about 85% identical to a Phi-29 DNA polymerase comprising the amino acid sequence of SEQ ID NO: 3, or biologically active fragment thereof. Optionally, the nucleotide polymerase lacks 3' to 5' exonuclease activity.

In some embodiments, the conjugate comprises one or more nucleotide polymerases or biologically active fragments operably linked to the at least one nanoparticle through a linker or chemical linkage comprising at least one bond selected from the group consisting of: a covalent bond, an electrostatic bond and a chelation bond.

In some embodiments, the bond is a covalent bond, which can be a bond through a functional group selected from the group consisting of: a hydroxyl, a carboxyl, a carbonyl, a sulfhydryl, an amine, an amide, a nitrile, a nitrogen with a free lone pair of electrons, an amino acid, a thiol, a polyethylene glycol, a sulfonic acid, a sulfonyl halide, and an acyl halide. In some embodiments, the bond is an amide bond formed through reaction of a carboxyl group of the nanoparticle and an amine group of the nucleotide polymerase or biologically active fragment.

In some embodiments, the bond is a thioether bond formed through a reaction involving the thiol group of a natural or engineered cysteine residue of the nucleotide polymerase or biologically active fragment.

In some embodiments, the enzyme is a Klenow DNA polymerase having the amino acid sequence of SEQ ID NO: 2 and further comprising an engineered cysteine introduced at amino acid positions 730, 748, 750, 751, 778, 922, 926, 927 and 928, or any combination thereof. In some embodiments, the enzyme is Phi-29 DNA polymerase having the amino acid sequence of SEQ ID NO: 3, and the cysteine at amino acid position 473 serves as an attachment site for the nanoparticle.

In some embodiments, the one or more nucleotide polymerases or biologically active fragments are operably linked to the at least one nanoparticle through a linker or chemical linkage comprising at least one chelation bond. The chelation bond can be formed between a metal group of the nanoparticle and a metal-chelating ligand attached to or otherwise associated with the nucleotide polymerase or biologically active fragment. The metal-chelating ligand can comprise one or more naturally occurring or engineered histidine residues of the enzyme. In some embodiments, the metal-chelating ligand comprises a histidine tag fused to the N-terminus or the C-terminus of the nucleotide polymerase or biologically active fragment.

In some embodiments, the one or more nucleotide polymerases or biologically active fragments thereof are operably linked to the at least one nanoparticle through a linker or chemical linkage comprising at least one electrostatic bond.

In some embodiments, the one or more nucleotide polymerases or biologically active fragments thereof are operably linked to the at least one nanoparticle through a linker or chemical linkage comprising a bond formed between a biotin moiety and an avidin moiety. In some embodiments, the bond can be formed between a biotin moiety operably linked to the nucleotide polymerase or biologically active fragment and an avidin moiety attached to or otherwise associated with the nanoparticle.

Also disclosed herein are methods for producing a biomolecule/nanoparticle conjugate, comprising the steps of: contacting a nanoparticle comprising a plurality of attachment sites on its surface with at least one accessory compound and a biomolecule or biologically active fragment thereof, the at least one accessory compound and the biomolecule or fragment both being capable of binding to one or more attachment sites, under conditions where the at least one accessory compound binds to one or more attachment sites, thereby reducing the number of attachment sites available for binding by the biomolecule or fragment, such that two or fewer biologically active biomolecules or fragments bind to the nanoparticle to form a biomolecule/nanoparticle conjugate comprising two or fewer biologically active biomolecules or fragments per nanoparticle.

In some embodiments, the biomolecule/nanoparticle conjugate can be formed as a 1:1 biomolecule:nanoparticle conjugate in a yield of about 30% to about 100%.

In some embodiments, the biomolecule is a nucleotide polymerase or biologically active fragment thereof, and the at least one accessory compound is selected from the group comprising uracil DNA glycosylase (UDG), uracil DNA glycosylase inhibitor (UGI), maltose binding protein (MBP), bovine serum albumin (BSA), horseradish peroxidase (HRP), glutathione S-transferase (GST) and mucin.

In some embodiments, the biomolecule and the at least one accessory compound each comprise a polyhistidine tag.

In some embodiments, the population of conjugates prepared according to the disclosed methods can comprise an average of between about 0.5-1.5 biomolecules or biologically active fragments per nanoparticle.

Also disclosed herein are compositions comprising a population of conjugates, each conjugate comprising one or more biomolecules or biologically active fragments thereof operably linked to a nanoparticle, the population comprising an average of between about 0.5-1.5 biomolecules or biologically active fragments per nanoparticle.

Also disclosed herein are systems for monitoring successive biomolecular interactions, comprising: one or more targets; a biomolecule that undergoes at least two successive and transient interactions with the one or more targets, and a nanoparticle operably linked to the biomolecule, wherein the nanoparticle emits, or causes to be emitted, one or more detectable signals upon each of the at least two transient and successive interactions. In some embodiments, the one or more targets can comprise one or more labeled nucleotides, each labeled nucleotide comprising a detectable label bonded to a portion of the nucleotide that is released during nucleotide incorporation; the biomolecule can comprise a nucleotide polymerase, and the at least two transient and successive interactions can each comprise a nucleotide incorporation.

In some embodiments, the enzyme of the labeled enzyme conjugate is a polymerase, the target is a nucleotide, and the one or more transient interactions each comprises a nucleotide incorporation catalyzed by the polymerase. When the biomolecule of the conjugate is a polymerase, the conjugate is typically referred as a "labeled polymerase conjugate".

One exemplary embodiment of the present disclosure is a labeled polymerase conjugate comprising a polymerase linked to a label, wherein the conjugate has polymerase activity. In some embodiments, the label can be a nanoparticle. In some embodiments, the label can be an organic dye.

In some embodiments, the label of the labeled polymerase conjugate is positioned to emit a signal during the interaction of the polymerase with a nucleotide. Optionally, the interaction comprises the incorporation of the nucleotide into a nucleic acid molecule by the polymerase. Optionally, the signal indicates the occurrence of the nucleotide incorporation. In some embodiments, the signal can indicate the identity of the nucleotide that is incorporated. Optionally, the signal can be detected to visualize and/or track the conjugate in real time. In some embodiments, a signal indicative of nucleotide incorporation is generated as each incoming nucleotide becomes incorporated by the polymerase of the conjugate.

In some embodiments, the conjugate may optionally comprise a polymerase linked to a label through a chemical linkage comprising a bond selected from the group consisting of: a covalent bond, an electrostatic bond and an affinity bond. In some embodiments, the linker or chemical linkage comprises a bond through a functional group, including, without limitation, a hydroxyl, a carboxyl, a carbonyl, a sulfhydryl, an amine, an amide, a nitrile, a nitrogen with a free lone pair of electrons, an amino acid, a thiol, a sulfonic acid, a sulfonyl halide, and an acyl halide.

In some embodiments, the labeled enzyme conjugate comprises a polymerase linked to the label through a covalent bond. The covalent bond can be formed using any suitable method, optionally including through use of crosslinking agents or linkers.

Optionally, the nucleotide comprises a label (referred to herein as "a nucleotide label"). The label can optionally be bonded to a portion of the nucleotide that is released during nucleotide incorporation. By releasing the label upon incorporation, successive extensions can each be detected without interference from nucleotides previously incorporated into the complementary strand.

In some embodiments, the nucleotide comprises a polyphosphate chain and the label is bonded to the beta, gamma or other terminal phosphate of the labeled nucleotide.

Also disclosed herein is a method for nucleotide incorporation, comprising: contacting the labeled polymerase conjugates of the present disclosure with a nucleotide under conditions where the polymerase catalyzes incorporation of the nucleotide into a nucleic acid molecule.

Also disclosed herein is kit for use in single molecule sequencing reactions, comprising a labeled polymerase conjugate according to the present disclosure. In some embodiments, the kit further comprises labeled nucleotides.

Also disclosed herein is a system for monitoring successive interactions of an enzyme (e.g., a polymerase), with one or more targets (e.g., nucleotides), comprising: a target; a labeled enzyme conjugate comprising an enzyme linked to a label, where the conjugate undergoes, or is capable of undergoing, a transient interaction with the target, and where the label of the conjugate emits, or is capable of emitting, a signal upon each such transient interaction. In some embodiments, the label of the conjugate induces, or is capable of inducing, the emission of a signal upon each such transient interaction. Optionally, the signal can be detected and analyzed to determine the identity of the target.

Optionally, the conjugate can undergo multiple transient interactions with the target, which can occur simultaneously or successively. In some embodiments, the conjugate undergoes a series of transient interaction with a series of targets in succession, and the label is capable of emitting (or inducing the emission of) a series of signals that can be detected and analyzed to determine a time series of interactions.

In some embodiments, the target is a labeled nucleotide. In some embodiments, the nucleotide label is bonded to a portion of the nucleotide that is released during incorporation of the nucleotide. Optionally, the nucleotide comprises a polyphosphate chain that is released during incorporation, and the nucleotide label is bonded to the beta, gamma or other terminal phosphate of the labeled nucleotide.

In some embodiments, the biomolecule of the system comprises a polymerase, and the at least two transient and successive interactions comprise nucleotide incorporations.

Also disclosed herein is system for single molecule sequencing, comprising: (a) a reaction chamber wherein the labeled polymerase conjugates of the present disclosure are contacted with a nucleotide under conditions where the nucleotide is polymerized by the polymerase such that a signal indicative of nucleotide incorporation are generated; (b) a detector for detecting the signal; and (c) an analyzer to analyze the signal to determine the identity of the incorporated nucleotide.

Also provided is a conjugate (herein, "polymerase-nanoparticle conjugate") comprising a polymerase linked to a nanoparticle, wherein the conjugate has polymerase activity and the nanoparticle of the conjugate is capable of producing a signal. Also provided are methods and systems for using such polymerase-nanoparticle conjugates in biological applications.

In some embodiments, the polymerase of the polymerase-nanoparticle conjugate is a polymerase. In some embodiments, the polymerase of the conjugate can be capable of catalyzing one or more incorporations of a labeled nucleotide. In some embodiments, the nanoparticle of the polymerase-nanoparticle conjugate will undergo FRET with the nucleotide label during nucleotide incorporation.

In the sequencing-based applications disclosed herein, the polymeric molecule to be sequenced is typically a nucleic acid. Suitable nucleic acid molecules that can be sequenced according to the present disclosure include without limitation single-stranded DNA, double-stranded DNA, single stranded DNA hairpins, DNA/RNA hybrids, RNA with an appropriate polymerase recognition site, and RNA hairpins. In a typical embodiment, the polymer is DNA, the polymerase is a DNA polymerase or an RNA polymerase, and the labeled monomer is a nucleotide selected from the group consisting of a nucleotide polyphosphate and an analog thereof. In another embodiment, the polymer to be sequenced is RNA and the polymerase is reverse transcriptase.

Provided herein are conjugate compositions comprising one or more biomolecules or biologically active fragments thereof operably linked to one or more nanoparticles, hereinafter referred to as "biomolecule/nanoparticle conjugates." Compositions comprising labeled biomolecule conjugates of the present disclosure can be useful in a wide variety of biological applications. For example, such conjugates can allow direct visualization of the biomolecule of the conjugate. Optionally, the biomolecule can be visualized and/or tracked in real time. In some embodiments, such visualization can be done in real time or near real time, optionally in high throughput and/or single molecule format. Such visualization can permit, for example, detection and evaluation of a wide range of biomolecular behavior over an extended period both in vivo and in vitro contexts, including but not limited to biomolecular movement and/or transport within a cell or living organism, association of dissociation of different biomolecules, protein expression patterns within living cells or organisms, approach and/or binding of a biomolecule to a particular target, detection of movement as a function of biomolecular activity such as, for example, polymerase movement along a template, etc. See, e.g., Jaiswal et al., "Use of quantum dots for live cell imaging", Nature Methods, 1(1):71-78. Observation of multiple different biomolecules or behaviors simultaneously can be achieved through use of different nanoparticles having different characteristic wavelengths, e.g., colors, and/or intensities.

Such conjugates can also be useful in applications requiring detection of biomolecular activity, including in single molecule and/or high-throughput format. For example, such conjugates can be useful in diagnostic assays involving detection of a signal generated as a result of biomolecular activity. In some embodiments, the biomolecule can be linked to the nanoparticle in such a manner that the nanoparticle is capable of functioning as a reporter of biomolecular activity in real time or near real time. Biomolecular activity can frequently involve interaction of the biomolecule with a specific target, such as, for example, the interaction of an enzyme with a substrate. In some embodiments, the biomolecule is capable of undergoing interactions with multiple targets either successively or simultaneously. Elucidating the nature of such biomolecule-target interactions can be important in determining the biological function of the biomolecule. Studies of such interactions have traditionally involved use of a labeled target, which is frequently degraded as a result of the interaction. This problem can be avoided or reduced by conjugating a label, e.g., a nanoparticle or an organic dye moiety, directly to the biomolecule. Such conjugation can allow for direct visualization of individual biomolecules, as well as the monitoring of multiple interactions of a biomolecule with multiple targets over time.

In some embodiments, the conjugates can permit not only visualization but also manipulation and sorting of biomolecules within a large population. For example, in some embodiments the conjugates can be sorted using suitable optical manipulation techniques such as "optical tweezers". See, e.g., Jauffred et al., "Three-dimensional optical control of individual quantum dots", Nano Lett. 8(10):3376-3380 (2008).

The labeled polymerase conjugates disclosed herein can be advantageously employed in the sequencing methods described in U.S. Pat. No. 7,329,492 to Hardin et al.; U.S. Pat. No. 6,982,146 to Schneider et al. The superior photostability and/or signal strength of the polymerase conjugates provided herein can be used to produce superior read length or accuracy in such single molecule sequence methods employing FRET between a labeled polymerase and labeled nucleotide.

Some additional disclosures relating to methods of making labeled polymerase conjugates and to modified polymerases that can be used to make the conjugates provided herein, are disclosed, for example, in U.S. provisional application Nos. 61/184,770, filed Jun. 5, 2009; 61/245,457, filed on Sep. 24, 2009; 61/299,919, filed on Jan. 29, 2010; 61/242,771, filed on Sep. 15, 2009; and 61/293,618, filed on Jan. 8, 2010, as well as in U.S. application Ser. No. 12/748,359 titled "Polymerase Compositions & Methods", filed concurrently herewith; and U.S. application Ser. No. 12/748,314 titled "Labeled Enzyme Compositions, Methods & Systems", filed concurrently herewith.

In some embodiments, the label of the labeled biomolecule conjugate comprises a nanoparticle, and the labeled biomolecule conjugate comprises a biomolecule or biologically active fragment thereof linked to a nanoparticle (a type of conjugate referred to herein as a "biomolecule/nanoparticle conjugate"). The superior detectability of nanoparticles as compared to conventional organic dye molecules can allow for increased signal in high-throughput in single molecule applications. Additionally, the conjugates of the present disclosure can be useful in highly multiplexed applications. For example, the size-tunable emission properties of labeled biomolecule conjugates comprising nanoparticle-based labels can also exploited to design assays involving wavelength and/or intensity multiplexing. Such conjugates can be useful in, e.g., performing multiple optical coding for biological assays. For example, the use of 10 different intensity levels and 6 colors could theoretically be used to code one million different biomolecules, opening new opportunities in gene expression, high throughput, diagnostic and other biological applications. See, e.g., Han et al., "Quantum-dot-tagged microbeads for multiplexed optical coding of biomolecules", Nat. Biotech. 19:631-635 (2001).

In some embodiments, the conjugate comprises one or more biomolecules or biologically active fragments thereof operably linked to at least one nanoparticle, wherein the at least one nanoparticle is capable of reporting one or more interactions of the associated biomolecule or fragment with specific targets. For example, the single label can be used to detect and monitor a time series of interactions between a biomolecule and a series of targets in succession.

In some embodiments, the nanoparticle of the conjugate can be configured to report one or more interactions of the biomolecule with one or more targets. In some embodiments, the interaction can be permanent, i.e., irreversible. Such permanent interactions are typically characterized by high-affinity binding events, such as the interaction between an antibody and an antigen. Alternatively, the interaction between the biomolecule can be transient, e.g., an enzyme-substrate interaction. Such "transient" interactions are typically reversible and are characterized by substantially lower affinity constants (e.g., orders of magnitude lower) than the affinity constants for permanent interactions.

In some embodiments, the biomolecule of the conjugate is capable of undergoing one or more transient interactions with at least one target. For example, the biomolecule can be an enzyme that is capable of undergoing a transient interaction with at least one substrate. In some embodiments, the biomolecule is capable of undergoing multiple transient interactions with one or more targets, which can occur simultaneously or successively.

In some embodiments, the biomolecule of the conjugate is capable of undergoing transient interactions with a plurality of targets, and the nanoparticle of the conjugate is capable of generating at least one detectable signal upon each interaction. Optionally, the detectable signal can be detected and analyzed to determine the identity of the target. In some embodiments, the biomolecule of the conjugate is capable of undergoing transient interaction with a series of targets in succession and the nanoparticle of the conjugate is capable of producing a series of detectable signals that can be detected and analyzed to determine a time series of interactions.

In some embodiments, the biomolecule of the conjugate is a protein, for example, an enzyme.

Also disclosed herein is a system for monitoring successive biomolecular interactions, comprising: one or more targets; a biomolecule that undergoes one or more transient interactions with the one or more targets, and a nanoparticle operably linked to the biomolecule, wherein the nanoparticle emits, or causes to be emitted, one or more detectable signals upon each of the one or more transient interactions.

In some embodiments, the biomolecule of the system is capable of undergoing one or more transient interactions with at least one target. For example, the biomolecule can be an enzyme that is capable of undergoing a transient interaction with at least one substrate. In some embodiments, the biomolecule of the system is capable of undergoing multiple transient interactions with one or more targets, which can occur simultaneously or successively.

In some embodiments, the biomolecule of the system is capable of undergoing transient interactions with a plurality of targets, and the nanoparticle of the system is capable of generating at least one detectable signal upon each interaction. Optionally, the detectable signal can be detected and analyzed to determine the identity of the target. In some embodiments, the biomolecule of the system is capable of undergoing transient interaction with a series of targets in succession and the nanoparticle of the system is capable of producing a series of detectable signals that can be detected and analyzed to determine a time series of interactions.

Also provided herein is a method for detecting one or more interactions of a biomolecule with a target, comprising: contacting a conjugate with at least one target, wherein the conjugate comprises one or more biomolecules or biologically active fragments thereof operably linked to a nanoparticle under conditions where the biomolecule of the conjugate undergoes one or more transient interactions with the at least one target and the nanoparticle of the conjugate emits, or causes to be emitted, one or more detectable signals upon each of the one or more transient interactions, detecting the one or more detectable signals and analyzing the one or more detectable signals to determine the occurrence of the interaction. In some embodiments, the one or more detectable signals can be further analyzed to determine the presence of the target. In some embodiments, the one or more detectable signals can be further analyzed to determine the identity of the target.

In some embodiments, the biomolecule of the method is capable of undergoing one or more transient interactions with at least one target. For example, the biomolecule can be an enzyme that is capable of undergoing a transient interaction with at least one substrate. In some embodiments, the biomolecule of the method is capable of undergoing multiple transient interactions with one or more targets, which can occur simultaneously or successively.

In some embodiments, the biomolecule is capable of undergoing transient interactions with a plurality of targets, and the nanoparticle is capable of generating at least one detectable signal upon each interaction. Optionally, the detectable signal can be detected and analyzed to determine the identity of the target. In some embodiments, the biomolecule is capable of undergoing transient interaction with a series of targets in succession and the nanoparticle is capable of producing a series of detectable signals that can be detected and analyzed to determine a time series of interactions.

In some embodiments, the biomolecule of the method is a nucleotide polymerase that is capable of undergoing transient interactions with a series of acceptor-labeled nucleotides in succession, and the nanoparticle is capable of undergoing FRET with the acceptor label of each acceptor-labeled nucleotide as it is incorporated, thereby generating a series of detectable signals that can be detected and analyzed to determine a time series of nucleotide incorporations.

Also provided herein are methods for preparing conjugates of biomolecules and nanoparticles, resulting in conjugates with improved properties suitable for use in single-molecule biological applications. These methods permit the production of conjugates characterized by stoichiometric ratios of biomolecule:nanoparticle approaching equivalency and exhibiting reduced aggregation. Also provided herein are methods and systems for using such compositions in real-time single molecule applications.

In some embodiments, the conjugates of the present disclosure comprise one or more biomolecules or biologically active fragments operably linked to at least one nanoparticle, wherein the one or more biomolecules or biologically active fragments are capable of selectively interacting with one or more particular targets. For example, the biomolecule or fragment can be an enzyme and the target can be one or more enzyme substrates. In some embodiments, the biomolecule or fragment is capable of undergoing one or more transient and successive interactions with at least one target, and the at least one nanoparticle can optionally be configured to produce a detectable signal upon each of one or more transient and successive interactions between the biomolecule or fragment and at least one target.

In some embodiments, the nanoparticle of the biomolecule/nanoparticle conjugate is capable of reporting a biological activity of the conjugate by emitting, or causing to be emitted, one or more detectable signals indicating of the biological activity.

In some embodiments, the nanoparticle of the biomolecule/nanoparticle conjugate is capable of reporting a biological activity of the conjugate by undergoing resonance energy transfer (RET) with the label of another moiety that is bound, reacted with, or brought into sufficient proximity with the biomolecule of the conjugate. Resonance energy transfer is typically a distance-dependent radiationless transmission of excitation energy from a first moiety, termed a donor moiety, to a second moiety termed an acceptor moiety. One type of RET includes Forster Resonance Energy Transfer (FRET), which can provide an on-off type signal indicating when the donor and acceptor moieties are within a particular distance of each other. Typically, such transfer is characterized by the generation of a detectable signal. The detectable signal can be an optically detectable signal, for example, an increase in acceptor fluorescence. Although the energy transfer from the donor to the acceptor itself does not involve emission of light, it may be thought of in the following terms: excitation of the donor produces energy in its emission spectrum that is then picked up by the acceptor in its excitation spectrum, leading to the emission of light from the acceptor in its emission spectrum. In effect, excitation of the donor sets off a chain reaction, leading to emission from the acceptor when the two are sufficiently close to each other. FRET efficiency typically depends on donor-acceptor distance. For example, FRET efficiency can be dependent on the separation of the donor and acceptor, r, and varies directly with the inverse sixth power of the separation distance, $1/r^6$, making it useful over distances comparable with the dimensions of biological macromolecules. The distance where FRET efficiency is 50% is termed $R_0$, also known as the Forster distance. $R_0$ is unique for each donor-acceptor combination and may be about 5 to 10 nm. The efficiency of FRET energy transfer can sometimes be dependent on energy transfer from a point to a plane which varies by the fourth power of distance separation (E. Jares-Erijman, et al., 2003 Nat. Biotechnol. 21:1387). Resonance energy transfer may be either an intermolecular or intramolecular event. Thus, the spectral properties of the energy transfer pair as a whole, change in some measurable way if the distance and/or orientation between the moieties are altered.

Also provided is a conjugate (herein, "polymerase/nanoparticle conjugate") comprising one or more polymerases or biologically active fragments thereof operably linked to at least one nanoparticle, wherein the conjugate has polymerase activity and the at least one nanoparticle of the conjugate is capable of producing one or more detectable signals. Also provided are methods and systems for using such polymerase/nanoparticle conjugates in biological applications.

In some embodiments, the polymerase of the polymerase/nanoparticle conjugate is a nucleotide polymerase. In some embodiments, the polymerase of the conjugate can be capable of catalyzing one or more incorporations of a labeled nucleotide. In some embodiments, the nanoparticle of the polymerase/nanoparticle conjugate will undergo FRET with the nucleotide label during nucleotide incorporation.

In some embodiments, the at least one nanoparticle of the polymerase/nanoparticle conjugate can report the interaction of a nucleotide polymerase with a series of nucleotides during a polymerization reaction. Under this strategy, conjugation of a nanoparticle to a nucleotide polymerase can allow direct visualization of the polymerase and monitoring of polymerase activity, thereby providing for high throughput single molecule real-time sequencing and/or PCR and ultimately allowing the sequencing of an entire genome rapidly and cheaply.

The polymerase/nanoparticle conjugates disclosed herein, and their use in the disclosed methods and systems, can provide significant advantages. For example, the use of such conjugates enables direct monitoring of polymerase activity during replication along the entire length of a template nucleic acid molecule. Such conjugates can also be used to simultaneously gather information from multiple priming points along a single template, thereby increasing the amount of sequence information obtainable from a single experiment and decreasing the cost of sequencing of an entire genome. Furthermore, by using nanoparticles operably linked to one or more polymerases, polymer sequence data can be generated as labeled monomers are incorporated into a newly synthesized polymer strand by a polymerase, thus enabling the sequencing of polymers in real time. The disclosed conjugates are additionally useful in probing molecular interactions between polymerase and other cellular factors, as well as in assessing polymerase enzymatic conformation and relation to biological function.

In some embodiments, the compositions, systems and methods provided herein permit real time sequencing of single nucleic acid molecule, either single or in parallel, via monitoring of polymerase activity in real or near real time. Provided herein are systems and methods for using the polymerase/nanoparticle conjugates of the present disclosure to detect one or more nucleotide incorporations in real or near real time. Methods for sequencing a single nucleic acid molecule in real or near real time, via monitoring of FRET emissions resulting from interaction of the nanoparticle with the label of an incorporating nucleotide during one or a series of nucleotide incorporations, are also provided.

Also disclosed herein is a system for monitoring successive biomolecular interactions, comprising: one or more targets; a biomolecule that undergoes one or more transient interactions with the one or more targets, and a nanoparticle operably linked to the biomolecule, wherein the nanoparticle emits, or causes to be emitted, one or more detectable signals upon each of the one or more transient interactions.

In some embodiments, the biomolecule of the system is capable of undergoing one or more transient interactions with at least one target. For example, the biomolecule can be an enzyme that is capable of undergoing a transient interaction with at least one substrate. In some embodiments, the biomolecule of the system is capable of undergoing multiple transient interactions with one or more targets, which can occur simultaneously or successively.

In some embodiments, the biomolecule of the system is capable of undergoing transient interactions with a plurality of targets, and the nanoparticle of the system is capable of generating at least one detectable signal upon each interaction. Optionally, the detectable signal can be detected and analyzed to determine the identity of the target. In some embodiments, the biomolecule of the system is capable of undergoing transient interaction with a series of targets in succession and the nanoparticle of the system is capable of producing a series of detectable signals that can be detected and analyzed to determine a time series of interactions.

In some embodiments, the one or more targets comprise one or more labeled nucleotides each comprising a detectable nucleotide label bonded to a portion of the nucleotide that is released during incorporation of the nucleotide. Typically, the releasable nucleotide label is bonded to the beta, gamma or other terminal phosphate of the labeled nucleotide.

In some embodiments, the biomolecule of the system comprises a nucleotide polymerase, and the at least two transient and successive interactions comprise nucleotide incorporations.

In the sequencing-based applications disclosed herein, the polymeric molecule to be sequenced is typically a nucleic acid. Suitable nucleic acid molecules that can be sequenced according to the present disclosure include without limitation single-stranded DNA, double-stranded DNA, single stranded DNA hairpins, DNA/RNA hybrids, RNA with an appropriate polymerase recognition site, and RNA hairpins. In a typical embodiment, the polymer is DNA, the polymerase is a DNA polymerase or an RNA polymerase, and the labeled monomer is a nucleotide, a nucleotide polyphosphate, or an analog. In another embodiment, the polymer to be sequenced is RNA and the polymerase is reverse transcriptase.

In some embodiments, the surfaces, labels (including, e.g., nanoparticles and organic dyes), polymerases, nucleotides and nucleic acid molecules (including, e.g., targets, primers and/or oligonucleotides) of the present disclosure can be linked to each other, in any combination and in any order, using well known linking chemistries. Such linkage can optionally include a covalent bond and/or a non-covalent bond selected from the group consisting of an ionic bond, a hydrogen bond, an affinity bond, a dipole-dipole bond, a van der Waals bond, and a hydrophobic bond.

In some embodiments, the linking procedure used to link the biomolecules, labels and/or surfaces of the present disclosure comprises a chemical reaction that includes formation of a covalent bond between a first and second moiety, resulting in the linkage of the first moiety to the second moiety. In some embodiments, the chemical reaction occurs between a first group of the moiety and a second group of the second moiety. Such chemical reaction can include, for example, reaction of activated esters, acyl azides, acyl halides, acyl nitriles, or carboxylic acids with amines or anilines to form carboxamide bonds. Reaction of acrylamides, alkyl halides, alkyl sulfonates, aziridines, haloacetamides, or maleimides with thiols to form thioether bonds. Reaction of acyl halides, acyl nitriles, anhydrides, or carboxylic acids with alcohols or phenols to form an ester bond. Reaction of an aldehyde with an amine or aniline to form an imine bond. Reaction of an aldehyde or ketone with a hydrazine to form a hydrazone bond. Reaction of an aldehyde or ketone with a hydroxylamine to form an oxime bond. Reaction of an alkyl halide with an amine or aniline to form an alkyl amine bond. Reaction of alkyl halides, alkyl sulfonates, diazoalkanes, or epoxides with carboxylic acids to form an ester bond. Reaction of an alkyl halides or alkyl sulfonates with an alcohol or phenol to form an ether bond. Reaction of an anhydride with an amine or aniline to form a carboxamide or imide bond. Reaction of an aryl halide with a thiol to form a thiophenol bond. Reaction of an aryl halide with an amine to form an aryl amine bond. Reaction of a boronate with a glycol to form a boronate ester bond. Reaction of a carboxylic acid with a hydrazine to form a hydrazide bond. Reaction of a carbodiimide with a carboxylic acid to form an N-acylurea or anhydride bond. Reaction of an epoxide with a thiol to form a thioether bond. Reaction of a haloplatinate with an amino or heterocyclic group to form a platinum complex. Reaction of a halotriazine with an amine or aniline to form an aminotriazine bond. Reaction of a halotriazines with an alcohol or phenol to form a triazinyl ether bond. Reaction of an imido ester with an amine or aniline to form an amidine bond. Reaction of an isocyanate with an amine or aniline to form a urea. Reaction of an isocyanate with an alcohol or phenol to form a urethane bond. Reaction of an isothiocyanate with an amine or aniline to form a thiourea bond. Reaction of a phosphoramidate with an alcohol to form a phosphite ester bond. Reaction of a silyl halide with an alcohol to form a silyl ether bond. Reaction of a sulfonate ester with an amine or aniline to form an alkyl amine bond. Reaction of a sulfonyl halide with an amine or aniline to form a sulfonamide bond. Reaction of a thioester with thiol group of a cysteine followed by rearrangement to form an amide bond. Reaction of an azide with an alkyne to form a 1,2,3-triazole. Reaction of an aldehyde with an N-terminal cysteine to form a 5-membered thiazolidine ring.

In some embodiments, water-insoluble substances can be chemically modified in an aprotic solvent such as dimethylformamide, dimethylsulfoxide, acetone, ethyl acetate, toluene, or chloroform. Similar modification of water-soluble substances can be accomplished using reactive compounds to make them more readily soluble in organic solvents.

In some embodiments the biomolecules and/or labels of the present disclosure are linked to a surface. Optionally, such linkage can result in reversible or non-reversible immobilization of the nanoparticles, polymerases, nucleotides, nucleic acid molecules, primers, and/or oligonucleotides onto the surface. Non-limiting examples of such linkage can include: nucleic acid hybridization, protein aptamer-target binding, non-specific adsorption, and solvent evaporation. In some embodiments, the biomolecule that is linked to a surface is a polymerase (such as, for example, a polymerase fusion protein). The polymerase can be attached to a surface via a linker comprising an anchor or tethering moiety. The anchor or tethering moiety can be flexible or rigid. The anchor or tether can orient the polymerase, or polymerase fusion protein, in a manner that does not interfere with the nucleotide binding and/or polymerase activity.

Linkage of biomolecules to labels, surfaces and/or to each other can be accomplished by any suitable method (for example, Brinkley et al., 1992 Bioconjugate Chem. 3: 2). In some embodiments, a biomolecule can comprise a single type of reactive site (as is typical for polysaccharides), or it can comprise multiple types of reactive sites, e.g., amines, thiols, alcohols, phenols, may be available (as is typical for proteins). Conjugation selectivity can be obtained by selecting an appropriate reactive moiety. For example, modification of thiols with a thiol-selective reagent such as a haloacetamide or maleimide, or modification of amines with an amine-reactive reagent such as 1-ethyl-3-(3-dimethyl-aminopropyl)carbodiimide (variously known as EDC or EDAC), an activated ester, acyl azide, isothiocyanate or 3,5-dichloro-2,4,6-triazine. Partial selectivity can also be obtained by careful control of the reaction conditions.

In some embodiments, the biomolecule of the labeled biomolecule conjugate is linked to the label through a bond selected from group consisting of: a covalent bond, a hydrogen bond, a hydrophilic bond, a hydrophobic bond, an electrostatic bond, a Van der Waals bond, and an affinity bond.

In some embodiments, the biomolecule comprises a peptide and the bond is a covalent bond formed between an amine group of a lysine residue of the biomolecule and an amine-reactive moiety, wherein the amine reactive moiety is linked to the label. In some embodiments, the biomolecule comprises a peptide and the bond is a covalent bond formed between a carboxy group of an amino acid residue of the biomolecule and a maleimide moiety, wherein the maleimide moiety is linked to the label.

In some embodiments, the label of the labeled biomolecule conjugate comprises a nanoparticle. Optionally, the nanoparticle further comprises a carboxyl group on its surface, and the biomolecule or fragment comprises a primary amine group, and the cross-linking agent EDC is employed to form a covalent amide bond between the nanoparticle and the biomolecules or fragment.

In some embodiments, the biomolecule can be attached to label (including, e.g., a FRET donor or acceptor moiety) using any suitable chemical linking procedure, including chemical linking procedures that are known in the art. In some embodiments, the biomolecule or biologically active fragment can be linked to the nanoparticle via chemical linking procedures. Many linking procedures are well known in the art, including: maleimide, iodoacetyl, or pyridyl disulfide chemistry which targets thiol groups on polypeptides; or succinimidyl esters (NHS), sulfonyl chlorides, iso(thio)cyanates, or carbonyl azide chemistry which targets primary amines in a polypeptide, and dichlorotriazine-based linking procedures. Additional exemplary linking procedures are described in more detail herein.

In some embodiments, the appropriate reactive compounds can be dissolved in a nonhydroxylic solvent (usually DMSO or DMF) in an amount sufficient to give a suitable degree of conjugation when added to a solution of the protein to be conjugated. These methods have been used to prepare protein conjugates from antibodies, antibody fragments, avidins, lectins, enzymes, proteins A and G, cellular proteins, albumins, histones, growth factors, hormones, and other proteins. The resulting protein (e.g., polymerase) attached to the energy transfer or reporter moiety can be used directly or enriched, e.g., chromatographically enriched to separate the desired linked compound from the undesired unlinked compound. Several linking procedures are described in U.S. Pat. No. 5,188,934. Other suitable linking procedures are also known in the art.

When conjugating biomolecules to nanoparticles, the residual, unreacted compound or a compound hydrolysis product can be removed by dialysis, chromatography or precipitation. The presence of residual, unconjugated moieties can be detected by methods such as thin layer chromatography which elutes the unconjugated forms away from its conjugate. In some embodiments, the reagents are kept concentrated to obtain adequate rates of conjugation.

In some embodiments, the surfaces, labels (including, e.g., dyes and/or nanoparticles) and/or biomolecules (including, e.g., polymerases, nucleotides and nucleic acid molecules) disclosed herein can be modified to facilitate their linkage to each other. Such modification can optionally include chemical or enzymatic modification. The modification can be practiced in any combination and in any order. In some embodiments, the modification can mediate covalent or non-covalent linkage of the surfaces, labels and/or biomolecules with each other.

In some embodiments, the biomolecule can be attached, fused or otherwise associated with a moiety that facilitates purification and/or isolation of the biomolecule. For example, the moiety can be a modification enzyme recognition site, an epitope or an affinity tag that facilitates purification of the biomolecule.

In some embodiments, the polymerase can include an amino acid analog which provides a reactive group for linking to the nanoparticle, target, substrate and/or surface. For example, the amino acid analog can be produced using a cell (e.g., bacterial cell) which is genetically engineered to have a 21 amino acid genetic code which is capable of inserting the amino acid analog into the encoded polymerase (or fusion protein). The inserted amino acid analog can be used in a linking chemistry procedure to attach the polymerase (or fusion protein) to the energy transfer donor moiety, biomolecule or the surface.

In some embodiments, the biomolecule is a protein and is modified with a His tag. In some embodiments, the His tag may be fused directly with the protein; alternatively, a linker comprising various lengths of amino acid residues can be placed between the protein and the His tag. The linker can be flexible or rigid.

Optionally, the presence of the His tag can facilitate purification of the protein. For example, His tagged protein can be purified from a raw bacterial lysate by contacting the lysate with any suitable affinity medium comprising bound metal ions to which the histidine residues of the His-tag can bind, typically via chelation. The bound metal ions can comprise, e.g., zinc, nickel or cobalt, to which the His tag can bind with micromolar affinity. Suitable affinity media include Ni Sepharose, NTA-agarose, HisPur® resin (Thermo Scientific, Pierce Protein Products, Rockford, Ill.), or Talon® resin (Clontech, Mountain View, Calif.). The affinity matrix can then be washed with suitable buffers, e.g., phosphate buffers, to remove proteins that do not specifically interact with the cobalt or nickel ion. Washing efficiency can be improved by the addition of 20 mM imidazole. The biomolecule can optionally be eluted from the proteins are usually eluted with 150-300 mM imidazole). The purity and amount of purified biomolecule can then be assessed using suitable methods, e.g., SDS-PAGE and Western blotting.

Optionally, the His tag can be fused to a suitable amino acid sequence that facilitates removal of the His-tag using a suitable endopeptidase. Alternatively, the His tag may be removed using a suitable exopeptidase, for example the Qiagen TAGZyme exopeptidase.

In some embodiments, the His tag can facilitate linkage of the biomolecule to a metal surface, for example, a surface comprising $Zn^{2+}$, $Ni^{2+}$, $Co^{2+}$, or $Cu^{2+}$ ions. Optionally, the His-tag can facilitate linkage of the biomolecule to the surface of a nanoparticle comprising a surface-bound metal ion, typically via chelation interactions, as described in more detail herein.

Any suitable linkers can be used to link the biomolecules (including, e.g., the polymerases, nucleotides and nucleic acid molecules), the labels (including, e.g., nanoparticles, organic dyes, energy transfer moieties and/or other reporter moieties) and/or the surfaces of the present disclosure to each other, in any combination. The linkers can be attached (to the surfaces, nanoparticles, polymerases, nucleotides, target nucleic acid molecules, primers, oligonucleotides, reporter moieties, and/or energy transfer moieties) via covalent bonding, non-covalent bonding, ionic bonding, hydrophobic interactions or any combination thereof. The type and length of the linker can be selected to optimize tethering, proximity, flexibility, rigidity, or orientation. The attachment can be reversible or non-reversible.

Suitable linkers include without limitation homobifunctional linkers and heterobifunctional linkers. For example, heterobifunctional linkers contain one end having a first reactive functionality to specifically link to a first molecule, and an opposite end having a second reactive functionality to specifically link to a second molecule. Depending on such factors as the molecules to be linked and the conditions in which the method of strand synthesis is performed, the linker can vary in length and composition for optimizing properties such as stability, length, FRET efficiency, resistance to certain chemicals and/or temperature parameters, and be of sufficient stereo-selectivity or size to link a label to the biomolecule such that the resultant conjugate is useful reporting biomolecular behavior such as approach, bonding, fusion or catalysis of a particular chemical reaction. Linkers can be employed using standard chemical techniques and include but not limited to, amine linkers for attaching labels to nucleotides (see, for example, U.S. Pat. No. 5,151,507); a linker containing a primary or secondary amine for linking a label to a nucleotide; and a rigid hydrocarbon arm added to a nucleotide base (see, for example, *Science* 282:1020-21, 1998).

In some embodiments, the linker comprises a polyethylene glycol (PEG) or PEG derivative. See, e.g., U.S. Provisional Applications 61/086,750; 61/102,709; 61/102,683; and 61/102,666. Such PEG moieties can be functionalized at one or both ends. In some embodiments, functionalization at both ends with the same reactive moiety can be employed to create a homobifunctional PEG derivative. Some examples of homobifunctional PEG derivatives include without limitation COOH-PEG-COOH; NH2-PEG-NH2; and MAL-PEG-MAL (where MAL denotes a maleimide group).

The linker moiety can optionally include: a covalent or non-covalent bond; amino acid tag; chemical compound (e.g., polyethylene glycol); protein-protein binding pair (e.g., biotin-avidin); affinity coupling; capture probes; or any combination of these.

Optionally, the linker can be selected such that it does not significantly interfere with the function or activity of the biomolecules, labels and/or surfaces that it links to each other. For example, when the biomolecule is a polymerase, the linker can be selected such that it does not significantly interfere with nucleotide binding to the polymerase, or with cleavage of the phosphodiester bonds, or with nucleotide incorporation, or with release of the polyphosphate product, or with translocation of the polymerase or with energy transfer, or with emission of a detectable signal.

In some embodiments, the linker can comprise a single covalent bond or a series of covalent bonds. Optionally, the linker can be linear, branched, bifunctional, trifunctional, homofunctional, or heterofunctional. The linker can be cleavable. The linkers can be rigid or flexible. The linker can be capable of energy transfer. The linker can be a chemical chain or a chemical compound. The linker can be resistant to heat, salts, acids, bases, light and chemicals. The linker can include a short or long spacer, a hydrophilic spacer, or an extended spacer.

In another embodiment, a rigid linker can be used link the biomolecule to the label. Examples of rigid linkers include benzyl linkers, proline or poly-proline linkers (S. Flemer, et al., 2008 Journal Org. Chem. 73:7593-7602), bis-azide linkers (M. P. L. Werts, et al., 2003 Macromolecules 36:7004-7013), and rigid linkers synthesized by modifying the so-called "click" chemistry scheme which is described by Megiatto and Schuster 2008 Journal of the Am. Chem. Soc.

130:12872-12873. In yet another embodiment, the linker can be an energy transfer linker synthesized using methods described in U.S. published patent application No. 2006/0057565, which is incorporated in its entirety. In yet another embodiment, the spacer linking moiety can be a cationic arginine spacer or an imidazolium spacer molecule.

In some embodiments, the linker moiety comprises about 1-40 plural valent atoms or more selected from the group consisting of C, N, O, S and P. The number of plural valent atoms in a linker may be, for example, 0, 1, 2, 3, 4, 5, 6, 7, 8, 9, 10, 20, 25, 30, or 40, or more. A linker may be linear or non-linear; some linkers have pendant side chains or pendant functional groups (or both). Examples of such pendant moieties are hydrophilicity modifiers, for example solubilizing groups like, e.g., sulfo ($—SO_3H—$ or $—SO^3—$). In some embodiments, a linker is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety which includes —C(O)NH—, —C(O)O—, —NH—, —S—, —O—, and the like. Linkers may by way of example consist of a combination of moieties selected from alkyl, alkylene, aryl, —C(O)NH—, —C(O)O—, —NH—, —S—, —O—, —C(O)—, —S(O)$_n$— where n is 0, 1, 2, 3, 4, 5, or 6-membered monocyclic rings and optional pendant functional groups, for example sulfo, hydroxy and carboxy.

In some embodiments, the linker can result from "click" chemistries schemes (see, e.g., Gheorghe, et al., 2008 Organic Letters 10:4171-4174) which can be used to attach any combination of biomolecules, labels and surfaces as disclosed herein to each other In one aspect, the linker can attach two or more energy transfer or reporter moieties to each other (the same type or different types of moieties).

In another aspect, a trifunctional linker (e.g., Graham, U.S. published patent application No. 2006/0003383) can be linked to two fluorescent dye moieties (the same type or different types) to amplify the fluorescent signal upon nucleotide binding or nucleotide incorporation. For example, a trifunctional linker can be linked to two energy transfer acceptor moieties, or to an energy transfer acceptor and a reporter moiety. In another example, multiple trifunctional linkers can be linked to each other, which can be linked to multiple fluorescent dyes for dendritic amplification of the fluorescent signal (e.g., Graham, U.S. published patent application No. 2007/0009980).

In some embodiments, the linker can be a cleavable linker such as, for example, a photocleavable linker, a chemically cleavable linker or a self-cleaving linker.

In some embodiments, the linker is a self-cleaving linker. Optionally, such linker can be a trimethyl lock or a quinone methide linker, which can each optionally link to two energy transfer acceptor and/or reporter moieties and the nucleotide.

In some embodiments, the linkers can be cleavable where cleavage is mediated by a chemical reaction, enzymatic activity, heat, acid, base, or light. For example, photo-cleavable linkers include nitrobenzyl derivatives, phenacyl groups, and benzoin esters. Many cleavable groups are known in the art and are commercially available. See, for example, J. W. Walker, et al., 1997 Bioorg. Med. Chem. Lett. 7:1243-1248; R. S. Givens, et al., 1997 Journal of the American Chemical Society 119:8369-8370; R. S. Givens, et al., 1997 Journal of the American Chemical Society 119:2453-2463; Jung et al., 1983 Biochem. Biophys. Acta, 761: 152-162; Joshi et al., 1990 J. Biol. Chem., 265: 14518-14525; Zarling et al., 1980 J. Immunol., 124: 913-920; Bouizar et al., 1986 Eur. J. Biochem., 155: 141-147; Park et al., 1986 J. Biol. Chem., 261: 205-210; and Browning et al., 1989 J. Immunol., 143: 1859-1867; see also U.S. Pat. No. 7,033,764. A broad range of cleavable, bifunctional (both homo- and hetero-bifunctional) spacer arms with varying lengths are commercially available.

In yet another embodiment, the linker can be an energy transfer linker synthesized using methods described in U.S. Published Patent Application No. 2006/0057565.

In yet another embodiment, the linker can comprise a spacer, for example a cationic arginine spacer or an imidazolium spacer molecule.

In some embodiments, the linker can be a fragmentable linker, including non-lamellar "detergent-like" micelles or lamellar vesicle-like micelles such as small unilamellar vesicles or liposomes ("SUVs"), small multilamellar vesicles or liposomes (SMVs"), large unilamellar vesicles or liposomes ("LUVs") and/or large multilamellar vesicles or liposomes ("LMVs") (see U.S. application Ser. No. 11/147,827) and see U.S. Application No. 60/577,995, and Ser. No. 12/188,165.

In some embodiments, the linker can include multiple amino acid residues (e.g., arginine) which serve as an intervening linker between an attachment site on the biomolecule and the label. For example, the linker can be can four arginine residues which connect a dye moiety to a nucleotide comprising a phosphate group, wherein the linker links the dye moiety to the terminal phosphate group of the nucleotide.

In some embodiments, linkers can be used to attach energy transfer or reporter moieties to biomolecules using any suitable linking procedure, including: amine linkers (see, for example, Hobbs, U.S. Pat. No. 5,151,507); a linker comprising a primary or secondary amine; and a rigid hydrocarbon arm (see, for example, R. F. Service, 1998 Science 282(5391): 1020-21). Some exemplary linking procedures for attaching energy transfer or reporters moieties to exemplary biomolecules are provided in European Patent Application 87310256.0; International Application PCT/US90/05565; Marshall, 1975 Histochemical Journal 7:299-303; and Barone et al., 2001 Nucleosides, Nucleotides, and Nucleic Acids, 20(4-7): 1141-1145. Other examples include linkers for attaching energy transfer or reporter moieties to exemplary biomolecules, using the specific example of oligonucleotides synthesized using phosphoramidate to incorporate amino-modified dT (see Mathies, U.S. Pat. No. 5,707,804).

In one aspect, a linker comprising a polymer of ethylene oxide can be used to attach the surfaces, labels (including, e.g., dyes and nanoparticles), polymerases, nucleotides and/or nucleic acid molecules of the present disclosure to each other in any combination. Non-limiting examples of such polymers of ethylene oxide include polyethylene glycol (PEG), including short to very long PEG, branched PEG, amino-PEG-acids, PEG-amines, PEG-hydrazines, PEG-guanidines, PEG-azides, biotin-PEG, PEG-thiols, and PEG-maleinimides. For example, PEG includes: PEG-1000, PEG-2000, PEG-12-OMe, PEG-8-OH, PEG-12-COOH, and PEG-12-NH$_2$. In some embodiments, the PEG molecule may be linear or branched. In some embodiments, it can have a molecular weight greater than or approximately equal to 1000, 2000, 3000, 4000, 5000 or greater.

In some embodiments, functionalization with different reactive moieties can be used create a heterobifunctional PEG derivative comprising different reactive groups at each end. Such heterobifunctional PEGs can be useful in linking two entities, where a hydrophilic, flexible and biocompatible spacer is needed. Some examples of heterobifunctional PEG derivatives include without limitation Hydroxyl PEG Carboxyl (HO-PEG-COOH): Thiol PEG Carboxyl (HS-PEG- COOH); Hydroxyl PEG Amine (HO-PEG-NH2); t-Boc Amine PEG Amine (TBOC-PEG-NH2); Amine PEG Carboxyl (NH2-PEG-COOH); t-Boc Amine PEG NHS Ester (TBOC-PEG-NHS); FMOC Amine PEG NHS Ester (FMOC-PEG-NHS): Acrylate PEG NHS Ester (ACLT-PEG-NHS); Maleimide PEG Carboxyl (MAL-PEG-COOH); Maleimide PEG Amine (MAL-PEG-NH2), including the TFA Salt thereof; Maleimide PEG NHS Ester (MAL-PEG-NHS); Biotin PEG NHS Ester (BIOTIN-PEG-NHS); Biotin Polyethylene Glycol Maleimide (BIOTIN-PEG-MAL); OPSS PEG NHS Ester (OPSS-PEG-NHS).

Optionally, the PEG derivative can be a multi-arm PEG derivative. In some embodiments, the multi-arm PEG derivative can be a PEG derivative having a core structure comprising pentaerythritol (including, for example, 4arm PEG Amine (4ARM-PEG-NH2); 4arm PEG Carboxyl (4ARM-PEG-COOH); 4arm PEG Maleimide (4ARM-PEG-MAL); 4arm PEG Succinimidyl Succinate (4ARM-PEG-SS); 4arm PEG Succinimidyl Glutarate (4ARM-PEG-SG)); a PEG derivative having a core structure comprising hexaglycerin (including, for example, 8arm PEG Amine (8ARM-PEG-NH2); 8arm PEG Carboxyl (8ARM-PEG-COOH); 8arm PEG Succinimidyl Succinate (8ARM-PEG-SS); 8arm PEG Amine (8ARM-PEG-SG); PEG derivative having a core structure comprising tripentaerythritol (including, for example, 8arm PEG Amine (8ARM(TP)-PEG-NH2); 8arm PEG Carboxyl (8ARM(TP)-PEG-COOH); 8arm PEG Succinimidyl Succinate (8ARM (TP)-PEG-SS); 8arm PEG Amine (8ARM(TP)-PEG-SG)). Optionally, end groups for heterobifunctional PEGs can include maleimide, vinyl sulfones, pyridyl disulfide, amine, carboxylic acids and NHS esters. The activated PEG derivatives can then be used to attach the PEG to the desired biomolecule and/or nanoparticle. Optionally, one or both ends of the PEG derivative can be attached to the N-terminal amino group or the C-terminal carboxylic acid of a protein-comprising biomolecule.

For methods, systems, compositions and kits comprising labeled biomolecule conjugates, the biomolecule can be linked to the label in any manner, and using any suitable linking procedures, that sufficiently preserves a particular biological activity of interest. Typically, when the biomolecule is a polymerase, the conjugate is a labeled polymerase conjugate and the biological activity of interest is polymerase activity. The polymerase of the labeled polymerase conjugate can be linked to the label using any suitable method that retains polymerase activity.

In some embodiments, the biomolecule and the label can be linked through a linker.

In some embodiments, the labeled biomolecule conjugate comprises a biomolecule covalently linked to a label through one or more covalent bonds.

In some embodiments, the label can be covalently linked to the biomolecule using any suitable method that permits linkage without loss of biological activity. Typically, the reagents employed are selected to allow the covalent linkage of the biomolecule to the label under defined reaction conditions. In some embodiments, the linkage can be performed in a site-specific manner.

In one exemplary embodiment, the label and the biomolecule can be reacted with each other in a suitable solvent in which both are soluble. The labels can optionally be treated or functionalized with suitable moieties to enhance their solubility in a suitable solvent.

In a typical embodiment, the biomolecule comprises a protein, more typically an enzyme, which can optionally be a polymerase. The various linking methods described herein have particular applicability for linking enzymes, e.g., polymerases, to labels such as nanoparticles or organic dyes.

In some embodiments, the label (e.g., nanoparticle or dye) can optionally be treated to create suitable sites for covalent attachment of the biomolecule. For example, the label and/or the biomolecule can be modified via introduction of a cysteine amino acid residue to create an attachment site comprising a free sulfhydryl group of the cysteine. In another embodiment, the label can be modified via introduction of a moiety comprising a reactive chemical group selected from any one of: a thiol group, an amino group (e.g., a primary or secondary amine) and a carboxyl group. The reactive chemical group of one member of the labeled biomolecule conjugate can then be reacted with a second reactive chemical group of a second member of the conjugate.

In one example, the label can be treated to introduce reactive chemical groups that form suitable attachment sites for the biomolecule. Optionally, the label can be linked to with a cysteine-rich compound such as bovine serum albumin (BSA) or ovalbumin, resulting in the association of the cysteine-rich compound with the label. The label can then be treated with reducing agents such as DTT, resulting in the formation of a large number of free sulfhydryl groups on the protein molecule to serve as potential sites for covalent attachment of the biomolecule. For example, reduction of a single BSA molecule on the nanoparticle surface results in the generation of approximately 34 free sulfhydryl groups, since a single BSA molecule typically comprises 17 disulfide bonds and one free thiol group. Such a poly-dentate thiol-modified protein could serve as a platform for initial modification of the label, onto which other biomolecules of interest can be added after the initial modification. In one embodiment, the BSA-treated label is a nanoparticle.

In another exemplary embodiment, CdSe—ZnS core-shell nanoparticles are capped with mercaptoacetic acid groups, and the resulting nanoparticles are covalently linked to the biomolecule. Optionally, the biomolecule can be engineered to include thiol-terminated residues that react with suitable groups within the capped layer of the nanoparticle.

In some embodiments, the biomolecule is a protein or polypeptide, for example an enzyme, that comprises naturally occurring amino acid side chains that can be modified or otherwise treated so as to generate attachment sites for the nanoparticle.

In some embodiments, the linker EDC is used to activate free —COOH ligands on the surface of nanoparticles. In one exemplary embodiment, the biomolecule and the nanoparticle are covalently linked through a condensation reaction between the amines on the biomolecule and the carboxyl groups on the nanoparticle using a suitable cross-linking agent. For example, the cross-linking agent 1-ethyl-3-(3-dimethyl-aminopropyl)carbodiimide (EDC) can be used to cross-link the polymerase with nanoparticles capped with ligands such as mercaptoacetic acid or dihydrolipoic acid (DHLA).

In some embodiments, the conjugation method can exploit the presence of cysteine residues within the biomolecule to be conjugated because such residues can serve as points of attachment to the label. For example, the thiol group of cysteine residues can be covalently linked to a label by using linking agents such as SMCC. In some embodiments, the biomolecule is a polymerase that is genetically modified to introduce one or more cysteine residues placed in strategic positions, e.g., proximal to the active site/NTP binding pocket of the polypeptide. The polymerase can then be linked to a nanoparticle using SMCC. The covalent bond(s) between the polymerase and the label will not only stabilize the conjugate but also orient the polypeptide with respect to the nanoparticle in the preferred orientation for binding, resulting both in an increase of conjugate stability (manifested as reduced propensity of the conjugate to disassociate) and preservation of high affinity binding.

In some embodiments, the labeled biomolecule conjugate is produced by covalently linking the biomolecule to the nanoparticle having one or more carboxyl groups on its surface using the heterobifunctional cross-linking agent succinimidyl-4-(N-maleimidomethyl)cyclohexane-1-carboxylate ("SMCC"). This agent comprises a maleimide reactive group capable of reacting with cysteine residues to form a thioether bond as well as an amine reactive NHS ester capable of reacting with primary amines to form an amide bond. Such a linker has utility in cross-linking, inter alia, biomolecules comprising one or more cysteines to nanoparticles comprising one or more amine groups. Under suitable conditions, the double bond of the maleimide can undergo an alkylation reaction with a sulfhydryl group of the biomolecule to form a stable thioether bond. The NHS ester contains an amine-reactive group that can react with, inter alia, amine groups on a suitable label, for example the surface of a nanoparticle. Optionally, the nanoparticle can be coated with a PEG amine, and the amine group that reacts with the NHS ester of SMCC can be the amine group of a surface PEG-amine.

In some embodiments, the biomolecule-nanoparticle conjugate comprises a biomolecule covalently linked to a nanoparticle. In one exemplary embodiment, the biomolecule comprises one or more primary amine groups and the nanoparticle is covalently linked to the one or more amine groups using the linking agents such as tris(hydroxymethyl)phosphine (TMP) and/or β-[tris(hydroxymethyl)phosphino]propionic acid (THPP). TMP and THPP are phosphine derivatives that can react with amines to form covalent linkages. See, e.g., Cochran, F., et al., "Application of tris(hydroxymethyl)phosphine as a coupling agent for alcohol dehydrogenase immobilization, Enzyme & Microbial Technology 18:373-378 (1996); Hermanson, G., *Bioconjugate Techniques*, Second Edition (2008). In one embodiment, a peptide-coated nanoparticle is prepared via self-assembly of imidazole-containing peptides comprising primary amines on the nanoparticle surface. The peptide-coated nanoparticle is then partially reacted with TMP or THPP, which is then removed via suitable techniques, e.g., washing. After removal of the TMP or THPP, a biomolecule comprising a primary amine group is added to the peptide-coated nanoparticle at a stochiometry of choice under suitable reaction conditions. The conjugate can then be purified using suitable techniques, for example, HPLC size exclusion chromatography, ultrafiltration and/or Ni/NTA column purification. In some embodiments, the biomolecule comprising a primary amine group is a protein, typically a His-tagged protein.

In one embodiment, a peptide-coated nanoparticle is prepared via self-assembly of imidazole-containing peptides comprising primary amines on the nanoparticle surface. The peptide-coated nanoparticle is then partially reacted with TMP or THPP, which is then removed via suitable techniques, e.g., washing. After removal of the TMP or THPP, a biomolecule comprising a primary amine group is added to the peptide-coated nanoparticle at a stochiometry of choice under suitable reaction conditions. The conjugate can then be purified using suitable techniques, for example, HPLC size exclusion chromatography, ultrafiltration and/or Ni/NTA column purification. In some embodiments, the biomolecule comprising a primary amine group is a protein, typically a His-tagged protein.

The nanoparticle can optionally be derivatized with PEG-amine. In some embodiments, the nanoparticle can be capped with ovalbumin or other proteinaceous coating using any suitable cross-linkers (e.g., EDC, BS3 SMCC).

In some embodiments, nanoparticles containing free —COOH ligands on their surface are derivatized via formation of amide bonds with the terminal amino group of PEG-amine. The PEG-ylated nanoparticles are activated by treatment with agents such as SMCC, and the activated nanoparticles are then conjugated to polymerase via formation of thioether bonds involving the maleimide group of SMCC and a cysteine thiol group on the polymerase.

In some embodiments, the biomolecule is linked to the nanoparticle via a covalent bond formed between a reactive α-thioester and an N-terminal cysteine residue. Such reactions are described, for example, in Dawson et al., Science 266:776-779 (1994); Dawson et al., Ann. Rev. Biochem. 69:923-960 (2000); Johnson et al., JACS 128:6640-6646 (2006). In some embodiments, a biomolecule that comprises, or is modified to comprise, an N-terminal cysteine group is linked to a nanoparticle comprising a thioester surface ligand. The chemistry of one such exemplary reaction, comprising the linkage of a protein including an N-terminal cysteine is linked to a quantum dot ("QD") including a surface thioester, is depicted in FIG. 32.

In one example, a thioester-comprising crosslinker is first attached to the surface of the nanoparticle using any suitable chemistry, resulting in a modified nanoparticle comprising a reactive thioester on its surface. This modified nanoparticle is then reacted with a biomolecule comprising, or modified to comprise, an N-terminal cysteine residue. Optionally, such reaction can be done in the presence of a suitable aromatic or aliphatic thiol catalyst. The thiol group of the cysteine reacts with the thioester on the surface of the nanoparticle, forming a second thioester that undergoes intramolecular rearrangement. Such rearrangement results in the formation of a natural peptide bond linking the biomolecule to the nanoparticle.

In another exemplary embodiment, a nanoparticle including a reactive aldehyde on its surface can be reacted with a biomolecule including an N-terminal cysteine residue. The reaction product is a five-membered thiazolidine ring that is stable over a pH range of 3-9. See, e.g., Shao & Tam, "*Unprotected Peptides as Building Blocks for the Synthesis of Peptide Dendrimers with Oxime, Hydrazone and Thiazolidine Linkages*," JACS 117(14):3893-3899 (1995); see also FIG. 33). Commercially available quantum dots typically comprise one or more surface amines, which can be converted to aldehydes through treatment with the heterobifunctional crosslinking reagent SFB (Pierce). Such aldehydes can then be reacted with an N-terminal cysteine group of a biomolecule to form a covalent linkage between the biomolecule and the nanoparticle.

In yet another embodiment, a biomolecule comprising a ketone can be reacted with a nanoparticle in the presence of a hydroxylamine to covalently link the biomolecule to the nanoparticle. One such reaction is depicted in FIG. 34.

In some embodiments, the biomolecule and the label can be linked using "click" chemistry. See, e.g., Huisgen, Rolf; Angewandte Chemie International Edition 2 (11): 633-645; Christian W. Tornøe, Caspar Christensen, and Morten Meldal, J. Org. Chem., 2002, 67 (9), pp 3057-3064; Rostovtsev, V. V.; Green, L. G.; Fokin, V. V.; Sharpless, K. B., Angew. Chem., Int. Ed. 2002, 41, (14), 2596-2599; Agard, N. J.; Prescher, J. A.; Bertozzi, C. R., J. Am. Chem. Soc. 2004, 126, (46), 15046-15047; John C. Jewett, Ellen M. Sletten and Carolyn R. Bertozzi, J. AM. CHEM. SOC. 2010, 132, 3688-3690.

In another exemplary embodiment, either the biomolecule or the label is modified to include an alkyne, and the other is labeled to include an azide. The alkyne and azide can undergo a "click" reaction to form a covalent conjugate. One such exemplary reaction between a biomolecule and a nanoparticle, wherein the biomolecule (BM) comprises an azide and the nanoparticle ("dot") comprises an alkyne, is depicted in FIG. 35. Optionally, the click reaction can be a "copperless" click reaction.

In some embodiments, the biomolecule of the labeled biomolecule conjugate can be non-covalently linked to the label. See, for example, Goldman et al., 2005, *Anal. Chim. Acta* 534:63-67. For example, in some embodiments the biomolecule can be linked to the label via a non-covalent interaction between a first and second member of a binding pair, as described further herein.

In some embodiments, the conjugation of biomolecules to labels can be achieved through a process of self-assembly, wherein suitably modified biomolecules and labels are contacted under conditions where they will spontaneously bind to each other. For example, one or more thiolated proteins can be conjugated to nanoparticles using dative thiol-bonding between the cysteine residues on the protein and the sulfur atoms on the nanoparticle surface. See, e.g., Akerman, M. E., et al., "Nanocrystal targeting in vivo", Proc. Natl. Acad. Sci. USA 99:12617-12621 (2002). Optionally, the conjugate can be formed through adsorption or non-covalent self-assembly of proteins on to the nanoparticle surface.

In some embodiments, the conjugate can be formed through self-assembly via electrostatic interactions, wherein biomolecules having either a natural positive surface charge or that are engineered to include positively charged domains, interact with nanoparticles having a negative surface charge, (e.g., nanoparticles capped with substances comprising COOH moieties). See, for example, Mattoussi et al., "Self-assembly of CdSe—ZnS nanoparticle bioconjugates using an engineered recombinant protein", J. Am. Chem. Soc. 122 (49):12142-50 (2000); Mattoussi et al., "Bioconjugation of highly luminescent colloidal CdSe—ZnS nanoparticles with an engineered two-domain recombinant protein", Phys. Status Solido B-Basic Res. 224:277-83 (2001). In some embodiments, the nanoparticle can be capped with —COOH ligands or other negatively charged moieties (for example, lipoic acid moieties), and the capped nanoparticle contacted with engineered recombinant polymerases comprising positively charged attachment domains (for example, leucine zippers, polylysine or polyarginine linkers or the like). It is theorized that the —COOH capping moieties not only promote dispersion of the nanoparticles in solution at basic pH, but also create a surface charge distribution that promotes direct self-assembly with other molecules that have a net positive charge.

Another assembly-based approach involves the use of affinity ligands. In some embodiments, conjugation is accomplished through use of binding pairs. Suitable binding pairs include: a biotin moiety (including, for example, biotin, desthiobiotin or photoactivatable biotin, bound with an avidin moiety, such as streptavidin or neutravidin); His-tag bound with nickel, zinc, cobalt or other metal ions; maltose bound with a maltose binding protein (MBP); lectin bound with a carbohydrate; calcium bound with a calcium binding protein (CBP); antigen or epitope tags bound with an antibody or antibody fragment; particular antigens such as digoxigenin, fluorescein, nitrophenol or bromodeoxyuridine and their respective antibodies; IgG bound with protein A; receptor bound with a receptor agonist or antagonist; enzyme bound with an enzyme cofactors; and thyroxine bound with cortisol.

The strong interaction between streptavidin (or avidin) and biotin (cis-hexahydro-2-oxo-1H-thieno[3,4]imidazole-4-pentanoic acid) is well known. The affinity binding between streptavidin and biotin, having a dissociation constant, $K_d$, of approximately $10^{-15}$M, is regarded as one of the strongest known, non-covalent, biochemical interactions. The biotin-avidin bond forms very rapidly and is considered to be stable under a wide range of pH, temperature and other denaturing conditions. See, e.g., Savage et al., Avidin-Biotin Chemistry: A Handbook, 1992:1-23, Rockford, Pierce Chemical Company; Goldman et al., "Avidin: A natural bridge for quantum dot-antibody conjugates", J. Am. Chem. Soc. 124:6378-6382 (2002). Without being bound by any particular theory, it is believed that biotin and avidin moieties bond with each other through a combination of ionic (electrostatic) and hydrophobic interactions.

In an exemplary embodiment, a biomolecule and a label can be linked to form a labeled biomolecule conjugate, where the linkage between the biomolecule and the label comprises one or more affinity interactions between a biotin moiety and an avidin moiety. In some embodiments, one member of the conjugate can be linked to a biotin moiety and another member of the conjugate can be linked to an avidin moiety. In an exemplary embodiment, a biotin moiety can linked to a first member of the conjugate, e.g., the biomolecule, and an avidin moiety is linked to a second member of the conjugate, e.g., the label, and the first and second members are linked to each other via an affinity interaction between the biotin and avidin moieties. The label can comprise, for example, a nanoparticle and/or an organic dye moiety.

In some embodiments, a biotin moiety is linked to either the biomolecule or the label through treatment with an enzyme that is capable of covalently attaching a biotin moiety to a substrate, such as a biotin ligase. For example, the biotin ligase can be the *E. coli* biotin ligase (EC 6.3.4.15) encoded by the birA gene of *E. coli*. The *E. coli* biotin ligase is also commonly referred to as biotin-protein ligase; other names for this enzyme include: biotin ligase; biotin operon repressor protein; birA; biotin holoenzyme synthetase; biotin-[acetyl-CoA carboxylase] synthetase. This enzyme can activate a biotin moiety to form a biotinyl-5' adenylate and can transfer the activated biotin moiety to a biotin-accepting protein, such as an acceptor peptide for biotin ligase (hereinafter, "a biotin acceptor peptide"). In some embodiments, the biotin acceptor site can comprise the amino acid sequence of SEQ ID NO: 10. See, e.g., Howarth et al., "Targeting quantum dots to surface proteins in living cells with biotin ligase", Proc. Natl. Acad. Sci. USA 102(21):7583-7588 (2005). In some embodiments, the biotin acceptor peptide can comprise the amino acid sequence of SEQ ID NO: 10 (GLNDIFEAQKIEWHE). Optionally, the biotin acceptor peptide is the AviTag™ peptide (Avidity, LLC). See, e.g., U.S. Pat. Nos. 5,723,584, 5,874,239 and 5,932,433.

In some embodiments, the biotin can be linked to a thiol group of the biomolecule. For example, the biomolecule can be a protein comprising a free cysteine residue (including but not limited to a naturally occurring or an engineered replacement cysteine residue), and the biotin moiety can be linked to the free cysteine residue. Optionally, the biotin moiety can be linked to the cysteine residue by use of a thiol-reactive reagent, such as a biotin-maleimide reagent, to form a biotin-labeled biomolecule. See, e.g., U.S. Pat. No. 7,521,541.

In one exemplary embodiment, the label of the conjugate is linked to an avidin moiety and contacted with a biomolecule linked to a biotin moiety.

In some embodiments, the label is linked to the biomolecule through use of an attachment site that is engineered or otherwise introduced into the biomolecule and serves as the site of attachment for one or more labels. In some embodiments, the introduced attachment site comprises an enzyme modification recognition sequence. In some embodiments, the modification enzyme recognition sequence can comprise a biotin ligase acceptor site, to which one or more biotin moieties can be attached by a biotin ligase, thus forming an attachment site for a label linked to an avidin moiety.

In some embodiments, the biomolecule of the conjugate is a protein that comprises a biotin ligase acceptor site, such that the biomolecule can be biotinylated via treatment with a suitable biotin ligase in the presence of a biotin. Typically, the biomolecule or the nanoparticle to be biotinylated comprises a biotin acceptor site.

In another embodiment, the modification enzyme recognition site is an N-terminal recognition site for the TEV (Tobacco Etch Virus) protease enzyme. Typically, such recognition site comprises the following amino acid sequence:

ENLYFQ SEQ ID NO: 37

The TEV protease can specifically cleave this modification enzyme recognition sequence after the glutamine (Q) residue. See, e.g., de Graaf et al., "Nonnatural Amino Acids for Site-Specific Protein Conjugation," 20(7): 1281-1295 (2009); Tolbert & Wong, "Conjugation of Glycopeptide Thioesters To Expressed Protein Fragments", Methods in Mol. Bio., Vol. 283 ("Bioconjugation Protocols"), pp. 255-266 (2004). Optionally the protein to be conjugated is fused at its N-terminus with a peptide tag comprising the TEV protease recognition sequence, and the recombinant protein is then cleaved with TEV protease to remove the tag and uncover an N-terminal cysteine. The amino acid sequences of exemplary polymerases comprising a TEV protease recognition sequence at their N-terminus are disclosed herein. Biomolecules comprising a N-terminal cysteine are especially desirable because the N-terminal cysteine group can serve as an attachment site for the site-specific attachment of a label using a variety of different chemistries. In one example, the N-terminal cysteine can be reacted with a thioester to form a peptide bond (see FIG. 32).

In another embodiment, the N-terminal cysteine can be reacted with an aldehyde to form a 5-membered thiazolidine ring (see FIG. 33). Specific examples using such conjugation strategies are described further herein.

In some embodiments, the enzyme can be labeled in a site-specific manner through incorporation of unnatural or modified amino acids during translation of the mRNA encoding the enzyme using modified aminoacyl tRNAs and/or modified tRNA synthetases. Briefly, such unnatural amino acids are genetically encoded in mammalian and other cells by using a mutant E. coli aminoacyl-tRNA synthetase that has been evolved to selectively aminoacylate its tRNA with the unnatural amino acid of interest. This mutant synthetase, together with an amber suppressor tRNA, can be used to selective incorporate the unnatural amino acid into a protein at selected sites in response to amber nonsense codes. See, e.g., Brustad et al., "A general and efficient method for the site-specific dual-labeling of proteins for single molecule fluorescence resonance energy transfer" J. Am. Chem. Soc. 130(52):17664-5 (2008); Liu et al., "Genetic incorporation of unnatural amino acids into proteins in mammalian cells" Nat. Methods, 4(3):239-244 (2007).

In another covalent conjugation approaches can also involve the insertion of other non-natural amino acids besides an N-terminal cysteine at defined sites within the biomolecule via site-specific engineering. Such introduced non-natural amino acids can then serve is attachment sites for a label. In one exemplary embodiment, an azido non-natural amino acid is engineered into the polymerase, which is then undergoes a click chemistry reaction with a DIBO moiety (DIBO being a reactive "click" complement to the azide). The DIBO moiety can optionally be linked to the termini of PEG surface ligands of a nanoparticle. In another embodiment, a heterobifunctional crosslinker can be used; one end of the linker can include a His-tag for metal affinity binding to the nanoparticle surface, and the other end can include a DIBO moiety for covalent coupling to the azido non-natural amino acid. The linker can optionally comprise peptide or PEG chains. Use of such a heterobifunctional crosslinker eliminates the need to develop nanoparticles with specific covalent chemistry.

In another embodiment, a ketone-comprising non-natural amino acid is introduced into a biomolecule, which can serve as an attachment site for a nanoparticle. For example, the introduced ketone group can allow site-specific modification of the biomolecule using chemistry unique to the ketone functional group. FIG. 34 depicts one exemplary pathway by which the insertion of the nonnatural amino acid, acetylphenyl alanine, into an exemplary biomolecule (Phi29 DNA polymerase) can be used to covalently couple a nanoparticle to the biomolecule.

In another embodiment, an azide-comprising non-natural amino acid such as, for example, azidophenyl alanine, can be introduced into a biomolecule; the introduced azide can then be used in a "click" reaction to covalently couple the biomolecule to an alkyne-comprising biomolecule. Normally, alkyne-azide click reactions utilize copper as a catalyst. In some embodiments, a "copperless click" reaction is utilized where a strained, eight-membered ring containing an alkyne can undergo reaction with an azide without the use of a copper catalyst. FIG. 35 depicts one exemplary pathway by which the insertion of the nonnatural amino acid, azidophenyl alanine, into an exemplary biomolecule (Phi29 DNA polymerase) can be used to covalently couple a nanoparticle to the biomolecule.

In some embodiments, the conjugate can be formed through self-assembly of the biomolecule with the label, where the self-assembly includes the formation of one or more metal affinity-based interactions, a phenomenon also referred to herein as "chelation". In some embodiments, a polypeptide can be conjugated to a label through metal-affinity coordination between a histidine residue of the polypeptide and a metal atom of the label. This strong interaction ($Zn^{2+}$-His) has a dissociation constant, $K_D$, stronger than most antigen-antibody bindings ($10^6$-$10^9$). See, e.g., Hainfeld at al., "Ni-NTA-gold clusters target his-tagged proteins", J. Struct. Biol. 127:185-198 (1999). Nanoparticles are one example of a label that comprises metal atoms that are accessible for binding by histidine residues of a biomolecule.

In some embodiments, the biomolecule can be engineered to contain, or otherwise fused to, a genetically encoded domain that exhibits chelation-based interactions with the surface of a nanoparticle label. See, for example, Clapp et al., Nature Protocols 1(3):1258 (2006). In some embodiments, such domain can comprise a His tag. For example, His tagged biomolecules, e.g., proteins, can bind via metal affinity-based interactions to the surface of CdSe—ZnS nanoparticles capped with lipoic acid or other negatively charged moieties. It is theorized that the strength of such binding is determined by the degree to which the imidazole side chains of the oligohistidine segment of the His tag interact with surface metal ions present in or on the nanoparticle shell. Without being bound to any particular theory or mechanism for linkage of His tagged proteins to nanoparticles, such methods are within the scope and spirit of the present disclosure. Overall, such methods can simplify the bioconjugation procedure and reduce the overall hydrodynamic size of the resulting conjugate by eliminating the need for a bridging protein. Such preparation methods can be particular suitable for FRET applications that require reduced spacing between the donor and acceptor moieties. The bioconjugate size can be further reduced by using only the shorter polymerase fragments that eliminate regions not required for core polymerase function.

In some embodiments, the biomolecule, e.g., polymerase, comprises one or more consecutive histidine residues, linked to the label, e.g., nanoparticle. In one exemplary embodiment, the biomolecule comprises between four and twelve consecutive histidine residues.

In some embodiments, the nanoparticle can be linked to a chelating compound, e.g., nickel-nitriloacetic acid, Ni-NTA) that quantitatively binds to His-tagged biomolecules with controlled molar ratio and biomolecular orientation. The $K_D$ for the hexahistidine tag ($His_6$) and Ni-NTA is $10^{-13}$.

In some embodiments, the conjugate comprises a polymerase fused to a His-tag and linked to a nanoparticle. The His-tag can comprise 3, 4, 5, 6, 7, 8, 9, 10, 11, 12 or more consecutive Histidine residues. The His-tag can be conjugated to the N-terminus of the polymerase, the C-terminus of the polymerase, or to any other suitable site within the polymerase. In some embodiments, a His-tag comprising six consecutive histidine residues is fused to the N-terminus of the polymerase. Optionally, the His-tag and the polymerase open reading frame can be separated by a peptide linker sequence, which can comprise the F-linker or H-linker sequence.

In some embodiments, the F-linker is situated between an N-terminal His-tag comprising six consecutive histidine residues and the protein.

Any suitable method capable of generating conjugates suitable for use in the desired applications, as well as by combination of such techniques, both covalent and non-covalent, may be employed to form conjugates according to the present disclosure. For example, a conjugate may be formed through a combination of both electrostatic and affinity-based interactions. In some embodiments, the polymerase can be engineered to include attachment domains that can mediate a range of interactions with the nanoparticle surface. For example, the polymerase can be fused both to a polyhistidine tag as well as a leucine zipper. Alternatively, the polymerase can be fused to a single attachment domain comprising histidines interspersed with, or flanked by, several lysine and/or arginine residues. Advantages of using such "multifunctional" attachment domains include increased strength of binding, the ability to orient binding between the polymerase and nanoparticle, and the ability to perform conjugations at ultra-high dilutions.

In addition to assembling the conjugate via direct interactions between the tagged peptide and unliganded areas of metal atoms (or metal ions) present on the nanoparticle surface, another option is to attach or cross-link ligands derivatized distally with species capable of interacting with and immobilizing a suitably modified peptide. A chelator molecule such as nitrilotriacetic acid (NTA) can be attached covalently to the surface of a nanoparticle, e.g., a quantum dot. This can be achieved by carbodiimide mediated coupling of one of the acetic acid side chains of NTA to surface functional groups such as amines. The resulting product can then be contacted with a solution of metal ions, such as $Ni^{2+}$, allowing some of the latter to bind to the chelating functional groups of NTA. After removal of the excess non-chelated metal ions, the metal-derivatized nanoparticles can be contacted with a solution of a His tag modified biomolecule, whereby the histidine residues of the poly-His tag will form additional coordinative chemical bonds with the NTA-chelated $Ni^{2+}$ ions. As a result, the His-tagged biomolecule will be immobilized to the nanoparticles' surface. This technique results in strong, oriented binding between the peptide and the nanoparticle, with only minor sacrifices in FRET $R_0$ distance compared to direct binding of the His tag to the nanoparticle surface, and creates a conjugate with a more fully protected surface that better withstands environmental stresses.

One general advantage of all assembly-based methods is that the need for complex linkers and/or cross-linking treatments is obviated, resulting in much greater simplicity and ease of synthesis. Unlike covalent cross-linking techniques, self-assembly of fusion peptides tagged with an attachment domain, such as a His tag, with capped nanoparticles eliminates the requirement for developing specific chemical synthetic routes for each organic dye on a case-by-case basis. Another advantage of self-assembly based conjugation methods is the minimal modification of nanoparticles and biomolecules involved, resulting in minimal disruption of their physical and biological properties. Yet another advantage of self-assembly based methods is the ability to selectively engineer the properties of the attachment domain, e.g., size, charge, and pH or temperature stability so as to control its binding properties. This also allows control of the assembly of individual peptides, e.g., into monomers, dimers, trimers, tetramers, etc., ultimately allowing control of the protein packing around the nanoparticles to form complex bioconjugates.

In some embodiments, the conjugate can be formed through a combination of methods, including self-assembly and covalent attachment. For example, the metal affinity- or chelation-based binding of fusion proteins to the nanoparticle surface can be reinforced by subsequent treatment to induce the formation of covalent bonds between the polymerase and the nanoparticle. In one exemplary embodiment a photoreactive crosslinker, such as substituted arylazide, diazirine or benzophenone derivatives, can be attached to the nanoparticle surface, which is subsequently contacted with a His-tagged polymerase. Following affinity-based assembly of the polymerase and nanoparticle, the assembled complex can be photoirradiated to generate a covalently linked polymerase-nanoparticle conjugate via crosslinking.

One important characteristic of the conjugate, which can be varied at will, is the relative proportion of biomolecule and nanoparticle present in a single conjugate. Typically, the conjugate is defined as a single nanoparticle along with any biomolecules that are linked thereto. In most biological applications, including, inter alia, single molecule sequencing, it can be desirable to achieve a 1:1 correspondence between the biomolecule and the nanoparticle by producing a "monoconjugate" i.e., a conjugate comprising an average of about one biomolecule, biomolecular complex or biomolecular fragment per conjugate. Such 1:1 correspondence can ensure that the signal from a single conjugate can be reliably correlated with the activity of a single biomolecule, complex or fragment.

In other applications, it can be desirable to use conjugates comprising an average of 2, 3, 4, 5, or more biomolecules per conjugate, or vice versa. In some embodiments, the relative ratio of either the polymerase or the nanoparticle with respect to the other can be 15:1, 25:1, 50:1, 100:1 or even higher.

Both covalent and non-covalent conjugation methods can be hampered by the difficulty of precisely controlling the number of active biomolecules conjugated to a given nanoparticle, resulting in the generation of conjugates comprising multiple biomolecules per conjugate. One method of increasing the yield of monoconjugates, i.e., conjugates comprising an average of about one biomolecule per conjugate, from a particular conjugation reaction is to rely on Poisson loading, wherein the concentration of nanoparticles is increased relative to the biomolecule, so that the nanoparticle is present in a stoichiometric excess relative to the biomolecule in the conjugation reaction. See, e.g., Clapp, A., et al., "Fluorescence resonance energy transfer between quantum dot donors and dye-labeled protein acceptors", J. Am. Chem. Soc. 126: 301-310; Medintz, I., et al., "Self-assembled nanoscale biosensors based on quantum dot FRET donors", Nat. Mater. 2:630-638 (2002); Medintz, I., et al., "A fluorescence resonance energy transfer-derived structure of a quantum dot-protein bioconjugate assembly", Proc. Natl. Acad. Sci. USA 101:9612-9617 (2004). Such methods, however, are not feasible for a wide range of biomolecules, whose activity is inhibited in the presence of an excess of nanoparticles and/or at low concentrations.

Disclosed herein are methods of preparing a population of biomolecule-nanoparticle conjugates comprising an average of about two or fewer biomolecules per conjugate, typically an average of approximately one biomolecule per conjugate, comprising contacting the biomolecule and the nanoparticle in the presence of an accessory compounds, where presence of the accessory compound results in an increased yield of conjugates comprising two or fewer biomolecules relative to the yield obtained in the absence of the accessory compound under otherwise identical reaction conditions.

Also disclosed herein are methods to control the stoichiometric ratio of conjugate compositions by varying the relative proportions of biomolecule, accessory compound(s) (if present) and/or nanoparticle added to the conjugation reaction.

In some embodiments, the conjugation is performed without an accessory compound, and the stochiometry of the conjugate is adjusted by varying the relative proportion of biomolecule and nanoparticle within the conjugate reaction. In one embodiment, a 15× Klenow-QDot conjugate, in which each conjugated complex contains an average of 15 molecules of Klenow polymerase per nanoparticle, can be synthesized by assembly-based methods wherein 15 moles of His-tagged polymerase are coincubated with 1 mole of nanoparticles.

However, it is normally not possible to prepare 1:1 biomolecule:nanoparticle conjugates simply by varying the relative loading of biomolecule and nanoparticle, because the biomolecule can frequently exhibits loss of activity in presence of excess nanoparticles/high dilutions.

Such problems can be avoided or reduced through conjugation methods that use nanoparticles treated with an accessory compound. Without being bound to any particular theory of mechanism or mode of operation, it is theorized that the nanoparticle surface presents a limited number of discrete attachment sites that can serve as points of attachment for the biomolecule.

The number and location of attachment sites available for attachment can vary with the method of conjugation employed. For example, for methods involving conjugation of a His tagged protein with a nanoparticle comprising bound metal ions via chelation/metal affinity binding, available attachment sites on the nanoparticle for attachment of the protein can comprise regions of exposed metal surface such as those, for example, appearing between gaps in the nanoparticle coating. For methods involving covalent coupling of the biomolecule to a thiol groups of the nanoparticle, the number of attachment sites will vary according to the density of thiol groups present on the nanoparticle surface.

Without being bound to any particular theory, the use of an accessory compound may increase the yield of biomolecule-nanoparticle monoconjugates obtained from a particular conjugation method by acting to reduce the number of attachment sites available to the biomolecule, thereby effectively preventing many biomolecules from binding to a given nanoparticle. Under another non-limiting theory, the accessory compound may directly compete with the biomolecule for binding to a given set of attachment sites. Additionally or alternatively, it is thought that in some embodiments the accessory compound can increase the yield of 1:1 biomolecule-nanoparticle conjugates obtained using a particular conjugation method by preventing or minimizing any toxic effect of the nanoparticle upon the biomolecule. For example, proximity and/or attachment to the nanoparticle surface can be detrimental to the biomolecule and reduce its ability to undergo interactions with a particular target. In some embodiments, the accessory compound increases the yield of monoconjugates obtained through a particular conjugation method by reducing the nanoparticle's toxicity for the biomolecule, such that an increased proportion of biomolecules remain active upon conjugation to the nanoparticle. Without being bound by any of these theories, the present disclosure relates to methods of preparing biomolecule-nanoparticle conjugates, wherein the nanoparticle of the conjugate is contacted with an accessory compound either prior to or during the conjugation of the biomolecule to the nanoparticle, thereby increasing the number of 1:1 biomolecule:nanoparticle conjugates that are formed as a result of the conjugation.

Also disclosed herein are methods for preparing 1:1 biomolecule:nanoparticle conjugates, comprising contacting a nanoparticle with an accessory compound and a biomolecule, wherein the relative ratios of biomolecule, nanoparticles and accessory compound are selected to maximize the percentage of 1:1 biomolecule:nanoparticle conjugates that are formed. In some embodiments, the accessory compound is present at a 10-fold, 5-fold or 2-fold molar excess relative to the biomolecule.

Also disclosed herein are methods for producing a biomolecule-nanoparticle conjugate, comprising the steps of: contacting a nanoparticle comprising a plurality of attachment sites on its surface with an accessory compound and a biomolecule, the accessory compound and the biomolecule both being capable of binding to an attachment site, under conditions where the two or less than two biomolecules bind to the nanoparticle to form a biomolecule-nanoparticle conjugate comprising two or less than two biomolecules per nanoparticle. In some embodiments, the nanoparticle can be contacted with the accessory compound before it is contacted with the biomolecule. In some embodiments, the nanoparticle is contacted with the biomolecule and the accessory compound simultaneously.

Also disclosed herein is a method for producing a biomolecule-nanoparticle conjugate, comprising the steps of: contacting a nanoparticle comprising with an accessory compound and a biomolecule, wherein the nanoparticle is capable of inhibiting a biological activity of the biomolecule, and wherein the accessory compound is capable of binding to the nanoparticle and thereby reducing its ability to inhibit the biological activity, under conditions where the accessory compound binds to the nanoparticle, thereby reducing its ability to inhibit the biological activity, such that two or less than two biomolecules bind to the nanoparticle to form a biomolecule-nanoparticle conjugate comprising two or less than two biomolecules per nanoparticle.

In some embodiments, the nanoparticle can be contacted with the accessory compound before it is contacted with the biomolecule. In some embodiments, the nanoparticle can be contacted with the accessory compound and the biomolecule simultaneously.

In some embodiments provided herein is a method for forming a biomolecule-nanoparticle conjugate, comprising the step of: contacting a nanoparticle capable of inhibiting the activity of a biomolecule when in sufficient proximity to the biomolecule with an accessory compound and a biomolecule, the accessory compound being capable of reducing the inhibitory effect of the nanoparticle upon biomolecular activity when in sufficient proximity to the nanoparticle, under conditions where two or fewer biomolecules bind to the nanoparticle to form a biomolecule-nanoparticle conjugate comprising two or fewer biomolecules per nanoparticle.

The accessory compound can be any composition that can be contacted with a nanoparticle either prior to or during conjugation of a biomolecule to a nanoparticle, such that the conjugation results in an increased proportion of monoconjugates, or an increased proportion of 1:1 biomolecule:nanoparticle conjugates, as compared to the proportion obtained using the same conjugation method in the absence of the accessory compound. In some embodiments, the accessory compound is preincubated or pre-attached to the nanoparticle prior to conjugation of the nanoparticle with the biomolecule to increase monoconjugate yield. In some embodiments, the accessory compound is contacted simultaneously with the nanoparticle and biomolecule to increase monoconjugate yield.

In some embodiments, the accessory compound can be a protein, typically a protein that by itself does not react with the biomolecule, the nanoparticle, nucleotides or nucleic acids, is not highly acidic or basic. In some embodiments, the accessory compound comprises a protein selected from the group consisting of: uracil DNA glycosylase ("UDG"), uracil DNA glycosylase inhibitor ("UGI"; New England Biolabs Catalog no. M0281L), maltose binding protein (MBP), bovine serum albumin (BSA), horseradish peroxidase (HRP), glutathione S-transferase ("GST"), mucin, or any combination thereof.

In some embodiments, the UGI protein is the bacteriophage PBS2 uracil-DNA glycosylase inhibitor (UGI). This UGI protein inactivates human and *Escherichia coli* uracil-DNA glycosylases (UDG) by forming an UDG-UGI protein complex with 1:1 stochiometry. UDG/UGI association can be described by a two-step (docking and locking) mechanism. The first step (docking) entails a rapid pre-equilibrium distinguished by the dissociation constant $K_d$=1.3 µM. The second step (locking) leads to the formation of an irreversibly stable complex.

In some embodiments, a single accessory compound or a plurality of different accessory compounds are contacted with the nanoparticle either prior to, or during, conjugation of the nanoparticle to a biomolecule.

In one exemplary embodiment involving conjugation of a His-tagged biomolecule to a nanoparticle, an accessory compound comprising a single His-tagged protein is contacted with the nanoparticle prior to, simultaneously with, or after the nanoparticle is contacted with the biomolecule. In some embodiments, multiple accessory compounds, each comprising a His-tagged protein, can be used. In some embodiments, two different accessory compounds are used together, one comprising His-tagged UDG and the other comprising UGI, which may or may not comprise a His-tag. In some embodiments, the biomolecule is a His-tagged polymerase.

In some embodiments, the yield of conjugates formed as a 1:1 biomolecule:nanoparticle conjugate is about 30% to about 100%, typically between 40% and 60%.

Provided herein are compositions comprises labeled biomolecule conjugates including a biomolecule linked to a nanoparticle, wherein the conjugate comprises four, three, two or one biomolecules linked to the nanoparticle.

Further provided herein are compositions comprising a population of biomolecule-nanoparticle conjugates, wherein an average of at least about 30%, 40%, 50%, 60%, 70%, 80%, 90%, 95%, 96%, 97% or 99% of the population includes an average of about four or less than four biomolecules per conjugate. As used herein, the term "population" in reference to conjugates refers to a solution or structure with more than one conjugate at a concentration suitable for single molecule analysis.

In some embodiments, an average of at least about 30%, 40%, 50%, 60%, 70%, 80%, 90%, 95%, 96%, 97% or 99% of the population of conjugates includes an average of about three or less than three biomolecules per conjugate.

In some embodiments, an average of at least about 30%, 40%, 50%, 60%, 70%, 80%, 90%, 95%, 96%, 97% or 99% of the population includes an average of about two or less than two biomolecules per conjugate.

In some embodiments, an average of at least about 30%, 40%, 50%, 60%, 70%, 80%, 90%, 95%, 96%, 97% or 99% of the population includes an average of about one biomolecule per conjugate.

In some embodiments, provided herein is a population of biomolecule-nanoparticle conjugates where at least 30%, at least 40%, at least 50%, at least 60% at least 70%, at least 80%, at least 90%, at least 95%, at least 96%, at least 98%, at least 99% or more of the biomolecule-nanoparticle conjugates in the population comprise an average of about one biomolecule and about one nanoparticle.

In some embodiments, provided herein is a population of biomolecule-nanoparticle conjugates where at least 30%, at least 40%, at least 50%, at least 60% at least 70%, at least 80%, at least 90%, at least 95%, at least 96%, at least 98%, at least 99% or more of the biomolecule-nanoparticle conjugates in the population comprise an average of about one biomolecule per conjugate.

Also disclosed herein is a population of conjugates, each conjugate comprising a biomolecule linked to a nanoparticle, the population comprising an average of between 0.5-1.5 biomolecules per nanoparticle.

Also disclosed herein is a method for preparing a 1:2 biomolecule-nanoparticle conjugate using linker moieties. For example, a nanoparticle dimer linked by a short organic molecule, for example, 4,4'-biphenyldithiol, can be attached to the biomolecule via a linker attached to any suitable moiety, e.g., a phenyl group, within the dimer linker. For example, the biomolecule could first be attached to the linker molecule using another linking moiety, and then each end of the linker can be attached to a nanoparticle. Dimers can be purified via size exclusion HPLC, filtration or other suitable techniques.

In some embodiments, the nanoparticle can be conjugated both to a biomolecule as well as other proteins, especially proteins known to enhance biomolecular activity or have other beneficial side effects. For example, the nanoparticle can optionally be conjugated both to a polymerase and to Single-Stranded DNA Binding Protein (SSBP), various processivity factors such as LEF-3, or the herpes simplex virus UL42 protein. The presence of such proteins on the nanoparticle surface can help to reduce the number of biomolecules on the nanoparticle surface and at the same time stabilize the QDot-polymerase complex, resulting in enhancement of DNA synthesis and increased read lengths. Alternatively, proteins that reduce the potential photodamage caused by reactive oxygen species, such as catalase or superoxide dismutase (SOD), can also be conjugated to the nanoparticle surface in combination with a biomolecule of interest, e.g., a polymerase.

A typical conjugate preparation can include individual conjugates that are of substantially identical size and shape. One challenge that can frequently arise during conjugation is that the resulting conjugate population can exhibit an unacceptably high level of aggregation, i.e., clumping or associate of two or more conjugates with each other. Such aggregation is undesirable because the aggregates comprise more then one conjugate, rendering it difficult to correlate the signal from one particular aggregate with the activity of any particular conjugate.

Disclosed herein are methods of preparing biomolecule-nanoparticle conjugates exhibiting reduced aggregation. In some embodiments, the population comprises at least about 30%, at least about 40%, at least about 50%, at least about 60%, at least about 70%, at least about 80%, at least about 90%, at least about 95%, at least about 97%, or at least about 99% monodisperse conjugates. The term "monodisperse" and its variants, as used herein, refer to a conjugate that is not aggregated with any other conjugate. The percentage of monodisperse conjugates can be measured as the percentage of conjugates that migrate within the single major peak during size exclusion chromatography, as described in Example 5 below.

In other embodiments, the percent of monodisperse conjugates can be measured through conjugate size analysis. Aggregation of a given conjugate with another conjugate typically results in an increase of the size and shape of the aggregate as compared to the original size and shape of the conjugates. In some embodiments, disclosed herein are conjugate populations wherein the degree in variation in size and shape between the individual conjugates is no more than 20%, no more than 15%, no more than 10%, no more than 8%, no more than 6%, no more than 5%, no more than 4%, no more than 3% or less in a measured dimension.

In some embodiments, disclosed herein is a population of conjugates, where at least about 60%, at least about 70%, at least about 80%, at least about 90%, at least about 95%, and ideally about 100% of the conjugates are of about the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values.

In some embodiments, use of the accessory compound provides the added benefit of reducing aggregation of the resulting conjugates. Without being bound to any particular theory, it is thought that the presence of the accessory compound may reduce the ability of conjugates to adhere or associate with each other, thereby increasing the percentage of monodisperse conjugates that are obtained.

In some embodiments, disclosed herein is a method of preparing a population of biomolecule-nanoparticle conjugates comprising, comprising: contacting the nanoparticle with an accessory compound and with a biomolecule under conditions resulting in formation of conjugates comprising a biomolecule linked to a nanoparticle, and purifying the conjugates without concentrating them.

In some embodiments, the accessory compound is selected from the group consisting of: uracil-DNA glycosylase (UDG), uracil-DNA glycosylase inhibitor (UGI), maltose binding protein (MBP), glutathione S-transferase (GST), bovine serum albumin (BSA), and chloramphenicol acetyl-transferase (CAT).

In some embodiments, the biomolecule comprises a His tagged protein, and the purifying step comprises passage of the conjugation reaction mixture through a $Ni^+/NTA$ column.

Figure 16A:
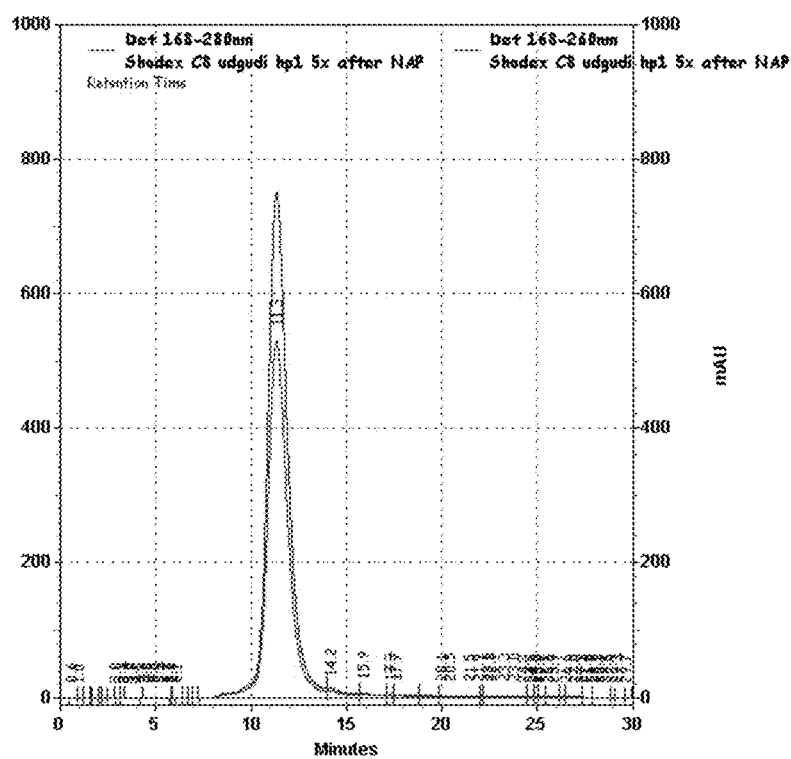
Figure 16B:
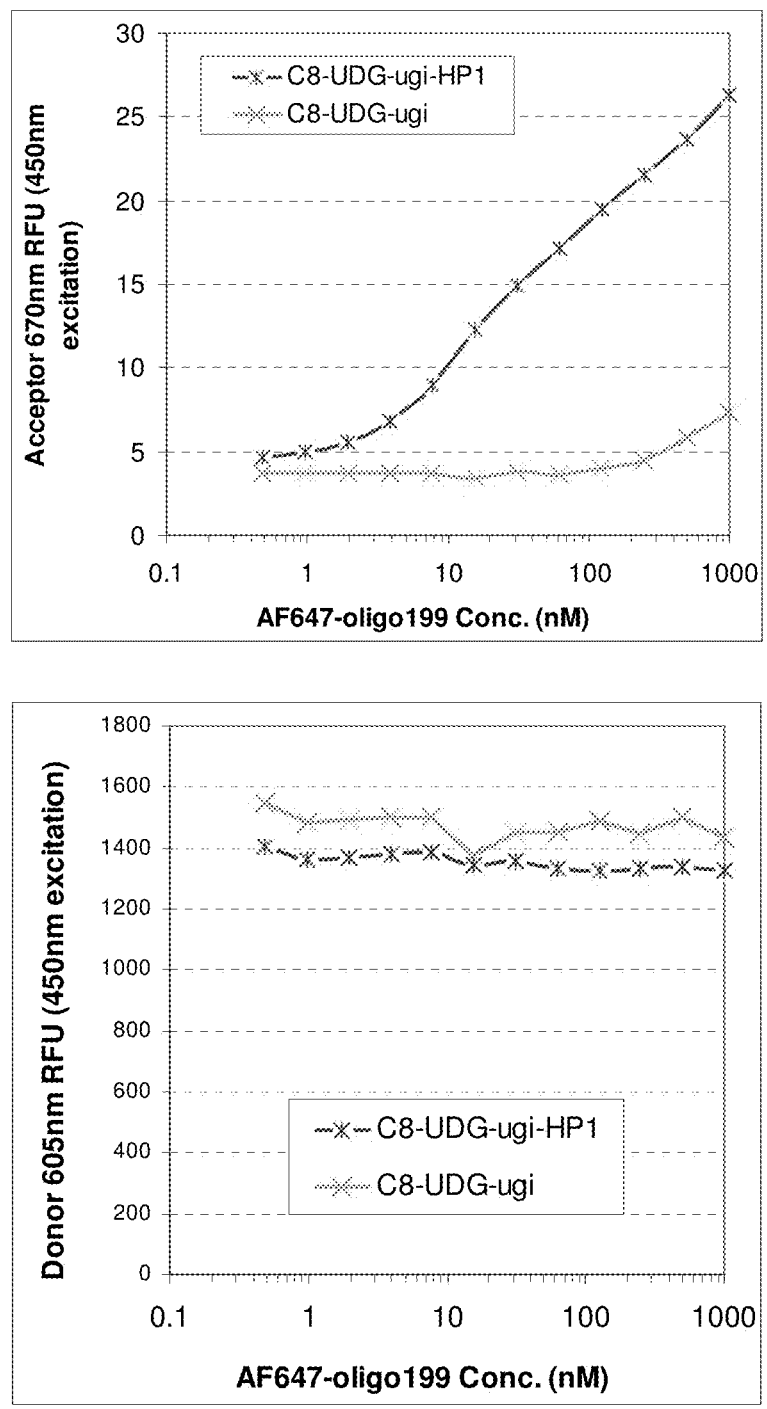
Figure 16C:
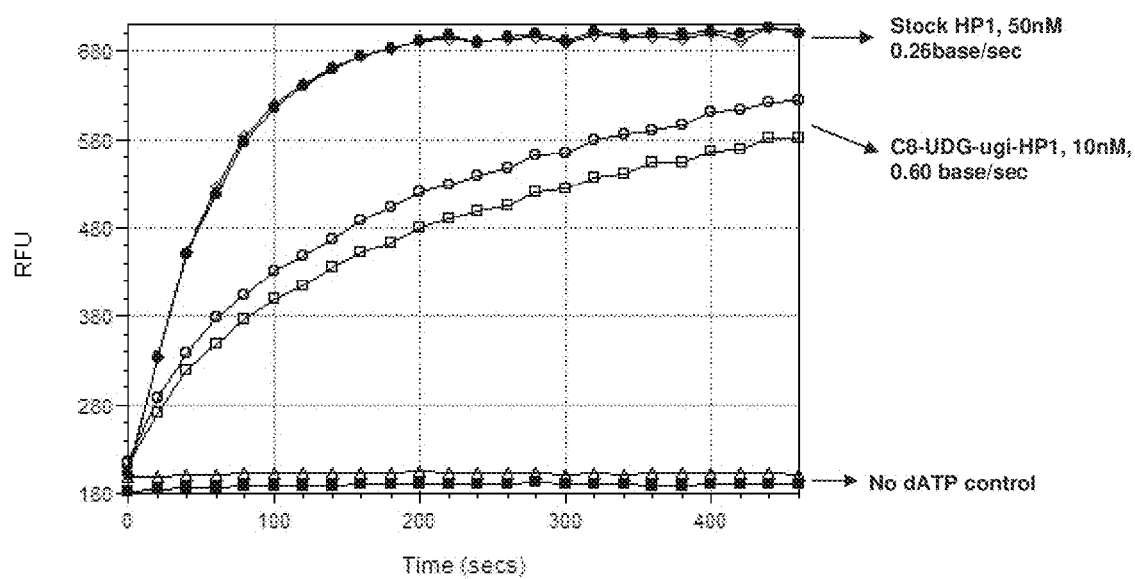
Figure 16D:
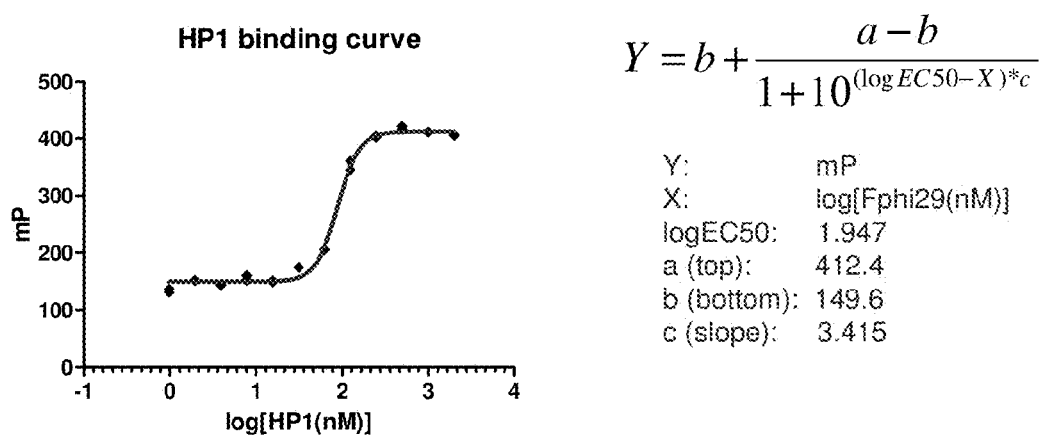
Figure 16E:
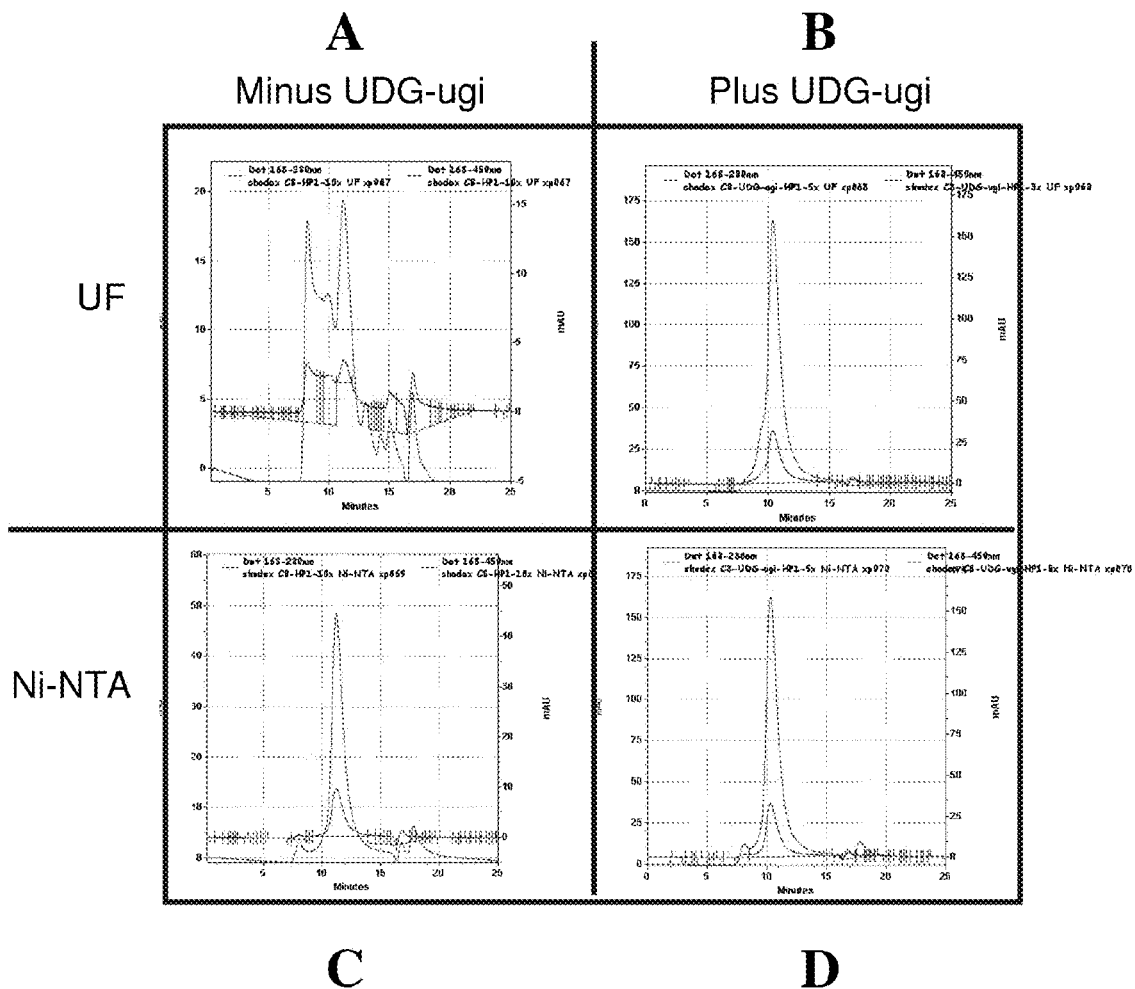

As described in the Examples and depicted in FIG. 16E, the conjugation methods disclosed herein can result in the formation of conjugate populations comprising at least 40%, 80%, 95% and 97% monodisperse conjugates.

Also disclosed herein are methods for simply and reliably estimating the number of biomolecules in a single conjugate using fluorescence polarization techniques. Fluorescence polarization (FP) measurements are based on the assessment of the rotational motions of species. FP can be considered a competition between the molecular motion and the fluorescence lifetime of fluorophores in solution. If linear polarized light is used to excite an ensemble of fluorophores only those fluorophores, aligned with the plane of polarization will be excited. There are 2 scenarios for the emission.

Provided the fluorescence lifetime of the excited fluorescent probe is much longer than the rotational correlation time θ of the molecule it is bound to ($\tau_{fl} \gg \theta_{rot}$) (θ is a parameter that describes how fast a molecule tumbles in solution), the molecules will randomize in solution during the process of emission, and, as a result, the emitted light of the fluorescent probe will be depolarized. If the fluorescence lifetime of the fluorophore is much shorter than the rotational correlation time θ ($\tau_{fl} \ll \theta_{rot}$) the excited molecules will stay aligned during the process of emission and as a result the emission will be polarized.

Typically, the fluorescence polarization (P) of a labeled macromolecule can depend on the fluorescence lifetime (τ) and the rotational correlation time (θ):

$$\left(\frac{1}{P} - \frac{1}{3}\right) = \left(\frac{1}{P_0} - \frac{1}{3}\right)\left(1 + \frac{\tau}{\Theta}\right)$$

where $P_0$ is the polarization observed in the absence of rotational diffusion. The effect of the molecular weight on the polarization values can be seen from an alternative form of the above equation:

$$\left(\frac{1}{P} - \frac{1}{3}\right) = \left(\frac{1}{P_0} - \frac{1}{3}\right)\left(1 + \frac{kT}{\eta V}\tau\right)$$

where k is the Boltzman constant, T is the absolute temperature, η the viscosity and V the molecular volume [2]. The molecular volume of the protein is related to the molecular weight (MW) and the rotational correlation time as given by $$\Theta = \frac{\eta V}{kT} = \frac{\eta MW}{RT}(\bar{v} + h)$$

where R is the ideal gas constant, v is the specific volume of the protein and h is the hydration, typically 0.2 g $H_2O$ per gram of protein. Generally, the observed correlation times are about two-fold longer than calculated for an anhydrous sphere due to the effects of hydration and the non-spherical shapes of most proteins. Hence, in aqueous solution at 20° C. (η=1 cP) one can expect a protein such as HSA (MW~65,000, with h=1.9) to display a rotational correlation time (θ) near 50 ns.

Figure 2A:
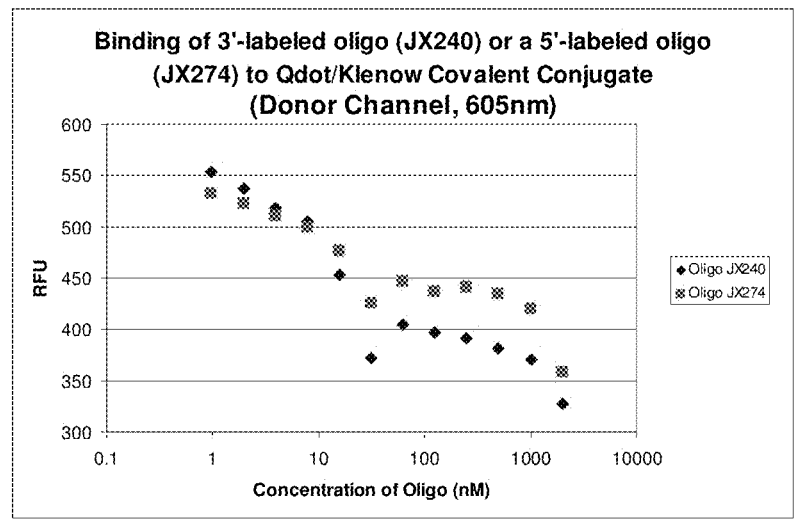
Figure 2B:
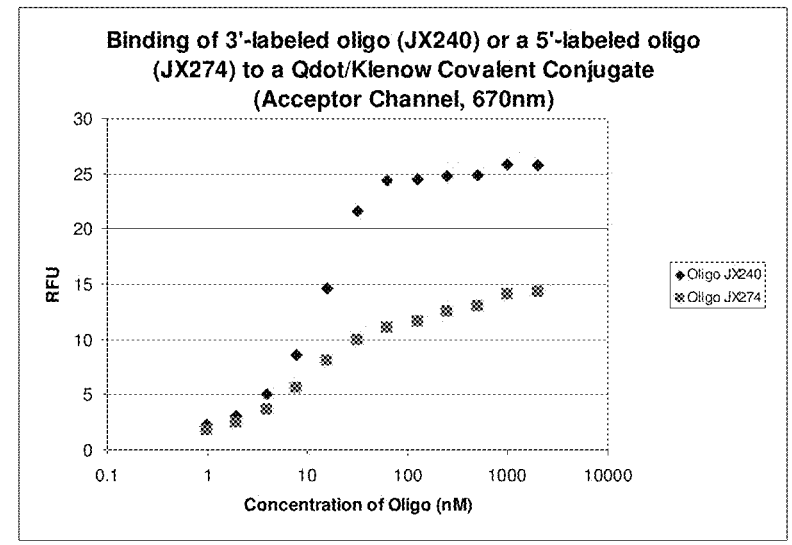
Figure 2C:
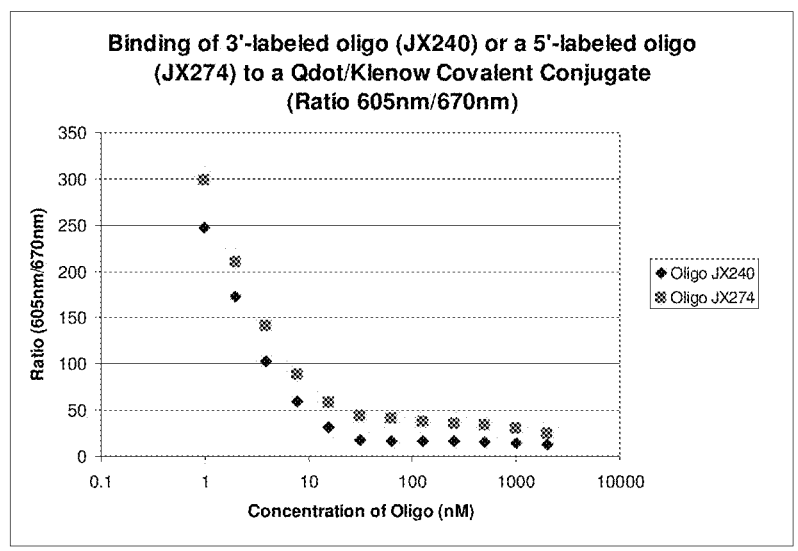

The measurement of fluorescence polarization is relatively straight-forward (FIG. 2). In a typical experiment the sample containing the fluorescent probe is excited with linear polarized light and the vertical and horizontal components of the intensity of the emitted light are measured and the polarization (P) or anisotropy (r) are calculated using the following equations:

$$\text{Polarization}(P) = (I_v - I_h)/(I_v + I_h)$$

$$\text{Anisotropy}(r) = (I_v - I_h)/(I_v + 2I_h)$$

where $I_v$ is the intensity parallel to the excitation plane and $I_h$ is the emission perpendicular to the excitation plane. They are interchangeable quantities and only differ in their normalization. Polarization P ranges from −0.33 to +0.5 while the range for anisotropy r is −0.25 to +0.4.

$$P = 3r/2 + r$$

$$r = 2P/3 - P$$

Fluorescence polarization measurements have been used in analytical and clinical chemistry [5,6] and as a biophysical research tool for studying membrane lipid mobility [7], domain motions in proteins, and interactions at the molecular level [8]. Fluorescence polarization based immunoassays are also extensively utilized for clinical diagnostics [9-11]. FP has the advantage that it requires only one labeled species for the assay (unlike energy-transfer based read outs that require two labeled species) and thus FP has become a very popular read out format for HTS (12-17). Many of these assays are based on the use of antibodies that provide the specificity needed to selectively detect a wide variety of antigens.

In some embodiments, provided herein is a method of measuring the average biomolecule:nanoparticle ratio of a population of biomolecule-nanoparticles, comprising: obtaining a population of biomolecule-nanoparticle conjugates, wherein each conjugate comprises a biomolecule linked to a nanoparticle; contacting the population with a labeled target for the biomolecule; measuring the resulting fluorescence polarization; comparing the observed fluorescence polarization of the population with the observed fluorescence polarization of a standard to determine the biomolecule or fragment concentration within the population; and determining the average biomolecule:nanoparticle ratio of the conjugate population based on the determined biomolecule or fragment concentration.

In some embodiments, the standard comprises the biomolecules of the conjugate. The standard can be contacted with the labeled substrate at various concentrations in order to obtain a standard fluorescence polarization curve, from which the concentration of an unknown sample can be extrapolated.

In some embodiments, the conjugate is a polymerase-nanoparticle conjugate comprising a polymerase linked to a nanoparticle and having polymerase activity, the labeled target is a fluorescein-labeled oligonucleotide, and the standard comprises free, i.e., unconjugated, polymerase.

In some embodiments, the labeled polymerase conjugates retain polymerase activity. For example, disclosed herein are compositions comprising a polymerase-nanoparticle conjugate including a polymerase linked to a nanoparticle, wherein the conjugate has polymerase activity. In some embodiments, the polymerase activity of the conjugate is at least about 1% relative to the polymerase activity of the unconjugated polymerase. In some embodiments, the polymerase activity of the conjugate is at least about 20%, 30%, 40%, 50%, 60%, 70%, 80%, 90%, 95%, 97% or 99% relative to the polymerase activity of the unconjugated polymerase.

In a typical embodiment, the polymerase activity is primer extension activity. Various methods of measuring primer extension activity are known in the art. Primer extension activity can be measured using any suitable assay that provides a quantitative indication of the amount of extension product obtained using defined reaction conditions comprising a known concentration of polymerase. Regardless of which assay is used, differences in primer extension activity between two samples, when obtained using identical reaction conditions, can be evaluated by simply comparing levels of observed primer activity obtained from each sample. Optionally, the observed primer extension activity can normalized for amount of polymerase by dividing the amount of incorporated radioactivity by the polymerase concentration in the reaction mixture, to allow comparison between reactions containing different polymerase concentrations.

In one exemplary embodiment, the primer extension activity of a polymerase can be measured using a radiometric assay that measures incorporation of a radioactively labeled nucleotide into acid-insoluble material in a polymerase reaction. The amount of incorporated radioactivity indicates the total number of nucleotides incorporated. See, e.g., Wu et al., Gene Biotechnology, 2nd Ed., CRC Press; Sambrook, J., Fritsch, E F, and Maniatis, T. (1989) Molecular Cloning A Laboratory Manual, 2nd ed., Cold Spring Harbor Laboratory Press, Cold Spring Harbor, N.Y.

In another exemplary embodiment, levels of primer extension activity in a sample can be measured by monitoring the fluorescence intensity change over time during extension of a fluorescein-labeled hairpin oligonucleotide.

In yet another exemplary embodiment, the primer extension activity can be quantified by quantifying the amount of pyrophosphate liberated after performing primer extension under defined reaction conditions for 5 minutes.

In yet another exemplary embodiment, the primer extension activity can be quantified by measuring the fraction of extended primer within a population of primer-template duplexes. In this exemplary embodiment, the template can comprise a radioactive ($^{32}$P) moiety or fluorescent (TAMRA) label to permit visualization of polymerase reaction products (e.g., extended primer). The primer extension products can be resolved on a gel, and the primer extension activity can then quantified as the proportion (%) of extended primer relative to total starting primer, by adding the intensities of all bands observed within a single lane as measured by densitometric analysis.

When comparing the primer extension activities of conjugates comprising multiple polymerases per conjugate and free (unconjugated) polymerase, the primer extension activities can be normalized for relative polymerase concentration before comparing them against each other.

The labeled biomolecule conjugates of the present disclosure can optionally comprise any polymerase suitable for use in the particular biological application of interest.

In some embodiments, the compositions, methods, systems and kits of the present disclosure relate to labeled biomolecule conjugates comprising a polymerase. In some embodiments, the polymerase incorporates one or more nucleotides into a nucleic acid molecule and the resulting one or more nucleotide incorporations is detected and/or analyzed in real time.

In some embodiments, the polymerase can bind a target nucleic acid molecule, which may or may not be base-paired with a polymerization initiation site (e.g., primer).

Typically, the polymerase can selectively bind to a nucleotide. Such nucleotide binding can occur in a template-dependent or non-template-dependent manner. Typically, the polymerase can mediate cleavage of the bound nucleotide. Typically, such cleavage of the nucleotide results in the formation of at least two nucleotide cleavage products. For polyphosphate-comprising nucleotides, such cleavage will typically occur between the α and β phosphate groups. Typically, the polymerase can mediate incorporation of one of the nucleotide cleavage products into a nucleic acid molecule, and release of another nucleotide cleavage product. When used in conjunction with polyphosphate-comprising nucleotides, the released nucleotide cleavage product can comprise one or more phosphates (for example, a polyphosphate chain); for nucleotides that are non-phosphate-comprising analogs, the nucleotide cleavage product may not comprise any phosphorus.

In some embodiments, the polymerase can mediate incorporation of a nucleotide on to a polymerization initiation site (e.g., terminal 3'OH of a primer).

In some embodiments, the polymerase can be unlabeled. Alternatively, the polymerase can be linked to a label. In some embodiments, the label comprises an energy transfer moiety.

The polymerase may be linked with an energy transfer donor moiety. One or more energy transfer donor moieties can be linked to the polymerase at the amino end or carboxyl end or may be inserted at any site therebetween. Optionally, the energy transfer donor moiety can be attached to the polymerase in a manner which does not significantly interfere with the nucleotide binding activity, or with the nucleotide incorporation activity of the polymerase. In such embodiments, the energy transfer moiety is attached to the polymerase in a manner that does not significantly interfere with polymerase activity.

In one aspect, a single energy transfer donor moiety can be linked to more than one polymerase and the attachment can be at the amino end or carboxyl end or may be inserted within the polymerase.

In another aspect, a single energy transfer donor moiety can be linked to one polymerase.

In one aspect, the energy transfer donor moiety can be a nanoparticle (e.g., a fluorescent nanoparticle) or a fluorescent dye. The polymerase, which can be linked to the nanoparticle or fluorescent dye, typically retains one or more activities that are characteristic of the polymerase, e.g., polymerase activity, exonuclease activity, nucleotide binding, and the like.

In one aspect, the polymerases can be replicases, DNA-dependent polymerases, primases, RNA-dependent polymerases (including RNA-dependent DNA polymerases such as, for example, reverse transcriptases), strand-displacement polymerases, or thermo-stable polymerases. In another aspect, the polymerase can be any Family A or B type polymerase. Many types of Family A (e.g., E. coli Pol I), B (e.g., E. coli Pol II), C (e.g., E. coli Pol III), D (e.g., Euryarchaeotic Pol II), X (e.g., human Pol beta), and Y (e.g., E. coli UmuC/DinB and eukaryotic RAD30/xeroderma pigmentosum variants) polymerases are described in Rothwell and Watsman 2005 Advances in Protein Chemistry 71:401-440.

In yet another aspect, the polymerases can be isolated from a cell, or generated using recombinant DNA technology or chemical synthesis methods. In another aspect, the polymerases can be expressed in prokaryote, eukaryote, viral, or phage organisms. In another aspect, the polymerases can be post-translationally modified proteins or fragments thereof.

In one aspect, the polymerase can be a recombinant protein which is produced by a suitable expression vector/host cell system. The polymerases can be encoded by suitable recombinant expression vectors carrying inserted nucleotide sequences of the polymerases. The polymerase sequence can be linked to a suitable expression vector. The polymerase sequence can be inserted in-frame into the suitable expression vector. The suitable expression vector can replicate in a phage host, or a prokaryotic or eukaryotic host cell. The suitable expression vector can replicate autonomously in the host cell, or can be inserted into the host cell's genome and be replicated as part of the host genome. The suitable expression vector can carry a selectable marker which confers resistance to drugs (e.g., kanamycin, ampicillin, tetracycline, chloramphenicol, or the like), or confers a nutrient requirement. The suitable expression vector can have restriction sites for inserting the nucleic acid molecule of interest. The suitable expression vector can include expression control sequences for regulating transcription and/or translation of the encoded sequence. The expression control sequences can include: promoters (e.g., inducible or constitutive), enhancers, transcription terminators, and secretion signals. The expression vector can be a plasmid, cosmid, or phage vector. The expression vector can enter a host cell which can replicate the vector, produce an RNA transcript of the inserted sequence, and/or produce protein encoded by the inserted sequence. The recombinant polymerase can include an affinity tag for enrichment or purification, including a poly-amino acid tag (e.g., poly His tag), GST, and/or HA sequence tag. Methods for preparing suitable recombinant expression vectors and expressing the RNA and/or protein encoded by the inserted sequences are well known (Sambrook et al, *Molecular Cloning* (1989)).

The polymerases may be DNA polymerases and include without limitation bacterial DNA polymerases, prokaryotic DNA polymerase, eukaryotic DNA polymerases, archaeal DNA polymerases, viral DNA polymerases and phage DNA polymerases. The polymerase can be a commercially available polymerase.

In some embodiments, the polymerase can be a DNA polymerase and include without limitation bacterial DNA polymerases, eukaryotic DNA polymerases, archaeal DNA polymerases, viral DNA polymerases and phage DNA polymerases.

Suitable bacterial DNA polymerase include without limitation *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase.

Suitable eukaryotic DNA polymerases include without limitation the DNA polymerases α, δ, ∈, η, ζ, γ, β, σ, λ, μ, τ, and κ, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as D29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase, PRD1 polymerase; Nf polymerase; M2Y polymerase; SF5 polymerase; f1 DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

Suitable RNA polymerases include, without limitation, T3, T5, T7, and SP6 RNA polymerases.

Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., Carlsbad, Calif.) and telomerases.

In some embodiments, the polymerase is selected from the group consisting of: Phi-29 DNA polymerase, a mutant or variant of Phi-29 DNA polymerase, B103 DNA polymerase and a mutant or variant of B103 DNA polymerase.

In another aspect, the polymerases can include a mutation that improves the performance of the polymerase in the particular biological assay of interest. The mutations can include amino acid substitutions, insertions, or deletions.

Selecting a Polymerase

The selection of the polymerase for use in the disclosed methods can be based on the desired polymerase behavior in the particular biological assay of interest. For example, the polymerase can be selected to exhibit enhanced or reduced activity in a particular assay, or enhanced or reduced interaction with a particular substrate.

For example, in some embodiments the polymerase is selected based on the polymerization kinetics of the polymerase either in unconjugated form or when linked to a label (labeled polymerase conjugate). Optionally, the label can be a nanoparticle or fluorescent dye; in some embodiments, the label can be energy transfer donor moiety. For example, the polymerase can be selected on the basis of kinetic behavior relating to nucleotide binding (e.g., association), nucleotide dissociation (intact nucleotide), nucleotide fidelity, nucleotide incorporation (e.g., catalysis), and/or release of the cleavage product. The selected polymerase can be wild-type or mutant.

In one embodiment, polymerases may be selected that retain the ability to selectively bind complementary nucleotides. In another embodiment, the polymerases may be selected which exhibit a modulated rate (faster or slower) of nucleotide association or dissociation. In another embodiment, the polymerases may be selected which exhibit a reduced rate of nucleotide incorporation activity (e.g., catalysis) and/or a reduced rate of dissociation of the cleavage product and/or a reduced rate of polymerase translocation (after nucleotide incorporation). Some modified polymerases which exhibit nucleotide binding and a reduced rate of nucleotide incorporation have been described (Rank, U.S. published patent application No. 2008/0108082; Hanzel, U.S. published patent application No. 2007/0196846).

In polymerases from different classes (including DNA-dependent polymerases), an active-site lysine can interact with the phosphate groups of a nucleoside triphosphate molecule bound to the active site. The lysine residue has been shown to protonate the pyrophosphate leaving-group upon nucleotidyl transfer. Mutant polymerases having this lysine substituted with leucine, arginine, histidine or other amino acids, exhibit greatly reduced nucleotide incorporation rates (Castro, et al., 2009 Nature Structural and Molecular Biology 16:212-218). One skilled in the art can use amino acid alignment and/or comparison of crystal structures of polymerases as a guide to determine which lysine residue to replace with alternative amino acids. The sequences of Phi29 polymerase (SEQ ID NO: 3), RB69 polymerase (SEQ ID NO: 29), an exemplary B103-like polymerase (SEQ ID NO: 33), and Klenow fragment (SEQ ID NO: 3) can be used as the basis for selecting the amino acid residues to be modified (for B103-like polymerase of SEQ ID NO: 33, see, e.g., Hendricks, et al., U.S. Ser. No. 61/242,771, filed on Sep. 15, 2009; U.S. Ser. No. 61/293,618, filed on Jan. 8, 2010; or Ser. No. 12/748,359 titled "Polymerase Compositions & Methods", filed concurrently herewith). In one embodiment, a modified phi29 polymerase can include lysine at position 379 and/or 383 substituted with leucine, arginine or histidine, wherein the numbering is relative to the amino acid sequence of SEQ ID NO: 3.

In other embodiments, the polymerase can be selected based on the combination of the polymerase and nucleotides, and the reaction conditions, to be used for the nucleotide binding and/or nucleotide incorporation reactions. For example, certain polymerases in combination with nucleotides which comprise 3, 4, 5, 6, 7, 8, 9, 10 or more phosphate groups can be selected for performing the disclosed methods. In another example, certain polymerases in combination with nucleotides which are linked to an energy transfer moiety can be selected for performing the nucleotide incorporation methods.

The polymerases, nucleotides, and reaction conditions, can be screened for their suitability for use in the nucleotide binding and/or nucleotide incorporation methods, using well known screening techniques. For example, the suitable polymerase may be capable of binding nucleotides and/or incorporating nucleotides. For example, the reaction kinetics for nucleotide binding, association, incorporation, and/or dissociation rates, can be determined using rapid kinetics techniques (e.g., stopped-flow or quench flow techniques). Using stopped-flow or quench flow techniques, the binding kinetics of a nucleotide can be estimated by calculating the $1/k_d$ value. Stopped-flow techniques which analyze absorption and/or fluorescence spectroscopy properties of the nucleotide binding, incorporation, or dissociation rates to a polymerase are well known in the art (Kumar and Patel 1997 Biochemistry 36:13954-13962; Tsai and Johnson 2006 Biochemistry 45:9675-9687; Hanzel, U.S. published patent application No. 2007/0196846). Other methods include quench flow (Johnson 1986 Methods Enzymology 134:677-705), time-gated fluorescence decay time measurements (Korlach, U.S. Pat. No. 7,485,424), plate-based assays (Clark, U.S. published patent application No. 2009/0176233), and X-ray crystal structure analysis (Berman 2007 EMBO Journal 26:3494).

Nucleotide incorporation by a polymerase can also be analyzed by gel separation of the primer extension products. In one embodiment, stopped-flow techniques can be used to screen and select combinations of nucleotides with polymerases having a $t_{pol}$ value (e.g., $1/k_{pol}$) which is less than a $t_{-1}$ (e.g., $1/k_{-1}$) value. Stopped-flow techniques for measuring $t_{pol}$ (MP Roettger 2008 Biochemistry 47:9718-9727; M Bakhtina 2009 Biochemistry 48:3197-320) and $t_{-1}$ (M Bakhtina 2009 Biochemistry 48:3197-3208) are known in the art.

For example, some phi29 or B103 polymerases (wild-type or mutant) exhibit $t_{pol}$ values which are less than $t_{-1}$ values, when reacted with nucleotide tetraphosphate or hexaphosphate molecules. In another embodiment, polymerases can be modified by binding it to a chemical compound or an antibody, in order to inhibit nucleotide incorporation.

In some embodiments, the selection of the polymerase may be determined by the level of processivity desired for conducting nucleotide incorporation or polymerization reactions. The polymerase processivity can be gauged by the number of nucleotides incorporated for a single binding event between the polymerase and the target molecule base-paired with the polymerization initiation site. For example, the processivity level of the polymerase may be about 1, 5, 10, 20, 25, 50, 100, 250, 500, 750, 1000, 2000, 5000, or 10,000 or more nucleotides incorporated with a single binding event. Processivity levels typically correlate with read lengths of a polymerase. Optionally, the polymerase can be selected to retain the desired level of processivity when conjugated to a label.

The selection of the polymerase may be determined by the level of fidelity desired, such as the error rate per nucleotide incorporation. The fidelity of a polymerase may be partly determined by the 3'→5' exonuclease activity associated with a DNA polymerase. The fidelity of a DNA polymerase may be measured using assays well known in the art (Lundburg et al., 1991 Gene, 108:1-6). The error rate of the polymerase can be one error per about 100, or about 250, or about 500, or about 1000, or about 1500 incorporated nucleotides. In some embodiments, the polymerase is selected to exhibit high fidelity. Such high-fidelity polymerases include those exhibiting error rates typically of about $5 \times 10^{-6}$ per base pair or lower.

In some embodiments, the selection of the polymerase may be determined by the rate of nucleotide incorporation such as about one nucleotide per 2-5 seconds, or about one nucleotide per second, or about 5 nucleotides per second, or about 10 nucleotides per second, or about 20 nucleotides per second, or about 30 nucleotides per second, or more than 40 nucleotides per second, or more than 50-100 per second, or more than 100 per second. In one embodiment, polymerases exhibiting reduced nucleotide incorporation rates include mutant phi29 polymerase having lysine substituted with leucine, arginine, histidine or other amino acids (Castro 2009 Nature Structural and Molecular Biology 16:212-218).

In some embodiments, the polymerase can be selected to exhibit either reduced or enhanced rates of incorporation for polyphosphate-comprising nucleotides comprising a label bonded to the terminal phosphate.

In some embodiments, the polymerase can be selected to exhibit either reduced or enhanced residence times for a particular nucleotide of interest. In some embodiments, the residence time of the selected polymerase for the particular labeled nucleotide of interest can be between about 20 msec and about 300 msec, typically between about 55 msec and about 100 msec. In some embodiments, the residence time of the selected polymerase for the particular labeled nucleotide of interest can be between about 1.5 and about 4 times the residence time of the corresponding wild-type polymerase for the labeled nucleotide.

In some embodiments, the polymerase can be selected, mutated, modified, evolved or otherwise engineered to exhibit either reduced or enhanced entry of nucleotides, particularly labeled nucleotides, into the polymerase active site. Some exemplary polymerases exhibiting altered residence times for labeled nucleotides are disclosed in U.S. Pub. No. 20080108082, published May 8, 2008.

In some embodiments, the polymerase can be selected to exhibit a reduced $K_{sub}$ for a substrate, particularly a labeled nucleotide analog. In some embodiments, the polymerase can comprise one or more mutations resulting in altered $K_{cat}/K_{sub}$ and/or $V_{max}/K_{sub}$ for a particular labeled nucleotide. In some embodiments, the $K_{cat}/K_{sub}$, the $V_{max}/K_{sub}$, or both, are increased as compared to the wild type polymerase.

Fusion Proteins

In one aspect, the polymerase can be a fusion protein comprising the amino acid sequence of a nucleic acid-dependent polymerase (the polymerase portion) linked to the amino acid sequence of a second enzyme or a biologically active fragment thereof (the second enzyme portion). The second enzyme portion of the fusion protein may be linked to the amino or carboxyl end of the polymerase portion, or may be inserted within the polymerase portion. The polymerase portion of the fusion protein may be linked to the amino or carboxyl end of the second enzyme portion, or may be inserted within the second enzyme portion. In some embodiments, the polymerase and second enzyme portions can be linked to each other in a manner which does not significantly interfere with polymerase activity of the fusion or with the ability of the fusion to bind nucleotides, or does not significantly interfere with the activity of the second enzyme portion. In the fusion protein, the polymerase portion or the second enzyme portions can be linked with a energy transfer donor moiety. The fusion protein can be a recombinant protein having a polymerase portion and a second enzyme portion. In some embodiments, the fusion protein can include a polymerase portion chemically linked to the second enzyme portion.

Evolved Polymerases

The polymerase can be a modified polymerase having certain desired characteristics, such as an evolved polymerase selected from a directed or non-directed molecular evolution procedure. The evolved polymerase can exhibit modulated characteristics or functions, such as changes in: affinity, specificity, or binding rates for substrates (e.g., target molecules, polymerization initiation sites, or nucleotides); binding stability to the substrates (e.g., target molecules, polymerization initiation sites, or nucleotides); nucleotide incorporation rate; nucleotide analog permissiveness; exonuclease activity (e.g., 3'→5' or 5'→3'); rate of extension; processivity; fidelity; stability; or sensitivity and/or requirement for temperature, chemicals (e.g., DTT), salts, metals, pH, or electromagnetic energy (e.g., excitation or emitted energy). Many examples of evolved polymerases having altered functions or activities can be found in U.S. provisional patent application No. 61/020,995, filed Jan. 14, 2008.

Methods for creating and selecting proteins and enzymes having the desired characteristics are known in the art, and include: oligonucleotide-directed mutagenesis in which a short sequence is replaced with a mutagenized oligonucleotide; error-prone polymerase chain reaction in which low-fidelity polymerization conditions are used to introduce point mutations randomly across a sequence up to about 1 kb in length (R. C. Caldwell, et al., 1992 PCR Methods and Applications 2:28-33; H. Gramm, et al., 1992 Proc. Natl. Acad. Sci. USA 89:3576-3580); and cassette mutagenesis in which a portion of a sequence is replaced with a partially randomized sequence (A. R. Oliphant, et al., 1986 Gene 44:177-183; J. D. Hermes, et al., 1990 Proc. Natl. Acad. Sci. USA 87:696-700; A. Arkin and D. C. Youvan 1992 Proc. Natl. Acad. Sci. USA 89:7811-7815; E. R. Goldman and D. C. Youvan 1992 Bio/Technology 10:1557-1561; Delagrave et al., 1993 Protein Engineering 6: 327-331; Delagrave et al., 1993 Bio/Technology 11: 1548-155); and domain shuffling.

Methods for creating evolved antibody and antibody-like polypeptides can be adapted for creating evolved polymerases, and include applied molecular evolution formats in which an evolutionary design algorithm is applied to achieve specific mutant characteristics. Many library formats can be used for evolving polymerases including: phage libraries (J. K. Scott and G. P. Smith 1990 Science 249:386-390; S. E. Cwirla, et al. 1990 Proc. Natl. Acad. Sci. USA 87:6378-6382; J. McCafferty, et al. 1990 Nature 348:552-554) and lad (M. G. Cull, et al., 1992 Proc. Natl. Acad. Sci. USA 89:1865-1869).

Another adaptable method for evolving polymerases employs recombination (crossing-over) to create the mutagenized polypeptides, such as recombination between two different plasmid libraries (Caren et al. 1994 Bio/Technology 12: 517-520), or homologous recombination to create a hybrid gene sequence (Calogero, et al., 1992 FEMS Microbiology Lett. 97: 41-44; Galizzi et al., WO91/01087). Another recombination method utilizes host cells with defective mismatch repair enzymes (Radman et al., WO90/07576). Other methods for evolving polymerases include random fragmentation, shuffling, and re-assembly to create mutagenized polypeptides (published application No. U.S. 2008/0261833, Stemmer). Adapting these mutagenesis procedures to generate evolved polymerases is well within the skill of the art.

In some embodiments, the polymerase can be fused with, or otherwise engineered to include, DNA-binding or other domains from other proteins that are capable of modulating DNA polymerase activity. For example, fusion of suitable portions of the Single-Stranded DNA Binding Protein (SSBP), thioredoxin and/or T7 DNA polymerase to bacterial or viral DNA polymerases has been shown to enhance both the processivity and fidelity of the DNA polymerase. Similarly, other groups have described efforts to engineer polymerases so as to broaden their substrate range. See, e.g., Ghadessy et al, Nat. Biotech., 22 (6):755-759 (2004). Similarly, the conjugates of the present disclosure can optionally comprise any polymerase engineered to provide suitable performance characteristics, including for example a polymerase fused to intact SSBP or fragments thereof, or to domains from other DNA-binding proteins (such as the herpes simplex virus UL42 protein.)

In some embodiments, a blend of different conjugates, each of which comprises a polymerase of unique sequence and characteristics, can be used according to the methods described herein. Use of such conjugate blends can additionally increase the fidelity and processivity of DNA synthesis. For example, use of a blend of processive and non-processive polymerases has been shown to result in increased overall read length during DNA synthesis, as described in U.S. Published App. No. 2004/0197800. Alternatively, conjugates comprising polymerases of different affinities for specific acceptor-labeled nucleotides can be used so as to achieve efficient incorporation of all four nucleotides.

Figure 7:
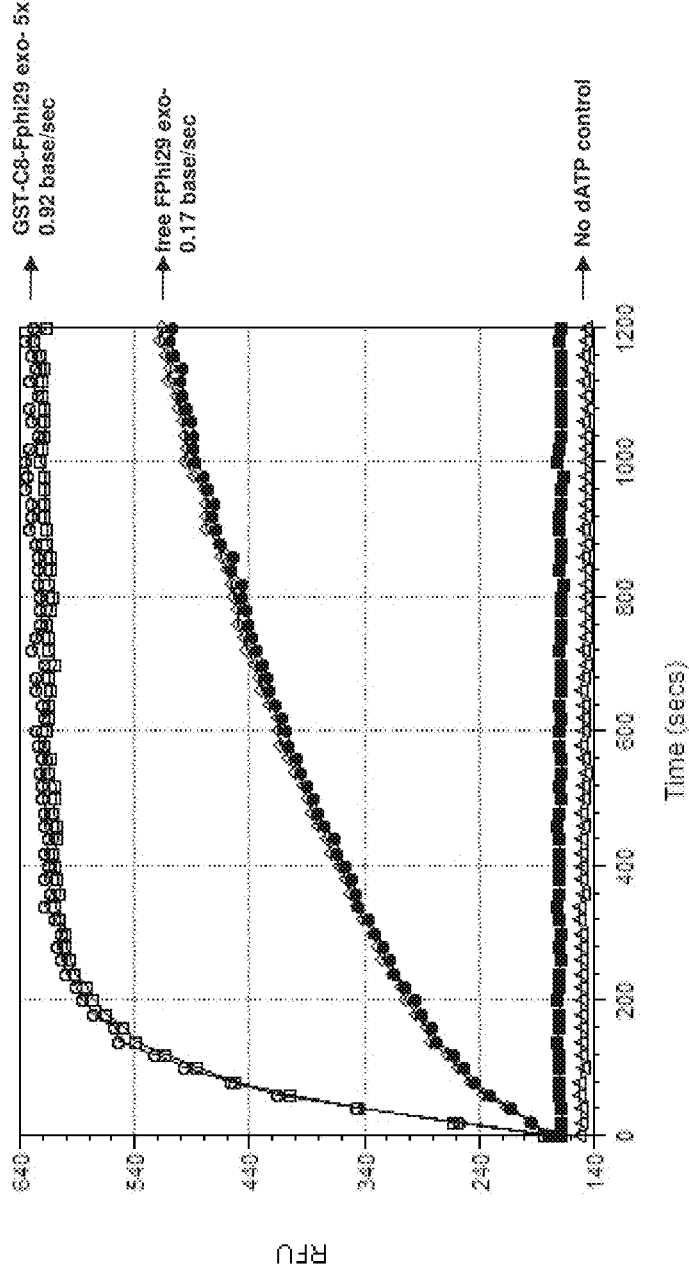

In one embodiment, the polymerase can be a mutant which retains nucleotide polymerization activity but lacks the 3'→5' or 5'→3' exonuclease activity (FIGS. 4 and 7). In another embodiment, the polymerase can be an exonuclease minus mutant which is based on wild type phi29 polymerase (Blanco, U.S. Pat. Nos. 5,001,050, 5,198,543, and 5,576,204; and Hardin PCT/US2009/31027 with an International filing date of Jan. 14, 2009) and comprising one or more substitution mutations, including: D12A, D66A, D169A, H61R, N62D, Q380A, and/or S388G, and any combination thereof.

In some embodiments, the polymerase can comprise the amino acid sequence of any polymerase disclosed in U.S. Provisional Application Nos. 61/242,771, filed on Sep. 15, 2009; 61/263,974, filed on Nov. 24, 2009 and 61/299,919, filed on Jan. 29, 2010, or any variant thereof.

In some embodiments, the polymerase is an *E. coli* K12 DNA polymerase I having the following amino acid sequence:

```
                                                        (SEQ ID NO: 1)
  1  MVQIPQNPLI LVDGSSYLYR AYHAFPPLTN SAGEPTGAMY
     GVLNMLRSLI MQYKPTHAAV

61  VFDAKGKTFR DELFEHYKSH RPPMPDDLRA QIEPLHAMVK
     AMGLPLLAVS GVEADDVIGT

121  LAREAEKAGR PVLISTGDKD MAQLVTPNIT LINTMTNTIL
     GPEEVVNKYG VPPELIIDFL

181  ALMGDSSDNI PGVPGVGEKT AQALLQGLGG LDTLYAEPEK
     IAGLSFRGAK TMAAKLEQNK

241  EVAYLSYQLA TIKTDVELEL TCEQLEVQQP AAEELLGLFK
     KYEFKRWTAD VEAGKWLQAK

301  GAKPAAKPQE TSVADEAPEV TATVISYDNY VTILDEETLK
     AWIAKLEKAP VFAFDTETDS

361  LDNISANLVG LSFAIEPGVA AYIPVAHDYL DAPDQISRER
     ALELLKPLLE DEKALKVGQN

421  LKYDRGILAN YGIELRGIAF DTMLESYILN SVAGRHDMDS
     LAERWLKHKT ITFEEIAGKG

481  KNQLTFNQIA LEEAGRYAAE DADVTLQLHL KMWPDLQKHK
     GPLNVFENIE MPLVPVLSRI

541  ERNGVKIDPK VLHNHSEELT LRLAELEKKA HEIAGEEFNL
     SSTKQLQTIL FEKQGIKPLK

601  KTPGGAPSTS EEVLEELALD YPLPKVILEY RGLAKLKSTY
     TDKLPLMINP KTGRVHTSYH

661  QAVTATGRLS STDPNLQNIP VRNEEGRRIR QAFIAPEDYV
     IVSADYSQIE LRIMAHLSRD

721  KGLLTAFAEG KDIHRATAAE VFGLPLETVT SEQRRSAKAI
     NFGLIYGMSA FGLARQLNIP

781  RKEAQKYMDL YFERYPGVLE YMERTRAQAK EQGYVETLDG
     RRLYLPDIKS SNGARRAAAE

841  RAAINAPMQG TAADIIKRAM IAVDAWLQAE QPRVRMIMQV
     HDELVFEVHK DDVDAVAKQI

901  HQLMENCTRL DVPLLVEVGS GENWDQAH
```

In some embodiments, the polymerase can comprise an amino acid sequence that is at least 70%, 80%, 85%, 90%, 95%, 99% or 100% identical to the above amino acid sequence, or a biologically active fragment thereof.

In some embodiments, the polymerase comprises an amino acid sequence at least 70% identical to the amino acid sequence of DNA polymerase I (SEQ ID NO: 1) or Klenow DNA polymerase (SEQ ID NO: 2), wherein the cysteine residue corresponding to the cysteine residue at position 907 is mutated to a serine or some other residue, the numbering being relative to *E. coli* K12 DNA polymerase I (SEQ ID NO: 1). In some embodiments, the mutant, variant, mutated or otherwise mutated polymerase lacks 3' to 5' exonuclease activity.

In some embodiments, the polymerase comprises an amino acid sequence at least 70%, 80%, 85%, 90%, 95%, 99% or 100% identical to the amino acid of DNA polymerase I (SEQ ID NO: 1) or Klenow DNA polymerase (SEQ ID NO: 2) and further comprises one or more substitutions wherein any amino acid residue is substituted with an engineered cysteine residue, which can serve as an attachment site for a label. Optionally, the label can be attached to the engineered cysteine residue using the linking agent SMCC.

In some embodiments, the engineered cysteine residue is substituted for the threonine residue at position 748, the numbering being relative to wild-type *E. coli* K12 DNA polymerase (SEQ ID NO: 1)

In some embodiments, the engineered cysteine residue is substituted for the threonine residue at position 750, the numbering being relative to wild-type *E. coli* K12 DNA polymerase (SEQ ID NO: 1).

In some embodiments, the engineered cysteine residue is substituted for the serine residue at position 751, the numbering being relative to wild-type *E. coli* K12 DNA polymerase (SEQ ID NO: 1).

In some embodiments, the engineered cysteine residue is substituted for the asparagine residue at position 778, the numbering being relative to wild-type *E. coli* K12 DNA polymerase (SEQ ID NO: 1).

In some embodiments, the engineered cysteine residue is substituted for the glycine residue at position 730, the numbering being relative to wild-type *E. coli* K12 DNA polymerase (SEQ ID NO: 1).

In some embodiments, the engineered cysteine residue is substituted for the asparagine residue at position 922, the numbering being relative to wild-type *E. coli* K12 DNA polymerase (SEQ ID NO: 1).

In some embodiments, the engineered cysteine residue is substituted for the Q (glutamine) residue at position 926, the numbering being relative to wild-type *E. coli* K12 DNA polymerase (SEQ ID NO: 1).

In some embodiments, the engineered cysteine residue is substituted for the alanine residue at position 927, the numbering being relative to wild-type *E. coli* K12 DNA polymerase (SEQ ID NO: 1).

In some embodiments, the engineered cysteine residue is substituted for the histidine residue at position 928, the numbering being relative to wild-type *E. coli* K12 DNA polymerase (SEQ ID NO: 1).

In some embodiments, the polymerase can comprise the Klenow form of DNA polymerase. In some embodiments, the polymerase comprises the Klenow truncated form of *E. coli* K12 DNA polymerase I ("Klenow DNA polymerase") having the following sequence:

```
                                          (SEQ ID NO: 2)
     MVISYDNY VTILDEETLK AWIAKLEKAP VFAFDTETDS

361  LDNISANLVG LSFAIEPGVA AYIPVAHDYL DAPDQISRER
     ALELLKPLLE DEKALKVGQN

421  LKYDRGILAN YGIELRGIAF DTMLESYILN SVAGRHDMDS
     LAERWLKHKT ITFEEIAGKG

481  KNQLTFNQIA LEEAGRYAAE DADVTLQLHL KMWPDLQKHK
     GPLNVFENIE MPLVPVLSRI

541  ERNGVKIDPK VLHNHSEELT LRLAELEKKA HEIAGEEFNL
     SSTKQLQTIL FEKQGIKPLK

601  KTPGGAPSTS EEVLEELALD YPLPKVILEY RGLAKLKSTY
     TDKLPLMINP KTGRVHTSYH

661  QAVTATGRLS STDPNLQNIP VRNEEGRRIR QAFIAPEDYV
     IVSADYSQIE LRIMAHLSRD

721  KGLLTAFAEG KDIHRATAAE VFGLPLETVT SEQRRSAKAI
     NFGLIYGMSA FGLARQLNIP

781  RKEAQKYMDL YFERYPGVLE YMERTRAQAK EQGYVETLDG
     RRLYLPDIKS SNGARRAAAE

841  RAAINAPMQG TAADIIKRAM IAVDAWLQAE QPRVRMIMQV
     HDELVFEVHK DDVDAVAKQI

901  HQLMENCTRL DVPLLVEVGS GENWDQAH
```

In some embodiments, the polymerase can comprise an amino acid sequence that is at least 70%, 80%, 85%, 90%, 95%, 99% or 100% identical to the above amino acid sequence, or a biologically active fragment thereof.

In some embodiments, the polymerase of the conjugate is a mutant or variant Klenow form of DNA polymerase comprising amino acid sequence at least about 85% identical to the amino acid sequence of SEQ ID NO: 2, or a biologically active fragment thereof. Optionally, the polymerase lacks 3' to 5' exonuclease activity.

In some embodiments, the modified polymerase is derived from a polymerase of any member of the Phi-29-like family of phages. The Phi-29-like phages are a genus of phages that are related to Phi-29 that includes the phages PZA, Φ15, BS32, B103, M2Y (M2), Nf1 and GA-1. Phages of this group have been sub-classified into three groups based on serological properties, DNA and/or polymerase maps and partial or complete DNA sequences, and share several characteristics in common. For example, such phages can typically undergo protein-primed DNA replication. See, for example, Meijer et al., "Phi-29 family of phages" Microbiol. & Mol. Biol. Revs. 65(2):261-287 (2001).

In some embodiments, the polymerase is homologous to a polymerase of one or more of the following organisms: B103, Phi-29, GA-1, PZA, Phi-15, BS32, M2Y, Nf, G1, Cp-1, PRD1, PZE, SF5, Cp-5, Cp-7, PR4, PR5, PR722, or L17. See, e.g., Meijer et al., "Phi-29 family of phages," Microbiol. & Mol. Biol. Revs. 65(2):261-287 (2001).

In some embodiments, the polymerase can comprise the Phi-29 DNA polymerase or a biologically active fragment thereof. (See, e.g., U.S. Pat. Nos. 5,001,050; 5,198,543 and 5,576,204). Typically, the Phi-29 polymerase comprises the following sequence:

```
                                                       (SEQ ID NO: 3)
MKHMPRKMYS CDFETTTKVE DCRVWAYGYM NIEDHSEYKI GNSLDEFMAW VLKVQADLYF
        70         80         90        100        110        120

HNLKFDGAFI INWLERNGFK WSADGLPNTY NTIISRMGQW YMIDICLGYK GKRKIHTVIY
       130        140        150        160        170        180

DSLKKLPFPV KKIAKDFKLT VLKGDIDYHK ERPVGYKITP EEYAYIKNDI QIIAEALLIQ
       190        200        210        220        230        240

FKQGLDRMTA GSDSLKGFKD IITTKKFKKV FPTLSLGLDK EVRYAYRGGF TWLNDRFKEK
       250        260        270        280        290        300

EIGEGMVFDV NSLYPAQMYS RLLPYGEPIV FEGKYVWDED YPLHIQHIRC EFELKEGYIP
       310        320        330        340        350        360

TIQIKRSRFY KGNEYLKSSG GEIADLWLSN VDLELMKEHY DLYNVEYISG LKFKATTGLF
       370        380        390        400        410        420

KDFIDKWTYI KTTSEGAIKQ LAKLMLNSLY GKFASNPDVT GKVPYLKENG ALGFRLGEEE
       430        440        450        460        470        480

TKDPVYTPMG VFITAWARYT TITAAQACYD RIIYCDTDSI HLTGTEIPDV IKDIVDPKKL
       490        500        510        520        530        540

GYWAHESTFK RAKYLRQKTY IQDIYMKEVD GKLVEGSPDD YTDIKFSVKC AGMTDKIKKE
       550        560        570

VTFENFKVGF SRKMKPKPVQ VPGGVVLVDD TFTIK
```

In some embodiments, the polymerase can comprise an amino acid sequence that is at least 70%, 80%, 85%, 90%, 95%, 99% or 100% identical to the amino acid sequence of SEQ ID NO: 3.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further including one or more amino acid mutations at positions selected from the group consisting of: 132, 135, 250, 266, 332, 342, 368, 370, 371, 372, 373, 375, 379, 380, 383, 387, 390, 458, 478, 480, 484, 486 and 512, wherein the numbering is relative to the amino acid sequence of SEQ ID NO: 3. In some embodiments, the Phi-29-like polymerase can comprise an amino acid deletion, wherein the deletion includes some of all of the amino acids spanning positions 306 to 311.

Without being bound to any particular theory, it is thought that the domain comprising amino acid residues 304-314 of the amino acid sequence of SEQ ID NO: 3 (Phi-29 polymerase), or homologs thereof, can reduce or otherwise interfere with DNA initiation and/or elongation by inhibiting access to the Phi-29 polymerase active site, and that this region must be displaced in order to allow access to the active site. See, e.g., Kamtekar et al., "The Φ29 DNA polymerase: protein primer structure suggests a model for the initiation to elongation transition", EMBO J., 25:1335-1343 (2005).

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further includes one or more amino acid mutations selected from the group consisting of: K132A, K135A, K135D, K135E, V250A, V250C, Y266F, D332Y, L342G, T368D, T368E, T368F, K370A, K371E, T372D, T372E, T372R, T372K, T373A, T373F, T373H, T373K, T373Q, T373R, T373S, T373W, T373Y, T373A, T373E, E375A, E375F, E375H, E375K, E375Q, E375R, E375S, E375W, E375Y, K379A, Q380A, K383E, K383H, K383L, K383R, N387Y, Y390F, D458N, K478D, K478E, K478R, L480K, L480R, A484E, E486A, E486D, K512A K512D, K512E, K512R, K512Y, K371E/K383E/N387Y/D458N, Y266F/Y390F, Y266F/Y390F/K379A/Q380A, K379A/Q380A, E375Y/Q380A/K383R, E375Y/Q380A/K383H, E375Y/Q380A/K383L, E375Y/Q380A/V250A, E375Y/Q380A/V250C, E375Y/K512Y/T368F, E375Y/K512Y/T368F/A484E, K379A/E375Y, K379A/K383R, K379A/K383H, K379A/K383L, K379A/Q380A, V250A/K379A, V250A/K379A/Q380A, V250C/K379A/Q380A, K132A/K379A and deletion of some or all of the amino acid residues spanning R306 to K311, wherein the numbering is relative to the amino acid sequence of SEQ ID NO: 3. In some embodiments, the mutant Phi-29-like polymerase can exhibit increased branching ratio and/or and increased $t_{-1}$ value in the presence of dye-labeled nucleotides relative to a reference polymerase having the amino acid sequence of SEQ ID NO: 3. In some embodiments, the branching ratio and/or $t_{-1}$ value of the polymerase is increased by at least about 105%, 110%, 125%, 150%, 175%, 200%, 250%, 500%, 750%, or 1000% relative to the reference polymerase. In some embodiments, the branching ratio and/or $t_{-1}$ value is increased in the presence of the dye-labeled nucleotide AF647-C6-dG6P. Optionally, the polymerase can further include one or more mutations reducing 3' to 5' exonuclease activity selected from the group consisting of: D12A, E14I, E14A, T15I, N62D, D66A, Y165F, Y165C, and D169A, wherein the numbering is relative to the amino acid sequence of SEQ ID NO: 3.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 3 and further includes the amino acid mutation H370R, wherein the numbering is relative to the amino acid sequence of SEQ ID NO: 3.

In other embodiments, the polymerase of the conjugate is a mutant or variant Phi-29 DNA polymerase comprising an N-terminal polyhistidine tag (His-tag) fused to an amino acid sequence at least about 85% identical to a Phi-29 DNA polymerase comprising the amino acid sequence of SEQ ID NO: 3, or biologically active fragment thereof. Optionally, the polymerase lacks 3' to 5' exonuclease activity. In some embodiments, the enzyme is a Klenow DNA polymerase having the amino acid sequence of SEQ ID NO: 2 and further comprising an engineered cysteine introduced at amino acid positions 730, 748, 750, 751, 778, 922, 926, 927 and 928, or any combination thereof. In some embodiments, the enzyme is Phi-29 DNA polymerase having the amino acid sequence of SEQ ID NO: 3, and the cysteine at amino acid position 473 serves as an attachment site for the label.

In some embodiments, the polymerase can be a deletion mutant which retains nucleotide polymerization activity but lacks the 3'→5' or 5'→3' exonuclease activity. For example, mutant phi29 polymerases having exonuclease-minus activity, or reduced exonuclease activity, can optionally comprise the amino acid sequence of SEQ ID NO: 3 and further comprise one or more amino acid substitutions at positions selected from the group consisting of: 12, 14, 15, 62, 66, 165 and 169 (wherein the numbering is relative to the amino acid sequence of SEQ ID NO: 3).

In some embodiments, the polymerase is derived from a Phi-29-like polymerase and comprises an amino acid sequence that is at least 70%, 80%, 90%, 95%, 97%, 98%, or 99% identical to the amino acid sequence of SEQ ID NO: 3 and comprises one or more of the following amino acid substitutions: D12A, E14I, E14A, T15I, N62D, D66A, Y165F, Y165C, and D169A, wherein the numbering is relative to SEQ ID NO: 3.

In some embodiments, the conjugate can comprise at least one biomolecule linked to a label through a peptide linker comprising a series of amino acid residues.

In some embodiments, the peptide linker can comprise the amino acid sequence: LLGAAAKGAAAKGSAA (SEQ ID NO: 4)

This linker is hereinafter referred to as the "H-linker".

In some embodiments, the peptide linker can comprise the amino acid sequence: LLGGGGSGGGGSAAAGSAA (SEQ ID NO: 5)

This linker is hereinafter referred to as the "F-linker".

Optionally, the peptide linker can be fused to the N-terminus of the biomolecule, the C-terminus of the biomolecule, or any suitable position along the length of the biomolecule.

In some embodiments, the conjugate comprises a protein or biologically active fragment thereof linked to a label, wherein the protein comprises one or more cysteine replacements, i.e., one or more cysteine residues of the protein have been selectively replaced through mutation, deletion or other suitable modification so as to reduce the number of thiol residues capable of acting as points of covalent attachment for the label. For example, the polymerase can comprise the Klenow form of DNA polymerase, having the sequence of SEQ ID NO: 2, or biologically active fragment or variant thereof. Klenow DNA polymerase typically comprises a single cysteine residue at amino acid position 907 of the protein. In some embodiments, this residue is selectively mutated to another residue, for example, serine. Alternatively, the polymerase can comprise Phi-29 DNA polymerase or variant thereof, having the sequence of SEQ ID NO: 3, which typically comprises at least seven different cysteine residues. In some embodiments, some or all of these cysteine residues are selectively mutated so as to replace them with another residue. For example, the polymerase can be a protein comprising an amino acid sequence that is 60%, 70%, 80%, 85%, 90%, 95% or 100% identical to the amino acid sequence of SEQ ID NO: 3, wherein cysteine residues at amino acid positions 47, 315, and 555 have been selectively replaced with non-cysteine residues.

In some embodiments, the protein can optionally be fused with a polycysteine tag comprising multiple cysteine residues, and the cysteine residues of the poly-cysteine tag can serve as sites of attachment of the label mediated by SMCC. For example, the biomolecule can be a fusion protein that comprises a polycysteine tag fused to the open reading frame of a protein or biologically active fragment thereof. The polycysteine tag can comprise a stretch of 6, 7, 8, 9, 10, 11, 12 or more consecutive cysteine residues. The polycysteine tag can be fused to the N-terminus, the C-terminus or any other suitable position of the protein.

Optionally, a polycysteine tag can be separated from the amino acid residues of the protein by a linker. In some embodiments, the linker comprises the amino acid sequence of SEQ ID NO: 4 and/or SEQ ID NO: 5.

In some embodiments, the fusion protein comprises a polycysteine tag fused to the N-terminus of the Klenow form of *E. coli* DNA polymerase. In some embodiments, the polycysteine tag and the Klenow polymerase peptide can be separated by a peptide linker. In some embodiments, the fusion protein comprises an amino acid sequence that is at least 70%, 80%, 85%, 90%, 95%, 99% or 100% identical to the following amino acid sequence:

```
                                                          (SEQ ID NO: 6)
         10         20         30         40         50         60
   MCCCCCCCCC CCCLLGGGGS GGGGSAAAGS AARKMYSCDF ETTTKVEDCR VWAYGYMNIE 70         80         90        100        110        120
   DHSEYKIGNS LDEFMAWVLK VQADLYFHNL KFDGAFIINW LERNGFKWSA DGLPNTYNTI 130        140        150        160        170        180
   ISRMGQWYMI DICLGYKGKR KIHTVIYDSL KKLPFPVKKI AKDFKLTVLK GDIDYHKERP 190        200        210        220        230        240
   VGYKITPEEY AYIKNDIQII AEALLIQFKQ GLDRMTAGSD SLKGFKDIIT TKKFKKVFPT 250        260        270        280        290        300
   LSLGLDKEVR YAYRGGFTWL NDRFKEKEIG EGMVFDVNSL YPAQMYSRLL PYGEPIVFEG 310        320        330        340        350        360
   KYVWDEDYPL HIQHIRCEFE LKEGYIPTIQ IKRSRFYKGN EYLKSSGGEI ADLWLSNVDL 370        380        390        400        410        420
   ELMKEHYDLY NVEYISGLKF KATTGLFKDF IDKWTYIKTT SEGAIKQLAK LMLNSLYGKF 430        440        450        460        470        480
   ASNPDVTGKV PYLKENGALG FRLGEEETKD PVYTPMGVFI TAWARYTTIT AAQACYDRII
```

```
            490        500        510        520        530        540
     YCDTDSIHLT GTEIPDVIKD IVDPKKLGYW AHESTFKRAK YLRQKTYIQD IYMKEVDGKL 550        560        570        580        590        600
     VEGSPDDYTD IKFSVKCAGM TDKIKKEVTF ENFKVGFSRK MKPKPVQVPG GVVLVDDTFT

IK
```

In some embodiments, covalent conjugation of a protein to a label comprising one or more carboxyl groups on its surface can be achieved through use of the homobifunctional cross-linking agent Bis(sulfosuccinimidyl)suberate (BS3), which can be useful in linking amines to amines. BS3 contains an amine-reactive N-hydroxysulfosuccinimide (NHS) ester at each end of an 8-carbon spacer arm. NHS esters can react with primary amines at pH 7-9 to form stable amide bonds, along with release of the N-hydroxysulfosuccinimide leaving group. Various proteins, including antibodies, generally have several primary amines in the side chain of lysine (K) residues and the N-terminus of each polypeptide that are available as targets for NHS-ester crosslinking reagents. Alternatively, the protein can be conjugated to a polylysine tag comprising In some embodiments, the polymerase of the conjugate is fused with a polylysine tag at its N-terminus, and then linked to labels coated with amine groups (e.g., PEG-amine) using the linking agent Bis(sulfosuccinimidyl)suberate (BS3), which is useful in linking amines to amines.

In some embodiments, the fusion protein comprises a polylysine tag fused to the N-terminus of the Klenow form of E. coli DNA polymerase. In some embodiments, the polylysine tag and the Klenow polymerase peptide are separated by a peptide linker. In some embodiments, the fusion protein comprises an amino acid sequence that is at least 70%, 80%, 85%, 90%, 95%, 99% or 100% identical to the following amino acid sequence:

```
                                                            (SEQ ID NO: 7)
             10         20         30         40         50         60
     MKKKKKKKKK KKKLLGGGGS GGGGSAAAGS AARKMYSCDF ETTTKVEDCR VWAYGYMNIE 70         80         90        100        110        120
     DHSEYKIGNS LDEFMAWVLK VQADLYFHNL KFDGAFIINW LERNGFKWSA DGLPNTYNTI 130        140        150        160        170        180
     ISRMGQWYMI DICLGYKGKR KIHTVIYDSL KKLPFPVKKI AKDFKLTVLK GDIDYHKERP 190        200        210        220        230        240
     VGYKITPEEY AYIKNDIQII AEALLIQFKQ GLDRMTAGSD SLKGFKDIIT TKKFKKVFPT 250        260        270        280        290        300
     LSLGLDKEVR YAYRGGFTWL NDRFKEKEIG EGMVFDVNSL YPAQMYSRLL PYGEPIVFEG 310        320        330        340        350        360
     KYVWDEDYPL HIQHIRCEFE LKEGYIPTIQ IKRSRFYKGN EYLKSSGGEI ADLWLSNVDL 370        380        390        400        410        420
     ELMKEHYDLY NVEYISGLKF KATTGLFKDF IDKWTYIKTT SEGAIKQLAK LMLNSLYGKF 430        440        450        460        470        480
     ASNPDVTGKV PYLKENGALG FRLGEEETKD PVYTPMGVFI TAWARYTTIT AAQACYDRII 490        500        510        520        530        540
     YCDTDSIHLT GTEIPDVIKD IVDPKKLGYW AHESTFKRAK YLRQKTYIQD IYMKEVDGKL 550        560        570        580        590        600
     VEGSPDDYTD IKFSVKCAGM TDKIKKEVTF ENFKVGFSRK MKPKPVQVPG GVVLVDDTFT

IK
``` multiple lysine residues, and the lysine residues of the polylysine tag can serve as sites of attachment of the label mediated by BS3. In some embodiments, the biomolecule is a fusion protein and comprises a polylysine tag fused to the open reading frame of a protein or biologically active fragment thereof. The polylysine tag can comprise a stretch of 6, 7, 8, 9, 10, 11, 12 or more consecutive lysine residues. The polylysine tag can be fused to the N-terminus, the C-terminus or any other suitable position of the protein. Optionally, a polylysine tag can be separated from the amino acid residues of the protein by a linker. In some embodiments, the linker comprises the amino acid sequence of SEQ ID NO: 5 or SEQ ID NO: 5.

In some embodiments, the biomolecule is a protein that is fused or otherwise coupled to a Transglutaminase tag comprising the amino acid sequence PKPQQF, which can be used as a site of attachment for amine reactive groups mediated by the enzyme transglutaminase. The transglutaminase tag can be fused to the N-terminus, the C-terminus or any other suitable position of the protein. Optionally, a transglutaminase tag can be separated from the amino acid residues of the protein by a peptide linker.

In some embodiments, the fusion protein comprises an amino acid sequence that is at least 70%, 80%, 85%, 90%, 95%, 99% or 100% identical to the following amino acid sequence:

```
                                                          (SEQ ID NO: 8)
MHHHHHHLLG GGGSGGGGSA AAPKPQQFGS AARKMYSCDF ETTTKVEDCR VWAYGYMNIE
        70         80         90        100        110        120

DHSEYKIGNS LDEFMAWVLK VQADLYFHNL KFDGAFIINW LERNGFKWSA DGLPNTYNTI
       130        140        150        160        170        180

ISRMGQWYMI DICLGYKGKR KIHTVIYDSL KKLPFPVKKI AKDFKLTVLK GDIDYHKERP
       190        200        210        220        230        240

VGYKITPEEY AYIKNDIQII AEALLIQFKQ GLDRMTAGSD SLKGFKDIIT TKKFKKVFPT
       250        260        270        280        290        300

LSLGLDKEVR YAYRGGFTWL NDRFKEKEIG EGMVFDVNSL YPAQMYSRLL PYGEPIVFEG
       310        320        330        340        350        360

KYVWDEDYPL HIQHIRCEFE LKEGYIPTIQ IKRSRFYKGN EYLKSSGGEI ADLWLSNVDL
       370        380        390        400        410        420

ELMKEHYDLY NVEYISGLKF KATTGLFKDF IDKWTYIKTT SEGAIKQLAK LMLNSLYGKF
       430        440        450        460        470        480

ASNPDVTGKV PYLKENGALG FRLGEEETKD PVYTPMGVFI TAWARYTTIT AAQACYDRII
       490        500        510        520        530        540

YCDTDSIHLT GTEIPDVIKD IVDPKKLGYW AHESTFKRAK YLRQKTYIQD IYMKEVDGKL
       550        560        570        580        590        600

VEGSPDDYTD IKFSVKCAGM TDKIKKEVTF ENFKVGFSRK MKPKPVQVPG GVVLVDDTFT

IK
```

In some embodiments, covalent conjugation of a biomolecule to a label can be accomplished via use of a Protein Kinase A (PKA) site fused, inserted or otherwise engineered into the biomolecular structure, which can permit more selectivity in choosing a point of attachment for the label to the biomolecule. For example, although a given protein may have several primary amines and cysteine thiols available for covalent conjugation, attempted modification of these reactive groups is not specific for one particular primary amine or thiol and frequently modification of the primary amine or thiol can result in decreased activity of the protein. Another method of conjugation that avoids such problems involves the engineering of a Protein Kinase A recognition sequence, typically comprising the amino acid sequence LRRASLG, into the protein at a desired location. After incubation of the engineered protein with Protein Kinase A and ATP-γS, the protein will contain a single reactive phosphorothioate at the desired location. This single phosphorothioate can be selectively modified to create a covalent conjugate linked at the sulfur atom of the phosphorothioate.

In some embodiments, the protein containing the single phosphorothioate can be covalently conjugated to labels containing residual carboxylate groups on their surface using the following synthetic route: The labels are first modified with an excess of adipic dihydrazide via EDC coupling. After purification, the hydrazide functionalized labels are then reacted in the dark with an excess of iodoacetic acid also using EDC as the coupling agent. The resulting purified product comprises an iodoacetal functional group that is reactive with thiols and phosphorothioates. Consequently, in the final reaction an excess of the phosphorothioate-containing protein is incubated with iodoacetal modified labels at pH 5.5. The reaction product can be purified by size exclusion chromatography and characterized for activity and binding.

In some embodiments, the biomolecule is a protein that is fused or otherwise coupled to a protein kinase A (PKA) tag comprising the amino acid sequence LRRASL, which can be used as a site of attachment mediated by the enzyme protein kinase A enzyme.

The PKA tag can be fused to the N-terminus, the C-terminus or any other suitable position of the protein. Optionally, the PKA tag can be separated from the amino acid residues of the protein by a linker, typically a peptide linker. In some embodiments, the fusion protein comprises an amino acid sequence that is at least 70%, 80%, 85%, 90%, 95%, 99% or 100% identical to the following amino acid sequence:

```
                                                           (SEQ ID NO: 9)
           10         20         30         40         50         60
    MGLRRASLHH LLGGGGSGGG GSAAAGSAAR KMYSCDFETT TKVEDCRVWA YGYMNIEDHS 70         80         90        100        110        120
    EYKIGNSLDE FMAWVLKVQA DLYFHNLKFD GAFIINWLER NGFKWSADGL PNTYNTIISR 130        140        150        160        170        180
    MGQWYMIDIC LGYKGKRKIH TVIYDSLKKL PFPVKKIAKD FKLTVLKGDI DYHKERPVGY 190        200        210        220        230        240
    KITPEEYAYI KNDIQIIAEA LLIQFKQGLD RMTAGSDSLK GFKDIITTKK FKKVFPTLSL 250        260        270        280        290        300
    GLDKEVRYAY RGGFTWLNDR FKEKEIGEGM VFDVNSLYPA QMYSRLLPYG EPIVFEGKYV
```

```
       310        320        330        340        350        360
WDEDYPLHIQ HIRCEFELKE GYIPTIQIKR SRFYKGNEYL KSSGGEIADL WLSNVDLELM 370        380        390        400        410        420
KEHYDLYNVE YISGLKFKAT TGLFKDFIDK WTYIKTTSEG AIKQLAKLML NSLYGKFASN 430        440        450        460        470        480
PDVTGKVPYL KENGALGFRL GEEETKDPVY TPMGVFITAW ARYTTITAAQ ACYDRIIYCD 490        500        510        520        530        540
TDSIHLTGTE IPDVIKDIVD PKKLGYWAHE STFKRAKYLR QKTYIQDIYM KEVDGKLVEG 550        560        570        580        590
SPDDYTDIKF SVKCAGMTDK IKKEVTFENF KVGFSRKMKP KPVQVPGGVV LVDDTFTIK
```

In some embodiments, the biomolecule comprises a Phi-29 polymerase further comprise a biotin ligase recognition sequence and optionally including a His-tag. The biotin ligase site and/or optionally the His-tag can be located at the N-terminus, the C-terminus or any other suitable position of the Phi-29 polymerase. Optionally, the biotin ligase sequence and/or the His-tag can be separated from the amino acid residues of the Phi-29 protein by a linker, typically a peptide linker. In some embodiments, the biotin ligase recognition site comprises a biotin acceptor peptide. In some embodiments, the biotin acceptor site can comprise the amino acid sequence of SEQ ID NO: 10:

```
    GLNDIFEAQKIEWHE            (SEQ ID NO: 10)
```

See, e.g., Howarth et al., "Targeting quantum dots to surface proteins in living cells with biotin ligase", Proc. Natl. Acad. Sci. USA 102(21):7583-7588 (2005).

In some embodiments, the fusion protein comprises an amino acid sequence that is at least 70%, 80%, 85%, 90%, 95%, 99% or 100% identical to the following amino acid sequence:

```
                                            (SEQ ID NO: 11)
MSHHHHHHSMSGLNDIFEAQKIEWHEGAPGARGSKHMPRKMYSCAFETTT

KVEDCRVWAYGYMNIEDHSEYKIGNSLDEFMAWVLKVQADLYFHNLKFAG

AFIINWLERNGFKWSADGLPNTYNTIISRMGQWYMIDICLGYKGKRKIHT

VIYDSLKKLPFPVKKIAKDFKLTVLKGDIDYHKERPVGYKITPEEYAYIK

NDIQIIAEALLIQFKQGLDRMTAGSDSLKGFKDIITTKKFKKVFPTLSLG

LDKEVRYAYRGGFTWLNDRFKEKEIGEGMVFDVNSLYPAQMYSRLLPYGE

PIVFEGKYVWDEDYPLHIQHIRCEFELKEGYIPTIQIKRSRFYKGNEYLK

SSGGEIADLWLSNVDLELMKEHYDLYNVEYISGLKFKATTGLFKDFIDKW

TYIKTTSEGAIKQLAKLMLNSLYGKFASNPDVTGKVPYLKENGALGFRLG

EEETKDPVYTPMGVFITAWARYTTITAAQACYDRIIYCDTDSIHLTGTEI

PDVIKDIVDPKKLGYWAHESTFKRAKYLRQKTYIQDIYMKEVDGKLVEGS

PDDYTDIKFSVKCAGMTDKIKKEVTFENFKVGFSRKMKPKPVQVPGGVVL

VDDTFTIK
```

Hereinafter, the protein of SEQ ID NO: 11 is referred to variously as "HBP1" or HBP-1." It comprises a His-tagged Phi-29 polymerase peptide comprising a biotin ligase site that is fused to the N-terminus of the Phi-29 polymerase, which is exonuclease-minus and includes the D12A and D66A mutations. In some embodiments, the polymerase of the labeled polymerase conjugate comprises an amino acid sequence that is at least 70%, 80%, 85%, 90%, 95%, 99% or 100% identical to the amino acid sequence of SEQ ID NO: 11.

In some embodiments, the polymerase comprises a fusion protein having an amino acid sequence that is at least 70%, 80%, 85%, 90%, 95%, 99% or 100% identical to the following amino acid sequence, which comprises a Phi-29 polymerase peptide comprising an N-terminal His-tag and an intervening H-linker sequence, as follows:

```
                                                     (SEQ ID NO: 12)
MHHHHHHLLG AAAKGAAAKG SAARKMYSCD FETTTKVEDC RVWAYGYMNI EDHSEYKIGN
        70         80         90        100        110        120

SLDEFMAWVL KVQADLYFHN LKFDGAFIIN WLERNGFKWS ADGLPNTYNT IISRMGQWYM
       130        140        150        160        170        180

IDICLGYKGK RKIHTVIYDS LKKLPFPVKK IAKDFKLTVL KGDIDYHKER PVGYKITPEE
       190        200        210        220        230        240

YAYIKNAIQI IAEALLIQFK QGLDRMTAGS DSLKGFKDII TTKKFKKVFP TLSLGLDKEV
       250        260        270        280        290        300

RYAYRGGFTW LNDRFKEKEI GEGMVFDVNS LYPAQMYSRL LPYGEPIVFE GKYVWDEDYP
       310        320        330        340        350        360

LHIQHIRCEF ELKEGYIPTI QIKRSRFYKG NEYLKSSGGE IADLWLSNVD LELMKEHYDL
       370        380        390        400        410        420

YNVEYISGLK FKATTGLFKD FIDKWTYIKT TSEGAIKQLA KLMLNSLYGK FASNPDVTGK
```

```
         430        440        450        460        470        480
VPYLKENGAL GFRLGEEETK DPVYTPMGVF ITAWARYTTI TAAQACYDRI IYCDTDSIHL
         490        500        510        520        530        540
TGTEIPDVIK DIVDPKKLGY WAHESTFKRA KYLRQKTYIQ DIYMKEVDGK LVEGSPDDYT
         550        560        570        580        590
DIKFSVKCAG MTDKIKKEVT FENFKVGFSR KMKPKPVQVP GGVVLVDDTF TIK
```

In some embodiments, the fusion protein comprises an amino acid sequence that is at least 70%, 80%, 85%, 90%, 95%, 99% or 100% identical to the following amino acid sequence, which comprises a Phi-29 polymerase peptide comprising an N-terminal His-tag and an intervening F-linker sequence, as follows:

```
                                                         (SEQ ID NO: 13)
MHHHHHHLLG GGGSGGGGSA AAGSAARKMY SCDFETTTKV EDCRVWAYGY MNIEDHSEYK
         70         80         90        100        110        120

IGNSLDEFMA WVLKVQADLY FHNLKFDGAF IINWLERNGF KWSADGLPNT YNTIISRMGQ
        130        140        150        160        170        180

WYMIDICLGY KGKRKIHTVI YDSLKKLPFP VKKIAKDFKL TVLKGDIDYH KERPVGYKIT
        190        200        210        220        230        240

PEEYAYIKNA IQIIAEALLI QFKQGLDRMT AGSDSLKGFK DIITTKKFKK VFPTLSLGLD
        250        260        270        280        290        300

KEVRYAYRGG FTWLNDRFKE KEIGEGMVFD VNSLYPAQMY SRLLPYGEPI VFEGKYVWDE
        310        320        330        340        350        360

DYPLHIQHIR CEFELKEGYI PTIQIKRSRF YKGNEYLKSS GGEIADLWLS NVDLELMKEH
        370        380        390        400        410        420

YDLYNVEYIS GLKFKATTGL FKDFIDKWTY IKTTSEGAIK QLAKLMLNSL YGKFASNPDV
        430        440        450        460        470        480

TGKVPYLKEN GALGFRLGEE ETKDPVYTPM GVFITAWARY TTITAAQACY DRIIYCDTDS
        490        500        510        520        530        540

IHLTGTEIPD VIKDIVDPKK LGYWAHESTF KRAKYLRQKT YIQDIYMKEV DGKLVEGSPD
        550        560        570        580        590

DYTDIKFSVK CAGMTDKIKK EVTFENFKVG FSRKMKPKPV QVPGGVVLVD DTFTIK
```

In some embodiments, the biomolecule comprises a fusion protein having an amino acid sequence that is at least 70%, 80%, 85%, 90%, 95%, 99% or 100% identical to the following amino acid sequence, which comprises a Phi-29 polymerase peptide that lacks exonuclease activity and comprises an N-terminal His-tag, an intervening linker sequence, and the D12A and D66A mutations, as follows:

```
                                                         (SEQ ID NO: 14)
MNHLVHHHHH HIEGRHMELG TLEGSMKHMP RKMYSCAFET TTKVEDCRVW AYGYMNIEDH
         70         80         90        100        110        120

SEYKIGNSLD EFMAWVLKVQ ADLYFHNLKF AGAFIINWLE RNGFKWSADG LPNTYNTIIS
        130        140        150        160        170        180

RMGQWYMIDI CLGYKGKRKI HTVIYDSLKK LPFPVKKIAK DFKLTVLKGD IDYHKERPVG
        190        200        210        220        230        240

YKITPEEYAY IKNDIQIIAE ALLIQFKQGL DRMTAGSDSL KGFKDIITTK KFKKVFPTLS
        250        260        270        280        290        300

LGLDKEVRYA YRGGFTWLND RFKEKEIGEG MVFDVNSLYP AQMYSRLLPY GEPIVFEGKY
        310        320        330        340        350        360

VWDEDYPLHI QHIRCEFELK EGYIPTIQIK RSRFYKGNEY LKSSGGEIAD LWLSNVDLEL
        370        380        390        400        410        420
```

```
                            -continued
MKEHYDLYNV EYISGLKFKA TTGLFKDFID KWTYIKTTSE GAIKQLAKLM LNSLYGKFAS
       430        440        450        460        470        480

NPDVTGKVPY LKENGALGFR LGEEETKDPV YTPMGVFITA WARYTTITAA QACYDRIIYC
       490        500        510        520        530        540

DTDSIHLTGT EIPDVIKDIV DPKKLGYWAH ESTFKRAKYL RQKTYIQDIY MKEVDGKLVE
       550        560        570        580        590        600

GSPDDYTDIK FSVKCAGMTD KIKKEVTFEN FKVGFSRKMK PKPVQVPGGV VLVDDTFTIK
```

This fusion polymerase of amino acid sequence of SEQ ID NO: 14 is herein variously referred to as "HP1" or "HP-1". See, e.g., U.S. Provisional Application No. 61/184,770, filed Jun. 5, 2009. This fusion polymerase comprises a Phi-29 polymerase peptide that lacks exonuclease activity and comprises an N-terminal His-tag, an intervening linker sequence, and the D12A and D66A mutations.

In some embodiments, the biomolecule comprises a fusion protein having an amino acid sequence that is at least 70%, 80%, 85%, 90%, 95%, 99% or 100% identical to the amino acid sequence of SEQ ID NO: 14 (HP-1).

In some embodiments, a naturally occurring or engineered cysteine of SEQ ID NO: 14 (HP1) is used as an attachment site for a label. In some embodiments, the attachment site is a site for covalent attachment of the label using the linking agent SMCC. In some embodiments, the cysteine occurring at amino acid position 473 of SEQ ID NO: 14 (HP1) is used as the attachment site.

In some embodiments, the polymerase can comprise a His-tagged version of a Phi-29 polymerase and an N-terminal linker as well as various mutations that reduce the exonuclease activity of the Phi-29 polymerase.

In some embodiments, the polymerase, or any biologically active fragment thereof, can be linked to a label through a peptide linker comprising a series of amino acid residues. In some embodiments, the peptide linker comprises the amino acid sequence of SEQ ID NO: 12 or SEQ ID NO: 13.

In some embodiments, the polymerase comprises mutated Phi-29 DNA polymerase that lacks 3' to 5' exonuclease activity. In some embodiments, the mutant Phi-29 DNA polymerase comprises the mutations D12A, D66A, the mutation D169A, the mutation H61R, the mutation N62D, the mutation Q380A, the mutation S388G, or any combination thereof, wherein the numbering is relative to wild-type Phi-29 polymerase (SEQ ID NO: 3). In some embodiments, the polymerase comprises any two, three, four, five or all of these mutations.

In some embodiments, the polymerase falls with the family of Family type-B delta polymerases, the Type B DNA polymerases, or the Family A T7 like polymerases.

In some embodiments, the polymerase is capable of withstanding exposure to laser irradiation and/or exposure to labels for a duration of at least 5, 10, 15, 20, 30, 45, 60, 90, 120, 180 or 240 minutes. Without being bound to any particular theory, it is believed that the polymerases of phototrophic and/or halotrophic organisms can exhibit enhanced tolerance to laser irradiation, fluorescent dyes, nanoparticles, photobreakdown products and/or excited state molecules such as superoxides, triplet oxygen, peroxides, etc. In some embodiments, the polymerase can be, for example, a polymerase isolated from a phototrophic and/or halotrophic organism. The polymerase can be a polymerase isolated from Cyanophage S-CBP1, Cyanophage S-CBP2, Cyanophage S-CBP3, Cyanophage Syn5, Cyanophage S-CBP42, Synechococcus phage P60, Roseobacter phage SIO1 DNA Polymerase, Oedogonium cardiacum chloroplast DNA Polymerase, Salterprovirus His1 Polymerase, Salterprovirus His2 Polymerase, Ostreococcus tauri V5, Ectocaipus siliculosus virus 1, or any combination of such polymerases.

In some embodiments, the biomolecule of the conjugate can be a Cyanophage S-CBP1 DNA polymerase having the following sequence:

```
                                                  (SEQ ID NO: 15)
  1 mtlifdietd glyndascih cigihdlnag etyvfndvgt
    qqpitkgiql ledadlivgh 61 niigydipvi sklfpwfsrt ngvldtivls rlyhtdlldi
    dqkrkwkhmp lqlygrhsle 121 aygyrlgeyk gsfgktadwk ewsqdmedym iqdvnvtrkl
    wkhfpqipew vqlehrvaqi 181 ltegeiygwy fdenaarela qtlytelddl kgvlrkrypy
    vagreftpkr vnrslgyveg 241 atctklvefs ptsrdhiawv mknlhgwkpd kktkagktai
    deivlkeigt eealqffrcl 301 eitkqlgmls egknawlkls rkdrvhhhcs vatvthrcah
    rnpnlaqvps dlnfrrlfca 361 spghimvgad lsgielrmla hylaryddgr ygdillhgdi
    hqenadkigi srrlvktvty 421 aflygagdqk iglsydqgls pdkakqkgke irqaymdaip
    gleklveatk kaadrgfirs 481 idgrhinvds shkalnmllq ssagciakrw mviandnfpt
    idneylahth glafihdelq 541 feclplyaed lkthlelcae lageyynlri piaaegkigs
    twadvh
```

In some embodiments, the biomolecule can comprise a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP1 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a Cyanophage S-CBP2 DNA polymerase. In some embodiments, this DNA polymerase can have the following sequence:

```
                                                  (SEQ ID NO: 16)
  1 mklvfdietd gflrklttvh cvvakdietg evfkfddsgr
    hqsvssgltl lmeaeelwgh 61 niigfdvpai qeiypffqpw estyydtlil srlfftdmld
    rdlrskpanm pgnlygrhsl
```

```
121  eawgyrlgvl kseygkqlhg dwatytpeml eyceqdvean
     lpivklfqpk leqyadaikt 181  ehdcalvmtr qeqagfpfdi dkaraleskl rseletlsde
     mratftfvag keftparnna 241  trgyitgcpf tkltefspts rdhiawafqq hrgwepiemt
     dtgkpkidee vlnaigteea 301  kkfgrilelq khvgmlsegk nswlqmvekd grihhscvln
     tatgrnahmr pnlaqvpsgh 361  efrelftpge gyvqvgadas glelrclahy larfdggkfg
     kvllegdiht dlaniygtdr 421  ktgktvtycl iygggdtklg lsagepkksa asrgkkirqa
     imkdldgfaq litavqeraq 481  sgvitgidgr pirmrkahaa lnyllqscga vickkwvvrs
     nellteagid ytplafvhde 541  qqlavrpdqv emastlisla mkdvehaikf rvpldcdvqs
     ganwgdth
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP2 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a Cyanophage S-CBP3 DNA polymerase. In some embodiments, the DNA polymerase can have the following sequence:

```
                                             (SEQ ID NO: 17)
1    mtlifdietd glyndvtcih cigihdlntk etyvfndvgt
     qqpitkgiql ledadiivgh 61   niigydlpvi rklypwfsnv grvldtlvls rlyhadllkt
     dqkrnwkhmp vqlwgrhsle 121  aygyrlgeyk gcfgkttdwk dwsqemedym vqdvnitrkl
     wkdfpeipew vglehrvaqi 181  lteqeihgwy fdepaawele stlrrelesl kavlrnrhpf
     ilgeeftpkr pnstqgyftg 241  atftrlkemn ptsrdhiayi lqkfydwept ertekgkpvv
     deivlkdigs eialqffrcl 301  eltkqigmlt egvnawlklv rndrihhhcs vatnthrcah
     rkpnlaqvpa eaefrklfra 361  tpgmvmvgad lagielrmla hylaqwdggr ygdvllngdi
     hqenadkigi srrlvktvty 421  aflygagnqk iglsydqsls pdkakkkgqe irqaymdaip
     glrklveatk kaanrgyira 481  idgrhisvds phkslnyllq ssagviakrw laltheaiir
     adikahqlaf ihdelqfett 541  pehvedlkfa llwgaasage yynlripiaa daksgndwse
     vh
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP3 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a Cyanophage Syn5 DNA polymerase. In some embodiments, the DNA polymerase can have the following sequence:

```
                                             (SEQ ID NO: 18)
1    mrlvtdietd gllrglsvih civardldtn eehrfephqt
     kaglqllkea delwghnivg 61   ydieaikely pkwttkakly dtlilsrlff tdlldrdfrs
     kpanmpgnly grhsleawgh 121  rlgvhksefg kqldgdwsty spemleycaq dvtvsvqvaq
     mfepkleqya dcidtehrla 181  timawqereg fpfdvtaaqq lesrlrteld alsdqmrstf
     lfvdggtftp rrnnkpqgyi 241  adapmcklke fnptsrhhia wafqqfrnwe pkeftdsgkp
     kideptltai gtdeakafar 301  ilelqkhlgq laegknawlk leskgrvhhs cvlntntgrq
     ahmrpnlaqv psaseyralf 361  gpgdsrvqvg adasglelrc lahylapfdn gsfaetvvng
     dihtelasiy gtdrksgkgv 421  tycliygggd hklgstagas kaqaskkgke irgrimrdld
     gfaalsdavs rrartgvlrg 481  ldgrpirlqg kshaalnyll qsagavickq wllrsyelld
     eanidywpla fvhdelqisv 541  apsqaematl litaamkdvq hnlkfrceld seaqtgnswa
     dch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage Syn5 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a Cyanophage S-CBP42 DNA polymerase. In some embodiments, the DNA polymerase can have the following sequence:

```
                                             (SEQ ID NO: 19)
1    mrlafdietd gllrnltkih civaqdldtn evykfdgtgd
     hpsireglal lkdadelwgh 61   niigydfeai kevfprwnys stvydtlils rlfftdlldr
     dfrsrpanmp aqlygrhsle 121  awghrlsvhk sefgkslsgd wstyspemld ycardvvvsv
     slarlftakv aeyrdciste
```

```
181 hrlatimawq esegfpfdva kaerlegqlr sellklseqm
    retfpyvdgg sftprtnngp 241 rgyvkgaamc rlkefnptsr qhiawafatf rdwepkeltd
    tgkpkidett lleygtdeak 301 tfarilelqk hlgqlsegan awlkkvesdg rihhscvlnt
    ntgrqahmkp nlaqvpsghe 361 yrelfhpgan rsqvgadasg lelrclghyl arfdggkfak
    evvqgdihta laeiygtdrk 421 sgkgvtycli ygggdsklgl tagaskaqav kkgkeirsri
    manldgfaal naavqeraks 481 gvlkgldgrp irlqgknhaa lnyllqsaga vicklwllrs
    yelldeagid yfpmafvhde 541 vhisvapsqa eqagqliqia mkdvehqikf rcaldseyqi
    gnswadch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Cyanophage S-CBP42 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a *Synechococcus* phage P60 DNA polymerase. In some embodiments, the DNA polymerase can have the following sequence:

```
                                        (SEQ ID NO: 20)
  1 mklafdietd glipdltiih civardidtd eefrfdgtgd
    ypsikeglel lskadelwgh 61 nivnydypai qklhpdwtpp sctrdtlils rlfftdlldr
    dfrsrpalmp gnlygrhsle 121 awghrlghhk sefgkslegd wstyspemle ycardvevsv
    alaktfvpki peyqwsvdte 181 heiarimswq eqmgfpfdvr aaqalegklr leldtlsddm
    retfhfvdgg vmtpkrsnkv 241 rhyfenapfc klrefnptsr hhiawafehh rgwepkerta
    ggqpkiddei lreintkesl 301 afarilelqk hlgqlsegkn awlklerkgr lhhscvlntn
    tgrqahmrpn laqvpsahey 361 rslfkpsdnh lqvgsdasgl elrclghyls rydggkfaee
    vvngdihtal aeiygtdrks 421 gkgvtycliy gggnhklglt agaskssasr kgqeirgkim
    qglsgfadln aaiqeraksg 481 vlkgldgrpi rlqgknhaal nyllqsagai icklwvirth
    ellqeagidy yplafvhdeq 541 qlsvradqae maaqlttlam kdvehqvkfr caldseyqig
    nswadch
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Synechococcus* phage P60 DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a *Roseobacter* phage SIO1 DNA polymerase. In some embodiments, the *Roseobacter* phage SIO1 DNA polymerase can have the following sequence:

```
                                        (SEQ ID NO: 21)
  1 mevvfdietd aldatvihvl vakrvgqkgf yvvrdaetfk
    rlakqvtlwi ghnvigfdip 61 qikklwgygi plkdvadtlv msrlldptrk gghsldalsg
    nekidfhdfs tytpemlayc 121 kqdvainekv ylqlkeelsn fgkasiqleh qmqaivceqe
    kngfmldtdi aeeiyttclr 181 etnrieaeik efmvpiavpv keviikrkkd gsiysnqlle
    gcnvqgdytk iaweefnlgs 241 paqvnkrldr lgwkptvktk sgnsykicpe nlatipdtap
    eavkglkawk vletrwklaq 301 ewlqksqetg rvhgrviltg avthraahqg pnmanipsvp
    hgkdgilwkm egmygaecrq 361 afkvpegkll vgtdaagiql rvlahymndp iyteqvidgd
    ihtfnkealg ryckdrptak 421 tfiyafllga gtgmiasilg cnnrqaneam anfyeaipsl
    kklksqasqa asmgwmkgld 481 grvlrigsdh lalsvylqgg etvimrlanv fwqrqakkeg
    infkqcawvh dewqtevded 541 qaqrlgeiqv qaikdagtff klncpmdgea kigknwleth
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Roseobacter* phage SIO1 DNA Polymerase DNA polymerase that lacks 3' to 5' exonuclease activity. For example, the so-called "DIET" motif comprising the amino acid residues DIET from positions 6-9 of the above amino acid sequence can be mutated via substitution of both the Asp and Glu residues of the DIET motif with Alanine, resulting in a polymerase that lacks 3' to 5' exonuclease activity.

In some embodiments, the biomolecule of the conjugate can be a DNA polymerase from *Oedogonium cardiacum*. In some embodiments, the *Oedogonium cardiacum* polymerase can be a *Oedogonium cardiacum* chloroplast DNA Polymerase. In some embodiments, this polymerase can have the following sequence:

```
                                        (SEQ ID NO: 22)
  1 miefyasfdk dkeieinked semnkediem nkedieidld
    evneeerfdv nremlqtnyf 61 vkrfknilfp iaasfytseg nknvsktfsl tsnifdkkip
    stinilkesq immqefliel 121 islaedllkk rnptnslfyg ddkviiymhn lssfdgffil
    qtllksriln ytfnlnkklk
```

```
181 vtsyegliyr ikignlcfqd syrvipmsln klsflllnkq
    kkdfdvenin sqklqhifkn 241 keilekmley clydsillye smiliqktfw delkfditse
    stisntainf ffskyyefpt 301 qyywhtttkk dglsaklkyd nkrvtvsthh naifytkpfl
    dqqlrsayfg grtelykpqt 361 sngyvfdins lyafalmydm pygspiyene yknwttnefe
    sffgflkiif itppnydilp 421 vlprrypppi shnvyclgig egwyfseeik larqkgyklk
    ilesikftph kgfekfvrdf 481 fsirqqypkg hplnllakli lnstygrfgi altthkqmkt
    fnqiklkekk nkkinini
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Oedogonium cardiacum* chloroplast DNA Polymerase DNA polymerase that lacks 3' to 5' exonuclease activity.

In some embodiments, the biomolecule of the conjugate can be a Salterprovirus His1 polymerase. In some embodiments, the polymerase can have the following sequence:

```
                                        (SEQ ID NO: 23)
  1 makcdkslea idldraytap rkakwaenkr ingldtetsd
    gdifcisvcw egekpmvqhn 61 drekltskqv wqvltdhkar sslnmwynld fdanvvlnhv
    cseeqlaelv vsgttlansd 121 rtyrqymdtd kelrkgeyli tyiqskflei kdhnshiyth
    ydasqffyts lenavtewlg 181 eskandglea glfgsqtpnq lretvaesdc vtwtnlslty
    nvskgdkwti hnaksyiskn 241 wsdilkyaqi daelvrdlwq eavnvgeeld ipmgrpfstg
    ylaesyldnr lrekpglgpm 301 pmakmawesy aggrfevlkr gnvgrvagpd insaypavla
    elpdpktlrw krakhasise 361 ietadygfmt vkvstdptre iqpfavkdek qdklvypspq
    nteitvvkdi fihaynqgyv 421 tdyevidcwl gyktegttfp fdfipelydn rktaeangle
    krglllkivl nsmygktcqt 481 tpkrrelaes telelhesyv pdmslpkmir ekysegfies
    ltagawfnpf lasyitgltr 541 lelhkqickh dleentvmla tdcvmieekp feesnfvenl
    vqdglgywdm eykgdafvlg 601 agvyqidfdt cqkgckdncn kfshkhkvkt rgfseadlek
    glvnaaekan ghieiestrp 661 qtiseiiwsn eelsqvgnfl eqerkikpem dtkrkwsent
    dfkkllstce tslplki
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Salterprovirus His1 DNA polymerase that lacks 3' to 5' exonuclease activity.

In some embodiments, the biomolecule of the conjugate can be a DNA polymerase from Salterprovirus His2. In some embodiments, this polymerase can have the following amino acid sequence:

```
                                        (SEQ ID NO: 24)
  1 maksdrnlde vnlypayqdq ysatfvdgkl inafdtetss
    gtvfmltsay gdktqayynr 61 dvseldaeti mdaltdyktr sniniwynld fdanailsgi
    lsqkemselv vtnettttva 121 gieyeifyik gkmlrivden gnisphydia qffytsldna
    aeewlgenkk egidtskfdd 181 keyikdnfde ilkyakkdas ltqdlaielt neaenldipm
    grpistgyls aeylrantee 241 kpslgneamq nlfwesyygg rfevfqrgnv gevvapdins
    aypaimkdlp dpttlnwnhy 301 lnevsdkepf shsinkfgye eienghygvv karvttdssr
    miqpfackid gkvkfpamtn 361 kvvtvikpif efavnnglvt dfelieawig nitdrtskpf
    efigdmyaer kvfeqlknkp 421 kkgqllkivl nssygktcqt tekrhkhdld kdgkkimqah
    etqyprfyls kkqrealgdd 481 eiiiteleag krfnpffasy itgltrlelh kqvvehdied
    stvmfatdcl mvekeayens 541 sfdeqihvpd dslpesefrk eatrslgawd fdyegsafiv
    gsgvyevdti qgktktktrg 601 fiesnlgdtl kglakhhkea ipldnerplt maevlinter
    gsvsefvens kklkpdfddk 661 rnwnrenpnf hdllndkeys kpidlqeqke emiqeqmdin
    ekmigdatpn gnetvvvkdd
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of Salterprovirus His2 DNA polymerase that lacks 3' to 5' exonuclease activity.

In some embodiments, the biomolecule of the conjugate can be a DNA polymerase from *Ostreococcus tauri* V5. In some embodiments, this DNA polymerase can have the following amino acid sequence:

```
                                        (SEQ ID NO: 25)
  1 mvvfqaltwe srdtddehli sifgkteegk svclttaftp
    yffiklpeki dagkirriyn 61 ildekckdsl vaysvmkskd vwgfqnneef vfmkvnfkhl
    qarrlvdsfl rkpldrtpel 121 fnifgvrnvk vyesnldpvl rlmhrtgiqs tgwldtgdkc
    irshlarvdl dlfcndwttl 181 kpvarddiap fvvasvdiec nsstgkfpda dvtgdacfqi
    aislckfgsd epydktclcy 241 kktdpnlegs tirsyetere mleafqkylh tkdvdiitgw
    nifgfdmeyi ykraqvnrch 301 yeffnlgklr dteselvikk lsssalgdnl lkllpmpgrf
    ifdmfhevkk gykldsykld 361 nvsklylgdq kidmapkemf aryreedpvk lrevaeycik
    dtllphrlmk klctllnmve
```

```
421  makatwvpan  flvergqqik  vfsqltkkar  elgfmvptir
     ygaipeepye  gatvleaqkg 481  ayytpitald  fealypsimm  ahnlcyssyv  mdekrygsvp
     gityetfnig  drtykfaqdv 541  psllpailae  lkqfrkqakr  dmaaatgfmk  evyngkqlay
     kvsmnsvygf  tgagkgilpc 601  vpiastttsk  grsmieetkn  yveknfpgak  vrygdtdsvm
     vefdvgdrkg  eeaiayswev 661  geraaeecsa  lfkkpnnlel  ekvywpyfly  skkryaaklw
     tkgkdgkmhm  dyidikglqv 721  vrrdntphvr  evckelldvi  ltssdpgppk  elakeraiel
     lsgdvpndkl  ilsqglsdty 781  kvggknvsvt  sadsvninqs  hvqvvtkmrq  rkpgsepqsg
     drvpylltkt  qdpkakayek 841  aedpkyveeh  gvpvdyhyyf  lnkflnpvcd  lldplyenvk
     edifgeiina  hkpvkppklp 901  slsgmkkddl  iaecqrlgle  etgtlailra  rlkdarhgsv
     edlfknyelt  qskdess
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Ostreococcus tauri* V5 DNA polymerase that lacks 3' to 5' exonuclease activity.

In some embodiments, the biomolecule of the conjugate can be a DNA polymerase from *Ectocarpus siliculosus* virus 1. In some embodiments, this polymerase can have the following amino acid sequence:

```
                                          (SEQ ID NO: 26)
  1  melylhdird  nsgsfqnptm  qlfameedgt  nvfvsvknfk
     tylyvgfdld  isedsvrsny 61  lekfkqekwe  rnvykmsvvk  rkrligfsng  dlfpyilmef
     tgtisfyivr  khlhelcger 121  dpgpntfvdl  nkypgmcvye  sksvdsilkf  fhasgvrpss
     yfrmenyvrv  adkarkthca 181  kefivdfvnv  rpvgeevvdr  kpppmticsy  dletsglntn
     edyifqasmi  fsrlgdpcpd 241  segsatghav  dsytdgvvic  vgdtesvdgt  pllivenelq
     lldkfreilv  ergcnilcgy 301  ntfkfdsafl  ykraerygfd  gfkklsfikd  lacdlevktl
     qsaalgknel  kqiiipgrve 361  idlfmvmrrs  qklssyklna  vcdkffggkk  ddvtyadilq
     actskdpkkl  gviakycyqd 421  sglvlklldk  ikevydatem  aklctvplty  ivgrgqqikc
     mslilnrihg  eyvcnyaaak
```

```
481  kkmaadgkqv  lnegykgasv  idakkgfyek  dpivtmdfas
     lypsimrlkq  lcyttivrdv 541  kyrgiegvny  edhqisdgvs  vtfahrpgsr  silceleeml
     geerkatkkl  mksekdpfay 601  slldskqkaq  kvtmnsiygf  tgtvnngmlp  lveiaaavts
     tgrdmikrtk  eyaekehgcn 661  viygdtdsvm  vifpehrnie  nlgdkmrycf  dmgtkvskei
     semfghpill  efeniyfkyl 721  lvskkryagl  swetvegppt  mtmkglvtvr  rdnapfvgrc
     aseaihmlmd  vdvtdgrgav 781  kkhltetllr  lergqisied  ltirkelkqw  vyktpsphat
     lalkilertk  eqavfrefik 841  payetiggyd  dsllssvwtk  mtnlksylsv  rakreiamsd
     mvesirgdtt  spfkaeayav 901  valrqlyddv  hsvlvgesfa  rvvglvmagi  gdvhklgery
     mafvrynivd  wdpptlgeri 961  pyvittgkgd  issraedprm  vnvgrcrpdf  lyyidhqlrn
     pmvdllqhvi  espsslfves 1021 qrrmsnlnhg  rkeittffkk  rkvteg
```

In some embodiments, the biomolecule can be a polymerase having an amino acid sequence that is at least 70%, 80%, 85%, 90%, 95%, 99% or 100% identical to the above amino acid sequence, or any biologically active fragment thereof. In some embodiments, the polymerase comprises a mutant or variant of *Ectocarpus siliculosus* virus 1 DNA polymerase that lacks 3' to 5' exonuclease activity.

In some embodiments, the biomolecule comprises the amino acid sequence of SEQ ID NO: 14 (HP1), further comprising a mutation of one, some or all of the cysteines occurring at amino acid positions 47, 315, 473 and/or 555 to any other amino acid. In some embodiments, the cysteine is replaced with a serine or alanine residue. In some embodiments, the cysteines at amino acid positions 47, 315 and 555 are mutated to another residue, e.g., alanine or serine, and the cysteine at position 473 is not mutated and can serve as a site for covalent attachment of a label.

In some embodiments, the biomolecule comprises the amino acid sequence of SEQ ID NO: 14 (HP1) and further comprises the mutation Q380A:

```
                                                        (SEQ ID NO: 27)
              10         20         30         40         50         60
         MNHLVHHHHH HIEGRHMELG TLEGSMKHMP RKMYSCAFET TTKVEDCRVW AYGYMNIEDH 70         80         90        100        110        120
         SEYKIGNSLD EFMAWVLKVQ ADLYFHNLKF AGAFIINWLE RNGFKWSADG LPNTYNTIIS 130        140        150        160        170        180
         RMGQWYMIDI CLGYKGKRKI HTVIYDSLKK LPFPVKKIAK DFKLTVLKGD IDYHKERPVG
```

```
                                                              -continued
        190        200        210        220        230        240
YKITPEEYAY IKNDIQIIAE ALLIQFKQGL DRMTAGSDSL KGFKDIITTK KFKKVFPTLS 250        260        270        280        290        300
LGLDKEVRYA YRGGFTWLND RFKEKEIGEG MVFDVNSLYP AQMYSRLLPY GEPIVFEGKY 310        320        330        340        350        360
VWDEDYPLHI QHIRCEFELK EGYIPTIQIK RSRFYKGNEY LKSSGGEIAD LWLSNVDLEL 370        380        390        400        410        420
MKEHYDLYNV EYISGLKFKA TTGLFKDFID KWTYIKTTSE GAIKALAKLM LNSLYGKFAS 430        440        450        460        470        480
NPDVTGKVPY LKENGALGFR LGEEETKDPV YTPMGVFITA WARYTTITAA QACYDRIIYC 490        500        510        520        530        540
DTDSIHLTGT EIPDVIKDIV DPKKLGYWAH ESTFKRAKYL RQKTYIQDIY MKEVDGKLVE 550        560        570        580        590        600
GSPDDYTDIK FSVKCAGMTD KIKKEVTFEN FKVGFSRKMK PKPVQVPGGV VLVDDTFTIK
```

This fusion polymerase having the amino acid sequence of SEQ ID NO: 27 is hereinafter referred to as HP1 Q380A. In some embodiments, the biomolecule comprises a fusion protein having an amino acid sequence that is at least 70%, 80%, 85%, 90%, 95%, 99% or 100% identical to the amino acid sequence of SEQ ID NO: 27.

In some embodiments, the biomolecule comprises the amino acid sequence of SEQ ID NO: 28, below, which is the HP1 sequence further comprising the mutation S388G:

amino acid sequence that is at least 70%, 80%, 85%, 90%, 95%, 99% or 100% identical to the amino acid sequence of SEQ ID NO: 28 (HP1 S388G).

In some embodiments, the biomolecule is a His-tagged version of a polymerase isolated from the phage RB69. The His-tag can be fused to the N-terminus, the C-terminus or any other suitable position of the RB69 polymerase. Optionally, the His-tag can be separated from the amino acid residues of the protein by a linker, typically a peptide linker. In some

```
                                                              (SEQ ID NO: 28)
         10         20         30         40         50         60
MNHLVHHHHH HIEGRHMELG TLEGSMKHMP RKMYSCAFET TTKVEDCRVW AYGYMNIEDH 70         80         90        100        110        120
SEYKIGNSLD EFMAWVLKVQ ADLYFHNLKF AGAFIINWLE RNGFKWSADG LPNTYNTIIS 130        140        150        160        170        180
RMGQWYMIDI CLGYKGKRKI HTVIYDSLKK LPFPVKKIAK DFKLTVLKGD IDYHKERPVG 190        200        210        220        230        240
YKITPEEYAY IKNDIQIIAE ALLIQFKQGL DRMTAGSDSL KGFKDIITTK KFKKVFPTLS 250        260        270        280        290        300
LGLDKEVRYA YRGGFTWLND RFKEKEIGEG MVFDVNSLYP AQMYSRLLPY GEPIVFEGKY 310        320        330        340        350        360
VWDEDYPLHI QHIRCEFELK EGYIPTIQIK RSRFYKGNEY LKSSGGEIAD LWLSNVDLEL 370        380        390        400        410        420
MKEHYDLYNV EYISGLKFKA TTGLFKDFID KWTYIKTTSE GAIKQLAKLM LNGLYGKFAS 430        440        450        460        470        480
NPDVTGKVPY LKENGALGFR LGEEETKDPV YTPMGVFITA WARYTTITAA QACYDRIIYC 490        500        510        520        530        540
DTDSIHLTGT EIPDVIKDIV DPKKLGYWAH ESTFKRAKYL RQKTYIQDIY MKEVDGKLVE 550        560        570        580        590        600
GSPDDYTDIK FSVKCAGMTD KIKKEVTFEN FKVGFSRKMK PKPVQVPGGV VLVDDTFTIK
```

This fusion polymerase of amino acid sequence of SEQ ID NO: 28 is herein referred to as HP1 S388G. In some embodiments, the biomolecule comprises a fusion protein having an embodiments, the fusion protein comprises an amino acid sequence that is at least 70%, 80%, 85%, 90%, 95%, 99% or 100% identical to the following amino acid sequence:

```
                                                              (SEQ ID NO: 29)
         10         20         30         40         50         60
MHHHHHHKHM KEFYLTVEQI GDSIFERYID SNGRERTREV EYKPSLFAHC PESQATKYFD 70         80         90        100        110        120
IYGKPCTRKL FANMRDASQW IKRMEDIGLE ALGMDDFKLA YLSDTYNYEI KYDHTKIRVA
```

-continued

```
        130        140        150        160        170        180
NFDIEVTSPD GFPEPSQAKH PIDAITHYDS IDDRFYVFDL LNSPYGNVEE WSIEIAAKLQ 190        200        210        220        230        240
EQGGDEVPSE IIDKIIYMPF DNEKELLMEY LNFWQQKTPV ILTGWNVESF DIPYVYNRIK 250        260        270        280        290        300
NIFGESTAKR LSPHRKTRVK VIENMYGSRE IITLFGISVL DYIDLYKKFS FTNQPSYSLD 310        320        330        340        350        360
YISEFELNVG KLKYDGPISK LRESNHQRYI SYNIIDVYRV LQIDAKRQFI NLSLDMGYYA 370        380        390        400        410        420
KIQIQSVFSP IKTWDAIIFN SLKEQNKVIP QGRSHPVQPY PGAFVKEPIP NRYKYVMSFD 430        440        450        460        470        480
LTSLYPSIIR QVNISPETIA GTFKVAPLHD YINAVAERPS DVYSCSPNGM MYYKDRDGVV 490        500        510        520        530        540
PTEITKVFNQ RKEHKGYMLA AQRNGEIIKE ALHNPNLSVD EPLDVDYRFD FSDEIKEKIK 550        560        570        580        590        600
KLSAKSLNEM LFRAQRTEVA GMTAQINRKL LINSLYGALG NVWFRYYDLR NATAITTFGQ 610        620        630        640        650        660
MALQWIERKV NEYLNEVCGT EGEAFVLYGD TDSIYVSADK IIDKVGESKF RDTNHWVDFL 670        680        690        700        710        720
DKFARERMEP AIDRGFREMC EYMNNKQHLM FMDREAIAGP PLGSKGIGGF WTGKKRYALN 730        740        750        760        770        780
VWDMEGTRYA EPKLKIMGLE TQKSSTPKAV QKALKECIRR MLQEGEESLQ EYFKEFEKEF 790        800        810        820        830        840
RQLNYISIAS VSSANNIAKY DVGGFPGPKC PFHIRGILTY NRAIKGNIDA PQVVEGEKVY 850        860        870        880        890        900
VLPLREGNPF GDKCIAWPSG TEITDLIKDD VLHWMDYTVL LEKTFIKPLE GFTSAAKLDY

910
EKKASLFDMF DF
```

In some embodiments, the biomolecule is a His-tagged version of a polymerase isolated from the GA-1 phage. The His-tag can be fused to the N-terminus, the C-terminus or any other suitable position of the GA-1 polymerase. Optionally, the His-tag can be separated from the amino acid residues of the protein by a linker. In some embodiments, the linker comprises the F-linker sequence LLGGGGSGGGGSAAAGSAA (SEQ ID NO: 5). In some embodiments, the fusion protein comprises an amino acid sequence that is at least 70%, 80%, 85%, 90%, 95%, 99% or 100% identical to the following amino acid sequence:

```
                                                      (SEQ ID NO: 30)
         10         20         30         40         50         60
MHHHHHHKHM ARSVYVCDFE TTTDPEDCRL WAWGWMDIYN TDKWSYGEDI DSFMEWALNS 70         80         90        100        110        120
NSDIYFHNLK FDGSFILPWW LRNGYVHTEE DRTNTPKEFT TTISGMGQWY AVDVCINTRG 130        140        150        160        170        180
KNKNHVVFYD SLKKLPFKVE QIAKGFGLPV LKGDIDYKKY RPVGYVMDDN EIEYLKHDLL 190        200        210        220        230        240
IVALALRSMF DNDFTSMTVG SDALNTYKEM LGVKQWEKYF PVLSLKVNSE IRKAYKGGFT 250        260        270        280        290        300
WVNPKYQGET VYGGMVFDVN SMYPAMMKNK LLPYGEPVMF KGEYKKNVEY PLYIQQVRCF 310        320        330        340        350        360
FELKKDKIPC IQIKGNARFG QNEYLSTSGD EYVDLYVTNV DWELIKKHYD IFEEEFIGGF 370        380        390        400        410        420
MFKGFIGFFD EYIDRFMEIK NSPDSSAEQS LQAKLMLNSL YGKFATNPDI TGKVPYLDEN 430        440        450        460        470        480
GVLKFRKGEL KERDPVYTPM GCFITAYARE NILSNAQKLY PRFIYADTDS IHVEGLGEVD 490        500        510        520        530        540
AIKDVIDPKK LGYWDHEATF QRARYVRQKT YFIETTWKEN DKGKLVVCEP QDATKVKPKI
```

```
         550        560        570        580
ACAGMSDAIK ERIRFNEFKI GYSTHGSLKP KNVLGGVVLM DYPFAIK
```

In some embodiments, the biomolecule is a His-tagged version of a polymerase isolated from the B103 phage. The His-tag can be fused to the N-terminus, the C-terminus or any other suitable position of the B103 polymerase. Optionally, the His-tag can be separated from the amino acid residues of the protein by a linker. In some embodiments, the linker comprises the amino acid sequence LLGGGGSGGGGSAAAGSAA (SEQ ID NO: 5). In some embodiments, the fusion protein comprises an amino acid sequence that is at least 70%, 80%, 85%, 90%, 95%, 99% or 100% identical to the following amino acid sequence:

```
                                              (SEQ ID NO: 31)
        10         20         30         40         50         60
MHHHHHHKHM PRKMFSCDFE TTTKLDDCRV WAYGYMEIGN LDNYKIGNSL DEFMQWVMEI 70         80         90        100        110        120
QADLYFHNLK FDGAFIVNWL EHHGFKWSNE GLPNTYNTII SKMGQWYMID ICFGYKGKRK 130        140        150        160        170        180
LHTVIYDSLK KLPFPVKKIA KDFQLPLLKG DIDYHAERPV GHEITPEEYE YIKNDIEIIA 190        200        210        220        230        240
RALDIQFKQG LDRMTAGSDS LKGFKDILST KKFNKVFPKL SLPMDKEIRR AYRGGFTWLN 250        260        270        280        290        300
DKYKEKEIGE GMVFDVNSLY PSQMYSRPLP YGAPIVFQGK YEKDEQYPLY IQRIRFEFEL 310        320        330        340        350        360
KEGYIPTIQI KKNPFFKGNE YLKNSGAEPV ELYLTNVDLE LIQEHYEMYN VEYIDGFKFR 370        380        390        400        410        420
EKTGLFKEFI DKWTYVKTHE KGAKKQLAKL MFDSLYGKFA SNPDVTGKVP YLKEDGSLGF 430        440        450        460        470        480
RVGDEEYKDP VYTPMGVFIT AWARFTTITA AQACYDRIIY CDTDSIHLTG TEVPEIIKDI 490        500        510        520        530        540
VDPKKLGYWA HESTFKRAKY LRQKTYIQDI YAKEVDGKLI ECSPDEATTT KFSVKCAGMT 550        560        570        580
DTIKKKVTFD NFRVGFSSTG KPKPVQVNGG VVLVDSVFTI K
```

In some embodiments, the polymerase of the labeled polymerase conjugate is derived from a DNA polymerase of the Phi-29-like phage B103. The genome of B103, including a gene encoding a B103 DNA polymerase, has been sequenced. See, e.g., Pecenkova et al., "Bacteriophage B103: complete DNA sequence of its genome and relationship to other *Bacillus* phages" Gene 199:157-163 (1999). The DNA polymerase of B103 is homologous to the DNA polymerase of Phi-29 and of other Phi-29-like phages. Collectively, these polymerases share several highly conserved regions. See, e.g., Meijer et al., "Phi-29 family of phages" Microbiol. & Mol. Biol. Revs. 65(2):261-287 (2001). These conserved regions are typically characterized by several conserved amino acid motifs. See, e.g., Blanco et al., Gene 100:27-38 (1991); Blasco et al., "Φ29 DNA polymerase Active Site" J. Biol. Chem. 268: 16763-16770 (1993) (describing regions of sequence homology and mutational analysis of consensus regions of Phi-29 and Phi-29-like DNA polymerases); Berman et al., "Structures of phi29 DNA polymerase complexed with substrate: the mechanism of translocation in B-family polymerases", EMBO J., 26:3494-3505 (2007). Site-directed mutagenesis indicates that these three regions can form an evolutionarily conserved polymerase active site.

In some embodiments, the polymerase of the labeled polymerase conjugate is derived from a B103 polymerase comprising the amino acid sequence of SEQ ID NO: 32 as follows:

```
                                              (SEQ ID NO: 32)
  1 mprkmfscdf etttklddcr vwaygymeig nldnykigns
    ldefmqwvme iqadlyfhnl 61 kfdgafivnw lehhgfkwsn eglpntynti iskmgqwymi
    dicfgykgkr klhtviydsl 121 kklpfpvkki akdfqlpllk gdidyhaerp vgheitpeey
    eyikndieii araldiqfkq 181 gldrmtagsd slkgfkdils tkkfnkvfpk lslpmdkeir
    rayrggftwl ndkykekeig 241 egmvfdvnsl ypsqmysrpl pygapivfqg kyekdeqypl
    yiqrirfefe lkegyiptiq 301 ikknpffkgn eylknsgaep velyltnvdl eliqehyemy
    nveyidgfkf rektglfkef 361 idkwtyvkth ekgakkqlak lmfdslygkf asnpdvtgkv
    pylkedgslg frvgdeeykd 421 pvytpmgvfi tawarfttit aaqacydrii ycdtdsihlt
    gtevpeiikd ivdpkklgyw 481 ahestfkrak ylrqktyiqd iyakevdgkl iecspdeatt
    tkfsvkcagm tdtikkkvtf 541 dnfrvgfsst gkpkpvqvng gvvlvdsvft ik
```

In some embodiments, the polymerase of the labeled polymerase conjugate is a variant of a B103 polymerase, wherein the modified polymerase comprises an amino acid sequence that is at least 80%, 85%, 90%, 95%, 97%, 98% or 99% identical to the amino acid sequence of SEQ ID NO: 32, or any biologically active fragment thereof.

In some embodiments, the polymerase of the labeled polymerase conjugate is homologous to a polymerase of one or more of the following organisms: B103, Phi-29, GA-1, PZA, Phi-15, BS32, M2Y, Nf, G1, Cp-1, PRD1, PZE, SF5, Cp-5, Cp-7, PR4, PR5, PR722, or L17. See, e.g., Meijer et al., "Phi-29 family of phages," Microbiol. & Mol. Biol. Revs. 65(2):261-287 (2001).

In some embodiments, the polymerase of the labeled polymerase conjugate comprises a B103 polymerase having the amino acid sequence of SEQ ID NO: 32 and further comprises one or more mutations in the amino acid sequence of SEQ ID NO: 32. In some embodiments, the one or more mutations can include, for example, substitution, chemical modification, addition, deletion and/or inversion of one or more amino acid residues, or any combination of the foregoing.

The mutant B103 polymerase can optionally further comprise the amino acid sequence of any of the polymerases disclosed in U.S. Ser. No. 61/242,771, filed on Sep. 15, 2009; U.S. Ser. No. 61/293,618, filed on Jan. 8, 2010 or U.S. Ser. No. 12/748,359 titled "Polymerase Compositions & Methods", filed concurrently herewith.

In some embodiments, the polymerase of the labeled polymerase conjugate comprises an amino acid modification at position 383, at position 384, or at both positions 383 and 384, wherein the numbering is relative to a B103 polymerase having the amino acid sequence of SEQ ID NO: 32. The modification can include, for example, one or more amino acid substitutions, additions, deletions or chemical modifications.

In some embodiments, the polymerase of the labeled polymerase conjugate is a variant of a B103 polymerase comprising the amino acid sequence of SEQ ID NO: 32, wherein the modified polymerase comprises an amino acid sequence that is at least 80%, 85%, 90%, 95%, 97%, 98% or 99% identical to the amino acid sequence of SEQ ID NO: 32, or any biologically active fragment thereof, wherein the amino acid at position 383 is not phenylalanine (F), where the numbering is relative to the amino acid sequence of SEQ ID NO: 32.

In some embodiments, the polymerase of the labeled polymerase conjugate comprises the amino acid sequence of SEQ ID NO: 32, and further comprises an amino acid substitution at position 383, wherein the numbering is relative to a B103 polymerase having the amino acid sequence of SEQ ID NO: 32. In some embodiments, the modified polymerase is a variant of B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the modified polymerase further comprises the amino acid mutation F383L.

In some embodiments, the polymerase of the labeled polymerase conjugate is a variant of a B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the amino acid at position 384 is not aspartic acid (D), where the numbering is relative to the amino acid sequence of SEQ ID NO: 32.

In some embodiments, the polymerase of the labeled polymerase conjugate comprises the amino acid sequence of SEQ ID NO: 32 and further comprises an amino acid substitution at position 384, wherein the numbering is relative to a B103 polymerase having the amino acid sequence of SEQ ID NO: 32. In some embodiments, the polymerase is a variant of B103 polymerase that comprises an amino acid sequence that is at least 80%, 85%, 90%, 95%, 97%, 98% or 99% identical to the amino acid sequence of SEQ ID NO: 32, or any biologically active fragment thereof, wherein the modified polymerase further comprises the amino acid mutation D384N.

In some embodiments, the polymerase of the labeled polymerase conjugate is a variant of B103 polymerase, or any biologically active fragment thereof, having the amino acid sequence of SEQ ID NO: 32, wherein the variant further comprises amino acid substitutions at positions 383 and 384, wherein the numbering is relative to the amino acid sequence of SEQ ID NO: 32. In some embodiments, the polymerase comprises the amino acid sequence of SEQ ID NO: 32 and further comprises the amino acid substitutions F383L and D384N, wherein the numbering is relative to the amino acid sequence of SEQ ID NO: 32. The amino acid sequence of this polymerase can be represented as follows:

(SEQ ID NO: 33)
```
  1 mprkmfscdf etttklddcr vwaygymeig nldnykigns
    ldefmqwvme iqadlyfhnl 61 kfdgafivnw lehhgfkwsn eglpntynti iskmgqwymi
    dicfgykgkr klhtviydsl 121 kklpfpvkki akdfqlpllk gdidyhaerp vgheitpeey
    eyikndieii araldiqfkq 181 gldrmtagsd slkgfkdils tkkfnkvfpk lslpmdkeir
    rayrggftwl ndkykekeig 241 egmvfdvnsl ypsqmysrpl pygapivfqg kyekdeqypl
    yiqrirfefe lkegyiptiq 301 ikknpffkgn eylknsgaep velyltnvdl eliqehyemy
    nveyidgfkf rektglfkef 361 idkwtyvkth ekgakkqlak lmlnslygkf asnpdvtgkv
    pylkedgslg frvgdeeykd 421 pvytpmgvfi tawarfttit aaqacydrii ycdtdsihlt
    gtevpeiikd ivdpkklgyw 481 ahestfkrak ylrqktyiqd iyakevdgkl iecspdeatt
    tkfsvkcagm tdtikkkvtf 541 dnfrvgfsst gkpkpvqvng gvvlvdsvft ik
```

In some embodiments, the polymerase of the labeled polymerase conjugate comprises an amino acid sequence that is at least 80%, 85%, 90%, 95%, 97%, 98% or 99% identical to the amino acid sequence of SEQ ID NO: 33, or any biologically active fragment thereof.

In some embodiments, the polymerase comprises an amino acid sequence that is at least 80%, 85%, 90%, 95%, 97%, 98%, 99% or 100% identical to the amino acid sequence of SEQ ID NO: 33 and further includes one or more mutations reducing the 3' to 5' exonuclease activity of the polymerase. In some embodiments, the one or more mutations reducing the 3' to 5' exonuclease activity are selected from the group consisting of: D9A, E11A, E11I, T12I, H58R, N59D, D63A, Y162F, Y162C, D166A, Q377A and S385G.

In some embodiments, the polymerase of the labeled polymerase conjugate comprises the amino acid of SEQ ID NO: 34, below:

(SEQ ID NO: 34)
```
  1 mprkmfscdf etttklddcr vwaygymeig nldnykigns
    ldefmqwvme iqadlyfhnl 61 kfdgafivnw lehhgfkwsn eglpntynti iskmgqwymi
    dicfgykgkr klhtviydsl
```

```
121 kklpfpvkki akdfqlpllk gdidyhaerp vgheitpeey
    eyiknaieii araldiqfkq 181 gldrmtagsd slkgfkdils tkkfnkvfpk lslpmdkeir
    rayrggftwl ndkykekeig 241 egmvfdvnsl ypsqmysrpl pygapivfqg kyekdeqypl
    yiqrirfefe lkegyiptiq 301 ikknpffkgn eylknsgaep velyltnvdl eliqehyemy
    nveyidgfkf rektglfkef 361 idkwtyvkth ekgakkqlak lmlnslygkf asnpdvtgkv
    pylkedgslg frvgdeeykd 421 pvytpmgvfi tawarfttit aaqacydrii ycdtdsihlt
    gtevpeiikd ivdpkklgyw 481 ahestfkrak ylrqktyiqd iyakevdgkl iecspdeatt
    tkfsvkcagm tdtikkkvtf 541 dnfrvgfsst gkpkpvqvng gvvlvdsvft ik
```

In some embodiments, the polymerase of the labeled polymerase conjugate comprises an amino acid sequence that is at least 70%, 75%, 80%, 85%, 90%, 95%, 97%, 98% or 99% identical to the amino acid sequence of SEQ ID NO: 34, or any biologically active fragment thereof. Typically, the polymerase of SEQ ID NO: 34 will exhibit reduced exonuclease activity relative to a reference polymerase comprising the amino acid sequence of SEQ ID NO: 3, SEQ ID NO: 32 or SEQ ID NO: 33.

In some embodiments, the polymerase of the labeled polymerase conjugate is a variant of a B103 polymerase comprising the amino acid sequence of SEQ ID NO: 32, SEQ ID NO: 33 or SEQ ID NO: 34, wherein the variant further comprises one, two, three or more modifications at amino acid positions 2, 9, 58, 59, 63, 129, 166, 246, 247, 339, 370, 371, 372, 373, 374, 375, 376, 377, 380, 383, 384, 385, 455, 507 and 509, or any combinations thereof, wherein the numbering is relative to the amino acid sequence of SEQ ID NO: 33.

In some embodiments, the polymerase can comprise a His-tagged version of a Phi-29 polymerase and an N-terminal linker as well as various mutations that reduce the exonuclease activity of the Phi-29 polymerase.

In some embodiments, the amino acid sequence of the polymerase of the labeled polymerase conjugate is fused to a peptide sequence that encodes a stretch of amino acid acids capable of functioning as a peptide linker to facilitate the formation of a linkage between the polymerase and another reactive moiety. The reactive moiety can in some embodiments be a label, or another attachment moiety that is itself linked to one or more labels. This peptide linker sequence can be fused to the N-terminus, the C-terminus or any suitable position between the N-terminus and the C-terminus of the polymerase.

In some embodiments, the polymerase is derived from a Phi-29-like polymerase and comprises an amino acid sequence that is at least 70%, 80%, 85%, 90%, 95%, 97%, 98%, 99% or 100% identical to the amino acid sequence of SEQ ID NO: 33 and further includes amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 33. In some embodiments, the modifications can include deletions, additions and substitutions. The substitutions can be conservative or non-conservative substitutions. In some embodiments, the polymerase comprises an amino acid sequence that is at least 80%, 85%, 90%, 95%, 97%, 98%, 99% or 100% identical to the amino acid sequence of SEQ ID NO: 33 and further includes one or more mutations reducing the 3' to 5' exonuclease activity of the polymerase. In some embodiments, the one or more mutations reducing the 3' to 5' exonuclease activity are selected from the group consisting of: D9A, E11A, E11I, T12I, H58R, N59D, D63A, Y162F, Y162C, D166A, Q377A and S385G.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, F383L, D384N, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 33. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, this polymerase comprises the amino acid substitution H370R and/or K380R.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increased $t_{-1}$ value in the presence of the dye-labeled nucleotides relative to a reference polymerase having the amino acid sequence of SEQ ID NO: 33. In some embodiments, the $t_{-1}$ value of the polymerase is increased by at least about 105%, 110%, 125%, 150%, 175%, 200%, 250%, 500%, 750%, or 1000% relative to the reference polymerase. In some embodiments, the $t_{-1}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 33. In some embodiments, the $t_{pol}$ value of the polymerase is increased by at least about 105%, 110%, 125%, 150%, 175%, 200%, 250%, 500%, 750%, or 1000% relative to the reference polymerase. In some embodiments, the $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation K380R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 3 and further includes an amino acid mutation selected from the group: T373G, T373E, T373T, T373S, T373R, T373A, K T373Q, T373W, T373Y and T373F, wherein the numbering is relative to the amino acid sequence of SEQ ID NO: 3. Typically, this polymerase can exhibit an increased $t_{-1}$ value in the presence of the dye-labeled nucleotides relative to a reference polymerase having the amino acid sequence of SEQ ID NO: 3. In some embodiments, the $t_{-1}$ value of the polymerase is increased by at least about 105%, 110%, 125%, 150%, 175%, 200%, 250%, 500%, 750%, or 1000% relative to the reference polymerase. In some embodiments, the $t_{-1}$ value is increased in the presence of the dye-labeled nucleotide AF647-C6-dG6P. Optionally, the polymerase can further include one or more mutations reducing 3' to 5' exonuclease activity selected from the group consisting of: D12A, E14I, E14A, T15I, N62D, D66A, Y165F, Y165C, and D169A, wherein the numbering is relative to the amino acid sequence of SEQ ID NO: 3. In some embodiments, the polymerase comprises an amino acid sequence that is at least 70%, 80%, 85%, 90%, 95%, 97%, 98%, 99% or 100% identical to the amino acid sequence of SEQ ID NO: 3 and further includes the amino acid mutation T373R, wherein the numbering is relative to the amino acid sequence of SEQ ID NO: 3. In some embodiments, the polymerase further includes the mutations D12A and D66A.

In some embodiments, the biomolecule is derived from a M2 polymerase (also known as M2Y DNA polymerase) having the amino acid sequence of the SEQ ID NO: 35 as follows:

```
                                          (SEQ ID NO: 35)
  1 msrkmfscdf etttklddcr vwaygymeig nldnykigns
    ldefmqwvme iqadlyfhnl 61 kfdgafivnw leqhgfkwsn eglpntynti iskmgqwymi
    dicfgykgkr klhtviydsl 121 kklpfpvkki akdfqlpllk gdidyhterp vgheitpeey
    eyikndieii araldiqfkq 181 gldrmtagsd slkgfkdils tkkfnkvfpk lslpmdkeir
    kayrggftwl ndkykekeig 241 egmvfdvnsl ypsqmysrpl pygapivfqg kyekdeqypl
    yiqrirfefe lkegyiptiq 301 ikknpffkgn eylknsgvep velyltnvdl eliqehyely
    nveyidgfkf rektglfkdf 361 idkwtyvkth eegakkqlak lmlnslygkf asnpdvtgkv
    pylkddgslg frvgdeeykd 421 pvytpmgvfi tawarfttit aaqacydrii ycdtdsihlt
    gtevpeiikd ivdpkklgyw 481 ahestfkrak ylrqktyiqd iyvkevdgkl kecspdeatt
    tkfsvkcagm tdtikkkvtf 541 dnfavgfssm gkpkpvqvng gvvlvdsvft ik
```

In some embodiments, the polymerase comprises an amino acid sequence that is at least 85%, 90%, 95%, 97%, 98% or 99% identical to the amino acid sequence of SEQ ID NO: 35 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 32. Typically, such a polymerase will exhibit reduced 3' to 5' exonuclease activity relative to reference polymerase having the amino acid sequence of SEQ ID NO: 35.

In some embodiments, the polymerase comprises an amino acid sequence that is at least 85%, 90%, 95%, 97%, 98% or 99% identical to the amino acid sequence of SEQ ID NO: 35 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the polymerase comprises any one, two, three, four, five or all of these mutations. In some embodiments, the polymerase comprises the amino acid substitution D166A. In some embodiments, the polymerase comprises the amino acid substitutions D9A and D63A. In some embodiments, the polymerase comprises the amino acid substitutions N59D and T12I. Typically, such polymerases will exhibit reduced 3' to 5' exonuclease activity relative to reference polymerase having the amino acid sequence of SEQ ID NO: 35.

In some embodiments, the polymerase comprises an amino acid sequence that is at least 80%, 85%, 90%, 95%, 97%, 98%, 99% or 100% identical to the amino acid sequence of SEQ ID NO: 35 and further comprises an amino acid substitution at one or more positions selected from the group consisting of: 2, 73, 147, 221, 318, 339, 359, 372, 405, 503, 511, 544 and 550, wherein the numbering is relative to the amino acid sequence of SEQ ID NO: 32.

In some embodiments, the polymerase comprises an amino acid sequence that is at least 80%, 85%, 90%, 95%, 97%, 98%, 99% or 100% identical to the amino acid sequence of SEQ ID NO: 35 and further includes any one, two, three or more amino acid mutations selected from the group consisting of: S2P, Q73H, T147A, K221R, V318A, L339M, D359E, E372K, D405E, V503A, K511I, A544R and M550T, wherein the numbering is relative to the amino acid sequence of SEQ ID NO: 32.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 32. Optionally, this polymerase comprises the amino acid mutation H370R. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 365, wherein the numbering is relative to the amino acid sequence of SEQ ID NO: 32. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 32. Optionally, this polymerase comprises the amino acid mutation T365F. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 372, wherein the numbering is relative to the amino acid sequence of SEQ ID NO: 32. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 32. Optionally, this polymerase comprises the amino acid mutation K372Y. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 481, wherein the numbering is relative to the amino acid sequence of SEQ ID NO: 32. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 32. Optionally, this polymerase comprises the amino acid mutation A481E. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes a mutation at position 509, wherein the numbering is relative to the amino acid sequence of SEQ ID NO: 32. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 32. Optionally, this polymerase comprises the amino acid mutation K509Y. Typically, this polymerase can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprise amino acid mutations at any one, two, three or more positions selected from the group consisting of: 2, 9, 12, 14, 15, 58, 59, 61, 63, 73, 98, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit an increased branching ratio and/or increased $t_{-1}$ value relative to a reference polymerase having the amino acid sequence of SEQ ID NO: 35. In some embodiments, the branching ratio and/or $t_{-1}$ value of the polymerase is increased by at least about 105%, 110%, 125%, 150%, 175%, 200%, 250%, 500%, 750%, or 1000% relative to the reference polymerase. In some embodiments, the branching ratio and/or $t_{-1}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the branching ratio and/or $t_{-1}$ value is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 365, 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions T365F, E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes amino acid mutations at positions 365, 372, 481 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 35 and further includes the amino acid substitutions T365F, E372Y, A481E and K509Y, wherein the numbering is relative to the amino acid sequence of SEQ ID NO: 32. Typically, such polymerases can exhibit an increased branching ratio and/or increased nucleotide binding affinity relative to a reference polymerase having the amino acid sequence of SEQ ID NO: 35. In some embodiments, the branching ratio and/or nucleotide binding affinity is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increased branching ratio and/or increased $t_{-1}$ value and/or $t_{-1}$ increased $t_{pol}$ value relative to a reference polymerase having the amino acid sequence of SEQ ID NO: 35. In some embodiments, the branching ratio and/or $t_{-1}$ value and/or $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes the amino acid mutation H370R, wherein the numbering is relative to the amino acid sequence of SEQ ID NO: 32. In some embodiments, the polymerase comprises an amino acid sequence that is at least 70%, 80%, 85%, 90%, 95%, 97%, 98%, 99% or 100% identical to the amino acid sequence of SEQ ID NO: 35 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. Optionally, the polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increase branching ratio in the presence of the dye-labeled nucleotide AF647-C6-dG6P relative to a reference polymerase having the amino acid sequence of SEQ ID NO: 35. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increase $t_{-1}$ value in the presence of the dye-labeled nucleotides relative to a reference polymerase having the amino acid sequence of SEQ ID NO: 35. In some embodiments, the $t_{-1}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. In some embodiments, the $t_{-1}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 35 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 35. In some embodiments, the $t_{pol}$ value of the polymerase is increased by at least about 105%, 110%, 125%, 150%, 175%, 200%, 250%, 500%, 750%, or 1000% relative to the reference polymerase. In some embodiments, the $t_{pol}$ value is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 33. In some embodiments, the polymerase comprises an amino acid sequence that is at least 70%, 80%, 85%, 90%, 95%, 97%, 98%, 99% or 100% identical to the amino acid sequence of SEQ ID NO: 33 and further includes the amino acid mutation K380R, wherein the numbering is relative to the amino acid sequence of SEQ ID NO: 33.

In some embodiments, the polymerase is derived from a bacteriophage Nf polymerase having the amino acid sequence of the SEQ ID NO: 36 as follows:

```
                                                (SEQ ID NO: 36)
  1 msrkmfscdf ettkldder vwaygymeig nldnykigns
    ldefmqwvme iqadlyfhnl 61 kfdgafivnw leqhgfkwsn eglpntynti iskmgqwymi
    dicfgyrgkr klhtviydsl 121 kklpfpvkki akdfqlpllk gdidyhterp vgheitpeey
    eyikndieii araldiqfkq 181 gldrmtagsd slkgfkdils tkkfnkvfpk lslpmdkeir
    kayrggftwl ndkykekeig 241 egmvfdvnsl ypsqmysrpl pygapivfqg kyekdeqypl
    yiqrirfefe lkegyiptiq 301 ikknpffkgn eylknsgvep velyltnvdl eliqehyely
    nveyidgfkf rektglfkdf 361 idkwtyvkth eegakkqlak lmlnslygkf asnpdvtgkv
    pylkddgslg frvgdeeykd 421 pvytpmgvfi tawarfttit aaqacydrii ycdtdsihlt
    gtevpeiikd ivdpkklgyw 481 ahestfkrak ylrqktyiqd iyvkevdgkl kecspdeatt
    tkfsvkcagm tdtikkkvtf 541 dnfavgfssm gkpkpvqvng gvvlvdsvft ik
```

In some embodiments, the polymerase can comprise an amino acid sequence that is at least 85%, 90%, 95%, 97%, 98% or 99% or 100% identical to the amino acid of SEQ ID NO: 36.

In some embodiments, the polymerase comprises an amino acid sequence that is at least 85%, 90%, 95%, 97%, 98% or 99% identical to the amino acid sequence of SEQ ID NO: 36 and further comprises an amino acid mutation at one, two, three or more amino acid positions selected from the group consisting of: 9, 11, 12, 58, 59, 63, 162, 162, 166, 377 and 385, wherein the numbering is relative to the amino acid sequence of SEQ ID NO: 32. Typically, such a polymerase will exhibit reduced 3' to 5' exonuclease activity relative to reference polymerase having the amino acid sequence of SEQ ID NO: 36.

In some embodiments, the polymerase comprises an amino acid sequence that is at least 85%, 90%, 95%, 97%, 98% or 99% identical to the amino acid sequence of SEQ ID NO: 36 and further comprises one, two, three or more amino acid mutations selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the polymerase comprises any one, two, three, four, five or all of these mutations. In some embodiments, the polymerase comprises the amino acid substitution D166A. In some embodiments, the polymerase comprises the amino acid substitutions D9A and D63A. In some embodiments, the polymerase comprises the amino acid substitutions N59D and T12I. Typically, such polymerases will exhibit reduced 3' to 5' exonuclease activity relative to reference polymerase having the amino acid sequence of SEQ ID NO: 36.

In some embodiments, the polymerase comprises an amino acid sequence that is at least 80%, 85%, 90%, 95%, 97%, 98%, 99% or 100% identical to the amino acid sequence of SEQ ID NO: 36 and further comprises an amino acid substitution at one or more positions selected from the group consisting of: 2, 73, 107, 147, 221, 318, 339, 359, 372, 405, 503, 511, 544 and 550, wherein the numbering is relative to the amino acid sequence of SEQ ID NO: 32.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 370. In some embodiments, the mutation is selected from the group consisting of: H370G, H370T, H370S, H370K, H370R, H370A, H370Q, H370W, H370Y and H370F, wherein the numbering is relative to the amino acid sequence of SEQ ID NO: 32. Optionally, this polymerase comprises the amino acid mutation H370R. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 365, wherein the numbering is relative to the amino acid sequence of SEQ ID NO: 32. In some embodiments, the mutation is selected from the group consisting of: T365H, T365F, T365G, T365S, T365K, T365R, T365A, T365Q, T365W and T365Y, wherein the numbering is relative to the amino acid sequence of SEQ ID NO: 32. Optionally, this polymerase comprises the amino acid mutation T365F. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 372, wherein the numbering is relative to the amino acid sequence of SEQ ID NO: 32. In some embodiments, the mutation is selected from the group consisting of: K372G, K372E, K372T, K372S, K372R, K372A, K372Q, K372W, K372Y and K372F, wherein the numbering is relative to the amino acid sequence of SEQ ID NO: 32. Optionally, this polymerase comprises the amino acid mutation K372Y. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 481, wherein the numbering is relative to the amino acid sequence of SEQ ID NO: 32. In some embodiments, the mutation is selected from the group consisting of: A481E, A481F, A481G, A481S, A481R, A481K, A481A, A481T, A481Q, A481W and A481Y, wherein the numbering is relative to the amino acid sequence of SEQ ID NO: 32. Optionally, this polymerase comprises the amino acid mutation A481E. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes a mutation at position 509, wherein the numbering is relative to the amino acid sequence of SEQ ID NO: 32. In some embodiments, the mutation is selected from the group consisting of: K509E, K509F, K509G, K509S, K509R, K509K, K509A, K509T, K509Q, K509W and K509Y, wherein the numbering is relative to the amino acid sequence of SEQ ID NO: 32. Optionally, this polymerase comprises the amino acid mutation K509Y. Typically, this polymerase can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes any one, two, three or more amino acid mutations selected from the group consisting of: S2P, Q73H, R107K, T147A, K221R, V318A, L339M, D359E, E372K, D405E, V503A, K511I, A544R and M550T, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation at any one, two, three or more positions selected from the group consisting of: 9, 12, 14, 15, 58, 59, 61, 63, 98, 129, 176, 185, 186, 187, 195, 208, 246, 247, 248, 251, 252, 256, 300, 302, 310, 357, 360, 362, 365, 367, 368, 369, 370, 371, 372, 373, 374, 375, 376, 377, 378, 380, 383, 384, 385, 386, 387, 389, 390, 392, 399, 411, 419, 430, 455, 475, 477, 481, 483, 493, 494, 497, 507, 509, 511, 526, 528, 529, 531, 535, 544, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprise amino acid mutations at any one, two, three or more positions selected from the group consisting of: 2, 9, 12, 14, 15, 58, 59, 61, 63, 73, 98, 107, 129, 147, 166, 176, 185, 186, 187, 195, 208, 221, 246, 247, 248, 251, 252, 256, 300, 302, 310, 318, 339, 357, 359, 360, 362, 367, 368, 369, 370, 371, 372, 373, 374, 375, 376, 377, 378, 380, 383, 384, 385, 386, 387, 389, 390, 392, 399, 405, 411, 419, 430, 455, 475, 477, 481, 483, 493, 494, 497, 503, 507, 509, 511, 526, 528, 529, 531, 535, 544, 550, 552, 555, 567, 569 and 572, wherein the numbering is relative to the amino acid sequence of SEQ ID NO: 32. In some embodiments, the modifications can include deletions, additions and substitutions. The substitutions can be conservative or non-conservative substitutions. Optionally, this polymerase comprises the amino acid substitution H370R. In some embodiments, the polymerase further comprises one or more mutations reducing the exonuclease activity as described herein such as, for example, the amino acid substitution D166A. Typically, this polymerase can exhibit increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes any one, two, three or more amino acid mutations selected from the group consisting of: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. In some embodiments, the polymerase comprises the amino acid mutations Typically, this polymerase can exhibit an increased branching ratio and/or increased nucleotide binding affinity relative to a reference polymerase having the amino acid sequence of SEQ ID NO: 36. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the branching ratio and/or nucleotide binding affinity is increased in the presence of the dye-labeled nucleotide AF647-C6-dG6P.

In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 365, 372 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions T365F, E372Y and K509Y, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes amino acid mutations at positions 365, 372, 481 and 509, wherein the numbering is relative to the amino acid sequence of SEQ ID NO: 32. In some embodiments, the polymerase comprises an amino acid sequence that is at least 80%, 85%, 90%, 95%, 97%, 98%, 99% or 100% identical to the amino acid sequence of SEQ ID NO: 36 and further includes the amino acid substitutions T365F, E372Y, A481E and K509Y, wherein the numbering is relative to the amino acid sequence of SEQ ID NO: 32. Typically, such polymerases can exhibit an increased branching ratio and/or increased nucleotide binding affinity relative to a reference polymerase having the amino acid sequence of SEQ ID NO: 36. In some embodiments, the branching ratio and/or nucleotide binding affinity is increased in the presence of the dye-labeled nucleotide AF647-C6-dG6P. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprises the amino acid mutation H370R. Optionally, the polymerase can further comprise any one, two, three or more amino acid mutations selected from the group consisting of: S2P, Q73H, R107K, T147A, K221R, V318A, L339M, D359E, E372K, D405E, V503A, K511I, A544R, M550T, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increased branching ratio, increased $t_{-1}$ and/or increased $t_{pol}$ values relative to a reference polymerase having the amino acid sequence of SEQ ID NO: 36. In some embodiments, the branching ratio, $t_{-1}$ value and/or $t_{pol}$ value is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes the amino acid mutation H370R, wherein the numbering is relative to the amino acid sequence of SEQ ID NO: 32. In some embodiments, the polymerase comprises an amino acid sequence that is at least 70%, 80%, 85%, 90%, 95%, 97%, 98%, 99% or 100% identical to the amino acid sequence of SEQ ID NO: 36 and further comprises any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. Optionally, the polymerase can further comprise one, two or three amino acid mutations selected from the group: T365G, T365F, T365G, T365S, T365K, T365R, T365A, T365Q, T365W, T365Y, T365H, H370G, H370T, H370S, H370K, H370R, H370A, H370Q, H370W, H370Y, H370F, E371G, E371H, E371T, E371S, E371K, E371R, E371A, E371Q, E371W, E371Y, E371F, K372G, K372E, K372T, K372S, K372R, K372A, K372Q, K372W, K372Y, K372F, K380E, K380T, K380S, K380R, K380A, K380Q, K380W, K380Y, K380F, A481E, A481F, A481G, A481S, A481R, A481K, A481A, A481T, A481Q, A481W, A481Y, D507H, D507G, D507E, D507T, D507S, D507R, D507A, D507R, D507Q, D507W, D507Y, D507F, K509H, K509G, K509D, K509R, K509E, K509T, K509S, K509R, K509A, K509Q, K509W, K509Y and K509F, wherein the numbering is relative to the amino acid sequence of SEQ ID NO: 32. Typically, this polymerase can exhibit increase branching ratio and/or increased $t_{-1}$ value and/or increased $t_{pol}$ value relative to a reference polymerase having the amino acid sequence of SEQ ID NO: 36. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 32. In some embodiments, the branching ratio, $t_{-1}$ value and/or $t_{pol}$ value is increased in the presence of the dye-labeled nucleotide AF647-C6-dG6P.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation selected from the group: H370G, H370T, H370S, H370K, H370R, H370A, H370Q, H370W, H370Y and H370F, wherein the numbering is relative to the amino acid sequence of SEQ ID NO: 33. Typically, this polymerase can exhibit an increase $t_{-1}$ value in the presence of the dye-labeled nucleotides relative to a reference polymerase having the amino acid sequence of SEQ ID NO: 36. In some embodiments, the $t_{-1}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 33. In some embodiments, the $t_{-1}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes the amino acid mutation H370R, wherein the numbering is relative to the amino acid sequence of SEQ ID NO: 33.

In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes an amino acid mutation selected from the group: K380G, K380E, K380T, K380S, K380R, K380A, K380Q, K380W, K380Y and K380F, wherein the numbering is relative to the amino acid sequence of SEQ ID NO: 33. Typically, this polymerase can exhibit an increased $t_{pol}$ value in the presence of the dye-labeled nucleotides relative to a reference polymerase having the amino acid sequence of SEQ ID NO: 36. In some embodiments, the $t_{pol}$ value of the polymerase is increased by at least about 105%, 110%, 125%, 150%, 175%, 200%, 250%, 500%, 750%, or 1000% relative to the reference polymerase. Optionally, the polymerase can further include one or more mutations reducing 3' to 5' exonuclease activity selected from the group consisting of: D9A, E11A, E11I, T12I, H58R, N59D, D63A, Y162F, Y162C, D166A, Q377A and S385G, wherein the numbering is relative to the amino acid sequence of SEQ ID NO: 33. Optionally, the polymerase can further include any one, two, three or more amino acid mutations selected from the group consisting of: S2P, Q73H, T147A, K221R, V318A, L339M, D359E, H370R, E372K, D405E, V503A, K511I, A544R and M550T, wherein the numbering is relative to the amino acid sequence of SEQ ID NO: 32. In some embodiments, the $t_{pol}$ value is increased in the presence of the dye-labeled nucleotide AF647-C6-dG6P. In some embodiments, the polymerase comprises an amino acid sequence that is at least 70%, 80%, 85%, 90%, 95%, 97%, 98%, 99% or 100% identical to the amino acid sequence of SEQ ID NO: 36 and further includes the amino acid mutation K380R, wherein the numbering is relative to the amino acid sequence of SEQ ID NO: 33.

In some embodiments, the biomolecule is a Phi-29 polymerase comprising the TEV protease recognition sequence at its N-terminal end. Optionally, the biomolecule can also comprise a His tag. The His-tag can be fused to the N-terminus, the C-terminus or any other suitable position of the Phi-29 polymerase. Optionally, the His-tag can be separated from the amino acid residues of the protein by a linker comprising the TEV protease recognition sequence. In some embodiments, the fusion protein comprises an amino acid sequence that is at least 70%, 80%, 85%, 90%, 95%, 99% or 100% identical to the following amino acid sequence:

```
                                                  (SEQ ID NO: 38)
         10         20         30         40         50         60
MNHKVHHHHH HIEGRENLYF QCMELGTLEG SMKHMPRKMY SCAFETTTKV EDCRVWAYGY 70         80         90        100        110        120
MNIEDHSEYK IGNSLDEFMA WVLKVQADLY FHNLKFAGAF IINWLERNGF KWSADGLPNT 130        140        150        160        170        180
YNTIISRMGQ WYMIDICLGY KGKRKIHTVI YDSLKKLPFP VKKIAKDFKL TVLKGDIDYH 190        200        210        220        230        240
KERPVGYKIT PEEYAYIKND IQIIAEALLI QFKQGLDRMT AGSDSLKGFK DIITTKKFKK 250        260        270        280        290        300
VFPTLSLGLD KEVRYAYRGG FTWLNDRFKE KEIGEGMVFD VNSLYPAQMY SRLLPYGEPI 310        320        330        340        350        360
VFEGKYVWDE DYPLHIQHIR CEFELKEGYI PTIQIKRSRF YKGNEYLKSS GGEIADLWLS 370        380        390        400        410        420
NVDLELMKEH YDLYNVEYIS GLKFKATTGL FKDFIDKWTY IKTTSEGAIK QLAKLMLNSL 430        440        450        460        470        480
YGKFASNPDV TGKVPYLKEN GALGFRLGEE ETKDPVYTPM GVFITAWARY TTITAAQACY 490        500        510        520        530        540
DRIIYCDTDS IHLTGTEIPD VIKDIVDPKK LGYWAHESTF KRAKYLRQKT YIQDIYMKEV 550        560        570        580        590        600
DGKLVEGSPD DYTDIKFSVK CAGMTDKIKK EVTFENFKVG FSRKMKPKPV QVPGGVVLVD

DTFTIK
```

In some embodiments, the biomolecule is a mutant Phi-29-like polymerase comprising the TEV protease recognition sequence at its N-terminal end. Optionally, the biomolecule can also comprise a His tag. The His-tag can be fused to the N-terminus, the C-terminus or any other suitable position of the mutant B103 polymerase. Optionally, the His-tag can be separated from the amino acid residues of the protein by a linker comprising the TEV protease recognition sequence. In some embodiments, the fusion protein comprises an amino acid sequence that is at least 70%, 80%, 85%, 90%, 95%, 99% or 100% identical to the following amino acid sequence:

In some embodiments, the biomolecule is a fusion protein comprising a mutant Phi-29-like polymerase comprising a His tag linked to its N-terminal end, and including one or more amino acid substitutions selected from the group consisting of D166A, H370R, F383L and D384N, wherein the numbering is relative to the amino acid sequence of wild type B103 having the amino acid sequence of SEQ ID NO: 32. In some embodiments, the fusion protein comprises all four amino acid substitutions. In some embodiments, the fusion protein comprises an amino acid sequence that is at least 70%,

```
                                                  (SEQ ID NO: 39)
         10         20         30         40         50         60
MHHHHHHLLG GGGENLYFQC GGGGSAAAGS AARKMFSCDF ETTTKLDDCR VWAYGYMEIG 70         80         90        100        110        120
NLDNYKIGNS LDEFMQWVME IQADLYFHNL KFDGAFIVNW LEHHGFKWSN EGLPNTYNTI 130        140        150        160        170        180
ISKMGQWYMI DICFGYKGKR KLHTVIYDSL KKLPFPVKKI AKDFQLPLLK GDIDYHAERP 190        200        210        220        230        240
VGHEITPEEY EYIKNAIEII ARALDIQFKQ GLDRMTAGSD SLKGFKDILS TKKFNKVFPK 250        260        270        280        290        300
LSLPMDKEIR RAYRGGFTWL NDKYKEKEIG EGMVFDVNSL YPSQMYSRPL PYGAPIVFQG 310        320        330        340        350        360
KYEKDEQYPL YIQRIRFEFE LKEGYIPTIQ IKKNPFFKGN EYLKNSGAEP VELYLTNVDL 370        380        390        400        410        420
ELIQEHYEMY NVEYIDGFKF REKTGLFKEF IDKWTYVKTH EKGAKKQLAK LMLNSLYGKF 430        440        450        460        470        480
ASNPDVTGKV PYLKEDGSLG FRVGDEEYKD PVYTPMGVFI TAWARFTTIT AAQACYDRII 490        500        510        520        530        540
YCDTDSIHLT GTEVPEIIKD IVDPKKLGYW AHESTFKRAK YLRQKTYIQD IYAKEVDGKL 550        560        570        580        590        600
IECSPDEATT TKFSVKCAGM TDTIKKKVTF DNFRVGFSST GKPKPVQVNG GVVLVDSVFT
```

80%, 85%, 90%, 95%, 99% or 100% identical to the following amino acid sequence:

```
                                                    (SEQ ID NO: 40)
         10         20         30         40         50         60
MSHHHHHHSM SGLNDIFEAQ KIEWHEGAPG ARGSKHMPRK MFSCDFETTT KLDDCRVWAY 70         80         90        100        110        120
GYMEIGNLDN YKIGNSLDEF MQWVMEIQAD LYFHNLKFDG AFIVNWLEHH GFKWSNEGLP 130        140        150        160        170        180
NTYNTIISKM GQWYMIDICF GYKGKRKLHT VIYDSLKKLP FPVKKIAKDF QLPLLKGDID 190        200        210        220        230        240
YHAERPVGHE ITPEEYEYIK NAIEIIARAL DIQFKQGLDR MTAGSDSLKG FKDILSTKKF 250        260        270        280        290        300
NKVFPKLSLP MDKEIRRAYR GGFTWLNDKY KEKEIGEGMV FDVNSLYPSQ MYSRPLPYGA 310        320        330        340        350        360
PIVFQGKYEK DEQYPLYIQR IRFEFELKEG YIPTIQIKKN PFFKGNEYLK NSGAEPVELY 370        380        390        400        410        420
LTNVDLELIQ EHYEMYNVEY IDGFKFREKT GLFKEFIDKW TYVKTREKGA KKQLAKLMLN 430        440        450        460        470        480
SLYGKFASNP DVTGKVPYLK EDGSLGFRVG DEEYKDPVYT PMGVFITAWA RFTTITAAQA 490        500        510        520        530        540
CYDRIIYCDT DSIHLTGTEV PEIIKDIVDP KKLGYWAHES TFKRAKYLRQ KTYIQDIYAK 550        560        570        580        590        600
EVDGKLIECS PDEATTTKFS VKCAGMTDTI KKKVTFDNFR VGFSSTGKPK PVQVNGGVVL

VDSVFTIK
```

As the skilled artisan will readily appreciate, the scope of the present disclosure encompasses not only the specific amino acid and/or nucleotide sequences disclosed herein, but also, for example, to many related sequences encoding genes and/or peptides with the functional properties described herein. For example, the nucleotide and amino acid sequence of the polymerase of the labeled polymerase conjugate can include any nucleotide and amino acid sequence encoding conservative variants of the polymerases disclosed herein are also within the scope of the present disclosure.

In some embodiments, the labeled polymerase conjugate includes a polymerase linked to a nanoparticle. "Nanoparticle" may refer to any particle with at least one major dimension in the nanosize range. In general, nanoparticles can be made from any suitable metal (e.g., noble metals, semiconductors, etc.) and/or non-metal atoms. Nanoparticles can have different shapes, each of which can have distinctive properties including spatial distribution of the surface charge; orientation dependence of polarization of the incident light wave; and spatial extent of the electric field. The shapes include, but are not limited to: spheres, rods, discs, triangles, nanorings, nanoshells, tetrapods, nanowires, etc.

In one embodiment, the nanoparticle can be a core/shell nanoparticle which typically comprises a core nanoparticle surrounded by at least one shell. For example, the core/shell nanoparticle can be surrounded by an inner and outer shell. In another embodiment, the nanoparticle is a core nanoparticle which has a core but no surrounding shell. The outmost surface of the core or shell can be coated with tightly associated ligands which are not removed by ordinary solvation.

Examples of a nanoparticle include a nanocrystal, such as a core/shell nanocrystal, plus any associated organic ligands (which are not removed by ordinary solvation) or other materials which may coat the surface of the nanocrystal. In one embodiment, a nanoparticle has at least one major dimension ranging from about 1 to about 1000 nm. In other embodiments, a nanoparticle has at least one major dimension ranging from about 1 to about 20 nm, about 1 to about 15 nm, about 1 to about 10 nm or about 1 to 5 nm.

In some embodiments, a nanoparticle can have a layer of ligands on its surface which can further be cross-linked to each other. In some embodiments, a nanoparticle can have other or additional surface coatings which can modify the properties of the particle, for example, increasing or decreasing solubility in water or other solvents. Such layers on the surface are included in the term 'nanoparticle.'

In one embodiment, nanoparticle can refer to a nanocrystal having a crystalline core, or to a core/shell nanocrystal, and may be about 1 nm to about 100 nm in its largest dimension, about 1 nm to about 20 nm, about 1 nm to about 15 nm, about 1 nm to about 10 nm or preferably about 5 nm to about 10 nm in its largest dimension. Small nanoparticles are typically less than about 20 nm in their largest dimension.

"Nanocrystal" as used herein can refer to a nanoparticle made out of an inorganic substance that typically has an ordered crystalline structure. It can refer to a nanocrystal having a crystalline core (core nanocrystal) or to a core/shell nanocrystal.

A core nanocrystal is a nanocrystal to which no shell has been applied. Typically, it is a semiconductor nanocrystal that includes a single semiconductor material. It can have a homogeneous composition or its composition can vary with depth inside the nanocrystal.

A core/shell nanocrystal is a nanocrystal that includes a core nanocrystal and a shell disposed over the core nanocrystal. Typically, the shell is a semiconductor shell that includes a single semiconductor material. In some embodiments, the core and the shell of a core/shell nanocrystal are composed of different semiconductor materials, meaning that at least one atom type of a binary semiconductor material of the core of a core/shell is different from the atom types in the shell of the core/shell nanocrystal.

The semiconductor nanocrystal core can be composed of a semiconductor material (including binary, ternary and quaternary mixtures thereof), from: Groups II-VI of the periodic table, including ZnS, ZnSe, ZnTe, CdS, CdSe, CdTe, HgS, HgSe, HgTe, MgTe; Groups III-V, including GaN, GaP, GaAs, GaSb, InN, InP, InAs, InSb, AlAs, AlP, AlSb, AlS; and/or Group IV, including Ge, Si, Pb.

The semiconductor nanocrystal shell can be composed of materials (including binary, ternary and quaternary mixtures thereof) comprising: ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, or AlSb.

Many types of nanocrystals are known, and any suitable method for making a nanocrystal core and applying a shell to the core may be employed. Nanocrystals can have a surface layer of ligands to protect the nanocrystal from degradation in use or during storage.

"Quantum dot" as used herein refers to a crystalline nanoparticle made from a material which in the bulk is a semiconductor or insulating material, which has a tunable photophysical property in the near ultraviolet (UV) to far infrared (IR) range.

"Water-soluble" or "water-dispersible" is used herein to mean the item can be soluble or suspendable in an aqueous-based solution, such as in water or water-based solutions or buffer solutions, including those used in biological or molecular detection systems as known by those skilled in the art. While water-soluble nanoparticles are not truly 'dissolved' in the sense that term is used to describe individually solvated small molecules, they are solvated (via hydrogen, electrostatic or other suitable physical/chemical bonding) and suspended in solvents which are compatible with their outer surface layer, thus a nanoparticle which is readily dispersed in water is considered water-soluble or water-dispersible. A water-soluble nanoparticle can also be considered hydrophilic, since its surface is compatible with water and with water solubility.

"Hydrophobic nanoparticle" as used herein refers to a nanoparticle which is readily dispersed in or dissolved in a water-immiscible solvent like hexanes, toluene, and the like. Such nanoparticles are generally not readily dispersed in water.

"Hydrophilic" as used herein refers to a surface property of a solid, or a bulk property of a liquid, where the solid or liquid exhibits greater miscibility or solubility in a high-dielectric medium than it does in a lower dielectric medium. By way of example, a material which is more soluble in methanol than in a hydrocarbon solvent such as decane would be considered hydrophilic.

"Coordinating solvents" as used herein refers to a solvent such as TDPA, OP, TOP, TOPO, carboxylic acids, and amines, which are effective to coordinate to the surface of a nanocrystal. 'Coordinating solvents' also include phosphines, phosphine oxides, phosphonic acids, phosphinic acids, amines, and carboxylic acids, which are often used in growth media for nanocrystals, and which form a coating or layer on the nanocrystal surface. Coordinating solvents can exclude hydrocarbon solvents such as hexanes, toluene, hexadecane, octadecene and the like, which do not have heteroatoms that provide bonding pairs of electrons to coordinate with the nanocrystal surface. Hydrocarbon solvents which do not contain heteroatoms such as O, S, N or P to coordinate to a nanocrystal surface are referred to herein as non-coordinating solvents. Note that the term 'solvent' is used in its ordinary way in these terms: it refers to a medium which supports, dissolves or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

As used herein, the term "population" refers to a plurality of nanoparticles having similar physical and/or optical properties. 'Population' can refer to a solution or structure with more than one nanoparticle at a concentration suitable for single molecule analysis. In some embodiments, the population can be monodisperse and can exhibit less than at least 15% rms deviation in diameter of the nanoparticles, and spectral emissions in a narrow range of no greater than about 75 nm full width at half max (FWHM). In the context of a solution, suspension, gel, plastic, or colloidal dispersion of nanoparticles, the nature of the population can be further characterized by the number of nanoparticles present, on average, within a particular volume of the liquid or solid, or the concentration. In a two-dimensional format such as an array of nanoparticles adhered to a solid substrate, the concept of concentration is less convenient than the related measure of particle density, or the number of individual particles per two-dimensional area. In this case, the maximum density would typically be that obtained by packing particles "shoulder-to-shoulder" in an array. The actual number of particles in this case would vary due to the size of the particles—a given array could contain a large number of small particles or a small number of larger particles.

As used herein, the terms "moderate to high excitation" refers to monochromatic illumination or excitation (e.g., laser illumination) having a high power intensity sufficiently high such that the absorbed photons per second for a given sample is between about 200,000 and about 1,600,000.

In one aspect, the nanoparticle is a semiconductor nanoparticle having size-dependent optical and electronic properties. For example, the nanoparticle can emit a fluorescent signal in response to excitation energy. The spectral emission of the nanoparticle can be tunable to a desired energy by selecting the particle size, size distribution, and/or composition of the semiconductor nanoparticle. For example, depending on the dimensions, the semiconductor nanoparticle can be a fluorescent nanoparticle which emits light in the UV-visible-IR spectrum. The shell material can have a bandgap greater than the bandgap of the core material.

In one aspect, the nanoparticle is an energy transfer donor. The nanoparticle can be excited by an electromagnetic source such as a laser beam, multi-photon excitation, or electrical excitation. The excitation wavelength can range between about 190 to about 800 nm including all values and ranges there in between. In some embodiments, the nanoparticle can be excited by an energy source having a wavelength of about 405 nm. In other embodiments, in response to excitation, the nanoparticle can emit a fluorescent signal at about 400-800 nm, or about 605 nm.

In one aspect, the nanoparticle can undergo Raman scattering when subjected to an electromagnetic source (incident photon source) such as a laser beam. The scattered photons have a frequency that is different from the frequency of the incident photons. As result, the wavelength of the scattered photons is different than the incident photon source. In one embodiment, the nanoparticle can be attached to a suitable tag or label to enhance the detectability of the nanoparticle via Raman spectroscopy. The associated tag can be fluorescent or nonfluorescent. Such approaches can be advantageous in avoiding problems that can arise in the context of fluorescent nanoparticles, such as photobleaching and blinking. See, e.g., Sun et al., "Surface-Enhanced Raman Scattering Based Nonfluorescent Probe for Multiplex DNA Detection", Anal. Chem. 79(11):3981-3988 (2007).

In one aspect, the nanoparticle is comprised of a multi-shell layered core which is achieved by a sequential shell material deposition process, where one shell material is added at a time, to provide a nanoparticle having a substantially uniform shell of desired thickness which is substantially free of defects. The nanoparticle can be prepared by sequential, controlled addition of materials to build and/or applying layers of shell material to the core. See e.g., U.S. PCT Application Serial No. PCT/US09/61951 which is incorporated herein by reference as if set forth in full.

In another aspect, a method is provided for making a nanoparticle comprising a core and a layered shell, where the shell comprises at least one inner shell layer and at least one outer shell layer. The method comprises the steps: (a) providing a mixture comprising a core, at least one coordinating solvent; (b) heating the mixture to a temperature suitable for formation of an inner shell layer; (c) adding a first inner shell precursor alternately with a second inner shell precursor in layer additions, to form an inner shell layer which is a desired number of layers thick; (d) heating the mixture to a temperature suitable for formation of an outer shell layer; and (e) adding a first outer shell precursor alternately with a second outer shell precursor in layer additions, to form an outer shell layer which is a desired number of layers thick. In one embodiment, if the coordinating solvent of (a) is not amine, the method further comprises an amine in (a).

In one aspect, at least one coordinating solvent comprises a trialkylphosphine, a trialkylphosphine oxide, phosphonic acid, or a mixture of these. In another aspect, at least one coordinating solvent comprises trioctylphosphine (TOP), trioctylphosphine oxide (TOPO), tetradecylphosphonic acid (TDPA), or a mixture of these. In yet another aspect, the coordinating solvent comprises a primary or secondary amine, for example, decylamine, hexadecylamine, or dioctylamine.

In one aspect, the nanoparticle comprises a core comprising CdSe. In another aspect, the nanoparticle shell can comprise YZ wherein Y is Cd or Zn, and Z is S, or Se. In one embodiment, at least one inner shell layer comprises CdS, and the at least one outer shell layer comprises ZnS.

In one aspect, the first inner shell precursor is $Cd(OAc)_2$ and the second inner shell precursor is bis(trimethylsilyl) sulfide ($TMS_2S$). In other aspects, the first and second inner shell precursors are added as a solution in trioctylphosphine (TOP). In other aspects, the first outer shell precursor is diethylzinc ($Et_2Zn$) and the second inner shell precursor is dimethyl zinc ($TMS_2S$). Sometimes, the first and second outer shell precursors are added as a solution in trioctylphosphine (TOP).

In one aspect, the nanoparticle can have ligands which coat the surface. The ligand coating can comprise any suitable compound(s) which provide surface functionality (e.g., changing physicochemical properties, permitting binding and/or other interaction with a biomolecule, etc.). In some embodiments, the disclosed nanoparticle has a surface ligand coating (in direct contact with the external shell layer) that adds various functionalities which facilitate it being water-dispersible or soluble in aqueous solutions. There are a number of suitable surface coatings which can be employed to permit aqueous dispersibility of the described nanoparticle. For example, the nanoparticle(s) disclosed herein can comprise a core/shell nanocrystal which is coated directly or indirectly with lipids, phospholipids, fatty acids, polynucleic acids, polyethylene glycol (PEG), primary antibodies, secondary antibodies, antibody fragments, protein or nucleic acid based aptamers, biotin, streptavidin, proteins, peptides, small organic molecules (e.g., ligands), organic or inorganic dyes, precious or noble metal clusters. Specific examples of ligand coatings can include, but are not limited to, amphiphilic polymer (AMP), bidentate thiols (i.e., DHLA), tridentate thiols, dipeptides, functionalized organophosphorous compounds (e.g., phosphonic acids, phosphinic acids), etc.

Non-Blinking Nanoparticles

Provided herein are nanoparticles which exhibit modulated, reduced, or no intermittent (e.g., continuous, non-blinking) fluorescence.

In one aspect, the nanoparticle or populations thereof exhibit modulated, reduced or non-detectable intermittent (e.g., continuous, etc.) fluorescence properties. The nanoparticles can have a stochastic blinking profile in a timescale which is shifted to very rapid blinking or very slow or infrequent blinking relative to a nanoparticle previously described in the art (conventional nanoparticles are described in the art as having on-time fractions of <0.2 in the best of conditions examined). For example, the nanoparticles may blink on and off on a timescale which is too rapid to be detected under the methods employed to study this behavior.

In one aspect the nanoparticle or populations thereof are photostable. The nanoparticles can exhibit a reduced or no photobleaching with long exposure to moderate to high intensity excitation source while maintaining a consistent spectral emission pattern.

In one aspect, the nanoparticle or populations thereof have a consistently high quantum yield. For example, the nanoparticles can have a quantum yield greater than: about 10%, or about 20%, or about 30%, or about 40%, or about 50%, or about 60%, or about 70% or about 80%.

As used herein, fluorescence (or Forster) resonance energy transfer (FRET) is a process by which a fluorophore (the donor) in an excited state transfers its energy to a proximal molecule (the acceptor) by nonradiative dipole-dipole interaction (Forster, T. "Intermolecular Energy Migration and Fluorescence", Ann. Phys., 2:55-75, 1948; Lakowicz, J. R., *Principles of Fluorescence Spectroscopy*, 2nd ed. Plenum, N.Y. 367-394., 1999).

FRET efficiency (E) can be defined as the quantum yield of the energy transfer transition, i.e. the fraction of energy transfer event occurring per donor excitation event. It is a direct measure of the fraction of photon energy absorbed by the donor which is transferred to an acceptor, as expressed in Equation 1: $E = k_{ET}/k_f + k_{ET} + \Sigma k_i$ where $k_{ET}$ is the rate of energy transfer, $k_f$ the radiative decay rate and the $k_i$ are the rate constants of any other de-excitation pathway.

FRET efficiency E generally depends on the inverse of the sixth power of the distance r (nm) between the two fluorophores (i.e., donor and acceptor pair), as expressed in Equation 2: $E = 1/1 + (r/R_0)^6$.

The distance where FRET efficiency is at 50% is termed $R_0$, also know as the Forster distance. $R_0$ can be unique for each donor-acceptor combination and can range from between about 5 nm to about 10 nm. Therefore, the FRET efficiency of a donor (i.e., nanoparticle) describes the maximum theoretical fraction of photon energy which is absorbed by the donor (i.e., nanoparticle) and which can then be transferred to a typical organic dye (e.g., fluoresceins, rhodamines, cyanines, etc.).

In some embodiments, the disclosed nanoparticles are relatively small (i.e., <15 nm) and thus may be particularly well suited to be used as a donor or an acceptor in a FRET reaction. That is, some embodiments of the disclosed nanoparticles exhibit higher FRET efficiency than conventional nanoparticles and thus are excellent partners (e.g., donors or acceptors) in a FRET reaction.

"Quantum yield" as used herein refers to the emission efficiency of a given fluorophore assessed by the number of times which a defined event, e.g., light emission, occurs per photon absorbed by the system. In other words, a higher quantum yield indicates greater efficiency and thus greater brightness of the described nanoparticle or populations thereof.

Any suitable method can be used to measure quantum yield. In one example, quantum yield can be obtained using standard methods such as those described in Casper et al (Casper, J.V.; Meyer, T.J. *J. Am. Chem. Soc.* 1983, 105, 5583) and can be analyzed relative to known fluorophores chosen as appropriate for maximal overlap between standard emission and sample emission (e.g., fluorescein, Rhodamine 6G, Rhodamine 101). Dilute solutions of the standard and sample can be matched or nearly matched in optical density prior to acquisition of absorbance and emission spectra for both. The emission quantum yield ($\phi_{em}$) then can be determined according to Equation 3:

$$\phi_{em} = \phi'_{em}\left(\frac{I}{I'}\right)\left(\frac{A'}{A}\right)$$

where A and A' are the absorbances at the excitation wavelength for the sample and the standard respectively and I and I' are the integrated emission intensities for the sample and standard respectively. In this case $\phi'_{em}$ can be the agreed upon quantum yield for the standard.

Disclosed herein are fluorescent nanoparticles with superior and robust properties which significantly expand the applications in which nanoparticles are useful. These nanoparticles are superior and surprisingly robust in that they are simultaneously stable, bright, and sensitive to environmental stimuli. Moreover, the disclosed nanoparticles have limited or no detectable blinking (i.e., where the nanoparticle emits light non-intermittently when subject to excitation), are highly photostable, have a consistently high quantum yield, are small (e.g., ≤20 nm) and can act as a donor which undergoes FRET with a suitable acceptor moiety (e.g., fluorescent dyes, etc.). The photostability of these nanoparticles is reflected in their exhibiting reduced or no photobleaching (i.e., fading) behavior when subjected to moderate to high intensity excitation for at least about 20 minutes. Additionally, the particles can remain substantially free from photo-induced color shifting.

Put another way, the nanoparticles can maintain a consistent spectral emission pattern (i.e., maintain the ability to fluoresce) even when exposed to a large quantity of photons (i.e., moderate to high intensity excitation) for a long period of time. This unique combination of characteristics makes these types of nanoparticles sensitive tools for single molecule analysis and other sensitive high throughput applications. Moreover, these properties make the nanoparticles particularly well suited for use as highly efficient donor fluorophores in energy transfer reactions such as FRET reactions (i.e., high FRET efficiency) or other reactions as well as applications which require or are enhanced by greater response to the environment.

Without being bound to a particular theory, blinking or fluorescence intermittency may arise during the nanoparticle charging process when an electron is temporarily lost to the surrounding matrix (Auger ejection or charge tunneling) or captured to surface-related trap states. The nanoparticle is "on" or fluorescing when all of the electrons are intact and the particle is "neutral" and the particle is "off" or dark when the electron is lost and the particle is temporarily (or in some cases permanently) charged. It is important to note that the complete suppression of blinking may not necessarily be required and in some instances may not be desirable. Blinking which occurs on a timescale much shorter or much longer than the interrogation period for a particular assay has relatively little impact on the performance of the system. Thus, nanoparticles and nanoparticle populations having modulated blinking properties, where blinking occurs on a very short or very fast timescale relative to the assay interrogation periods are also useful and fall within the scope of the present disclosure. Localization of timescale or simply pushing timescale to one side (e.g., to where the blinking is undetectable within the assay system) can provide substantial benefit in application development.

The blinking behavior of the nanoparticles described herein can be analyzed and characterized by any suitable number of parameters using suitable methodologies. The probability distribution function of the "on" and "off" blinking time durations (i.e., blinking behavior) can be determined using the form of an inverse power law. A value, alpha ($\alpha$) can be calculated, wherein $\alpha$ represents an exponent in the power law. As the percentage of the population which is non-blinking increases, the value of $\alpha_{on}$ theoretically approaches zero. In conventional nanoparticle populations previously described, $\alpha_{on}$ typically ranges from about 1.5 to about 2.5, under moderate to high excitation energy.

Most alpha calculations can use a predetermined threshold to determine the "on" and "off" values of alpha-on and alpha-off (i.e., $\alpha_{on}$ and $\alpha_{off}$). Typically, an alpha estimator which calculates the on/off threshold for each dot individually can be employed. The data can be represented by a plot of signal versus frequency, and typically appears as a series of Gaussian distributions around the "off state" and one or more "on states." A log-log plot of frequency versus time for each period of time that the dot is "on" provides a straight line having a slope of $\alpha_{on}$. The value of alpha-off ($\alpha_{off}$) can be similarly determined.

In a specific example (the "TIRF example"), the fluorescent intermittency measurements can be made using a Total Internal Reflection Fluorescence (TIRF) microscope fitted with a 60× oil immersion objective lens, using a dual view with a longpass filter on the acceptor side and a bandpass filter on the donor side. Using the TIRF setup, the nanoparticles were imaged at 30 Hz (33 ms), typically for 5 minutes, to produce a movie showing the time and intensity of the emitted light for each individual spot (corresponding to a single particle) within a binned frame which was 33 ms long; the intensity for each binned frame can be integrated. Each data set can be manually analyzed dot-by-dot, and aggregates and other artifacts were excluded. From the edited results, the following parameters can be calculated: alpha-on ("$\alpha_{on}$"); alpha-off ("$\alpha_{off}$"); the percent on; longest on/longest off; overlap scores; and the median values for each of these parameters.

In some aspects, provided herein is a nanoparticle or population thereof which has an $\alpha_{on}$ of less than about 1.5, $\alpha_{on}$ of less than about 1.4, $\alpha_{on}$ of less than about 1.3, $\alpha_{on}$ of less than about 1.2, or an $\alpha_{on}$ of less than about 1.1, under moderate to high excitation energy. In some embodiments, at least about 50%, at least about 60%, at least about 70%, at least about 80%, at least about 90%, at least about 95%, at least about 98%, at least about 99% or more of the population has an $\alpha_{on}$ of less than about 1.5, $\alpha_{on}$ of less than about 1.4, $\alpha_{on}$ of less than about 1.3, $\alpha_{on}$ of less than about 1.2, or $\alpha_{on}$ of less than about 1.1 for the time observed, under moderate to high excitation energy. The observation time can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy. Compositions comprising such a nanoparticle and populations thereof also are contemplated.

In some aspects, provided herein is a nanoparticle or a population thereof having a stochastic blinking profile which is either undetectable or rare (e.g., no more than 1-2 events during the interrogation period) over an observed timescale. In this case, "undetectable" encompasses the situation in which evidence might exist for ultra-fast blinking on a timescale which is faster than the binning timescale (e.g., dimming and brightening from bin to bin) but there are no "off" events persisting for longer than the bin time. Therefore, in some embodiments, a nanoparticle or population thereof has a stochastic blinking profile which is undetectable for at least about 50%, at least about 60%, at least about 70%, at least about 80%, at least about 85%, at least about 90%, at least about 95%, at least about 98%, at least about 99% or more of the time observed, under moderate to high excitation energy. In other embodiments, at least about 50%, at least about 60%, at least about 70%, at least about 80%, at least about 90%, at least about 95%, at least about 98%, at least about 99% or more of the individual nanoparticles in a population have a stochastic blinking on a timescale which is undetectable for the time observed, under moderate to high excitation energy. The timescale can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

In some aspects, the longest on and longest off values can relate to the longest period of time a nanoparticle is observed to be in either the "on" or the "off" state. In particular, the longest on value can be important to determining the length of time and amount of data which may be measured in a particular assay.

Thus, the blinking characteristics of the nanoparticles herein can also be characterized by their on-time fraction, which represents the (total on-time)/(total experiment time). Under the TIRF example disclosed herein, the total on time can be determined by the total number of frames "on" multiplied by 33 ms, and the total experiment time is 5 minutes. For example, the blinking properties of the disclosed nanoparticles or populations thereof can be determined under continuous irradiation conditions using a 405 nm laser with an intensity of about 1 watt per $cm^2$ during an experimental window of at least 5 minutes.

On-time fractions can be used to characterize the blinking behavior of a single nanoparticle or of a population of nanoparticles. It is important to note that the on-time fraction for a particular nanoparticle or population of nanoparticles is a function of the specific conditions under which the percent of blinking or "non-blinking" nanoparticles is determined.

In some aspects, provided herein is a nanoparticle or population thereof having an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. In some embodiments, a nanoparticle or populations thereof having a percent on-time of about 98%, about 99% (i.e., on-time fraction of about 0.99) can be considered to be "non-blinking," under moderate to high excitation energy. In some embodiments, at least about 50%, at least about 60%, at least about 70%, at least about 80%, at least about 90%, at least about 95%, at least about 98%, at least about 99%, or more of the individual nanoparticles in a population of nanoparticles can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. The on-times of the nanoparticles are typically for at least about 5 minutes, at least about 10 minutes, at least about 15 minutes, at least about 20 minutes, at least about 30 minutes, at least about 45 minutes, at least about 60 minutes, at least about 70 minutes, at least about 80 minutes, at least about 90 minutes, at least about 120 minutes under moderate to high intensity excitation of the nanoparticle or nanoparticle population. Under one set of conditions, continuous irradiation with 405 nm laser with an approximate intensity of 1 watt per $cm^2$ was used to determine the stochastic blinking profile.

In some embodiments, nanoparticles which have a stochastic (i.e., random) blinking profile in a timescale which shifts from very rapid blinking or very slow/infrequent blinking (relative to a nanoparticle previously described in the art) can be considered to have modulated blinking properties. In some embodiments, these nanoparticles may blink on and off on a timescale which is too rapid to be detected under the methods employed to study this behavior. Thus, certain nanoparticles can effectively appear to be "always on" or to have on-time fractions of about 0.99, when in fact they flicker on and off at a rate too fast or too slow to be detected. Such flickering has relatively little impact on the performance of a system, and for practical purposes such nanoparticles can be considered to be non-blinking.

In some instances, the disclosed nanoparticles and populations thereof are not observed to blink off under the analysis conditions, and such particles can be assessed as "always on" (e.g., non-blinking). The percent of usable dots which are "always on" can be a useful way to compare nanoparticles or populations of nanoparticles. However, a determination of "always on" may mean that the "off" time was insufficient to provide enough a signal gap for accurate determination and thus the value in the regime of particles is insufficient to calculate. Even these "non-blinking" nanoparticles may flicker on and off on a timescale which is not detected under the conditions used to assess blinking. For example, certain particles may blink on a timescale which is too fast to be detected, or they may blink very rarely, and, in some embodiments, such particles may also be considered to be "always-on" or non-blinking, as the terms are used herein.

In one aspect, provided herein is a nanoparticle or population thereof which demonstrate some fluctuation in fluorescence intensity. In some embodiments, the change in fluorescence intensity for the nanoparticle is less than about 5%, less than about 10%, less than about 20%, or less than about 25% of the nanoparticle or populations thereof at its greatest intensity, under moderate to high excitation energy. In some embodiments, such changes in fluorescence intensity of less than about 5%, less than about 10%, less than about 20%, or less than about 25% of the highest intensity can occur in at least about 50%, at least about 60%, at least about 70%, at least about 80%, at least about 85%, at least about 90%, at least about 95%, at least about 98%, at least about 99% of the nanoparticles in the population, under moderate to high excitation energy.

In some aspects, the nanoparticles with modulated, reduced or no intermittent (e.g., continuous, non-blinking) fluorescence provided herein can comprise of a core and a layered gradient shell. In some embodiments, the nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed nanoparticle(s) is less than about 15 nm. See for example, PCT Application Serial No. PCT US/09/61951. See also PCT/US09/061,951 and PCT/US09/061,953 both filed on Oct. 23, 2009.

As discussed previously, the disclosed nanoparticles may be particularly well suited for use as a donor or acceptor which undergoes FRET with a suitable complementary partner (donor or acceptor). A "FRET capable" nanoparticle refers to a nanoparticle which can undergo a measurable FRET energy transfer event with a donor or an acceptor moiety. In some embodiments, a FRET capable nanoparticle is one which has at least about 25% efficiency in a FRET reaction.

Thus, in one aspect, a FRET capable fluorescent nanoparticle or population thereof with modulated, reduced or non intermittent (e.g., continuous, etc.) fluorescence is provided. In some embodiments, the nanoparticle is the donor in a FRET reaction. In some embodiments, the nanoparticle is the acceptor in the FRET reaction.

In some embodiments, the FRET capable non-blinking fluorescent nanoparticle(s) disclosed herein can comprise a core and a layered gradient shell. In some embodiments, the FRET capable non-blinking nanoparticle(s) disclosed herein can be comprised of a nanocrystal core (e.g., CdSe, etc.), at least one inner (intermediate) shell layer (e.g., CdS, etc.), and at least one outer (external) shell layer (e.g., ZnS, etc.). In some embodiments, the inner and/or outer shell layers are each comprised of two or more discrete monolayers of the same material. In some embodiments, the largest dimension of the disclosed FRET capable nanoparticle(s) is less than about 15 nm.

In some embodiments, the nanoparticle or population thereof has a FRET efficiency of at least about 20%, at least about 40%, at least about 50%, at least about 60%, at least about 70%, at least about 80%, at least about 90%, at least about 95%, at least about 98%, at least about 99%, or greater.

In some embodiments, at least about 30%, at least about 40%, at least about 50%, at least about 60% at least about 70%, at least about 80%, at least about 90%, at least about 95%, at least about 98%, at least about 99% or more of the individual nanoparticles in the population have a FRET efficiency of at least about 20%, at least about 40%, at least about 50%, at least about 60%, at least about 70%, at least about 80%, at least about 90%, at least about 95%, at least about 98%, at least about 99% or more.

In some embodiments, the FRET efficiency of the disclosed nanoparticle or population thereof can be maintained for at least about the first 10%, at least about the first 20%, at least about the first 30%, at least about the first 40%, at least about the first 50%, at least about the first 60%, at least about the first 70%, at least about the first 80%, at least about the first 90% or more of the total emitted photons under conditions of moderate to high excitation.

As discussed above, the nanoparticle(s) provided herein can be considered to be surprisingly photostable. In particular, the nanoparticle and populations described herein can be photostable over an extended period of time while maintaining the ability to effectively participate in energy transfer (i.e., FRET) reactions. The disclosed nanoparticles can be stable under high intensity conditions involving prolonged or continuous irradiation over an extended period of time from a moderate to high excitation source.

Thus, in one aspect, provided herein is a non-blinking fluorescent nanoparticle and population thereof which is photostable.

In some embodiments, the disclosed photostable nanoparticle and population thereof can have an emitted light or energy intensity sustained for at least about 10 minutes and does not decrease by more than about 20% of maximal intensity achieved during that time. Further, these nanoparticles and populations thereof can have a wavelength spectrum of emitted light which does not change more than about 10% upon prolonged or continuous exposure to an appropriate energy source (e.g. irradiation).

In one embodiment, the photostable nanoparticles disclosed herein can remain photostable under moderate to high intensity excitation from at least about 10 minutes to about 2 hours. In another embodiment, the photostable nanoparticles disclosed herein can remain photostable under moderate to high intensity excitation from at least about 10 minutes to about 10 hours. In still another embodiment, the photostable nanoparticles disclosed herein can remain photostable under moderate to high from about 10 minutes to about 48 hours. However, it should be appreciated, that these are just example photostable times for the disclosed nanoparticles, in practice the nanoparticles can remain photostable for longer periods of time depending on the particular application.

It should be appreciated that nanoparticles which are photostable over longer timescales in combination with moderate to high excitation energy sources are well suited for more sensitive and broad-ranging applications such as the real-time monitoring of single molecules involving FRET. That is, the nanoparticle and population thereof described herein can be photostable over an extended period of time while maintaining the ability to effectively participate in energy transfer (i.e., FRET) reactions, which makes the subject nanoparticles particularly useful for many applications involving the real-time monitoring of single molecules. As such, in some embodiments the photostable nanoparticles disclosed herein have FRET efficiencies of at least about 20%.

In some embodiments, the disclosed nanoparticles are stable upon prolonged or continuous irradiation (under moderate to high excitation rate) in which they do not exhibit significant photo-bleaching on the timescales indicated. Photobleaching can result from the photochemical destruction of a fluorophore (and can be characterized by the nanoparticles losing the ability to produce a fluorescent signal) by the light exposure or excitation source used to stimulate the fluorescence. Photobleaching can complicate the observation of fluorescent molecules in microscopy and the interpretation of energy transfer reactions because the signals can be destroyed or diminished increasingly as timescales for the experiment increase or the energy intensity increases.

Photobleaching can be assessed by measuring the intensity of the emitted light or energy for a nanoparticle or nanoparticle population using any suitable method. In some embodiments, the intensity of emitted light or energy from the disclosed nanoparticle or population thereof does not decrease by more than about 20% (and in some embodiments, not more than about 10%) upon prolonged or continuous irradiation (under moderate to high excitation rate). In some embodiments, the intensity of emitted light from the disclosed nanoparticle or population thereof does not decrease by more than about 20%, about 15%, about 10%, about 5% or less upon irradiation from about 10 minutes, about 20 minutes, about 30 minutes, about 45 minutes, about 60 minutes, about 90 minutes, about 2 hours, about 3 hours to about 4 hours, under moderate to high excitation energy.

In some embodiments, the photostable nanoparticles provided herein further demonstrate enhanced stability in which they exhibit a reduction in or absence of spectral shifting during prolonged excitation. In the conventional nanoparticles previously described in the art, increased exposure to an excitation source—whether via increase time or power—results in a spectral shift of the wavelength emission wavelength profile of a nanoparticle and populations thereof from a longer wavelength to an increasingly shorter wavelength. Such spectral shifting of emission wavelength represents a significant limitation as precise resolution of emission spectra is required for applications which require rapid detection, multi-color analysis, and the like. Shifting of any significance then requires that the wavelength emissions used in an assay be sufficiently separated to permit resolution, thus reducing the number of colors available as well as increasing signal to noise ratio to an unacceptable level as the initial spectral profile cannot be relied upon once spectral shifting begins. Such shifting may require shortened observation times or use of fluorophores with widely separated emission spectra. The nanoparticles provided herein have little to no spectral shift, particularly over extended periods of excitation.

Wavelength emission spectra can be assessed by any suitable method. For example, spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Thus, in some embodiments, the photostable nanoparticle and population thereof has a wavelength spectrum of emitted light which does not change more than about 10% upon prolonged or continuous exposure to an appropriate energy source (e.g. irradiation) over about 4 minutes to about 10 minutes, under moderate to high excitation energy. In some embodiments, the wavelength emission spectra does not change more than about 5%, more than about 10%, more than about 20% over 10 minutes, about 20 minutes, about 30 minutes, about 45 minutes, about 60 minutes, about 90 minutes, about 2 hours, about 3 hours to about 4 hours.

It should be appreciated that there can be various other objective indicia of nanoparticle photostability. For example, a nanoparticle can be classified as photostable when the nanoparticle, under moderate to high excitation, emits about 1,000,000 to about 100,000,000 photons or more preferably about 100,000,001 to about 100,000,000,000 photons or even more preferably more than about 100,000,000,000 photons before becoming non-emissive (i.e., bleached).

A nanoparticle with modulated, reduced or no fluorescent intermittency (e.g., continuous, non-blinking, etc.); reduced or absent spectral shifting; low to no photobleaching; high quantum yield; and sufficient FRET efficiency can be of any suitable size. Typically, it is sized to provide fluorescence in the UV-visible portion of the electromagnetic spectrum as this range is convenient for use in monitoring biological and biochemical events in relevant media. The disclosed nanoparticle and population thereof can have any combination of the properties described herein.

Thus, in some embodiments the nanoparticle or population thereof has modulated or no blinking, are photostable (e.g., limited or no photobleaching, limited or no spectral shift), has high quantum yield, have high FRET efficiency, has a diameter of less than about 15 nm, is spherical or substantially spherical shape, or any combination of all these properties as described herein.

Likewise, in some embodiments, at least about 50%, at least about 60%, at least about 70%, at least about 80%, at least about 90%, at least about 95%, at least about 98%, at least about 99%, or more of the individual nanoparticles in a population of nanoparticles have modulated or no blinking, are photostable (e.g., limited or no photobleaching, limited or no spectral shift), have high quantum yield, have high FRET efficiency, have diameters of less than about 15 nm, are spherical or substantially spherical shape, or any combination of or all of these properties as described herein.

In one aspect, the FRET capable, non-blinking and/or photostable nanoparticle or population thereof provided herein has a maximum diameter of less than about 20 nm. In some embodiments, the nanoparticle(s) can be less than about 15 nm, less than about 10 nm, less than about 8 nm, less than about 6 nm, less than about 5 nm, less than about 4 nm, less than about 3 nm or less in its largest diameter when measuring the core/shell structure. Any suitable method may be used to determine the diameter of the nanoparticle(s). The nanoparticle(s) provided herein can be grown to the desired size using any of the methods disclosed herein. In some embodiments, at least about 50%, at least about 60%, at least about 70%, at least about 80%, at least about 90%, at least about 95%, at least about 98%, at least about 99%, or more of the individual members of a population of nanoparticles have maximum diameters (when measuring the core, core/shell or core/shell/ligand structure) which are less than about 20 nm, less than about 15 nm, less than about 10 nm, less than about 8 nm, less than about 6 nm, less than about 5 nm, less than about 4 nm, less than about 3 nm or less.

The FRET capable, non-blinking and/or photostable nanoparticle(s) provided herein and populations thereof can be spherical or substantially spherical. In some embodiments, a substantially spherical nanoparticle can be one where any two radius measurements do not differ by more than about 10%, about 8%, about 5%, about 3% or less. In some embodiments, at least about 50%, at least about 60%, at least about 70%, at least about 80%, at least about 90%, at least about 95%, at least about 98%, at least about 99%, or more of the individual members of a population of nanoparticles are spherical or substantially spherical.

Nanoparticles can be synthesized in shapes of different complexity such as spheres, rods, discs, triangles, nanorings, nanoshells, tetrapods, nanowires and so on. Each of these geometries can have distinctive properties: spatial distribution of the surface charge, orientation dependence of polarization of the incident light wave, and spatial extent of the electric field. In some embodiments, the nanoparticles are substantially spherical or spheroidal.

For embodiments where the nanoparticle is not spherical or spheroidal, e.g. rod-shaped, it may be from about 1 to about 15 nm, from about 1 nm to about 10 nm, or 1 nm to about 5 nm in its smallest dimension. In some such embodiments, the nanoparticles may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm and ranges between any two of these values.

The single-color preparation of the nanoparticles disclosed herein can have individual nanoparticles which are of substantially identical size and shape. Thus, in some embodiments, the size and shape between the individual nanoparticles in a population of nanoparticles vary by no more than about 20%, no more than about 15%, no more than about 10%, no more than about 8%, no more than about 6%, no more than about 5%, no more than about 4%, no more than about 3% or less in at least one measured dimension. In some embodiments, disclosed herein is a population of nanoparticles, where at least about 60%, at least about 70%, at least about 80%, at least about 90%, at least about 95%, and ideally about 100% of the particles are of the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values. Such a collection of particles is sometimes referred to as being a "monodisperse" population.

The color (emitted light) of a nanoparticle can be "tuned" by varying the size and composition of the particle. Nanoparticles as disclosed herein can absorb a wide spectrum of wavelengths, and emit a relatively narrow wavelength of light. The excitation and emission wavelengths are typically different, and non-overlapping. The nanoparticles of a monodisperse population may be characterized in that they produce a fluorescence emission having a relatively narrow wavelength band. Examples of emission widths include less than about 200 nm, less than about 175 nm, less than about 150 nm, less than about 125 nm, less than about 100 nm, less than about 75 nm, less than about 60 nm, less than about 50 nm, less than about 40 nm, less than about 30 nm, less than about 20 nm, and less than about 10 nm. In some embodiments, the width of emission is less than about 60 nm full width at half maximum (FWHM), or less than about 50 nm FWHM, and sometimes less than about 40 nm FWHM, less than about 30 nm FWHM or less than about 20 nm FWHM. In some embodiments, the emitted light preferably has a symmetrical emission of wavelengths.

The emission maxima of the disclosed nanoparticle and population thereof can generally be at any wavelength from about 200 nm to about 2,000 nm. Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

As discussed previously, the disclosed nanoparticle or populations thereof can comprise a core and a layered shell, wherein the shell includes at least one inner (intermediate) shell layer comprising a first shell material and at least one outer (external) shell layer comprising a second shell material, and wherein the layered shell is substantially uniform in coverage around the core and is substantially free of defects.

Thus, in one aspect, the nanoparticle or population thereof comprises a core ($M^1Y$) and a layered shell, wherein the shell comprises m inner shell monolayers comprising a first shell material ($M^1X$)$_m$ and n outer shell monolayers comprising a second shell material ($M^2X$)$_n$, wherein M can be a metal atom and X can be a non-metal atom, each of m and n is independently an integer from 1 to 10, and the layered shell is substantially uniform in coverage around the core and is substantially free of defects. In specific embodiments, the sum of m+n is 3-20, or 5-14, or 6-12, or 7-10.

In certain embodiments, the disclosed nanoparticles can further comprise one or more additional shell layers between the at least one inner shell layer and the at least one outer shell layer.

In some embodiments, the nanoparticle core and population thereof can have a first bandgap energy and the first shell material can have a second bandgap energy, wherein the second bandgap energy can be greater than the first bandgap energy.

In a further aspect, provided herein is a nanoparticle or population thereof comprising a core and a layered shell, wherein the shell comprises sequential monolayers comprising an alloyed multi-component shell material of the form $M^1_xM^2_yX$, where $M^1$ and $M^2$ can be metal atoms and X can be a non metal atom, where the composition becomes successively enriched in $M^2$ as the monolayers of shell material are deposited, where x and y represent the ratio of $M^1$ and $M^2$ in the shell material, and wherein the monolayered shell is substantially uniform in coverage around the core and is substantially free of defects. In some embodiments, the layered shell sometimes has about 3-20 monolayers of shell material, sometimes about 5-14 monolayers of shell material, sometimes about 6-12 monolayers of shell material, or sometimes about 7-10 monolayers of shell material.

In one aspect, provided herein is a nanoparticle or population thereof comprising a core and a layered shell having a gradient potential, wherein the shell comprises at least one inner shell layer and at least one outer shell layer, and wherein the layered shell is substantially uniform in coverage around the core and is substantially free of defects.

The layered shell may be engineered such that the sequential monolayers are selected to provide a gradient potential from the nanoparticle core to the outer surface of the nanoparticle shell. The steepness of the potential gradient may vary depending on the nature of the shell materials selected for each monolayer or group of monolayers. For example, a nanoparticle comprising several sequential monolayers of the same shell material may reduce the potential through a series of steps, while a more continuous gradient may be achievable through the use of sequential monolayers of a multi-component alloyed shell material. In some embodiments, both single component and multi-component shell materials may be applied as different monolayers of a multi-layer shell on a nanoparticle.

The nanoparticles can be synthesized as disclosed to the desired size by sequential, controlled addition of materials to build and/or apply monolayers of shell material to the core. This is in contrast to conventional methods of adding shells where materials (e.g., diethylzinc and bis(trimethylsilyl)sulfide) are added together. Sequential addition permits the formation of thick (e.g., >2 nm) relatively uniform individual shells (e.g., uniform size and depth) on a core. The layer additions generally require the addition of an appropriate amount of the shell precursors to form a single monolayer, based on the starting size of the underlying core. This means that as each monolayer of shell material is added, a new "core" size must be determined by taking the previous "core" size and adding to it the thickness of just-added shell monolayer. This leads to a slightly larger volume of the following shell material needing to be added for each subsequent monolayer of shell material being added.

Each monolayer of shell material can be independently selected, and may be made up of a single component, or may comprise a multi-component (e.g., alloyed, etc.) shell material. In some embodiments, it is suitable to apply one or more sequential monolayers of a first shell material, followed by one or more sequential monolayers of a second shell material. This approach allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited.

In some embodiments, the layered shell can be about 3-20 monolayers of shell material thick, sometimes about 5-14 monolayers of shell material thick, sometimes about 6-12 monolayers of shell material thick or sometimes about 7-10 monolayers of shell material thick. In some embodiments, at least one inner shell layer can be comprised of about 3-5 monolayers, sometimes about 3-7 monolayers, of the first shell material. In other embodiments, at least one outer shell layer can be comprised of about 3-5 monolayers, sometimes about 3-7 monolayers, of the second shell material. In some embodiments, the inner shell layer can be at least 3 monolayers thick; in other embodiments, the outer shell layer can be at least 3 monolayers thick. The individual monolayers can be formed by the controlled, sequential addition of the layer materials methods described herein. The monolayers may not always be completely distinct as they may, in some embodiments, be a latticing between the surfaces of contacting monolayers.

In certain embodiments, provided herein are nanoparticles having a thick, uniform, layered shell, as described herein, wherein the core comprises CdSe, the at least one inner shell layer comprises CdS, and the at least one outer shell layer comprises ZnS. In a particular embodiment, provided herein is a nanoparticle or population thereof having a CdSe core and a layered shell comprising 4CdS+3.5ZnS layers. In some embodiments, provided herein is a nanoparticle which consists essentially of CdSe/4CdS–3.5ZnS.

Also disclosed herein are methods of making a nanoparticle and population thereof with modulated, reduced or no fluorescence intermittency or "blinking". These nanoparticles can be small, photostable, bright, highly FRET efficient or some combination thereof. These nanoparticles can have a multi-shell layered core achieved by a sequential shell material deposition process, whereby one shell material is added at a time, to provide a nanoparticle having a substantially uniform shell of desired thickness which is substantially free of defects.

In one aspect, provided herein is a method for making a nanoparticle or population thereof with modulated, reduced or no fluorescence intermittency, comprising: providing a mixture comprising a core and at least one coordinating solvent; adding a first inner shell precursor alternately with a second inner shell precursor in layer additions, to form an inner shell layer which is a desired number of layers thick; and adding a first outer shell precursor alternately with a second outer shell precursor in layer additions, to form an outer shell layer which is a desired number of layers thick. If the coordinating solvent of is not amine, the method further comprises an amine in.

In some embodiments, the mixture can be heated to a temperature which is suitable for shell formation before and/or after every sequential addition of a shell precursor. In some embodiments, the shell is substantially uniform in coverage around the core and is substantially free of defects. In some embodiments, the resulting nanoparticles have a diameter of less than about 15 nm. In other embodiments, the nanoparticles have a diameter of between about 6 nm to about 10 nm. The nanoparticles made by this method can have quantum yields greater than about 80%. The nanoparticle made by this method can have on-time fractions (i.e., ratio of the time which nanoparticle emission is turned "on" when the nanoparticle is excited) of greater than about 0.80 (under moderate to high excitation energy).

In another aspect, provided herein is a method for making a FRET capable nanoparticle and populations thereof with modulated, reduced or no fluorescence intermittency, comprising: (a) providing a mixture comprising a plurality of nanocrystal cores and at least one coordinating solvent; (b) adding a first intermediate shell precursor alternately with a second intermediate shell precursor in layer additions to form an intermediate shell layer on each of the plurality of nanocrystal cores, wherein the intermediate shell layer is comprised of more than one monolayer; (c) adding a first external shell precursor alternately with a second external shell precursor in layer additions to form an external shell layer on each of the plurality of nanocrystal cores, wherein the external shell layer is disposed on top of the intermediate shell layer and is comprised of more than one monolayer; (d) adding an aqueous solution comprising a hydrophilic ligand; and (e) maintaining the mixture under conditions which cause the plurality of nanocrystals to migrate into an aqueous phase. If the coordinating solvent is not an amine, at least one amine can be included in step (a). In some embodiments, the resulting population of FRET capable non-blinking nanoparticles has a $\alpha_{on}$ value which is less than about 1.4. In other embodiments, the resulting population of FRET capable non-blinking nanoparticles has an on-time fraction of least about 0.8 (under moderate to high excitation energy). In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the methods disclosed above utilize a one step or a two step ligand exchange process to replace the hydrophobic ligands on the nanoparticles with hydrophilic ligands to cause the plurality of nanocrystals to migrate into the aqueous phase. See PCT Application Serial No. PCT/US09/53018 and PCT/US09/59456 which are expressly incorporated herein by reference as if set forth in full.

In another aspect, provided herein is a method for making a FRET capable nanoparticle and populations thereof with modulated, reduced or no fluorescence intermittency, comprising: providing a mixture comprising a plurality of nanocrystal cores, functionalized organophosphorous-based hydrophilic ligands and at least one coordinating solvent; adding a first intermediate shell precursor alternately with a second intermediate shell precursor in layer additions to form an intermediate shell layer on each of the plurality of nanocrystal cores; and adding a first external shell precursor alternately with a second external shell precursor in layer additions to form an external shell layer on each of the plurality of nanocrystal cores. In some embodiments, the resulting population of FRET capable non-blinking nanoparticles has an $\alpha_{on}$ value which is less than about 1.4. In other embodiments, the resulting population of FRET capable non-blinking nanoparticles has an on-time fraction of least about 0.8. In some embodiments, the resulting population of FRET capable non-blinking nanoparticles has diameters which are less than about 15 nm. In some embodiments, the resulting population of FRET capable non-blinking nanoparticles has a FRET efficiency of at least 20%. In some embodiments, the resulting population of FRET capable non-blinking nanoparticles has a quantum yield of at least about 40%.

In some embodiments, the functionalized organophosphorous-based hydrophilic ligands are multi-functional surface ligands which include a phosphonate/phosphinate nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the FRET capable and non-blinking nanoparticles produced by the disclosed methods may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See PCT Application Serial No. PCT/US09/59117 which is expressly incorporated herein by reference as if set forth in full.

In another aspect, provided herein is a method of making a nanoparticle or population thereof comprising a core and a layered gradient shell, wherein the shell comprises an multi-component (e.g., alloy, etc.) shell material of the form $M^1_xM^2_yX$, where x and y represent the ratio of $M^1$ and $M^2$ in the shell material. The method comprising: (a) providing a mixture comprising a core, at least one coordinating solvent; (b) heating said mixture to a temperature suitable for formation of the shell layer; and (c) adding a first inner shell precursor comprising $M^1_x$ and $M^2_y$ alternately with a second inner shell precursor comprising X in layer additions, wherein the ratio of y to x gradually increases in sequential layer additions, such that the shell layers becomes successively enriched in $M^2$, to form a layered gradient shell which is a desired number of monolayers thick. If the coordinating solvent is not an amine, at least one amine can be included in step (a).

In one embodiment, the method described above provides a nanoparticle having a layered gradient shell, wherein the core comprises CdSe and the shell comprises sequential layers of $Cd_xZn_yS$, where the ratio of y to x increases gradually from the innermost shell layer to the outermost shell layer, to provide a layered gradient shell with a finely graded potential. In some such embodiments, the outermost shell layer is essentially pure ZnS. In some embodiments, the percent of Zn in the gradient shell varies from less than about 10% at the innermost shell layer to greater than about 80% at the outermost shell layer.

Typically, the heating steps in the disclosed methods are conducted at a temperature within the range of about 150-350° C., more preferably within the range of about 200-300° C. In some embodiments, the temperature suitable for formation of at least one inner shell layer is about 215° C. In some embodiments, the temperature suitable for formation of at least one outer shell layer is about 245° C. It is understood that the above ranges are merely exemplary and are not intended to be limiting in any manner as the actual temperature ranges may vary, dependent upon the relative stability of the precursors, ligands, and solvents. Higher or lower temperatures may be appropriate for a particular reaction. The determination of suitable time and temperature conditions for providing nanoparticles is within the level of skill in the art using routine experimentation.

It can be advantageous to conduct the nanoparticle-forming reactions described herein with the exclusion of oxygen and moisture. In some embodiments the reactions are conducted in an inert atmosphere, such as in a dry box. The solvents and reagents are also typically rigorously purified to remove moisture and oxygen and other impurities, and are generally handled and transferred using methods and apparatus designed to minimize exposure to moisture and/or oxygen. In addition, the mixing and heating steps can be conducted in a vessel which is evacuated and filled and/or flushed with an inert gas such as nitrogen. The filling can be periodic or the filling can occur, followed by continuous flushing for a set period of time.

In some embodiments, the at least one coordinating solvent comprises a trialkylphosphine, a trialkylphosphine oxide, a phosphonic acid, or a mixture of these. Sometimes, the at least one coordinating solvent comprises TOP, TOPO, TDPA, OPA or a mixture of these. The solvent for these reactions often comprises a primary or secondary amine, for example, decylamine, hexadecylamine, or dioctylamine. In some embodiments, the amine is decylamine. In some embodiments, the first inner shell precursor is $Cd(OAc)_2$ and the second inner shell precursor is bis(trimethylsilyl)sulfide ($TMS_2S$). Sometimes, the first and second inner shell precursors are added as a solution in TOP. In some embodiments, the first outer shell precursor is $Et_2Zn$ and the second inner shell precursor is $TMS_2S$. Sometimes, the first and second outer shell precursors are added as a solution in TOP.

In certain embodiments, the disclosed nanoparticles may be prepared using the method described herein to build a layered CdS—ZnS shell on a CdSe quantum size core. The shells for these materials can have varying numbers of layers of CdS and ZnS. Prototypical materials containing a CdSe core and approximately 4 monolayers CdS and 3.5 monolayers of ZnS (the final 0.5 monolayer is essentially pure Zn), or a CdSe core and 9 monolayers CdS and 3.5 monolayers of ZnS were prepared as described in the examples.

In some embodiments, for either the inner or outer layer, or both, less than a full layer of the appropriate first shell precursor can be added alternately with less than a full layer of the appropriate second shell precursor, so the total amount of the first and second shell precursor required is added in two or more portions. Sometimes, the portion is about 0.25 monolayers of shell material, so that the 4 portions of 0.25 monolayer of first shell precursor are added alternately with 4 portions of 0.25 monolayer of second shell precursor; sometimes the portion is about 0.5 monolayers of shell material, and sometimes about 0.75 monolayers of shell material.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethylzinc ($Et_2Zn$) or dimethyl cadmium are typically considered to be a source of neutral zinc atoms ($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn(oleate)_2$), zinc chloro(oleate), zinc undecylenate, zinc salicylate, and other zinc salts. In some embodiments, the first precursor is salt of Cd or Zn. In some embodiments, it is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a C4-C24 alkyl group which is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

When the first precursor comprises a metal cation, the second precursor can provide an uncharged (i.e., neutral) non-metal atom in solution. In frequent embodiments, when the first precursor comprises a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and trialkylphosphine adducts of S, Se and Te. Such trialkylphosphine adducts are sometimes described herein as R3P=X, wherein X is S, Se or Te, and each R is independently H, or a C1-C24 hydrocarbon group which can be straight-chain, branched, cyclic, or a combination of these, and which can be unsaturated. Exemplary second precursors of this type include tri-n-(butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors which provide anionic species under the reaction conditions are typically used with a first precursor which provides a neutral metal atom, such as alkylmetal compounds and others described above or known in the art.

In some embodiments, the second precursor provides a negatively charged non-metal ion in solution (e.g., S-2, Se-2 or Te-2). Examples of suitable second precursors providing an ionic species include silyl compounds such as bis(trimethylsilyl)selenide (($TMS)_2Se$), bis(trimethylsilyl)sulfide (($TMS)_2S$) and bis(trimethylsilyl)telluride (($TMS)_2Te$). Also included are hydrogenated compounds such as H2Se, H2S, H2Te; and metal salts such as NaHSe, NaSH or NaHTe. In this situation, an oxidant can be used to oxidize a neutral metal species to a cationic species which can react with the anionic precursor in a 'matched' reaction, or an oxidant can be used increase the oxidation state of the anionic precursor to provide a neutral species which can undergo a 'matched' reaction with a neutral metal species.

Other exemplary organic precursors are described in U.S. Pat. Nos. 6,207,229 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

Both the first and the second precursors can be combined with an appropriate solvent to form a solution for use in the disclosed methods. The solvent or solvent mixture used to form a first precursor solution may be the same or different from that used to form a second precursor solution. Typical coordinating solvents include alkyl phosphines, alkyl phosphine oxides, alkyl phosphonic acids, alkyl phosphinic acids, or carboxylic acid containing solvents, or mixtures of these.

Suitable reaction solvents include, by way of illustration and not limitation, hydrocarbons, amines, alkyl phosphines, alkyl phosphine oxides, carboxylic acids, ethers, furans, phosphoacids, pyridines and mixtures thereof. The solvent may actually comprise a mixture of solvents, often referred to in the art as a "solvent system". In some embodiments, the solvent comprises at least one coordinating solvent. In some embodiments, the solvent system comprises a secondary amine and a trialkyl phosphine (e.g., TBP or TOP) or a trialkylphosphine oxide (e.g., TOPO). If the coordinating solvent is not an amine, an amine can be included.

A coordinating solvent might be a mixture of an essentially non-coordinating solvent such as an alkane and a ligand as defined below.

Suitable hydrocarbons include alkanes, alkenes and aromatic hydrocarbons from 10 to about 30 carbon atoms; examples include octadecene and squalane. The hydrocarbon may comprise a mixture of alkane, alkene and aromatic moieties, such as alkylbenzenes (e.g., mesitylene).

Suitable amines include, but are not limited to, monoalkylamines, dialkylamines, and trialkylamines, for example dioctylamine, oleylamine, decylamine, dodecylamine, hexyldecylamine, and so forth. Alkyl groups for these amines typically contain about 6-24 carbon atoms per alkyl, and can include an unsaturated carbon-carbon bond, and each amine typically has a total number of carbon atoms in all of its alkyl groups combined of about 10-30 carbon atoms.

Exemplary alkyl phosphines include, but are not limited to, the trialkyl phosphines, tri-n-butylphosphine (TBP), tri-n-octylphosphine (TOP), and so forth. Alkyl groups for these phosphines contain about 6-24 carbon atoms per alkyl, and can contain an unsaturated carbon-carbon bond, and each phosphine has a total number of carbon atoms in all of its alkyl groups combined of about 10-30 carbon atoms.

Suitable alkyl phosphine oxides include, but are not limited to, the trialkyl phosphine oxide, tri-n-octylphosphine oxide (TOPO), and so forth. Alkyl groups for these phosphine oxides contain about 6-24 carbon atoms per alkyl, and can contain an unsaturated carbon-carbon bond, and each phosphine oxide has a total number of carbon atoms in all of its alkyl groups combined of about 10-30 carbon atoms.

Exemplary fatty acids include, but are not limited to, stearic, oleic, palmitic, myristic and lauric acids, as well as other carboxylic acids of the formula R—COOH, wherein R is a C6-C24 hydrocarbon group and can contain an unsaturated carbon-carbon bond. It will be appreciated that the rate of nanocrystal growth generally increases as the length of the fatty acid chain decreases.

Exemplary ethers and furans include, but are not limited to, tetrahydrofuran and its methylated forms, glymes, and so forth.

Suitable phosphonic and phosphinic acids include, but are not limited to hexylphosphonic acid (HPA), tetradecylphosphonic acid (TDPA), and octylphosphinic acid (OPA), and are frequently used in combination with an alkyl phosphine oxide such as TOPO. Suitable phosphonic and phosphinic acids are of the formula $RPO_3H_2$ or $R_2PO_2H$, wherein each R is independently a C6-C24 hydrocarbon group and can contain an unsaturated carbon-carbon bond.

Exemplary pyridines include, but are not limited to, pyridine, alkylated pyridines, nicotinic acid, and so forth.

Suitable alkenes include, e.g., octadecene and other C4-C24 hydrocarbons which are unsaturated.

Nanoparticle core or shell precursors can be represented as a M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo)(oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a C8-C20 alkyl amine) The X donor can include, for example, a phosphine chalcogenide, a bis(trialkylsilyl)chalcogenide, a dioxygen species, an ammonium salt, or a tris(trialkylsilyl) phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a $C_6$-$C_{20}$ alkyl diol or a $C_6$-$C_{20}$ aldehyde.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or C1-C8 alkyl or lower alkenyl.

The X donor is a compound capable of reacting with the M-containing salt to form a material with the general formula MX. The X donor is generally a chalcogenide donor or a phosphine donor, such as a phosphine chalcogenide, a bis (silyl)chalcogenide, dioxygen, an ammonium salt, or a tris (trialkylsilyl) phosphine. Suitable X donors include dioxygen, elemental sulfur, bis(trimethylsilyl)selenide (($TMS)_2$ Se), trialkyl phosphine selenides such as (tri-n-octylphosphine)selenide (TOPSe) or (tri-n-butylphosphine)selenide (TBPSe), trialkyl phosphine tellurides such as (tri-n-octylphosphine)telluride (TOPTe) or hexapropylphosphorustriamide telluride (HPPTTe), bis(trimethylsilyl)telluride (($TMS)_2Te$), sulfur, bis(trimethylsilyl)sulfide (($TMS)_2S$), a trialkyl phosphine sulfide such as (tri-n-octylphosphine)sulfide (TOPS), tris(dimethylamino) arsine, an ammonium salt such as an ammonium halide (e.g., $NH_4Cl$), tris(trimethylsilyl) phosphide (($TMS)_3P$), tris(trimethylsilyl) arsenide (($TMS)_3As$), or tris(trimethylsilyl) antimonide (($TMS)_3Sb$). In certain embodiments, the M donor and the X donor can be moieties within the same molecule.

Ligand Exchange Processes for Coating Nanoparticles

Provided herein are ligand exchange processes that permit efficient conversion of a conventional hydrophobic nanoparticle or population thereof into a water-dispersible and functionalized nanoparticle or population of nanoparticles. It also permits preparation of small nanoparticles which are highly stable and bright enough to be useful in biochemical and biological assays. The resulting nanoparticles can also be linked to a target molecule or cell or enzyme (e.g., polymerase) of interest.

Typically, the nanoparticle used for this process is a core/shell nanocrystal which is coated with a hydrophobic ligand such as tetradecylphosphonic acid (TDPA), trioctylphosphine oxide (TOPO), trioctyl phosphine (TOP), octylphosphonic acid (OPA), and the like, or a mixture of such ligands; these hydrophobic ligands typically have at least one long-chain alkyl group, i.e. an alkyl group having at least 8 carbons, or for the phosphine/phosphine oxide ligands, this hydrophobic character may be provided by two or three alkyl chains on a single ligand molecule having a total of at least 10 carbon atoms. Therefore, in some embodiments, the surface of the core/shell nanocrystal or population thereof can be coated with varying quantities of TDPA hydrophobic ligands prior to replacement with hydrophilic ligand(s). For example, TDPA can represent at least about 10%, at least about 20%, at least about 30%, at least about 40%, at least about 50%, at least about 80%, at least about 95%, at least about 98%, at least about 99% or more of the total surface ligands coating the core/shell nanoparticles. Moreover, certain hydrophobic ligands show an unexpected and apparent ease of replacement with the hydrophilic ligand. For example, nanoparticles with OPA on the surface have been observed to transfer into aqueous buffer more readily and more completely than the same type of core-shell with TDPA on the surface. Therefore, in some embodiments, the surface of the core/shell nanocrystal or populations thereof can be coated with varying quantities of OPA hydrophobic ligands prior to replacement with hydrophilic ligand(s). For example, OPA can represent at least about 10%, at least about 20%, at least about 30%, at least about 40%, at least about 50%, at least about 80%, at least about 95%, at least about 98%, at least about 99% or more of the total surface ligands coating the core/shell nanocrystal.

In one aspect, provided herein is a "one-step" ligand exchange process to apply various types of ligands to the surface of a nanoparticle, by substituting a desired hydrophilic ligand for a conventional hydrophobic ligand like TOPO, TOP, TDPA, OPA, and the like. The process steps, comprising: providing a nanocrystal coated with a surface layer comprising a hydrophobic ligand, and dissolved or dispersed in a non-aqueous solvent, contacting the nanocrystal dispersion with a phase transfer agent and an aqueous solution comprising a hydrophilic ligand, to form a biphasic mixture having an aqueous phase and a non-aqueous phase and maintaining the mixture under conditions that cause the nanocrystal to migrate from the non-aqueous solvent into the aqueous phase. See PCT Application Serial No. PCT/US09/53018 which is expressly incorporated herein by reference as if set forth in full.

The 'one-step' ligand exchange process described herein utilizes phase transfer catalysts which are particularly effective, and provide faster exchange reactions. Butanol has been utilized as a phase transfer catalyst for this type of exchange reaction; however, the reaction takes several days typically, and requires heating to about 70° C. The time for this reaction exposes the nanoparticles to these reaction conditions for a long period of time, which may contribute to some reduction in its ultimate stability. The embodiments disclosed herein provide more efficient conditions which achieve ligand exchange more rapidly, thus better protecting the nanoparticles. As a result of accelerating the exchange reaction and allowing use of milder conditions, these phase transfer catalysts produce higher quality nanoparticles.

The phase transfer agent for this process can be a crown ether, a PEG, a trialkylsulfonium, a tetralkylphosphonium, and an alkylammonium salt, or a mixture of these. In some embodiments, the phase transfer agent is 18-crown-6,15-crown-5, or 12-crown-4. In some embodiments, the phase transfer agent is a PEG, which can have a molecular weight from about 500 to about 5000. In some embodiments, the phase transfer agent is a trialkylsulfonium, tetralkylphosphonium, or alkylammonium (including monoalkylammonium, dialkylammonium, trialkylammonium and tetralkylammonium) salt.

Tetralkylammonium salts are sometimes preferred as phase transfer agents. Examples of suitable tetralkylammonium salts include triethylbenzyl ammonium, tetrabutylammonium, tetraoctylammonium, and other such quaternary salts. Other tetralkylammonium salts, where each alkyl group is a C1-C12 alkyl or arylalkyl group, can also be used. Typically, counting all of the carbons on the alkyl groups of a trialkylsulfonium, tetralkylphosphonium, and alkylammonium salt, the phase transfer agent will contain a total of at least 2 carbons, at least 10 carbons and preferably at least 12 carbon atoms. Each of the trialkylsulfonium, tetralkylphosphonium, and alkylammonium salts has a counterion associated with it; suitable counterions include halides, preferably chloride or fluoride; sulfate, nitrate, perchlorate, and sulfonates such as mesylate, tosylate, or triflate; mixtures of such counterions can also be used. The counterion can also be a buffer or base, such as borate, hydroxide or carbonate; thus, for example, tetrabutylammonium hydroxide can be used to provide the phase transfer catalyst and a base. Specific phase transfer salts for use in these methods include tetrabutylammonium chloride (or bromide) and tetraoctylammonium bromide (or chloride).

Suitable hydrophilic ligands are organic molecules which provide at least one binding group to associate tightly with the surface of a nanocrystal. The hydrophilic ligand typically is an organic moiety having a molecular weight between about 100 and 1500, and contains enough polar functional groups to be water soluble. Some examples of suitable hydrophilic ligands include small peptide having 2-10 amino acid residues (preferably including at least one histidine or cysteine residue), mono- or polydentate thiol containing compounds.

Following ligand exchange, the surface layer can optionally be crosslinked.

In another aspect, provided herein is a "two-step" ligand exchange process to apply various types of ligands to the surface of a nanoparticle, by substituting a desired hydrophilic ligand for a conventional hydrophobic ligand like TOPO, TOP, TDPA, OPA, and the like. The process involves the removal of phosphonate or phosphinate ligands from the surface of a nanoparticle or nanocrystal by treatment with sulfonate reagents, particularly silylsulfonate derivatives of weak bases or other poorly coordinating groups.

The process steps, comprising: providing a nanocrystal whose surface comprises a phosphonate ligand, contacting the nanocrystal with a sulfonate reagent in an organic solvent, contacting the sulfonate ligand coated nanocrystal with a functionalized organic molecule (i.e., hydrophilic ligand) comprising at least one nanocrystal surface attachment group, contacting the nanocrystal dispersion with an aqueous solution to form a biphasic mixture having an aqueous phase and a non-aqueous phase, and maintaining the biphasic mixture under conditions which cause the nanocrystal to migrate from the non-aqueous phase into the aqueous phase. See PCT Application Serial No. PCT/US09/59456 which is expressly incorporated herein by reference as if set forth in full.

The result of this removal of phosphonate ligands is replacement of the phosphonates with the weakly coordinating groups. One example is the use of silyl sulfonates, such as trimethylsilyl triflate, to form a sulfonate-coated nanoparticle. Triflate is a conventional/common name for a trifluoromethanesulfonyloxy group, $CF_3SO_2O$—.

The same type of replacement process can also occur on nanoparticles having phosphinic acid ligands of the formula $R_2P(=O)$—OH or on nanoparticles having carboxylic acid ligands of the formula $RC(=O)$—OH, which could be incorporated on the surface of a nanocrystal by known methods; R can be a $C_1$-$C_{24}$ hydrocarbon group in these phosphinates, and the two R groups can be the same or different. Thus, it is understood that when phosphonate-containing nanocrystals are described herein, phosphinate-containing nanocrystals can be used instead, with similar results.

This process provides a mild and selective method for removing phosphonate, phosphinate, and carboxylate ligands from the surface of a nanocrystal. As a result, it provides a way for a user to remove these groups and replace them, without removing other ligands which are not displaced or affected by the silylsulfonate.

The sulfonate ligands can comprise an alkyl or aryl moiety linked to —SO₃X, where X can represent whatever the sulfonate group is attached to. For example, where the sulfonate ligand is a sulfonate anion (i.e., triflate), X would represent a nanocrystal, or the surface of a nanocrystal. Some of the sulfonate embodiments disclosed herein can also be described with reference to feature 'A' of Formula I, as set forth below.

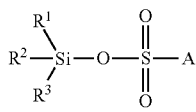

I wherein $R^1$, $R^2$, $R^3$ and A are each, independently, C1-C10 alkyl or C5-C10 aryl; and each alkyl and aryl is optionally substituted.

The alkyl groups for Formula I compounds are independently selected, and can be straight chain, branched, cyclic, or combinations of these, and optionally can include a C1-C4 alkoxy group as a substituent. Typically, the alkyl groups are lower alkyls, e.g., C1-C4 alkyl groups which are linear or branched. Methyl is one suitable example.

The aryl group for the compounds of Formula I can be phenyl, naphthyl or a heteroaryl having up to 10 ring members, and can be monocyclic or bicyclic, and optionally contain up to two heteroatoms selected from N, O and S as ring members in each ring. (It will be understood by those skilled in the art that the 5-membered aryl is a heteroaryl ring.) Phenyl is a preferred aryl group; and an aryl group is typically only present if the other organic groups on the silicon other than the sulfonate are lower alkyls, and preferably they are each Me.

Examples of silylsulfonate ligands can include, but are not limited to: (trimethylsilyl)triflate, (triethylsilyl)triflate, (t-butyldimethylsilyl)triflate, (phenyldimethylsily)triflate, trimethylsilyl fluoromethanesulfonate, trimethylsilyl methanesulfonate, trimethylsilyl nitrophenylsulfonate, trimethylsilyl trifluoroethylsulfonate, trimethylsilyl phenylsulfonate, trimethylsilyl toluenesulfonate, diisopropylsilyl bis(trifluoromethanesulfonate), tertbutyldimethylsilyl trifluoromethanesulfonate, triisopropylsilyl trifluoromethanesulfonate and trimethylsilyl chlorosulfonate.

Examples of other sulfonate ligands can include, but are not limited to: trifluoromethanesulfonate (triflate), fluoromethanesulfonate, methanesulfonate (mesylate), nitrophenylsulfonate (nosylate), trifluorethylsulfonate, phenylsulfonate (besylate) and toluenesulfonate (tosylate).

Some suitable examples of the hydrophilic ligand are disclosed, for example, in Naasani, U.S. Pat. Nos. 6,955,855; 7,198,847; 7,205,048; 7,214,428; and 7,368,086. Suitable hydrophilic ligands also include imidazole containing compounds such as peptides, particularly dipeptides, having at least one histidine residue, and peptides, particularly dipeptides, having at least one cysteine residue. Specific ligands of interest for this purpose can include carnosine (which contains beta-alanine and histidine); His-Leu; Gly-His; His-Lys; His-Glu; His-Ala; His-His; His-Cys; Cys-His; His-Ile; His-Val; and other dipeptides where His or Cys is paired with any of the common alpha-amino acids; and tripeptides, such as Gly-His-Gly, His-Gly-His, and the like. The chiral centers in these amino acids can be the natural L-configuration, or they can be of the D-configuration or a mixture of L and D. Thus a dipeptide having two chiral centers such as His-Leu can be of the L,L-configuration, or it can be L,D- or D,L; or it can be a mixture of diastereomers.

Furthermore, suitable hydrophilic ligands can also include mono- or polydentate thiol containing compounds, for example: monodentate thiols such as mercaptoacetic acid, bidentate thiols such as dihydrolipoic acid (DHLA), tridentate thiols such as compounds of Formula II-VII as shown below, and the like.

II

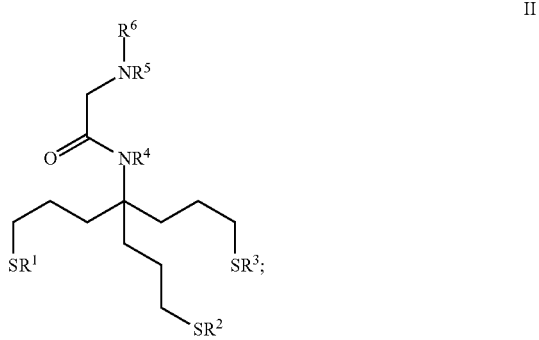

III

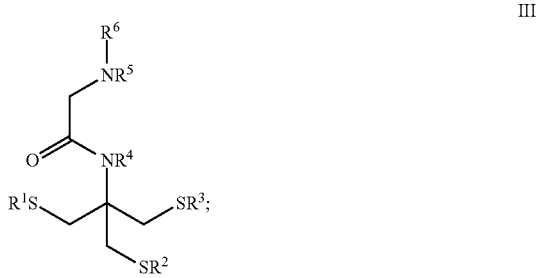

IV

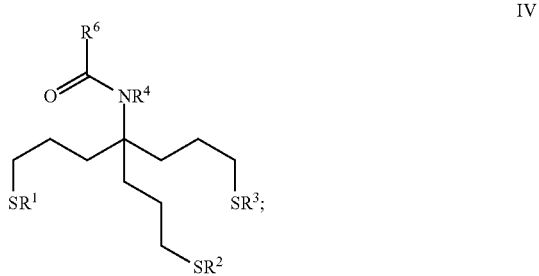

V

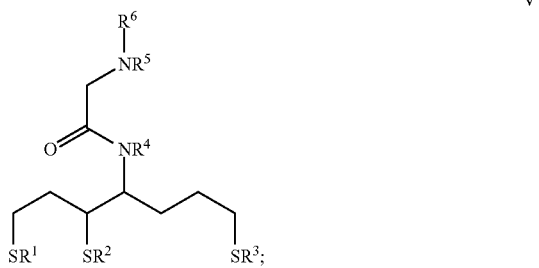

VI

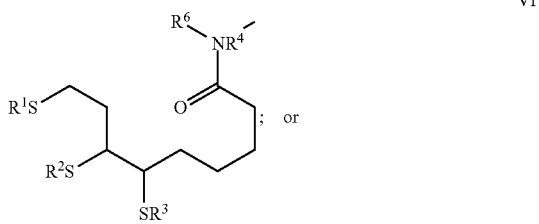

; or

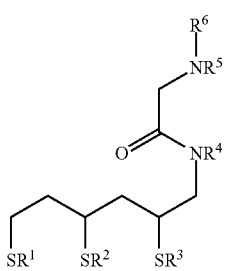

VII

In compounds of Formula II-VII, $R^1$, $R^2$, $R^3$ can independently be H, halo, hydroxyl, (—(C=O)—$C_1$-$C_{22}$, —(C=O) $CF_3$) alkanoyl, $C_1$-$C_{22}$ alkyl, $C_1$-$C_{22}$ heteroalkyl, ((CO)O$C_1$-$C_{22}$) alkylcarbonato, alkylthio ($C_1$-$C_{22}$) or (—(CO)NH($C_1$-$C_{20}$) or —(CO)N($C_1$-$C_{20}$)$_2$) alkylcarbamoyl. In some embodiments, $R^1$, $R^2$, and $R^3$ are different. In other embodiments, $R^1$, $R^2$, and $R^3$ are the same.

In compounds of Formula II-VII, $R^4$, and $R^5$ can independently be H, $C_1$-$C_{20}$ alkyl, $C_6$-$C_{18}$ aryl, $C_1$-$C_{22}$ heteroalkyl or $C_1$-$C_{22}$ heteroaryl. In some embodiments, $R^4$ and $R^5$ are different. In other embodiments, $R^4$ and $R^5$ are the same.

In compounds of Formula II-VII, $R^6$ can be H or a polyethylene glycol based moiety of Formula VIII:

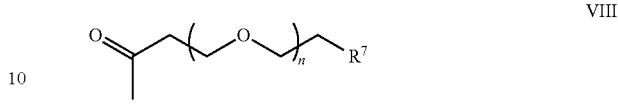

VIII

In certain embodiments of Formula VIII, $R^7$ can be —$NH_2$, —$N_3$, —NHBoc, —NHFmoc, —NHCbz, —COOH, —COOt-Bu, —COOMe, iodoaryl, hydroxyl, alkyne, boronic acid, allylic alcohol carbonate, —NHBiotin, —(CO)NHNHBoc, —(CO)NHNHFmoc or —OMe. In some embodiments, n can be an integer from 1 to 100.

In still further embodiments, the tridentate thiol ligands can be a compound of Formula IX, X, XI, XII, XIII, XIV, XV, XVI, XVII, XVIII, XIX, XX, XXI, XXII, XXIII or XXIV:

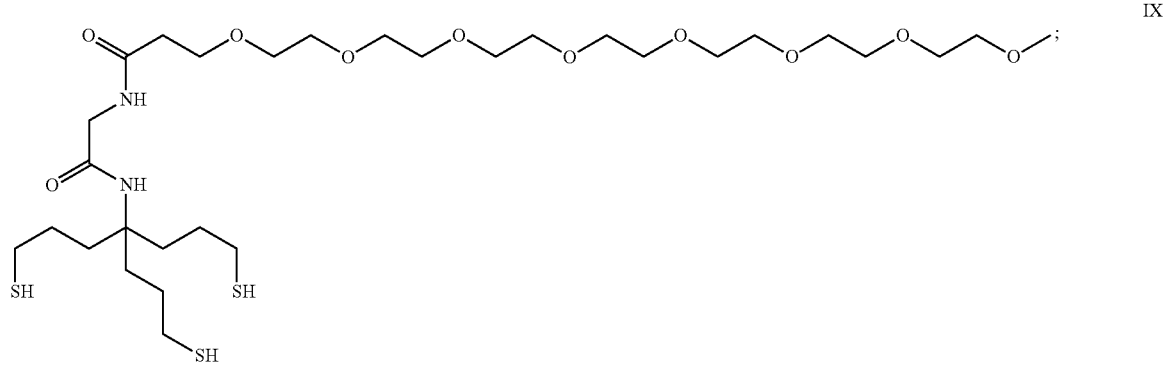

IX

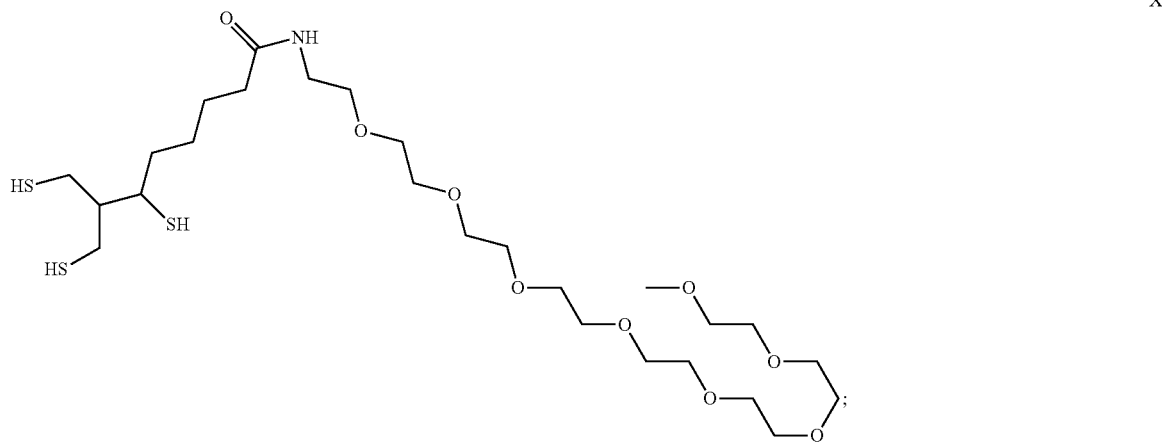

X

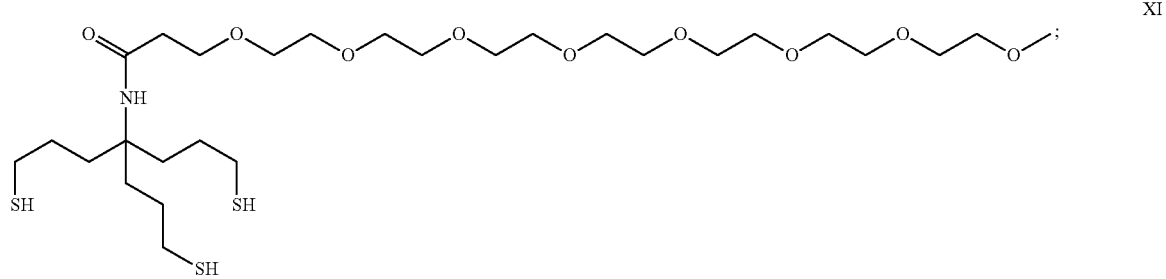

XI

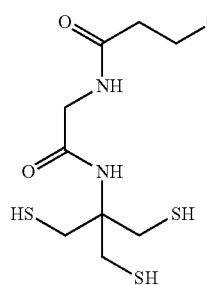
XII
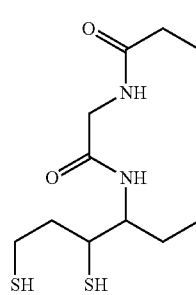
XIII
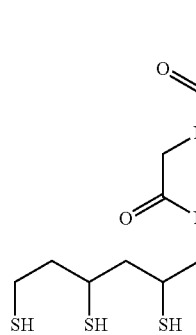
XIV
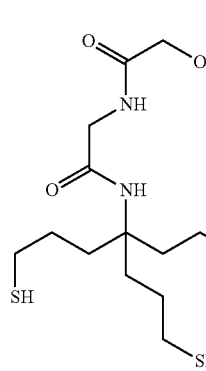
XV
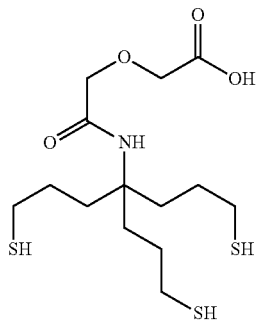
XVI
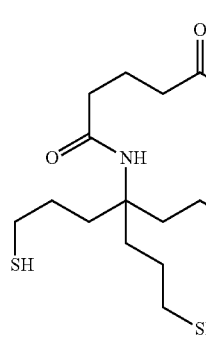
XVII
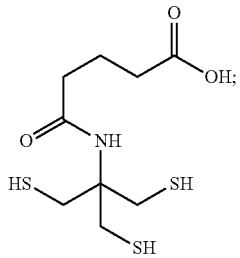
XVIII -continued

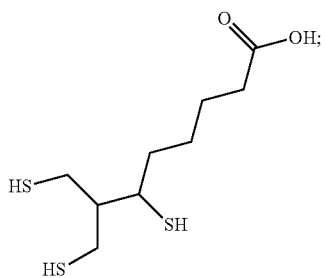
XIX

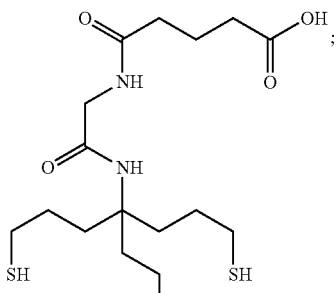
XX

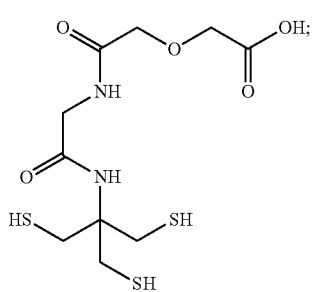
XXI

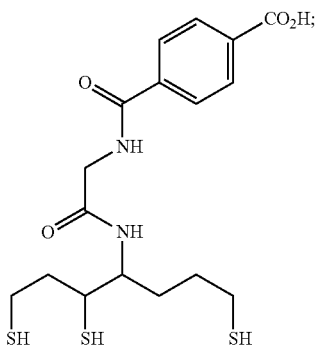
XXII

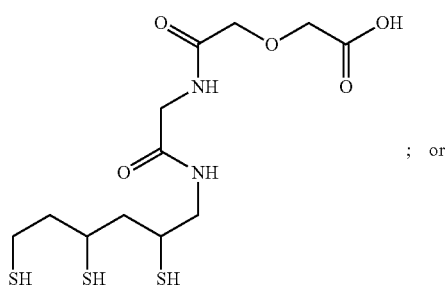
XXIII ; or

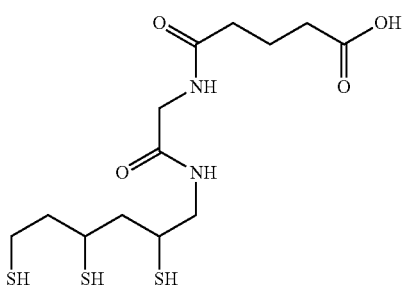
XXIV

Functionalized TDPA Ligands on Nanoparticles

Provided herein are methods for preparing water-soluble semi-conducting, insulating, or metallic nanoparticles including the steps of admixing one or more nanocrystal precursors and one or more multi-functional surface ligands with a solvent to form a solution and heating the solution to a suitable temperature, and in certain embodiments, methods may include the steps of admixing nanocrystal cores, one or more nanocrystal precursors, and one or more multi-functional surface ligands with a solvent to form a solution and heating the solution to a suitable temperature. In such embodiments, the one or more multi-functional surface ligands may at least include a nanocrystal binding center, a linker, and a functional group, which imparts functionality on the nanocrystal. As used herein the term "functional group" may refer to a group which affects reactivity, solubility, or both reactivity and solubility when present on a multi-functional surface ligand. Embodiments can include a wide variety of functional groups which can impart various types of functionality on the nanocrystal including hydrophilicity, water-solubility, or dispersibility and/or reactivity, and the functionality may generally not include only hydrophobicity or only solubility in organic solvents without increasing reactivity. For example, a functional group which is generally hydrophobic but which increases reactivity such as an alkene or alkyne and certain esters and ethers can be encompassed by embodiments, whereas alkyl groups, which do not generally impart reactivity but increase hydrophobicity may be excluded.

In certain embodiments, the nanoparticles produced by the methods of such embodiments may be coated with ligands which impart water solubility and/or reactivity on the nanoparticle obviating the need for ligand replacement. Without wishing to be bound by theory, eliminating ligand replacement may provide more consistent thermodynamic properties, which may lead to reduction in variability of coating and less loss of quantum yield, among other improvements in the properties of nanoparticles produced by the methods embodied herein. Eliminating ligand replacement may also allow for the production of nanoparticles having a wide variety of functional groups associated with the coating. In particular, while ligand replacement is generally limited to production of nanoparticles having amine and/or carboxylic acid functional groups, in various embodiments, the skilled artisan may choose among numerous functional groups when preparing the multi-functional ligands and may, therefore, generate nanoparticles which provide improved water-solubility or water-dispersity and/or support improved crosslinking and/or improved reactivity with cargo molecules. See for example PCT Application Serial No. PCT/US09/59117 filed Sep. 30, 2009 which are expressly incorporated herein by reference as if set forth in full.

Also disclosed herein are populations of biomolecule nanoparticle conjugates wherein the nanoparticle of at least about 10%, 20%, 30%, 40%, 50% 60%, 70%, 80% or 90% of the conjugates can be about 1 nm to about 100 nm in its largest dimension, about 1 nm to about 20 nm, about 1 nm to about 15 nm, about 1 nm to about 10 nm or preferably about 5 nm to about 10 nm in its largest dimension. Nanoparticles of such reduced dimensions can provide superior performance in FRET-based assays where the nanoparticle of the conjugate undergoes FRET with a labeled nucleotide bound to an active site of the polymerase. Such conjugates may perform such FRET with higher efficiencies and/or intensities because their smaller size effectively reduces the distance between the nanoparticle and the nucleotide label. Nanoparticles having reduced dimensions are described further herein.

Any suitable nanoparticle can be used in the conjugates of the present disclosure, including, for example, those described in U.S. Provisional Appl. Nos. 61/086,750, filed Aug. 6, 2008; 61/102,631, filed Oct. 3, 2008; 61/102,693, filed Oct. 3, 2008; 61/102,709, filed Oct. 3, 2008; 61/102,666, filed Oct. 3, 2008; 61/102,642, filed Oct. 3, 2008; 61/108,425, filed Oct. 24, 2008; 61/144,613, filed Jan. 14, 2009; 61/102,613, filed Oct. 3, 2008; 61/102,589, filed Oct. 3, 2008; 61/102,599, filed Oct. 3, 2008; 61/076,833, filed Jun. 30, 2008; 61/076,910, filed Jun. 30, 2008; 60/941,211, filed May 31, 2007 and Intl. Appl. No. PCT/US08/65425, filed May 30, 2008, as well as any other nanoparticle-related disclosures cited herein. Without being bound to any particular theory, it is believed that at least some of the compositions and methods disclosed in these applications relate to nanoparticles having reduced size relative to typical commercially available nanoparticles. Such nanoparticles having reduced size can allow the production of biomolecule-nanoparticle conjugates having improved performance in FRET-based assays. Such reduced sizes are thought to enhance FRET efficiency by reducing the effective distance between the donor and acceptor moieties such that the effective distance is less than or equal to the Forster distance, $R_0$.

In some embodiments, the methods, compositions, systems and/or kits disclosed herein can involve the use of moieties capable of undergoing energy transfer. Such energy transfer moieties can include energy transfer donors and acceptors. The energy transfer moieties can be linked to the solid surfaces, nanoparticles, polymerases, nucleotides, target nucleic acid molecules, primers, and/or oligonucleotides.

In one exemplary embodiment, the labeled biomolecule conjugates of the present disclosure comprise a polymerase linked to a label that includes an energy transfer moiety, wherein the conjugate has polymerase activity. In some embodiments, the energy transfer moiety of the conjugate performs energy transfer, which can be RET or FRET. In some embodiments, the energy transfer moiety of the conjugate performs energy transfer with the label of a nucleotide.

In one aspect, the energy transfer moiety can be an energy transfer donor. For example, the energy transfer donor can be a nanoparticle or an energy transfer donor moiety (e.g., fluorescent dye). In another aspect, the energy transfer moiety can be an energy transfer acceptor. For example, the energy transfer acceptor can be an energy acceptor dye. In another aspect, the energy transfer moiety can be a quencher moiety.

In one aspect, the energy transfer pair can be linked to the same molecule. For example, the energy transfer donor and acceptor pair can be linked to a single polymerase, which can provide detection of conformational changes in the polymerase. In another aspect, the donor and acceptor can be linked to different molecules in any combination. For example, the donor can be linked to the polymerase, target molecule, or primer molecule, and/or the acceptor can be linked to the nucleotide, the target molecule, or the primer molecule.

The energy transfer donor is capable of absorbing electromagnetic energy (e.g., light) at a first wavelength and emitting excitation energy in response. The energy acceptor is capable of absorbing excitation energy emitted by the donor and fluorescing at a second wavelength in response.

The donor and acceptor moieties can interact with each other physically or optically in a manner which produces a detectable signal when the two moieties are in proximity with each other. A proximity event includes two different moieties (e.g., energy transfer donor and acceptor) approaching each other, or associating with each other, or binding each other.

The donor and acceptor moieties can transfer energy in various modes, including: fluorescence resonance energy transfer (FRET) (L. Stryer 1978 Ann. Rev. Biochem. 47: 819-846; Schneider, U.S. Pat. No. 6,982,146; Hardin, U.S. Pat. No. 7,329,492; Hanzel U.S. published patent application No. 2007/0196846), scintillation proximity assays (SPA) (Hart and Greenwald 1979 Molecular immunology 16:265-267; U.S. Pat. No. 4,658,649), luminescence resonance energy transfer (LRET) (G. Mathis 1995 Clin. Chem. 41:1391-4397), direct quenching (Tyagi et al, 1998 Nature Biotechnology 16:49-53), chemiluminescence energy transfer (CRET) (Campbell and Patel 1983 Biochem. Journal 216: 185-194), bioluminescence resonance energy transfer (BRET) (Y. Xu, et al., 1999 Proc. Natl. Acad. Sci. 96:151-156), and excimer formation (J. R. Lakowicz 1999 "Principles of Fluorescence Spectroscopy", Kluwer Academic/Plenum Press, New York).

In one exemplary embodiment, the energy transfer moieties can be a FRET donor/acceptor pair. FRET is a distance-dependent radiationless transmission of excitation energy from a first moiety, referred to as a donor moiety, to a second moiety, referred to as an acceptor moiety. Typically, the efficiency of FRET energy transmission is dependent on the inverse sixth-power of the separation distance between the donor and acceptor, r. For a typical donor-acceptor pair, r can vary between approximately 10-100 Angstroms. FRET is useful for investigating changes in proximity between and/or within biological molecules. In some embodiments, FRET efficiency may depend on donor-acceptor distance r as $1/r^6$ or $1/r^4$. The efficiency of FRET energy transfer can sometimes be dependent on energy transfer from a point to a plane which varies by the fourth power of distance separation (E. Jares-Erijman, et al., 2003 Nab Biotechnol. 21:1387). The distance where FRET efficiency is 50% is termed $R_0$, also know as the Forster distance. $R_0$ is unique for each donor-acceptor combination and may be about 5 to 10 nm. A change in fluorescence from a donor or acceptor during a FRET event (e.g., increase or decrease in the signal) can be an indication of proximity between the donor and acceptor.

In biological applications, FRET can provide an on-off type signal indicating when the donor and acceptor moieties are proximal (e.g., within $R_0$) of each other. Additional factors affecting FRET efficiency include the quantum yield of the donor, the extinction coefficient of the acceptor, and the degree of spectral overlap between the donor and acceptor. Procedures are well known for maximizing the FRET signal and detection by selecting high yielding donors and high absorbing acceptors with the greatest possible spectral overlap between the two (D. W. Piston and G. J. Kremers 2007 Trends Biochem. Sci. 32:407). Resonance energy transfer may be either an intermolecular or intramolecular event. Thus, the spectral properties of the energy transfer pair as a whole, change in some measurable way if the distance and/or orientation between the moieties are altered.

The production of signals from FRET donors and acceptors can be sensitive to the distance between donor and acceptor moieties, the orientation of the donor and acceptor moieties, and/or a change in the environment of one of the moieties (Deuschle et al. 2005 Protein Science 14: 2304-2314; Smith et al. 2005 Protein Science 14:64-73). For example, a nucleotide linked with a FRET moiety (e.g., acceptor) may produce a detectable signal when it approaches, associates with, or binds a polymerase linked to a FRET moiety (e.g., donor). In another example, a FRET donor and acceptor linked to one protein can emit a FRET signal upon conformational change of the protein. Some FRET donor/acceptor pairs exhibit changes in absorbance or emission in response to changes in their environment, such as changes in pH, ionic strength, ionic type ($NO_2$, $Ca^{+2}$, $Zn^{+2}$, $Na^+$, $Cl^-$, $K^+$), oxygen saturation, and solvation polarity.

The FRET donor and/or acceptor may be a fluorophore, luminophore, chemiluminophore, bioluminophore, or quencher (P. Selvin 1995 Methods Enzymol 246:300-334; C. G. dos Remedios 1995 J. Struct. Biol. 115:175-185; P. Wu and L. Brand 1994 Anal Biochem 218:1-13).

In some embodiments, the energy transfer moieties may not undergo FRET, but may undergo other types of energy transfer with each other, including luminescence resonance energy transfer, bioluminescence resonance energy transfer, chemiluminescence resonance energy transfer, and similar types of energy transfer not strictly following the Forster's theory, such as the non-overlapping energy transfer when non-overlapping acceptors are utilized (Laitala and Hemmila 2005 Anal. Chem. 77: 1483-1487).

In one embodiment, the polymerase can be linked to an energy transfer donor moiety. In another embodiment, the nucleotide can be linked to an energy transfer acceptor moiety. For example, in one embodiment the nucleotide comprises a polyphosphate chain and an energy transfer moiety linked to the terminal phosphate group of the polyphosphate chain. A change in a fluorescent signal can occur when the labeled nucleotide is proximal to the labeled polymerase.

In one embodiment, when an acceptor-labeled nucleotide is proximal to a donor-labeled polymerase, the signal emitted by the donor moiety decreases. In another embodiment, when the acceptor-labeled nucleotide is proximal to the donor-labeled polymerase, the signal emitted by the acceptor moiety increases. In another embodiment, a decrease in donor signal and increase in acceptor signal correlates with nucleotide binding to the polymerase and/or correlates with polymerase-dependent nucleotide incorporation.

Quenchers

The energy transfer moiety can be a FRET quencher. Typically, quenchers have an absorption spectrum with large extinction coefficients, however the quantum yield for quenchers is reduced, such that the quencher emits little to no light upon excitation. Quenching can be used to reduce the background fluorescence, thereby enhancing the signal-to-noise ratio. In one aspect, energy transferred from the donor may be absorbed by the quencher which emits moderated (e.g., reduced) fluorescence. In another aspect, the acceptor can be a non-fluorescent chromophore which absorbs the energy transferred from the donor and emits heat (e.g., the energy acceptor is a dark quencher).

For an example, a quencher can be used as an energy acceptor with a nanoparticle donor in a FRET system, see I. L. Medintz, et al., 2003 Nature Materials 2:630. One exemplary method involves the use of quenchers in conjunction with reporters comprising fluorescent reporter moieties. In this strategy, certain nucleotides in the reaction mixture are labeled with a reporter comprising a fluorescent label, while the remaining nucleotides are labeled with a quencher. Alternatively, each of the nucleotides in the reaction mixture is labeled with a quencher. Discrimination of the nucleotide bases is based on the wavelength and/or intensity of light emitted from the FRET acceptor, as well as the intensity of light emitted from the FRET donor. If no signal is detected from the FRET acceptor, a corresponding reduction in light emission from the FRET donor indicates incorporation of a nucleotide labeled with a quencher. The degree of intensity reduction may be used to distinguish between different quenchers.

Examples of fluorescent donors and non-fluorescent acceptor (e.g., quencher) combinations have been developed for detection of proteolysis (Matayoshi 1990 Science 247: 954-958) and nucleic acid hybridization (L. Morrison, in: Nonisotopic DNA Probe Techniques, ed., L. Kricka, Academic Press, San Diego, (1992) pp. 311-352; S. Tyagi 1998 Nat. Biotechnol. 16:49-53; S. Tyagi 1996 Nat. Biotechnol. 14:947-8). FRET donors, acceptors and quenchers can be moieties which absorb electromagnetic energy (e.g., light) at about 300-900 nm, or about 350-800 nm, or about 390-800 nm.

Materials for Energy Transfer Moieties

Energy transfer donor and acceptor moieties can be made from materials which typically fall into four general categories (see the review in: K. E. Sapford, et al., 2006 Angew. Chem. Int. Ed. 45:4562-4588), including: (1) organic fluorescent dyes, dark quenchers and polymers (e.g., dendrimers); (2) inorganic material such as metals, metal chelates and semiconductors: nanoparticles; (3) biomolecules such as proteins and amino acids (e.g., green fluorescent protein and derivatives thereof); and (4) enzymatically catalyzed bioluminescent molecules. The material for making the energy transfer donor and acceptor moieties can be selected from the same or different categories.

The FRET donor and acceptor moieties which are organic fluorescent dyes, quenchers or polymers can include traditional dyes which emit in the UV, visible, or near-infrared region. The UV emitting dyes include coumarin-, pyrene-, and naphthalene-related compounds. The visible and near-infrared dyes include xanthene-, fluorescein-, rhodol-, rhodamine-, and cyanine-related compounds. The fluorescent dyes also includes DDAO ((7-hydroxy-9H-(1,3-dichloro-9, 9-dimethylacridin-2-one)) resorufin, ALEXA FLUOR and BODIPY dyes (both. Molecular Probes), HILYTE Fluors (AnaSpec), ATTO dyes (Atto-Tec). DY dyes (Dyomics GmbH), TAMRA (Perkin Elmer), tetramethylrhodamine (TMR), TEXAS RED, DYLIGHT (Thermo Fisher Scientific), PAM (AnaSpec), JOE and ROX (both Applied Biosystems), and Tokyo Green.

Additional fluorescent dyes which can be used as quenchers includes: DNP, DABSYL, QSY (Molecular Probes), ATTO (Atto-Tec), BHQ (Biosearch Technologies), QXL (AnaSpec), BBQ (Berry and Associates) and CY5Q/7Q (Amersham Biosciences).

The FRET donor and acceptor moieties which comprise inorganic materials include gold (e.g., quencher), silver, copper, silicon, semiconductor nanoparticles, and fluorescence-emitting metal such as a lanthanide complex, including those of Europium and Terbium.

Suitable FRET donor/acceptor pairs include: FAM as the donor and JOE, TAMRA, and ROX as the acceptor dyes. Other suitable pairs include: CYA as the donor and R6G, TAMRA, and ROX as the donor dyes. Other suitable donor/acceptor pairs include: a nanoparticle as the donor, and ALEXA FLUORS dyes (e.g., 610, 647, 660, 680, 700). DYOMICS dyes, such as 634 and 734 can be used as energy transfer acceptor dyes.

The compositions, methods, systems and kits of the present disclosure have particular use in single molecule sequencing reactions. Typically, such applications comprise the performance of a polymerase reaction using the a conjugate comprising a polymerase linked to a label and having polymerase activity according to the present disclosure.

In one exemplary embodiment, the temporal order of nucleotide incorporations during the polymerase reaction is detected and monitored in real time based on detection of FRET signals resulting from FRET between the labeled polymerase conjugates and the nucleotide label of an incorporating acceptor-labeled nucleotide.

In some embodiments, the polymerase is linked to a FRET donor and contacted with a nucleotide comprising a FRET acceptor. In some embodiments, the donor performs FRET with the acceptor when the polymerase and nucleotide are bought into sufficient proximity (for example, during a productive incorporation, a non-productive incorporation or during association of a nucleotide with the polymerase active site), resulting in the emission of a FRET signal. The FRET signal can optionally be detected and analyzed to determine the occurrence of a polymerase-nucleotide interaction.

In some embodiments, the FRET can occur prior to, during or after productive incorporation of the nucleotide into a nucleic acid molecule. Alternatively, the FRET can occur prior to binding of the nucleotide to the polymerase active site, or while the nucleotide resides within the polymerase active site, during a non-productive incorporation.

In some embodiments, the FRET acceptor moiety can in some embodiments be attached to, or comprise part of, the nucleotide sugar, the nucleobase, or analogs thereof. In some embodiments, the FRET acceptor is attached to a phosphate group of the nucleotide that is cleaved and released upon incorporation of the underlying nucleotide into the primer strand, for example the γ-phosphate, the β-phosphate or some other terminal phosphate of the incoming nucleotide. When this acceptor-labeled nucleotide polyphosphate is incorporated by the labeled polymerase conjugate into a nucleic acid molecule, the polymerase cleaves the bond between the alpha and beta phosphate, thereby releasing a pyrophosphate moiety comprising the acceptor that diffuses away. Thus, in these embodiments, a signal indicative of nucleotide incorporation is generated through FRET between the nanoparticle and the acceptor bonded to the gamma, beta or other terminal phosphate as each incoming nucleotide is incorporated into the newly synthesized strand. By releasing the label upon incorporation, successive incorporation of labeled nucleotides can each be detected without interference from nucleotides previously incorporated into the complementary strand. Alternatively, the nucleotide may be labeled with a FRET acceptor moiety on an internal phosphate, for example, the alpha phosphate, the beta phosphate, or another internal phosphate. Although such alpha-phosphate adducts are not cleaved and released during the polymerization process, they can be removed and/or rendered inoperable through appropriate treatments, e.g., chemical cleavage or photobleaching, later in the sequencing process.

The polymerase reaction conditions can comprise any suitable reaction conditions that permit nucleotide polymerization by labeled polymerase conjugates of the present disclosure. In one non-limiting example of nucleotide polymerization, the steps of polymerization can comprise: (1) complementary base-pairing of a target DNA molecule (e.g., a template molecule) with a primer molecule having a terminal 3' OH (the terminal 3' OH provides the polymerization initiation site for the polymerase); (2) binding of the polymerase of the conjugate to the base-paired target DNA/primer duplex to form a complex (e.g., open complex); (3) binding of the candidate nucleotide by the polymerase of the conjugate, which polymerase interrogates the candidate nucleotide for complementarity with the template nucleotide on the target DNA molecule; (4) catalysis of nucleotide polymerization by the polymerase of the conjugate.

In one embodiment, the polymerase of the conjugate comprises cleavage of the incorporating nucleotide by the polymerase, accompanied by liberation of a nucleotide cleavage product. When the nucleotide is a phosphate-comprising nucleotide, the cleavage product can include one or more phosphate groups. In other embodiments, where the polymerase incorporates a nucleotide analog having substituted phosphate groups, the cleavage product may include one or more substituted phosphate groups.

The candidate nucleotide may or may not be complementary to the template nucleotide on the target molecule. The candidate nucleotide may dissociate from the polymerase. If the candidate nucleotide dissociates from the polymerase, it can be liberated; in some embodiments, the liberated nucleotide carries intact polyphosphate groups. When the candidate nucleotide dissociates from the DNA polymerase, the event is known as a "non-productive binding" event. The dissociating nucleotide may or may not be complementary to the template nucleotide on the target molecule.

The incorporated nucleotide may or may not be complementary to the template nucleotide on the target. When the candidate nucleotide binds the DNA polymerase and is incorporated, the event is a "productive binding" event. The incorporated nucleotide may or may not be complementary to the template nucleotide on the target molecule.

The length of time, frequency, or duration of the binding of the complementary candidate nucleotide to the polymerase can differ from that of the non-complementary candidate nucleotide. This time difference can be used to distinguish between the complementary and non-complementary nucleotides, and/or can be used to identify the incorporated nucleotide, and/or can be used to deduce the sequence of the target molecule.

The signal (or change in signal) generated by the energy transfer donor and/or acceptor can be detected before, during, and/or after any nucleotide incorporation event.

In some embodiments, the polymerase reaction includes RNA polymerization which does not require a 3' polymerization initiation site. Polymerase reactions involving RNA polymerization are well known in the art.

Productive and Non-Productive Binding

Also provided herein are energy transfer compositions and methods for distinguishing between the productive and non-productive binding events. The compositions and methods can also provide base identity information during nucleotide incorporation. The compositions include nucleotides and polymerases each attached to a energy transfer moiety.

The compositions and methods provided herein can be used to distinguish events such as productive and non-productive nucleotide binding to the polymerase. In a productive binding event, the nucleotide can bind/associate with the polymerase for a time period which is distinguishable (e.g., longer or shorter time period), compared to a non-productive binding event. In a non-productive binding event, the nucleotide can bind/associate with the polymerase and then dissociate. The donor and acceptor energy transfer moieties produce detectable signals when they are in proximity to each other and can be associated with productive and non-productive binding events. Thus, the time-length difference between signals from the productive and non-productive binding events can provide distinction between the two types of events.

The detectable signals can be classified into true positive and false positive signals. For example, the true positive signals can arise from productive binding in which the nucleotide binds the polymerase and is incorporated. The incorporated nucleotide can be complementary to the template nucleotide. In another example, the false positive signals can arise from different binding events, including: non-specific binding, non-productive binding, and any event which brings the energy transfer donor and acceptor into sufficient proximity to induce a detectable signal.

Optionally, polymerase reactions performed using the methods, systems, compositions and kits of the present disclosure can be performed under any conditions which are suitable for: forming the complex (target/polymerase or target/initiation site/polymerase); binding the nucleotide to the polymerase; permitting the energy transfer and reporter moieties to generate detectable signals when the nucleotide binds the polymerase; incorporating the nucleotide; permitting the energy transfer and reporter moieties to generate a signal upon close proximity and/or nucleotide incorporation; and/or detecting the signal, or change in the signal, from the energy transfer or reporter moieties. The suitable conditions include well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. The buffer can include Tris, Tricine, HEPES, MOPS, ACES, or MES, which can provide a pH range of about 5.0 to about 9.5. The buffer can include chelating agents such as EDTA and EGTA, and the like.

Reducing Photo-Damage

The suitable polymerase reaction conditions can also include compounds which reduce photo-damage. For example, the compounds may reduce oxygen-damage or photo-damage. Illuminating the nucleotide binding and/or nucleotide incorporation reactions with electromagnetic radiation at an excitation wavelength can induce formation of reactive oxygen species from the fluorophore or other components in the reaction. The reactive oxygen species can cause photo-damage to the fluorophores, polymerases, or any other component of the binding or incorporation reactions. The nucleotide binding or nucleotide incorporation reactions can include compounds which are capable of reducing photo-damage, including: protocatechuate-3,4-dioxygenase, protocatechuic acid; 6-Hydroxy-2,5,7,8-tetramethylchroman-2-carboxylic Acid (TROLOX); or cyclooctatetraene (COT).

Other compounds for reducing photo-damage include: ascorbic acid, astazanthin, bilirubin, biliverdin, bixin, captopril, canthazanthin, carotene (alpha, beta, and gamma), cysteine, beta-dimethyl cysteine, N-acetyl cysteine, diazobicyclooctane (DABCO), dithiothreitol (DTT), ergothioneine, glucose oxidase/catalase (GO/Cat), glutathione, glutathione peroxidase, hydrazine ($N_2H_4$), hydroxylamine, lycopene, lutein, polyene dialdehydes, melatonin, methionine, mercaptopropionylglycine, 2-mercaptoethane sulfonate (MESNA), pyridoxine1 and its derivatives, mercaptoethylamine (MEA), β-mercaptoethanol (BME), n-propyl gallate, p-phenylenediamene (PPD), hydroquinone, sodium azide ($NaN_3$), sodium sulfite ($Na_2SO_3$), superoxide dismutase, tocopherols, α-tocopheryl succinate and its analogs, and zeaxanthin.

Also provided herein are methods of using the labeled biomolecule conjugates of the present disclosure.

For example, disclosed herein are methods for incorporation of one or more nucleotides onto the end of a nucleic acid molecule, comprising: contacting a conjugate including a polymerase linked to a label with a nucleotide under conditions where the nucleotide is incorporated into a nucleic acid molecule by the conjugate. The nucleic acid molecule can be any suitable target nucleic acid molecule of interest. In some embodiments, the nucleotide can be become incorporated onto the 3' end of an extending nucleic acid molecule by the polymerase. In some embodiments, the nucleotide can be a labeled nucleotide analog. The labeled nucleotide analog can further comprise a label linked to the base, sugar, phosphate or any other portion of the nucleotide analog. In some embodiments, the nucleotide can also comprise a blocking group that inhibits, slows down or blocks further incorporation of nucleotides onto the end of the nucleic acid molecule until the blocking group is removed from the nucleotide. In some embodiments, the nucleotide comprising a blocking group is a reversible terminator for nucleic acid synthesis, as described further below. In some embodiments, the blocking group can be removed from the nucleotide by chemical, enzymatic, or photocleaving reactions.

In some embodiments, the method further includes the step of adding one or more divalent cations to the polymerase reaction mixture in an amount sufficient for inhibiting further incorporation of nucleotides onto the end of the nucleic acid molecule by the labeled polymerase. In some embodiments, the divalent cation that inhibits nucleotide incorporation is calcium. In another embodiment, omitting, reducing, or chelating cations that permit nucleotide incorporation (e.g, manganese and/or magnesium) can be employed. Such methods are described, for example, in U.S. Provisional Application 61/242,762, filed Sep. 15, 2009; and in U.S. Provisional Application No. 61/184,774, filed on Jun. 5, 2009. In some embodiments, the polymerase can be linked to a label, as, for example, disclosed herein and in U.S. Provisional Application No. 61/184,770, filed Jun. 5, 2009.

Also provided herein is a method for detecting one or more nucleotide incorporations, comprising: contacting a conjugate including a polymerase linked to a label with a labeled nucleotide under conditions where the labeled nucleotide is incorporated by the conjugate into a nucleic acid molecule, and where the label of the labeled nucleotide emits a signal indicative of such nucleotide incorporation; and detecting the signal indicative of such nucleotide incorporation. In some embodiments, the detecting can be performed in real or near real time. In some embodiments, the method can further include analyzing the detected signal indicative of nucleotide incorporation to determine the identity of the incorporated nucleotide. In some embodiments, the labeled polymerase conjugate catalyzes a time series of nucleotide incorporations, which can collectively be detected and analyzed to determine some or all of the sequence of the target nucleic acid molecule.

Also disclosed herein is a method for determining a nucleotide sequence of a single nucleic acid molecule, comprising: (a) conducting a polymerase reaction comprising a labeled biomolecule conjugate and a labeled nucleotide under conditions where the conjugate incorporates the labeled nucleotide into a nucleic acid molecule and a signal indicative of such nucleotide incorporation is generated; (b) detecting the signal indicative of such nucleotide incorporation; and (c) analyzing the signal to determine the identity of the incorporated nucleotide. Optionally, a time series of nucleotide incorporation signals can be detected and analyzed, thereby determining some or all of the nucleotide sequence of a single nucleic acid molecule.

Also provided herein are methods of sequencing a nucleic acid molecule, comprising: (a) performing a polymerase reaction comprising a labeled polymerase conjugate and labeled nucleotides under conditions resulting in a series of labeled nucleotide incorporations by the polymerase and the generation of a signal indicative of each nucleotide incorporation the series; (b) detecting a time sequence of nucleotide incorporations; and (c) determining the identity of one or more incorporated nucleotides, thereby determining some or all of the nucleotide sequence of a single nucleic acid molecule.

In some embodiments, the polymerase is attached to or associated with a substrate or surface. In some embodiments, the polymerase can be attached to or associated with a nucleic acid molecule (termed a template), and polymerize one or more nucleotides in a template-dependent fashion. In some embodiments, the template can be attached to or associated with a substrate or surface. In some embodiments, the polymerase, template, nucleotide, substrate or surface, or some combination thereof, can also be labeled.

In some embodiments, the methods of the present disclosure can be performed in multiplex and/or "high-throughput" format wherein multiple units of the labeled polymerase conjugates of the present disclosure can each be visualized and monitored in parallel with each other. For example, in some embodiments, multiple labeled polymerase conjugates may be positioned, associated with, or attached to different locations on a substrate, and a polymerase activity of one or more of these polymerases may be detected in isolation. In some embodiments, the polymerase or the template nucleic acid molecule are associated with or attached to a substrate or surface in array format. The array can be spatially addressable.

In some embodiments, the sequencing reaction can be performed using buffer conditions comprising 50 mM Tris buffer pH 7.5, 50 mM NaCl, 0-10 mM $MgCl_2$, 2 mM $MnCl_2$, 330 nM polymerase, 100 nM primed template and 4 µM labeled nucleotide hexaphosphate. Optionally, 0.3% BSA and/or 0.05% Tween20 can be included in the reaction mix. In some embodiments, the reaction mix is further supplemented with 2 mM DTT and/or single stranded binding protein (SSBP) at a concentration of 100 µg/ml.

Alternatively, in some embodiments the sequencing reaction can be performed using buffer conditions comprising 50 mM Tris pH 8.0, 50 mM NaCl and 10 mM $MgCl_2$.

In one exemplary embodiment, a nucleic acid sequencing system can comprise a template nucleic acid molecule attached to a substrate, a labeled polymerase conjugate comprising a FRET donor label linked to a polymerase, and labeled nucleotides each comprising a nucleotide linked to one or more FRET acceptor labels.

The template nucleic acid molecule of this sequencing system can be attached to any suitable substrate or surface using any suitable method. in some embodiments, the template nucleic acid molecule can comprise one or more biotin moieties, the surface can comprise an avidin moiety, and the template nucleic acid is linked to the surface via one or more biotin-avidin bonds. In some embodiments, the template and surface can each comprise one or more biotin moieties, and be linked to each other through a linkage comprising an avidin moiety.

Figure 1:
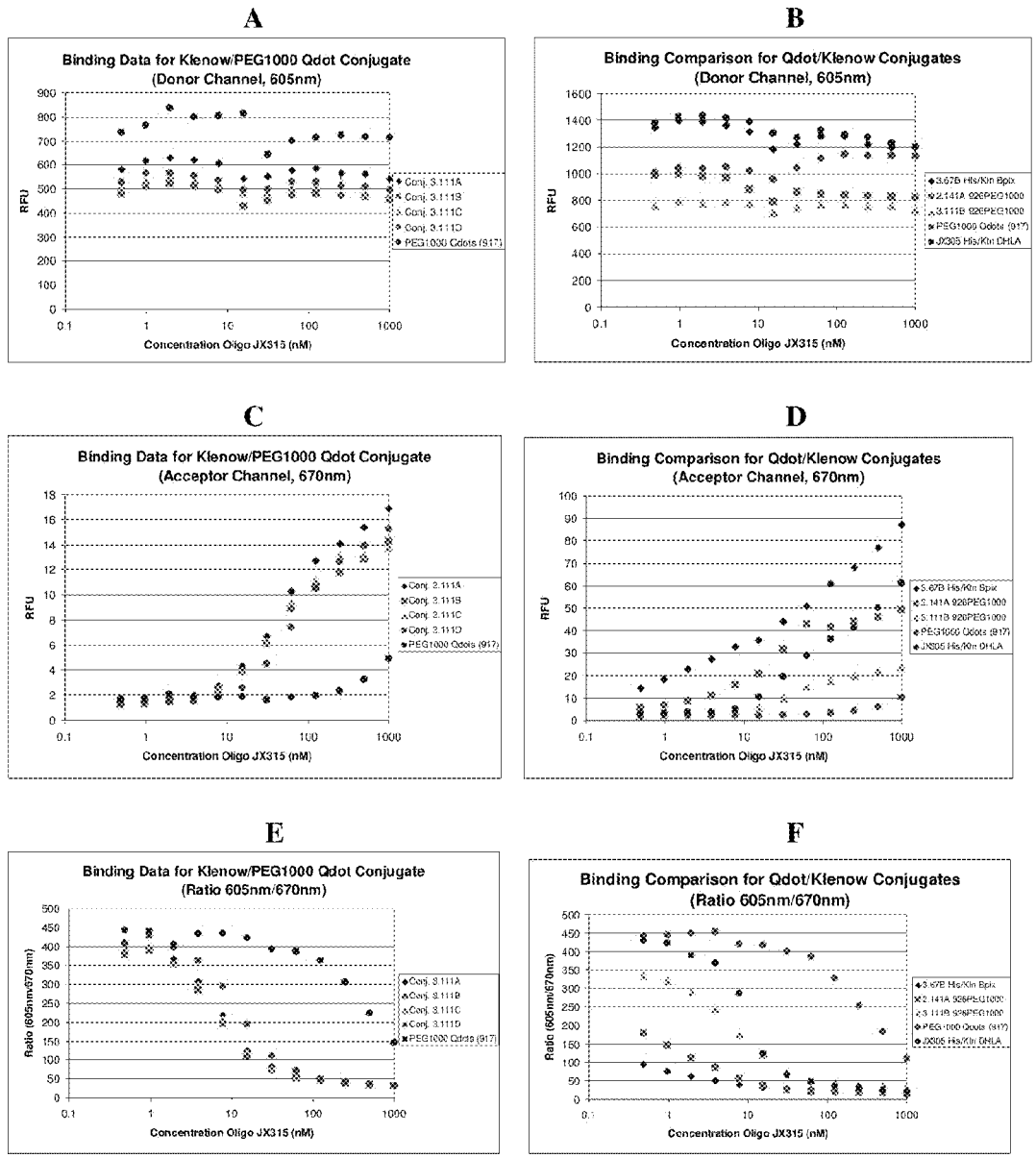

An exemplary sequencing system according to the present disclosure is depicted in FIG. 1. This exemplary system comprises a biotinylated nucleic acid template (here, a hairpin oligonucleotide) linked to a surface though one or more biotin-avidin bonds, a labeled polymerase conjugate comprising biotinylated Phi-29 linked to dye-labeled streptavidin, and acceptor-labeled nucleotides.

In some embodiments, the polymerase of the labeled polymerase conjugate initiations polymerization at a polymerization initiation site. In some embodiments, the polymerization initiation site can be a terminal 3' OH group of a nucleic acid molecule. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication.

In some embodiments, the polymerization initiation site can be provided by an accessory protein (e.g., RNA polymerase or helicase/primase). The polymerization initiation site can be provided by a terminal protein which can be bound (covalently or non-covalently) to the end of the target nucleic, including terminal protein (e.g., TP) found in phage (e.g., TP from phi29 phage). Thus, the polymerization initiation site may be at a terminal end or within a base-paired nucleic acid molecule.

In other embodiments, the polymerization initiation site used by some polymerases (e.g., RNA polymerase) may not include a 3'OH group.

The portion of the target molecule which is base paired with the primer or with the oligonucleotide, or the self-primed portion of the target molecule, can form hydrogen bonding by Watson-Crick or Hoogstein binding to form a duplex nucleic acid structure. The primer, oligonucleotide, and self-priming sequence may be complementary, or partially complementary, to the nucleotide sequence of the target molecule. The complementary base pairing can be the standard A-T or C-G base pairing, or can be other forms of base-pairing interactions.

Primer Molecules

In some embodiments, the primer molecule can hybridize with the target nucleic acid molecule. The sequence of the primer molecule can be complementary or non-complementary with the sequence of the sequence of the target molecule. The 3' terminal end of the primer molecule can provide the polymerization initiation site.

Optionally, the primers can be modified with a chemical moiety to protect the primer from serving as a polymerization initiation site or as a restriction enzyme recognition site. The chemical moiety can be a natural or synthetic amino acid linked through an amide bond to the primer.

The primer, oligonucleotide, or self-priming portion, may be naturally-occurring, or may be produced using enzymatic or chemical synthesis methods. The primer, oligonucleotide, or self-priming portion may be any suitable length including 5, 10, 15, 20, 25, 30, 40, 50, 75, or 100 nucleotides or longer in length. The primer, oligonucleotide, or self-priming portion may be linked to an energy transfer moiety (e.g., donor or acceptor) or to a reporter moiety (e.g., a dye) using methods well known in the art.

The primer molecule, oligonucleotide, and self-priming portion of the target molecule, may comprise ribonucleotides, deoxyribonucleotides, ribonucleotides, deoxyribonucleotides, peptide nucleotides, modified phosphate-sugar backbone nucleotides including phosphorothioate and phosphoramidate, metallonucleosides, phosphonate nucleosides, and any analogs or variants thereof, or combinations thereof.

In one embodiment, the primer molecule can be a recombinant DNA molecule. The primer can be linked at the 5' or 3' end, or internally, with a binding partner, such as biotin. The biotin can be used to immobilize the primer molecule to the surface (via an avidin-like molecule), or for attachment to a reporter moiety. The primer can be linked to a energy transfer moiety, such as a fluorescent dye or a nanoparticle, or to a reporter moiety. The primer molecule can hybridize to the target nucleic acid molecule. The primer molecule can be used as a capture probe to immobilize the target molecule.

The compositions, methods, systems, apparatuses and kits disclosed herein can be practiced using nucleotides. In some embodiments, the nucleotides can be linked with at least one energy transfer moiety. The energy transfer moiety can be an energy transfer acceptor moiety. The different types of nucleotides (e.g., adenosine, thymidine, cytidine, guanosine, and uridine) can be labeled with different energy transfer acceptor moieties so that the detectable signals from each of the different types of nucleotides can be distinguishable to permit base identity. The nucleotides can be labeled in a way that does not interfere with the events of polymerization. For example the attached energy transfer acceptor moiety does not interfere with nucleotide binding and/or does not interfere with nucleotide incorporation and/or does not interfere with cleavage of the phosphodiester bonds and/or does not interfere with release of the polyphosphate product. See for example, U.S. Ser. No. 61/164,091, Ronald Graham, concurrently filed Mar. 27, 2009. See for example U.S. Pat. Nos. 7,041,812, 7,052,839, 7,125,671, and 7,223,541; U.S. Pub. Nos. 2007/072196 and 2008/0091005; Sood et al., 2005, J. Am. Chem. Soc. 127:2394-2395; Arzumanov et al., 1996, J. Biol. Chem. 271:24389-24394; and Kumar et al., 2005, Nucleosides, Nucleotides & Nucleic Acids, 24(5):401-408.

In one aspect, the energy transfer acceptor moiety may be linked to any position of the nucleotide. For example, the energy transfer acceptor moiety can be linked to any phosphate group (or derivatized phosphate group), the sugar or the base. In another example, the energy transfer moiety can be linked to any phosphate group (or derivatized phosphate group) which is released as part of a phosphate cleavage product upon incorporation. In yet another example, the energy transfer acceptor moiety can be linked to the terminal phosphate group (or derivatized phosphate group). In another aspect, the nucleotide may be linked with an additional energy transfer acceptor moiety, so that the nucleotide is attached with two or more energy transfer acceptor moieties. The additional energy transfer acceptor moiety can be the same or different as the first energy transfer acceptor moiety. In one embodiment, the energy transfer acceptor moiety can be a FRET acceptor moiety.

In one aspect, the nucleotide may be linked with a reporter moiety which is not an energy transfer moiety. For example, the reporter moiety can be a fluorophore.

In one aspect, the energy transfer acceptor moieties and/or the reporter moiety can be attached to the nucleotide via a linear or branched linker moiety. An intervening linker moiety can connect the energy transfer acceptor moieties with each other and/or to the reporter moiety, any combination of linking arrangements.

In another aspect, the nucleotides comprise a sugar moiety, base moiety, and at least three, four, five, six, seven, eight, nine, ten, or more phosphate groups linked to the sugar moiety by an ester or phosphoramide linkage. The phosphates can be linked to the 3' or 5' C of the sugar moiety. The nucleotides can be incorporated and/or polymerized into a growing nucleic acid strand by a naturally occurring, modified, or engineered nucleic acid dependent polymerase.

In one aspect, different linkers can be used to operably link the different nucleotides (e.g., A, G, C, or T/U) to the energy transfer moieties or reporter moieties. For example, adenosine nucleotide can be attached to one type of energy transfer moiety using one type of linker, and guanosine nucleotide can be linked to a different type of energy transfer moiety using a different type of linker. In another example, adenosine nucleotide can be attached to one type of energy transfer moiety using one type of linker, and the other types of nucleotides can be attached to different types of energy transfer moieties using the same type of linker. One skilled in the art will appreciate that many different combinations of nucleotides, energy transfer moieties, and linkers are possible.

In one aspect, the distance between the nucleotide and the energy transfer moiety can be altered. For example, the linker length and/or number of phosphate groups can lengthen or shorten the distance from the sugar moiety to the energy transfer moiety. In another example, the distance between the nucleotide and the energy transfer moiety can differ for each type of nucleotide (e.g., A, G, C, or T/U).

In another aspect, the number of energy transfer moieties which are linked to the different types of nucleotides (e.g., A, G, C, or T/U) can be the same or different. For example: A can have one dye, and G, C, and T have two; A can have one dye, C has two, G has three, and T has four; A can have one dye, C and G have two, and T has four. One skilled in the art will recognize that many different combinations are possible.

In another aspect, the concentration of the labeled nucleotides used to conduct the nucleotide binding or nucleotide incorporation reactions can be about 0.0001 nM-1 µM, or about 0.0001 nM-0.001 nM, or about 0.001 nM-0.01 nM, or about 0.01 nM-0.1 nM, or about 0.1 nM-1.0 nM, or about 1 nM-25 nM, or about 25 nM-50 nM, or about 50 nM-75 nM, or about 75 nM-100 nM, or about 100 nM-200 nM, or about 200 nM-500 nM, or about 500 nM-750 nM, or about 750 nM-1000 nM, or about 0.1 µM-20 µM, or about 20 µM-50 µM, or about 50 µM-75 µM, or about 75 µM-100 µM, or about 100 µM-200 µM, or about 200 µM-500 µM, or about 500 µM-750 µM, or about 750 µM-1000 µM.

In another aspect, the concentration of the different types of labeled nucleotides, which are used to conduct the nucleotide binding or incorporation reaction, can be the same or different from each other.

Sugar Moieties

The nucleotides typically comprise suitable sugar moieties, such as carbocyclic moieties (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In one aspect, the 3'-position has a hydroxyl group, for strand/chain elongation.

Base Moieties

The nucleotides can include a hetero cyclic base which includes substituted or unsubstituted nitrogen-containing parent heteroaromatic ring which is commonly found in nucleic acids, including naturally-occurring, substituted, modified, or engineered variants. The base is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2 ms61A), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in: *Practical Handbook of Biochemistry and Molecular Biology*, pp. 385-394, CRC Press, Boca Raton, Fla., and the references cited therein.

Examples of nucleotides include ribonucleotides, deoxyribonucleotides, modified ribonucleotides, modified deoxyribonucleotides, ribonucleotides, deoxyribonucleotides, modified ribonucleotides, modified deoxyribonucleotides, peptide nucleotides, modified peptide nucleotides, metallonucleosides, phosphonate nucleosides, and modified phosphate-sugar backbone nucleotides, and any variants of the foregoing.

Phosphate Groups

The nucleotides can optionally include phosphate groups which can be linked to the 2', 3' and/or 5' position of the sugar moiety. The phosphate groups include analogs, such as phosphoramidate, phosphorothioate, phosphorodithioate, and O-methylphosphoroamidite groups. In one embodiment, at least one of the phosphate groups can be substituted with a fluoro and/or chloro group. The phosphate groups can be linked to the sugar moiety by an ester or phosphoramide linkage. Typically, the nucleotide comprises three, four, five, six, seven, eight, nine, ten, or more phosphate groups linked to the 5' position of the sugar moiety.

The disclosed compositions and methods can be practiced using any nucleotide which can be incorporated by a polymerase, including naturally-occurring or recombinant polymerases. In one embodiment, the nucleotides can include a nucleoside linked to a chain of 1-10 phosphorus atoms. The nucleoside can include a base (or base analog) linked to a sugar (or sugar analog). The phosphorus chain can be linked to the sugar, for example linked to the 5' position of the sugar. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)$ $CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotides are described in Xu, U.S. Pat. No. 7,405,281.

In some embodiments, the nucleotide is a dye-labeled nucleotide that comprises a polyphosphate chain and a dye moiety linked to the terminal phosphate group. In some embodiments, the dye-labeled nucleotide comprises a dye moiety linked to the terminal phosphate through an alkyl linker. Optionally, the linker comprises a 6-carbon chain and has a reactive amine group, and the dye moiety is linked to the terminal phosphate bond though a covalent bond formed with the amine group of the linker. In some embodiments, the polyphosphate chain comprises 4, 5, 6, 7, 8, 9, 10 or more phosphates. One exemplary dye-labeled nucleotide that can be used in the disclosed methods and systems has the general structure shown in FIG. 39. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In some embodiments, the dye moiety can optionally comprise any one or more of the following dyes: rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives) and Cy5 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610 (N-succinimidyl ester), ATTO 635 (NHS ester); ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED (phosphoramidate), EPOCH YAKIMA YELLOW (phosphoramidate), EPOCH GIG HARBOR GREEN (phosphoramidate); Tokyo green (M. Kamiya, et al., 2005 Angew. Chem. Int. Ed. 44:5439-5441); and CF dyes including CF 647 and CF555 (Biotium).

In some embodiments, such dye-labeled nucleotides can be used to assay for the nucleotide incorporation kinetics of a particular polymerase according to the procedures described herein (see, e.g., Example 30).

Non-Hydrolyzable Nucleotides

The nucleotide binding and nucleotide incorporation methods can be practiced using incorporatable nucleotides and non-hydrolyzable nucleotides. In the presence of the incorporatable nucleotides (e.g., labeled), the non-hydrolyzable nucleotides (e.g., non-labeled) can compete for the polymerase binding site to permit distinction between the complementary and non-complementary nucleotides, or for distinguishing between productive and non-productive binding events. In the nucleotide incorporation reaction, the presence of the non-hydrolyzable nucleotides can alter the length of time, frequency, and/or duration of the binding of the labeled incorporatable nucleotides.

The non-hydrolyzable nucleotides can be non-labeled or can be linked to a reporter moiety (e.g., energy transfer moiety). The labeled non-hydrolyzable nucleotides can be linked to a reporter moiety at any position, such as the sugar, base, or any phosphate (or substituted phosphate group). For example, the non-hydrolyzable nucleotides can have the general structure:

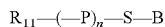

Where B can be a base moiety, such as a hetero cyclic base which includes substituted or unsubstituted nitrogen-containing heteroaromatic ring. Where S can be a sugar moiety, such as a ribosyl, riboxyl, or glucosyl group. Where n can be 1-10, or more. Where P can be one or more substituted or unsubstituted phosphate or phosphonate groups. Where $R_{11}$, if included, can be a reporter moiety (e.g., a fluorescent dye). In one embodiment, the non-hydrolyzable nucleotide having multiple phosphate or phosphonate groups, the linkage between the phosphate or phosphonate groups can be non-hydrolyzable by the polymerase. The non-hydrolyzable linkages include, but are not limited to, amino, alkyl, methyl, and thio groups. Non-hydrolyzable nucleotide tetraphosphates having alpha-thio or alpha boreno substitutions having been described (Rank, U.S. published patent application No. 2008/0108082; and Gelfand, U.S. published patent application No. 2008/0293071).

The phosphate or phosphonate portion of the non-hydrolyzable nucleotide can have the general structure:

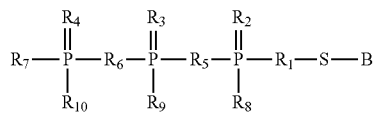

Where B can be a base moiety and S can be a sugar moiety. Where any one of the $R_1$-$R_7$ groups can render the nucleotide non-hydrolyzable by a polymerase. Where the sugar C5 position can be $CH_2$, $CH_2O$, $CH=$, CHR, or $CH_2CH_2$. Where the $R_1$ group can be O, S, $CH=$, CH(CN), or NH. Where the $R_2$, $R_3$, and $R_4$, groups can independently be O, $BH_3$, or SH. Where the $R_5$ and $R_6$ groups can independently be an amino, alkyl, methyl, thio group, or CHF, $CF_2$, CHBr, $CCl_2$, O—O, or —C≡C—. Where the $R_7$ group can be oxygen, or one or more additional phosphate or phosphonate groups, or can be a reporter moiety. Where $R_8$ can be SH, $BH_3$, $CH_3$, $NH_2$, or a phenyl group or phenyl ring. Where $R_9$ can be SH. Where $R_{10}$ can be $CH_3$, $N_3CH_2CH_2$, $NH_2$, ANS, $N_3$, MeO, SH, Ph, F, PhNH, PhO, or RS (where Ph can be a phenyl group or phenyl ring, and F can be a fluorine atom or group). The substituted groups can be in the S or R configuration.

The non-hydrolyzable nucleotides can be alpha-phosphate modified nucleotides, alpha-beta nucleotides, beta-phosphate modified nucleotides, beta-gamma nucleotides, gamma-phosphate modified nucleotides, caged nucleotides, or dinucleotides.

Many examples of non-hydrolyzable nucleotides are known (Rienitz 1985 Nucleic Acids Research 13:5685-5695), including commercially-available ones from Jena Bioscience (Jena, Germany).

In some embodiments, the nucleotide comprises a nucleotide analog that is capable of acting as a reversible terminator of nucleic acid synthesis. Typically, reversible terminators can be incorporated by a polymerase onto the end of an extending nucleic acid molecule, but then "terminate" further synthesis by blocking further addition of nucleotides. In some embodiments, this "termination" capability can be manipulated by adjusting the reaction conditions and/or by suitable treatment. The ability to terminate can result from the presence of a moiety or group, typically named a "blocking" group, which is linked to the nucleotide. In some embodiments, the ability of the nucleotide to terminate nucleic acid synthesis can be eliminated through physical removal, cleavage, structural modification or disruption of the blocking group. The blocking group can be attached to any portion of the nucleotide including, for example, a base moiety, sugar moiety or phosphate moiety. The blocking group can be attached to the nucleotide via a linker. The linkage between the blocking group and the nucleotide can be a photocleavable, chemically cleavable, enzymatically cleavable, thermocleavable (i.e., cleavable upon adjustment of temperature) or pH-sensitive linkage. In some embodiments, the label (which is linked to the nucleotide) is the blocking group.

In some embodiments, the reversible terminator further comprises a label or tag that facilitates detection of nucleotide. The label can be a fluorescent label. In some embodiments, the label can also be removed via suitable treatment. In some embodiments, the label is released from the nucleotide during incorporation of the nucleotide into the extending nucleic acid molecule. Alternatively, the label becomes incorporated into the extending nucleic acid molecule and is then removed via suitable treatment. In some embodiments, the label is attached to the nucleotide via a cleavable linkage. The cleavable linkage can be a photocleavable, chemically cleavable, enzymatically cleavable, thermocleavable (i.e., cleavable upon adjustment of temperature) or pH-sensitive linkage.

The removal of the blocking group can be accomplished in a variety of ways. In some embodiments, the blocking group is attached to the nucleotide via a photocleavable linkage and can be removed from the nucleotide via exposure to photocleaving radiation. In some embodiments, the linkage is a chemically or enzymatically cleavable linkage. In some embodiments, the linkage can be disrupted by varying reaction conditions, e.g., pH, temperature, concentrations of divalent cations, etc.

Non-limiting examples of suitable reversible terminators include, inter alia, nucleotide base-labeled nucleotides comprising one or more blocking groups attached to 3' hydroxyl group, the base moiety or a phosphate group. For example, the nucleotide can comprise an azidomethyl group linked to the 3' hydroxyl group and a fluorescent label linked to the base of the nucleotide. In some embodiments, the reversible terminator can comprise one or more blocking groups attached to the phosphate group. In some embodiments, the nucleotide can comprise a blocking group and a label. In some embodiments, both the blocking group and the label can be linked to the base moiety, while the 3' hydroxyl group is not modified. In some embodiments, the blocking group can be a photocleavable group linked to the base of the nucleotide. See, e.g., U.S. Publication No. 2008/0132692, published Jun. 5, 2008. Further examples of nucleotides comprising extension blocking groups and methods of their use in polymerase-based applications can be found, for example, in U.S. Pat. No. 7,078,499 issued Jul. 18, 2006; as well as in U.S. Published Application Nos. 2004/0048300 published Mar. 11, 2004; 2008/0132692 published Jun. 5, 2008; 2009/0081686, published Mar. 26, 2009; and 2008/0131952, published Jun. 5, 2008; Tsien, WO/1991/006678; Stemple, U.S. Pat. No. 7,270,951, Balasubramanian, U.S. Pat. No. 7,427,673; Milton, U.S. Pat. No. 7,541,444.

In some embodiments, the nucleotide comprises a cleavable label linked to the base. In some embodiments, the blocking group and the label can be removed via the same cleavage treatment. See, e.g., U.S. Pat. No. 7,553,949, issued Jun. 30, 2009. Alternatively, different treatments can be required to remove the blocking group and the label. In some embodiments, the label of the reversible terminator correlates with the base identity of the nucleotide. In some embodiments, each reversible terminator is added sequentially to the polymerase reaction; alternatively, different kinds of reversible terminators can be present simultaneously in the reaction mixture.

In some embodiments, the blocking group is linked to the 2' hydroxyl group of the sugar moiety. See, e.g., U.S. Pat. No. 7,553,949, issued Jun. 30, 2009.

In some embodiments, the reversible terminator can comprise more than one blocking group. In some embodiments, these multiple blocking groups may function cooperatively by enhancing the termination efficiency of the nucleotide. In one exemplary embodiment, the nucleotide comprises a blocking group linked to the base moiety, while another group linked to the terminal phosphate group further suppresses the incorporation of a nucleotide onto the free 3' hydroxyl group. See, e.g., U.S. patent application Ser. No. 12/355,487, filed Jan. 16, 2009.

Typically, the labeled polymerase conjugates of the present disclosure can be used to sequence one or more nucleic acid molecules of interest. In an exemplary method, the reversible terminator is incorporated in a template-dependent manner onto the 3' end of an extending nucleic acid molecule by a labeled polymerase conjugate. The incorporated reversible terminator is detected and identified; and the blocking group of the reversible terminator is then removed. In some embodiments, the unincorporated reversible terminators can be washed away; in some embodiments, it is not necessary to wash or otherwise remove the unincorporated reversible terminators prior to detection, identification or subsequent extension of the extending nucleic acid molecule. In some embodiments, incorporation of the reversible terminator onto the end of a nucleic acid molecule can involve the formation of a covalent bond between the reversible terminator and the nucleotide moiety at the 3' end of the nucleic acid molecule. Alternatively, incorporation of reversible terminator onto the end of a nucleic acid molecule will not involve formation of any covalent bond between the reversible terminator and the nucleotide moiety at the 3' end of the nucleic acid molecule; instead, the reversible terminator is bound in a template-dependent fashion and positioned within the active site of the polymerase until the blocking group is cleaved or otherwise removed, following which the remaining portion of the reversible terminator can remain as a portion of the extending nucleic acid molecule or alternatively will also dissociate from the polymerase active site and diffuse away.

In some embodiments, the nucleic acid molecule, the polymerase, or both, may be isolated within a suitable nanostructure. In some embodiments, the nanostructure can be useful in elongating the nucleic acid molecule to permit visualization of nucleotide synthesis along some or all of the length of the nucleic acid molecule. In some embodiments, the nanostructure is also useful in limiting the amount of background signal ("noise") in the system by reducing the excitation or detection volume, and/or by reducing the amount of labeled moieties present within the reaction chamber. In some embodiments, the nanostructure is designed to admit only a single polymeric molecule and elongate it as it flows through the nanostructure. Suitable devices comprising nanostructures that may be used to practice the inventions disclosed herein are described, for example, in U.S. Pat. No. 6,635,163; U.S. Pat. No. 7,217,562, U.S. Pub. No. 2004/0197843 and U.S. Pub. No. 2007/0020772. In some embodiments, the nanostructures of the nanofluidic device will satisfy three requirements: (1) they will have a sufficiently small dimension to elongate and isolate macromolecules; (2) they will be sufficient length to permit instantaneous observation of the entire elongated macromolecule; and (3) the nanochannels or other nanostructures will be sufficiently numerous to permit simultaneous and parallel observation of a large population of macromolecules. In one embodiment, the radius of the component nanostructures of the nanofluidic device will be roughly equal to or less than the persistence length of the target DNA. Suitable methods of detecting nucleotide incorporations using nanostructures are disclosed, for example, in U.S. Provisional Application Nos. 61/077,090, filed Jun. 30, 2008; 61/089,497, filed Aug. 15, 2008; and 61/090,346, filed Aug. 20, 2008; and International Application No. PCT/US09/49324, filed Jun. 30, 2009.

In some embodiments, the label of the disclosed labeled conjugates can emit, or cause to be emitted, a signal that permits visualization of the conjugate and/or provides an indication of biomolecular activity.

Particular disclosed herein are compositions, methods and systems relating to labeled polymerase conjugates, wherein the conjugate emits, or causes the emission of, a signal indicating a nucleotide incorporation by the polymerase of the conjugate.

In some embodiments, the signal is an optically detectable signal. Optionally, the optically detectable signal can be a fluorescent signal.

The signal emitted, or caused to be emitted by the labeled conjugates of the disclosed compositions, methods and systems can be detected and analyzed using any suitable methods and related devices. A wide variety of detectors are available in the art. Representative detectors include but are not limited to optical readers, high-efficiency photon detection systems, photodiodes (e.g. avalanche photo diodes (APD); APD arrays, etc.), cameras, charge couple devices (CCD), electron-multiplying charge-coupled device (EMCCD), intensified charge coupled device (ICCD), photomultiplier tubes (PMT), a multi-anode PMT, and a confocal microscope equipped with any of the foregoing detectors. Where desired, the subject arrays can contain various alignment aides or keys to facilitate a proper spatial placement of each spatially addressable array location and the excitation sources, the photon detectors, or the optical transmission element as described below.

The systems and methods can detect and/or measure a change or an amount of change of an optical or spectral characteristic of a signal (e.g., fluorescence or quenching) from a label. In some embodiments, the label can be the label of the conjugate or a nucleotide label. The change in the signal can include changes in the: intensity of the signal; duration of the signal; wavelength of the signal; amplitude of the signal; duration between the signals; and/or rate of the change in intensity, duration, wavelength or amplitude. The change in the signal can include a change in the ratio of the change of the energy transfer donor relative to change of the energy transfer acceptor signals.

In some embodiments, the detection system comprises: excitation illumination, optical transmission elements, detectors, and/or computers.

The detection system can comprise excitation illumination which can excite the energy transfer or reporter moieties which produce a detectable signal. The excitation illumination can be electromagnetic energy, such as radio waves, infrared, visible light, ultraviolet light, X-rays or gamma rays. The source of the electromagnetic radiation can be a laser, which possesses properties of mono-chromaticity, directionality, coherence, polarization, and/or intensity. The laser can produce a continuous output beam (e.g., continuous wave laser) or produce pulses of light (e.g., Q-switching or mode-locking). The laser can be used in a one-photon or multi-photon excitation mode. The laser can produce a focused laser beam. The wavelength of the excitation electromagnetic radiation can be between about 325-850 nm, or between about 325-752 nm, or between about 330-752 nm, or between about 405-752 nm. The laser can be generated by a mercury, xenon, halogen, or other lamps.

The wavelength and/or power of the excitation illumination can be selected to avoid interfering with or damaging the polymerase enzymatic activities. The excitation illumination can be focused on a stationary position or moved to a different field of view (FOV). The excitation illumination can be directed at a nucleotide incorporation reaction which is: in a liquid volume (e.g., aqueous or oil); on a surface; in or on a nanodevice; in a waveguide; or in an evanescent illumination system (e.g., total internal reflection illumination). The excitation illumination can pass through a transparent or partially transparent surface which is conjugated (covalently or non-covalently) with the components of the nucleotide incorporation reaction.

The energy transfer moiety (e.g., a FRET donor) can be excited by the excitation illumination at a particular wavelength, and transmit the excitation energy to an acceptor moiety which is excited and emits a signal at a longer wavelength. The energy transfer moiety or reporter moiety can undergo multi-photon excitation with a longer wavelength, typically using a pulsed laser.

The detection system comprises suitable optical transmission elements which are capable of transmitting light from one location to another with the desired refractive indices and geometries. The optical transmission elements transmit the excitation illumination and/or the emitted energy in an unaltered or altered form. The optical transmission elements include: lens, optical fibers, polarization filters (e.g., dichroic filters), diffraction gratings (e.g., etched diffraction grating), arrayed waveguide gratings (AWG), optical switches, mirrors, dichroic mirrors, dichroic beam splitter, lenses (e.g., microlens and nanolens), collimators, filters, prisms, optical attenuators, wavelength filters (low-pass, band-pass, or high-pass), wave-plates, and delay lines, or any combination thereof.

The detection system comprises suitable detectors which are capable of detecting and/or distinguishing the excitation illumination and/or the emitted energy. A wide variety of detectors are available in the art, including: single or multiple channel detectors, high-efficiency photon detection systems, optical readers, charge couple devices (CCD), photodiodes (e.g. avalanche photo diodes (APD)), APD arrays, cameras, electron-multiplying charge-coupled device (EMCCD), intensified charge coupled device (ICCD), photomultiplier tubes (PMT), multi-anode PMT, complementary metal oxide semiconductor (CMOS) chip(s), and a confocal microscope equipped with any of the foregoing detectors. The location of the nucleotide incorporation reaction can be aligned, with respect to the excitation illumination and/or detectors, to facilitate proper optical transmission.

Suitable detection methods can be used for detecting and/or distinguishing the excitation illumination (or change in excitation illumination) and/or the emitted energy (or change in emitted energy), including: confocal laser scanning microscopy, Total Internal Reflection (TIR), Total Internal Reflection Fluorescence (TIRF), near-field scanning microscopy, far-field confocal microscopy, wide-field epi-illumination, light scattering, dark field microscopy, photoconversion, wide field fluorescence, single and/or multi-photon excitation, spectral wavelength discrimination, evanescent wave illumination, scanning two-photon, scanning wide field two-photon, Nipkow spinning disc, multi-foci multi-photon, or any combinations thereof.

The signals emitted from different energy transfer moieties can be resolved using suitable discrimination methods which are based on: fluorescence resonance energy transfer measurements; photoconversion; fluorescent lifetime measurements; polarization; fluorescent lifetime determination; correlation/anti-correlation analysis; Raman; intensity; ratiometric; time-resolved methods; anisotropy; near-field or far field microscopy; fluorescence recovery after photobleaching (FRAP); spectral wavelength discrimination; measurement and separation of fluorescence lifetimes; fluorophore identification; background suppression, parallel multi-color imaging, or any combination thereof. See, for example, J. R. Lakowitz 2006, in: "Principles of Fluorescence Spectroscopy", Third Edition. If the different nucleotides are labeled with different energy transfer or reporter moieties, then resolving the emitted signals can be used to distinguish between the different nucleotides which bind the polymerase and/or which are incorporated by the polymerase.

In one embodiment, a system and method for detecting radiation emitted by an excited energy transfer or reporter moiety comprises: an illumination source (e.g., a laser) which produces the excitation energy (e.g., one or multi-photon excitation radiation) which is directed, via a dichroic beam splitter, through a lens, and through a transparent surface or onto a surface, where the nucleotide binding reaction or the nucleotide incorporation reaction is attached to the surface or is in a solution. The excitation illumination excites the energy transfer or reporter moiety (e.g., fluorescent dye and/or nanoparticle) resulting in emitted radiation (or a change in radiation) which passes back through the dichroic beam splitter and is directed to the detector (or an array of detectors) which is capable of identifying and/or resolving the type of emission. Information about the detected emitted signals is directed to the computer where the information is registered and/or stored. The computer can process the registered and/or stored information to determine the identity of the nucleotide which bound the polymerase or the identity of the incorporated nucleotide.

In one aspect, the system and method for detecting radiation emitted by an excited energy transfer or reporter moiety includes a multifluorescence imaging system. For example, the different nucleotides may each be linked to different FRET acceptor moieties. The FRET acceptor moieties can be selected to have minimal overlap between the absorption and emission spectra, and the absorption and emission maxima. The multifluorescence imaging system can simultaneously (or substantially simultaneously) detect signals from the FRET acceptor moieties, and resolve the signals. Such multifluorescent imaging can be accomplished using suitable filters, including: band pass filters, image splitting prisms, band cutoff filters, wavelength dispersion prisms, dichroic mirrors, or diffraction gratings, or any combination thereof.

In another aspect, the multifluorescence imaging system is capable of detecting the signals emitted by the different energy transfer and reporter moieties attached to the different nucleotides. Such a system can include special filter combinations for each excitation line and/or each emission band. In one embodiment, the detection system includes tunable excitation and/or tunable emission fluorescence imaging. For tunable excitation, light from a light source can pass through a tuning section and condenser prior to irradiating the sample. For tunable emissions, emissions from the sample can be imaged onto a detector after passing through imaging optics and a tuning section. The tuning sections can be controlled to improve performance of the system.

In yet another aspect, the detection system comprises an optical train which directs signals emitted from an organized array onto different locations of an array-based detector to detect multiple optical signals from multiple locations. The optical trains typically include optical gratings and/or wedge prisms to simultaneously direct and separate signals having differing spectral characteristics from different addressable locations in an array to different locations on an array-based detector, e.g., a CCD.

In another aspect, the detection methods include detecting photon bursts from the labeled nucleotides during incorporation. The photon bursts can be the fluorescent signals emitted by the energy transfer moiety which is linked to the nucleotide. The photon bursts can be a FRET event. The methods can additionally include analyzing the time trace of the photon bursts. The methods can be practiced using time-resolved fluorescence correlation spectroscopy.

Nucleotide incorporation reactions using nucleotides labeled at the terminal phosphate with a fluorescent dye have been previously demonstrated (Sood, U.S. published patent application No. 2004/0152119; and Kumar, U.S. Pat. No. 7,393,640). Furthermore, fluorescence detection of single molecule nucleotide incorporation reactions has been routinely obtained (Kao, U.S. Pat. No. 6,399,335; and Fuller, U.S. Pat. No. 7,264,934).

The nucleotide labeling strategy can be used as a basis for selecting any suitable detection system for detecting and/or resolving signals emitted by the nucleotide binding reaction or the nucleotide incorporation reaction. Exemplary labeling and detection strategies include but are not limited to optical train and TIRF detection methods such as those disclosed by Harris in U.S. Pat. No. 6,423,551; and U.S. Pub. Nos. 2006/0176479, 2007/0109536, 2007/0111350, and 2007/0250274.

Following detection of the sample emissions, the raw emission data can be analyzed to identify events involving nucleotide polymerization. In some embodiments, the emissions can be analyzed in single molecule format to identify nucleotide polymerization.

In one aspect, a labeled enzyme conjugate is a labeled polymerase conjugate, and a time series of nucleotide incorporations by the labeled polymerase conjugate is detected and analyzed to deduce the ordered sequence of nucleotides in the single nucleic acid substrate that is being replicated by the polymerase.

In one exemplary embodiment, the labeled polymerase conjugate comprises an energy transfer moiety that undergoes FRET with the label of an incoming labeled nucleotide that is polymerized by the polymerase of the conjugate. Nucleic acid sequence analysis is performed by first analyzing the raw emission data to computationally determine the occurrence of a FRET event. In some embodiments, FRET events can be identified using a Hidden Markov Model (HMM)-based or equivalent generalized likelihood ratio test that determines the location of an intensity change point based on individual photon arrival times; this test can then be applied recursively to an entire single molecule intensity trajectory, thus finding each change points. The true number of states accessible to the system is then computed. See, e.g., Watkins et al., "Detection of Intensity Change Points in Time-Resolved Single-Molecule Measurements" J. Phys. Chem. B., 109(1):617-628 (2005). An exemplary FRET detection method using this technique is described herein in Example 6.

In one aspect, a system can collect and analyze chemical and/or physical event data occurring at one or a plurality of locations within a viewing volume or field of an imagining apparatus. In some embodiments, the system comprises a sample subsystem for containing a sample to be detected and analyzed, where the sample includes at least one moiety (e.g., enzyme, substrate, label, etc) having detectable property that undergoes a change before, during or after one or a sequence of chemical and/or physical events involving the moiety. The system can also includes a detection apparatus having a viewing field that permits the detection of changes in the detectable property of the moiety within the viewing field. The system also includes a data processing subsystem connected to the imagining for collecting, storing and analyzing data corresponding to the chemical and/or physical events occurring at definable locations in the viewing field involving one or more moieties within the viewing field of the imagining subsystem. The data processing subsystem converts the data into classifications of events according the event type determined by a set of parameters defining or characterizing each event type. See, e.g., U.S. Published Patent Application No. 2007/0250274, Volkov et al. which is incorporated herein as if set forth in full.

In one aspect, FRET events can be identified by computationally determining the occurrence of an anticorrelated FRET event (typically involving a correlated decrease in donor signal and increase in acceptor signal). In one exemplary embodiment, FRET events corresponding to interactions between a donor fluorophore associated with a first moiety, e.g., a polymerase and an acceptor fluorophore associated with a second moiety, e.g., a nucleotide can be analyzed by first collecting or receiving data from a viewing volume of an imaging apparatus such as an CCD or iCCD detection system. In some embodiments, the data can be in a single data channel or a plurality of data channels, each data channel representing a different frequency range of emitted fluorescent light, e.g., one channel can include fluorescent light data emitted by a donor, a donor channel, while other channels include fluorescent light data emitted by an acceptor, an acceptor channel, or by another donor, a second donor channel. In certain embodiments, a channel will exit for each different fluorophore being detected simultaneously. In some embodiments, the acceptors are selected so that they can be separately identified based on detectable attributes of their signals e.g., intensity, frequency shifts, signal duration, attenuation, etc. After data collection, the separate data channels are spatially correlated within the viewing volume so that active fluorophores can be spatially and temporally related, called calibration or registration. The goal of calibration is to determine the pixel coordinates in each quadrant that correspond to a single position on the slide or a single location within the viewing field—to make sure that the data in each channel is spatially coincident over the viewing field and through time of detection. After reading the configuration file and the open log file, calibrations, if any, are loaded from the command line. After loading the calibration information, a corresponding directory is read as specified in the command line with all subdirectories, for each one. This read step includes: (1) scanning for calibration stacks, and if there are some not matched by the available calibrations, generate new calibrations out of them; (2) scanning for stacks; if there are some, assume this directory is a slide; and (3) scanning the directory path for a date and slide name comprising reaction conditions such as donor identity, acceptor identity, buffers, etc. See, for example, U.S. Published Patent Application No. 2007/0250274, Volkov et al.

Once FRET events have been identified, they can be analyzed to determine the order and sequence of nucleotide incorporations.

Analysis of Fluorescence Data to Extrapolate Sequence Information

To convert the observed fluorescence emissions detected during the sequencing reaction into nucleotide sequence information, the raw data comprising a movie of observed emissions was first processed by using a Hidden Markov Model (HMM)-based algorithm or equivalent to detect and identify FRET events. The subsequent detected FRET events were filtered and filtered sequences were aligned. Each of these two steps, FRET event detection and sequence analysis, are described in more detail below.

Detection of FRET Events

The analysis underlying FRET event detection is designed to process spatially correlated movie(s) comprising sequence fluorescence emission data, and extract time-series of interest from those data. A movie typically contains one or more channels where each channel represents the same spatial location at different wavelengths. The analysis chain begins with the submission of one or more movies to the analysis machine via a comprehensive user interface. The user interface requires the user to input various parameters that describe the movie(s) (e.g. channel regions, dye emission properties . . . ). Once this data is submitted the movie(s) are then processed by the image analysis software where a sliding window of N frames propagates through the movie calculating a temporal local average of the frames within the window. At each position of the window in the movie, the local average image is then further processed and enhanced using well known image processing algorithms and a record of the maximum projection of all the local average images is recorded to produce a global image of the movie. This global image is the input into a spot identification algorithm which produces a set of spots identified by a unique spot id, its x and y location and its corresponding channel. Each set of spots for a given channel is then registered to the set of spots in every other channel. In this way a set of spot tuples is constructed. If a detected spot in one channel does not have a corresponding detected spot in another channel, then the position of the undetected spot using the transformation between the two channels and the location of the detected spot is inferred. Once a complete set of spot tuples is constructed the movie is iterated over and at each frame the amplitude of each spot is calculated and appended to the appropriate time-series.

The collection of time-series from a spot tuple consists of time-series from donor and corresponding acceptor channels. This collection is called a Vector Time-Series (VTS). The FRET detection process starts with a data segmentation step using a Markov Chain Monte-Carlo (MCMC) algorithm. Each segment of VTS is modeled by a multivariate Gaussian model, with each of the channel modeled by a mean and a standard deviation. This model establishes a baseline for each channel, from which quantities such as "Donor Down" and "Acceptor Up" can be calculated. A Hidden Markov Model (HMM) or equivalent algorithm is used to model the observed data. The underlying states consist of a null state, a blink state and a number of FRET states (one for each acceptor channel). Each state has its emission probability, which reflects the state's corresponding physical concept. FRET states are characterized by significant "donor down" and "acceptor up" signals. Blink state is characterized by significant "donor down" with no "acceptor up". Null state is characterized by no "donor down" and no "acceptor up". Given the observed VTS signal, the emission matrix, and a state transition probability matrix, the most probable state path can be computed using the Viterbi algorithm. This state path assigns each of the frames to a state. Temporally neighboring FRET frames are grouped into FRET events. For each of the detected FRET events, a list of event features are calculated, including event duration, signal average, signal to noise ratio, FRET efficiency, probability of event, color calling and other features. This list of events and corresponding features are stored in a file.

The final stage of the automated analysis generates a report summarizing the results in the form of a web page containing summary image, statistics of the spots and FRET detection, together with line intensity plots and base call plots.

Using the above process, the movie data obtained from the sequencing reactions was analyzed to detect and identify FRET events according to the process described above. The FRET events were then processed to identify sequences as described below.

Sequence Analysis

The string of FRET events from the same spot-tuple are then aligned to a reference sequence. Each color call in the string is associated with a nucleotide, creating a DNA sequence. That DNA sequence and a reference sequence are fed into a Smith-Waterman alignment or equivalent algorithm to determine where the read comes from in the template sequence and what the similarity between the sequences is.

Also provided herein are kits for conducting the nucleotide binding reactions and/or the nucleotide incorporation reactions described herein. The kits can include, in one or more containers, the components of nucleotide binding and/or nucleotide incorporation disclosed herein, including: labeled biomolecule conjugates, labeled polymerase conjugates, nucleotides, target nucleic acid molecules (e.g., a control test target molecules), primers, and/or oligonucleotides.

In some embodiments, the kit comprises a labeled polymerase conjugate according to the present disclosure. Optionally, the kit can further include a nucleotide. The nucleotide can be a labeled nucleotide. In some embodiments, the nucleotide includes a polyphosphate chain. The nucleotide label can optionally be attached to the terminal phosphate group of the nucleotide.

In the kits, the solid surfaces, energy transfer moieties, reporter moieties, nanoparticles, polymerases, nucleotides, target nucleic acid molecules, primers, and/or oligonucleotides can be attached to each other in any combination, and/or be unattached. The kits can include positive and/or negative control samples.

Additional components can be included in the kit, such as buffers and reagents. For example, the buffers can include Tris, Tricine, HEPES, or MOPS, or chelating agents such as EDTA or EGTA. In another example, the reagents can include monovalent ions, such as KCl, K-acetate, $NH_4$-acetate, K-glutamate, $NH_4Cl$, or ammonium sulfate. In yet another example, the reagents can include divalent ions, such as $Ca^{2+}$, $CaCl_2$, $Mg^{2+}$, $MgCl_2$, Mg-acetate, $Mn^{2+}$, $MnCl_2$, and the like. The kits can include the components in pre-measured unit amounts. The kits can include instructions for performing the nucleotide binding reactions and/or the nucleotide incorporation reactions. Where the kit is intended for diagnostic applications, the kits may further include a label indicating regulatory approval for the diagnostic application.

All of the compositions and methods disclosed and claimed herein can be made and executed without undue experimentation in light of the present disclosure. While the compositions and methods of this invention have been described in terms of embodiments, these embodiments are in no way intended to limit the scope of the claims, and it will be apparent to those of skill in the art that variations can be applied to the compositions and/or methods and in the steps or in the sequence of steps of the methods described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

EXAMPLES

In the following examples, Klenow and Phi-29 polymerase proteins were expressed and purified. The purified proteins were then assayed for DNA binding and primer extension activity as described in the succeeding examples.

Example 1

Conjugate Comprising Cysteine-Containing Protein Linked to Nanoparticle

This example illustrates the conjugation of a cysteine-containing protein, specifically Klenow DNA polymerase, to a quantum dot.

The three-dimensional structure of the Klenow DNA polymerase was modeled using RAS-MOL software, and naturally occurring cysteine residues 906 and 730 were visually selected as attachment points for conjugation with a quantum dot nanoparticle as described further below. In addition, various non-conserved amino acid residues having side chains spatially oriented close to the polymerase active site, including residues 926, 927 and 928, were selected as potential points of attachment for the quantum dot. These selected residues were converted to cysteine residues via site-directed mutagenesis, and the newly introduced cysteine residues conjugated to quantum dots using the heterobifunctional crosslinker SMCC, as described in further detail below. A list of the various mutant forms of Klenow DNA polymerase used in these studies is provided in Table 1. Both the wild-type and the mutant versions of Klenow DNA polymerase were expressed and purified as follows. Briefly, expression constructs comprising the open reading frame of Klenow DNA polymerase (or mutants thereof) under control of the β-galactosidase promoter were constructed using standard DNA recombination techniques and transformed into the bacterial strain TOP10. Transformants were selected and cultured at 37° C. to a final A60 absorbance of 0.6, following which IPTG was added to a final concentration of 1 mM and culture continued for a further 2 to 4 hours. Cells were harvested by centrifugation and resuspended in 50 mM Tris pH 7.5, 100 mM NaCl, 5 mM BME, 0.1 mM EDTA and 0.02 mM PMSF, lysed by sonication, and then treated with Polymin P at final concentration of 0.4%. The treated lysate was centrifuged for 30 min at 13K rpm, and the supernatant was treated to two successive rounds of ammonium sulfate purification. First, ammonium sulfate was added to the supernatant at a final concentration of 45% W/V, and precipitates were removed by centrifugation. Next, ammonium sulfate was added to 75% W/V and the polymerase-containing precipitate collected by centrifugation. The precipitated polymerase was resuspended in 20 mM KPi pH 7.0, 0.1 mM EDTA and 5 mM BME and dialyzed against the same buffer to remove traces of ammonium sulfate. The dialysate was then loaded onto a 15 mL EMD sulfate column, and fractions were eluted with increasing concentrations of salt (0-1M NaCl in 20 mM KPi pH 7.0, 0.1 mM EDTA and 5 mM BME) over ten column volumes. Polymerase-containing fractions were pooled and dialyzed into 100 mM KPi pH 7 containing 1 mM DTT. The protein concentration of the final preparation was determined using standard techniques.

A quantum dot was covalently conjugated to residue 926 of Klenow polymerase. Residue 926 was selected as a site for covalent conjugation because it was visually determined to be situated close to the polymerase active site using RAS-MOL protein modeling software. Briefly, a mutant form of Klenow polymerase, Klenow-926 polymerase, wherein residue 926 of SEQ ID NO: 2 is selectively mutated to a cysteine residue, was created using standard site-directed mutagenesis techniques and expressed and purified as described above. The purified mutant polymerase was then treated with the reducing agent DTT to ensure that all sulfhydryl groups were fully reduced prior to conjugation. Briefly, 500 ul of purified Klenow-926 polymerase (concentration: 7.1 mg/ml) with 125 ul 1M Tris HCl, pH 8.5 and 12.5 ul 1M DTT, and incubating the mixture for 30 minutes at room temperature to fully reduce all sulfhydryl groups on the peptide. The mixture was then partially concentrated by ultrafiltration (molecular weight cut-off: 50 KD), and then subjected to gel filtration through a NAP-5 column (GE Healthcare; Cat#17-0853-01). The flow-through was collected in 5-drop fractions. Each fraction was mixed with 3 ul of 5M NaCl and centrifuged at 16K r.c.f. for 2 minutes to redissolve any precipitated protein. The protein concentration of the supernatant was estimated using UV absorption at 280 nm.

To prepare the quantum dots for conjugation, quantum dots (Qdot 605 ITK carboxy quantum dots, (Life Technologies Corp., Carlsbad, Calif. (formerly known as Invitrogen Corp.); catalog no. Q21301MP, concentration: 8 µM) were first coated with PEG-amine, and then activated using the linking agent EDC. To coat the dots, a reaction mixture containing 200 µl of quantum dots (concentration: 8 µM), 200 µl of PEG diamine (average MW=1000; concentration: 125 mM), 2 ml of 50 mM Borate, pH 7.4 and 12.3 µl of 80 mM EDC was mixed in a glass vial and incubated for 48 hours at room temperature. 90 minutes after initiation of the reaction, another 12.3 µl aliquot of 80 mM EDC was added to the reaction mixture. The coated dots were then concentrated by spin ultrafiltration using a membrane with a molecular weight cut-off of 100 KD, then purified over a NAP5 column using PBS as the elution buffer. The PEG-amine coated dots were then stored at 4° C. until the conjugation step was performed as described below.

For the conjugation reaction, the PEG-amine coated quantum dots were first activated using the heterobifunctional cross linker SMCC. Briefly, 450 µl of 4.3 µM PEG-coated quantum dots, 450 µl 1M NaHCO$_3$ and 100 µl of 20 mM SMCC (in DMSO) were mixed and incubated at room temperature. After 1 hour, the mixture was concentrated by ultrafiltration and then purified on a NAP-5 column with exchange buffer. These activated dots were then conjugated to purified reduced Klenow-926 polymerase, prepared as described above. Briefly, 280 µl of 2.0 µM activated dots were mixed with 20 equivalents of purified reduced Klenow-926 peptide (140 µl of 81.1 µM Klenow-926) and incubated at room temperature for 2 hours. The reaction mix was concentrated by ultrafiltration (molecular weight cut-off: 100 KD). The concentrated conjugates were then purified by size exclusion using a Superdex column and eluted using PBS. The conjugate concentration of each fraction was measured using UV/VIS absorbance at 405 nm. Each fraction was then characterized for DNA binding activity and primer extension activity as described below.

Characterization of DNA Binding Abilities of Polymerase-Nanoparticle Conjugates

In preliminary experiments, various polymerase-nanoparticle conjugates were analyzed for DNA binding ability, as indicated by increased fluorescence at the acceptor wavelength (670 nm) following co-incubation of an acceptor-labeled oligonucleotide with the purified conjugate. The quantum dot of the conjugate becomes excited at 405 nm or 450 nm. Various acceptor-labeled oligonucleotides, each comprising a self-complementary "hairpin" sequence and a single dye molecule, were used to evaluate the DNA binding ability of the polymerase-quantum dot conjugates. Results of an exemplary study are provided in FIG. 1. In this experiment, DNA binding was assayed using oligonucleotide JX315, a hairpin oligonucleotide that comprises a single molecule of the dye Alexa Fluor 647 ("AF647") at the 3' end of the oligonucleotide. The AF647 dye maximally absorbs at 647 nm and emits fluorescence at 670 nm. The sequence of JX315 is as follows:

Hairpin oligonucleotide JX315 sequence:

5'-TTTTTGCGGGTGACAGGTTTTTCCTGTCACCX-3' where X=ALEXA FLUOR 647-dC

To evaluate the DNA binding abilities of the purified polymerase-nanoparticle conjugates, the purified conjugates were co-incubated with template DNA in 100 µl of 1× extension buffer comprising 50 mM Tris pH 8.0, 50 mM NaCl 10 mM MgCl$_2$ and optionally including 0.5 mM MnCl$_2$. Each conjugate was incubated with the hairpin oligonucleotide JX315, serially diluted starting at 1 µM). The fluorescence intensity of the mixture was simultaneously measured at 605 nm and 670 nm using a Molecular Devices SpectraMax M5 microtiter plate reader. Fluorescence emission was detected at 670 nM, thus indicating the presence of an active polymerase attached to the quantum dot. Results of a typical binding assay are depicted in FIG. 1, which depicts fluorescence data obtained using various Klenow/quantum dot conjugates. The left column of charts shows the oligonucleotide binding of four different fractions (3.111A-D) of a covalent conjugate preparation where the 926 mutant Klenow was covalently attached to a PEG1000-coated quantum dot. The right column of charts shows the binding behavior of two covalent conjugates (2.141A and 3.111B) and two conjugates where the His-tagged Klenow is bound to the quantum dot through metal affinity binding (3.67B and JX305). PEG1000 Qdots (917) serve as the negative controls. The two top graphs depict donor emission at 605 nm. The two graphs in the middle depict acceptor emissions at 670 nm, while the bottom two panels depict the ratio of donor to acceptor emissions. Only conjugates having detectable DNA binding activity were selected for primer extension assays as described below.

FIG. 2 shows another example of oligonucleotide binding to a covalent conjugate consisting of mutant 926 Klenow (Cys-) attached to 605-PEG1000 quantum dots. The conjugate was purified essentially as described above. The binding assay was performed using two different oligonucleotides to compare the effect of dye attachment position (3' vs. 5') on binding results. Oligonucleotide JX240 comprises a dye label at the 3' position, whereas oligo JX274 comprises a dye label at the 5' position. The oligo concentrations started at 2 µM and were serially diluted. The conjugate concentration was 10 nM. As depicted in FIG. 2, the assay using oligonucleotide labeled at the 3' position resulting in enhanced fluorescence as compared to the 5'-labeled oligonucleotide. The top panel shows the (Qdot; donor) fluorescence intensity at 605 nm. The middle panel shows the acceptor fluorescence intensity observed at 670 nm. The lower panel shows the ratio of the donor to acceptor signal.

Characterization of Polymerase-Nanoparticle Conjugates Via Primer Extension Assay Primer extension reactions using purified preparations of polymerase-nanoparticle conjugates were performed to determine whether the conjugate retained polymerization activity. The primer used in these assays was JX315, a hairpin oligonucleotide comprising a dye label at its 3' end. Complete extension of the hairpin primer/template results in the insertion of the bases GCAAAAA (see sequence provided above)

Figure 3:
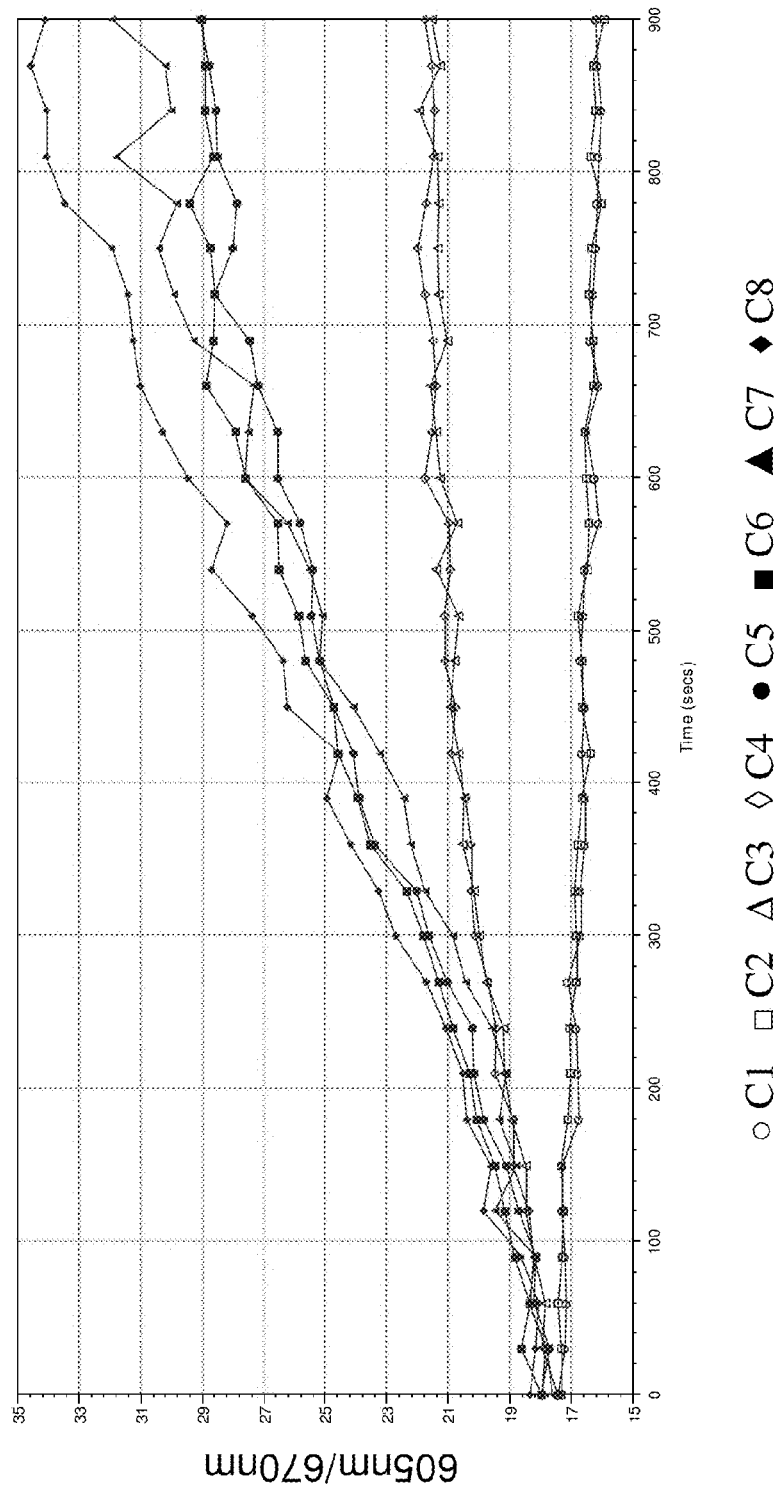

To perform the assay, in eight wells of a microtiter plate was placed 100 µl of a solution containing 120 nM of 3' dye-labeled hairpin primer JX315 and 10 nM of purified Klenow-nanoparticle conjugate in 1× extension buffer (50 mM Tris pH 8, 50 mM NaCl, 10 mM MgCl$_2$). To start the extension reaction, 41 of the appropriate 1 mM dNTP solution was added to each well. The progress of primer extension was monitored by detecting and analyzing changes in fluorescence intensity at both donor (605 nm) and acceptor (670 nm) wavelengths as a function of time. Results of a typical experiment are depicted in FIG. 3, which shows the ratio of the donor to acceptor signal (referred to in FIG. 3 as "Ilm1/Ilm2") as a function of time. Curves C1 (open circles) and C2 (open squares) in FIG. 3 represent a control where all components to the extension reaction were added except the nucleotides, wherein no extension or consequent FRET should occur. Curves C3 (open triangles) and C4 (open diamonds) depict the results of an extension reaction where only dGTP has been added. This causes extension by only a single base. Curves C5 (solid circles) and C6 (solid squares) represent the extension by two bases due to the addition of dGTP and dCTP. Curves C7 (solid triangles) and C8 (solid diamonds) show extension by 7 bases due to the addition of dGTP, dCTP and dATP.

Example 2

Conjugate Comprising his-Tagged Protein Linked to Nanoparticle

This example illustrates the conjugation of various proteins comprising a polyhistidine tag ("His-tag"), specifically His-tagged Klenow DNA polymerase and His-tagged Phi-29 DNA polymerase, with a quantum dot.

For the first study, the His-tagged Klenow polymerase, expression vectors comprising the Klenow polymerase open reading frame fused in-frame to a His tag at its N-terminus under control of the inducible β-galactosidase promoter were constructed using standard recombinant DNA techniques and transformed into TOP10 cells. Expression of the recombinant protein was induced, cells were harvested and subjected to lysis via sonication, and the lysate subjected to two successive rounds of ammonium sulfate precipitation using the same conditions as described above for Klenow polymerase. Following the second ammonium sulfate precipitation step, the pellet was resuspended in 20 mM KPi pH 7.0, and loaded onto a 5 mL HIS-TRAP® column equilibrated with 20 mM Kpi pH7.0, 100 mM NaCl and 20 mM Imidazole. His-tagged Klenow polymerase was eluted using an imidazole concentration gradient from 0-500 mM Imidazole in 20 mM KPi pH 7.0 over ten column volumes. The eluate was then loaded onto a 15 mL EMD sulfate column, and fractions were eluted with increasing concentrations of salt (0-1M NaCl in 20 mM KPi pH 7.0) over ten column volumes. Polymerase-containing fractions were pooled and dialyzed into 100 mM KPi pH 7 containing 1 mM DTT. The protein concentration of the final preparation was determined using standard techniques.

To obtain purified Phi-29 polymerase protein, the expression construct comprising the Phi-29 polymerase open reading frame under control of the inducible β-galactosidase promoter, using standard recombinant DNA techniques. The expression constructs were transformed into the bacterial strain BL21 DE3 (PLYS S). Transformants were selected and cultured at 37° C. to a final A60 absorbance of 0.4-0.5, following which IPTG was added to a final concentration of 1 mM. The mixture was further cultured at 18° C. overnight. Cells were harvested by centrifugation and resuspended in 30 mM Tris pH 7.5, 100 mM NaCl, 5 mM BME, 1 mM EDTA and 8% glycerol, lysed by sonication, and then treated with Polymin P at final concentration of 0.4%. The treated lysate was centrifuged for 30 min at 13K rpm, and the supernatant was then loaded onto a 15 mL EMD sulfate column Fractions were eluted with increasing concentrations of salt (0-1M NaCl in 30 mM Tris pH 7.5, 100 mM NaCl, 5 mM BME, 1 mM EDTA and 8% glycerol) over ten column volumes. Polymerase-containing fractions were pooled and loaded onto Q XL Hi Trap column. The flow-through was collected and loaded onto a 1 mL Heparin Hi Trap column Fractions were eluted with increasing concentrations of salt (0-1M NaCl in 30 mM Tris pH 7.5, 100 mM NaCl, 5 mM BME, 1 mM EDTA and 8% glycerol) over ten column volumes. The cleanest fractions (as determined by UV absorbance and SDS-PAGE) were pooled and dialyzed into 10 mM Tris pH7.5, 100 mM KCL, 0.5% Tween 20, 0.1 mM EDTA, 1 mM DTT containing 50% glycerol. The protein concentration of the final preparation was determined using standard techniques.

His-tagged Phi-29 polymerase variants were expressed using constructs comprising the Phi-29 polymerase open reading frame fused in-frame to a His tag under control of the inducible β-galactosidase promoter, made according to standard recombinant DNA techniques. Expression of the recombinant protein was induced, cells were harvested, subjected to lysis via sonication and treated with Polymin P using the same conditions as described above for non-tagged Phi-29 polymerase. The treated lysate was centrifuged for 30 min at 13K rpm and the supernatant was loaded onto a 15 mL EMD sulfate column Fractions were eluted with increasing concentrations of salt (0-1M NaCl in 30 mM Tris pH 7.5, 100 mM NaCl, 5 mM BME, 1 mM EDTA and 8% glycerol) over ten column volumes. Polymerase-containing fractions were pooled and loaded onto Q XL Hi Trap column. The flow-through was collected and loaded onto a 5 mL His Trap column. Fractions were eluted with increasing concentrations of salt (0-1M NaCl in 30 mM Tris pH 7.5, 100 mM NaCl, 5 mM BME, 1 mM EDTA and 8% glycerol) over ten column volumes. The cleanest fractions (as determined by UV absorbance and SDS-PAGE) were pooled and dialyzed into 10 mM Tris pH7.5, 100 mM KCL, 0.5% Tween 20, 0.1 mM EDTA, 1 mM DTT containing 50% glycerol. The protein concentration of the final preparation was determined using standard techniques.

A purified His-tagged Klenow polymerase selectively modified to lack any cysteine residue via mutation of the single cysteine at amino acid position 907 of SEQ ID NO: 2 ("N-His Kle(cys-)") was then conjugated with a peptide-coated quantum dot, herein referred to as a "Bpix dot", in the presence of the Bovine Serum Albumin Briefly, 4.5 nanomoles of Bpix dots were coincubated for 3 hours at room temperature with 22.5 nanomoles of N-His Kle(cys-) peptide and 90 nanomoles of BSA in a total volume of 1955 ul. Conjugates were then concentrated by ultrafiltration and then purified via size exclusion chromatography by passage through a Superdex 200 column using 50 mM borate, pH 7.4 as the elution buffer. The concentrations of the eluted conjugate fractions were measured using UV absorbance at 405 nm and then tested in a DNA binding assay, as described below. Active fractions were pooled, diluted to a total volume of 1.5 ml and stored.

Figure 4A:
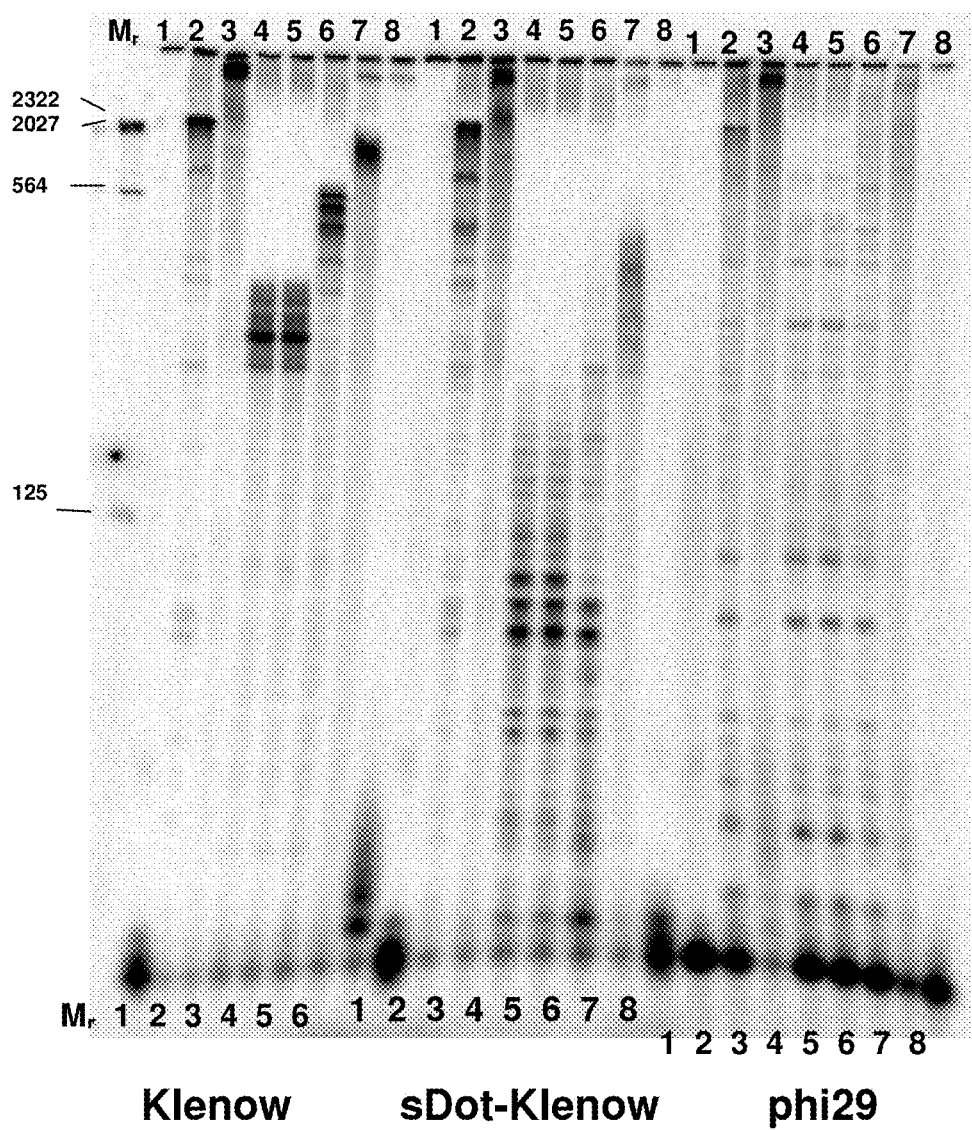

Evaluation of Processivity and Read Length of Polymerase-Nanoparticle Conjugates Purified conjugates that showed primer extension activity were selected for inclusion in studies to evaluate their processivity and read length. Briefly, 100 nM of purified conjugate was incubated with 9 nM of primed template in the presence of omega labeled nucleotides at 37° C. for 15 minutes in 50 mM Tris pH 7.5, 50 mM NaCl, 2 mM DTT, 0.3% BSA and 0.05% Tween20, following which extension products were resolved on urea-polyacrylamide gels. Typical results obtained using the 5×Kle(cys-):Bpix conjugate are depicted in FIG. 4A. The length of extension products synthesized by the conjugate using natural, i.e., unlabeled, nucleotides in some cases was greater than 2300 base pairs, and corresponded to read lengths obtained using native, i.e., unconjugated, Klenow and Phi-29 polymerases. Read lengths using omega-labeled nucleotides were typically several hundred base pairs long. Read lengths were improved by the inclusion of 3 mM $MnCl_2$ and Single Stranded Binding Protein (SSBP; concentration: 100 μg/ml) in the reaction. The results for Klenow, sDot-Klenow, and phi29 are depicted in FIG. 4A. Lanes 1 are negative controls (no nucleotides); Lanes 2 include $MgCl_2$ (at 10 mM), $MnCl_2$ (at 0.5 mM) and unlabeled dTNPs at 20 μM concentration; Lanes 3 include $MgCl_2$ (at 10 mM), $MnCl_2$ (at 0.5 mM), unlabeled dNTPs at 20 μM concentration, and SSBs at 100 nM; Lanes 4 and 5 include $MgCl_2$ (at 10 mM), $MnCl_2$ (at 0.5 mM) and omega-labeled nucleoside tetraphosphates (ωdN4P) at 12 μM concentration; Lanes 6 include $MnCl_2$ (at 3.0 mM) and omega-labeled nucleoside tetraphosphates (ωdN4P) at 12 μM concentration; Lanes 7 include $MnCl_2$ (at 3.0 mM), omega-labeled nucleoside tetraphosphates (ωdN4P) at 12 μM concentration, and SSBs at 100 nM concentration; Lane 8 is an additional negative control containing SSBs at 100 nM but does not contain nucleotides. As shown in FIG. 4A, extension products measuring several hundred base pairs in length were detected in lanes 2-7, indicating that both free (unconjugated) Klenow and phi29 as well as Klenow:BPix conjugates can incorporate nucleoside tetraphosphates in the presence of a primed template.

In another experiment, three different conjugate preparations, named XP0057, XP0061 and XP0064, respectively, comprising a protein having the amino acid sequence of SEQ ID NO: 14 (HP1) linked to UDG/UGI-treated quantum dots (conjugates XP0057 and XP0061) or MBP-treated quantum dots (conjugate XP0064) were prepared using the methods described in Example 8 (for conjugates XP0057 and XP0061) or Example 10 (using conjugate XP0064). Each conjugate was tested for the ability to incorporate unlabeled nucleoside tetraphosphates in the presence of a $^{32}$P-labeled primed template including unlabeled M13 DNA annealed with a 5' $^{32}$P-labeled primer comprising the following sequence:

```
5'-GGCCAGTGAATTCGAGCTCGGTACCCGG-3'
```

Figure 4B:
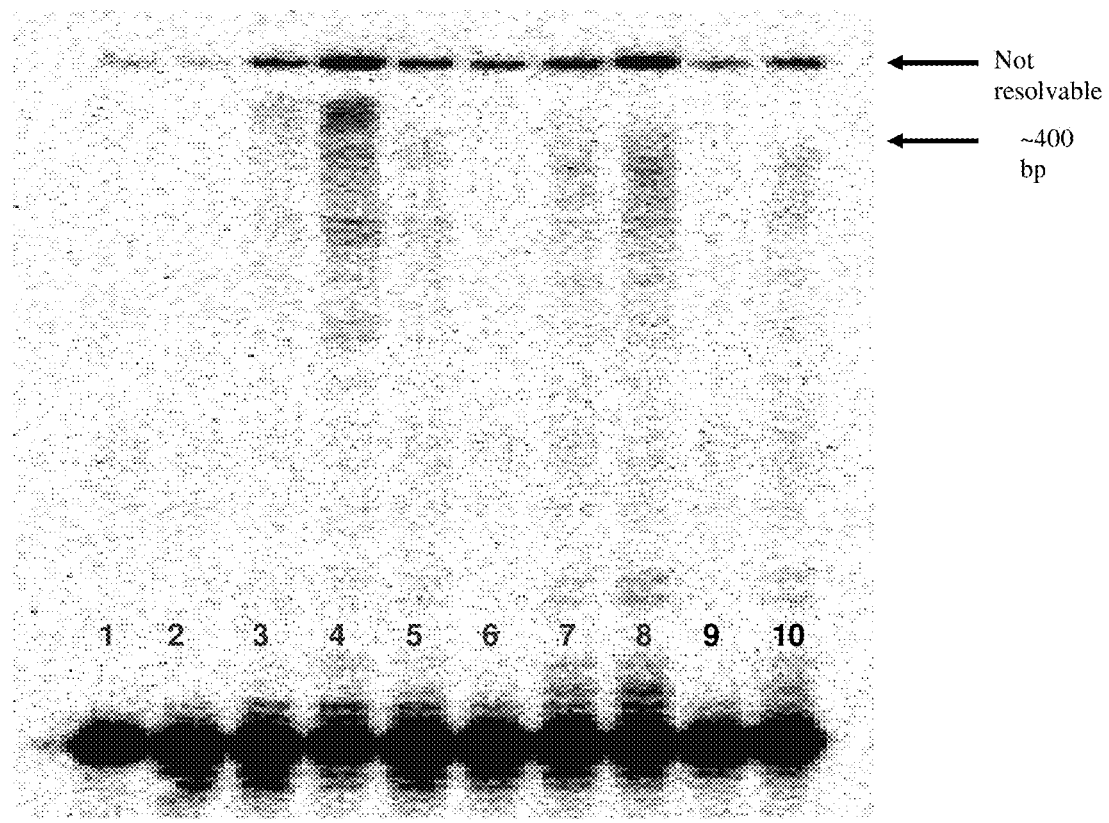

The M13 DNA was annealed with the above 5' $^{32}$P-labeled primer via heating the mixture to 95 C, followed by cooling to 4 C at a rate of 1 C per minute. (FIG. 4B). Briefly, various concentrations of unconjugated HP1 or each of the three different conjugates XP0057, XP0061 and XP0064, respectively, were incubated with 1 nm of $^{32}$P-labeled primed template and 10 mM linker-associated dN4Ps (which comprise a 6-carbon linker attached to the omega phosphate of the dN4P, but no dye) in 50 mM Tris-HCl, pH 7.5, 50 mM NaCl, 2.0 mM MnCl$_2$, 0.2% BSA, and 100 µg/ml purified SSBP (single strand binding protein, concentration: 100 µg/ml) at 22° C. for 20 minutes, following which the labeled extension products were resolved on urea gels. The results are depicted in FIG. 4B. Lane 1 included the negative control (no nucleotides); Lane 2 included HP1 at 1 nM concentration; Lane 3 included HP1 at 10 nM concentration; Lane 4 included HP1 at 100 nM concentration; Lane 5 included conjugate XP0057 at 20 nM concentration; Lane 6 included conjugate XP0061 at 20 nM concentration; Lane 7 included conjugate XP0064 at 20 nM concentration; Lane 8 included conjugate XP0057 at 40 nM concentration; Lane 9 included conjugate XP0061 at 40 nM concentration; and Lane 10 included conjugate XP0064 at 40 nM concentration. As depicted in FIG. 4B, extension products measuring several hundred base pairs in length were detected in lanes 3-5, 7, 8 and 10, indicating that both free (unconjugated) HP1 as well as various Phi-29:C8 conjugates can incorporate nucleoside tetraphosphates in the presence of a primed template.

The ability to incorporate omega-labeled nucleoside tetraphosphates (ωdN4P) of Phi-29:C8 conjugates comprising peptide having the amino acid sequence of SEQ ID NO: 13 (His-tagged Phi-29 polymerase peptide comprising the F-linker sequence) linked to C8 nanoparticles was tested in another experiment. Briefly, 50 nM Phi-29:C8 conjugate, prepared according to the method of Example 3, below, was incubated with 5 nM of labeled primed template DNA and increasing concentrations (0, 0.1, 0.25, 0.5, 1, 2 and 4 µM) of the omega-labeled nucleoside tetraphosphate compounds (AF680)$_2$-dC4P (left gel) or (AF647)$_2$-dG4P (right gel) in 1× extension buffer for 5 seconds at 22° C. The extension products were resolved on a urea gel (data not shown). These results indicate that the conjugate is able to incorporate omega-labeled nucleoside tetraphosphates.

Example 3

Conjugate Comprising his-Tagged Protein Linked to Nanoparticle

Preparing Nanoparticles Attached with his-Tagged Polymerase

Hairpin ALEXA FLUOR 647 labeled-oligonucleotide 192 sequence:

```
(SEQ ID NO: 42)
5'-TTTTTTTGCCCCCAGGGTGACAGGTTTTTCCTGTCACCC-3'
``` where the 192 oligo is labeled at the 3' end with ALEXA FLUOR 647.

Hairpin ALEXA FLUOR 647 labeled-oligonucleotide 199 sequence:

```
5'-TTATCTTTGTGGGTGACAGGTTTTTCCTGTCACCX-3'
``` where X=ALEXA FLUOR 647-dC.

Hairpin fluorescein labeled-oligonucleotide 221 sequence:

```
(SEQ ID NO: 43)
5'-TTTTTTTGCAGGTGACAGGTTTTTCCTGTCACCXGC-3'
``` where X=fluorescein dT.

Hairpin ALEXA FLUOR 647 labeled-oligonucleotide 229 sequence:

```
(SEQ ID NO: 48)
5'-TTTTTGCGGGTGACAGGTTTTTCCTGTCACCC-3'
``` where the 229 oligo is labeled at the 3' end with ALEXA FLUOR 647.

1× extension buffer: 50 mM Tris pH 7.5, 50 mM NaCl, 10 mM MgCl$_2$, 0.5 mM MnCl$_2$.

Preparing Nanoparticles Attached with Phi29 Polymerase

300 µL of a 56 µM stock solution of His-tagged Phi29 polymerase peptide (SEQ ID NO: 13), which comprises the mutation D169A and is exonuclease minus, fused to the F-linker, in 10 mM Tris (pH 7.5) buffer with 100 mM NaCl, 1 mM DTT, 0.5% Tween-20, 0.1 mM EDTA and 50% v/v glycerol, was buffer exchanged into 100 mM Tris (pH 7.5) buffer with 300 mM NaCl using an NAP-5 column.

A suspension of C8 dots (160 µL, 4.9 µM in 50 mM borate buffer pH 8.0) was concentrated to approximately 30 µL by ultrafiltration (VivaSpin, at 100K MWCO), and mixed with the buffer exchanged Phi29 polymerase (440 µL, 26.9 µM in buffer comprising 100 mM Tris pH 7.5 and 300 mM NaCl) in a 1:15 molar ratio (nanoparticle to polymerase). The resulting solution was incubated overnight at 4° C., concentrated to ~30 µL by ultra-filtration with a 100K MWCO VivaSpin centrifugal concentrator, further purified on SUPERDEX 200 column using 100 mM Tris (pH 7.5) buffer with 300 mM NaCl as the eluent.

The conjugated nanoparticle-Phi29 was assayed to determine nucleotide incorporation activity and DNA binding as described previously. The incorporation reaction contained: 1× extension buffer (50 mM Tris pH 7.5, 50 mM NaCl, 10 mM MgCl$_2$, 0.5 mM MnCl$_2$), 10 nM Phi29-nanoparticle conjugates (or free, i.e., unconjugated, phi29 as a positive control), 150 nM oligonucleotide 221 and 20 µM dATP.

Figure 5:
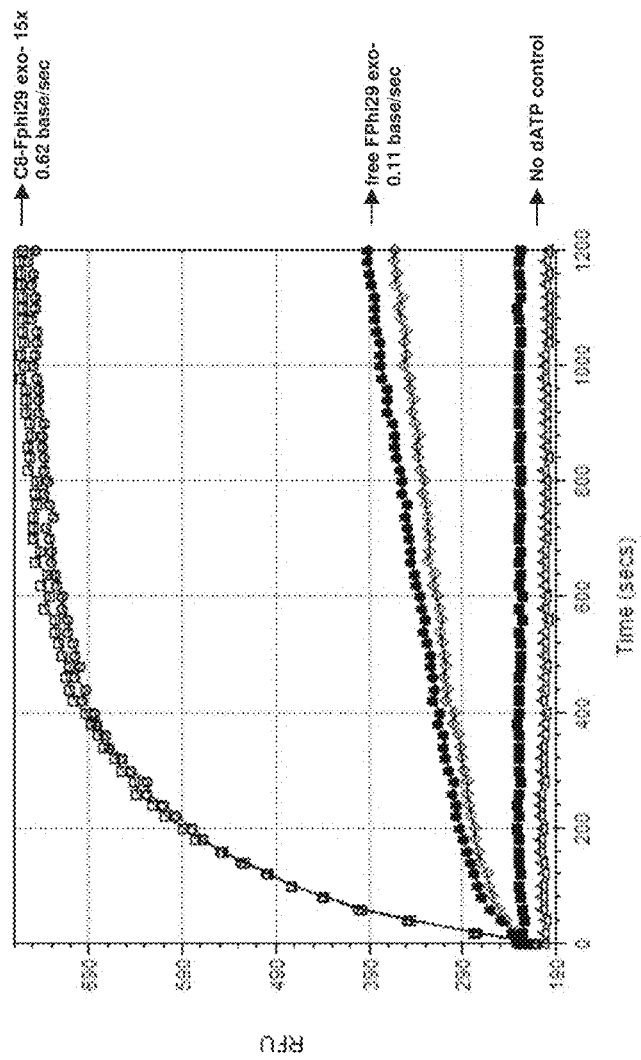

The results in FIG. 5 indicate that both free (unconjugated) Phi29 polymerase, as well as the Phi-29:C8 conjugate, can incorporate nucleotides (open circles and squares).

Figure 6A:
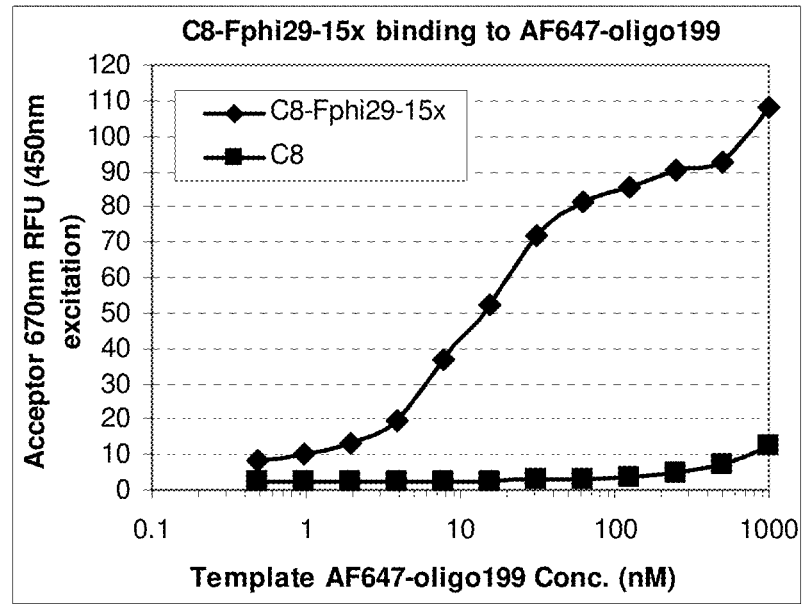
Figure 6B:
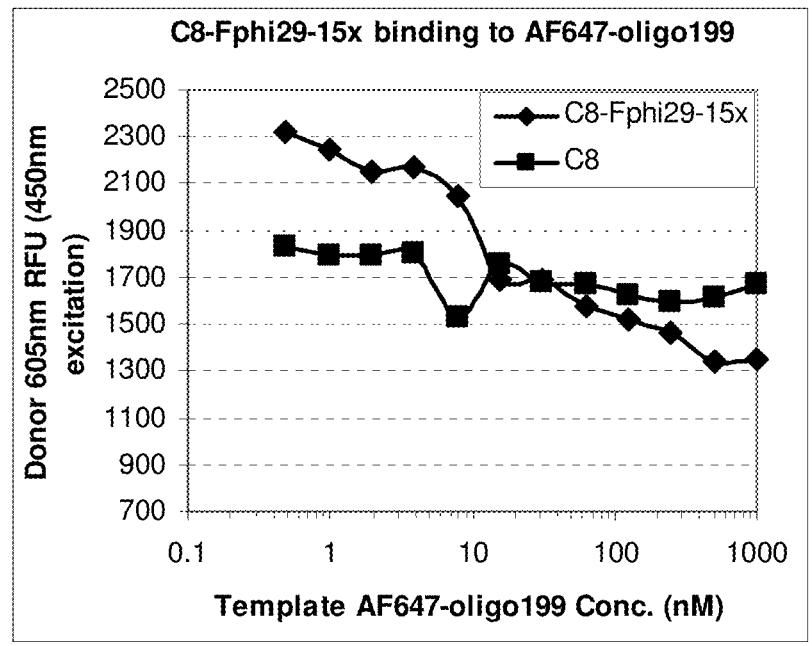
Figure 6C:
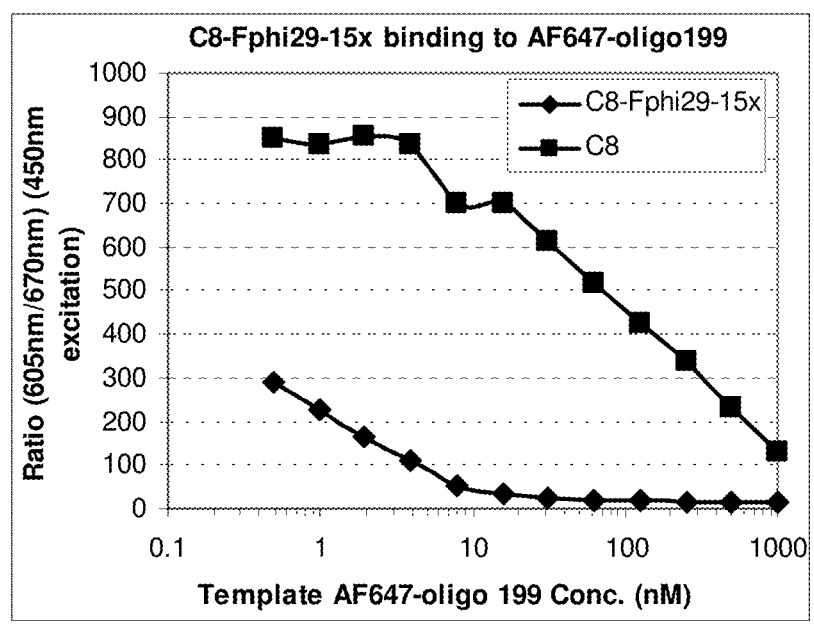

The fluorescence intensities in donor and acceptor channels from these binding reactions were also monitored. The results in FIG. 6A show an increase in FRET acceptor signal with an increase in the amount of the labeled oligonucleotide-199, or a decrease in FRET donor signal (FIG. 6B). The ratio of 605 nm/670 nm signals is depicted in FIG. 6C.

Example 4

Conjugate Comprising Phi-29 Polymerase Linked to Nanoparticle Treated with Glutathione S-Transferase (GST)

C8 dots (50 µL, 3.5 µM in 50 mM borate buffer pH 8.0) were diluted with 100 µL of 100 mM Tris buffer pH 7.5 with 300 mM NaCl and concentrated to ~20 µL by ultrafiltration (VivaSpin, 100K MWCO). The concentrated nanoparticle solution was mixed with His-tagged glutathione S-transferase ("GST") (184 µL, 19 µM in 50 mM Tris pH7.5 with 200 mM NaCl) in a 1:20 molar ratio (nanoparticle to His-tagged-GST). The resulting solution was incubated at room temperature for 5 hours. His-tagged Phi29 polymerase comprising the F-linker sequence between the N-terminal His-tag and the Phi-29 polymerase (SEQ ID NO: 13) (60 µL, 14.5 µM in 100 mM Tris (pH 7.5) buffer with 300 mM NaCl) was added to the nanoparticles in a 5:1 molar ratio (Phi29 to nanoparticle). The resulting solution was incubated overnight at 4° C., concentrated to ~30 µL by ultra-filtration with 100K MWCO VivaSpin centrifugal concentrator, purified on a SUPERDEX 200 column using 100 mM Tris (pH 7.5) buffer with 300 mM NaCl as the eluent.

The GST-nanoparticle-Phi29 conjugates were assayed to determine template extension activity and DNA binding according to the protocol provided in Example 1. The incorporation reaction contained: 1× extension buffer (50 mM Tris pH 7.5, 50 mM NaCl, 10 mM MgCl$_2$, 0.5 mM MnCl$_2$, 10 nM Phi29-nanoparticle conjugates (or free, i.e., unconjugated, Phi29 as a positive control), 150 nM oligonucleotide 221 and 20 µM dATP.

The results in FIG. 7 show that phi29 polymerase, attached to GST-treated nanoparticles, can incorporate nucleotides (open circles and squares).

Figure 8A:
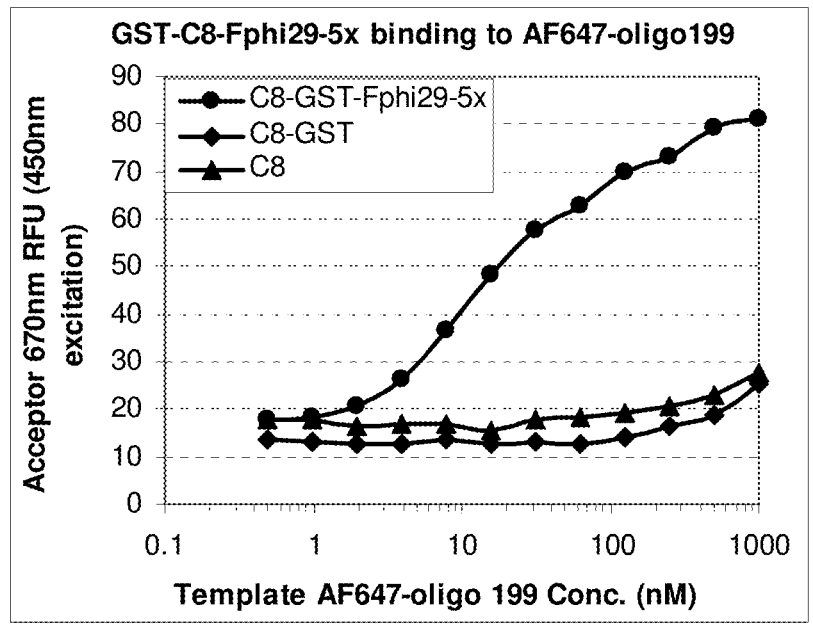
Figure 8B:
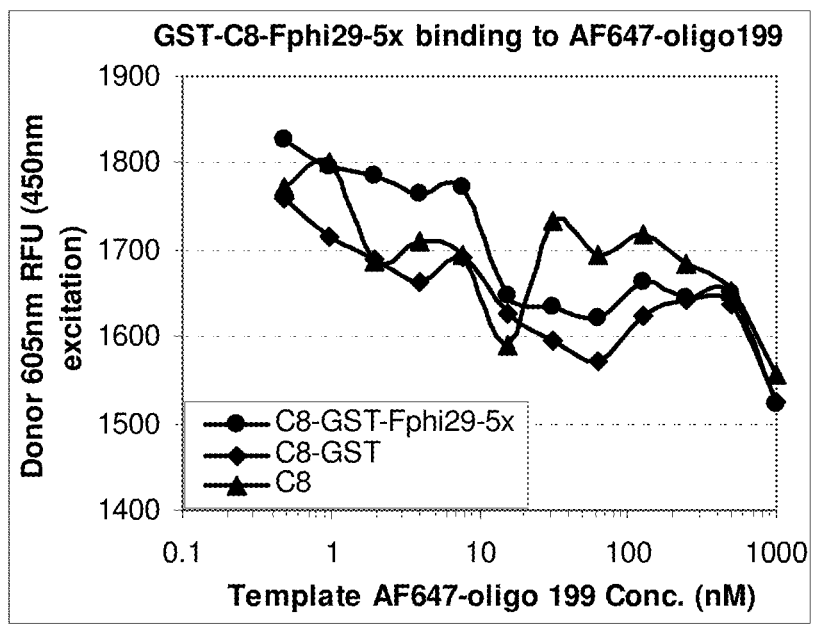
Figure 8C:
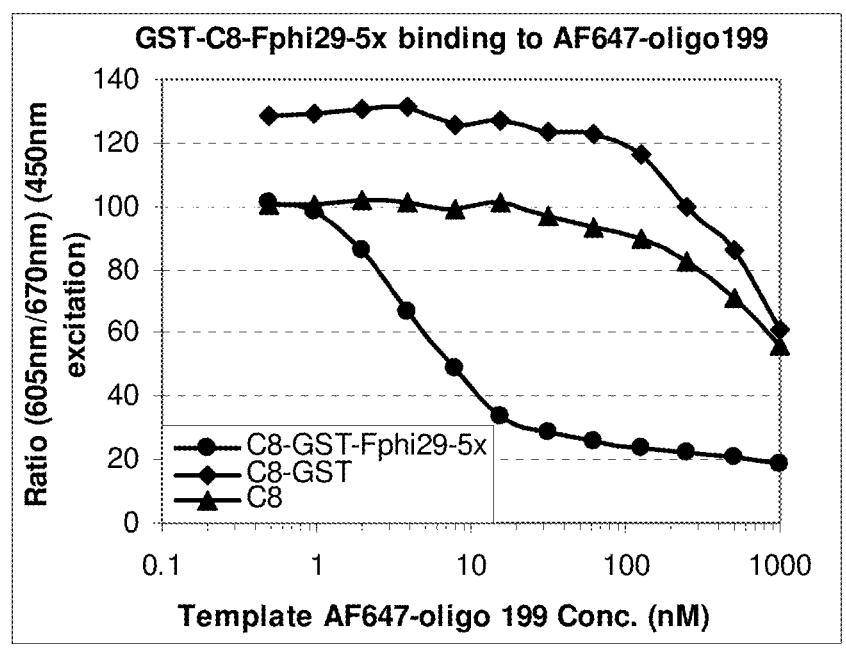

The fluorescence intensities in donor and acceptor channels from these binding reactions were also monitored. The results are depicted in FIG. 8. FIG. 8A shows an increase in FRET acceptor signal with an increase in the amount of the labeled oligonucleotide-199. FIG. 8B shows a decrease in FRET donor signal. The ratio of 605 nm/670 nm signals is depicted in FIG. 8C).

Example 5

Conjugate Comprising Phi-29 Polymerase Linked to Nanoparticle Treated with Glutathione S-Transferase (GST)

C8 dots (450 µL, 2.88 µM in 50 mM borate buffer pH 8.0 with 1 M Betaine) was buffer exchanged into 100 mM Tris (pH 7.5) buffer with 300 mM NaCl and 1 mM DTT using an NAP-10 column, aliquoted for immediate usage. The buffer exchanged C8 nanoparticles aliquot (250 µL, 1.2 µM in 100 mM Tris (pH 7.5) buffer with 300 mM NaCl and 1 mM DTT) was mixed with a His-tagged-GST (glutathione S-transferase) protein solution (237 µL, 19 µM in 50 mM Tris buffer (pH 8.0) with 200 mM NaCl and 0.5 mM EDTA) in a 1:15 molar ratio (nanoparticle to His-tagged-GST) to prepare the GST-nanoparticles. The resulting solution was rotated on a tube rotator for 2 hours at 4° C. Most of the GST-nanoparticles (430 µL) made was then mixed with the buffer exchanged His-tagged HP1-Phi29 polymerase (110 µL, 12.3 µM in 100 mM Tris (pH 7.5) buffer with 300 mM NaCl and 1 mM DTT) in a 1:5 molar ratio (nanoparticle to polymerase). HP1 is a His-tagged phi29 polypeptide which is exonuclease-minus, and includes the D12A and D66A mutations (SEQ ID NO: 14).

The resulting solution was rotated on a tube rotator overnight at 4° C., centrifuged for 5 minutes at 16.8K ref. The conjugate solution was purified on Ni$^{2+}$-NTA Agarose column using 100 mM Tris (pH 7.5) buffer with 300 mM NaCl, 1 mM DTT and 0.5 M imidazole as the eluent, centrifuged and transferred into a 10K MWCO dialysis cassette. The conjugate was then dialyzed into 50 mM Tris buffer pH7.5 with 150 mM NaCl, 0.2 mM EDTA, 0.5% v/v Tween-20, 5 mM DTT and 50% v/v glycerol. The resulting GST-nanoparticle-HP1-Phi29 conjugate was assayed to determine concentration, conjugate purity by HPLC size exclusion chromatography (SEC-HPLC), primer extension activity, the active number of Phi29 per conjugate (measured via fluorescence polarization assays) and DNA binding. Details regarding each of these assay techniques were as follows:

SEC-HPLC Assay

Figure 9A:
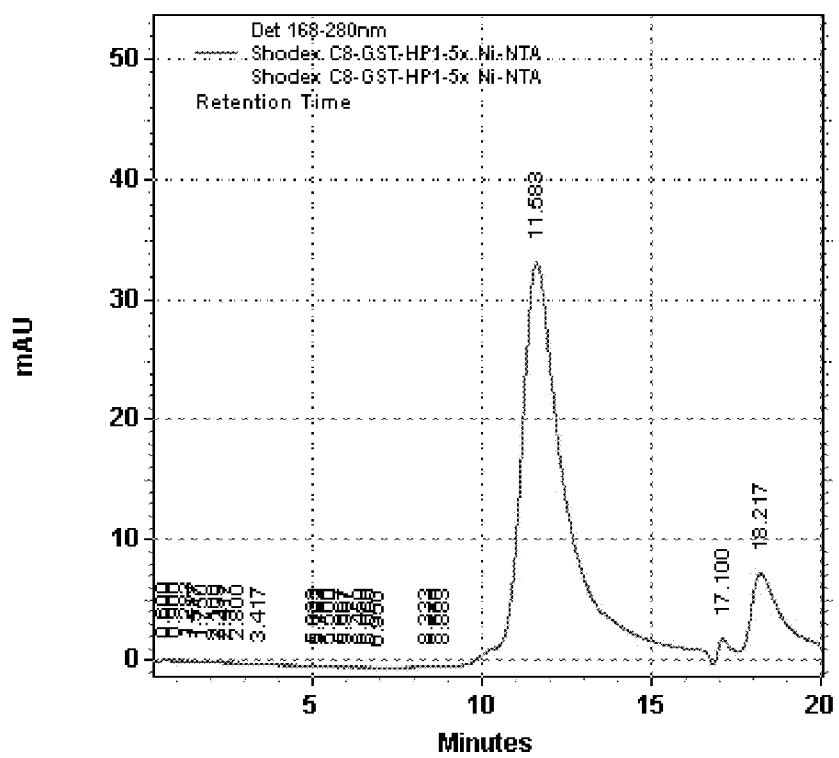

Aggregate formation was assayed via size exclusion-HPLC chromatography using a Shodex KW404-4F column in conjunction with a Shodex KW400G-4A guard column. The mobile phase was 1×PBS pH7.4 supplemented with 250 mM NaCl and 5% v/v isopropanol. The flow rate was 0.25 mL/min. The absorption of the elution stream was monitored at 280 nm to determine the appearance of protein-containing conjugates. The number of peaks and the retention time of each peak was observed and compared to the retention time (~12 minutes) of the single peak appearing when a control sample consisting of nanoparticles was loaded into the column. Aggregated conjugates typically appear as additional peaks with retention times lower than 12 minutes. As depicted in FIG. 9A, the presence of a single peak appearing around 12 minutes of retention time indicated the presence of relatively pure and non-aggregated conjugates.

DNA Binding Assay

DNA binding assays were performed to measure the ability of the polymerase-nanoparticle conjugates to bind a DNA template. The assay buffer was 50 mM Tris buffer pH 7.5, 50 mM NaCl, 10 mM MgCl$_2$ and 0.5 mM MnCl$_2$. 50 µL of 20 nM nanoparticle-polymerase conjugate was added into a well containing either 50 µL of ALEXA FLUOR 647 (AF647) labeled oligonucleotide 199 or ALEXA FLUOR 647 (AF647) labeled oligonucleotide 192 at various concentrations (2-fold dilution series with concentrations ranging from 1000 nM to 0.49 nM). The sequence of these oligonucleotides was as follows:

ALEXA FLUOR 647 labeled oligonucleotide 199:

```
                                        (SEQ ID NO: 49)
5'-TTATCTTTGTGGGTGACAGGTTTTTCCTGTCACCC-3'-AF647
```

ALEXA FLUOR 647 labeled oligonucleotide 192:

```
                                        (SEQ ID NO: 50)
5'-TTTTTTTGCCCCCAGGGTGACAGGTTTTTCCTGTCACCC-3'-
AF647
```

Figure 9B:
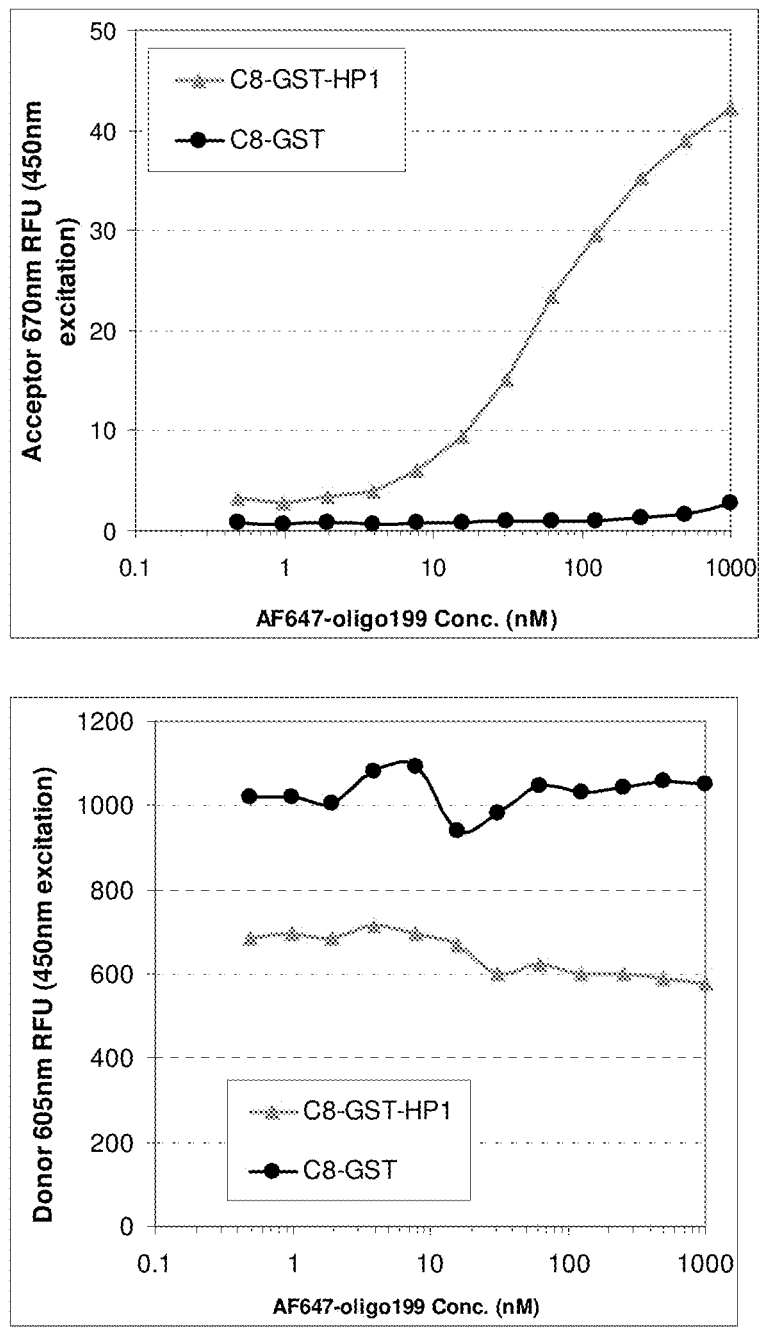

The binding of conjugate to the dye-labeled oligo was detected by measuring the fluorescence intensity at 670 nm and 605 nm with 450 nm excitation at each oligonucleotide concentration. The negative control comprised nanoparticles with no Phi29 attached. Representative results are depicted in FIG. 9B, indicating that the conjugate exhibits increasing fluorescence intensity at 670 nm with increasing oligonucleotide concentration, whereas the control nanoparticles exhibit little change in fluorescence at 670 nm over the same concentration range.

Primer Extension Assay

Primer extension assays were performed to measure the extension activity of the polymerase-nanoparticle conjugates. To reaction wells containing 100 µL of 150 nM of a fluorescein-labeled hairpin oligonucleotide, oligo221, having the sequence:

```
(5'-TTTTTTTGCAGGTGACAGGTTTTTCCTGTCACC(fluorescein-

T)GC-3'),
``` and 10 nM of the polymerase-nanoparticle conjugate in the 1× extension buffer (50 mM Tris buffer pH 7.5, 50 mM NaCl, 10 mM MgCl$_2$, 0.5 mM MnCl$_2$). 2 µL of 1 mM dATP was added to initiate the reactions, which were also exposed to excitation radiation of with 490 nm excitation. The fluorescence intensity in the wells was recorded at 525 nm fluorescence every 20 seconds for the 10 minute period immediately following the addition of dATP. Control reaction wells contained the same components, except that no dATP was added.

Figure 9C:
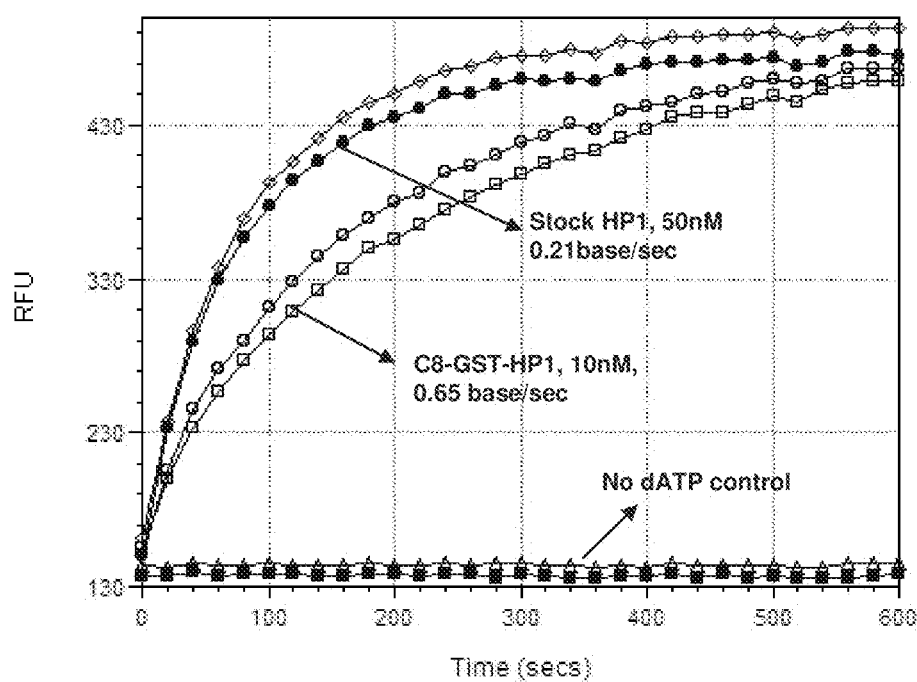

Representative results are depicted FIG. 9C. The control reaction wells exhibit a steady fluorescence level over time compared to reaction wells, which exhibit increasing fluorescence level over time.

To calculate the rate of enzyme activity, reference polymerase reaction/control wells were included that contained 150 nM fluorescein-labeled oligo-221 and 50 nM free polymerase with 20 µM dATP (positive control reaction) or without dATP (negative control reactions) in 1× extension buffer as above. The time course data for conjugate reaction/control and reference polymerase reaction/control is used to calculate the conjugate activity rate, in bases/sec, using the following equations:

$$\text{turnover\_rate(base/sec)} = \frac{\Delta RFU_{sample}\_\text{per\_sec}}{\Delta RFU_{max}\_\text{per\_nMsubs}} \times \frac{1}{10 \text{ nM}} \times 7 \text{(base)}$$

$$\Delta RFU_{max}\_\text{per\_nMsubs} = \frac{RFU_{max} - RFU_{min}}{\text{substr\_conc.(nM)}}$$

where: $RFU_{max}$ is the average maximal RFU in the reference polymerase reaction wells; $RFU_{min}$ is the average minimal RFU in the reference polymerase control wells; and Substr_conc. (nM) is the oligo 221 concentration, which is 150 nM.

$$\Delta RFU_{sample}\_\text{per\_sec} = \frac{RFU_t - RFU_0}{t(sec)}$$

where t (sec) is the time period where the fluorescence intensity increases in conjugate reaction well linearly from the start; $RFU_t$ is the average RFU of the conjugate extension wells for the tested sample at t second point; and $RFU_0$ is the average RFU of the conjugate extension wells for the tested sample at the start point. Using these methods and equations, the activity of the conjugate preparation was determined to be 0.42 bases/sec.

Fluorescence Polarization Assay

This procedure measures the active number of Phi29 per conjugate (i.e., per nanoparticle) based on evaluating the binding of active Phi29 to a fluorescein-labeled template, as indicated by the degree of fluorescence polarization observed. In this assay, the mP values of a conjugate at several concentrations are measured and a standard curve is also generated of mP values at known concentrations of free Phi29 polymerase. By fitting the experimental mP values into the standard curve, the number of Phi29 polymerases per conjugate can be calculated.

For this assay, 50 µL of 1× extension buffer (50 mM Tris pH7.5, 50 mM NaCl, 10 mM $MgCl_2$ and 0.5 mM $MnCl_2$) was added into the first two rows of a 96-well microtiter plate. Control calibration wells were prepared by adding 50 µL of 4000 nM free Phi29 in 1× extension buffer to the first well of the each row. The solution was mixed and 50 µL of the resulting mixture was transferred to the second well of the each row. Serial 2-fold dilutions (at concentrations ranging from 4000 nM to 1.95 nM) of the free Phi-29 were then prepared in the two rows by sub-sequentially transferring and mixing as described. 50 µL of solution was removed from the last well of each row to make 50 µL volume for each well. These two rows of wells served as the calibration wells.

For the sDot-Phi-29 conjugate reaction wells, 50 µL of conjugate solution comprising various conjugate concentrations (e.g. 40 nM, 80 nM, 120 nM; prepared by diluting conjugate into 1× extension buffer) were added to each well.

To both the control calibration wells and the conjugate reaction wells was added 50 µL of a solution comprising a fluorescein-labeled oligonucleotide substrate, oligo221, at 300 nM concentration in 1× extension buffer. The contents of each well were mixed, and the mP value of each well was measured using a plate reader.

The fluorescence polarization value, mP, was calculated as follows:

$$mP = \frac{I_v - I_h}{I_v + I_h} \times 1000$$

Where $I_v$ is the fluorescence intensity parallel to the excitation plane and $I_h$ is the fluorescence intensity perpendicular to the excitation plane.

The fluorescence polarization mP was directly measured on a plate reader (Molecular Devices). In this assay, the polarization (mP) of free Phi29 at various known concentrations from 2000 nM to 0.98 nM was measured as served as a calibration standard curve. The mP values for conjugate of interest at various concentrations were also measured in this assay. The mP values of certain conjugate concentration were fitted into the calibration standard curve and the number of phi29 per conjugate was calculated accordingly.

To calculate the active number of phi29 per conjugate, the results for the standard curve (obtained using the control calibration wells) was fitted into a non-linear regression equation:

$$Y = b + \frac{a-b}{1 + 10^{(\log EC50 - X)*c}}$$

Where

Y is the mP value;

X is the log [phi29(nM)];

a is the top value of the standard curve;

b is the bottom value of the standard curve;

c is the slope of the curve

EC50 is the concentration that gives 50% of the total response.

Based on the standard curve fitting results, the active Phi29 concentration at certain conjugate concentration can be calculated by entering the mP value at particular conjugate concentration into the equation. The active number of active Phi29 molecules (or fragments) per conjugate is then determined by dividing the calculated active Phi29 concentration by the conjugate concentration.

Figure 9D:
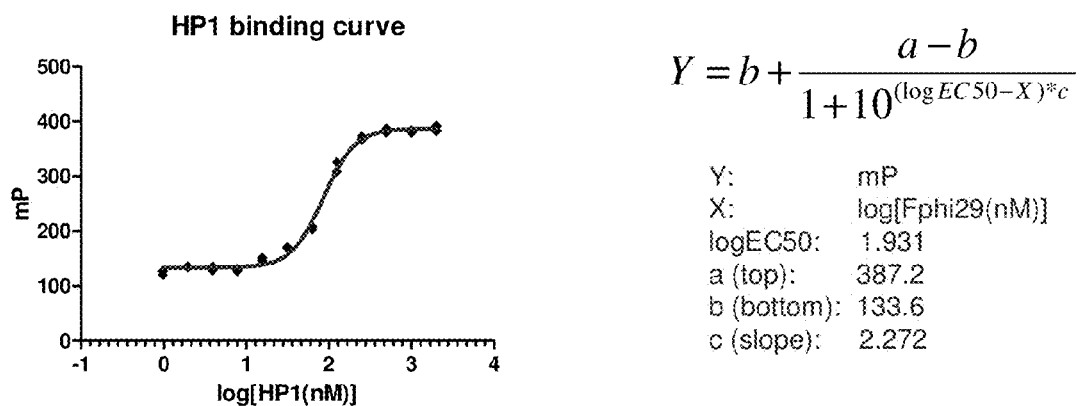

Results of these assays are depicted in FIG. 9D, which depicts the HP1 binding curve that was obtained. Based on this binding curve, the estimated values of a, b and c, were 387.2, 133.6 and 2.272, respectively. The number of active HP1 per conjugate in four separate trials was estimated as 1.9, 2.0, 1.3, and 1.5, respectively.

Example 6

Conjugate Comprising Protein Including a Protein Kinase a (PKA) Recognition Site Linked to Nanoparticle This example describes the preparation of a conjugate comprising the protein kinase A recognition sequence LRRASLG fused to the N-terminus of Phi-29 polymerase linked to a quantum dot. Phi29 polymerase protein, comprising the protein kinase A recognition sequence LRRASLG at the N-terminus (SEQ ID NO: 9), was incubated with kinase and ATP-γS to form a phosphorothioate functional group on the serine residue of the recognition sequence.

Modifying the Nanoparticles with Adipic Dihydrazide

C8 dots having outer shells that are pre-modified with methoxy-terminated PEG were obtained from Molecular Probes. These nanoparticles have residual carboxylate functional groups. 300 µl of 4.1 µM the nanoparticles were buffer exchanged into 100 mM MES, 300 mM NaCl, pH 5.5 using ultrafiltration (VivaSpin 100K MWCO spin filters). The reaction was started by adding: 260 µl of 4.08 µM buffer exchanged nanoparticles, 10.6 µl of 20 mM adipic dihydrazide (dissolved in water) and 13.5 µl of 10 mM EDC (1-ethyl-3-(3-dimethylaminopropyl)carbodiimide hydrochloride dissolved in water). 25 minutes after the start of the reaction another 13.5 µl aliquot of 10 mM EDC was added to the reaction mix. After two hours incubation at room temperature, the reaction mix was concentrated by ultrafiltration (VivaSpin 100K MWCO) then washed three times with 200 µl of 100 mM MES, 300 mM NaCl, pH 5.5 using the same ultrafiltration unit. The nanoparticles have hydrazide functional groups.

Reacting the Nanoparticles with Iodoacetic Acid

The nanoparticles (having hydrazide reactive groups) were modified with iodoacetic acid. The following reagents were added: 185 µl of 3.98 µM hydrazide-modified nanoparticles, 14.7 µl of 10 mM iodoacetic acid (sodium salt, dissolved in water) and 10 µl of 10 mM EDC (dissolved in water). 25 minutes after the start of the reaction another 10 µl aliquot of 10 mM EDC was added to the reaction mix. The reaction mix was allowed to incubate at room temperature, in the dark for three hours. After incubation, the reaction mix was concentrated by ultrafiltration and washed 5×200 µl with 100 mM MES, 300 mM NaCl, pH 5.5 also using ultrafiltration. The nanoparticles have iodoacetyl functional groups.

Attaching Iodoacetyl Nanoparticles with Phi29 Polymerases

The phosphorothioated Phi29 polymerase was buffer exchanged into 100 mM MES, 300 mM NaCl, pH 5.5 using a NAP5 column (GE Healthcare). For the conjugation reaction, 392 µl of 13.2 µM phosphorothioated Phi29 polymerase was added to 95 µl of 2.73 µM iodoacetyl modified nanoparticles. The reaction mix was allowed to incubate overnight at room temperature in the dark. The reaction mix was concentrated to approximately 30 µl then purified over a SUPERDEX 200 (GE Healthcare) 8 mm×5.5 cm column (2 mL disposable column from Thermo Scientific) using 100 mM TRIS, 300 mM NaCl, pH 7.5 as the elution buffer. Three fractions were collected and assayed for concentration, extension activity and template binding.

Materials:
Hairpin oligonucleotide 221 sequence:

(SEQ ID NO: 43)
5'-TTTTTTTGCAGGTGACAGGTTTTTCCTGTCACCXGC-3' where X=fluorescein dT.

Hairpin oligonucleotide ALEXA FLUOR-647-labeled 199 sequence:

(SEQ ID NO: 49)
5'-TTATCTTTGTGGGTGACAGGTTTTTCCTGTCACCC-3'

Hairpin oligonucleotide ALEXA FLUOR-647-labeled 199 sequence (oligo JX338):

(SEQ ID NO: 51)
5'-TTATCTTTGTGGGTGACAGGTTTTTCCTGTCACCX-3' where X=ALEXA FLUOR 647-dC

1× extension buffer: 50 mM Tris (pH 8), 50 mM NaCl, and 10 mM MgCl$_2$.

Hairpin oligonucleotide JX274 sequence:

(SEQ ID NO: 52)
5'-TTTTTTAGTCTGGGTGACAGGTTXTTCCTGTCACCY-3' where X=biotin TEG, Y=ALEXA FLUOR 647-dC.

Hairpin oligonucleotide JX240 sequence:

(SEQ ID NO: 53)
5'-TTTTTGAGGGTGACAGGTTTTTCCTGTCACCX-3' where X=ALEXA FLUOR 647-dC.

Hairpin oligonucleotide JX315 sequence:

(SEQ ID NO: 54)
5'-TTTTTGCGGGTGACAGGTTTTTCCTGTCACCX-3' where X=ALEXA FLUOR 647-dC

Activity Assay

A 150 nM master mix solution of a labeled hairpin oligonucleotide 221 was prepared by diluting the appropriate quantity of a 50 µM stock solution with 1× extension buffer (50 mM Tris, pH 8, 50 mM NaCl, 10 mM MgCl$_2$). 450 µl of a master mix was prepared for each sample being tested.

The conjugate being tested was diluted in 450 µl of the master mix such that the final concentration of the conjugate was in the range of 10 nM to 50 nM. The positive control samples containing free PKAΦ$_{29}$ were similarly diluted. The sample solution was deposited in four microtiter plate wells, at 100 µl/well.

Figure 10:
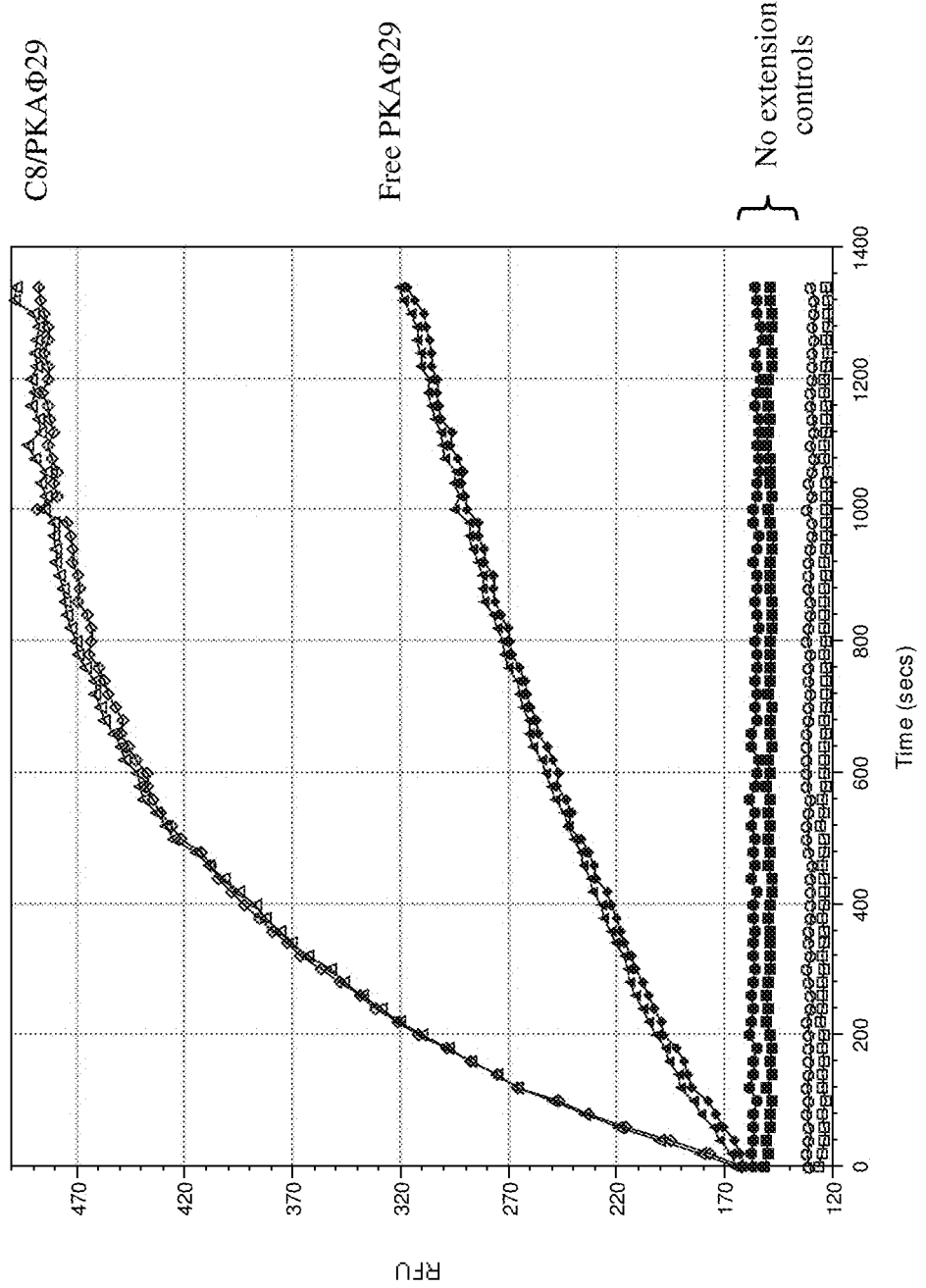

The microtiter plate was placed in a plate reader (Molecular Devices, SpectraMax M5) and set up to monitor the fluorescence as function of time (excitation 490 nm, emission 535 nm, cutoff filter 515 nm). Just prior to starting the plate reader, 2 µl of 1 mM dATP was added to each of two microtiter wells to start the extension reaction. The other two microtiter wells with sample represent no extension controls. The plate was read for an hour or until the samples reached saturation. The results in FIG. 10 indicate that Phi29 polymerase, attached to nanoparticles, can incorporate nucleotides.

Binding Assay

Each sample to be tested was diluted to 20 nM in 650 µl of 1× extension buffer. 50 µl of the sample was pipetted into each well of the top row of a microtiter plate.

A 2 µM solution of an ALEXA FLUOR-labeled hairpin oligonucleotide JX338, which comprises the same sequence as oligo 199 above with an ALEXA FLUOR 647 dye moiety attached to the 3' end of the oligonucleotide, was prepared by dissolving the appropriate amount of stock oligonucleotide in 1× extension buffer. 140 µl of each sample to be tested was prepared. The hairpin primer/template solution was pipetted into the first well of the second row in the microtiter plate. Into the remaining 11 wells of the second row of the microtiter plate, 70 µl of extension buffer was pipetted. 70 µl of the hairpin primer/template was removed from the first well of the second row and mixed with the extension buffer in the second well. 70 µl from the second well was removed and mixed with the extension buffer in the third well. The serial dilution was prepared up to the last well in row two.

50 µl of the primer/template was transferred from each well of row two into 50 µl of the sample in each well of row one.

Figure 11A:
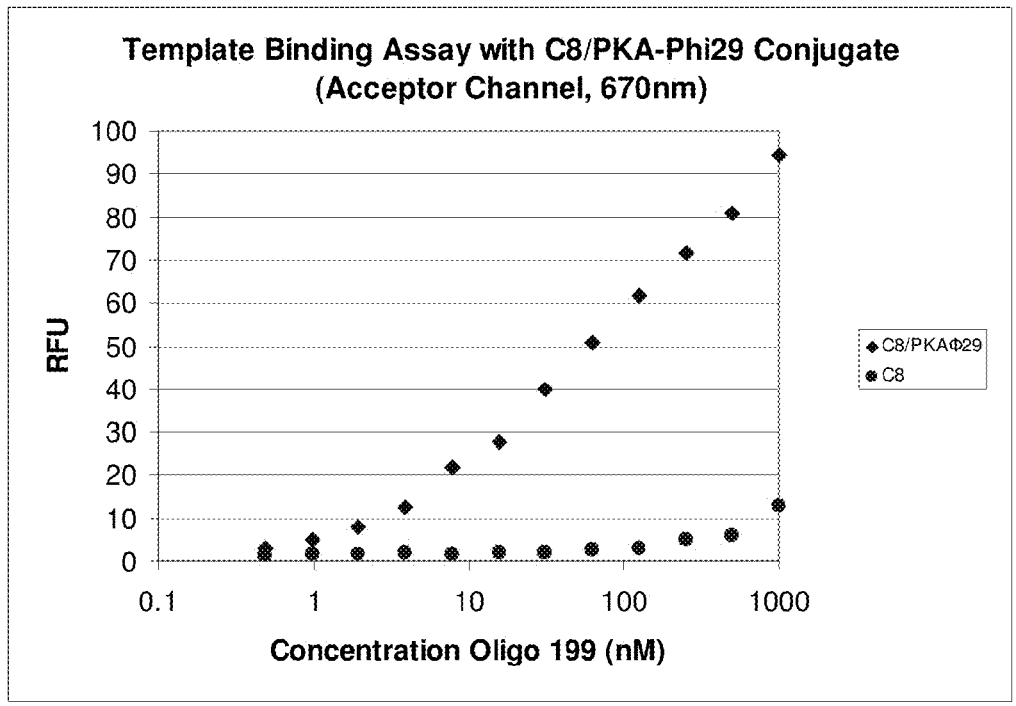
Figure 11B:
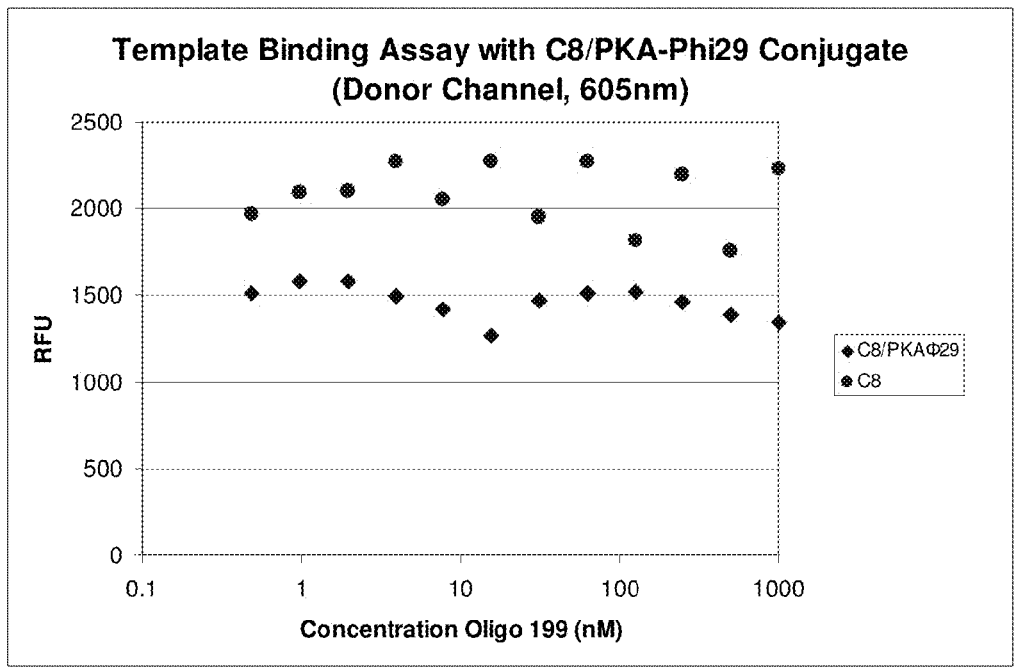
Figure 11C:
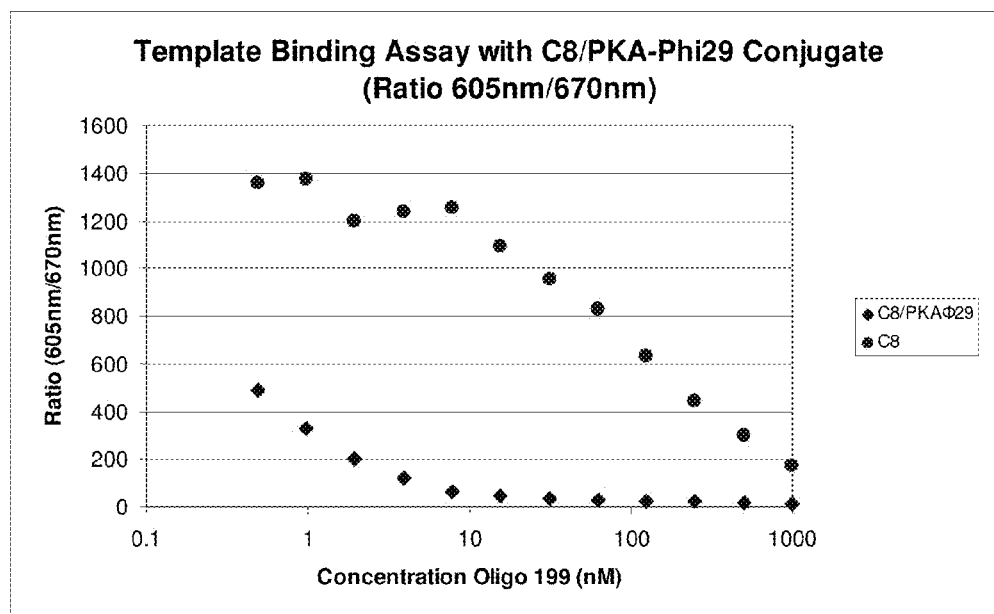

The microtiter plate was placed on the plate reader which was set to measure fluorescence at 605 nm and 670 nm with excitation at 450 nm. The results are depicted in FIG. 11. FIG. 11A depicts an increase in FRET acceptor signal with an increase in the amount of the labeled oligonucleotide-JX338, or a decrease in FRET donor signal (FIG. 11B). The ratio of 605 nm/670 nm signals is depicted in FIG. 11C.

Example 7

Conjugate Comprising his-Tagged Polymerase Linked to Nanoparticle Treated with UDG/UGI His-tagged UDG protein (uracil DNA glycosylase) (500 µL, 27 mM in 30 mM Tris buffer (pH 7.5) with 200 mM NaCl) was mixed with UGI (uracil-DNA glycosylase inhibitor) (50 µL, 347 µM in 30 mM Tris buffer (pH 7.5) with 200 mM NaCl) in 1:1.2 molar ratio (His-tagged-UDG to UGI protein), and incubated at 4° C. overnight.

C8 dots (140 µL, 4.9 µM in 50 mM borate buffer pH 8.0) was diluted by 200 µL of 100 mM Tris buffer (pH 7.5) with 300 mM NaCl and concentrated to ~30 µL by ultrafiltration (VivaSpin, 100K MWCO). The concentrated nanoparticle solution was mixed with the His-tagged-UDG-ugi protein conjugate (550 µL, 24.7 µM in 30 mM Tris buffer (pH 7.5) with 200 mM NaCl) in a 1:20 molar ratio (nanoparticle to His-tagged-UDG-ugi) to prepare the UDG-ugi-nanoparticles. The resulting solution was incubated at room temperature for 5 hours.

The His-tagged Phi29 polymerase of SEQ ID NO: 13 was added (220 µL, 15.4 µM in 100 mM Tris (pH 7.5) buffer with 300 mM NaCl) in a 1:5 molar ratio (UDG-ugi-nanoparticle to phi29). The resulting solution was incubated overnight at 4° C., concentrated to ~30 µL by ultra-filtration with 100K MWCO VivaSpin centrifugal concentrator, and purified on a SUPERDEX 200 column using 100 mM Tris (pH 7.5) buffer with 300 mM NaCl as the eluent.

The conjugated UDG-ugi-nanoparticle-phi29 was assayed to determine template extension activity and DNA binding. The conjugated nanoparticle-Phi29 was assayed to determine nucleotide incorporation activity and DNA binding as described previously. The incorporation reaction contained: 1× extension buffer (50 mM Tris pH 7.5, 50 mM NaCl, 10 mM MgCl$_2$, 0.5 mM MnCl$_2$), 10 nM Phi29-nanoparticle conjugates (or free, i.e., unconjugated, phi29 as a positive control), 150 nM oligonucleotide 221 and 20 µM dATP.

Figure 12:
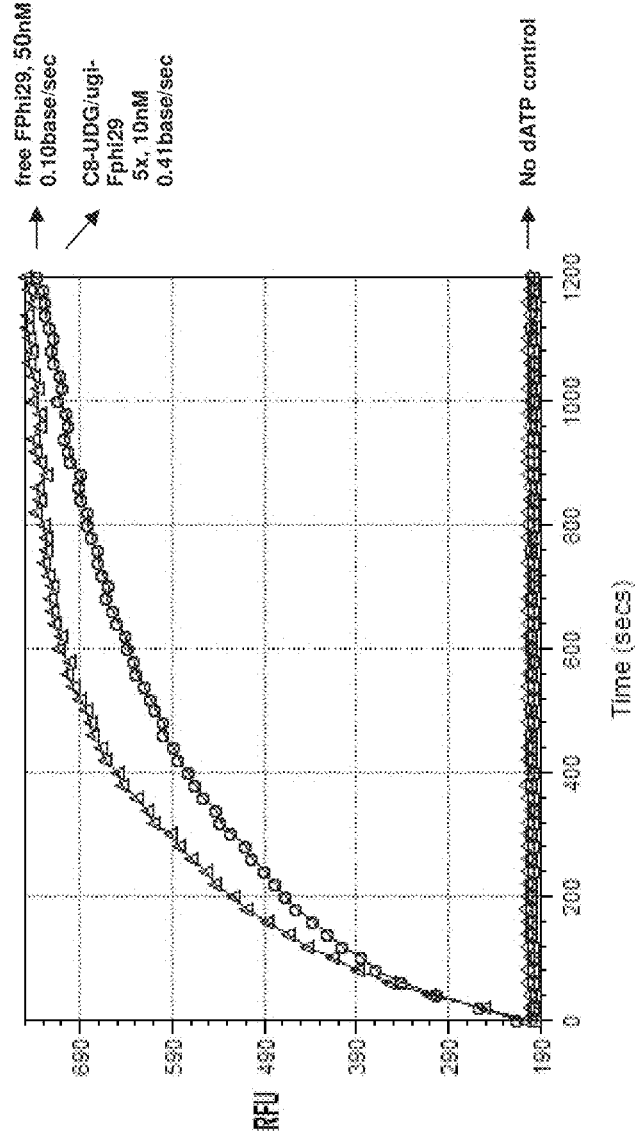

The results in FIG. 12 indicate that Phi29 polymerase, attached to UDG/ugi-treated nanoparticles, can incorporate nucleotides (open circles).

Figure 13A:
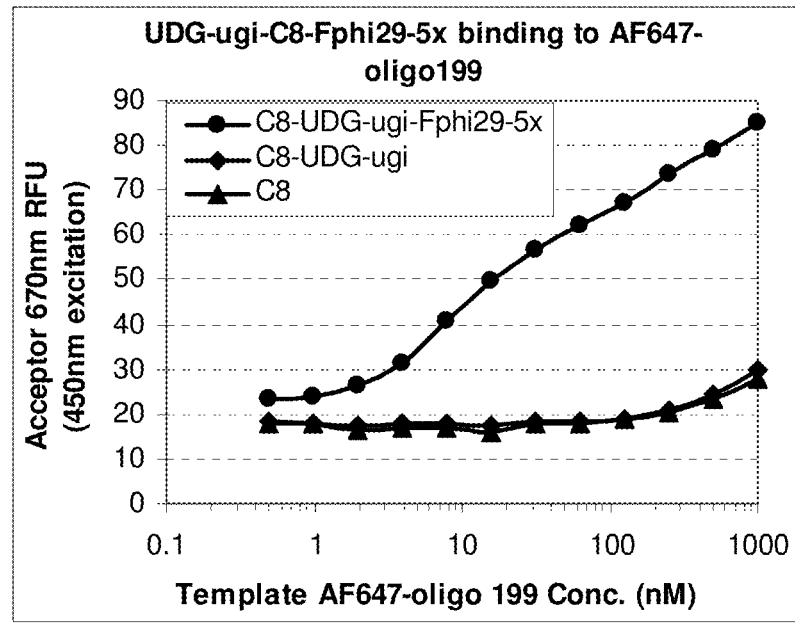
Figure 13B:
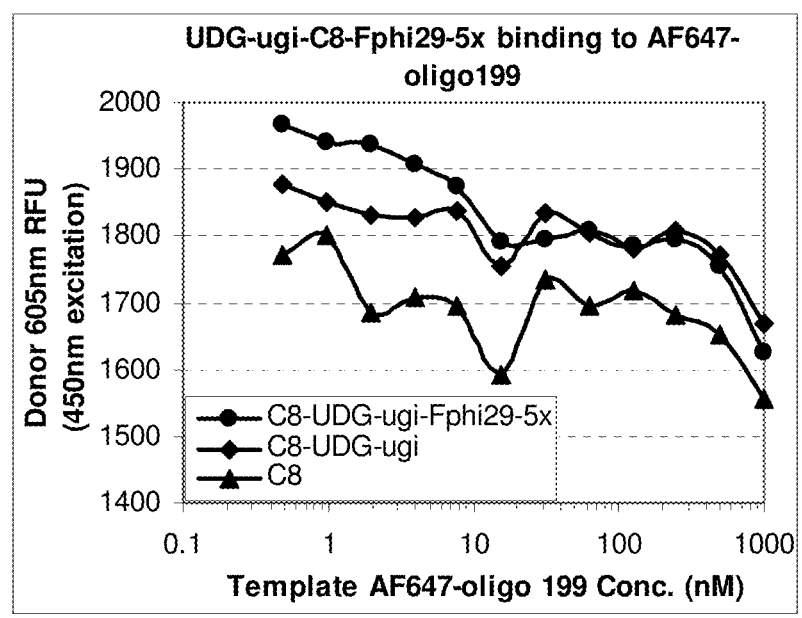
Figure 13C:
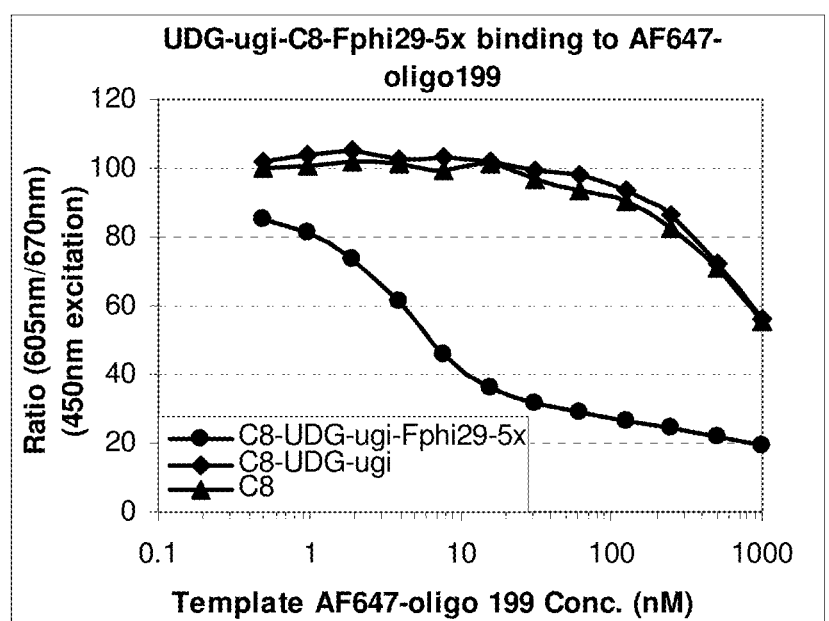

The fluorescence intensities in donor and acceptor channels from these binding reactions were also monitored. The results in FIG. 13A indicate an increase in FRET acceptor signal with an increase in the amount of the labeled oligonucleotide-199, or a decrease in FRET donor signal (FIG. 13B). The ratio of 605 nm/670 nm signals is depicted in FIG. 13C.

Preparing BSA-Nanoparticles Attached with Phi29 Polymerase

Bovine serum albumin (BSA) (20 mg, catalog no. B4287, Sigma) was dissolved in 2 mL deionized water. The BSA solution (200 µL, 10 mg/mL in H$_2$O was mixed with DTT (8 µL, 1M), and incubated at room temperate overnight. The resulting solution was purified on an NAP-5 column using deionized water as the eluent.

A1 dots (100 µL, 1.0 µM in 50 mM Tris buffer (pH 8)) was diluted by 100 µL of 100 mM Tris buffer (pH 7.5) with 300 mM NaCl and concentrated to ~30 µL by ultrafiltration (VivaSpin, 100K MWCO).

The concentrated nanoparticle solution was mixed with DTT (1.0 µL, 100 mM), and with the above-described BSA solution (27 µL, 75.8 µM in deionized water) in a 1:20 molar ratio (nanoparticle to BSA). The resulting solution was incubated at room temperature overnight, concentrated to ~30 µL by ultra-filtration 100K MWCO VivaSpin centrifugal concentrator.

The concentrated nanoparticle-BSA solution was mixed with the His-tagged phi29 polymerase (48 µL, 20.8 µM in 100 mM Tris (pH 7.5) buffer with 300 mM NaCl) in a 1:10 molar ration (BSA-nanoparticles to phi29). The resulting solution was incubated overnight at 4° C., concentrated to ~30 µL by ultra-filtration with 100K MWCO VivaSpin centrifugal concentrator, and purified on a SUPERDEX 200 column using 100 mM Tris (pH 7.5) buffer with 300 mM NaCl as the eluent.

The conjugated BSA-nanoparticle-phi29 was assayed to determine template extension activity and DNA binding by detecting FRET signals. The incorporation reaction contained: 1× extension buffer, 10 nM nanoparticle-phi29 conjugates (or non-conjugated phi29 as a control), 150 nM oligonucleotide 229, and 20 µM dATP.

Figure 14:
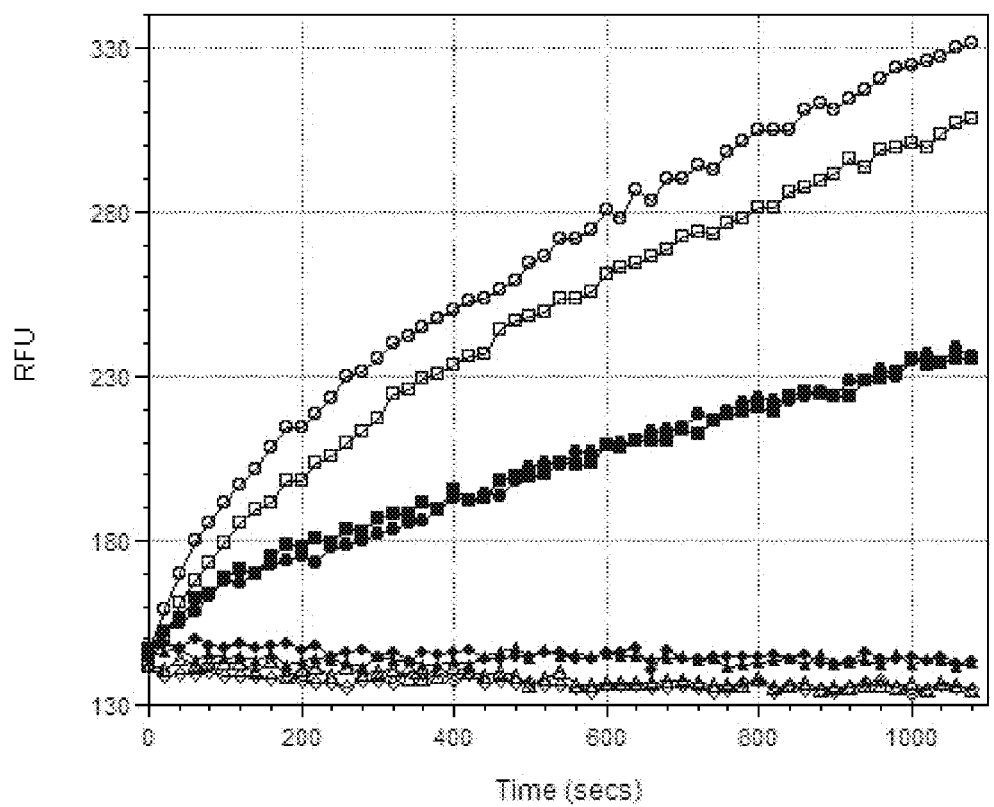

The results in FIG. 14 indicate that phi29 polymerase, attached to BSA-treated nanoparticles, can incorporate nucleotides (open circles).

Figure 15A:
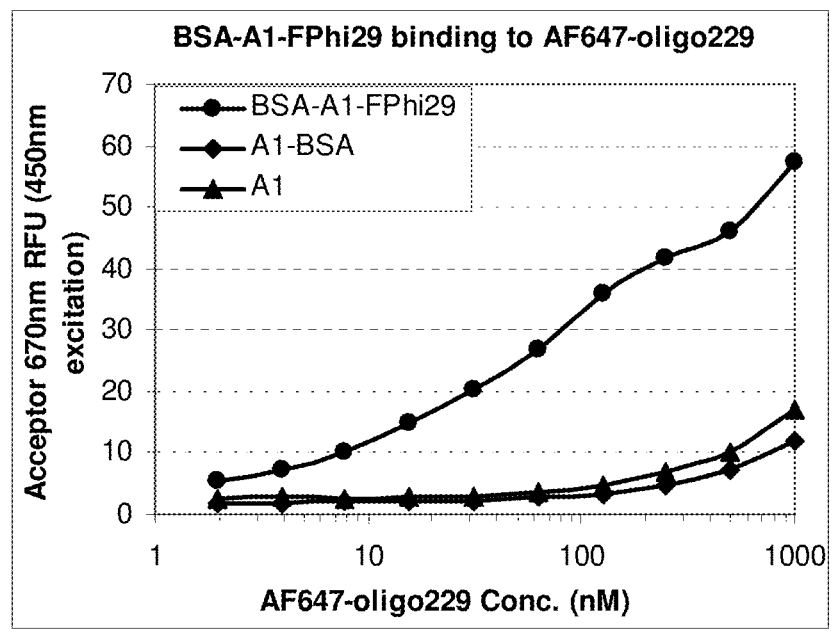
Figure 15B:
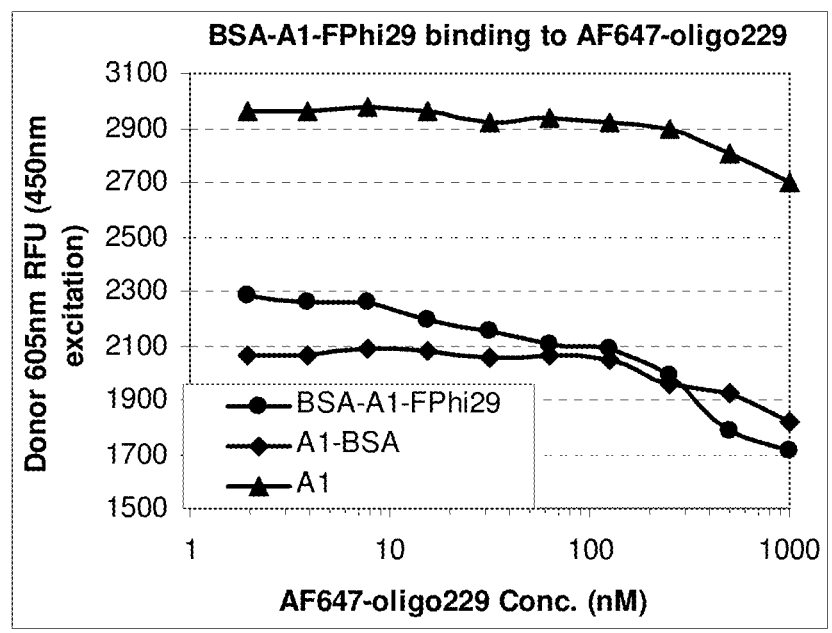
Figure 15C:
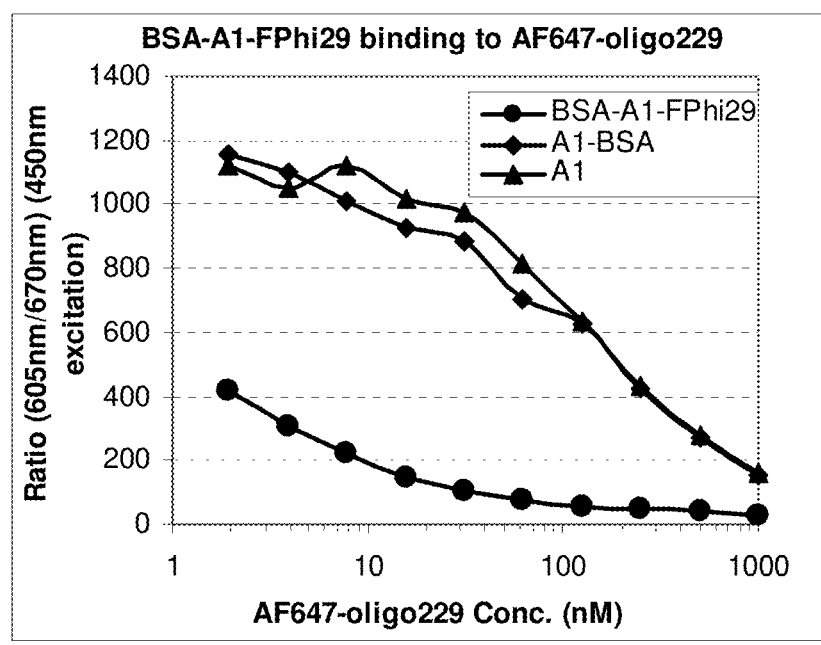

The binding reactions contained: 1× extension buffer, A1 nanoparticles-phi29 conjugates (or phi29 non-conjugated), oligonucleotide 229, and dATP. The binding reactions were serially diluted. The results in FIG. 15A indicate an increase in FRET acceptor signal with an increase in the amount of the labeled oligonucleotide-229, or a decrease in FRET donor signal (FIG. 15B). The ratio of 605 nm/670 nm signals is depicted in FIG. 15C.

Example 8

Conjugate Comprising his-Tagged Polymerase Linked to a Nanoparticle Treated with UDG/UGI His-tagged UDG protein (uracil DNA glycosylase) (1.72 mL, 14.3 µM in 30 mM Tris buffer (pH 8.0) with 200 mM NaCl, 0.5 mM EDTA and 1 mM DTT) was mixed with UGI (uracil-DNA glycosylase inhibitor) (85 µL, 347 µM in 30 mM Tris buffer (pH 7.5) with 200 mM NaCl) in 1:1.2 molar ratio (His-tagged-UDG to UGI protein), and incubated at 4° C. overnight.

A stock solution of His-tagged HP1-Phi29 polymerase (100 µL, 57 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl and 1 mM DTT using an NAP-5 column.

C8 dots (210 µL, 4.0 µM in 50 mM borate buffer pH 8.0 with 1.0 M Betaine) was buffer exchanged into 100 mM Tris (pH 7.5) buffer with 300 mM NaCl and 1 mM DTT using an NAP-5 column. The buffer exchanged C8 dots (455 µL, 1.59 µM in 100 mM Tris (pH 7.5) buffer with 300 mM NaCl and 1 mM DTT) was mixed with the His-tagged-UDG-UGI protein complex (798 µL, 13.6 µM in 30 mM Tris buffer (pH 8.0) with 200 mM NaCl, 0.5 mM EDTA and 1 mM DTT) in a 1:15 molar ratio (nanoparticle to His-tagged-UDG-UGI) to prepare the UDG-UGI-nanoparticles. The resulting solution was rotated on a tube rotator for 3 hours at 4° C. The resulting UDG-UGI-nanoparticles was then mixed with the buffer exchanged His-tagged HP1-Phi29 polymerase (650 µL, 5.57 µM in 100 mM Tris (pH 7.5) buffer with 300 mM NaCl and 1 mM DTT) in a 1:5 molar ratio (nanoparticle to polymerase). The resulting solution was rotated on a tube rotator overnight at 4° C., centrifuged for 5 minutes at 16.8K ref. The conjugate solution was purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed into 50 mM Tris buffer pH7.5 with 150 mM NaCl, 0.2 mM EDTA, 0.5% v/v Tween-20, 5 mM DTT and 50% v/v glycerol. The resulting UDG-ugi-nanoparticle-HP1-Phi29 conjugate was assayed to determine protein concentration via UV absorbance (results not shown).

The conjugate was then assayed for purity and non-aggregation using SEC-HPLC, DNA binding, primer extension activity, and stochiometry, i.e., active number of Phi29 per conjugate measured via fluorescence polarization assay, using the procedures described in Example 5. Representative results are depicted in FIG. 16A (purity), FIG. 16B (DNA binding), FIG. 16C (primer extension) and FIG. 16D (stochiometry).

Using the methods and equations described in Example 5, the activity of the conjugate preparation was determined to be 0.32 bases/sec.

Based on the HP1 binding curve depicted in FIG. 16D, the estimated values of a, b and c were 412.4, 149.6 and 3.415, respectively. The number of active HP1 per conjugate in five separate trials was estimated as 1.6, 1.2, 1.3, 1.1, 1.0 and 1.1, respectively.

Finally, the degree of aggregation observed in various conjugate preparations prepared by different conjugation methods was compared. The degree of aggregation was measured using HPLC size exclusion chromatography (SEC-HPLC) according to the method described in Example 5. Representative results for four different conjugate preparations, prepared according to the methods of Examples 3, 7, 8 and 12, are depicted in FIG. 16E. Panel A (top left) shows the SEC-HPLC profile of Phi-29:C8 conjugates prepared according to the method of Example 3; the observed percentage of monodisperse conjugates in the conjugate preparation was 42%. Panel B (top right) shows the SEC-HPLC profile of Phi-29:C8 conjugates prepared according to the method of Example 7; the observed percentage of monodisperse conjugates in the conjugate preparation was 80%. Panel C (bottom left) shows the SEC-HPLC profile of Phi-29:C8 conjugates prepared according to the method of Example 12; the observed percentage of monodisperse conjugates in the conjugate preparation was 95%. Panel D (bottom right) shows the SEC-HPLC profile of Phi-29:C8 conjugates prepared according to the method of Example 8; the observed percentage of monodisperse conjugates in the conjugate preparation was 97%.

Example 9

Formation of a 1:1 Polymerase:Nanoparticle Conjugate

In another study, three different C8-UDG-ugi-FPhi29 conjugates, each comprising F-linker-Phi-29 polymerase linked to quantum dots treated with UDG and UGI, were prepared and the activity and stoichiometric composition of each conjugate was assessed in order to evaluate conditions favoring the formation of 1:1 Phi-29:nanoparticle monoconjugates.

The three conjugates were prepared according to the following method:

Preparing UDG-ugi-Nanoparticles Attached with Various Numbers of Phi29 Polymerase His-tagged UDG protein (uracil DNA glycosylase) (1000 µL, 57 µM in 10 mM Tris buffer (pH 7.5) with 100 mM NaCl, 1 mM DTT, 0.5% v/v Tween-20, 0.1 mM EDTA, 50% v/v Glycerol) was mixed ugi (uracil-DNA glycosylase inhibitor) (125 µL, 445 µM in 50 mM Tris buffer (pH 7.5) with 1 mM DTT and 5% Glycerol) in 1:1 molar ratio (His-tagged-UDG to ugi protein), and incubated at 4° C. overnight. The formed His-tagged UDG-ugi protein complex was buffer exchanged into 100 mM Tris (pH 7.5) buffer with 300 mM NaCl using an NAP-5 column.

A stock solution of His-tagged F linker-Phi29 polymerase (SEQ ID NO: 13) (200 µL, 65 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl using an NAP-5 column.

Preparing UDG-ugi-Nanoparticles-4×Phi29 Polymerase

C8 dots (100 µL, 4.1 µM in 50 mM borate buffer pH 8.0) was diluted by 100 µL of 100 mM Tris buffer (pH 7.5) with 300 mM NaCl and concentrated to ~10 µL by ultrafiltration (VivaSpin, 100K MWCO). The concentrated nanoparticle solution was mixed with the His-tagged-UDG-ugi protein complex (216 µL, 30.4 µM in 100 mM Tris buffer (pH 7.5) with 300 mM NaCl) in a 1:16 molar ratio (nanoparticle to His-tagged-UDG-ugi) to prepare the UDG-ugi-nanoparticles. The resulting solution was incubated at room temperature for 6 hours.

The His-tagged F linker-Phi29 polymerase (SEQ ID NO: 13) was added (104 µL, 15.8 µM in 100 mM Tris (pH 7.5) buffer with 300 mM NaCl) in a 1:4 molar ratio (UDG-ugi-nanoparticle to phi29). The resulting solution was incubated overnight at 4° C., concentrated to ~10 µL by ultra-filtration with 100K MWCO VivaSpin centrifugal concentrator, and purified on a SUPERDEX 200 column using 100 mM Tris (pH 7.5) buffer with 300 mM NaCl as the eluent.

Preparing UDG-ugi-Nanoparticles-2×Phi29 Polymerase

C8 dots (50 µL, 4.1 µM in 50 mM borate buffer pH 8.0) was diluted by 100 µL of 100 mM Tris buffer (pH 7.5) with 300 mM NaCl and concentrated to ~10 µL by ultrafiltration (VivaSpin, 100K MWCO). The concentrated nanoparticle solution was mixed with the His-tagged-UDG-ugi protein complex (135 µL, 27.4 µM in 100 mM Tris buffer (pH 7.5) with 300 mM NaCl) in a 1:18 molar ratio (nanoparticle to His-tagged-UDG-ugi) to prepare the UDG-ugi-nanoparticles. The resulting solution was incubated at room temperature for 6 hours.

The His-tagged F linker-Phi29 polymerase (SEQ ID NO: 13) was added (26 µL, 15.8 µM in 100 mM Tris (pH 7.5) buffer with 300 mM NaCl) in a 1:2 molar ratio (UDG-ugi-nanoparticle to phi29). The resulting solution was incubated overnight at 4° C., concentrated to ~10 µL by ultra-filtration with 100K MWCO VivaSpin centrifugal concentrator, and purified on a SUPERDEX 200 column using 100 mM Tris (pH 7.5) buffer with 300 mM NaCl as the eluent.

Preparing UDG-ugi-Nanoparticles-1×Phi29 Polymerase.

C8 dots (50 µL, 4.1 µM in 50 mM borate buffer pH 8.0) was diluted by 100 µL of 100 mM Tris buffer (pH 7.5) with 300 mM NaCl and concentrated to ~10 µL by ultrafiltration (VivaSpin, 100K MWCO). The concentrated nanoparticle solution was mixed with the His-tagged-UDG-ugi protein complex (103 µL, 37.8 µM in 100 mM Tris buffer (pH 7.5) with 300 mM NaCl) in a 1:19 molar ratio (nanoparticle to His-tagged-UDG-ugi) to prepare the UDG-ugi-nanoparticles. The resulting solution was incubated at room temperature for 6 hours.

The His-tagged F linker-Phi29 polymerase (SEQ ID NO: 13) was added (13 µL, 15.8 µM in 100 mM Tris (pH 7.5) buffer with 300 mM NaCl) in a 1:1 molar ratio (UDG-ugi-nanoparticle to phi29). The resulting solution was incubated overnight at 4° C., concentrated to ~10 µL by ultra-filtration with 100K MWCO VivaSpin centrifugal concentrator, and purified on a SUPERDEX 200 column using 100 mM Tris (pH 7.5) buffer with 300 mM NaCl as the eluent.

Each of the three conjugates was assayed to determine protein concentration via UV absorbance (results not shown).

Figure 17A:
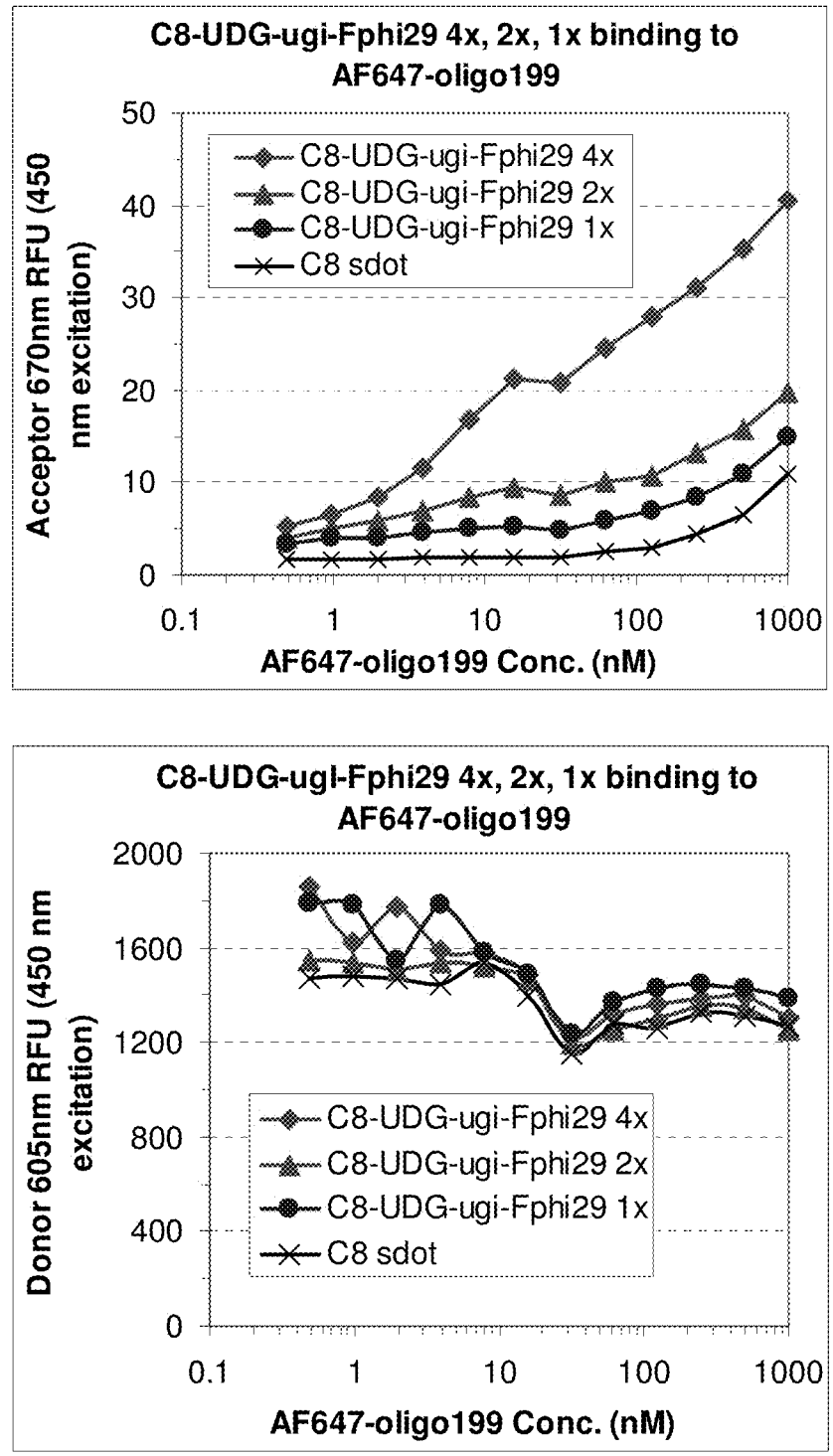
Figure 17B:
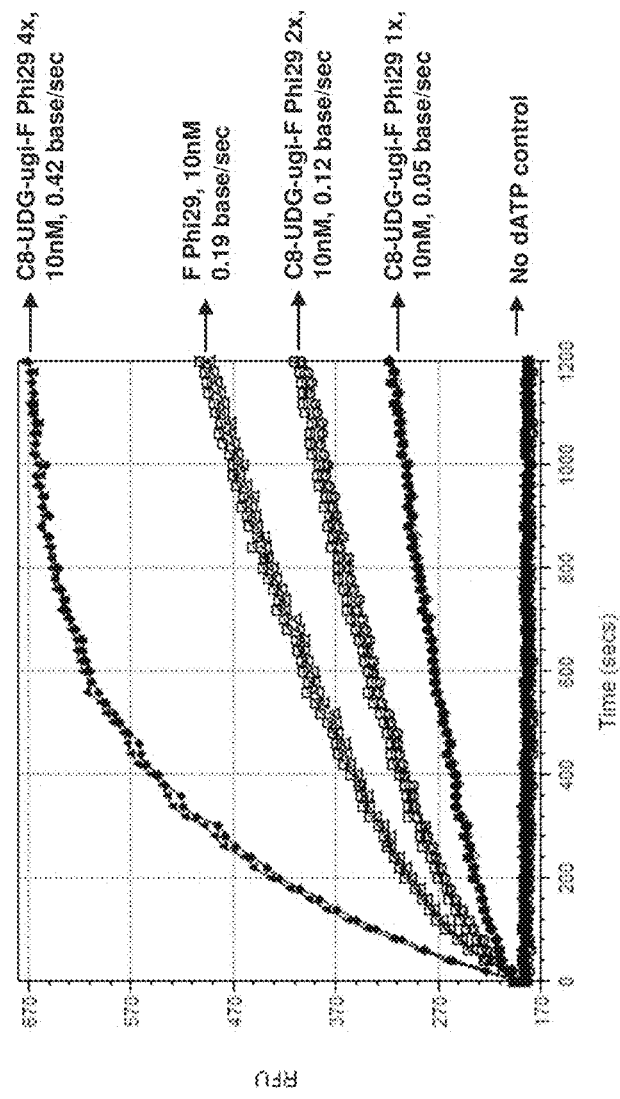
Figure 17C:
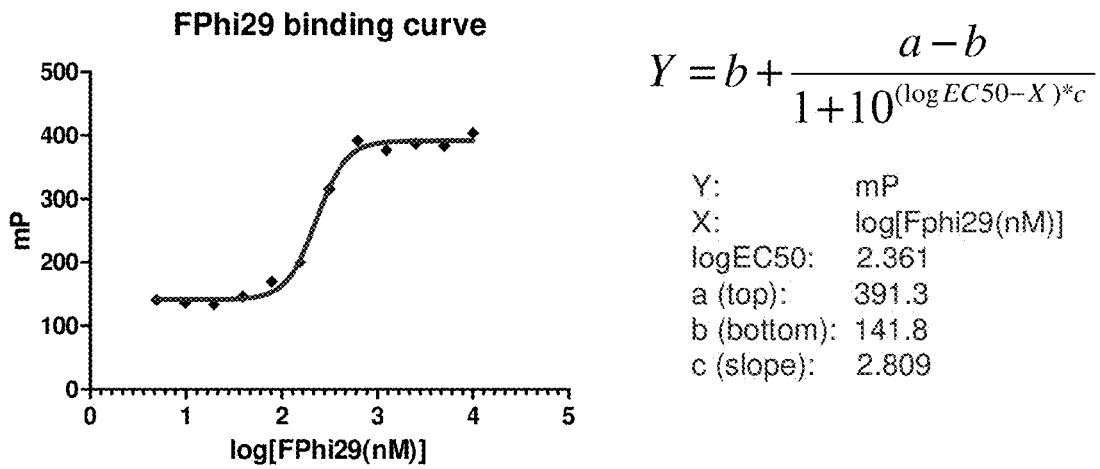

Each of the three conjugates was then assayed for DNA binding, primer extension activity, and stochiometry, i.e., active number of Phi29 per conjugate measured via fluorescence polarization assay, using the procedures described in Example 5. Representative results are depicted in FIG. 17A (DNA binding), FIG. 17B (primer extension), and FIG. 17C (stochiometry).

Figure 17D:
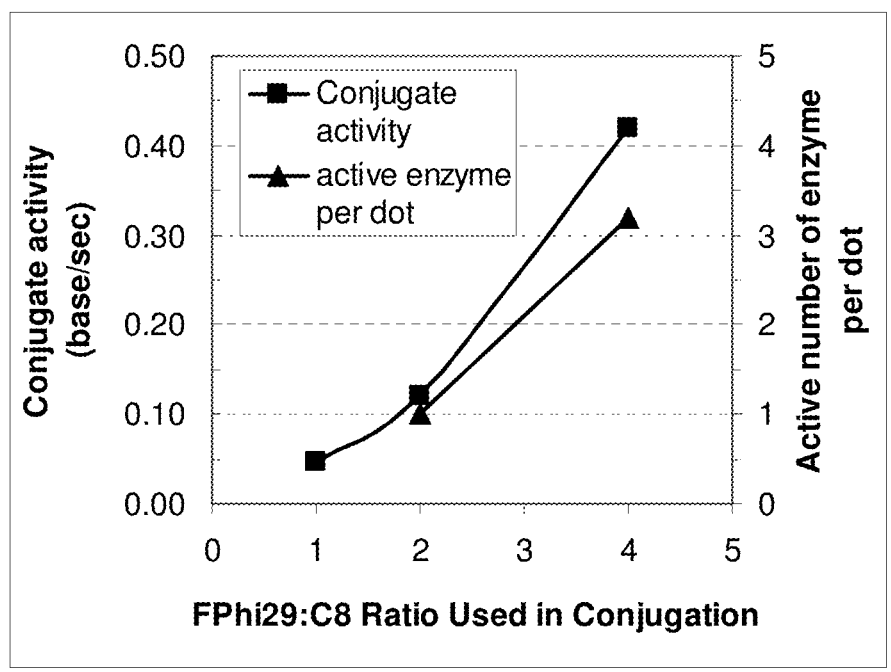

In addition, the effect of Phi29:C8 ratios on conjugate activity, as measured in bases/second (measured in the primer extension assay; left Y axis) or on the number of active polymerases observed per conjugate (measured in the fluorescence polarization assay, right Y axis) against the ratio of protein to nanoparticle (F-Phi29:C8) used in the conjugation reaction mixture (X axis) was evaluated. As depicted in FIG. 17D, correlation between the phi29:C8 ratio and the conjugate activity was observed. Similar correlation between the phi29:C8 ratio and the active number of phi29 per conjugate was also observed. As depicted in FIG. 17D, 1:1 polymerase:nanoparticle (i.e., F-Phi29:C8) conjugates were obtained by adjusting the phi29:C8 ratio in the conjugation reaction mixture to ~2. The yield of 1:1 biomolecule:nanoparticle conjugates was approximately 48%. In other similar experiments, the yield ranged from 40% to 60% (results not shown).

Example 10

Conjugate Comprising Phi 29 Polymerase and Maltose Binding Protein (MBP) Linked to Nanoparticle His-MBP (maltose-binding protein) (200 µL, 147.7 µM) (stock solution in 10 mM Tris (pH 7.5) buffer with 100 mM NaCl, 4 mM DTT, 0.5% Tween-20, 0.1 mM EDTA and 50% v/v glycerol) was buffer exchanged into 100 mM Tris (pH 7.5) buffer with 300 mM NaCl using an NAP-10 column.

A stock solution of His-tagged HP1-Phi29 polymerase (SEQ ID NO: 14) (150 µL, 70.4 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl and 1 mM DTT using an NAP-5 column.

C8 dots (450 µL, 2.88 µM in 50 mM borate buffer pH 8.0 with 1 M Betaine) was buffer exchanged into 100 mM Tris (pH 7.5) buffer with 300 mM NaCl and 1 mM DTT using an NAP-10 column, aliquoted for immediate usage. The buffer exchanged C8 nanoparticles aliquot (250 µL, 1.2 µM in 100 mM Tris (pH 7.5) buffer with 300 mM NaCl and 1 mM DTT) was mixed with the buffer exchanged His-MBP protein (66 µL, 68.2 µM in 100 mM Tris buffer (pH 7.5) with 300 mM NaCl) in a 1:15 molar ratio (nanoparticle to His-tagged-MBP) to prepare the MBP-nanoparticles. The resulting solution was rotated on a tube rotator for 2 hours at 4° C. Most of the MBP-nanoparticles (270 µL) made was then mixed with the buffer exchanged His-tagged HP1-Phi29 polymerase (110 µL, 12.3 µM in 100 mM Tris (pH 7.5) buffer with 300 mM NaCl and 1 mM DTT) in a 1:5 molar ratio (nanoparticle to polymerase). The resulting solution was rotated on a tube rotator overnight at 4° C., centrifuged for 5 minutes at 16.8K rd. The conjugate solution was purified on Ni$^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed into 50 mM Tris buffer pH7.5 with 150 mM NaCl, 0.2 mM EDTA, 0.5% v/v Tween-20, 5 mM DTT and 50% v/v glycerol. The resulting MBP-nanoparticle-HP1-Phi29 conjugate was assayed to determine protein concentration (data not shown).

Figure 18A:
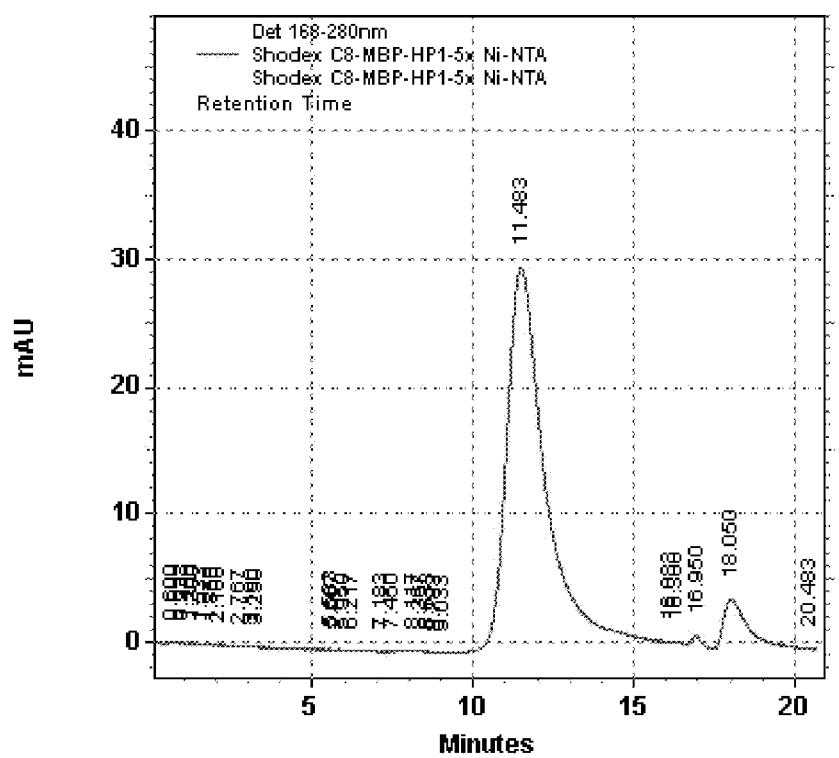
Figure 18B:
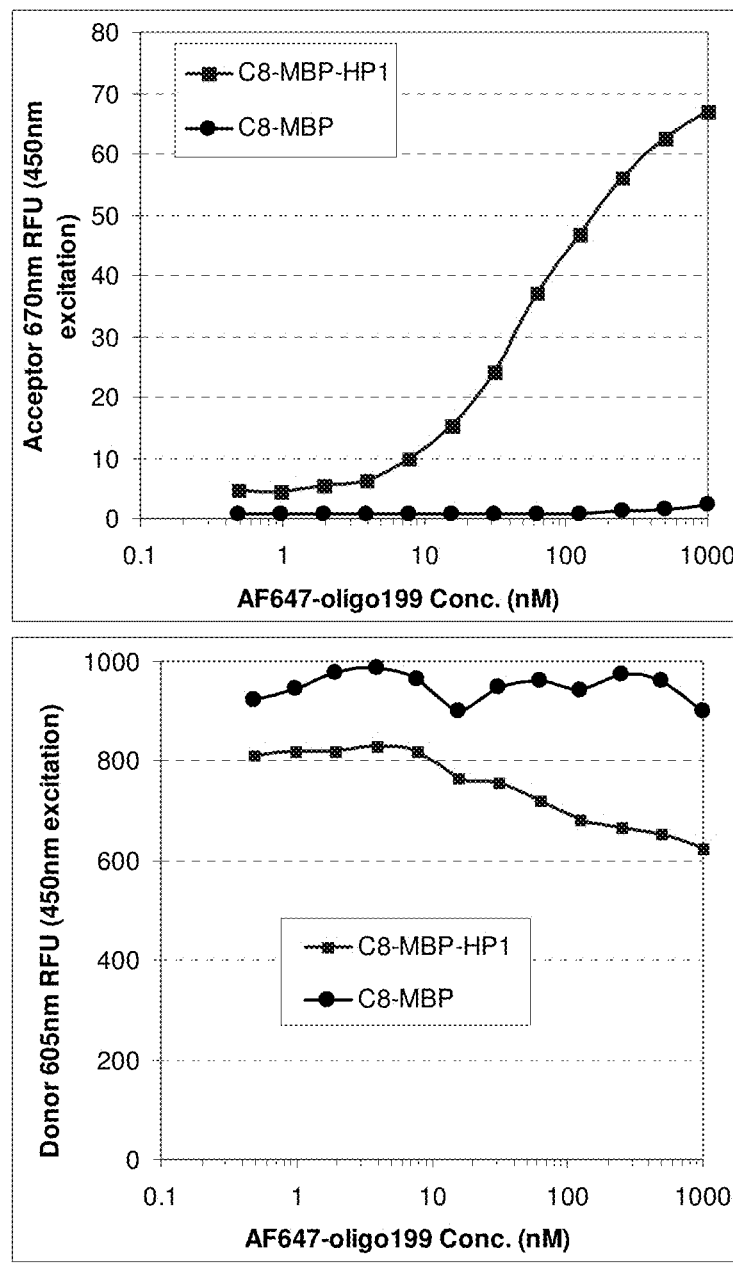
Figure 18C:
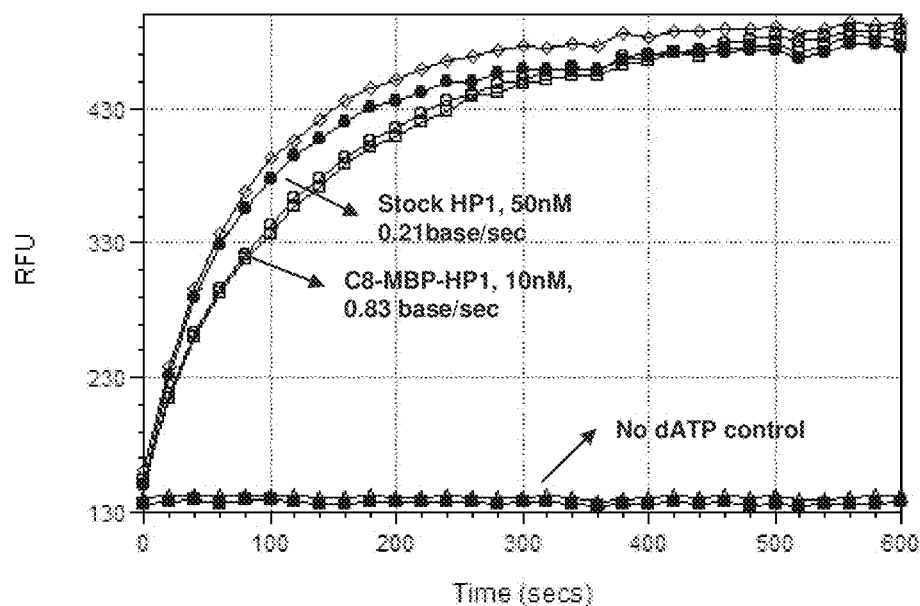

The conjugate was then assayed for purity and non-aggregation using SEC-HPLC, DNA binding, primer extension activity, and stochiometry, i.e., active number of Phi29 per conjugate measured via fluorescence polarization assay, using the procedures described in Example 5. Representative results are depicted in FIG. 18A (purity), FIG. 18B (DNA binding), FIG. 18C (primer extension), and FIG. 18D (stochiometry).

Using the methods and equations described in Example 5, the activity of the conjugate preparation was determined to be 0.83 bases/sec.

Figure 18D:
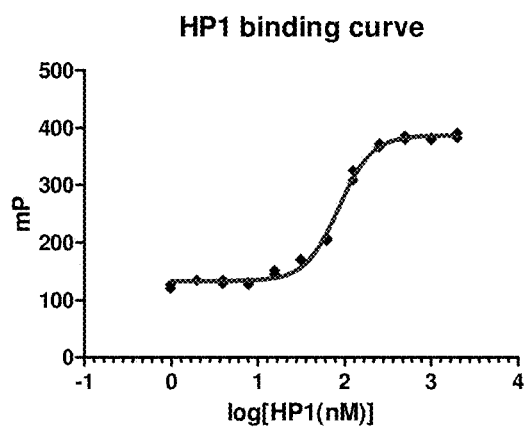

Based on the HP1 binding curve depicted in FIG. 18D, the estimated values of a, b and c were 387.2, 133.6 and 2.272, respectively. The number of active HP1 per conjugate in four separate trials was estimated as 2.0, 2.1, 2.3 and 2.1, respectively.

Example 11

Conjugate Comprising Phi 29 Polymerase and Chloramphenicol Acetyl Transferase (CAT) Linked to Nanoparticle A stock solution of His-tagged HP1-Phi29 polymerase (SEQ ID NO: 14) (150 µL, 70.4 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl and 1 mM DTT using an NAP-5 column.

C8 dots (450 µL, 2.88 µM in 50 mM borate buffer pH 8.0 with 1 M Betaine) was buffer exchanged into 100 mM Tris (pH 7.5) buffer with 300 mM NaCl and 1 mM DTT using an NAP-10 column, aliquoted for immediate usage. The buffer exchanged C8 nanoparticles aliquot (250 µL, 1.2 µM in 100 mM Tris (pH 7.5) buffer with 300 mM NaCl and 1 mM DTT) was mixed with a His-tagged-CAT (chloramphenicol acetyl transferase) protein solution (87 µL, 52 µM in 50 mM Tris buffer (pH 8.0) with 200 mM NaCl) in a 1:15 molar ratio (nanoparticle to His-tagged-CAT) to prepare the CAT-nanoparticles. The resulting solution was rotated on a tube rotator for 2 hours at 4° C. Most of the CAT-nanoparticles (290 µL) made was then mixed with the buffer exchanged His-tagged HP1-Phi29 polymerase (107 µL, 12.3 µM in 100 mM Tris (pH 7.5) buffer with 300 mM NaCl and 1 mM DTT) in a 1:5 molar ratio (nanoparticle to polymerase). The resulting solution was rotated on a tube rotator overnight at 4° C., centrifuged for 5 minutes at 16.8K ref. The conjugate solution was purified on $Ni^{2+}$-NTA Agarose column using 100 mM Tris (pH 7.5) buffer with 300 mM NaCl, 1 mM DTT, centrifuged and transferred into a 10K MWCO dialysis cassette. The conjugate was then dialyzed into 50 mM Tris buffer pH7.5 with 150 mM NaCl, 0.2 mM EDTA, 0.5% v/v Tween-20, 5 mM DTT and 50% v/v glycerol. The resulting CAT-nanoparticle-HP1-Phi29 conjugate was assayed to determine protein concentration (data not shown).

Figure 19A:
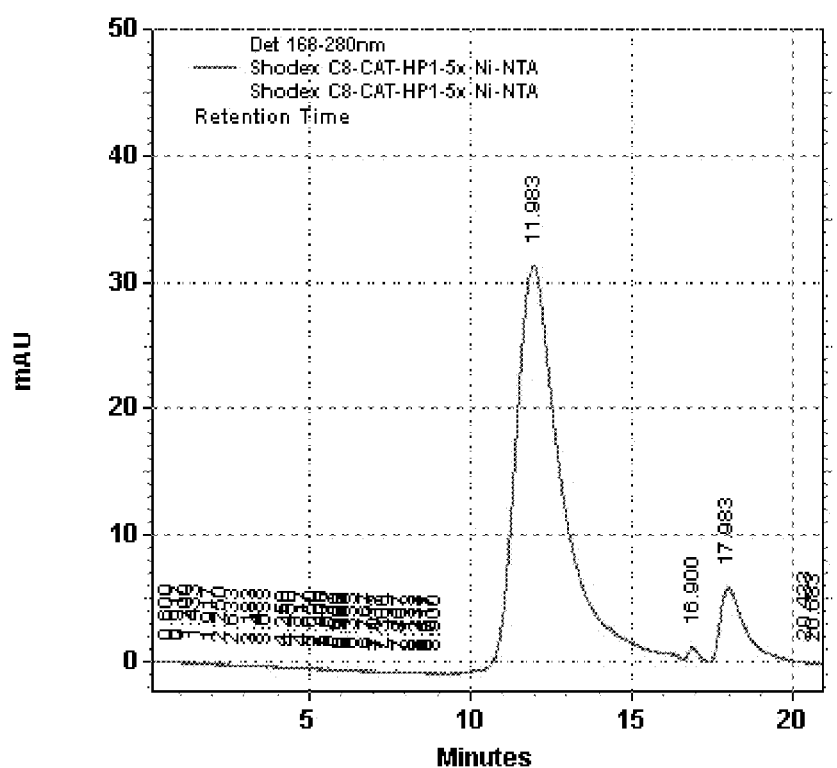
Figure 19B:
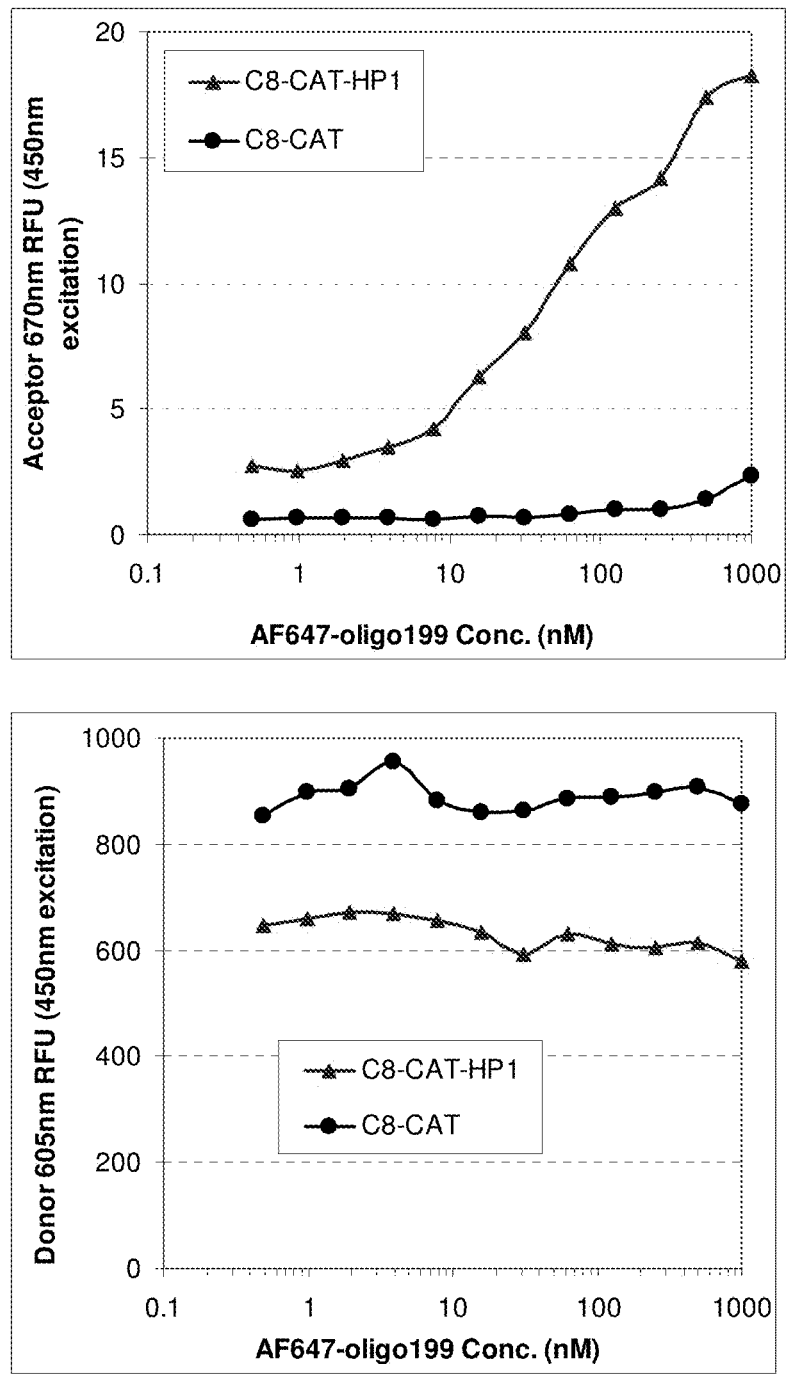
Figure 19C:
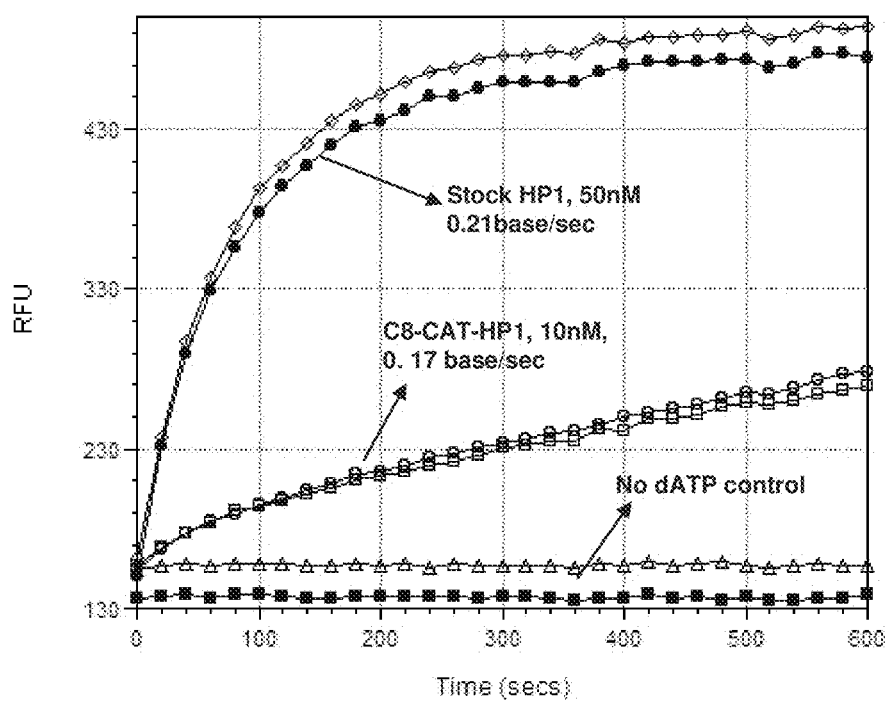

The conjugate was then assayed for purity and non-aggregation using SEC-HPLC, DNA binding, primer extension activity, and stochiometry, i.e., active number of Phi29 per conjugate measured via fluorescence polarization assay, using the procedures described in Example 5. Representative results are depicted in FIG. 19A (purity), FIG. 19B (DNA binding), FIG. 19C (primer extension), and FIG. 19D (stochiometry). Using the methods and equations described in Example 5, the activity of the conjugate preparation was determined to be 0.17 bases/sec.

Figure 19D:
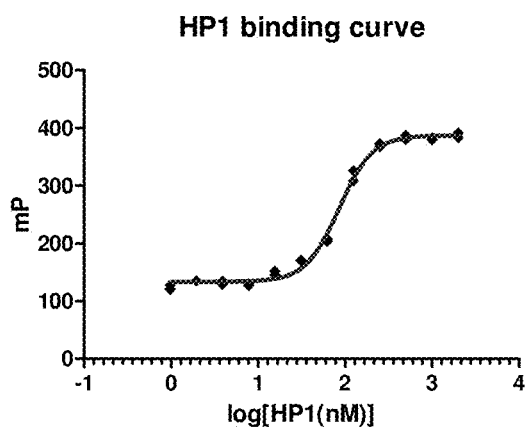

Based on the HP1 binding curve depicted in FIG. 19D, the estimated values of a, b and c were 387.2, 133.6 and 2.272, respectively. The number of active HP1 per conjugate in two separate trials was estimated as 0.5 and 0.6, respectively.

Example 12

Conjugate Comprising his-Tagged Phi29 Polymerase Linked to Nanoparticle

A stock solution of His-tagged HP1-Phi29 polymerase (SEQ ID NO: 14) (300 μL, 57 μM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl and 1 mM DTT using an NAP-5 column.

C8 dots (400 μL, 4.0 μM in 50 mM borate buffer pH 8.0 with 1 M Betaine) was buffer exchanged into 100 mM Tris (pH 7.5) buffer with 300 mM NaCl and 1 mM DTT using an NAP-10 column, aliquoted for immediate usage. The buffer exchanged C8 nanoparticles aliquot (860 μL, 1.7 μM in 100 mM Tris (pH 7.5) buffer with 300 mM NaCl and 1 mM DTT) was mixed with the buffer exchanged His-tagged HP1-Phi29 polymerase (1070 μL, 13.7 μM in 100 mM Tris (pH 7.5) buffer with 300 mM NaCl and 1 mM DTT) in a 1:10 molar ratio (nanoparticle to polymerase). The resulting solution was incubated overnight at 4° C., centrifuged for 5 minutes at 16.8K ref. The conjugate solution was purified on $Ni^{2+}$-NTA Agarose column using 100 mM Tris (pH 7.5) buffer with 300 mM NaCl, 1 mM DTT, centrifuged and transferred into a 10K MWCO dialysis cassette. The conjugate was then dialyzed into 50 mM Tris buffer pH7.5 with 150 mM NaCl, 0.2 mM EDTA, 0.5% v/v Tween-20, 5 mM DTT and 50% v/v glycerol. The resulting nanoparticle-HP1-Phi29 conjugate was assayed to determine protein concentration (data not shown).

Figure 20A:
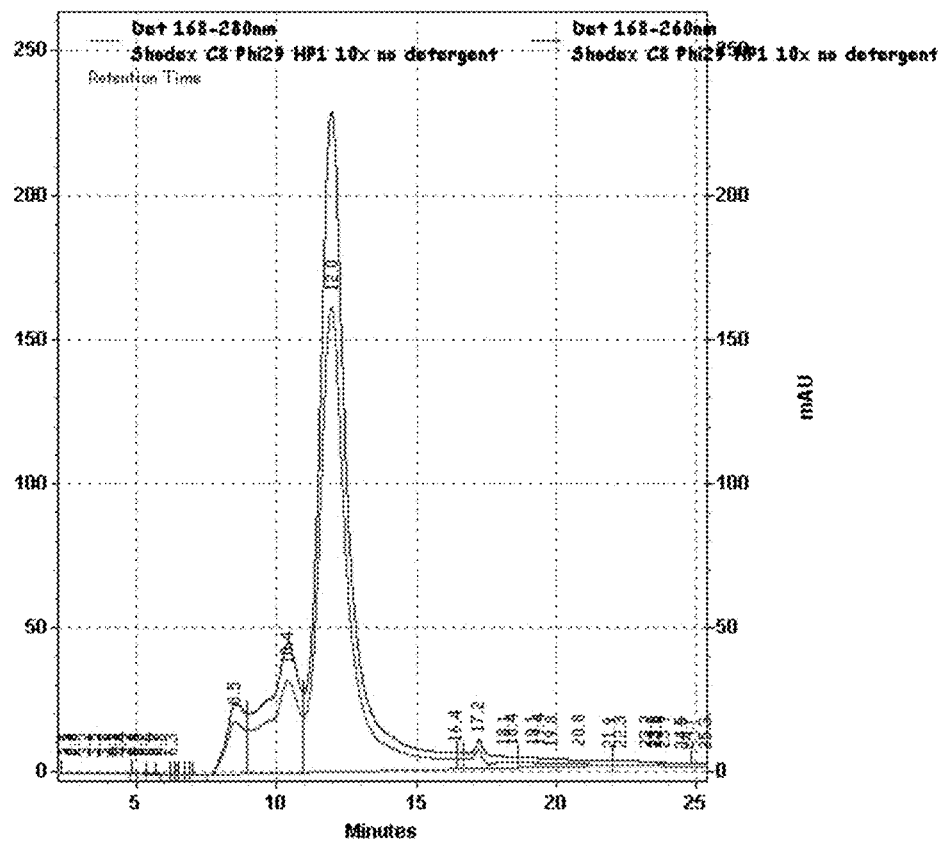
Figure 20B:
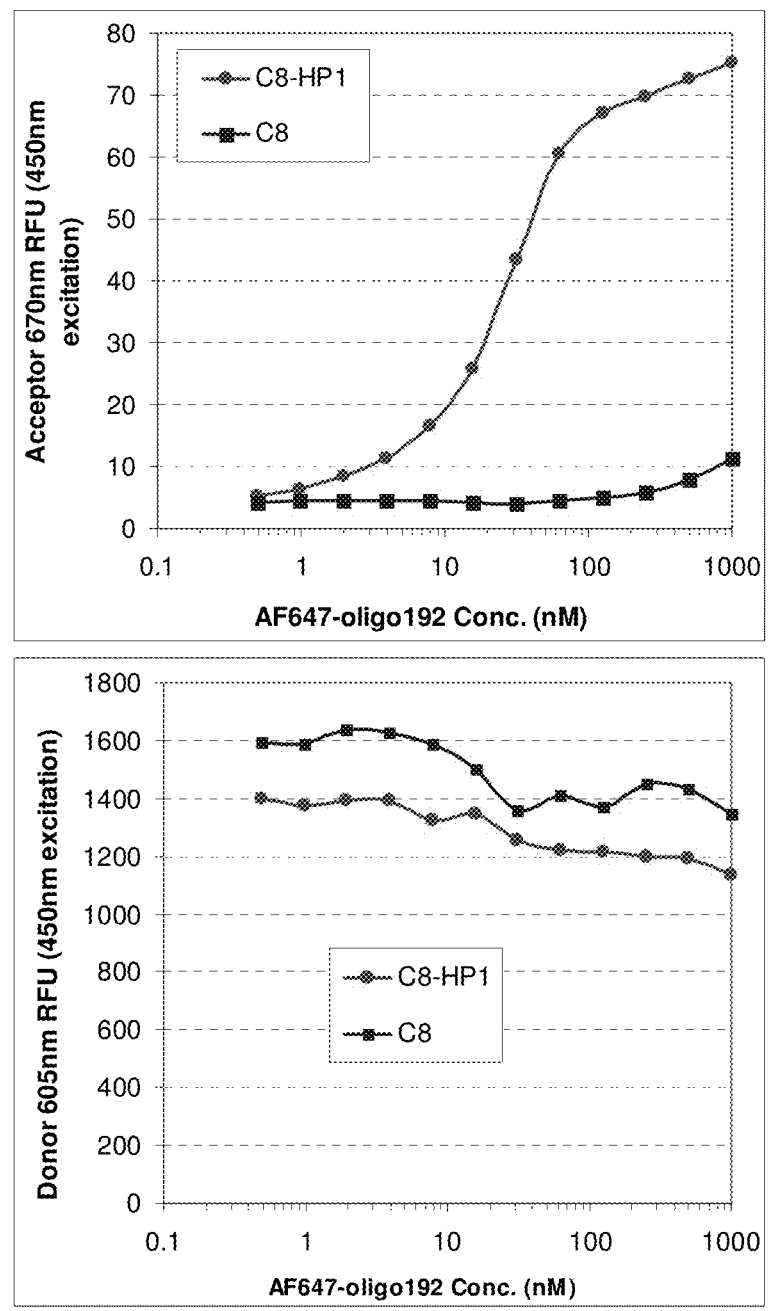
Figure 20C:
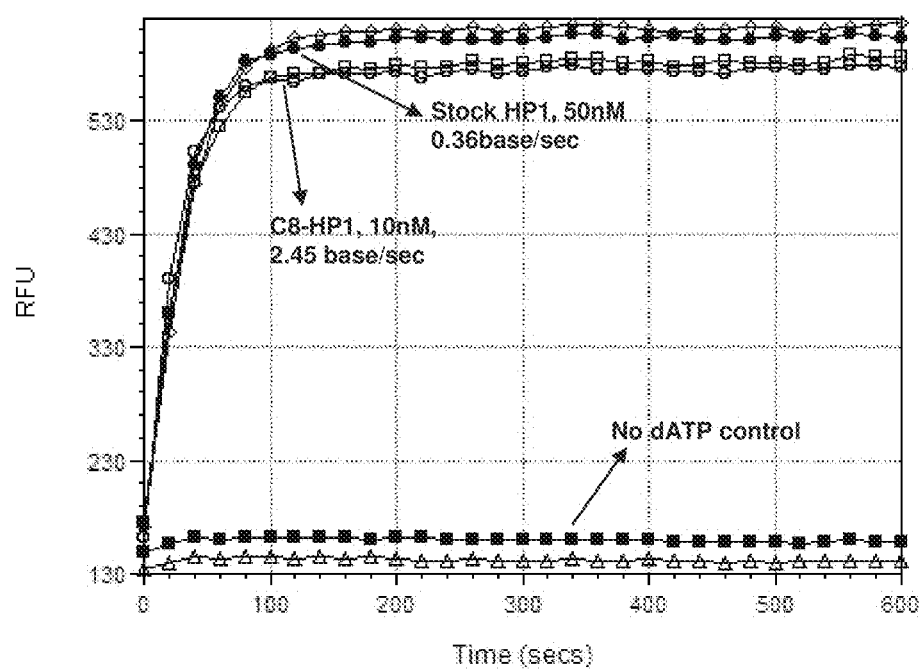
Figure 20D:
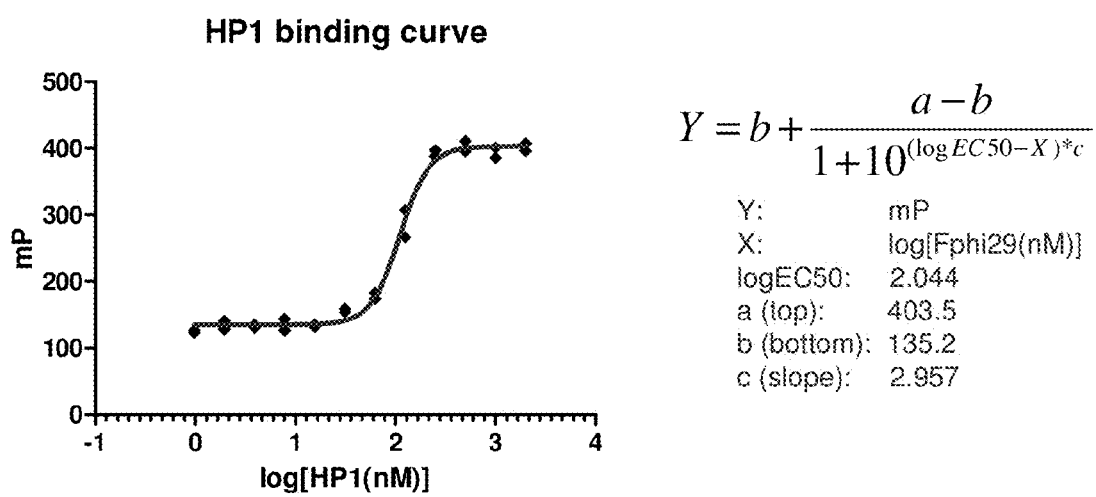

The conjugate was then assayed for purity and non-aggregation using SEC-HPLC, DNA binding, primer extension activity, and stochiometry, i.e., active number of Phi29 per conjugate measured via fluorescence polarization assay, using the procedures described in Example 5. Representative results are depicted in FIG. 20A (purity), FIG. 20B (DNA binding), FIG. 20C (primer extension), and FIG. 20D (stochiometry). Based on the HP1 binding curve depicted in FIG. 20D, the estimated values of a, b and c were 403.5, 135.2 and 2.957, respectively. The number of active HP1 per conjugate in four separate trials was estimated as 5.6, 5.9, 4.1 and 3.8, respectively.

Example 13

Conjugate Comprising a Biotinylated Protein Linked to a Nanoparticle Comprising Avidin To 100 microliters of commercially available Qdot 605-PEG streptavidin conjugate (1 μM; Life Technologies Corp., catalog No: Invitrogen Q10101MP) was added 19 microliters of a 15.5 μM solution of biotinylated Phi29 polymerase. The molar ratio of streptavidin conjugated dots to protein was approx. 3.5. The mixture was left at room temperature for 30 min, then centrifuged at 15000 ref in a benchtop centrifuge for 2 minutes. The small pellet obtained was removed and the supernatant was concentrated to about 25 microliters by ultrafiltration through a Vivaspin 500 (Sartorius-Stedim, Catalog No. VS0142) cartridge having a molecular weight cut-off (MWCO) of 50,000. This solution was then passed over a small Superdex200 size exclusion column to remove any free unconjugated polymerase. The buffer used for elution was phosphate buffered saline (PBS). The colored, quantum dot-containing fraction form this size-exclusion column was collected, and the concentration was measured by absorbance. Approx. 100 microliters of conjugate were obtained, having a concentration of approx. 0.6 μM. This material was then tested for polymerase activity in a primer extension assay as described below.

Primer Extension Assay

Figure 21:
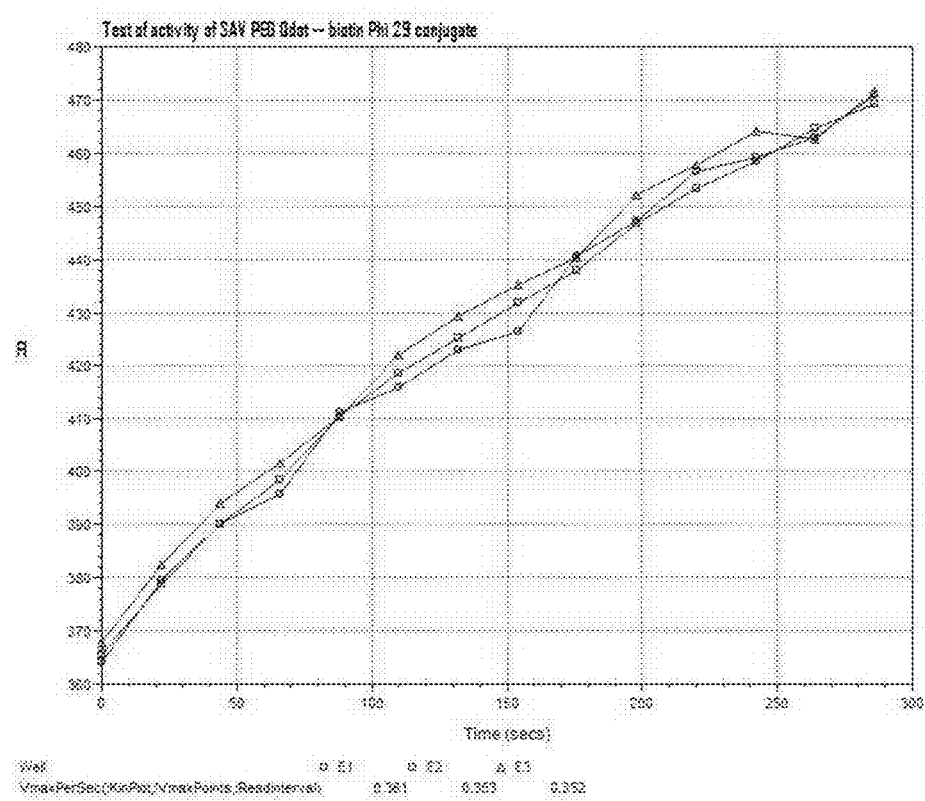
FIG. 21 depicts the results of nucleotide incorporation by conjugates comprising biotinylated Phi-29 polymerase linked with avidin-treated nanoparticles.

The primer extension assay was performed in a buffer containing 50 mM Tris HCl, pH 7.5, 50 mM NaCl and 10 mM $MgCl_2$. A mixture was prepared containing 150 nM of a fluorescein labeled oligo (oligo "221") having the following sequence:

(SEQ ID NO: 43)
3'-TTTTTTTGCAGGTGACAGGTTTTTCCTGTCACCXGC-5' where X=fluorescein dT), and 20 nM of the biotin Phi29-Qdot 605 PEG streptavidin conjugate prepared as described above. One hundred microliter aliquots of this mixture were added to three wells of a 96 well plate and the reaction was initiated by the addition of dATP to 20 μM final concentration. The increase in fluorescence was measured over the course of 5 minutes using an excitation wavelength of 490 nm and an emission wavelength of 525 nm. The increase of fluorescence signal detected is depicted in FIG. 21, which shows different fluorescence traces obtained using triplicate samples E1, E2 and E3. A negative control performed in the absence of any added dATP did not result in any measurable increase in the fluorescence signal (data not shown).

Example 14

Conjugation of Phi-29 Polymerase to Nanoparticles Using the Linking Agent BS3

Phi29 exo- was covalently attached to C2 dots using the linking agent Bis[sulfosuccinimidyl]suberate, BS3, (Thermo Scientific; Catalog no. 21580) as a crosslinking agent. The conjugation protocol is described below.

First, Phi29 exo- storage buffer was exchanged through dialysis into a buffer containing 10 mM HEPES (instead of TRIS in storage buffer), 100 mM NaCl, 0.1 mM EDTA, 0.5% Tween 20, 50% glycerol, with no DTT (to avoid interaction with dots). The dialysis was performed overnight in a fridge. Then, C2 dots (1 eq.) were reacted for 5 min with an excess of BS3 (about 1,000 eq.; fresh solution in water) in presence of 100 mM HEPES+250 mM NaCl buffer, pH 7.4 (50% of total volume). The reaction mixture was quickly purified over a NAP-5 column (GE Healthcare; Catalog no. 17-0853-01) using the HEPES+NaCl buffer as an eluent. The buffer exchanged Phi29 exo- (15 eq.) was added to the purified activated C2 dots for 20-25 min at 4° C. The reaction mixture was concentrated using a Vivaspin 500 100 KDa MWCO ultrafiltration unit (VWR; Catalog no. 14005-008) before being purified over Superdex (VWR; Catalog no. 95017-068) using the HEPES+NaCl buffer as an eluent. The purified conjugate solution was finally concentrated using a Vivaspin 500 100 KDa filter.

Figure 22:
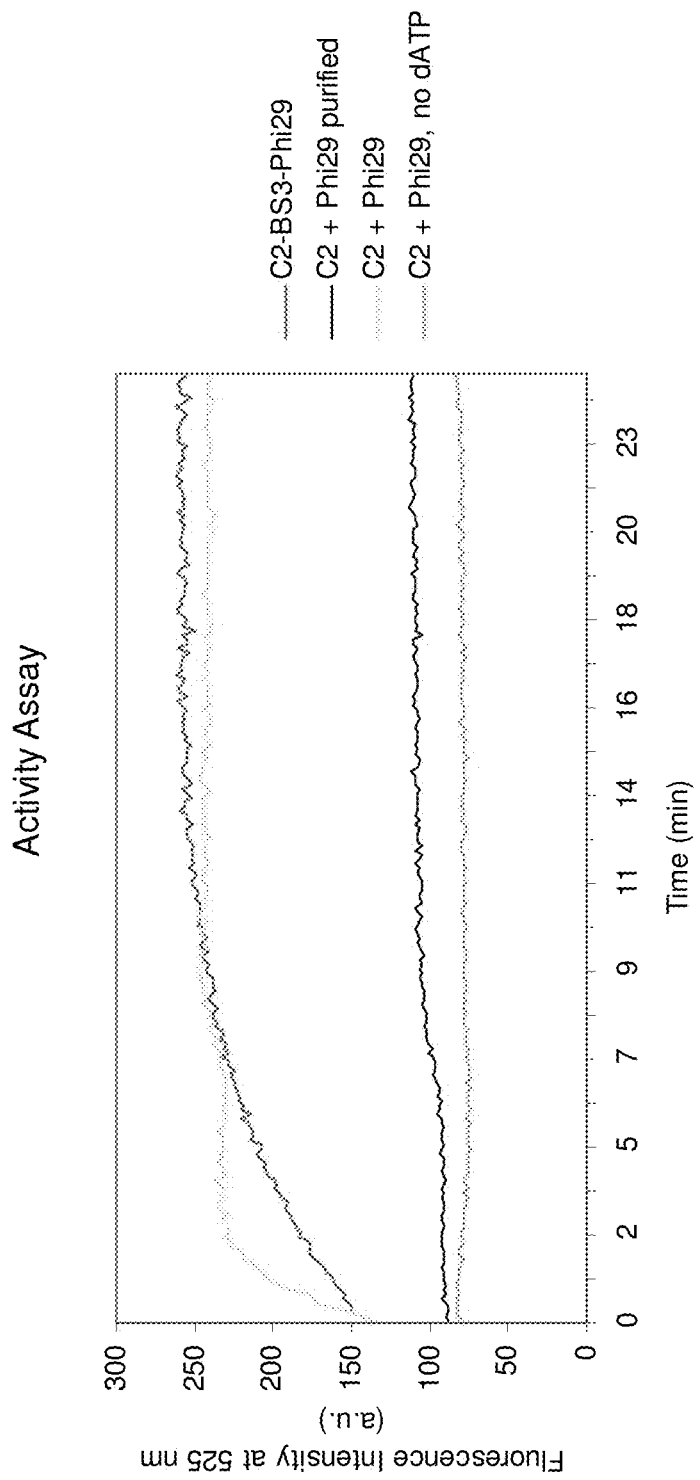
FIG. 22 depicts the results of nucleotide incorporation by conjugates comprising Phi-29 polymerase linked with nanoparticles in the presence of the linking agent Bis[sulfosuccinimidyl]suberate (BS3).

The conjugates were tested for activity to determine whether or not they can incorporate nucleotides. An extension assay was performed using 150 nM of a fluorescein labeled hairpin oligonucleotide, oligo-221, 40 nM of the C2-BS3-Phi29 conjugates, and 20 µM dATP in 50 mM Tris, 50 mM NaCl, and 10 mM $MgCl_2$ buffer. The reaction was monitored using a fluorometer for an increase in fluorescein signal as nucleotides are being incorporated. The mixture was excited at 490 nm and emission was detected at 525 nm. Results are displayed in FIG. 22. As a negative control, C2 dots had been mixed with Phi29 exo- in absence of BS3 and had undergone the same purification as the conjugates. It was used during the activity assay and showed no increase in fluorescein signal, along the baseline signal obtained with the conjugates in absence of dATP. A positive control (free Phi29 exo-) was included as well in the assay. These results indicated that the C2-BS3-Phi29 conjugate retained its nucleotide incorporation activity, which was not observed in absence of BS3 crosslinking agent.

Example 15

Conjugate Comprising his-Tagged Protein and Horse Radish Peroxidase (HRP) or Mucin Linked to Nanoparticle Nanoparticle shapes: A1 are spherical, and A2 and A4 are rod-shaped. The spherical nanoparticles are about 8 nm in diameter, and the rod-shaped ones are about 5×12 nm (width× length). These nanoparticles have ligand coatings which include: L-carnosine; dipeptides (e.g., His-Leu and Gly-His); 4-aminobenzophenone; citric acid; glycine; tris(hydroxymethyl)phosphine; and amino-dPEG24-acid.

The nanoparticles were reacted with HRP, BSA, biotin, and conjugated with one of three different phi29 polymerases: HP1, HP1-Q380A or HP1-S388G. HP1 is a 6×His-tagged phi29 polypeptide which is exonuclease-minus, and includes D12A and D66A mutations. HP1-Q380A is a 6×His-tagged phi29 mutant polypeptide which is exonuclease-minus and includes D12A, D66A, and Q380A mutations. HP1-S388G is a 6×His-tagged phi29 mutant polypeptide which is exonuclease-minus and includes D12A, D66A, and S388G mutations.

Attaching Nanoparticles Attached with Polymerases

Horseradish peroxidase (HRP; Life Technologies Corp., Catalog no. Invitrogen 01-2001) reduction reaction: 3 mg of HRP was reacted with 150 mg of Cleland's REDUCTACRYL Reagent (VWR; Catalog no. 80056-208) in 600 µl of 50 mM sodium borate buffer, pH 8.2 for 45 minutes at room temperature. The reaction was filtered through a Micro Bio-Spin Empty Column (Bio-Rad; Catalog no. 732-6204). 360 µmol of spherical (A1) or rod-shaped (A2 or A4) nanoparticles (1 eq.) were added in 50 µl of 50 mM sodium borate buffer, pH 8.2 containing 5 µL of 10% BSA (Life Technologies; Catalog no. P2489) for 1 hour at room temperature. The reaction mixture was concentrated using a VivaSpin 500 100 KDa MWCO ultrafiltration unit (VWR; Catalog no. 14005-008) and washed (5 times) with 50 mM sodium borate buffer (pH 8.2). 3 mg of LC-sulfo-NHS-Biotin (Molecular Biosciences; Catalog no. 00598) was added in 300 µl of 50 mM sodium borate buffer, pH 8.2 for 30 min at room temperature. The reaction was filtered and washed again as above (5 times), diluted with 100 µl of sodium borate buffer containing 300 mM NaCl (final concentration in a final reaction volume). Phi29 polymerase (HP1 or HP1-Q380A (15 eq.) was added and incubated at 4° C. overnight. Reaction mixtures were purified using a SUPERDEX column (VWR; Catalog no. 95017-068) eluting with a borate buffer containing 300 mM NaCl and concentrated to 1-2 µM of conjugation products using VivaSpin 500 100 KDa MWCO filters and centrifugation at 6,000×G.

In a second set of experiments, mucin was substituted for HRP: 1 mg of mucin (MP Biomedicals; Catalog no. 155742) was dissolved in 60 µl of 50 mM sodium borate buffer, pH 8.2 followed by addition of 30 µl of 4.15 µM A2 nanoparticles. A reaction mixture was kept for 15 min and subjected to a SUPERDEX column (VWR; Catalog no. 95017-068) purification eluting with 50 mM sodium borate buffer, pH 8.2. Fractions containing modified A2 nanoparticles were concentrated using a VivaSpin 500 100 KDa MWCO filter (VWR; Catalog no. 14005-008) followed by addition of NaCl and HBP1 Q380A to a final concentration of 300 mM NaCl and 15 equivalents of enzyme. For biotinylated preparations, 200 equivalents of LC-sulfo-NHS-Biotin (Molecular Biosciences; Catalog no. 00598) was added in 300 µl of 50 mM sodium borate buffer, pH 8.2 for 30 min at room temperature. The reaction was filtered and washed again as above (5 times) and concentrated using a VivaSpin 500 100 KDa MWCO filter (VWR; Cat#14005-008) followed by addition of NaCl and HBP1 Q380A to a final concentration of 300 mM NaCl and 15 equivalents of enzyme. The reaction mixture was kept at +4° C. and used for 2-3 days.

Polymerase conjugated nanoparticles were stored in 10 mM Tris pH 7.5, 220 mM NaCl, 0.1 mM EDTA, 1 mM DTT, 0.5% Tween-20, and 50% Glycerol at −20° C. for more than 30 days without any detectable decrease in polymerase activity or nanoparticle stability.

Assay: Confirming Nanoparticles are Conjugated with Polymerases

Assays were performed to confirm that the Phi29 polymerases were attached to the nanoparticles. The assay included 250 nM of ALEXA FLUOR 647 labeled oligonucleotide:

(SEQ ID NO: 55)
(5'-TTATCTTTGTGGGTGACAGGTTTTTCCTGTCACC-3'-ALEXA

FLUOR 647)

and 40 nM of the nanoparticle-polymerase conjugates in 50 mM Tris, 50 mM NaCl and 10 mM $MgCl_2$. The reaction was excited at 450 nm and emission (e.g., FRET) was detected as a ratio of intensities at 605/670 (dot emission/ ALEXA FLUOR 647 emission). Control nanoparticles were reacted with HRP, BSA, biotin, and ALEXA FLUOR 647, but no Phi29 polymerase.

Figure 23:
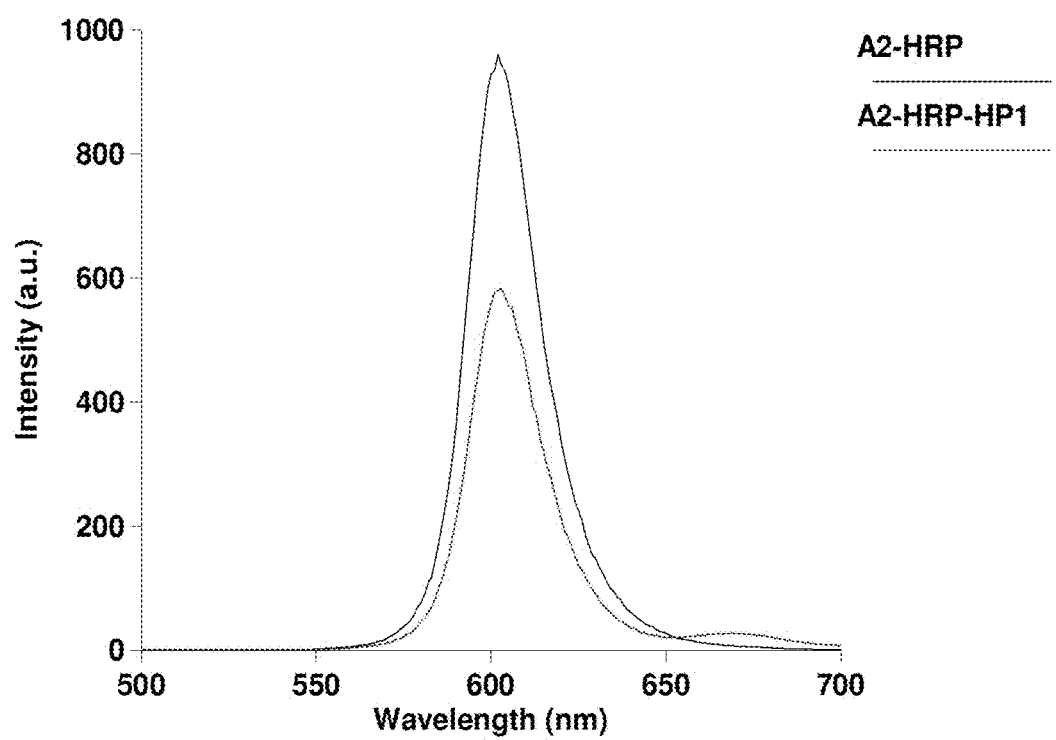
FIG. 23 depicts the binding of a fluorescently labeled oligonucleotide to conjugates comprising Phi-29 polymerase linked to nanoparticles treated with horseradish peroxidase (HRP).

The results in FIG. 23 show that the control nanoparticles exhibit a higher intensity peak compared to the nanoparticles conjugated with Phi29 polymerase and dye-labeled oligonucleotides (lower intensity peak) at the same concentration, and the signal intensity peaks at 670 nm. This demonstrates that the nanoparticles are bound with the Phi29 polymerase and with the ALEXA FLUOR 647-labeled oligonucleotide.

Figure 24:
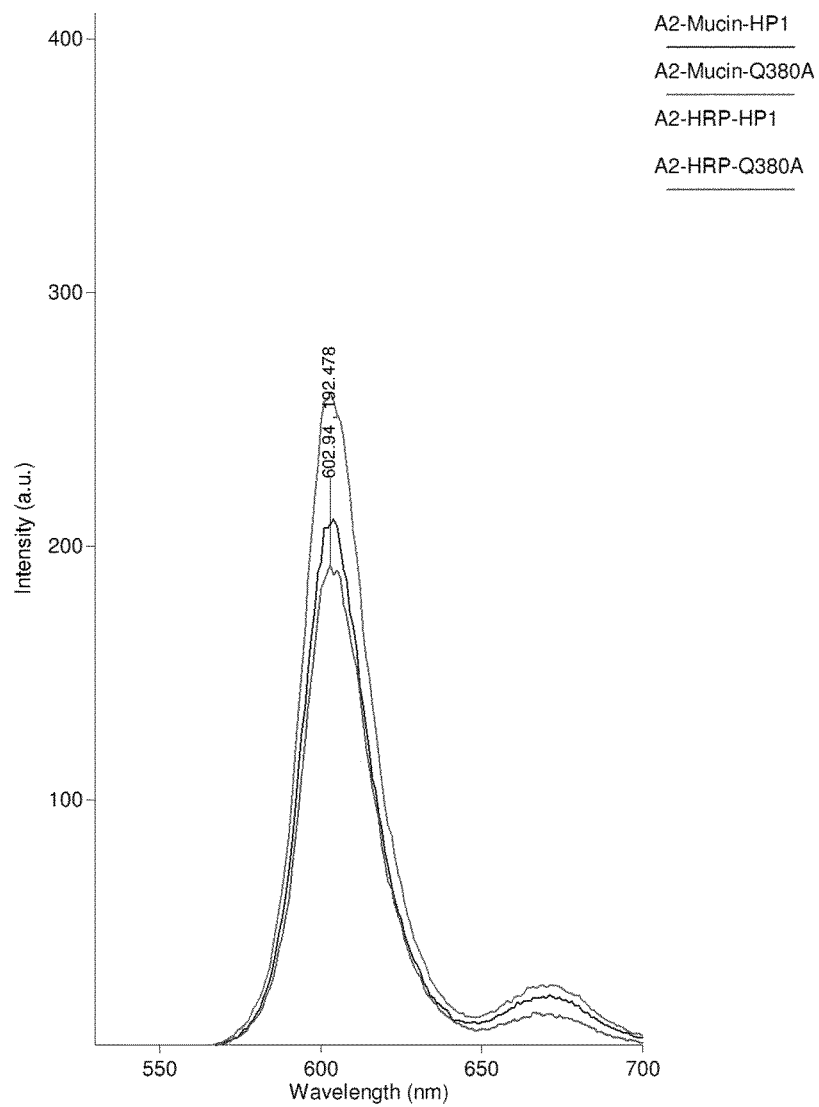
FIG. 24 depicts the binding of a fluorescently labeled oligonucleotide to conjugates comprising Phi-29 polymerase linked to nanoparticles treated with mucin.

The results in FIG. 24 show that the A2-mucin coated dots conjugated to Phi29 showed similar binding as compared with a corresponding A2-HRP-HBP1 Q380 conjugate.

Assay: Nucleotide Incorporation

Assays were performed to determine if the polymerases, which are attached to the nanoparticles, could incorporate nucleotides. The assay included 150 nM of a hairpin oligonucleotide, fluorescein-labeled oligo-221:

```
                                            (SEQ ID NO: 43)
(5'-TTTTTTTGCAGGTGACAGGTTTTTCCTGTCACC(fluorescein-
T)GC-3')
```

Figure 25:
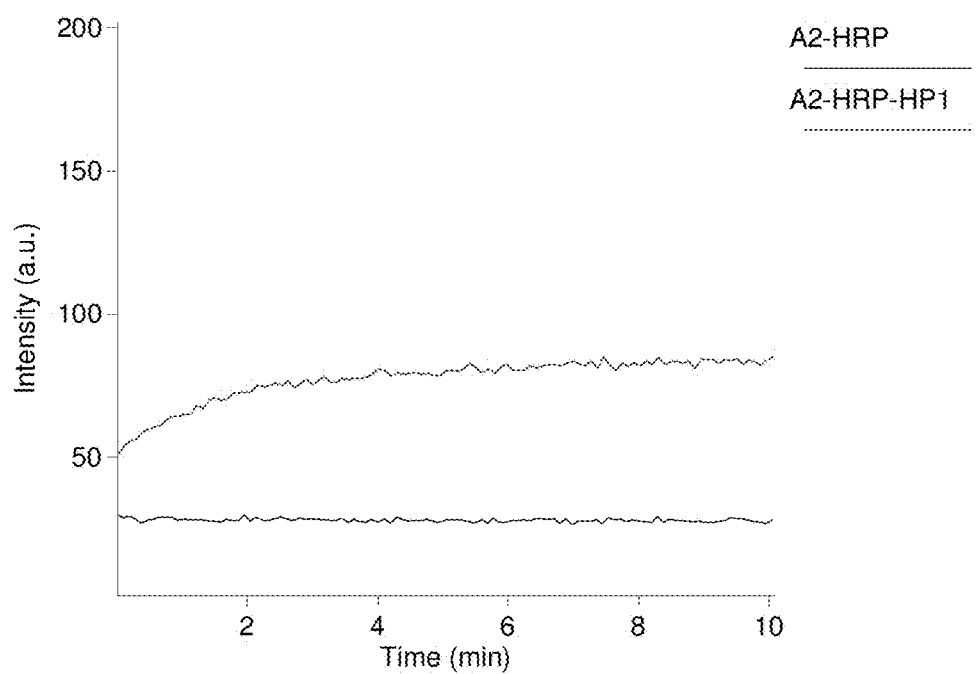
FIG. 25 depicts nucleotide incorporation by a conjugates comprising Phi-29 polymerase linked to nanoparticles treated with horseradish peroxidase (HRP).

The assay also included 40 nM of the polymerase-nanoparticle conjugates, 20 µM dATP in 50 mM Tris, 50 mM NaCl, and 10 mM MgCl$_2$ buffer. The reaction was excited at 490 nm and emission was detected at 525 nm. The results in FIG. 25 show the control nanoparticles exhibit baseline intensity fluorescence levels compared to nanoparticles bound with phi29 polymerase and fluorescein-labeled oligonucleotides (higher intensity levels). These results demonstrate that phi29 enzyme conjugated with a nanoparticle retains its nucleotide incorporation activity.

Assay: Nucleotide Incorporation and DNA Extension

Figure 26:
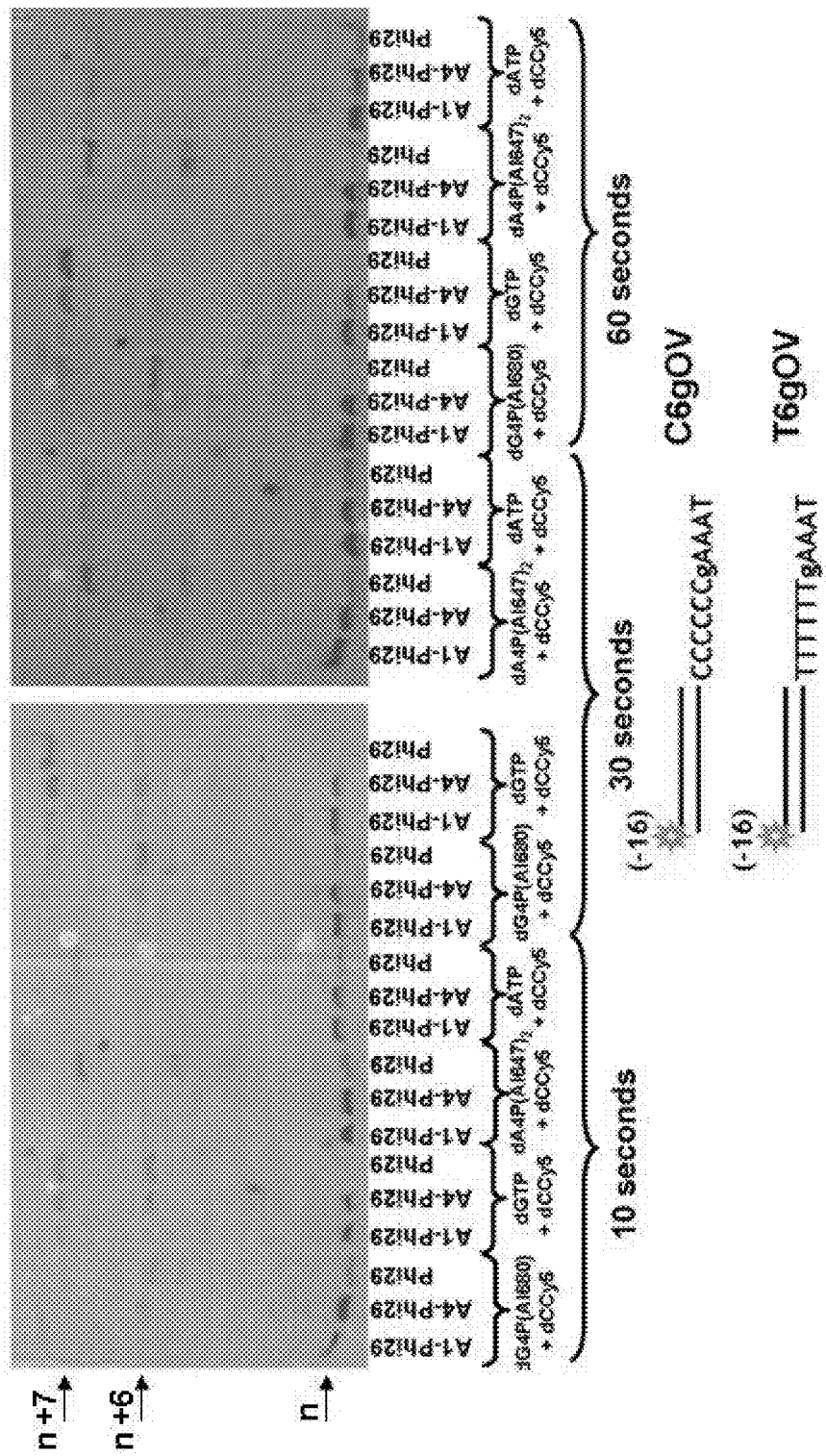
FIG. 26 depicts incorporation of fluorescent dye labeled deoxynucleoside tetraphosphate molecules by conjugates comprising Phi-29 polymerase linked to nanoparticles.

Assays were performed to determine if the polymerases, which are attached to the nanoparticles, could polymerize nucleotides. The assay included 50 mM Tris (pH 7.0), 2 mM MnCl$_2$, 62.5-70 mM NaCl (from the various polymerase-nanoparticle conjugate stocks), 0.5% BSA, 1 µM each dNTP, 50 nM duplex (primer Top: 5'-GGTACTAAGCGGCCG-CATG-3', (SEQ ID NO: 56) with either one of the following templates:

```
C6gOV:
                                            (SEQ ID NO: 57)
5'-TAAAGCCCCCCCATGCGGCCGCTTAGTACC-3',

T6gOV:
                                            (SEQ ID NO: 58)
5'-TAAAGTTTTTTCATGCGGCCGCTTAGTACC-3').
``` and 100 nM of HP1 phi29 polymerase (no nanoparticles), 100 nM A1/HRP-HP1 (A1 spherical nanoparticles conjugated with phi29 polymerase), or 100 nM A4/HRP-HP1 (A4 rod-shaped nanoparticles conjugated with phi29 polymerase). The reaction was initiated with the addition of dNTPs (1 µM) including dA4P labeled at the terminal phosphate group with one ALEXA FLUOR 647, dG4P labeled at the terminal phosphate group with ALEXA FLUOR 680, and dCTP labeled at the nucleo-base with Cy5 dye (GE Healthcare Biosciences; catalog no. PA55021). The reaction was quenched with EDTA and analyzed by electrophoresis in a 20% 7M urea denaturing gel followed by fluorescence imaging. The data in FIG. 26 (left and right gel) show extension products from Phi29 polymerase in all three forms (unbound; bound to spherical nanoparticles (A1); and bound to rod nanoparticles (A4)). The data in FIG. 26 shows extension products produced by Phi29 polymerase, bound to nanoparticles, and incorporating fluorescent dye labeled deoxynucleoside tetraphosphate molecules (dA4P and dG4P).

Assay: Nucleotide Incorporation and DNA Extension

Figure 27:
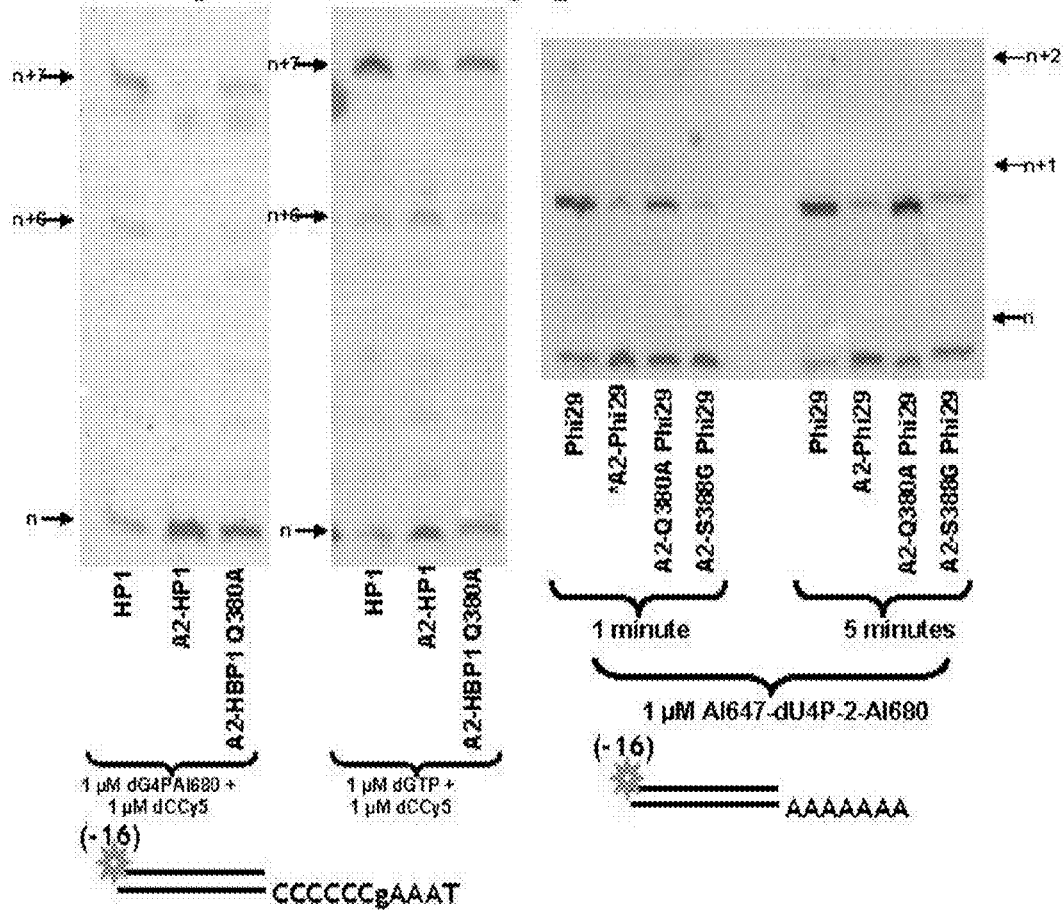
FIG. 27 depicts incorporation of fluorescent dye labeled deoxynucleoside tetraphosphate molecules by conjugates comprising various mutants of Phi-29 polymerase linked to nanoparticles.

Assays were performed to determine if the polymerases, which are attached to the nanoparticles, could polymerize nucleotides. The assay included 50 mM Tris (pH 7.0), 2 mM MnCl$_2$, 42.5-167.5 mM NaCl (from various polymerase-nanoparticle conjugate stocks), 0.5% BSA, 1 µM each dNTP, 100 nM duplex (primer Top: 5'-GGTACTAAGCGGCCG-CATG-3' (SEQ ID NO: 59) with template C6gOV: 5'-TAAAGCCCCCCCATGCGGCCGCTTAGTACC-3' or with template A6A: 5'-AAAAAAACATGCGGCCGCT-TAGTACC-3') (SEQ ID NO: 60), and 200 nM of HP1 phi29 polymerase (no nanoparticles) or 200 nM of A2/HRP-HP1 (rod-shaped nanoparticles conjugated with phi29 polymerase). The reaction was initiated with the addition of 1 µM of dNTPs, including dCTP labeled at the nucleo-base with Cy5 dye (GE Healthcare Biosciences; catalog No. PA55021) in combination with dG4P labeled at the terminal phosphate group with ALEXA FLUOR 680 or with dGTP. For the A6A template, the reaction was conducted in the presence of dU4P labeled at the terminal phosphate group with ALEXA FLUOR 680 and labeled at the nucleo-base with ALEXA FLUOR 647. The reactions were quenched with EDTA and analyzed by gel electrophoresis in a 20% 7M urea denaturing gel followed by fluorescence imaging. The results in FIG. 27 show extension products from Phi29 polymerase in four forms: (1) unbound HP1 polymerase, (2) HP1 polymerase bound to A2 rod-shaped nanoparticles (A2-HP1), (3) HP1 polymerase mutant Q380A bound to A2 rod-shaped nanoparticles A2-HP1-Q380A), and (4) HP1 polymerase mutant S388G bound to A2 rod-shaped nanoparticles (A2-S388G-Phi29). The data in FIG. 27 shows extension products produced by Phi29 polymerase bound to nanoparticles and incorporating deoxynucleoside tetraphosphate molecules (dG4P) (FIG. 27, left gel) and fluorescent-dye labeled deoxynucleoside tetraphosphate molecules (dG4P-Alexa 680) (FIG. 27, right gel).

Detecting FRET Signals in a Single Molecule Assay

Chambered glass cover slips were prepared to facilitate injection and multiple experiments data collection from several chambers using a single slide. The PEG-neutravidin glass coverslips were functionalized as described by Taekjip Ha (2002 Nature 419:638-641) but using neutravidin instead of streptavidin. Duplexes of primer/template strands were prepared by reacting 1 µM of the template and 1 µM of the primer strands in 1× Duplexing buffer (50 mM Tris (pH 7.2), 10 mM NaCl).

```
Reaction 1:
Primer:
                                            (SEQ ID NO: 61)
5'-TGATAGAACCTCCGTGT-3'
Template:
5'-GGAACACGGAGGTTCTATCATCGTCATCGTCATCGTCATCG-3';

Reactions 2 and 3:
Primer:
                                            (SEQ ID NO: 62)
5'-GGTACTAAGCGGCCGCATG-3'
Template:
                                            (SEQ ID NO: 63)
5'-TTTTACCCATGCGGCCGCTTAGTACC-3';

Reaction 4:
Primer:
                                            (SEQ ID NO: 64)
5'-GGTACTAAGCGGCCGC-dd-3'
Template:
                                            (SEQ ID NO: 65)
5'-TTTTACCCATGCGGCCGCTTAGTACC-3'.
```

10 nM of the A2 nanoparticles coated with biotinylated-HRP/biotinylated-BSA (which were conjugated with phi29 polymerase mutant Q380A) were reacted with 300 nM of the DNA primer/template duplex on ice for 30 minutes in 1×
pre-complexing buffer (50 mM Tris (pH 7.2), 100 mM NaCl)
in a total volume of 100 mL. Without being bound to any
particular theory, it is thought that this reaction forms the
binary complex of polymerase/nanocrystal bound to template/primer.

The binary complex was diluted to a nanoparticle concentration of 100 μM and template/primer duplex concentration of 3000 μM in a ratio of 1:30. 100 μL of the diluted binary complex was injected into a chamber and was allowed to immobilize on the PEG-neutravidin surface for 5 minutes. An extension mix was injected and the reaction was allowed to occur for 2 minutes, followed by a 200 μL buffer wash of EDTA and an oxygen scavenging system. The extension mix consisted of 50 mM Tris (pH 7.2), 2 mM MnCl$_2$, 100 mM NaCl, 0.5% BSA and natural dNTPs (dGTP) plus Cy5 base labeled dUTO or dye-labeled dNTPs (dG4P labeled at the terminal phosphate group with ALEXA FLUOR 680 plus Cy5 base-labeled dUTP) at 1 μM each. The oxygen scavenging system consisted of 50 nM protocatechuate-3,4-dioxygenase, 2.5 mM protocatechuic acid and 1 mM TROLOX (6-Hydroxy-2,5,7,8-tetramethylchroman-2-carboxylic Acid; Hoffmann-LaRoche).

Four separate reactions were performed: Reaction #1 included Cy5 base-labeled dUTP (GE Healthcare Biosciences; Catalog No. PA55022). Reaction 2 included dGTPs and Cy5 base-labeled dUTP (GE Healthcare Biosciences; catalog no. PA55022). Reaction #3 included dG4P labeled at the terminal phosphate group with ALEXA FLUOR 680 and Cy5 base-labeled dUTP (GE Healthcare Biosciences; catalog no. PA55022). Reaction #4 included dG4P labeled at the terminal phosphate group with ALEXA FLUOR 680 and Cy5 base-labeled dUTP (GE Healthcare Biosciences; catalog no. PA55022), and the primer having a dideoxynucleotide (ddG) at the 3' end (negative control).

The data were collected on the single molecule detection system, which included an ANDOR back-illuminated EMCCD camera (iXonEM), and an inverted Olympus microscope (IX71), with a 100×TIRF objective. The samples were excited using a 405 nm laser (Coherent; Catalog no. 1069413) at 460 μW, and the data were collected at 100 ms integration time for 2000 frames and 3 to 5 consecutive streams were collected by moving to new fields of views (FOVs). The signals were separated using dichroics (535 nm, 667 nm) before forming an image on the camera.

Figure 28:
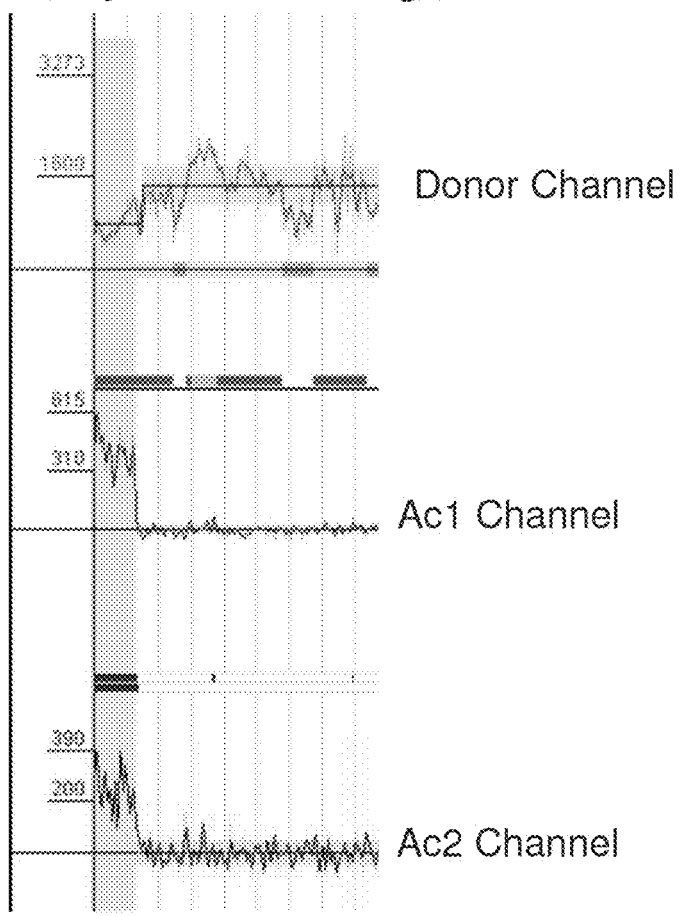
FIG. 28 depicts the results of single-molecule assays for nucleotide incorporation by conjugates comprising biotinylated Phi-29 DNA polymerase linked to HRP-treated nanoparticles in the presence of avidin-coated surfaces.

FRETAN software (Volkov et al., U.S. Ser. No. 11/671, 956) was used to obtain donor and acceptor FRET traces. Custom-designed MATLAB scripts were used to extract the data and obtain percent FRET or percent activity data. Only signals where the acceptor signal preceded the donor signals and acceptor signals had a signal to noise ratio (S/N) greater than 2 were counted for the percent activity numbers. FIG. 28 shows data from reaction #3.

Example 16

Detection of FRET in Single Molecule Assays Using a Polymerase-Nanoparticle Conjugate Chambered glass cover slips were prepared to facilitate injection and multiple experiments data collection from several chambers using a single slide. The PEG-biotin glass coverslips were purchased from Microsurfaces Inc. The PEG-biotin surfaces were coated with NeutrAvidin Protein (Pierce Biotechnology, Catalog no. 31000). Duplexes of primer/template strands were prepared by reacting 1 μM of the template and 1 μM of the primer strands in 1× Duplexing buffer (50 mM Tris (pH 7.2), 10 mM NaCl).

```
Reaction 1:
Primer:
                                        (SEQ ID NO: 66)
    5'-GGTACTAAGCGGCCGCATG-3'

Template:
                                        (SEQ ID NO: 67)
    5'-TGGACCCATGCGGCCGCTTAGTACC-3';

Reaction 2:
Primer:
                                        (SEQ ID NO: 68)
    5'-GGTACTAAGCGGCCGCATG-dd-3'

Template:
                                        (SEQ ID NO: 69)
    5'-TGGACCCATGCGGCCGCTTAGTACC-3';

Reaction 3:
Primer:
                                        (SEQ ID NO: 70)
    5'-GGTACTAAGCGGCCGCATG-3'

Template:
                                        (SEQ ID NO: 71)
    5'-TGGACCCCCCCATGCGGCCGCTTAGTACC-3'

Reaction 4:
Primer:
                                        (SEQ ID NO: 72)
    5'-GGTACTAAGCGGCCGCATG-dd-3'

Template:
                                        (SEQ ID NO: 73)
    5'-TGGACCCCCCCATGCGGCCGCTTAGTACC-3'

Reaction 5:
NO DNA (control)
```

10 nM of the A2 nanocrystals coated with biotinylated-HRP/biotinylated-BSA, or 10 nM of the A4 nanocrystals coated with biotinylated-mucin, were then conjugated with Phi29 polymerase mutant Q380A according to the procedure of Example 15.

The conjugates were then incubated with 300 nM of the DNA primer/template duplex (except for the no DNA control reaction) on ice for 10 minutes in 1× pre-complexing buffer (50 mM Tris (pH 7.2), 0.2% BSA) in a total volume of 50 μL.

The mixture was then diluted to a nanoparticle concentration of 10 pM. 100 μL of the diluted mixture was injected into a chamber and was allowed to immobilize on the PEG-neutravidin surface for 5 minutes. The surface was then washed with 100 μl of 1× wash buffer (50 mM Tris (pH 7.2), 0.2% BSA). An extension mix consisting of 50 mM Tris (7.2), 0.2% BSA, 3.45 mM Asp4, 2 mM MnCl$_2$, Oxygen Scavenging System [1 mM 4-OH-TEMPO; 80 μg/ml Glucose oxidase; 2K U/ml catalase (Sigma; catalog no. 02071); 0.4% glucose] and 1 μM dGTP plus 1 μM of Cy5 base-labeled dUTP (or: 1 μM dG4P labeled at the terminal phosphate group with ALEXA FLUOR 680 plus 1 μM of Cy5 base-labeled dUTP) was injected and data were collected for 2 min in real time. After 2 min the extension reaction was stopped with 20 mM EDTA containing buffer, and then buffer containing Oxygen Scavenging System was re-injected for post-wash imaging.

The data were collected on the single molecule detection system, which included a Photometrics back-illuminated EMCCD camera (Cascade11), and an inverted Nikon microscope (Nikon; Catalog no. TE2000-U), with a 60×TIRF objective. The samples were excited using a 457 nm Ar-ion tunable laser (Melles Griot; Catalog no. 35-LAP-321-120) at 830-860 μW, and the data were collected at 10 or 100 ms integration time for a total time of 2 min. The signals were separated using a QuadView Micro Imager (Roper Scientific; Catalog no. MSMI-QV-C) with dichroics (635 nm, 685 nm) and band pass filters (605/40 nm, 670/30 nm, and 715/60 nm).

FRETAN software (Volkov et al., U.S. Ser. No. 11/671,956) was used to obtain donor and acceptor FRET traces. Custom-designed MATLAB and PERL scripts were used to extract the data and obtain percent FRET or percent activity data.

Figure 29:
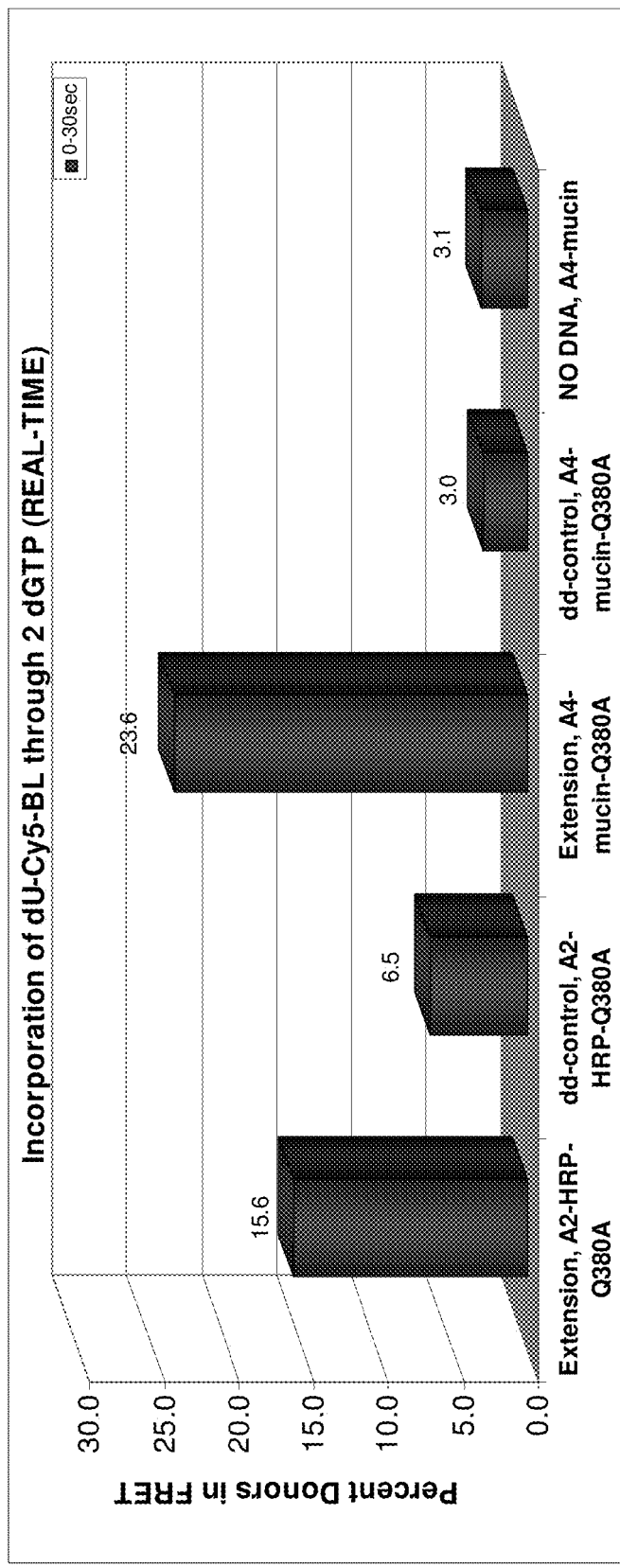
FIG. 29 depicts the results of single-molecule assays for nucleotide incorporation by conjugates comprising biotinylated Phi-29 DNA polymerase linked to nanoparticles treated with HRP or mucin, in the presence of avidin-coated surfaces.

The results in FIG. 29 show that the A4-mucin coated dots conjugated to HBP1-Q380A showed increased activity over A2-HRP coated dots conjugated to HBP1-Q380A in live reactions where a dU-Cy5-BL (GE Healthcare Biosciences; catalog #PA55021) was incorporated following two natural dNTPs and a more prominent difference between the reaction and control. Base label incorporation was detected based on detection of fluorescence traces having a signal to noise (S/N) ratio exceeding a selected threshold value of ≥2 as well as signal lasting for duration exceeding a selected threshold value of ≥2 seconds.

Figure 30:
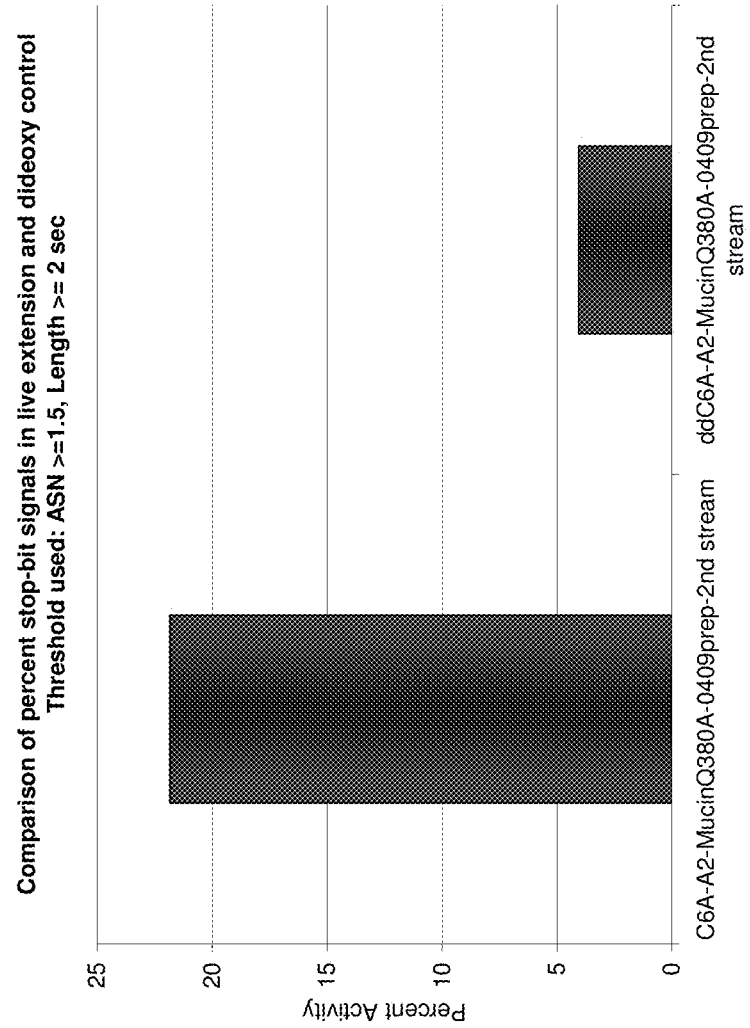
FIG. 30 depicts the results of single-molecule assays for nucleotide incorporation by conjugates comprising biotinylated Phi-29 DNA polymerase linked to nanoparticles treated with HRP or mucin, in the presence of avidin-coated surfaces.
Figure 31:
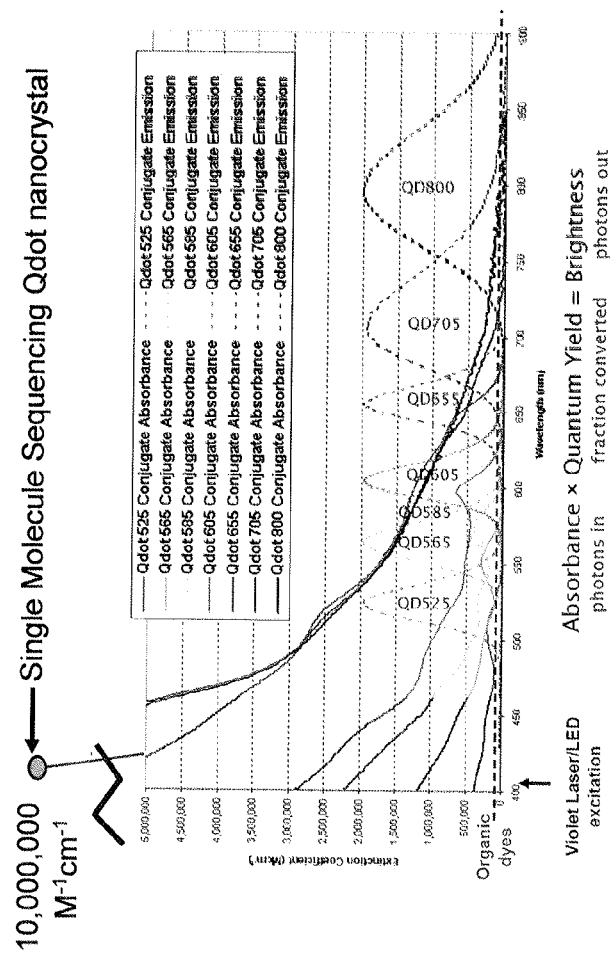
FIG. 31 depicts the absorbance and emission spectra for a variety of conjugates as indicated.

The results in FIG. 30 show that the A2-non-biotinylated-mucin coated dots conjugated to HBP1-Q380A showed incorporation of dU-Cy5-BL following the incorporation of six dG4P labeled at the terminal phosphate group with ALEXA FLUOR 680. Base label incorporation was detected based on detection of fluorescence traces having a signal to noise (S/N) ratio exceeding a selected threshold value of ≥1.5 as well as signal lasting for duration exceeding a selected threshold value of ≥2 seconds.

Example 17

Covalent Conjugation of a Polymerase Comprising an N-Terminal Cysteine to a Nanoparticle Having a Thioester Surface Ligand An expression construct encoding a recombinant Phi-29 DNA polymerase comprising a TEV cleavage site at its N-terminus was transformed and expressed in bacteria. The recombinant protein comprising the amino acid sequence of SEQ ID NO: 38 was purified and treated with TEV protease to uncover the N-terminal cysteine residue using methods known in the art.

To prepare nanoparticles comprising thioester surface ligands, amino-containing dots were dissolved in Borate buffer pH 7.4 50 mM to concentration ranging from 3 to 8 uM. A solution of a thioester-comprising crosslinker in DMF (0.2M) was added to the solution of amino-dots to at a ratio of approximately 1:2000 (nanoparticles:crosslinker). The reaction was stirred overnight at room temperature. The reaction was then diluted with ligation buffer (45 mM MES pH 6.11, 400 mM NaCl) and passed through a 50 kD spin-filter. The filter was washed several times with ligation buffer, and the resulting solution was concentrated to the original concentration of 3-8 uM. The thioester-comprising nanoparticles were purified on a Biogel P30 column with ligation buffer. The nanoparticles were concentrated to concentration of 3-8 uM.

The thioester-comprising nanoparticles were then conjugated a Phi-29 polymerase modified to include an N-terminal cysteine. A solution of N-Cys-Protein ligation buffer (~180-200 uM) was combined at 4° C. with solution of MPAA in ligation buffer; the final ratio of the reactions was approximately 1:300:60 (nanoparticle:MPAA:polymerase). The reaction mixture was stirred at 4° C. for 48 h. A solution of thioester biotin in water was added to adjust the biotin:protein ratio to 1:30. The reaction mixture was kept for 24 h at 4° C. A solution of hydroxylamine (1M) in 50 mM Tris, pH 7.5 was added to a final concentration of 100 uM. The reaction mixture was kept at 4° C. for 1 hr. The reaction mixture was then purified on a P30 column and washed with ligation buffer supplemented with 1 mM DTT to remove unreacted biotin reagent. The nanoparticle fraction was collected and was passed through avidin-agarose column in at 4° C. The visible nanoparticle fraction was collected, concentrated to ~5 uM and separated on a Superdex S-200 column using Ligation buffer supplemented with 1 mM DTT at 4° C. Fractions that visibly included nanoparticles were collected and concentrated to an appropriate concentration (~1 uM). This conjugate preparation was observed to induce a detectable FRET signal upon contact with an acceptor-labeled oligonucleotide, indicating that the conjugate had DNA-binding activity (data not shown).

Example 18

Covalent Conjugation of a Polymerase Comprising an N-Terminal Cysteine to a Nanoparticle Having an Aldehyde Surface Ligand Conversion of Qdots to Contain Aldehyde Functional Group:

Lot SLN2010-0018 Qdots were prepared in Eugene and contain approximately 70% PEG16-OMe and 30% PEG20-NH$_2$. 300 µl of 3.3 µM of lot SLN2010-0018 Qdots were buffer exchanged into 1M NaHCO$_3$ by four rounds of ultra-filtration using a 30 kD MWCO Amicon spin filter yielding 0.98 nmole of buffer exchanged Qdots. 19.6 µl of 20 mM SFB (Pierce heterobifunctional crosslinker that adds aldehydes to amines) in DMSO was added to 0.98 nmole of buffer exchanged Qdots. The reaction mix was incubated at room temperature for 3 hours. After incubation, the reaction product was purified into 50 mM borate buffer, pH 7.3 using ultra-filtration (Amicon, 30 kD MWCO). The yield of aldehyde modified Qdots was ~0.9 nmoles.

Buffer Exchange and Reduction of Cleaved TEV-Φ29:

Cleaved TEV-Φ29 was protein engineered to contain cysteine on the N-terminus. The amino acid sequence of this recombinant Phi-29 polymerase is provided herein as SEQ ID NO: 38. 1.1 ml of 27 µM TEV-Φ29 was buffer exchanged over two NAP10 size exclusion columns (GE Health Sciences) into 100 mM MES, 700 mM NaCl, pH 6.0 buffer (herein referred to as MES pH 6 buffer). Five-drop fractures were collected. The fractions containing protein were pooled and concentrated by ultra-filtration (Amicon, 10 kD MWCO). The final concentrated volume was 400 µl of 57.7 µM TEV-Φ29. 2 µl of 1 M TCEP (reductant) was added to the 400 µl of buffer exchanged TEV-Φ29 to give a final concentration of 5 mM TCEP. The TEV-Φ29 was reduced for 1 hour on ice.

Conjugation of Reduced TEV-Φ29 with Aldehyde-Containing Qdots:

200 µl of 57.7 µl of reduced TEV-Φ29 (11.5 nmoles) was added to 70 µl of 4.98 µM aldehyde-containing Qdots (0.35 nmoles) and 50 µl of MES pH 6 buffer. The conjugation mix was incubated overnight at 4° C. After incubation, the conjugation mix was purified by 10 washes with 200 µl of 100 mM TRIS, 300 mM NaCl, pH 7.5 buffer (herein referred to as TRIS pH 7.5 buffer) using ultra-filtration (Amicon, 100 kD MWCO). Next, the conjugate was further purified over a Superdex 200 size exclusion column (GE Health Sciences) using TRIS pH 7.5 buffer as the elution buffer. When the orange conjugate began to elute from the column three, two-drop fractions were collected. The conjugate was measured in a plate-based (ensemble) template binding assay and an onscope (single molecule) based template binding assay. Prior to storage at −20° C., neat glycerol was added to the conjugate fractions to give a conjugate/glycerol mixture of approximately 50% glycerol.

Plate-Based (Ensemble) Template Binding Assay:

The conjugate was tested for its ability to bind a fluorescently labeled DNA template (Oligo 1555). Detection of binding was achieved by exciting the Qdot with 450 nm excitation light and observing the emitted light at 670 nm due to fluorescence resonance energy transfer (FRET) between the Qdot and the fluorescent dye on the template. Only conjugates bound to the DNA template are in close enough proximity for FRET-based detection of binding. Briefly, the assay is run by pipeting 50 µl of 20 nM conjugate into each of twelve wells in one row of a micro-titer plate. Using a multi-channel pipeter, 50 µl of a serial dilution of the labeled DNA template, starting at 2 µM, is added to each well of the conjugate. The fluorescence is then measured in a Molecular Devices SpectraMax M5 plate reader. A plot of the emitted light at 670 nm versus the concentration of the DNA template should show an increase in the emitted light as the concentration of the DNA template increases. FIG. 36 shows the results of a template binding assay (conjugate—blue diamond; negative controls—pink square and green triangle).

```
Oligo 1555
                                          (SEQ ID NO: 73)
    TTATCTTTGTGGGTGACAGGTTTTTCCTGTCACCX
``` where X=AF647-dC

Example 19

Analysis of Nucleotide Incorporation Using a Conjugate Including a Polymerase Linked to a Nanoparticle Having a Tridentate Thiol Surface Ligand Preparing Tripod Nanoparticle-his-Mutant B103-H370R (Exo-) Polymerase Conjugates Mutant B103 polymerase having the amino acid sequence of SEQ ID NO: 40 was conjugated to nanoparticles comprising a tridentate thiol surface ligand (referred to herein as "tripod nanocrystals"). The preparation of tripod nanocrystals is also described herein.

To prepare the conjugate, tripod nanocrystals (50 µL, 2.7 µM in 50 mM borate buffer pH 8.0) were mixed with a stock solution of His-tagged HP1-mutantB103 H370R exo- polymerase having the amino acid sequence of SEQ ID NO: 40 (25 µL, 16 µM in 10 mM Tris (pH 7.5) buffer with 100 mM NaCl, 4 mM DTT, 0.5% v/v Tween-20, 0.1 mM EDTA and 50% v/v glycerol) and 40 µL of 100 mM Tris (pH 7.5) buffer with 300 mM NaCl and 1 mM DTT in a 1:3 molar ratio (nanocrystal to polymerase). The conjugation solution was incubated overnight at 4° C. The resulting conjugate solution was centrifuged for 5 minutes at 16.8K rcf, purified on $Ni^{2+}$-NTA Agarose columns using 100 mM Tris (pH 7.5) buffer with 300 mM NaCl and 1 mM DTT as the eluent, centrifuged and transferred into a 10K MWCO dialysis cassette. The conjugate was dialyzed into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-B103 H370R exo- conjugate was assayed to determine nucleotide concentration, template extension activity, active number of Phi29 per conjugate and DNA binding by FRET. In a DNA extension assay, the Tripod-nanoparticle-HP1-B103-H370R (exo-) conjugates exhibited a nucleotide incorporation rate of about 0.35 base/sec/conjugate, and the stock HP1-B104-H370R (exo-) polymerase exhibited a nucleotide incorporation rate of about 0.29 base/sec/enzyme (data not shown). The average number of polymerases per nanoparticle in the purified conjugate preparation was estimated to be approximately about 1.0 using the fluorescence polarization assay described herein.

Nucleotide Incorporation Using the Conjugates

The template nucleic acid used in this assay had the following sequence:

```
Biotin-5'-
                                          (SEQ ID NO: 41)
TTTTTCCCCGCGTAACTCTTTACCCCgACACggAggTTCTATCA-3'-
amine)
```

The primer used in this assay had the following sequence:

```
5'-TGATAGAACCTCCGTGTC-3'      (SEQ ID NO: 42)
```

50 µL of 10 µM template comprising the sequence of SEQ ID NO: 41 was mixed with 50 µL of 50 µM primer comprising the SEQ ID NO: of SEQ ID NO: 42 (sequences shown above). The mixture was heated at 98° C. for 1 minute and chilled on ice. The annealed template/primer was diluted to 200 µM using 500 mM borate buffer (pH 8.2), and injected into lanes of a microfluidic device with coverslip containing NHS ester reactive groups on the surface, incubated at room temperature for 10 minutes. The coverslip surface was deactivated by incubating with 50 mM glycine in 500 mM borate buffer (pH 8.2) for 10 minutes, washed with 50 mM Tris buffer (pH 7.5) with 50 mM NaCl, 0.5% BSA and 0.05% Tween-20.

The microfluidic device was secured on a TIRF (total internal reflection fluorescence) microscope. The TIRF microscope was setup on TIRF mode with power density at ~15 W/cm² for the 405 nm excitation laser. Nanoparticle-polymerase conjugate solution (10 nM in GO-Cat OSS buffer system, 50 mM MOPS buffer pH 7.2 with 50 mM KOAc, 0.1% Tween-20, 10 mM Trolox, 0.3% BSA, 0.5 mg/mL glucose oxidase, 10 unit/uL catalase, 2 mM tetra-aspartic acid and 0.5% freshly added glucose) was injected into a lane of the microfluidic, incubated at room temperature for ~1 minute, then washed with the GO-Cat OSS buffer system (50 mM MOPS buffer pH 7.2 with 50 mM KOAc, 0.1% Tween-20, 10 mM Trolox, 0.3% BSA, 0.5 mg/mL glucose oxidase, 10 unit/uL catalase, 2 mM tetra-aspartic acid and 0.5% freshly added glucose). The successive nucleotide incorporation was captured on a movie, which was recorded for 100 seconds at 30 ms per frame rate on a new FOV (field of view) when injecting into the lane of a primer extension reaction mixture (e.g. 150 nM dG6P-C6-AF647, 150 nM dA6P-C6-AF680, 1000 nM dTTP, 1000 nM dCTP and 0.5 mM $MnCl_2$ in GO-Cat OSS buffer system containing freshly added 0.5% glucose. The movie was analyzed to identify the order of incorporated nucleotides using time series extraction and base calling software.

Example 20

Conjugation Specificity of Various Conjugates

C8 Dots-His Phi29 Conjugation Attachment Specificity

A stock solution of His-tagged F linker-Phi29 polymerase having the amino acid sequence of SEQ ID NO: 13 (200 µL, 108 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl using an NAP-5 column C8 Nanocrystals (150 µL, 3.5 µM in 50 mM borate buffer pH 8.0) was concentrated to ~10 µL by ultrafiltration (VivaSpin, 100K MWCO); diluted by 150 µL of 100 mM Tris buffer (pH 7.5) with 300 mM NaCl; and concentrated again to ~10 µL by ultrafiltration (VivaSpin, 100K MWCO). The concentrated C8 nanocrystal solution was mixed with the buffer-exchanged His-tagged F linker-Phi29 polymerase (240 µL, 33 µM in 100 mM Tris (pH 7.5) buffer with 300 mM NaCl) in a 1:15 molar ratio (nanocrystal to polymerase). The conjugation solution was incubated overnight at 4° C.

A stock solution of His-tagged H linker-Phi29 polymerase (400 µL, 25 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl using an NAP-5 column. The buffer-exchanged His-tagged H linker-Phi29 polymerase was stored on ice for immediate use in the following conjugation reaction. C8 Nanocrystals (50 µL, 3.5 µM in 50 mM borate buffer pH 8.0) was concentrated to ~10 µL by ultrafiltration (VivaSpin, 100K MWCO); diluted by 150 µL of 100 mM Tris buffer (pH 7.5) with 300 mM NaCl; and concentrated again to ~10 µL by ultrafiltration (VivaSpin, 100K MWCO). The concentrated C8 nanocrystal solution was mixed with the buffer-exchanged His-tagged H linker-Phi29 polymerase (180 mL, 14.6 µM in 100 mM Tris (pH 7.5) buffer with 300 mM NaCl) in a 1:15 molar ratio (nanocrystal to polymerase). The conjugation solution was incubated overnight at 4° C.

A stock solution of His-tagged (no linker)-Phi29 polymerase (400 µL, 25 µM) (stock solution in: 10 mM Tris (pH 7.5) buffer with 100 mM NaCl, 4 mM DTT, 0.5% v/v Tween-20, 0.1 mM EDTA and 50% v/v glycerol) was buffer exchanged into 100 mM Tris (pH 7.5) buffer with 300 mM NaCl using an NAP-5 column. The buffer-exchanged His-tagged (no linker)-Phi29 polymerase was stored on ice for immediate use in the following conjugation reaction. C8 Nanocrystals (150 µL, 3.5 µM in 50 mM borate buffer pH 8.0) was concentrated to ~10 µL by ultrafiltration (VivaSpin, 100K MWCO); diluted by 150 µL of 100 mM Tris buffer (pH 7.5) with 300 mM NaCl; and concentrated again to ~10 µL by ultrafiltration (VivaSpin, 100K MWCO). The concentrated C8 nanocrystal solution was mixed with the buffer-exchanged His-tagged (no linker)-Phi29 polymerase (159 µL, 16.5 µM in 100 mM Tris (pH 7.5) buffer with 300 mM NaCl) in a 1:15 molar ratio (nanocrystal to polymerase). The conjugation solution was incubated overnight at 4° C.

The three conjugation solutions were examined by electrophoresis using 0.8% Agarose E-gel and by primer extension assay.

All three conjugation solutions were centrifuged for 5 minutes at 16.8K rcf, purified on Ni$^{2+}$-NTA Agarose column using 100 mM Tris (pH 7.5) buffer with 300 mM NaCl as the eluent, centrifuged and transferred into individual 10K MWCO dialysis cassettes. The conjugates were then dialyzed overnight at 4° C. into 50 mM Tris buffer pH7.5 with 150 mM NaCl, 0.2 mM EDTA, 0.5% v/v Tween-20 and 50% v/v glycerol. The resulting conjugate solutions were removed from dialysis cassettes and measured the concentration by UV/vis absorption spectroscopy. The conjugate solutions were assayed to measure primer extension activity and DNA binding by FRET.

Example 21

First Method for Conjugating a Mutant B103 Polymerase to Nanoparticles Including Surface Tridentate Thiol Ligands at Controlled Ratios In this assay, mutant B103 polymerase having the amino acid sequence of SEQ ID NO: 40 was conjugated to tripod nanocrystals to produce different conjugate populations having controlled ratios of polymerase to nanoparticle.

Preparing Tripod Dot-10×his-B104 H370R Exo- Polymerase Conjugate

To prepare the first conjugate population, Tripod Nanocrystals (50 µL, 2.7 µM in 50 mM borate buffer pH 8.0) were mixed with stock His-tagged HP1-B104 H370R exo- polymerase having the amino acid sequence of SEQ ID NO: 40 (82 µL, 16 µM in 10 mM Tris (pH 7.5) buffer with 100 mM NaCl, 4 mM DTT, 0.5% v/v Tween-20, 0.1 mM EDTA and 50% v/v glycerol) and 80 µL of 100 mM Tris (pH 7.5) buffer with 300 mM NaCl and 1 mM DTT in a 1:10 molar ratio (nanocrystal to polymerase). The conjugation solution was incubated overnight at 4° C. The resulting conjugate solution was centrifuged for 5 minutes at 16.8K rcf, purified on Ni$^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-10×B104 H370R exo- conjugate solution was removed from dialysis cassette and measured the concentration by Uv-Vis absorption spectroscopy. The conjugate product (600 µL, 0.2 µM) was obtained at approximately 89% yield based on Tripod Nanocrystals starting material used)

Preparing Tripod Dot-5×his-B104 H370R Exo- Polymerase Conjugate

A second conjugate population was prepared as follows: Tripod Nanocrystals (50 µL, 2.7 µM in 50 mM borate buffer pH 8.0) was mixed with a stock solution of His-tagged HP1-B104 H370R exo- polymerase (42 mL, 16 nM in 10 mM Tris (pH 7.5) buffer with 100 mM NaCl, 4 mM DTT, 0.5% v/v Tween-20, 0.1 mM EDTA and 50% v/v glycerol) and 60 µL of 100 mM Tris (pH 7.5) buffer with 300 mM NaCl and 1 mM DTT in a 1:5 molar ratio (nanocrystal to polymerase). The conjugation solution was incubated overnight at 4° C. The resulting conjugate solution was centrifuged for 5 minutes at 16.8K rcf, purified on Ni$^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-5×B104 H370R exo- conjugate solution was removed from dialysis cassette and measured the concentration by Uv-Vis absorption spectroscopy. The conjugate product (500 µL, 0.26 µM) was obtained at approximately 96% yield based on Tripod Nanocrystals starting material used.

Preparing Tripod Dot-3×his-B104 H370R Exo- Polymerase Conjugate

A third conjugate population was prepared as follows: Tripod Nanocrystals (50 µL, 2.7 µM in 50 mM borate buffer pH 8.0) was mixed with a stock solution of His-tagged HP1-B104 H370R exo- polymerase having the amino acid sequence of SEQ ID NO: 40 (25 µL, 16 µM in 10 mM Tris (pH 7.5) buffer with 100 mM NaCl, 4 mM DTT, 0.5% v/v Tween- 20, 0.1 mM EDTA and 50% v/v glycerol) and 40 µL of 100 mM Tris (pH 7.5) buffer with 300 mM NaCl and 1 mM DTT in a 1:3 molar ratio (nanocrystal to polymerase). The conjugation solution was incubated overnight at 4° C. The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-3×B104 H370R exo- conjugate solution was removed from dialysis cassette and measured the concentration by Uv-Vis absorption spectroscopy. The mono-pol-dot conjugate product (500 µL, 0.19 µM) was obtained at approximately 70% yield based on Tripod Nanocrystals starting material used. Tests indicated that approximately 30% of the resulting population was comprised of 1:1 polymerase:nanoparticle conjugates (monoconjugates).

Tripod Dot-3×his-B104 H370R Exo- Polymerase Conjugate

A fourth conjugate population was produced using the accessory compound uracil DNA glycosylase (UDG) as follows:

His-tagged UDG protein (uracil DNA glycosylase) (2800 µL, 41 µM in 30 mM Tris buffer (pH 7.5) with 300 mM NaCl, 1 mM DTT, 0.5% v/v Tween-20, 0.1 mM EDTA, 50% v/v Glycerol) was mixed ugi (uracil-DNA glycosylase inhibitor) (809 µL, 173 µM in 50 mM Tris buffer (pH 7.5) with 1 mM DTT and 5% Glycerol) in 1:1.2 molar ratio (His-tagged-UDG to ugi protein), and incubated at 4° C. overnight. The formed His-tagged UDG-ugi protein complex was stored at 4° C. for future use without further purification.

Tripod Nanocrystals (50 µL, 2.7 µM in 50 mM borate buffer pH 8.0) was mixed with stock His-tagged HP1-B104 H370R exo- polymerase (25 µL, 16 µM in 10 mM Tris (pH 7.5) buffer with 100 mM NaCl, 4 mM DTT, 0.5% v/v Tween-20, 0.1 mM EDTA and 50% v/v glycerol) and 40 µL of 100 mM Tris (pH 7.5) buffer with 300 mM NaCl and 1 mM DTT in a 1:3 molar ratio (nanocrystal to polymerase). The conjugation solution was incubated overnight at 4° C.; mixed with His-tagged UDG-ugi (83 µL, 32 µM in 30 mM Tris (pH 7.5) buffer with 300 mM NaCl, 1 mM DTT); and further incubated at 4° C. for 6.5 hours. The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting Tripod-nanocrystal-HP1-3×B104 H370R exo- conjugate solution was removed from dialysis cassette and measured the concentration by Uv-Vis absorption spectroscopy. The mono-pol-dot conjugate product (500 µL, 0.20 µM, 74% yield based on Tripod Nanocrystals starting material used, ~30% 1:1 pol-dot conjugate population in the product).

All four resulting conjugate populations where then assayed to measure primer extension activity, active number of polymerase per conjugate and DNA binding by FRET. Representative results are shown in FIG. 37, which depicts histograms indicating the FRET 605/670 ratio, the estimated average number of active polymerases per nanoparticle, the primer extension activity (bases/sec per conjugate, or bases/sec per free enzyme.

Example 22

Second Method of Conjugating a Mutant B103 Polymerase to Nanoparticles at Controlled Ratios Using Accessory Compounds In this assay, mutant B103 polymerase having the amino acid sequence of SEQ ID NO: 40 was conjugated to nanoparticles (C8 quantum dots) in the presence of the accessory compound uracil DNA glycoslyase (UDG) to produce different conjugate populations having controlled ratios of polymerase to nanoparticle.

C8 Dot-his-UDG-Ugi-10×his-B104 H370R Exo- Polymerase Conjugate

A first conjugate population was prepared as follows:

His-tagged UDG protein (uracil DNA glycosylase) (2800 µL, 41 µM in 30 mM Tris buffer (pH 7.5) with 300 mM NaCl, 1 mM DTT, 0.5% v/v Tween-20, 0.1 mM EDTA, 50% v/v Glycerol) was mixed ugi (uracil-DNA glycosylase inhibitor) (809 µL, 173 µM in 50 mM Tris buffer (pH 7.5) with 1 mM DTT and 5% Glycerol) in 1:1.2 molar ratio (His-tagged-UDG to ugi protein), and incubated at 4° C. overnight. The formed His-tagged UDG-ugi protein complex was stored at 4° C. for future use without further purification.

C8 Nanocrystals (100 µL, 5.3 µM in 50 mM borate buffer pH 8.0 with 1 M Betaine stored at −20° C.) was thawed and mixed with stock His-tagged HP1-B104 H370R exo- polymerase (332 µL, 16 µM in 10 mM Tris (pH 7.5) buffer with 100 mM NaCl, 4 mM DTT, 0.5% v/v Tween-20, 0.1 mM EDTA and 50% v/v glycerol) and 400 µL of 100 mM Tris (pH 7.5) buffer with 300 mM NaCl and 1 mM DTT in a 1:10 molar ratio (nanocrystal to polymerase). The conjugation solution was incubated at 4° C. for 2 hours; mixed with His-tagged UDG-ugi (166 µL, 32 µM in 30 mM Tris (pH 7.5) buffer with 300 mM NaCl, 1 mM DTT); and further incubated overnight at 4° C. The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting C8-nanocrystal-HP1-10×B104 H370R exo- conjugate solution was removed from dialysis cassette and measured the concentration by Uv-Vis absorption spectroscopy. The conjugate product (950 µL, 0.45 µM) was obtained at approximately 81% yield based on C8 Nanocrystals starting material used.

C8 Dot-his-UDG-Ugi-5×his-B104 H370R Exo- Polymerase Conjugate

A second conjugate population was prepared as follows:

His-tagged UDG protein (uracil DNA glycosylase) (2800 µL, 41 µM in 30 mM Tris buffer (pH 7.5) with 300 mM NaCl, 1 mM DTT, 0.5% v/v Tween-20, 0.1 mM EDTA, 50% v/v Glycerol) was mixed ugi (uracil-DNA glycosylase inhibitor) (809 µL, 173 µM in 50 mM Tris buffer (pH 7.5) with 1 mM DTT and 5% Glycerol) in 1:1.2 molar ratio (His-tagged-UDG to ugi protein), and incubated at 4° C. overnight. The formed His-tagged UDG-ugi protein complex was stored at 4° C. for future use without further purification.

C8 Nanocrystals (100 µL, 5.3 µM in 50 mM borate buffer pH 8.0 with 1 M Betaine stored at −20° C.) was thawed and mixed with stock His-tagged HP1-B104 H370R exo- polymerase (166 μL, 16 μM in 10 mM Tris (pH 7.5) buffer with 100 mM NaCl, 4 mM DTT, 0.5% v/v Tween-20, 0.1 mM EDTA and 50% v/v glycerol), and His-tagged UDG-ugi (165 μL, 32 μM in 30 mM Tris (pH 7.5) buffer with 300 mM NaCl, 1 mM DTT), and 300 μL of 100 mM Tris (pH 7.5) buffer with 300 mM NaCl and 1 mM DTT in a 1:5:10 molar ratio (nanocrystal to polymerase to his-UDG-ugi). The conjugation solution was incubated at 4° C. for 4 hours. The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting C8-nanocrystal-HP1-5×B104 H370R exo- conjugate solution was removed from dialysis cassette and measured the concentration by Uv-Vis absorption spectroscopy. The conjugate product (850 μL, 0.53 μM) was obtained at approximately 85% yield based on C8 Nanocrystals starting material used.

C8 Dot-his-UDG-Ugi-3×his-B104 H370R Exo- Polymerase Conjugate

A third conjugate population was obtained as follows:

His-tagged UDG protein (uracil DNA glycosylase) (2800 μL, 41 μM in 30 mM Tris buffer (pH 7.5) with 300 mM NaCl, 1 mM DTT, 0.5% v/v Tween-20, 0.1 mM EDTA, 50% v/v Glycerol) was mixed ugi (uracil-DNA glycosylase inhibitor) (809 μL, 173 μM in 50 mM Tris buffer (pH 7.5) with 1 mM DTT and 5% Glycerol) in 1:1.2 molar ratio (His-tagged-UDG to ugi protein), and incubated at 4° C. overnight. The formed His-tagged UDG-ugi protein complex was stored at 4° C. for future use without further purification.

C8 Nanocrystals (100 μL, 5.3 μM in 50 mM borate buffer pH 8.0 with 1 M Betaine stored at −20° C.) was thawed and mixed with stock His-tagged HP1-B104 H370R exo- polymerase (99.4 μL, 16 μM in 10 mM Tris (pH 7.5) buffer with 100 mM NaCl, 4 mM DTT, 0.5% v/v Tween-20, 0.1 mM EDTA and 50% v/v glycerol), and His-tagged UDG-ugi (165 μL, 32 μM in 30 mM Tris (pH 7.5) buffer with 300 mM NaCl, 1 mM DTT), and 150 μL of 100 mM Tris (pH 7.5) buffer with 300 mM NaCl and 1 mM DTT in a 1:3:10 molar ratio (nanocrystal to polymerase to his-UDG-ugi). The conjugation solution was incubated overnight at 4° C.; centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO The resulting conjugate solution was centrifuged for 5 minutes at 16.8K rcf, purified on $Ni^{2+}$-NTA Agarose column using 100 mM Tris (pH 7.5) buffer with 300 mM NaCl and 1 mM DTT as the eluent, centrifuged and transferred into a 10K MWCO dialysis cassette. The conjugate was then dialyzed overnight at 4° C. into 50 mM Tris buffer pH7.5 with 150 mM NaCl, 0.2 mM EDTA, 0.5% v/v Tween-20, 5 mM DTT and 50% v/v glycerol. The resulting C8-nanocrystal-HP1-3×B104 H370R exo- conjugate solution was removed from dialysis cassette and measured the concentration by Uv-Vis absorption spectroscopy. The conjugate product (1200 μL, 0.44 μM) was obtained at approximately 99% yield based on C8 Nanocrystals starting material used. Based on fluorescence polarization assays, approximately 30% of the resulting population included conjugates comprising an average ratio of 1:1 (polymerase to nanoparticle).

All three conjugate populations where then assayed to measure primer extension activity, active number of Phi29 per conjugate and DNA binding by FRET. Representative results are shown in FIG. 38, which depicts histograms indicating the FRET 605/670 ratio, the estimated average number of active polymerases per nanoparticle, the primer extension activity (bases/sec per conjugate, or bases/sec per free enzyme.

Example 23

Measurement of Primer Extension Activity of a Sample Polymerase Using a Fluorescein-Labeled Oligonucleotide This example provides an exemplary assay for primer extension activity in a sample. Primer extension activity is quantified by monitoring the fluorescence intensity change over time during extension of a fluorescein-labeled hairpin oligonucleotide, comprising the following nucleotide sequence, known as "oligo 221"): The fluorescence intensity correlates with the level of primer extension activity in the sample.

```
                                     (SEQ ID NO: 43)
       (5'-TTTTTTTGCAGGTGACAGGTTTTTCCTGTCA-

CC(fluorescein-T)GC-3').
```

The extension reactions are performed in 1× extension buffer (50 mM Tris buffer pH 7.5, 50 mM NaCl, 10 mM $MgCl_2$ and 0.5 mM $MnCl_2$). To reaction wells that contain 100 μL of 150 nM of a fluorescein-labeled hairpin oligonucleotide, oligo221 (SEQ ID NO: 43, above) and 10 nM of polymerase (or conjugated polymerase) in extension buffer, 2 μL of 1 mM dATP (final concentration: 20 μM) is added to initiate the enzymatic reaction and the fluorescence intensity in each well is recorded at 525 nm fluorescence with 490 nm excitation for every 20 seconds for the next 10 minutes. Control reaction wells include the same components without any dATP. The fluorescence intensity at 525 nm (as measured in arbitrary fluorescence units, RFU, y axis) is plotted against time (seconds, X axis) for each sample, as well as the control wells (no nucleotide). The fluorescence time course data from each well is used to calculate the primer extension activity of each sample using the following equations:

$$\text{Activity(base/sec/enz)} = \frac{\Delta RFU_{sample}\_\text{per\_sec}}{\Delta RFU_{max}\_\text{per\_nMsubs}} \times \frac{1}{50\text{ nM}} \times 7(\text{base})$$

$$\text{and } \Delta RFU_{max}\_\text{per\_nMsubs} = \frac{RFU_{max} - RFU_{min}}{\text{substr\_conc.(nM)}}$$

Where: $RFU_{max}$ is the average maximal RFU in the reference polymerase reaction wells; $RFU_{min}$ is the average minimal RFU in the reference polymerase control wells; Substr_conc. (nM) is the oligo 221 concentration in assay, which is 150 nM; and:

$$\Delta RFU_{sample}\_\text{per\_sec} = \frac{RFU_t - RFU_0}{t(sec)}$$

Where: t (sec) is the time period where the fluorescence intensity increases in the reference enzyme reaction well linearly from the start; $RFU_t$ is the average RFU of the reference enzyme extension wells at t second point; and $RFU_0$ is the average RFU of the reference enzyme extension wells at the start point.

Example 24

Comparing the Primer Extension Activities of Conjugated and Unconjugated Polymerases This assay describes how to measure and compare the primer extension activity of a labeled polymerase conjugate comprising multiple polymerases per conjugate, with the primer extension activity of unconjugated (free) enzyme. Primer extension activity is quantified by monitoring the fluorescence intensity change over time during extension of a fluorescein-labeled hairpin oligonucleotide, comprising the following nucleotide sequence. The fluorescence intensity correlates with the level of primer extension activity in the sample.

Step 1: Measure the Primer Extension Activities of the Conjugate and the Free (Unconjugated) Enzyme Conjugate primer extension activity is measured by monitoring the fluorescence intensity change over time during extension of a fluorescein-labeled hairpin oligonucleotide, oligo 221 comprising the nucleotide sequence of SEQ ID NO: 43, below:

```
                                       (SEQ ID NO: 43)
(5'-TTTTTTTGCAGGTGACAGGTTTTTCCTGTCA-

CC(fluorescein-T)GC-3')
```

The extension reactions are performed in 1× extension buffer (50 mM Tris buffer pH 7.5, 50 mM NaCl, 10 mM $MgCl_2$ and 0.5 mM $MnCl_2$). To reaction wells that contain 100 µL of 150 nM of a fluorescein-labeled hairpin oligonucleotide, oligo221 (SEQ ID NO: 43, above) and 10 nM of polymerase (or conjugated polymerase) in extension buffer, 2 µL of 1 mM dATP (final concentration: 20 µM) is added to initiate the enzymatic reaction and the fluorescence intensity in each well is recorded at 525 nm fluorescence with 490 nm excitation for every 20 seconds for the next 10 minutes. Control reaction wells include the same components without any addition of dATP. The fluorescence intensity at 525 nm (as measured in arbitrary fluorescence units, RFU, y axis) is plotted against time (seconds, X axis) for each sample, as well as the control wells (no nucleotide). The fluorescence time course data from each well is used to calculate the primer extension activity of each sample.

For conjugate activity (base/sec/conj), the activity is calculated according to the following equations:

$$\text{Activity(base/sec/}enz\text{)} = \frac{\Delta RFU_{sample}\_\text{per\_sec}}{\Delta RFU_{max}\_\text{per\_nMsubs}} \times \frac{1}{10 \text{ nM}} \times 7(\text{base})$$

$$\text{and } \Delta RFU_{max}\_\text{per\_nMsubs} = \frac{RFU_{max} - RFU_{min}}{\text{substr\_conc.(nM)}}$$

Where: $RFU_{max}$ is the average maximal RFU in the reference polymerase reaction wells; $RFU_{min}$ is the average minimal RFU in the reference polymerase control wells; Substr_conc. (nM) is the oligo 221 concentration in assay, which is 150 nM; and:

$$\Delta RFU_{sample}\_\text{per\_sec} = \frac{RFU_t - RFU_0}{t(sec)}$$

Where: t (sec) is the time period where the fluorescence intensity increases in the reference enzyme reaction well linearly from the start; $RFU_t$ is the average RFU of the reference enzyme extension wells at t second point; and $RFU_0$ is the average RFU of the reference enzyme extension wells at the start point.

For activity of free enzyme (base/sec/enzyme), the activity is calculated according to the following equations:

$$\text{Free-enzyme}\_activity(\text{base/sec/}enz) =$$

$$\frac{\Delta RFU_{sample}\_\text{per\_sec}}{\Delta RFU_{max}\_\text{per\_nMsubs}} \times \frac{1}{50 \text{ nM}} \times 7(\text{base})$$

$$\text{and } \Delta RFU_{max}\_\text{per\_nMsubs} = \frac{RFU_{max} - RFU_{min}}{\text{substr\_conc.(nM)}}$$

Where: $RFU_{max}$ is the average maximal RFU in the reference polymerase reaction wells; $RFU_{min}$ is the average minimal RFU in the reference polymerase control wells; and Substr_conc. (nM) is the oligo 221 concentration in assay, which is 150 nM; and $$\Delta RFU_{sample}\_\text{per\_sec} = \frac{RFU_t - RFU_0}{t(sec)}$$

Where: t (sec) is the time period where the fluorescence intensity increases in the reference enzyme reaction well linearly from the start; $RFU_t$ is the average RFU of the reference enzyme extension wells at t second point; $RFU_0$ is the average RFU of the reference enzyme extension wells at the start point.

Step 2: Measure the Number of Active Enzyme Per Conjugate

This procedure describes a method to measure the active number of polymerase per conjugate based on the active polymerase binding to fluorescein-labeled template using FP as the readout. In this assay, the mP values of a conjugate at several concentrations are measured and a standard curve is also generated for the mP values at known concentrations of free polymerase. By fitting the mP values into the standard curve, the number of polymerase per conjugate can be calculated Extension buffer (50 mM Tris pH7.5 with 50 mM NaCl, 10 mM MgCl2 and 0.5 mM MnCl2) is added into the first two rows of a 96-well microtiter plate for 50 µL per well. To the first well of the above each row, 50 µL of 4000 nM free polymerase (polymerase used in the tested conjugate) in extension buffer is added, mixed and transferred 50 µL per well into the second well of the above each row. A 2-fold dilution (concentration from 4000 nM to 1.95 nM) of the free polymerase is then prepared in the above two rows by subsequentially transferring and mixing as described. 50 µL of solution is removed from the last well of each row to make 50 µL volume for each well. These two rows are served as the free polymerase standard wells.

For the wells containing conjugate, 50 µL of conjugate is added to each well with various concentrations (e.g. 20 nM, 40 nM, 60 nM, 80 nM) that are prepared by diluting conjugate into the extension buffer.

To all wells including either free enzyme or conjugated enzyme, 50 μL of 300 nM oligo221 in 1× extension buffer is added. The plate is then mixed and the mP value of each well is measured using a plate reader.

To calculate the active number of polymerase per conjugate, the standard curve is fitted into a non-linear regression equation:

$$Y = b + \frac{a-b}{1 + 10^{(\log EC50 - X)*c}}$$

Where Y is the mP value;
X is the log [phi29(nM)];
a is the top value of the standard curve;
b the bottom value of the standard curve;
c is the slope of the curve
EC50 is the concentration that gives 50% of the total response.

Based on the standard curve fitting results, the active polymerase concentration at certain conjugate concentration can be calculated by inputting the mP value at particular conjugate concentration into the equation. The actual number of active polymerase per conjugate is then determined by dividing the calculated active polymerase concentration by the corresponding conjugate concentration.

Step 3: Calculate the "Ratio of Activity for Conjugated-Enzyme to Free-Enzyme"

Based on the results of the measurements for "conjugate activity", "Free-enzyme activity" and the "Nan active polymerase per conjugate", the ratio of activity of conjugated enzyme to free enzyme ("Ratio of Activity for Conj-enzyme to Free-enzyme") can be calculated as follows:

$$\text{Ratio\_Activity\_of\_Conj-Enzyme-to-FreeEnzyme} = \frac{\text{Conjugate\_activity}}{\text{Nn\_active} - \text{Pol-per-Conjugate}} \times \frac{1}{\text{Free-polymerase\_activity}}$$

Example 25

Preparation of Core-Shell Nanoparticle CdSe/4CdS-3.5ZnS

Core Synthesis

Cores are prepared using standard methods, such as those described in U.S. Pat. No. 6,815,064, the only change being that the growth is halted at 535 nm emission. These cores were precipitated and cleaned in the standard methods and resuspended into hexane for use in the shell reaction.

Shell Synthesis:

A 1:1 (w:v) mixture of tri-n-octylphosphine oxide (TOPO) and tri-n-octylphosphine (TOP) was introduced into a flask. Tetradecylphosphonic acid (TDPA) was added to the flask in an amount suitable to fully passivate the final material, as can be calculated from the reaction scale and the expected final nanoparticle size. The contents of the flask were heated to 125° C. under vacuum and then the flask was refilled with $N_2$ and cooled.

Inside the glovebox, a solution of a suitable cadmium precursor (such as dimethylcadmium or cadmium acetate) in TOP was prepared in a quantity sufficient to produce a desired thickness of shell, as can be calculated by one of ordinary skill in the art. When a zinc shell was also desired, a solution of a suitable zinc precursor (such as diethylzinc or zinc stearate) was prepared in TOP in a quantity sufficient to produce the desired shell thickness. Separately, a solution of trimethylsilylsulfide [$(TMS)_2S$] in TOP was prepared in a quantity sufficient to produce the desired shell thickness. Each of these solutions was taken up in separate syringes and removed from the glove box.

Of the previously prepared core/hexane solution, 17 mL (at an optical density of 21.5 at the band edge) was added to the reaction flask and the hexane was removed by vacuum; the flask was then refilled with $N_2$. The flask was heated to the desired synthesis temperature, typically about 200 to about 250° C. During this heat-up, 17 mL of decylamine was added.

The cadmium and sulfur precursor solutions were then added alternately in layer additions, which were based upon the starting size of the underlying cores. So this means that as each layer of shell material was added, a new "core" size was determined by taking the previous "core" size and adding to it the thickness of just-added shell material. This leads to a slightly larger volume of the following shell material needing to be added for each subsequent layer of shell material.

After a desired thickness of CdS shell material was added, the cadmium precursor solution was replaced with the zinc precursor solution. Zinc and sulfur solutions were then added alternately in layer additions until a desired thickness of ZnS was added. A final layer of the zinc solution was added at the end, the reaction flask was cooled, and the product was isolated by conventional precipitation methods.

Example 26

Exchange Process Using Dipeptide Ligands and Butanol as a Cosolvent

Core/shell nanocrystals (quantum dots) were prepared by standard methods, and were washed with acetic acid/toluene several times, and suspended in hexanes. 10 nmol of core/shell nanocrystals were suspended in 40 mL hexane. This was mixed with 10 mL of a 300 mM solution of carnosine and 10 mL of 1 M sodium carbonate solution. n-Butanol (14 mL) was added, and the vessel was flushed with argon. The mixture was mixed vigorously overnight at room temperature. The mixture was then heated and allowed to cool to room temperature. The aqueous phase was then removed and filtered through a 0.2/0.8 micron syringe filter.

Excess carnosine was removed by dialyzing against 3.5 L of 25 mM NaCl for one hour. The solution was concentrated to 1 mL using a 10K MWCO (10,000 molecular weight cut-off) Amicon centricon. A solution was then prepared with 568 mg of His-Leu dipeptide plus 212 mg of Gly-His dipeptide in 9 mL sodium carbonate solution, and this solution was combined with the aqueous solution of quantum dots. This mixture was stirred overnight at room temperature. The mixture of water-soluble quantum dots was then dialyzed against 3.5 L of 25 mM NaCl for one hour.

To crosslink the peptide ligands (clarify) A solution of 0.5 mM 4-aminobenzophenone in ethanol was then added to the aqueous quantum dots mixture, and the mixture was irradiated at 365 nm for 4 hours to effect reaction of the aminobenzophenone with the surface molecules on the quantum dots. To this, 5 mmol of THP (tris(hydroxymethyl)phosphine) was added, and the mixture was stirred at RT overnight, to induce crosslinking. Another 5 mmol of THP was added, and again the mixture was stirred overnight at RT. Another 5 mmol of THP was added the next day, along with 300 micromoles of PEG1000-COOH. This was mixed overnight at room temperature, then another 5 mmol of THP was added along with 30 mmol of glycine, and the mixture was stirred overnight at RT.

The material was purified by dialysis using the 10K MWCO Amicon centricon, and was washed with 50 mM borate buffer (pH 9). The final material was dispersed into 50 mM borate buffer to a final concentration of 2.5 micromolar for storage.

Example 27

Exchange Process Using Trithiol Ligands

A solution of hydrophobic phosphonate-coated quantum dots in organic solvent (e.g. toluene, chloroform, etc) with a concentration of between about 0.1 and 10 micromolar quantum dots was prepared. Approximately 1000 to 1000000 equivalents of a suitable trithiol ligand was added, optionally as a solution in a suitable organic solvent (e.g. acetone, methanol, etc). The reaction mixture was stirred for 1-48 hours and then the solution was basicified by addition of an organic base (e.g. tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 28

Two-Step Ligand Exchange: Process for Exchanging Phosphonate Ligands with Sulfonate (Triflate) Ligands A nanoparticle comprising a core/shell nanocrystal having TDPA ligands on its surface is dissolved in dichloromethane, and excess TMS triflate is added to it. After 1-2 hours at room temperature, analysis indicates that the TDPA ligands have been removed, and the nanoparticle remains dispersed in the solvent. It is dialyzed against dichloromethane using a 10K MWCO (10,000 molecular-weight cut-off) dialysis membrane to remove excess TMS triflate and the TMS-TDPA produced by the reaction of TMS triflate with the TDPA ligands. This produces a solution/suspension of nanoparticles comprising triflate ligands on the surface of nanocrystals. These triflate-containing nanoparticles are soluble in many organic solvents, but may not be readily soluble in hexanes, depending upon the complement of ligands present.

Two-Step Process for Exchanging Sulfonate (Triflate) Ligands with PEG Conjugated Dithiol (DHLA) Ligands Using n-Butanol as an Intermediate Ligand and DMF as a Co-Solvent The triflate-containing nanoparticle solution, described above, can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. This intermediate nanoparticle is contacted with an excess of a dihydrolipoic acid-PEG conjugate of this formula:

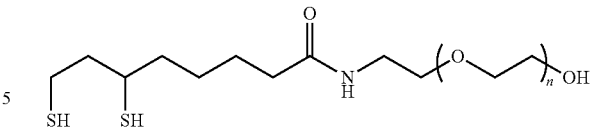

where n is 1-100.

The product is a water-soluble, stable nanoparticle. It can be collected by extraction into a pH 9 buffer, and isolated by conventional methods, including dialysis with a 10K MWCO dialysis filter, or by size exclusion (gel filtration) chromatography.

Two-Step Process for Exchanging Sulfonate (Triflate) Ligands with Nucleophilic Reactant Group Containing Ligands Using n-Butanol as an Intermediate Ligand and DMF as a Co-Solvent The triflate-containing nanoparticle solution from can be contacted with excess n-butanol in acetonitrile, using DMF as a co-solvent, to provide an intermediate nanoparticle believed to comprise butanol ligands in place of the triflates which were on the nanoparticle. This intermediate nanoparticle can be isolated from the medium, or it can be further modified without isolation. To further modify it, it is treated with a new ligand containing at least one nucleophilic reactant group: suitable ligands include HS—$CH_2$—$CH_2$-PEG; aminomethyl phosphonic acid; dihydrolipoic acid; omega-thio-alkanoic acids, and carboxymethylphosphonic acid. The mixture is then treated with TMEDA (tetramethylethylene diamine), and monitored until triflate is displaced, then the nanocrystal product is extracted into pH 9 buffer and purified by conventional methods.

Process for Exchanging Sulfonate (Triflate) Ligands with Carboxylate Functionalized Dithiol (DHLA) Ligands The triflate-containing nanoparticle is contacted with neat dihydrolipoic acid (DHLA) for an hour at room temperature, and is then dispersed into pH 9 buffer and isolated by conventional methods. This provides a nanoparticle having carboxylate groups to provide water solubility, and having two thiol groups binding the carboxylate to the nanocrystal surface. The product is water soluble and stable in aqueous buffer. It provides good colloidal stability, and a moderate quantum yield. This composition containing DHLA as a ligand contains free carboxyl groups which can be used to attach other groups such as a PEG moiety, optionally linked to a functional group or a biomolecule. The same reaction can be performed to replace triflate groups on a nanoparticle with thioglycolic acid (HS—$CH_2$—COOH) ligands. This provides a highly stabilized nanoparticle which produces a high quantum yield, but has lower colloidal stability than the product having DHLA on its surface.

Process for Exchanging Sulfonate (Triflate) Ligands with Amine Ligands

The triflate-containing nanoparticle is dispersed in dichloromethane plus hexanes, and an alkylamine is added. Suitable alkylamines are preferably primary amines, and include, e.g., $H_2N$—$(CH_2)_r$-PEG (r=2-10), p-aminomethylbenzoic acid, and lysine ethyl ester. After an hour at room temperature, the exchange process is completed, and the nanoparticle product can be isolated by conventional methods.

Process for Pre-treating Phosphonate Coated Nanocrystals with Toluene Acetic Acid to Remove Impurities Prior to Exchanging with Sulfonate (Triflate) Ligands TDPA-covered nanocrystals were synthesized which emitted light at 605 nm and had shells of CdS and of ZnS. These when treated with 200,000 equivalents of TMS triflate in hexanes did not produce a precipitate. This was attributed to excess TDPA-derived impurities in the nanocrystals. This was alleviated by dissolving the nanocrystals in toluene-acetic acid and precipitating them with methanol, to remove TDPA salts or related by-products. The resultant TDPA nanocrystals behaved as described above, demonstrating that impurities were causing the nanocrystals to behave differently when made with excess TDPA present, and that those impurities can be removed by precipitation under conditions better suited to dissolving TDPA-related impurities.

Process for Exchanging Activated (Sulfonate Coated) Nanocrystals with Dithiol (DHLA) Ligands Using Butanol, DMF or Isopropyl Alcohol as Dispersants Three different methods of depositing the DHLA ligands were employed, each of which was considerably more rapid than the classic approach using non-activated dots. In the first approach, the activated dot powder was dispersed in butanol and stirred with DHLA, then precipitated with hexane and collected in aqueous buffer. In the second approach, the activated dot powder was dispersed in dimethylformamide (DMF) and stirred with DHLA, then precipitated with toluene and collected in aqueous buffer. In the third approach, the activated dot powder was stirred as a slurry in neat DHLA, then dispersed in isopropyl alcohol, precipitated with hexane, and collected in aqueous buffer and purified with a filtration membrane.

These three samples, plus a sample derived from non-activated dots were diluted to 60 nM for a colloidal stability challenge, wherein the absorbance is monitored over the course of days to watch for precipitation. Samples 1 (butanol-mediated), 2 (DMF-mediated), and 4 (classic) all precipitated on day 3 or 4 of the stability challenge, but sample 3 (neat DHLA) lasted twice as long, coming out of solution on day 7. HPLC measurements indicated that the DHLA-coated particles produced from activated dots showed even less aggregation than the classic DHLA particles made by the displacement of TOPO or pyridine ligands from nanocrystals. Thus the invention provided rapid reactions leading to improved colloidal stability and comparable or lower aggregation levels than conventional ligand replacement methods of putting DHLA on a nanocrystal. Similar treatment with other thiol ligands like mercaptoundecanoic acid (MUA) or the PEGylated thiol also provided water-dispersible nanocrystals. Reacting triflate-coated nanoparticles with MUA or PEG-thiol gave particles which were readily dispersible in water, indicating that ligand exchange had occurred. The observed quantum yield was over 70% in each case.

Process for Exchanging Activated (Sulfonate Coated) Nanocrystals with Hydrophilic Phosphonate Ligands Triflate-coated dots were dispersed in butanol and then stirred with phosphonoacetic acid. Triethylamine was added to form the triethylammonium salt of both the phosphonate and carboxylate functionalities, and then pH 9 aqueous borate buffer was added to extract the hydrophilic particles. The result was a bright orange aqueous dispersion of quantum dots, with no remaining color observed in the butanol layer. The particles were purified by centrifugal filtration and the quantum yield was measured to be 72%. Multiple batches of particles were prepared and remained in solution through room temperature storage for at least eight weeks. The same method can be successfully employed with DHLA, MUA, and PEGylated thiol ligands.

Process for Exchanging Activated (Sulfonate Coated) Nanocrystals with a Variety of Hydrophilic Phosphonate Ligands via Biphasic Exchange Using a biphasic exchange method, dispersing the quantum dots in organic solvents such as chloroform and the exchangeable ligands in aqueous solution, quantum dots were made water soluble and stable after ligand exchange with N,N-Bis(phosphonomethyl)glycine (1) or phosphonoacetic acid (2). In a typical biphasic ligand exchange experiment, 1 nmol of quantum dots were dispersed in 1 mL of chloroform and placed in a vial with 2 mL of 300 mM phosphonic acid in basic buffer and the mixture was rapidly stirred at room temperature for 2 days. Quantum yields as high as 53% were achieved; however the quantum yields achieved were dependent on core-shell batch employed, probably as a result of variable amounts of long-chain alkyl phosphonates remaining on the nanocrystal surface post-ligand exchange. This demonstrated that complete removal of TDPA from nanocrystals is important for successful modification of the surface. Though the dots were rendered water stable by the above phosphonate-containing ligands, they were not successfully modified with PEG2000-diamine using standard EDC condensation chemistry.

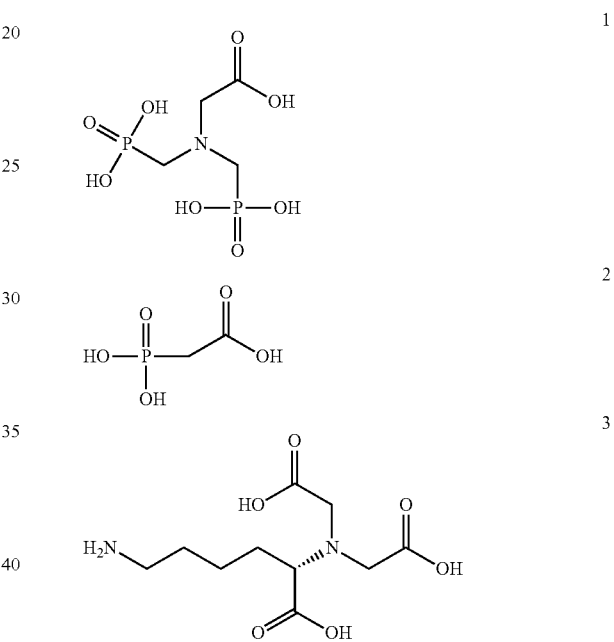

Nanocrystals coated with compounds 1, 2, or 3 were readily prepared by this method, as well as nanocrystals having a mixture of compounds 1 and 2, or 1 and 3, or 2 and 3. In each case, the nanocrystals were stable, bright and water-soluble. Using mixed ligands, it was found that PEGylation (with PEG2000-diamine using standard EDC condensation chemistry) could be achieved with these phosphonate-containing ligands to produce highly stable, bright, water soluble nanoparticles. These nanoparticles can be further stabilized by at least partially cross-linking the ligands using a diamine such as putrescine, cadaverine, 1,2-diaminoethane, bis(hexamethylene)triamine, PAMAM dendrimer, and cystamine.

Two-Step Ligand Exchange Process with Tridentate Thiol Ligands

Triflate exchange step was performed following the procedure described above. Next, the triflate nanoparticles were dispersed in organic solvent (e.g. toluene, chloroform, etc) with a concentration of between about 0.1 and 10 micromolar quantum dots. Approximately 1000 to 1000000 equivalents of a suitable tridentate thiol ligand was added, optionally as a solution in a suitable organic solvent (e.g. acetone, methanol, etc). The reaction mixture was stirred for 1-48 hours and then the solution was basicified by addition of an organic base (e.g.

tetramethylammonium hydroxide, tetrabutylammonium hydroxide, etc). After a shorter second stirring period, water or aqueous buffer was used to extract the dots with hydrophilic ligands. The aqueous solution was washed with additional organic solvent (e.g. toluene, chloroform, etc) and purified by filtration.

Example 29

Functionalized Ligands on Nanoparticles

General Core Reaction Procedure

Into a 25 mL 3 neck flask with 14/20 joints, 1.575 g of >99% tri-n-octylphosphine oxide (TOPO) was weighed. To this, 1-1000 micromoles of a bi-functional phosphonate ligand was added. A stir bar was added to this flask. The flask was connected to an inert atmosphere manifold and evacuated thoroughly, then refilled with nitrogen. A solution of a suitable cadmium salt in tri-n-octylphosphine (TOP) was prepared with a concentration of 0.5 mol Cd per kg solution. A desired amount of cadmium as required for growth of nanoparticles of a desired size was extracted from this solution, diluted with 0.9 mL of additional TOP, and added to the flask. The flask was stirred and heated to ~200-350° C. under nitrogen flow. A 1 molar solution of selenium in TOP was prepared and a desired amount as required for growth of nanoparticles of a desired size was added to the solution, optionally with addition of a reaction promoter to achieve desired levels of particle nucleation. One minute after the reaction was initiated by adding these final reagents, a 20 microliter sample was removed from the reaction, mixed with 5 mL of hexane, and an emission spectrum was collected. This aliquot removal and measurement process was repeated after 2, 3, 4, 5, 6, 7, 8, 10, 12, and 14 minutes. After 14 minutes, the reaction was rapidly cooled and the products were isolated by methods understood in the art.

Control Core Reaction with Tetradecylphosphonic Acid [TDPA]

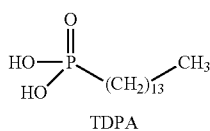

TDPA

The core reaction using TDPA as the phosphonate ligand was demonstrated as a control reaction. This reaction proceeded with an initial emission reading at 1 minute of ~490 nm and progressing to a final emission reading of ~544 nm at 14 minutes. The full width at half maximum intensity (FWHM) never got above 28 nm. The final "growth solution" of the cores was yellow/light orange in appearance by eye. The aliquoted samples of this reaction remained dispersed and clear solutions in hexane.

Core Reaction with 11-methoxy-11-oxo-undecylphosphonic acid

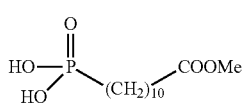

The reaction using 11-methoxy-11-oxo-undecylphosphonic acid as the phosphonate ligand proceeded with an initial emission reading at 1 minute was ~560 nm; this was redder than the final emission of the control reaction. The final emission of this reaction was ~610 nm. The FWHM of this reaction started at ~35 nm and steadily got more broad throughout the reaction for a final FWHM of ~50 nm.

The aliquoted samples were not soluble in hexane, and became almost instantly flocculated and settled to the bottom of the vials within minutes.

Core Reaction with 6-ethoxy-6-oxohexylphosphonic acid

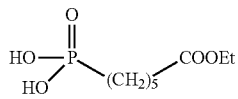

The core reaction using 6-ethoxy-6-oxohexylphosphonic acid as the phosphonate ligand had an initial emission reading at 1 minute of ~560 nm and a final emission reading of ~606 nm. The FWHM of this reaction started out at 1 minute at ~43 nm and narrowed to a final FWHM of ~40.5 nm.

The solubility of the aliquoted samples was observed. The hexane samples were immediately cloudy, however the flocculation did not settle to the bottom of the vials. Six of the aliquoted samples were centrifuged and the resulting clear, colorless supernatants were discarded. The pellets were soluble in toluene, dichloromethane ($CH_2Cl_2$), dimethylformamide (DMF), and methanol (MeOH). The pellets were not soluble in water, 50 mM borate buffer at pH=8.3 or hexane.

Particles synthesized in the presence of TDPA are soluble in hexane, toluene, $CH_2Cl_2$, DMF and hexane. The 6-ethoxy-6-oxohexylphosphonic acid itself is not soluble in hexane, and neither were the resulting particles from this reaction, suggesting that the ligand was indeed coating the nanoparticles—a suggestion which was confirmed with infrared and NMR spectroscopy indicating the expected ester functionality. Using a solvent system of toluene as the solubilizing solvent and hexane as a precipitating solvent, a pellet can be formed along with a clear, colorless supernatant. The resulting pellet can be re-solubilized in toluene. This resulting toluene solution allowed an absorbance spectrum of these cores to be obtained.

These data suggest that quantum confined nanoparticles have been formed with 6-ethoxy-6-oxohexylphosphonic acid on the particle surface. The resulting core particles were taken further into a shell reaction.

Shell Reaction Procedure using 6-ethoxy-6-oxohexylphosphonic acid

Core Precipitation

Three (3) mL of growth solution cores using 6-ethoxy-6-oxohexylphosphonic acid ligand (prepared according to the procedure of Example 28) was solubilized into 3 mL toluene in a 250 mL conical bottom centrifuge tube. A total of 135 mL of hexane was added to precipitate the cores. The tube was centrifuged at 3000 RPM for 5 min. The resulting clear, colorless supernatant was discarded and the pellet was dispersed into 3 mL of toluene.

Shell Reaction

Into a 25 mL 3 neck flask with 14/20 joints, 1.4 g of TOPO was weighed. To this, 1-1000 mg of 6-ethoxy-6-oxohexylphosphonic acid was added. A stir bar and 1.4 mL of TOP were added to the flask. The flask was connected to an inert atmosphere manifold and evacuated thoroughly, then refilled with nitrogen. 2.6 mL of the toluene solution of cores was added to the flask and the flask was warmed and evacuated to remove the toluene, then refilled with nitrogen. Approximately 1 mL of a suitably high-boiling amine was added to the flask and the flask was heated to 200-350° C. Solutions of suitable cadmium and zinc precursors in TOP were prepared with a concentration of 0.5 mol metal ion per kg of solution. A solution of 10% trimethylsilylsulfide in TOP by weight was prepared as well. The metal and sulfur precursor solutions were added slowly over the course of several hours to minimize additional nanoparticle nucleation. Sufficient shell precursors were added to grow a shell of a desired thickness, as can be calculated by one of ordinary skill in the art. When the desired shell thickness was reached, the reaction was cooled and the core/shell nanoparticles were isolated by conventional means. Aliquots taken during the reaction permitted monitoring of the progress of the shell reaction. It was observed that the emission maximum after heating but before addition of shell precursors was very similar to that of the initial cores (~600 nm), suggesting that the bi-functional phosphonate was sufficiently strongly coordinated to the nanoparticle surface to minimize Ostwald ripening. A redshift during shell precursor addition of ~50 nm was typical of a shell as deposited in a reaction employing TDPA, suggesting that the shell formed as expected. In addition, the nanoparticle solution became much more intensely emissive, as would be expected of successful deposition of an insulating shell Infrared and NMR spectroscopy confirmed that the functionalized phosphonates were present on the nanoparticles.

Example 30

Measurement of $t_{-1}$ and $t_{pol}$ Values of Modified Phi-29 and B103 Polymerases In this example, the $t_{-1}$ and $t_{pol}$ values of a Phi-29 polymerase comprising the amino acid sequence of SEQ ID NO: 3 and a B103 polymerase comprising the amino acid sequence of SEQ ID NO: 34 (referred to as "mB103" in the table below) and including amino acid substitutions at various positions were measured using a stopped-flow procedure. The stopped-flow techniques for measuring $t_{pol}$ ($1/k_{pol}$) followed the techniques described by MP Roettger (2008 Biochemistry 47:9718-9727; M. Bakhtina 2009 Biochemistry 48:3197-320).

Stopped-Flow Measurements of $t_{pol}$

```
Template C sequence:
                                    (SEQ ID NO: 44)
5'-CGTTAACCGCCCGCTCCTTTGCAAC-3'

Primer sequence:
                                    (SEQ ID NO: 45)
5'-GTTGCAAAGGAGCGGGCG-3'
```

The template sequence (SEQ ID NO: 44) further included an Alexa Fluor 546 dye moiety bonded to the 5' position of the template.

The kinetics of nucleotide incorporation by each polymerase was measured in an Applied Photophysics SX20 stopped-flow spectrometer by monitoring changes in fluorescence from the dye-labeled primer-template duplex complexed to enzyme, following the mixing of the enzyme-DNA complex with dye-labeled nucleotides. These dye-labeled nucleotides comprise terminal-phosphate-labeled nucleotides having an alkyl linker with a functional amine group attached to the dye, and have the general structure shown in FIG. 39. This structure includes a sugar bonded to a hexaphosphate chain at the 5' carbon position, and to a nucleotide base (denoted as "N"). The terminal phosphate group of the hexaphosphate is linked to a 6-carbon linker, and the other end of the 6-carbon linker is attached to a dye moiety (denoted as "dye"), typically through an amide bond. In this example, the particular dye-labeled nucleotide added was a labeled nucleotide hexaphosphate comprising a guanine base at the N (base) position and an Alexa Fluor 647 (AF647) at the dye position, and is referred to herein as "AF647-C6-dG6P".

The primer and template were annealed to form a dye-labeled primer-template duplex using standard methods. This duplex was preincubated with polymerase. The mixture included 330 nM recombinant DNA polymerase, 100 nM template/primer duplex in buffer ("reaction buffer") comprising 50 mM Tris-HCl, pH 7.5, 50 mM NaCl, 4 mM DTT, 0.2% BSA, and 2 mM MnCl$_2$. The dye-labeled nucleotide AF647-C6-dG6P was then added to a final concentration of 7 µM, and the resulting fluorescence was monitored over time.

The averaged (5 traces) stopped-flow fluorescence traces (>1.5 ms) were fitted with a double exponential equation (1) to extrapolate the rates of the nucleotide binding and product release, $$\text{Fluorescence} = A_1 * e^{-k1*t} + A_2 * e^{-kpol*t} + C \quad \text{(equation 1)}$$

where $A_1$ and $A_2$ represent corresponding fluorescence amplitudes, C is an offset constant, and k1 and kpol are the observed rate constants for the fast and slow phases of the fluorescence transition, respectively.

Stopped-Flow Measurements of $t_{-1}$

The stopped-flow techniques for measuring $t_{-1}$ ($1/k_{-1}$) followed the techniques described by M. Bakhtina (2009 Biochemistry 48:3197-3208).

```
Template C sequence:
                                    (SEQ ID NO: 46)
5'-CAGTAACGG AGT TGG TTG GAC GGC TGC GAG GC-3'

Dideoxy-primer sequence:
                                    (SEQ ID NO: 47)
5'-GCC TCG CAG CCG TCC AAC CAA CTC ddC-3'
```

The rate of the nucleotide dissociation ($k_1$) from the ternary complex of [enzyme.DNA.nucleotide] was measured in an Applied Photophysics SX20 stopped-flow spectrometer by monitoring changes in fluorescence from in fluorescence from a duplex Alexa fluor 546 dye-labeled-DNA template following the mixing of the [enzyme.DNA.labeled nucleotide] ternary complex with 50 µM cognate non-labeled deoxynucleoside triphosphate in a buffer containing 50 mM Tris-HCl (pH 7.5), 50 mM NaCl, 4 mM DTT, 0.2% BSA, and 2 mM MnCl$_2$.

The ternary complexes were prepared using: 330 nM polymerase, 100 nM template/primer duplex, and 7 µM terminal phosphate-labeled nucleotides (AF647-C6-dG6P).

The averaged stopped-flow fluorescence traces (>1.5 msec) were fitted with a single exponential equation (2) to extrapolate the rate of the nucleotide dissociation ($k_{-1}$) from the [enzyme.DNA.nucleotide] ternary complex.

$$\text{Fluorescence} = A_1 * e^{-k-1*t} C \quad \text{(equation 2)}$$

where $A_1$ represents the corresponding fluorescence amplitude, C is an offset constant, and $k_{-1}$ and the observed rate constants for the fluorescence transition.

Some representative results of the stopped flow data are shown in the Table below:

TABLE

Summary of $t_{pol}$ and $t_{-1}$ measurements for various exemplary modified Phi-29 and B103 polymerases

| Protein | $t_{pol}$ | $t_{-1}$ |
|---|---|---|
| mB103 (SEQ ID: 8) | 14 | 16 |
| mB103 + H370R | 17 | 43 |
| mB103 + H370Y | 15 | 12 |
| mB103 + E371R | 11 | 17 |
| mB103 + E371Y | 11 | 7 |
| K372R | 14 | 12 |
| K380R | 783 | 17 |
| mB103 + D507G | 11 | 13 |
| mB103 + D507H | 7 | 16 |
| mB103 + K509Y | 10 | 20 |
| Phi-29 (exo−) | 11 | 27 |
| Phi-29 (exo−) + T373R | 15 | 81 |
| Phi-29 (exo−) + T373Y | 14 | 45 |

What is claimed is:

1. A composition, comprising a polymerase-nanoparticle conjugate including a polymerase linked to a nanoparticle, wherein the conjugate has polymerase activity, and wherein the polymerase-nanoparticle conjugate includes a template nucleic acid molecule, a polymerization initiation site, and lacks a helicase.

2. The composition of claim 1, wherein the polymerase activity of the conjugate is at least 1% relative to the polymerase activity of the unconjugated polymerase.

3. The composition of claim 2, wherein the polymerase activity is at least 70% relative to the polymerase activity of the unconjugated polymerase.

4. The composition of claim 1, wherein the polymerase comprises a His tag.

5. The composition of claim 1, wherein the polymerase comprises one member of a binding pair and the nanoparticle comprises a complementary member of the binding pair.

6. The composition of claim 1, wherein the polymerase is a DNA polymerase.

7. The composition of claim 6, wherein the DNA polymerase is at least 95% identical to a DNA polymerase selected from the group consisting of: Phi-29 DNA polymerase, B103 DNA polymerase, the Klenow fragment of *E. coli* DNA polymerase and HIV reverse transcriptase.

8. The composition of claim 1, wherein the polymerase link is selected from one of a group consisting of: covalent bonding, affinity bonding and electrostatic bonding.

9. The composition of claim 1, wherein the nanoparticle has a surface coating including a ligand selected from the group consisting of: a DHLA-based ligand, a polycyclic acid-based ligand, a bipeptide ligand and a tridentate thiol-based ligand.

10. The composition of claim 1, wherein the nanoparticle includes a DHLA-based ligand coating.

11. The composition of claim 1, wherein the nanoparticle includes a polycyclic acid-based ligand coating.

12. The composition of claim 1, wherein the nanoparticle includes a tripodal thiol-based ligand coating.

13. The composition of claim 1, wherein the nanoparticle includes a dipeptide-based coating.

14. The composition of claim 1, wherein the nanoparticle is positioned relative to the polymerase to perform an energy transfer reaction.

15. The composition of claim 1, wherein the nanoparticle is positioned to undergo FRET with a labeled nucleotide bound to the nucleotide binding site of the polymerase.

16. The composition of claim 15, wherein labeled nucleotide further comprises an Alexa Fluor dye linked to the terminal phosphate of the nucleotide, and the nanoparticle undergoes FRET with the Alexa Fluor dye with a FRET efficiency of at least 20%.

17. The composition of claim 1, where the polymerase includes an N-terminal cysteine, and where N-terminal cysteine is linked to the nanoparticle through a covalent bond.

18. The composition of claim 17, wherein the covalent bond is formed between a thioester surface ligand of the nanoparticle and a thiol group of the N-terminal cysteine.

19. The composition of claim 17, wherein the covalent bond is formed between an aldehyde surface ligand of the nanoparticle and a thiol group of the N-terminal cysteine.

20. The composition of claim 1, further comprising a template nucleic acid molecule and a nucleotide.

* * * * *

SEQUENCE LISTING

<160> NUMBER OF SEQ ID NOS: 91

<210> SEQ ID NO 1
<211> LENGTH: 928
<212> TYPE: PRT
<213> ORGANISM: Escherichia coli

<400> SEQUENCE: 1

Met Val Gln Ile Pro Gln Asn Pro Leu Ile Leu Val Asp Gly Ser Ser
1               5                   10                  15

Tyr Leu Tyr Arg Ala Tyr His Ala Phe Pro Leu Thr Asn Ser Ala
            20                  25                  30

Gly Glu Pro Thr Gly Ala Met Tyr Gly Val Leu Asn Met Leu Arg Ser
            35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
    210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

```
Glu Glu Leu Leu Gly Leu Phe Lys Lys Tyr Glu Phe Lys Arg Trp Thr
        275                 280                 285

Ala Asp Val Glu Ala Gly Lys Trp Leu Gln Ala Lys Gly Ala Lys Pro
290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
        355                 360                 365

Val Gly Leu Ser Phe Ala Ile Glu Pro Gly Val Ala Ala Tyr Ile Pro
370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
                405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
        435                 440                 445

Leu Asn Ser Val Ala Gly Arg His Asp Met Asp Ser Leu Ala Glu Arg
450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
                485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
        515                 520                 525

Ile Glu Met Pro Leu Val Pro Val Leu Ser Arg Ile Glu Arg Asn Gly
530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
                565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
        595                 600                 605

Thr Ser Glu Glu Val Leu Glu Glu Leu Ala Leu Asp Tyr Pro Leu Pro
610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
                645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
        675                 680                 685
```

Ile Arg Gln Ala Phe Ile Ala Pro Glu Asp Tyr Val Ile Ser Ala
690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
            725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met
            755                 760                 765

Ser Ala Phe Gly Leu Ala Arg Gln Leu Asn Ile Pro Arg Lys Glu Ala
770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
            805                 810                 815

Thr Leu Asp Gly Arg Arg Leu Tyr Leu Pro Asp Ile Lys Ser Ser Asn
            820                 825                 830

Gly Ala Arg Arg Ala Ala Ala Glu Arg Ala Ala Ile Asn Ala Pro Met
            835                 840                 845

Gln Gly Thr Ala Ala Asp Ile Ile Lys Arg Ala Met Ile Ala Val Asp
850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Asp Val Asp Ala Val
            885                 890                 895

Ala Lys Gln Ile His Gln Leu Met Glu Asn Cys Thr Arg Leu Asp Val
            900                 905                 910

Pro Leu Leu Val Glu Val Gly Ser Gly Glu Asn Trp Asp Gln Ala His
            915                 920                 925

<210> SEQ ID NO 2
<211> LENGTH: 606
<212> TYPE: PRT
<213> ORGANISM: Escherichia coli

<400> SEQUENCE: 2

Met Val Ile Ser Tyr Asp Asn Tyr Val Thr Ile Leu Asp Glu Glu Thr
1               5                   10                  15

Leu Lys Ala Trp Ile Ala Lys Leu Glu Lys Ala Pro Val Phe Ala Phe
            20                  25                  30

Asp Thr Glu Thr Asp Ser Leu Asp Asn Ile Ser Ala Asn Leu Val Gly
            35                  40                  45

Leu Ser Phe Ala Ile Glu Pro Gly Val Ala Ala Tyr Ile Pro Val Ala
            50                  55                  60

His Asp Tyr Leu Asp Ala Pro Asp Gln Ile Ser Arg Glu Arg Ala Leu
65                  70                  75                  80

Glu Leu Leu Lys Pro Leu Leu Glu Asp Glu Lys Ala Leu Lys Val Gly
            85                  90                  95

Gln Asn Leu Lys Tyr Asp Arg Gly Ile Leu Ala Asn Tyr Gly Ile Glu
            100                 105                 110

Leu Arg Gly Ile Ala Phe Asp Thr Met Leu Glu Ser Tyr Ile Leu Asn
            115                 120                 125

Ser Val Ala Gly Arg His Asp Met Asp Ser Leu Ala Glu Arg Trp Leu
130                 135                 140

```
Lys His Lys Thr Ile Thr Phe Glu Glu Ile Ala Gly Lys Gly Lys Asn
145                 150                 155                 160

Gln Leu Thr Phe Asn Gln Ile Ala Leu Glu Glu Ala Gly Arg Tyr Ala
            165                 170                 175

Ala Glu Asp Ala Asp Val Thr Leu Gln Leu His Leu Lys Met Trp Pro
        180                 185                 190

Asp Leu Gln Lys His Lys Gly Pro Leu Asn Val Phe Glu Asn Ile Glu
    195                 200                 205

Met Pro Leu Val Pro Val Leu Ser Arg Ile Glu Arg Asn Gly Val Lys
210                 215                 220

Ile Asp Pro Lys Val Leu His Asn His Ser Glu Leu Thr Leu Arg
225                 230                 235                 240

Leu Ala Glu Leu Glu Lys Lys Ala His Glu Ile Ala Gly Glu Phe
                245                 250                 255

Asn Leu Ser Ser Thr Lys Gln Leu Gln Thr Ile Leu Phe Glu Lys Gln
            260                 265                 270

Gly Ile Lys Pro Leu Lys Lys Thr Pro Gly Gly Ala Pro Ser Thr Ser
        275                 280                 285

Glu Glu Val Leu Glu Glu Leu Ala Leu Asp Tyr Pro Leu Pro Lys Val
    290                 295                 300

Ile Leu Glu Tyr Arg Gly Leu Ala Lys Leu Lys Ser Thr Tyr Thr Asp
305                 310                 315                 320

Lys Leu Pro Leu Met Ile Asn Pro Lys Thr Gly Arg Val His Thr Ser
                325                 330                 335

Tyr His Gln Ala Val Thr Ala Thr Gly Arg Leu Ser Ser Thr Asp Pro
                340                 345                 350

Asn Leu Gln Asn Ile Pro Val Arg Asn Glu Glu Gly Arg Arg Ile Arg
            355                 360                 365

Gln Ala Phe Ile Ala Pro Glu Asp Tyr Val Ile Val Ser Ala Asp Tyr
        370                 375                 380

Ser Gln Ile Glu Leu Arg Ile Met Ala His Leu Ser Arg Asp Lys Gly
385                 390                 395                 400

Leu Leu Thr Ala Phe Ala Glu Gly Lys Asp Ile His Arg Ala Thr Ala
                405                 410                 415

Ala Glu Val Phe Gly Leu Pro Leu Glu Thr Val Thr Ser Glu Gln Arg
            420                 425                 430

Arg Ser Ala Lys Ala Ile Asn Phe Gly Leu Ile Tyr Gly Met Ser Ala
        435                 440                 445

Phe Gly Leu Ala Arg Gln Leu Asn Ile Pro Arg Lys Glu Ala Gln Lys
    450                 455                 460

Tyr Met Asp Leu Tyr Phe Glu Arg Tyr Pro Gly Val Leu Glu Tyr Met
465                 470                 475                 480

Glu Arg Thr Arg Ala Gln Ala Lys Glu Gln Gly Tyr Val Glu Thr Leu
                485                 490                 495

Asp Gly Arg Arg Leu Tyr Leu Pro Asp Ile Lys Ser Ser Asn Gly Ala
            500                 505                 510

Arg Arg Ala Ala Ala Glu Arg Ala Ala Ile Asn Ala Pro Met Gln Gly
        515                 520                 525

Thr Ala Ala Asp Ile Ile Lys Arg Ala Met Ile Ala Val Asp Ala Trp
    530                 535                 540

Leu Gln Ala Glu Gln Pro Arg Val Arg Met Ile Met Gln Val His Asp
545                 550                 555                 560
```

```
Glu Leu Val Phe Glu Val His Lys Asp Asp Val Asp Ala Val Ala Lys
                565                 570                 575

Gln Ile His Gln Leu Met Glu Asn Cys Thr Arg Leu Asp Val Pro Leu
                580                 585                 590

Leu Val Glu Val Gly Ser Gly Glu Asn Trp Asp Gln Ala His
            595                 600                 605

<210> SEQ ID NO 3
<211> LENGTH: 575
<212> TYPE: PRT
<213> ORGANISM: Bacillus sp.
<220> FEATURE:
<223> OTHER INFORMATION: Phage Phi-29

<400> SEQUENCE: 3

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
            130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320
```

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Gly Ala Ala Ala Lys Gly Ala Ala Lys Gly Ser Ala Ala
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Leu Gly Gly Gly Ser Gly Gly Gly Ser Ala Ala Gly
1               5                   10                  15

Ser Ala Ala

<210> SEQ ID NO 6
<211> LENGTH: 602
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Cys Cys Cys Cys Cys Cys Cys Cys Cys Cys Leu Leu Gly
1               5                   10                  15

Gly Gly Gly Ser Gly Gly Gly Ser Ala Ala Ala Gly Ser Ala Ala
            20                  25                  30

Arg Lys Met Tyr Ser Cys Asp Phe Glu Thr Thr Thr Lys Val Glu Asp
        35                  40                  45

Cys Arg Val Trp Ala Tyr Gly Tyr Met Asn Ile Glu Asp His Ser Glu
    50                  55                  60

Tyr Lys Ile Gly Asn Ser Leu Asp Glu Phe Met Ala Trp Val Leu Lys
65                  70                  75                  80

Val Gln Ala Asp Leu Tyr Phe His Asn Leu Lys Phe Asp Gly Ala Phe
                85                  90                  95

Ile Ile Asn Trp Leu Glu Arg Asn Gly Phe Lys Trp Ser Ala Asp Gly
            100                 105                 110

Leu Pro Asn Thr Tyr Asn Thr Ile Ile Ser Arg Met Gly Gln Trp Tyr
        115                 120                 125

Met Ile Asp Ile Cys Leu Gly Tyr Lys Gly Lys Arg Lys Ile His Thr
    130                 135                 140

Val Ile Tyr Asp Ser Leu Lys Lys Leu Pro Phe Pro Val Lys Lys Ile
145                 150                 155                 160

Ala Lys Asp Phe Lys Leu Thr Val Leu Lys Gly Asp Ile Asp Tyr His
                165                 170                 175

Lys Glu Arg Pro Val Gly Tyr Lys Ile Thr Pro Glu Glu Tyr Ala Tyr
            180                 185                 190

Ile Lys Asn Asp Ile Gln Ile Ile Ala Glu Ala Leu Leu Ile Gln Phe
        195                 200                 205

Lys Gln Gly Leu Asp Arg Met Thr Ala Gly Ser Asp Ser Leu Lys Gly
    210                 215                 220

Phe Lys Asp Ile Ile Thr Thr Lys Lys Phe Lys Lys Val Phe Pro Thr
225                 230                 235                 240

Leu Ser Leu Gly Leu Asp Lys Glu Val Arg Tyr Ala Tyr Arg Gly Gly
                245                 250                 255

Phe Thr Trp Leu Asn Asp Arg Phe Lys Glu Lys Glu Ile Gly Glu Gly
            260                 265                 270

Met Val Phe Asp Val Asn Ser Leu Tyr Pro Ala Gln Met Tyr Ser Arg
        275                 280                 285

Leu Leu Pro Tyr Gly Glu Pro Ile Val Phe Glu Gly Lys Tyr Val Trp
    290                 295                 300

Asp Glu Asp Tyr Pro Leu His Ile Gln His Ile Arg Cys Glu Phe Glu
305                 310                 315                 320

Leu Lys Glu Gly Tyr Ile Pro Thr Ile Gln Ile Lys Arg Ser Arg Phe
                325                 330                 335

Tyr Lys Gly Asn Glu Tyr Leu Lys Ser Ser Gly Gly Glu Ile Ala Asp
            340                 345                 350

Leu Trp Leu Ser Asn Val Asp Leu Glu Leu Met Lys Glu His Tyr Asp
        355                 360                 365
```

```
Leu Tyr Asn Val Glu Tyr Ile Ser Gly Leu Lys Phe Lys Ala Thr Thr
    370                 375                 380

Gly Leu Phe Lys Asp Phe Ile Asp Lys Trp Thr Tyr Ile Lys Thr Thr
385                 390                 395                 400

Ser Glu Gly Ala Ile Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asn Gly Ala Leu Gly Phe Arg Leu Gly Glu Glu Glu Thr
        435                 440                 445

Lys Asp Pro Val Tyr Thr Pro Met Gly Val Phe Ile Thr Ala Trp Ala
450                 455                 460

Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
                485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Met Lys Glu Val Asp Gly Lys Leu Val Glu Gly Ser
    530                 535                 540

Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
                565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
        595                 600

<210> SEQ ID NO 7
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Lys Lys Lys Lys Lys Lys Lys Lys Lys Leu Leu Gly
1               5                   10                  15

Gly Gly Gly Ser Gly Gly Gly Ser Ala Ala Ala Gly Ser Ala Ala
                20                  25                  30

Arg Lys Met Tyr Ser Cys Asp Phe Glu Thr Thr Thr Lys Val Glu Asp
            35                  40                  45

Cys Arg Val Trp Ala Tyr Gly Tyr Met Asn Ile Glu Asp His Ser Glu
        50                  55                  60

Tyr Lys Ile Gly Asn Ser Leu Asp Glu Phe Met Ala Trp Val Leu Lys
65                  70                  75                  80

Val Gln Ala Asp Leu Tyr Phe His Asn Leu Lys Phe Asp Gly Ala Phe
                85                  90                  95

Ile Ile Asn Trp Leu Glu Arg Asn Gly Phe Lys Trp Ser Ala Asp Gly
            100                 105                 110

Leu Pro Asn Thr Tyr Asn Thr Ile Ile Ser Arg Met Gly Gln Trp Tyr
        115                 120                 125
```

```
Met Ile Asp Ile Cys Leu Gly Tyr Lys Gly Lys Arg Lys Ile His Thr
            130                 135                 140

Val Ile Tyr Asp Ser Leu Lys Lys Leu Pro Phe Pro Val Lys Lys Ile
145                 150                 155                 160

Ala Lys Asp Phe Lys Leu Thr Val Leu Lys Gly Asp Ile Asp Tyr His
                165                 170                 175

Lys Glu Arg Pro Val Gly Tyr Lys Ile Thr Pro Glu Glu Tyr Ala Tyr
            180                 185                 190

Ile Lys Asn Asp Ile Gln Ile Ala Glu Ala Leu Leu Ile Gln Phe
        195                 200                 205

Lys Gln Gly Leu Asp Arg Met Thr Ala Gly Ser Asp Ser Leu Lys Gly
    210                 215                 220

Phe Lys Asp Ile Ile Thr Thr Lys Lys Phe Lys Lys Val Phe Pro Thr
225                 230                 235                 240

Leu Ser Leu Gly Leu Asp Lys Glu Val Arg Tyr Ala Tyr Arg Gly Gly
                245                 250                 255

Phe Thr Trp Leu Asn Asp Arg Phe Lys Glu Lys Glu Ile Gly Glu Gly
            260                 265                 270

Met Val Phe Asp Val Asn Ser Leu Tyr Pro Ala Gln Met Tyr Ser Arg
    275                 280                 285

Leu Leu Pro Tyr Gly Glu Pro Ile Val Phe Glu Gly Lys Tyr Val Trp
    290                 295                 300

Asp Glu Asp Tyr Pro Leu His Ile Gln His Ile Arg Cys Glu Phe Glu
305                 310                 315                 320

Leu Lys Glu Gly Tyr Ile Pro Thr Ile Gln Ile Lys Arg Ser Arg Phe
                325                 330                 335

Tyr Lys Gly Asn Glu Tyr Leu Lys Ser Ser Gly Gly Glu Ile Ala Asp
            340                 345                 350

Leu Trp Leu Ser Asn Val Asp Leu Glu Leu Met Lys Glu His Tyr Asp
        355                 360                 365

Leu Tyr Asn Val Glu Tyr Ile Ser Gly Leu Lys Phe Lys Ala Thr Thr
    370                 375                 380

Gly Leu Phe Lys Asp Phe Ile Asp Lys Trp Thr Tyr Ile Lys Thr Thr
385                 390                 395                 400

Ser Glu Gly Ala Ile Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asn Gly Ala Leu Gly Phe Arg Leu Gly Glu Glu Thr
        435                 440                 445

Lys Asp Pro Val Tyr Thr Pro Met Gly Val Phe Ile Thr Ala Trp Ala
    450                 455                 460

Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
                485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Met Lys Glu Val Asp Gly Lys Leu Val Glu Gly Ser
    530                 535                 540
```

```
Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
                565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
            595                 600

<210> SEQ ID NO 8
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met His His His His His Leu Leu Gly Gly Gly Ser Gly Gly
1               5                   10                  15

Gly Gly Ser Ala Ala Pro Lys Pro Gln Gln Phe Gly Ser Ala Ala
            20                  25                  30

Arg Lys Met Tyr Ser Cys Asp Phe Glu Thr Thr Thr Lys Val Glu Asp
                35                  40                  45

Cys Arg Val Trp Ala Tyr Gly Tyr Met Asn Ile Glu Asp His Ser Glu
            50                  55                  60

Tyr Lys Ile Gly Asn Ser Leu Asp Glu Phe Met Ala Trp Val Leu Lys
65                  70                  75                  80

Val Gln Ala Asp Leu Tyr Phe His Asn Leu Lys Phe Asp Gly Ala Phe
                85                  90                  95

Ile Ile Asn Trp Leu Glu Arg Asn Gly Phe Lys Trp Ser Ala Asp Gly
            100                 105                 110

Leu Pro Asn Thr Tyr Asn Thr Ile Ile Ser Arg Met Gly Gln Trp Tyr
        115                 120                 125

Met Ile Asp Ile Cys Leu Gly Tyr Lys Gly Lys Arg Lys Ile His Thr
130                 135                 140

Val Ile Tyr Asp Ser Leu Lys Lys Leu Pro Phe Pro Val Lys Lys Ile
145                 150                 155                 160

Ala Lys Asp Phe Lys Leu Thr Val Leu Lys Gly Asp Ile Asp Tyr His
                165                 170                 175

Lys Glu Arg Pro Val Gly Tyr Lys Ile Thr Pro Glu Glu Tyr Ala Tyr
            180                 185                 190

Ile Lys Asn Asp Ile Gln Ile Ile Ala Glu Ala Leu Leu Ile Gln Phe
        195                 200                 205

Lys Gln Gly Leu Asp Arg Met Thr Ala Gly Ser Asp Ser Leu Lys Gly
    210                 215                 220

Phe Lys Asp Ile Ile Thr Thr Lys Lys Phe Lys Lys Val Phe Pro Thr
225                 230                 235                 240

Leu Ser Leu Gly Leu Asp Lys Glu Val Arg Tyr Ala Tyr Arg Gly Gly
                245                 250                 255

Phe Thr Trp Leu Asn Asp Arg Phe Lys Glu Lys Glu Ile Gly Glu Gly
            260                 265                 270

Met Val Phe Asp Val Asn Ser Leu Tyr Pro Ala Gln Met Tyr Ser Arg
        275                 280                 285

Leu Leu Pro Tyr Gly Glu Pro Ile Val Phe Glu Gly Lys Tyr Val Trp
    290                 295                 300
```

```
Asp Glu Asp Tyr Pro Leu His Ile Gln His Ile Arg Cys Glu Phe Glu
305                 310                 315                 320

Leu Lys Glu Gly Tyr Ile Pro Thr Ile Gln Ile Lys Arg Ser Arg Phe
            325                 330                 335

Tyr Lys Gly Asn Glu Tyr Leu Lys Ser Ser Gly Gly Ile Ala Asp
            340                 345                 350

Leu Trp Leu Ser Asn Val Asp Leu Glu Leu Met Lys Glu His Tyr Asp
        355                 360                 365

Leu Tyr Asn Val Glu Tyr Ile Ser Gly Leu Lys Phe Lys Ala Thr Thr
    370                 375                 380

Gly Leu Phe Lys Asp Phe Ile Asp Lys Trp Thr Tyr Ile Lys Thr Thr
385                 390                 395                 400

Ser Glu Gly Ala Ile Lys Gln Leu Ala Lys Leu Met Leu Asn Ser Leu
            405                 410                 415

Tyr Gly Lys Phe Ala Ser Asn Pro Asp Val Thr Gly Lys Val Pro Tyr
            420                 425                 430

Leu Lys Glu Asn Gly Ala Leu Gly Phe Arg Leu Gly Glu Glu Thr
        435                 440                 445

Lys Asp Pro Val Tyr Thr Pro Met Gly Val Phe Ile Thr Ala Trp Ala
450                 455                 460

Arg Tyr Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Ile Pro Asp
            485                 490                 495

Val Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Met Lys Glu Val Asp Gly Lys Leu Val Glu Gly Ser
    530                 535                 540

Pro Asp Asp Tyr Thr Asp Ile Lys Phe Ser Val Lys Cys Ala Gly Met
545                 550                 555                 560

Thr Asp Lys Ile Lys Lys Glu Val Thr Phe Glu Asn Phe Lys Val Gly
                565                 570                 575

Phe Ser Arg Lys Met Lys Pro Lys Pro Val Gln Val Pro Gly Gly Val
            580                 585                 590

Val Leu Val Asp Asp Thr Phe Thr Ile Lys
            595                 600

<210> SEQ ID NO 9
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Leu Arg Arg Ala Ser Leu His His Leu Leu Gly Gly Gly Gly
1               5                   10                  15

Ser Gly Gly Gly Gly Ser Ala Ala Gly Ser Ala Ala Arg Lys Met
            20                  25                  30

Tyr Ser Cys Asp Phe Glu Thr Thr Thr Lys Val Glu Asp Cys Arg Val
            35                  40                  45

Trp Ala Tyr Gly Tyr Met Asn Ile Glu Asp His Ser Glu Tyr Lys Ile
```

-continued

```
                    50                  55                  60
Gly Asn Ser Leu Asp Glu Phe Met Ala Trp Val Leu Lys Val Gln Ala
 65                  70                  75                  80

Asp Leu Tyr Phe His Asn Leu Lys Phe Asp Gly Ala Phe Ile Ile Asn
                 85                  90                  95

Trp Leu Glu Arg Asn Gly Phe Lys Trp Ser Ala Asp Gly Leu Pro Asn
            100                 105                 110

Thr Tyr Asn Thr Ile Ile Ser Arg Met Gly Gln Trp Tyr Met Ile Asp
        115                 120                 125

Ile Cys Leu Gly Tyr Lys Gly Lys Arg Lys Ile His Thr Val Ile Tyr
130                 135                 140

Asp Ser Leu Lys Lys Leu Pro Phe Pro Val Lys Ile Ala Lys Asp
145                 150                 155                 160

Phe Lys Leu Thr Val Leu Lys Gly Asp Ile Asp Tyr His Lys Glu Arg
                165                 170                 175

Pro Val Gly Tyr Lys Ile Thr Pro Glu Glu Tyr Ala Tyr Ile Lys Asn
            180                 185                 190

Asp Ile Gln Ile Ile Ala Glu Ala Leu Leu Ile Gln Phe Lys Gln Gly
        195                 200                 205

Leu Asp Arg Met Thr Ala Gly Ser Asp Ser Leu Lys Gly Phe Lys Asp
210                 215                 220

Ile Ile Thr Thr Lys Lys Phe Lys Lys Val Phe Pro Thr Leu Ser Leu
225                 230                 235                 240

Gly Leu Asp Lys Glu Val Arg Tyr Ala Tyr Arg Gly Gly Phe Thr Trp
                245                 250                 255

Leu Asn Asp Arg Phe Lys Glu Lys Glu Ile Gly Glu Gly Met Val Phe
            260                 265                 270

Asp Val Asn Ser Leu Tyr Pro Ala Gln Met Tyr Ser Arg Leu Leu Pro
        275                 280                 285

Tyr Gly Glu Pro Ile Val Phe Glu Gly Lys Tyr Val Trp Asp Glu Asp
290                 295                 300

Tyr Pro Leu His Ile Gln His Ile Arg Cys Glu Phe Glu Leu Lys Glu
305                 310                 315                 320

Gly Tyr Ile Pro Thr Ile Gln Ile Lys Arg Ser Arg Phe Tyr Lys Gly
                325                 330                 335

Asn Glu Tyr Leu Lys Ser Ser Gly Gly Glu Ile Ala Asp Leu Trp Leu
            340                 345                 350

Ser Asn Val Asp Leu Glu Leu Met Lys Glu His Tyr Asp Leu Tyr Asn
        355                 360                 365

Val Glu Tyr Ile Ser Gly Leu Lys Phe Lys Ala Thr Thr Gly Leu Phe
370                 375                 380

Lys Asp Phe Ile Asp Lys Trp Thr Tyr Ile Lys Thr Thr Ser Glu Gly
385                 390                 395                 400

Ala Ile Lys Gln Leu Ala Lys Leu Met Leu Asn Ser Leu Tyr Gly Lys
                405                 410                 415

Phe Ala Ser Asn Pro Asp Val Thr Gly Lys Val Pro Tyr Leu Lys Glu
            420                 425                 430

Asn Gly Ala Leu Gly Phe Arg Leu Gly Glu Glu Thr Lys Asp Pro
        435                 440                 445

Val Tyr Thr Pro Met Gly Val Phe Ile Thr Ala Trp Ala Arg Tyr Thr
450                 455                 460

Thr Ile Thr Ala Ala Gln Ala Cys Tyr Asp Arg Ile Ile Tyr Cys Asp
465                 470                 475                 480
```

```
Thr Asp Ser Ile His Leu Thr Gly Thr Glu Ile Pro Asp Val Ile Lys
            485                 490                 495

Asp Ile Val Asp Pro Lys Lys Leu Gly Tyr Trp Ala His Glu Ser Thr
        500                 505                 510

Phe Lys Arg Ala Lys Tyr Leu Arg Gln Lys Thr Tyr Ile Gln Asp Ile
    515                 520                 525

Tyr Met Lys Glu Val Asp Gly Lys Leu Val Glu Gly Ser Pro Asp Asp
530                 535                 540

Tyr Thr Asp Ile Lys Phe Ser Val Lys Cys Ala Gly Met Thr Asp Lys
545                 550                 555                 560

Ile Lys Lys Glu Val Thr Phe Glu Asn Phe Lys Val Gly Phe Ser Arg
                565                 570                 575

Lys Met Lys Pro Lys Pro Val Gln Val Pro Gly Gly Val Val Leu Val
            580                 585                 590

Asp Asp Thr Phe Thr Ile Lys
            595
```

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Gly Leu Asn Asp Ile Phe Glu Ala Gln Lys Ile Glu Trp His Glu
1               5                   10                  15
```

<210> SEQ ID NO 11
<211> LENGTH: 608
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Ser His His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Tyr Ser Cys Ala Phe Glu Thr
        35                  40                  45

Thr Thr Lys Val Glu Asp Cys Arg Val Trp Ala Tyr Gly Tyr Met Asn
    50                  55                  60

Ile Glu Asp His Ser Glu Tyr Lys Ile Gly Asn Ser Leu Asp Glu Phe
65                  70                  75                  80

Met Ala Trp Val Leu Lys Val Gln Ala Asp Leu Tyr Phe His Asn Leu
                85                  90                  95

Lys Phe Ala Gly Ala Phe Ile Ile Asn Trp Leu Glu Arg Asn Gly Phe
            100                 105                 110

Lys Trp Ser Ala Asp Gly Leu Pro Asn Thr Tyr Asn Thr Ile Ile Ser
        115                 120                 125

Arg Met Gly Gln Trp Tyr Met Ile Asp Ile Cys Leu Gly Tyr Lys Gly
    130                 135                 140

Lys Arg Lys Ile His Thr Val Ile Tyr Asp Ser Leu Lys Lys Leu Pro
145                 150                 155                 160
```

```
Phe Pro Val Lys Lys Ile Ala Lys Asp Phe Lys Leu Thr Val Leu Lys
            165                 170                 175

Gly Asp Ile Asp Tyr His Lys Glu Arg Pro Val Gly Tyr Lys Ile Thr
        180                 185                 190

Pro Glu Glu Tyr Ala Tyr Ile Lys Asn Asp Ile Gln Ile Ile Ala Glu
        195                 200                 205

Ala Leu Leu Ile Gln Phe Lys Gln Gly Leu Asp Arg Met Thr Ala Gly
        210                 215                 220

Ser Asp Ser Leu Lys Gly Phe Lys Asp Ile Ile Thr Thr Lys Lys Phe
225                 230                 235                 240

Lys Lys Val Phe Pro Thr Leu Ser Leu Gly Leu Asp Lys Glu Val Arg
                245                 250                 255

Tyr Ala Tyr Arg Gly Gly Phe Thr Trp Leu Asn Asp Arg Phe Lys Glu
                260                 265                 270

Lys Glu Ile Gly Glu Gly Met Val Phe Asp Val Asn Ser Leu Tyr Pro
                275                 280                 285

Ala Gln Met Tyr Ser Arg Leu Leu Pro Tyr Gly Glu Pro Ile Val Phe
                290                 295                 300

Glu Gly Lys Tyr Val Trp Asp Glu Asp Tyr Pro Leu His Ile Gln His
305                 310                 315                 320

Ile Arg Cys Glu Phe Glu Leu Lys Glu Gly Tyr Ile Pro Thr Ile Gln
                325                 330                 335

Ile Lys Arg Ser Arg Phe Tyr Lys Gly Asn Glu Tyr Leu Lys Ser Ser
                340                 345                 350

Gly Gly Glu Ile Ala Asp Leu Trp Leu Ser Asn Val Asp Leu Glu Leu
                355                 360                 365

Met Lys Glu His Tyr Asp Leu Tyr Asn Val Glu Tyr Ile Ser Gly Leu
                370                 375                 380

Lys Phe Lys Ala Thr Thr Gly Leu Phe Lys Asp Phe Ile Asp Lys Trp
385                 390                 395                 400

Thr Tyr Ile Lys Thr Thr Ser Glu Gly Ala Ile Lys Gln Leu Ala Lys
                405                 410                 415

Leu Met Leu Asn Ser Leu Tyr Gly Lys Phe Ala Ser Asn Pro Asp Val
                420                 425                 430

Thr Gly Lys Val Pro Tyr Leu Lys Glu Asn Gly Ala Leu Gly Phe Arg
                435                 440                 445

Leu Gly Glu Glu Glu Thr Lys Asp Pro Val Tyr Thr Pro Met Gly Val
450                 455                 460

Phe Ile Thr Ala Trp Ala Arg Tyr Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Ile Pro Asp Val Ile Lys Asp Ile Val Asp Pro Lys Lys
                500                 505                 510

Leu Gly Tyr Trp Ala His Glu Ser Thr Phe Lys Arg Ala Lys Tyr Leu
                515                 520                 525

Arg Gln Lys Thr Tyr Ile Gln Asp Ile Tyr Met Lys Glu Val Asp Gly
                530                 535                 540

Lys Leu Val Glu Gly Ser Pro Asp Asp Tyr Thr Asp Ile Lys Phe Ser
545                 550                 555                 560

Val Lys Cys Ala Gly Met Thr Asp Lys Ile Lys Lys Glu Val Thr Phe
                565                 570                 575
```

```
Glu Asn Phe Lys Val Gly Phe Ser Arg Lys Met Lys Pro Lys Pro Val
                580                 585                 590

Gln Val Pro Gly Gly Val Val Leu Val Asp Asp Thr Phe Thr Ile Lys
        595                 600                 605
```

<210> SEQ ID NO 12
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met His His His His His Leu Leu Gly Ala Ala Lys Gly Ala
1               5                   10                  15

Ala Ala Lys Gly Ser Ala Ala Arg Lys Met Tyr Ser Cys Asp Phe Glu
                20                  25                  30

Thr Thr Thr Lys Val Glu Asp Cys Arg Val Trp Ala Tyr Gly Tyr Met
                35                  40                  45

Asn Ile Glu Asp His Ser Glu Tyr Lys Ile Gly Asn Ser Leu Asp Glu
50                  55                  60

Phe Met Ala Trp Val Leu Lys Val Gln Ala Asp Leu Tyr Phe His Asn
65                  70                  75                  80

Leu Lys Phe Asp Gly Ala Phe Ile Ile Asn Trp Leu Glu Arg Asn Gly
                85                  90                  95

Phe Lys Trp Ser Ala Asp Gly Leu Pro Asn Thr Tyr Asn Thr Ile Ile
                100                 105                 110

Ser Arg Met Gly Gln Trp Tyr Met Ile Asp Ile Cys Leu Gly Tyr Lys
                115                 120                 125

Gly Lys Arg Lys Ile His Thr Val Ile Tyr Asp Ser Leu Lys Lys Leu
130                 135                 140

Pro Phe Pro Val Lys Lys Ile Ala Lys Asp Phe Lys Leu Thr Val Leu
145                 150                 155                 160

Lys Gly Asp Ile Asp Tyr His Lys Glu Arg Pro Val Gly Tyr Lys Ile
                165                 170                 175

Thr Pro Glu Glu Tyr Ala Tyr Ile Lys Asn Ala Ile Gln Ile Ile Ala
                180                 185                 190

Glu Ala Leu Leu Ile Gln Phe Lys Gln Gly Leu Asp Arg Met Thr Ala
                195                 200                 205

Gly Ser Asp Ser Leu Lys Gly Phe Lys Asp Ile Ile Thr Thr Lys Lys
210                 215                 220

Phe Lys Lys Val Phe Pro Thr Leu Ser Leu Gly Leu Asp Lys Glu Val
225                 230                 235                 240

Arg Tyr Ala Tyr Arg Gly Gly Phe Thr Trp Leu Asn Asp Arg Phe Lys
                245                 250                 255

Glu Lys Glu Ile Gly Glu Gly Met Val Phe Asp Val Asn Ser Leu Tyr
                260                 265                 270

Pro Ala Gln Met Tyr Ser Arg Leu Leu Pro Tyr Gly Glu Pro Ile Val
                275                 280                 285

Phe Glu Gly Lys Tyr Val Trp Asp Glu Asp Tyr Pro Leu His Ile Gln
                290                 295                 300

His Ile Arg Cys Glu Phe Glu Leu Lys Glu Gly Tyr Ile Pro Thr Ile
305                 310                 315                 320

Gln Ile Lys Arg Ser Arg Phe Tyr Lys Gly Asn Glu Tyr Leu Lys Ser
                325                 330                 335
```

-continued

Ser Gly Gly Glu Ile Ala Asp Leu Trp Leu Ser Asn Val Asp Leu Glu
        340                 345                 350

Leu Met Lys Glu His Tyr Asp Leu Tyr Asn Val Glu Tyr Ile Ser Gly
        355                 360                 365

Leu Lys Phe Lys Ala Thr Thr Gly Leu Phe Lys Asp Phe Ile Asp Lys
        370                 375                 380

Trp Thr Tyr Ile Lys Thr Thr Ser Glu Gly Ala Ile Lys Gln Leu Ala
385                 390                 395                 400

Lys Leu Met Leu Asn Ser Leu Tyr Gly Lys Phe Ala Ser Asn Pro Asp
            405                 410                 415

Val Thr Gly Lys Val Pro Tyr Leu Lys Glu Asn Gly Ala Leu Gly Phe
        420                 425                 430

Arg Leu Gly Glu Glu Thr Lys Asp Pro Val Tyr Thr Pro Met Gly
        435                 440                 445

Val Phe Ile Thr Ala Trp Ala Arg Tyr Thr Thr Ile Thr Ala Ala Gln
    450                 455                 460

Ala Cys Tyr Asp Arg Ile Ile Tyr Cys Asp Thr Asp Ser Ile His Leu
465                 470                 475                 480

Thr Gly Thr Glu Ile Pro Asp Val Ile Lys Asp Ile Val Asp Pro Lys
            485                 490                 495

Lys Leu Gly Tyr Trp Ala His Glu Ser Thr Phe Lys Arg Ala Lys Tyr
        500                 505                 510

Leu Arg Gln Lys Thr Tyr Ile Gln Asp Ile Tyr Met Lys Glu Val Asp
        515                 520                 525

Gly Lys Leu Val Glu Gly Ser Pro Asp Asp Tyr Thr Asp Ile Lys Phe
    530                 535                 540

Ser Val Lys Cys Ala Gly Met Thr Asp Lys Ile Lys Lys Glu Val Thr
545                 550                 555                 560

Phe Glu Asn Phe Lys Val Gly Phe Ser Arg Lys Met Lys Pro Lys Pro
            565                 570                 575

Val Gln Val Pro Gly Gly Val Val Leu Val Asp Asp Thr Phe Thr Ile
        580                 585                 590

Lys

<210> SEQ ID NO 13
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met His His His His His Leu Leu Gly Gly Gly Ser Gly Gly
1               5                   10                  15

Gly Gly Ser Ala Ala Ala Gly Ser Ala Ala Arg Lys Met Tyr Ser Cys
            20                  25                  30

Asp Phe Glu Thr Thr Thr Lys Val Glu Asp Cys Arg Val Trp Ala Tyr
        35                  40                  45

Gly Tyr Met Asn Ile Glu Asp His Ser Glu Tyr Lys Ile Gly Asn Ser
    50                  55                  60

Leu Asp Glu Phe Met Ala Trp Val Leu Lys Val Gln Ala Asp Leu Tyr
65                  70                  75                  80

Phe His Asn Leu Lys Phe Asp Gly Ala Phe Ile Ile Asn Trp Leu Glu
            85                  90                  95

```
Arg Asn Gly Phe Lys Trp Ser Ala Asp Gly Leu Pro Asn Thr Tyr Asn
            100                 105                 110

Thr Ile Ile Ser Arg Met Gly Gln Trp Tyr Met Ile Asp Ile Cys Leu
            115                 120                 125

Gly Tyr Lys Gly Lys Arg Lys Ile His Thr Val Ile Tyr Asp Ser Leu
            130                 135                 140

Lys Lys Leu Pro Phe Pro Val Lys Lys Ile Ala Lys Asp Phe Lys Leu
145                 150                 155                 160

Thr Val Leu Lys Gly Asp Ile Asp Tyr His Lys Glu Arg Pro Val Gly
                165                 170                 175

Tyr Lys Ile Thr Pro Glu Glu Tyr Ala Tyr Ile Lys Asn Ala Ile Gln
                180                 185                 190

Ile Ile Ala Glu Ala Leu Leu Ile Gln Phe Lys Gln Gly Leu Asp Arg
            195                 200                 205

Met Thr Ala Gly Ser Asp Ser Leu Lys Gly Phe Lys Asp Ile Ile Thr
            210                 215                 220

Thr Lys Lys Phe Lys Lys Val Phe Pro Thr Leu Ser Leu Gly Leu Asp
225                 230                 235                 240

Lys Glu Val Arg Tyr Ala Tyr Arg Gly Gly Phe Thr Trp Leu Asn Asp
                245                 250                 255

Arg Phe Lys Glu Lys Glu Ile Gly Glu Gly Met Val Phe Asp Val Asn
                260                 265                 270

Ser Leu Tyr Pro Ala Gln Met Tyr Ser Arg Leu Leu Pro Tyr Gly Glu
            275                 280                 285

Pro Ile Val Phe Glu Gly Lys Tyr Val Trp Asp Glu Asp Tyr Pro Leu
            290                 295                 300

His Ile Gln His Ile Arg Cys Glu Phe Glu Leu Lys Glu Gly Tyr Ile
305                 310                 315                 320

Pro Thr Ile Gln Ile Lys Arg Ser Arg Phe Tyr Lys Gly Asn Glu Tyr
                325                 330                 335

Leu Lys Ser Ser Gly Gly Glu Ile Ala Asp Leu Trp Leu Ser Asn Val
            340                 345                 350

Asp Leu Glu Leu Met Lys Glu His Tyr Asp Leu Tyr Asn Val Glu Tyr
            355                 360                 365

Ile Ser Gly Leu Lys Phe Lys Ala Thr Thr Gly Leu Phe Lys Asp Phe
            370                 375                 380

Ile Asp Lys Trp Thr Tyr Ile Lys Thr Thr Ser Glu Gly Ala Ile Lys
385                 390                 395                 400

Gln Leu Ala Lys Leu Met Leu Asn Ser Leu Tyr Gly Lys Phe Ala Ser
                405                 410                 415

Asn Pro Asp Val Thr Gly Lys Val Pro Tyr Leu Lys Glu Asn Gly Ala
                420                 425                 430

Leu Gly Phe Arg Leu Gly Glu Glu Thr Lys Asp Pro Val Tyr Thr
            435                 440                 445

Pro Met Gly Val Phe Ile Thr Ala Trp Ala Arg Tyr Thr Thr Ile Thr
            450                 455                 460

Ala Ala Gln Ala Cys Tyr Asp Arg Ile Ile Tyr Cys Asp Thr Asp Ser
465                 470                 475                 480

Ile His Leu Thr Gly Thr Glu Ile Pro Asp Val Ile Lys Asp Ile Val
                485                 490                 495

Asp Pro Lys Lys Leu Gly Tyr Trp Ala His Glu Ser Thr Phe Lys Arg
            500                 505                 510
```

```
Ala Lys Tyr Leu Arg Gln Lys Thr Tyr Ile Gln Asp Ile Tyr Met Lys
            515                 520                 525

Glu Val Asp Gly Lys Leu Val Glu Gly Ser Pro Asp Asp Tyr Thr Asp
        530                 535                 540

Ile Lys Phe Ser Val Lys Cys Ala Gly Met Thr Asp Lys Ile Lys Lys
545                 550                 555                 560

Glu Val Thr Phe Glu Asn Phe Lys Val Gly Phe Ser Arg Lys Met Lys
                565                 570                 575

Pro Lys Pro Val Gln Val Pro Gly Gly Val Val Leu Val Asp Asp Thr
            580                 585                 590

Phe Thr Ile Lys
            595

<210> SEQ ID NO 14
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asn His Leu Val His His His His His Ile Glu Gly Arg His
1               5                   10                  15

Met Glu Leu Gly Thr Leu Glu Gly Ser Met Lys His Met Pro Arg Lys
            20                  25                  30

Met Tyr Ser Cys Ala Phe Glu Thr Thr Thr Lys Val Glu Asp Cys Arg
        35                  40                  45

Val Trp Ala Tyr Gly Tyr Met Asn Ile Glu Asp His Ser Glu Tyr Lys
50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
        115                 120                 125

Asp Ile Cys Leu Gly Tyr Lys Gly Lys Arg Lys Ile His Thr Val Ile
    130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
        195                 200                 205

Gly Leu Asp Arg Met Thr Ala Gly Ser Asp Ser Leu Lys Gly Phe Lys
    210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270
```

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
    290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Glu Ile Ala Asp Leu Trp
            340                 345                 350

Leu Ser Asn Val Asp Leu Glu Leu Met Lys Glu His Tyr Asp Leu Tyr
            355                 360                 365

Asn Val Glu Tyr Ile Ser Gly Leu Lys Phe Lys Ala Thr Thr Gly Leu
    370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
            435                 440                 445

Pro Val Tyr Thr Pro Met Gly Val Phe Ile Thr Ala Trp Ala Arg Tyr
    450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
    515                 520                 525

Ile Tyr Met Lys Glu Val Asp Gly Lys Leu Val Glu Gly Ser Pro Asp
530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
            580                 585                 590

Val Asp Asp Thr Phe Thr Ile Lys
            595                 600

<210> SEQ ID NO 15
<211> LENGTH: 586
<212> TYPE: PRT
<213> ORGANISM: Unknown
<220> FEATURE:
<223> OTHER INFORMATION: Description of Unknown: Cyanophage S-CBP1
      polypeptide

<400> SEQUENCE: 15

Met Thr Leu Ile Phe Asp Ile Glu Thr Asp Gly Leu Tyr Asn Asp Ala
1               5                   10                  15

Ser Cys Ile His Cys Ile Gly Ile His Asp Leu Asn Ala Gly Glu Thr

```
                20                  25                  30
Tyr Val Phe Asn Asp Val Gly Thr Gln Gln Pro Ile Thr Lys Gly Ile
                35                  40                  45
Gln Leu Leu Glu Asp Ala Asp Leu Ile Val Gly His Asn Ile Ile Gly
                50                  55                  60
Tyr Asp Ile Pro Val Ile Ser Lys Leu Phe Pro Trp Phe Ser Arg Thr
65                  70                  75                  80
Asn Gly Val Leu Asp Thr Leu Val Leu Ser Arg Leu Tyr His Thr Asp
                85                  90                  95
Leu Leu Asp Ile Asp Gln Lys Arg Lys Trp Lys His Met Pro Leu Gln
                100                 105                 110
Leu Tyr Gly Arg His Ser Leu Glu Ala Tyr Gly Tyr Arg Leu Gly Glu
                115                 120                 125
Tyr Lys Gly Ser Phe Gly Lys Thr Ala Asp Trp Lys Glu Trp Ser Gln
                130                 135                 140
Asp Met Glu Asp Tyr Met Ile Gln Asp Val Asn Val Thr Arg Lys Leu
145                 150                 155                 160
Trp Lys His Phe Pro Gln Ile Pro Glu Trp Val Gln Leu Glu His Arg
                165                 170                 175
Val Ala Gln Ile Leu Thr Glu Gln Glu Ile Tyr Gly Trp Tyr Phe Asp
                180                 185                 190
Glu Asn Ala Ala Arg Glu Leu Ala Gln Thr Leu Tyr Thr Glu Leu Asp
                195                 200                 205
Asp Leu Lys Gly Val Leu Arg Lys Arg Tyr Pro Tyr Val Ala Gly Arg
                210                 215                 220
Glu Phe Thr Pro Lys Arg Val Asn Arg Ser Leu Gly Tyr Val Glu Gly
225                 230                 235                 240
Ala Thr Cys Thr Lys Leu Val Glu Phe Ser Pro Thr Ser Arg Asp His
                245                 250                 255
Ile Ala Trp Val Met Lys Asn Leu His Gly Trp Lys Pro Asp Lys Lys
                260                 265                 270
Thr Lys Ala Gly Lys Thr Ala Ile Asp Glu Ile Val Leu Lys Glu Ile
                275                 280                 285
Gly Thr Glu Glu Ala Leu Gln Phe Phe Arg Cys Leu Glu Ile Thr Lys
                290                 295                 300
Gln Leu Gly Met Leu Ser Glu Gly Lys Asn Ala Trp Leu Lys Leu Ser
305                 310                 315                 320
Arg Lys Asp Arg Val His His His Cys Ser Val Ala Thr Val Thr His
                325                 330                 335
Arg Cys Ala His Arg Asn Pro Asn Leu Ala Gln Val Pro Ser Asp Leu
                340                 345                 350
Asn Phe Arg Arg Leu Phe Cys Ala Ser Pro Gly His Ile Met Val Gly
                355                 360                 365
Ala Asp Leu Ser Gly Ile Glu Leu Arg Met Leu Ala His Tyr Leu Ala
                370                 375                 380
Arg Tyr Asp Asp Gly Arg Tyr Gly Asp Ile Leu Leu His Gly Asp Ile
385                 390                 395                 400
His Gln Glu Asn Ala Asp Lys Ile Gly Ile Ser Arg Arg Leu Val Lys
                405                 410                 415
Thr Val Thr Tyr Ala Phe Leu Tyr Gly Ala Gly Asp Gln Lys Ile Gly
                420                 425                 430
Leu Ser Tyr Asp Gln Gly Leu Ser Pro Asp Lys Ala Lys Gln Lys Gly
                435                 440                 445
```

```
Lys Glu Ile Arg Gln Ala Tyr Met Asp Ala Ile Pro Gly Leu Glu Lys
        450                 455                 460

Leu Val Glu Ala Thr Lys Lys Ala Ala Asp Arg Gly Phe Ile Arg Ser
465                 470                 475                 480

Ile Asp Gly Arg His Ile Asn Val Asp Ser Ser His Lys Ala Leu Asn
                    485                 490                 495

Met Leu Leu Gln Ser Ser Ala Gly Cys Ile Ala Lys Arg Trp Met Val
                500                 505                 510

Ile Ala Asn Asp Asn Phe Pro Thr Ile Asp Asn Glu Tyr Leu Ala His
                515                 520                 525

Thr His Gln Leu Ala Phe Ile His Asp Glu Leu Gln Phe Glu Cys Leu
                530                 535                 540

Pro Leu Tyr Ala Glu Asp Leu Lys Thr His Leu Glu Leu Cys Ala Glu
545                 550                 555                 560

Leu Ala Gly Glu Tyr Tyr Asn Leu Arg Ile Pro Ile Ala Ala Glu Gly
                    565                 570                 575

Lys Ile Gly Ser Thr Trp Ala Asp Val His
                580                 585
```

<210> SEQ ID NO 16
<211> LENGTH: 588
<212> TYPE: PRT
<213> ORGANISM: Unknown
<220> FEATURE:
<223> OTHER INFORMATION: Description of Unknown: Cyanophage S-CBP2
      polypeptide

<400> SEQUENCE: 16

```
Met Lys Leu Val Phe Asp Ile Glu Thr Asp Gly Phe Leu Arg Lys Leu
1               5                   10                  15

Thr Thr Val His Cys Val Val Ala Lys Asp Ile Glu Thr Gly Glu Val
                20                  25                  30

Phe Lys Phe Asp Asp Ser Gly Arg His Gln Ser Val Ser Ser Gly Leu
                35                  40                  45

Thr Leu Leu Met Glu Ala Glu Glu Leu Trp Gly His Asn Ile Ile Gly
50                  55                  60

Phe Asp Val Pro Ala Ile Gln Glu Ile Tyr Pro Phe Phe Gln Pro Trp
65                  70                  75                  80

Glu Ser Thr Tyr Tyr Asp Thr Leu Ile Leu Ser Arg Leu Phe Phe Thr
                85                  90                  95

Asp Met Leu Asp Arg Asp Leu Arg Ser Lys Pro Ala Asn Met Pro Gly
                100                 105                 110

Asn Leu Tyr Gly Arg His Ser Leu Glu Ala Trp Gly Tyr Arg Leu Gly
                115                 120                 125

Val Leu Lys Ser Glu Tyr Gly Lys Gln Leu His Gly Asp Trp Ala Thr
130                 135                 140

Tyr Thr Pro Glu Met Leu Glu Tyr Cys Glu Gln Asp Val Glu Ala Asn
145                 150                 155                 160

Leu Pro Ile Val Lys Leu Phe Gln Pro Lys Leu Glu Gln Tyr Ala Asp
                165                 170                 175

Ala Ile Lys Thr Glu His Asp Cys Ala Leu Val Met Thr Arg Gln Glu
                180                 185                 190

Gln Ala Gly Phe Pro Phe Asp Ile Asp Lys Ala Arg Ala Leu Glu Ser
                195                 200                 205

Lys Leu Arg Ser Glu Leu Glu Thr Leu Ser Asp Glu Met Arg Ala Thr
```

```
                 210                 215                 220
Phe Thr Phe Val Ala Gly Lys Glu Phe Thr Pro Ala Arg Asn Asn Ala
225                 230                 235                 240

Thr Arg Gly Tyr Ile Thr Gly Cys Pro Phe Thr Lys Leu Thr Glu Phe
                245                 250                 255

Ser Pro Thr Ser Arg Asp His Ile Ala Trp Ala Phe Gln Gln His Arg
                260                 265                 270

Gly Trp Glu Pro Ile Glu Met Thr Asp Thr Gly Lys Pro Lys Ile Asp
            275                 280                 285

Glu Glu Val Leu Asn Ala Ile Gly Thr Glu Ala Lys Lys Phe Gly
290                 295                 300

Arg Ile Leu Glu Leu Gln Lys His Val Gly Met Leu Ser Glu Gly Lys
305                 310                 315                 320

Asn Ser Trp Leu Gln Met Val Glu Lys Asp Gly Arg Ile His His Ser
                325                 330                 335

Cys Val Leu Asn Thr Ala Thr Gly Arg Asn Ala His Met Arg Pro Asn
                340                 345                 350

Leu Ala Gln Val Pro Ser Gly His Glu Phe Arg Glu Leu Phe Thr Pro
                355                 360                 365

Gly Glu Gly Tyr Val Gln Val Gly Ala Asp Ala Ser Gly Leu Glu Leu
            370                 375                 380

Arg Cys Leu Ala His Tyr Leu Ala Arg Phe Asp Gly Gly Lys Phe Gly
385                 390                 395                 400

Lys Val Leu Leu Glu Gly Asp Ile His Thr Asp Leu Ala Asn Ile Tyr
                405                 410                 415

Gly Thr Asp Arg Lys Thr Gly Lys Thr Val Thr Tyr Cys Leu Ile Tyr
                420                 425                 430

Gly Gly Gly Asp Thr Lys Leu Gly Leu Ser Ala Gly Pro Lys Lys
            435                 440                 445

Ser Ala Ala Ser Arg Gly Lys Lys Ile Arg Gln Ala Ile Met Lys Asp
                450                 455                 460

Leu Asp Gly Phe Ala Gln Leu Ile Thr Ala Val Gln Glu Arg Ala Gln
465                 470                 475                 480

Ser Gly Val Ile Thr Gly Ile Asp Gly Arg Pro Ile Arg Met Arg Lys
                485                 490                 495

Ala His Ala Ala Leu Asn Tyr Leu Leu Gln Ser Cys Gly Ala Val Ile
                500                 505                 510

Cys Lys Lys Trp Val Val Arg Ser Asn Glu Leu Leu Thr Glu Ala Gly
            515                 520                 525

Ile Asp Tyr Thr Pro Leu Ala Phe Val His Asp Glu Gln Gln Leu Ala
530                 535                 540

Val Arg Pro Asp Gln Val Glu Met Ala Ser Thr Leu Ile Ser Leu Ala
545                 550                 555                 560

Met Lys Asp Val Glu His Ala Ile Lys Phe Arg Val Pro Leu Asp Cys
                565                 570                 575

Asp Val Gln Ser Gly Ala Asn Trp Gly Asp Thr His
                580                 585

<210> SEQ ID NO 17
<211> LENGTH: 582
<212> TYPE: PRT
<213> ORGANISM: Unknown
<220> FEATURE:
<223> OTHER INFORMATION: Description of Unknown: Cyanophage S-CBP3
      polypeptide
```

<400> SEQUENCE: 17

```
Met Thr Leu Ile Phe Asp Ile Glu Thr Asp Gly Leu Tyr Asn Asp Val
1               5                   10                  15

Thr Cys Ile His Cys Ile Gly Ile His Asp Leu Asn Thr Lys Glu Thr
                20                  25                  30

Tyr Val Phe Asn Asp Val Gly Thr Gln Gln Pro Ile Thr Lys Gly Ile
            35                  40                  45

Gln Leu Leu Glu Asp Ala Asp Ile Ile Val Gly His Asn Ile Ile Gly
        50                  55                  60

Tyr Asp Leu Pro Val Ile Arg Lys Leu Tyr Pro Trp Phe Ser Asn Val
65                  70                  75                  80

Gly Arg Val Leu Asp Thr Leu Val Leu Ser Arg Leu Tyr His Ala Asp
                85                  90                  95

Leu Leu Lys Thr Asp Gln Lys Arg Asn Trp Lys His Met Pro Val Gln
            100                 105                 110

Leu Trp Gly Arg His Ser Leu Glu Ala Tyr Gly Tyr Arg Leu Gly Glu
        115                 120                 125

Tyr Lys Gly Cys Phe Gly Lys Thr Thr Asp Trp Lys Asp Trp Ser Gln
    130                 135                 140

Glu Met Glu Asp Tyr Met Val Gln Asp Val Asn Ile Thr Arg Lys Leu
145                 150                 155                 160

Trp Lys Asp Phe Pro Glu Ile Pro Glu Trp Val Gln Leu Glu His Arg
                165                 170                 175

Val Ala Gln Ile Leu Thr Glu Gln Glu Ile His Gly Trp Tyr Phe Asp
            180                 185                 190

Glu Pro Ala Ala Trp Glu Leu Glu Ser Thr Leu Arg Arg Glu Leu Glu
        195                 200                 205

Ser Leu Lys Ala Val Leu Arg Asn Arg His Pro Phe Ile Leu Gly Glu
    210                 215                 220

Glu Phe Thr Pro Lys Arg Pro Asn Ser Thr Gln Gly Tyr Phe Thr Gly
225                 230                 235                 240

Ala Thr Phe Thr Arg Leu Lys Glu Met Asn Pro Thr Ser Arg Asp His
                245                 250                 255

Ile Ala Tyr Ile Leu Gln Lys Phe Tyr Asp Trp Glu Pro Thr Glu Arg
            260                 265                 270

Thr Glu Lys Gly Lys Pro Val Val Asp Glu Ile Val Leu Lys Asp Ile
        275                 280                 285

Gly Ser Glu Ile Ala Leu Gln Phe Phe Arg Cys Leu Glu Leu Thr Lys
    290                 295                 300

Gln Ile Gly Met Leu Thr Glu Gly Val Asn Ala Trp Leu Lys Leu Val
305                 310                 315                 320

Arg Asn Asp Arg Ile His His Cys Ser Val Ala Thr Asn Thr His
                325                 330                 335

Arg Cys Ala His Arg Lys Pro Asn Leu Ala Gln Val Pro Ala Glu Ala
            340                 345                 350

Glu Phe Arg Lys Leu Phe Arg Ala Thr Pro Gly Met Val Met Val Gly
        355                 360                 365

Ala Asp Leu Ala Gly Ile Glu Leu Arg Met Leu Ala His Tyr Leu Ala
    370                 375                 380

Gln Trp Asp Gly Gly Arg Tyr Gly Asp Val Leu Leu Asn Gly Asp Ile
385                 390                 395                 400

His Gln Glu Asn Ala Asp Lys Ile Gly Ile Ser Arg Arg Leu Val Lys
```

```
                       405                 410                 415
Thr Val Thr Tyr Ala Phe Leu Tyr Gly Ala Gly Asn Gln Lys Ile Gly
            420                 425                 430

Leu Ser Tyr Asp Gln Ser Leu Ser Pro Asp Lys Ala Lys Lys Lys Gly
            435                 440                 445

Gln Glu Ile Arg Gln Ala Tyr Met Asp Ala Ile Pro Gly Leu Arg Lys
    450                 455                 460

Leu Val Glu Ala Thr Lys Lys Ala Ala Asn Arg Gly Tyr Ile Arg Ala
465                 470                 475                 480

Ile Asp Gly Arg His Ile Ser Val Asp Ser Pro His Lys Ser Leu Asn
                485                 490                 495

Tyr Leu Leu Gln Ser Ser Ala Gly Val Ile Ala Lys Arg Trp Leu Ala
            500                 505                 510

Leu Thr His Glu Ala Ile Ile Arg Ala Asp Ile Lys Ala His Gln Leu
            515                 520                 525

Ala Phe Ile His Asp Glu Leu Gln Phe Glu Thr Thr Pro Glu His Val
    530                 535                 540

Glu Asp Leu Lys Phe Ala Leu Leu Trp Gly Ala Ala Ser Ala Gly Glu
545                 550                 555                 560

Tyr Tyr Asn Leu Arg Ile Pro Ile Ala Ala Asp Ala Lys Ser Gly Asn
                565                 570                 575

Asp Trp Ser Glu Val His
            580

<210> SEQ ID NO 18
<211> LENGTH: 583
<212> TYPE: PRT
<213> ORGANISM: Unknown
<220> FEATURE:
<223> OTHER INFORMATION: Description of Unknown: Cyanophage Syn5
      polypeptide

<400> SEQUENCE: 18

Met Arg Leu Val Phe Asp Ile Glu Thr Asp Gly Leu Leu Arg Gly Leu
1               5                   10                  15

Ser Val Ile His Cys Ile Val Ala Arg Asp Leu Asp Thr Asn Glu Glu
            20                  25                  30

His Arg Phe Glu Pro His Gln Thr Lys Ala Gly Leu Gln Leu Leu Lys
        35                  40                  45

Glu Ala Asp Glu Leu Trp Gly His Asn Ile Val Gly Tyr Asp Ile Glu
    50                  55                  60

Ala Ile Lys Glu Leu Tyr Pro Lys Trp Thr Thr Lys Ala Lys Leu Tyr
65                  70                  75                  80

Asp Thr Leu Ile Leu Ser Arg Leu Phe Phe Thr Asp Leu Leu Asp Arg
                85                  90                  95

Asp Phe Arg Ser Lys Pro Ala Asn Met Pro Gly Asn Leu Tyr Gly Arg
            100                 105                 110

His Ser Leu Glu Ala Trp Gly His Arg Leu Gly Val His Lys Ser Glu
        115                 120                 125

Phe Gly Lys Gln Leu Asp Gly Asp Trp Ser Thr Tyr Ser Pro Glu Met
    130                 135                 140

Leu Glu Tyr Cys Ala Gln Asp Val Thr Val Ser Val Gln Val Ala Gln
145                 150                 155                 160

Met Phe Glu Pro Lys Leu Glu Gln Tyr Ala Asp Cys Ile Asp Thr Glu
                165                 170                 175
```

His Arg Leu Ala Thr Ile Met Ala Trp Gln Glu Arg Glu Gly Phe Pro
            180                 185                 190

Phe Asp Val Thr Ala Ala Gln Gln Leu Glu Ser Arg Leu Arg Thr Glu
                195                 200                 205

Leu Asp Ala Leu Ser Asp Gln Met Arg Ser Thr Phe Leu Phe Val Asp
        210                 215                 220

Gly Gly Thr Phe Thr Pro Arg Arg Asn Asn Lys Pro Gln Gly Tyr Ile
225                 230                 235                 240

Ala Asp Ala Pro Met Cys Lys Leu Lys Glu Phe Asn Pro Thr Ser Arg
                245                 250                 255

His His Ile Ala Trp Ala Phe Gln Gln Phe Arg Asn Trp Glu Pro Lys
            260                 265                 270

Glu Phe Thr Asp Ser Gly Lys Pro Lys Ile Asp Glu Pro Thr Leu Thr
        275                 280                 285

Ala Ile Gly Thr Asp Glu Ala Lys Ala Phe Ala Arg Ile Leu Glu Leu
        290                 295                 300

Gln Lys His Leu Gly Gln Leu Ala Glu Gly Lys Asn Ala Trp Leu Lys
305                 310                 315                 320

Leu Glu Ser Lys Gly Arg Val His His Ser Cys Val Leu Asn Thr Asn
                325                 330                 335

Thr Gly Arg Gln Ala His Met Arg Pro Asn Leu Ala Gln Val Pro Ser
            340                 345                 350

Ala Ser Glu Tyr Arg Ala Leu Phe Gly Pro Gly Asp Ser Arg Val Gln
        355                 360                 365

Val Gly Ala Asp Ala Ser Gly Leu Glu Leu Arg Cys Leu Ala His Tyr
370                 375                 380

Leu Ala Pro Phe Asp Asn Gly Ser Phe Ala Glu Thr Val Val Asn Gly
385                 390                 395                 400

Asp Ile His Thr Glu Leu Ala Ser Ile Tyr Gly Thr Asp Arg Lys Ser
            405                 410                 415

Gly Lys Gly Val Thr Tyr Cys Leu Ile Tyr Gly Gly Asp His Lys
        420                 425                 430

Leu Gly Ser Thr Ala Gly Ala Ser Lys Ala Gln Ala Ser Lys Lys Gly
        435                 440                 445

Lys Glu Ile Arg Gly Arg Ile Met Arg Asp Leu Asp Gly Phe Ala Ala
450                 455                 460

Leu Ser Asp Ala Val Ser Arg Arg Ala Arg Thr Gly Val Leu Arg Gly
465                 470                 475                 480

Leu Asp Gly Arg Pro Ile Arg Leu Gln Gly Lys Ser His Ala Ala Leu
                485                 490                 495

Asn Tyr Leu Leu Gln Ser Ala Gly Ala Val Ile Cys Lys Gln Trp Leu
            500                 505                 510

Leu Arg Ser Tyr Glu Leu Leu Asp Glu Ala Asn Ile Asp Tyr Trp Pro
        515                 520                 525

Leu Ala Phe Val His Asp Glu Leu Gln Ile Ser Val Ala Pro Ser Gln
        530                 535                 540

Ala Glu Met Ala Thr Leu Leu Ile Thr Ala Ala Met Lys Asp Val Gln
545                 550                 555                 560

His Asn Leu Lys Phe Arg Cys Glu Leu Asp Ser Glu Ala Gln Thr Gly
                565                 570                 575

Asn Ser Trp Ala Asp Cys His
            580

```
<210> SEQ ID NO 19
<211> LENGTH: 588
<212> TYPE: PRT
<213> ORGANISM: Unknown
<220> FEATURE:
<223> OTHER INFORMATION: Description of Unknown: Cyanophage S-CBP42
      polypeptide

<400> SEQUENCE: 19
```

| | | | | | | | | | | | | | | | |
|---|---|---|---|---|---|---|---|---|---|---|---|---|---|---|---|
| Met | Arg | Leu | Ala | Phe | Asp | Ile | Glu | Thr | Asp | Gly | Leu | Leu | Arg | Asn | Leu |
| 1 | | | | 5 | | | | | 10 | | | | | 15 | |
| Thr | Lys | Ile | His | Cys | Ile | Val | Ala | Gln | Asp | Leu | Asp | Thr | Asn | Glu | Val |
| | | | 20 | | | | | 25 | | | | | 30 | | |
| Tyr | Lys | Phe | Asp | Gly | Thr | Gly | Asp | His | Pro | Ser | Ile | Arg | Glu | Gly | Leu |
| | | 35 | | | | | 40 | | | | | 45 | | | |
| Ala | Leu | Leu | Lys | Asp | Ala | Asp | Glu | Leu | Trp | Gly | His | Asn | Ile | Ile | Gly |
| | 50 | | | | | 55 | | | | | 60 | | | | |
| Tyr | Asp | Phe | Glu | Ala | Ile | Lys | Glu | Val | Phe | Pro | Arg | Trp | Asn | Tyr | Ser |
| 65 | | | | | 70 | | | | | 75 | | | | | 80 |
| Ser | Thr | Val | Tyr | Asp | Thr | Leu | Ile | Leu | Ser | Arg | Leu | Phe | Phe | Thr | Asp |
| | | | | 85 | | | | | 90 | | | | | 95 | |
| Leu | Leu | Asp | Arg | Asp | Phe | Arg | Ser | Arg | Pro | Ala | Asn | Met | Pro | Ala | Gln |
| | | | 100 | | | | | 105 | | | | | 110 | | |
| Leu | Tyr | Gly | Arg | His | Ser | Leu | Glu | Ala | Trp | Gly | His | Arg | Leu | Ser | Val |
| | | 115 | | | | | 120 | | | | | 125 | | | |
| His | Lys | Ser | Glu | Phe | Gly | Lys | Ser | Leu | Ser | Gly | Asp | Trp | Ser | Thr | Tyr |
| | 130 | | | | | 135 | | | | | 140 | | | | |
| Ser | Pro | Glu | Met | Leu | Asp | Tyr | Cys | Ala | Arg | Asp | Val | Val | Ser | Val |
| 145 | | | | | 150 | | | | | 155 | | | | | 160 |
| Ser | Leu | Ala | Arg | Leu | Phe | Thr | Ala | Lys | Val | Ala | Glu | Tyr | Arg | Asp | Cys |
| | | | | 165 | | | | | 170 | | | | | 175 | |
| Ile | Ser | Thr | Glu | His | Arg | Leu | Ala | Thr | Ile | Met | Ala | Trp | Gln | Glu | Ser |
| | | | 180 | | | | | 185 | | | | | 190 | | |
| Glu | Gly | Phe | Pro | Phe | Asp | Val | Ala | Lys | Ala | Glu | Arg | Leu | Glu | Gly | Gln |
| | | 195 | | | | | 200 | | | | | 205 | | | |
| Leu | Arg | Ser | Glu | Leu | Leu | Lys | Leu | Ser | Glu | Gln | Met | Arg | Glu | Thr | Phe |
| | 210 | | | | | 215 | | | | | 220 | | | | |
| Pro | Tyr | Val | Asp | Gly | Gly | Ser | Phe | Thr | Pro | Arg | Thr | Asn | Asn | Gly | Pro |
| 225 | | | | | 230 | | | | | 235 | | | | | 240 |
| Arg | Gly | Tyr | Val | Lys | Gly | Ala | Ala | Met | Cys | Arg | Leu | Lys | Glu | Phe | Asn |
| | | | | 245 | | | | | 250 | | | | | 255 | |
| Pro | Thr | Ser | Arg | Gln | His | Ile | Ala | Trp | Ala | Phe | Ala | Thr | Phe | Arg | Asp |
| | | | 260 | | | | | 265 | | | | | 270 | | |
| Trp | Glu | Pro | Lys | Glu | Leu | Thr | Asp | Thr | Gly | Lys | Pro | Lys | Ile | Asp | Glu |
| | | 275 | | | | | 280 | | | | | 285 | | | |
| Thr | Thr | Leu | Leu | Glu | Tyr | Gly | Thr | Asp | Glu | Ala | Lys | Thr | Phe | Ala | Arg |
| | 290 | | | | | 295 | | | | | 300 | | | | |
| Ile | Leu | Glu | Leu | Gln | Lys | His | Leu | Gly | Gln | Leu | Ser | Glu | Gly | Ala | Asn |
| 305 | | | | | 310 | | | | | 315 | | | | | 320 |
| Ala | Trp | Leu | Lys | Lys | Val | Glu | Ser | Asp | Gly | Arg | Ile | His | His | Ser | Cys |
| | | | | 325 | | | | | 330 | | | | | 335 | |
| Val | Leu | Asn | Thr | Asn | Thr | Gly | Arg | Gln | Ala | His | Met | Lys | Pro | Asn | Leu |
| | | | 340 | | | | | 345 | | | | | 350 | | |
| Ala | Gln | Val | Pro | Ser | Gly | His | Glu | Tyr | Arg | Glu | Leu | Phe | His | Pro | Gly |
| | | 355 | | | | | 360 | | | | | 365 | | | |

```
Ala Asn Arg Ser Gln Val Gly Ala Asp Ala Ser Gly Leu Glu Leu Arg
        370                 375                 380

Cys Leu Gly His Tyr Leu Ala Arg Phe Asp Gly Gly Lys Phe Ala Lys
385                 390                 395                 400

Glu Val Val Gln Gly Asp Ile His Thr Ala Leu Ala Glu Ile Tyr Gly
                405                 410                 415

Thr Asp Arg Lys Ser Gly Lys Gly Val Thr Tyr Cys Leu Ile Tyr Gly
                420                 425                 430

Gly Gly Asp Ser Lys Leu Gly Leu Thr Ala Gly Ala Ser Lys Ala Gln
                435                 440                 445

Ala Val Lys Lys Gly Lys Glu Ile Arg Ser Arg Ile Met Ala Asn Leu
450                 455                 460

Asp Gly Phe Ala Ala Leu Asn Ala Ala Val Gln Glu Arg Ala Lys Ser
465                 470                 475                 480

Gly Val Leu Lys Gly Leu Asp Gly Arg Pro Ile Arg Leu Gln Gly Lys
                485                 490                 495

Asn His Ala Ala Leu Asn Tyr Leu Leu Gln Ser Ala Gly Ala Val Ile
                500                 505                 510

Cys Lys Leu Trp Leu Leu Arg Ser Tyr Glu Leu Leu Asp Glu Ala Gly
        515                 520                 525

Ile Asp Tyr Phe Pro Met Ala Phe Val His Asp Glu Val His Ile Ser
        530                 535                 540

Val Ala Pro Ser Gln Ala Glu Gln Ala Gly Gln Leu Ile Gln Ile Ala
545                 550                 555                 560

Met Lys Asp Val Glu His Gln Ile Lys Phe Arg Cys Ala Leu Asp Ser
                565                 570                 575

Glu Tyr Gln Ile Gly Asn Ser Trp Ala Asp Cys His
                580                 585

<210> SEQ ID NO 20
<211> LENGTH: 587
<212> TYPE: PRT
<213> ORGANISM: Synechococcus sp.
<220> FEATURE:
<223> OTHER INFORMATION: Phage P60

<400> SEQUENCE: 20

Met Lys Leu Ala Phe Asp Ile Glu Thr Asp Gly Leu Ile Pro Asp Leu
1               5                   10                  15

Thr Ile Ile His Cys Ile Val Ala Arg Asp Ile Asp Thr Asp Glu Glu
                20                  25                  30

Phe Arg Phe Asp Gly Thr Gly Asp Tyr Pro Ser Ile Lys Glu Gly Leu
            35                  40                  45

Glu Leu Leu Ser Lys Ala Asp Glu Leu Trp Gly His Asn Ile Val Asn
        50                  55                  60

Tyr Asp Tyr Pro Ala Ile Gln Lys Leu His Pro Asp Trp Thr Pro Pro
65                  70                  75                  80

Ser Cys Thr Arg Asp Thr Leu Ile Leu Ser Arg Leu Phe Phe Thr Asp
                85                  90                  95

Leu Leu Asp Arg Asp Phe Arg Ser Arg Pro Ala Leu Met Pro Gly Asn
            100                 105                 110

Leu Tyr Gly Arg His Ser Leu Glu Ala Trp Gly His Arg Leu Gly His
        115                 120                 125

His Lys Ser Glu Phe Gly Lys Ser Leu Glu Gly Asp Trp Ser Thr Tyr
    130                 135                 140
```

```
Ser Pro Glu Met Leu Glu Tyr Cys Ala Arg Asp Val Glu Val Ser Val
145                 150                 155                 160

Ala Leu Ala Lys Thr Phe Val Pro Lys Ile Pro Glu Tyr Gln Trp Ser
            165                 170                 175

Val Asp Thr Glu His Glu Ile Ala Arg Ile Met Ser Trp Gln Glu Gln
        180                 185                 190

Met Gly Phe Pro Phe Asp Val Arg Ala Ala Gln Ala Leu Glu Gly Lys
    195                 200                 205

Leu Arg Leu Glu Leu Asp Thr Leu Ser Asp Asp Met Arg Glu Thr Phe
210                 215                 220

His Phe Val Asp Gly Gly Val Met Thr Pro Lys Arg Ser Asn Lys Val
225                 230                 235                 240

Arg His Tyr Phe Glu Asn Ala Pro Phe Cys Lys Leu Arg Glu Phe Asn
            245                 250                 255

Pro Thr Ser Arg His His Ile Ala Trp Ala Phe Glu His His Arg Gly
        260                 265                 270

Trp Glu Pro Lys Glu Arg Thr Ala Gly Gln Pro Lys Ile Asp Asp
    275                 280                 285

Glu Ile Leu Arg Glu Ile Asn Thr Lys Glu Ser Leu Ala Phe Ala Arg
290                 295                 300

Ile Leu Glu Leu Gln Lys His Leu Gly Gln Leu Ser Glu Gly Lys Asn
305                 310                 315                 320

Ala Trp Leu Lys Leu Glu Arg Lys Gly Arg Leu His His Ser Cys Val
            325                 330                 335

Leu Asn Thr Asn Thr Gly Arg Gln Ala His Met Arg Pro Asn Leu Ala
        340                 345                 350

Gln Val Pro Ser Ala His Glu Tyr Arg Ser Leu Phe Lys Pro Ser Asp
    355                 360                 365

Asn His Leu Gln Val Gly Ser Asp Ala Ser Gly Leu Glu Leu Arg Cys
370                 375                 380

Leu Gly His Tyr Leu Ser Arg Tyr Asp Gly Gly Lys Phe Ala Glu Glu
385                 390                 395                 400

Val Val Asn Gly Asp Ile His Thr Ala Leu Ala Glu Ile Tyr Gly Thr
            405                 410                 415

Asp Arg Lys Ser Gly Lys Gly Val Thr Tyr Cys Leu Ile Tyr Gly Gly
        420                 425                 430

Gly Asn His Lys Leu Gly Leu Thr Ala Gly Ala Ser Lys Ser Ser Ala
    435                 440                 445

Ser Arg Lys Gly Gln Glu Ile Arg Gly Lys Ile Met Gln Gly Leu Ser
450                 455                 460

Gly Phe Ala Asp Leu Asn Ala Ala Ile Gln Glu Arg Ala Lys Ser Gly
465                 470                 475                 480

Val Leu Lys Gly Leu Asp Gly Arg Pro Ile Arg Leu Gln Gly Lys Asn
            485                 490                 495

His Ala Ala Leu Asn Tyr Leu Gln Ser Ala Gly Ala Ile Ile Cys
        500                 505                 510

Lys Leu Trp Val Ile Arg Thr His Glu Leu Leu Gln Glu Ala Gly Ile
    515                 520                 525

Asp Tyr Tyr Pro Leu Ala Phe Val His Asp Glu Gln Leu Ser Val
530                 535                 540

Arg Ala Asp Gln Ala Glu Met Ala Ala Gln Leu Thr Thr Leu Ala Met
545                 550                 555                 560

Lys Asp Val Glu His Gln Val Lys Phe Arg Cys Ala Leu Asp Ser Glu
```

Tyr Gln Ile Gly Asn Ser Trp Ala Asp Cys His
            580                 585

<210> SEQ ID NO 21
<211> LENGTH: 580
<212> TYPE: PRT
<213> ORGANISM: Roseobacter sp.
<220> FEATURE:
<223> OTHER INFORMATION: Phage SIO1

<400> SEQUENCE: 21

Met Glu Val Val Phe Asp Ile Glu Thr Asp Ala Leu Asp Ala Thr Val
1               5                   10                  15

Ile His Val Leu Val Ala Lys Arg Val Gly Gln Lys Gly Phe Tyr Val
            20                  25                  30

Val Arg Asp Ala Glu Thr Phe Lys Arg Leu Ala Lys Gln Val Thr Leu
        35                  40                  45

Trp Ile Gly His Asn Val Ile Gly Phe Asp Ile Pro Gln Ile Lys Lys
    50                  55                  60

Leu Trp Gly Tyr Gly Ile Pro Leu Lys Asp Val Ala Asp Thr Leu Val
65                  70                  75                  80

Met Ser Arg Leu Leu Asp Pro Thr Arg Lys Gly Gly His Ser Leu Asp
                85                  90                  95

Ala Leu Ser Gly Asn Glu Lys Ile Asp Phe His Asp Phe Ser Thr Tyr
            100                 105                 110

Thr Pro Glu Met Leu Ala Tyr Cys Lys Gln Asp Val Ala Ile Asn Glu
        115                 120                 125

Lys Val Tyr Leu Gln Leu Lys Glu Glu Leu Ser Asn Phe Gly Lys Ala
    130                 135                 140

Ser Ile Gln Leu Glu His Gln Met Gln Ala Ile Val Cys Glu Gln Glu
145                 150                 155                 160

Lys Asn Gly Phe Met Leu Asp Thr Asp Ile Ala Glu Glu Ile Tyr Thr
                165                 170                 175

Thr Cys Leu Arg Glu Thr Asn Arg Ile Glu Ala Glu Ile Lys Glu Phe
            180                 185                 190

Met Val Pro Ile Ala Val Pro Val Lys Glu Val Ile Ile Lys Arg Lys
        195                 200                 205

Lys Asp Gly Ser Ile Tyr Ser Asn Gln Leu Leu Glu Gly Cys Asn Val
    210                 215                 220

Gln Gly Asp Tyr Thr Lys Ile Ala Trp Glu Glu Phe Asn Leu Gly Ser
225                 230                 235                 240

Pro Ala Gln Val Asn Lys Arg Leu Asp Arg Leu Gly Trp Lys Pro Thr
                245                 250                 255

Val Lys Thr Lys Ser Gly Asn Ser Tyr Lys Ile Cys Pro Glu Asn Leu
            260                 265                 270

Ala Thr Ile Pro Asp Thr Ala Pro Glu Ala Val Lys Gly Leu Lys Ala
        275                 280                 285

Trp Lys Val Leu Glu Thr Arg Trp Lys Leu Ala Gln Glu Trp Leu Gln
    290                 295                 300

Lys Ser Gln Glu Thr Gly Arg Val His Gly Arg Val Ile Leu Thr Gly
305                 310                 315                 320

Ala Val Thr His Arg Ala Ala His Gln Gly Pro Asn Met Ala Asn Ile
                325                 330                 335

Pro Ser Val Pro His Gly Lys Asp Gly Ile Leu Trp Lys Met Glu Gly

```
                340                 345                 350
Met Tyr Gly Ala Glu Cys Arg Gln Ala Phe Lys Val Pro Glu Gly Lys
            355                 360                 365

Leu Leu Val Gly Thr Asp Ala Ala Gly Ile Gln Leu Arg Val Leu Ala
        370                 375                 380

His Tyr Met Asn Asp Pro Ile Tyr Thr Glu Gln Val Ile Asp Gly Asp
385                 390                 395                 400

Ile His Thr Phe Asn Lys Glu Ala Leu Gly Arg Tyr Cys Lys Asp Arg
                405                 410                 415

Pro Thr Ala Lys Thr Phe Ile Tyr Ala Phe Leu Leu Gly Ala Gly Thr
            420                 425                 430

Gly Met Ile Ala Ser Ile Leu Gly Cys Asn Asn Arg Gln Ala Asn Glu
        435                 440                 445

Ala Met Ala Asn Phe Tyr Glu Ala Ile Pro Ser Leu Lys Lys Leu Lys
    450                 455                 460

Ser Gln Ala Ser Gln Ala Ala Ser Met Gly Trp Met Lys Gly Leu Asp
465                 470                 475                 480

Gly Arg Val Leu Arg Ile Gly Ser Asp His Leu Ala Leu Ser Val Tyr
                485                 490                 495

Leu Gln Gly Gly Glu Thr Val Ile Met Arg Leu Ala Asn Val Phe Trp
            500                 505                 510

Gln Arg Gln Ala Lys Lys Glu Gly Ile Asn Phe Lys Gln Cys Ala Trp
        515                 520                 525

Val His Asp Glu Trp Gln Thr Glu Val Asp Glu Asp Gln Ala Gln Arg
    530                 535                 540

Leu Gly Glu Ile Gln Val Gln Ala Ile Lys Asp Ala Gly Thr Phe Phe
545                 550                 555                 560

Lys Leu Asn Cys Pro Met Asp Gly Glu Ala Lys Ile Gly Lys Asn Trp
                565                 570                 575

Leu Glu Thr His
            580

<210> SEQ ID NO 22
<211> LENGTH: 538
<212> TYPE: PRT
<213> ORGANISM: Oedogonium cardiacum

<400> SEQUENCE: 22

Met Ile Glu Phe Tyr Ala Ser Phe Asp Lys Asp Lys Glu Ile Glu Ile
1               5                   10                  15

Asn Lys Glu Asp Ser Glu Met Asn Lys Glu Asp Ile Glu Met Asn Lys
            20                  25                  30

Glu Asp Ile Glu Ile Asp Leu Asp Glu Val Asn Glu Glu Glu Arg Phe
        35                  40                  45

Asp Val Asn Arg Glu Met Leu Gln Thr Asn Tyr Phe Val Lys Arg Phe
    50                  55                  60

Lys Asn Ile Leu Phe Pro Ile Ala Ala Ser Phe Tyr Thr Ser Glu Gly
65                  70                  75                  80

Asn Lys Asn Val Ser Lys Thr Phe Ser Leu Thr Ser Asn Ile Phe Asp
                85                  90                  95

Lys Lys Ile Pro Ser Thr Ile Asn Ile Leu Lys Glu Ser Gln Ile Met
            100                 105                 110

Met Gln Glu Phe Leu Ile Glu Leu Ile Ser Leu Ala Glu Asp Leu Leu
        115                 120                 125
```

```
Lys Lys Arg Asn Pro Thr Asn Ser Leu Phe Tyr Gly Asp Asp Lys Val
    130                 135                 140

Ile Ile Tyr Met His Asn Leu Ser Ser Phe Asp Gly Phe Phe Ile Leu
145                 150                 155                 160

Gln Thr Leu Leu Lys Ser Arg Ile Leu Asn Tyr Thr Phe Asn Leu Asn
                165                 170                 175

Lys Lys Leu Lys Val Thr Ser Tyr Glu Gly Leu Ile Tyr Arg Ile Lys
            180                 185                 190

Ile Gly Asn Leu Cys Phe Gln Asp Ser Tyr Arg Val Ile Pro Met Ser
        195                 200                 205

Leu Asn Lys Leu Ser Phe Leu Leu Leu Asn Lys Gln Lys Lys Asp Phe
    210                 215                 220

Asp Val Glu Asn Ile Asn Ser Gln Lys Leu Gln His Ile Phe Lys Asn
225                 230                 235                 240

Lys Glu Ile Leu Glu Lys Met Leu Glu Tyr Cys Leu Tyr Asp Ser Ile
                245                 250                 255

Leu Leu Tyr Glu Ser Met Ile Leu Ile Gln Lys Thr Phe Trp Asp Glu
            260                 265                 270

Leu Lys Phe Asp Ile Thr Ser Glu Ser Thr Ile Ser Asn Thr Ala Ile
        275                 280                 285

Asn Phe Phe Phe Ser Lys Tyr Tyr Glu Phe Pro Thr Gln Tyr Tyr Trp
    290                 295                 300

His Thr Thr Thr Lys Lys Asp Gly Leu Ser Ala Lys Leu Lys Tyr Asp
305                 310                 315                 320

Asn Lys Arg Val Thr Val Ser Thr His His Asn Ala Ile Phe Tyr Thr
                325                 330                 335

Lys Pro Phe Leu Asp Gln Gln Leu Arg Ser Ala Tyr Phe Gly Gly Arg
            340                 345                 350

Thr Glu Leu Tyr Lys Pro Gln Thr Ser Asn Gly Tyr Val Phe Asp Ile
        355                 360                 365

Asn Ser Leu Tyr Ala Phe Ala Leu Met Tyr Asp Met Pro Tyr Gly Ser
    370                 375                 380

Pro Ile Tyr Glu Asn Glu Tyr Lys Asn Trp Thr Thr Asn Glu Phe Glu
385                 390                 395                 400

Ser Phe Phe Gly Phe Leu Lys Ile Ile Phe Ile Thr Pro Pro Asn Tyr
                405                 410                 415

Asp Ile Leu Pro Val Leu Pro Arg Arg Tyr Pro Pro Ile Ser His
            420                 425                 430

Asn Val Tyr Cys Leu Gly Ile Gly Glu Gly Trp Tyr Phe Ser Glu Glu
    435                 440                 445

Ile Lys Leu Ala Arg Gln Lys Gly Tyr Lys Leu Lys Ile Leu Glu Ser
    450                 455                 460

Ile Lys Phe Thr Pro His Lys Gly Phe Glu Lys Phe Val Arg Asp Phe
465                 470                 475                 480

Phe Ser Ile Arg Gln Gln Tyr Pro Lys Gly His Pro Leu Asn Leu Leu
                485                 490                 495

Ala Lys Leu Ile Leu Asn Ser Thr Tyr Gly Arg Phe Gly Ile Ala Leu
            500                 505                 510

Thr Thr His Lys Gln Met Lys Thr Phe Asn Gln Ile Lys Leu Lys Glu
        515                 520                 525

Lys Lys Asn Lys Lys Ile Asn Ile Asn Ile
    530                 535
```

<210> SEQ ID NO 23
<211> LENGTH: 717
<212> TYPE: PRT
<213> ORGANISM: Salterprovirus His1

<400> SEQUENCE: 23

```
Met Ala Lys Cys Asp Lys Ser Leu Glu Ala Ile Asp Leu Asp Arg Ala
 1               5                  10                  15

Tyr Thr Ala Pro Arg Lys Ala Lys Trp Ala Glu Asn Lys Arg Ile Asn
            20                  25                  30

Gly Leu Asp Thr Glu Thr Ser Asp Gly Asp Ile Phe Cys Ile Ser Val
        35                  40                  45

Cys Trp Glu Gly Glu Lys Pro Met Val Gln His Asn Asp Arg Glu Lys
 50                  55                  60

Leu Thr Ser Lys Gln Val Trp Gln Val Leu Thr Asp His Lys Ala Arg
 65                  70                  75                  80

Ser Ser Leu Asn Met Trp Tyr Asn Leu Asp Phe Asp Ala Asn Val Val
                85                  90                  95

Leu Asn His Val Cys Ser Glu Glu Gln Leu Ala Glu Leu Val Val Ser
            100                 105                 110

Gly Thr Thr Leu Ala Asn Ser Asp Arg Thr Tyr Arg Gln Tyr Met Asp
        115                 120                 125

Thr Asp Lys Glu Leu Arg Lys Gly Glu Tyr Leu Ile Thr Tyr Ile Gln
130                 135                 140

Ser Lys Phe Leu Glu Ile Lys Asp His Asn Ser His Ile Tyr Thr His
145                 150                 155                 160

Tyr Asp Ala Ser Gln Phe Phe Tyr Thr Ser Leu Glu Asn Ala Val Thr
                165                 170                 175

Glu Trp Leu Gly Glu Ser Lys Ala Asn Asp Gly Leu Glu Ala Gly Leu
            180                 185                 190

Phe Gly Ser Gln Thr Pro Asn Gln Leu Arg Glu Thr Val Ala Glu Ser
        195                 200                 205

Asp Cys Val Thr Trp Thr Asn Leu Ser Leu Thr Tyr Asn Val Ser Lys
210                 215                 220

Gly Asp Lys Trp Thr Ile His Asn Ala Lys Ser Tyr Ile Ser Lys Asn
225                 230                 235                 240

Trp Ser Asp Ile Leu Lys Tyr Ala Gln Ile Asp Ala Glu Leu Val Arg
                245                 250                 255

Asp Leu Trp Gln Glu Ala Val Asn Val Gly Glu Leu Asp Ile Pro
            260                 265                 270

Met Gly Arg Pro Phe Ser Thr Gly Tyr Leu Ala Glu Ser Tyr Leu Asp
        275                 280                 285

Asn Arg Leu Arg Glu Lys Pro Gly Leu Gly Pro Met Pro Met Ala Lys
        290                 295                 300

Met Ala Trp Glu Ser Tyr Ala Gly Gly Arg Phe Glu Val Leu Lys Arg
305                 310                 315                 320

Gly Asn Val Gly Arg Val Ala Gly Pro Asp Ile Asn Ser Ala Tyr Pro
                325                 330                 335

Ala Val Leu Ala Glu Leu Pro Asp Pro Lys Thr Leu Arg Trp Lys Arg
            340                 345                 350

Ala Lys His Ala Ser Ile Ser Glu Ile Glu Thr Ala Asp Tyr Gly Phe
        355                 360                 365

Met Thr Val Lys Val Ser Thr Asp Pro Thr Arg Glu Ile Gln Pro Phe
        370                 375                 380
```

Ala Val Lys Asp Glu Lys Gln Asp Lys Leu Val Tyr Pro Ser Pro Gln
385                 390                 395                 400

Asn Thr Glu Ile Thr Val Val Lys Asp Ile Phe Ile His Ala Tyr Asn
            405                 410                 415

Gln Gly Tyr Val Thr Asp Tyr Glu Val Ile Asp Cys Trp Leu Gly Tyr
        420                 425                 430

Lys Thr Glu Gly Thr Thr Phe Pro Phe Asp Phe Ile Pro Glu Leu Tyr
    435                 440                 445

Asp Asn Arg Lys Thr Ala Glu Ala Asn Gly Leu Glu Lys Arg Gly Leu
450                 455                 460

Leu Leu Lys Ile Val Leu Asn Ser Met Tyr Gly Lys Thr Cys Gln Thr
465                 470                 475                 480

Thr Pro Lys Arg Arg Glu Leu Ala Glu Ser Thr Glu Leu Glu Leu His
            485                 490                 495

Glu Ser Tyr Val Pro Asp Met Ser Leu Pro Lys Met Ile Arg Glu Lys
        500                 505                 510

Tyr Ser Glu Gly Phe Ile Glu Ser Leu Thr Ala Gly Ala Trp Phe Asn
    515                 520                 525

Pro Phe Leu Ala Ser Tyr Ile Thr Gly Leu Thr Arg Leu Glu Leu His
530                 535                 540

Lys Gln Ile Cys Lys His Asp Leu Glu Glu Asn Thr Val Met Leu Ala
545                 550                 555                 560

Thr Asp Cys Val Met Ile Glu Glu Lys Pro Phe Glu Ser Asn Phe
            565                 570                 575

Val Glu Asn Leu Val Gln Asp Gly Leu Gly Tyr Trp Asp Met Glu Tyr
        580                 585                 590

Lys Gly Asp Ala Phe Val Leu Gly Ala Gly Val Tyr Gln Ile Asp Phe
    595                 600                 605

Asp Thr Cys Gln Lys Gly Cys Lys Asp Asn Cys Asn Lys Phe Ser His
610                 615                 620

Lys His Lys Val Lys Thr Arg Gly Phe Ser Glu Ala Asp Leu Glu Lys
625                 630                 635                 640

Gly Leu Val Asn Ala Ala Glu Lys Ala Asn Gly His Ile Glu Ile Glu
            645                 650                 655

Ser Thr Arg Pro Gln Thr Ile Ser Glu Ile Ile Trp Ser Asn Glu Glu
        660                 665                 670

Leu Ser Gln Val Gly Asn Phe Leu Gln Glu Arg Lys Ile Lys Pro
    675                 680                 685

Glu Met Asp Thr Lys Arg Lys Trp Ser Glu Asn Thr Asp Phe Lys Lys
690                 695                 700

Leu Leu Ser Thr Cys Glu Thr Ser Leu Pro Leu Lys Ile
705                 710                 715

<210> SEQ ID NO 24
<211> LENGTH: 720
<212> TYPE: PRT
<213> ORGANISM: Salterprovirus His2

<400> SEQUENCE: 24

Met Ala Lys Ser Asp Arg Asn Leu Asp Glu Val Asn Leu Tyr Pro Ala
1               5                   10                  15

Tyr Gln Asp Gln Tyr Ser Ala Thr Phe Val Asp Gly Lys Leu Ile Asn
            20                  25                  30

Ala Phe Asp Thr Glu Thr Ser Ser Gly Thr Val Phe Met Leu Thr Ser
        35                  40                  45

Ala Tyr Gly Asp Lys Thr Gln Ala Tyr Tyr Asn Arg Asp Val Ser Glu
 50                  55                  60

Leu Asp Ala Glu Thr Ile Met Asp Ala Leu Thr Asp Tyr Lys Thr Arg
 65                  70                  75                  80

Ser Asn Ile Asn Ile Trp Tyr Asn Leu Asp Phe Asp Ala Asn Ala Ile
                     85                  90                  95

Leu Ser Gly Ile Leu Ser Gln Lys Glu Met Ser Glu Leu Val Val Thr
            100                 105                 110

Asn Glu Thr Thr Thr Val Ala Gly Ile Glu Tyr Glu Ile Phe Tyr
        115                 120                 125

Ile Lys Gly Lys Met Leu Arg Ile Val Asp Glu Asn Gly Asn Ile Ser
130                 135                 140

Pro His Tyr Asp Ile Ala Gln Phe Phe Tyr Thr Ser Leu Asp Asn Ala
145                 150                 155                 160

Ala Glu Glu Trp Leu Gly Glu Asn Lys Lys Glu Gly Ile Asp Thr Ser
                165                 170                 175

Lys Phe Asp Asp Lys Glu Tyr Ile Lys Asp Asn Phe Asp Glu Ile Leu
            180                 185                 190

Lys Tyr Ala Lys Lys Asp Ala Ser Leu Thr Gln Asp Leu Ala Ile Glu
        195                 200                 205

Leu Thr Asn Glu Ala Glu Asn Leu Asp Ile Pro Met Gly Arg Pro Ile
210                 215                 220

Ser Thr Gly Tyr Leu Ser Ala Glu Tyr Leu Arg Ala Asn Thr Glu Glu
225                 230                 235                 240

Lys Pro Ser Leu Gly Asn Glu Ala Met Gln Asn Leu Phe Trp Glu Ser
                245                 250                 255

Tyr Tyr Gly Gly Arg Phe Glu Val Phe Gln Arg Gly Asn Val Gly Glu
            260                 265                 270

Val Val Ala Pro Asp Ile Asn Ser Ala Tyr Pro Ala Ile Met Lys Asp
        275                 280                 285

Leu Pro Asp Pro Thr Thr Leu Asn Trp Asn His Tyr Leu Asn Glu Val
290                 295                 300

Ser Asp Lys Glu Pro Phe Ser His Ser Ile Asn Lys Phe Gly Tyr Glu
305                 310                 315                 320

Glu Ile Glu Asn Gly His Tyr Gly Val Val Lys Ala Arg Val Thr Thr
                325                 330                 335

Asp Ser Ser Arg Met Ile Gln Pro Phe Ala Cys Lys Ile Asp Gly Lys
            340                 345                 350

Val Lys Phe Pro Ala Met Thr Asn Lys Val Val Thr Val Ile Lys Pro
        355                 360                 365

Ile Phe Glu Phe Ala Val Asn Asn Gly Leu Val Thr Asp Phe Glu Leu
370                 375                 380

Ile Glu Ala Trp Ile Gly Asn Ile Thr Asp Arg Thr Ser Lys Pro Phe
385                 390                 395                 400

Glu Phe Ile Gly Asp Met Tyr Ala Glu Arg Lys Val Phe Glu Gln Leu
                405                 410                 415

Lys Asn Lys Pro Lys Lys Gly Gln Leu Leu Lys Ile Val Leu Asn Ser
            420                 425                 430

Ser Tyr Gly Lys Thr Cys Gln Thr Thr Glu Lys Arg His Lys His Asp
        435                 440                 445

Leu Asp Lys Asp Gly Lys Lys Ile Met Gln Ala His Glu Thr Gln Tyr
450                 455                 460

```
Pro Arg Phe Tyr Leu Ser Lys Lys Gln Arg Glu Ala Leu Gly Asp Asp
465                 470                 475                 480

Glu Ile Ile Ile Thr Glu Leu Glu Ala Gly Lys Arg Phe Asn Pro Phe
            485                 490                 495

Phe Ala Ser Tyr Ile Thr Gly Leu Thr Arg Leu Glu Leu His Lys Gln
        500                 505                 510

Val Val Glu His Asp Ile Glu Asp Ser Thr Val Met Phe Ala Thr Asp
    515                 520                 525

Cys Leu Met Val Glu Lys Glu Ala Tyr Glu Asn Ser Ser Phe Asp Glu
        530                 535                 540

Gln Ile His Val Pro Asp Asp Ser Leu Pro Glu Ser Glu Phe Arg Lys
545                 550                 555                 560

Glu Ala Thr Arg Ser Leu Gly Ala Trp Asp Phe Asp Tyr Glu Gly Ser
                565                 570                 575

Ala Phe Ile Val Gly Ser Gly Val Tyr Glu Val Asp Thr Ile Gln Gly
            580                 585                 590

Lys Thr Lys Thr Lys Thr Arg Gly Phe Ile Glu Ser Asn Leu Gly Asp
        595                 600                 605

Thr Leu Lys Gly Leu Ala Lys Lys His Lys Glu Ala Ile Pro Leu Asp
610                 615                 620

Asn Glu Arg Pro Leu Thr Met Ala Glu Val Leu Ile Asn Thr Glu Arg
625                 630                 635                 640

Gly Ser Val Ser Glu Phe Val Glu Asn Ser Lys Lys Leu Lys Pro Asp
                645                 650                 655

Phe Asp Asp Lys Arg Asn Trp Asn Arg Glu Asn Pro Asn Phe His Asp
            660                 665                 670

Leu Leu Asn Asp Lys Glu Tyr Ser Lys Pro Ile Asp Leu Gln Glu Gln
        675                 680                 685

Lys Glu Glu Met Ile Gln Glu Gln Met Asp Ile Asn Glu Lys Met Ile
690                 695                 700

Gly Asp Ala Thr Pro Asn Gly Asn Glu Thr Val Val Lys Asp Asp
705                 710                 715                 720

<210> SEQ ID NO 25
<211> LENGTH: 957
<212> TYPE: PRT
<213> ORGANISM: Ostreococcus tauri

<400> SEQUENCE: 25

Met Val Val Phe Gln Ala Leu Thr Trp Glu Ser Arg Asp Thr Asp Asp
1               5                   10                  15

Glu His Leu Ile Ser Ile Phe Gly Lys Thr Glu Glu Gly Lys Ser Val
            20                  25                  30

Cys Leu Thr Thr Ala Phe Thr Pro Tyr Phe Phe Ile Lys Leu Pro Glu
        35                  40                  45

Lys Ile Asp Ala Gly Lys Ile Arg Arg Ile Tyr Asn Ile Leu Asp Glu
    50                  55                  60

Lys Cys Lys Asp Ser Leu Val Ala Tyr Ser Val Met Lys Ser Lys Asp
65                  70                  75                  80

Val Trp Gly Phe Gln Asn Asn Glu Glu Phe Val Phe Met Lys Val Asn
                85                  90                  95

Phe Lys His Leu Gln Ala Arg Arg Leu Val Asp Ser Phe Leu Arg Lys
            100                 105                 110

Pro Leu Asp Arg Thr Pro Glu Leu Phe Asn Ile Phe Gly Val Arg Asn
        115                 120                 125
```

-continued

```
Val Lys Val Tyr Glu Ser Asn Leu Asp Pro Val Leu Arg Leu Met His
        130                 135                 140

Arg Thr Gly Ile Gln Ser Thr Gly Trp Leu Asp Thr Gly Asp Lys Cys
145                 150                 155                 160

Ile Arg Ser His Leu Ala Arg Val Asp Leu Asp Leu Phe Cys Asn Asp
                165                 170                 175

Trp Thr Thr Leu Lys Pro Val Ala Arg Asp Asp Ile Ala Pro Phe Val
            180                 185                 190

Val Ala Ser Val Asp Ile Glu Cys Asn Ser Ser Thr Gly Lys Phe Pro
        195                 200                 205

Asp Ala Asp Val Thr Gly Asp Ala Cys Phe Gln Ile Ala Ile Ser Leu
210                 215                 220

Cys Lys Phe Gly Ser Asp Glu Pro Tyr Asp Lys Thr Cys Leu Cys Tyr
225                 230                 235                 240

Lys Lys Thr Asp Pro Asn Leu Glu Gly Ser Thr Ile Arg Ser Tyr Glu
                245                 250                 255

Thr Glu Arg Glu Met Leu Glu Ala Phe Gln Lys Tyr Leu His Thr Lys
            260                 265                 270

Asp Val Asp Ile Ile Thr Gly Trp Asn Ile Phe Gly Phe Asp Met Glu
        275                 280                 285

Tyr Ile Tyr Lys Arg Ala Gln Val Asn Arg Cys His Tyr Glu Phe Phe
290                 295                 300

Asn Leu Gly Lys Leu Arg Asp Thr Glu Ser Glu Leu Val Ile Lys Lys
305                 310                 315                 320

Leu Ser Ser Ser Ala Leu Gly Asp Asn Leu Leu Lys Leu Leu Pro Met
                325                 330                 335

Pro Gly Arg Phe Ile Phe Asp Met Phe His Glu Val Lys Lys Gly Tyr
            340                 345                 350

Lys Leu Asp Ser Tyr Lys Leu Asp Asn Val Ser Lys Leu Tyr Leu Gly
        355                 360                 365

Asp Gln Lys Ile Asp Met Ala Pro Lys Glu Met Phe Ala Arg Tyr Arg
370                 375                 380

Glu Glu Asp Pro Val Lys Leu Arg Glu Val Ala Glu Tyr Cys Ile Lys
385                 390                 395                 400

Asp Thr Leu Leu Pro His Arg Leu Met Lys Lys Leu Cys Thr Leu Leu
                405                 410                 415

Asn Met Val Glu Met Ala Lys Ala Thr Trp Val Pro Ala Asn Phe Leu
            420                 425                 430

Val Glu Arg Gly Gln Gln Ile Lys Val Phe Ser Gln Leu Thr Lys Lys
        435                 440                 445

Ala Arg Glu Leu Gly Phe Met Val Pro Thr Ile Arg Tyr Gly Ala Ile
450                 455                 460

Pro Glu Glu Pro Tyr Glu Gly Ala Thr Val Leu Glu Ala Gln Lys Gly
465                 470                 475                 480

Ala Tyr Tyr Thr Pro Ile Thr Ala Leu Asp Phe Glu Ala Leu Tyr Pro
                485                 490                 495

Ser Ile Met Met Ala His Asn Leu Cys Tyr Ser Ser Tyr Val Met Asp
            500                 505                 510

Glu Lys Arg Tyr Gly Ser Val Pro Gly Ile Thr Tyr Glu Thr Phe Asn
        515                 520                 525

Ile Gly Asp Arg Thr Tyr Lys Phe Ala Gln Asp Val Pro Ser Leu Leu
530                 535                 540
```

```
Pro Ala Ile Leu Ala Glu Leu Lys Gln Phe Arg Lys Gln Ala Lys Arg
545                 550                 555                 560

Asp Met Ala Ala Thr Gly Phe Met Lys Glu Val Tyr Asn Gly Lys
                565                 570                 575

Gln Leu Ala Tyr Lys Val Ser Met Asn Ser Val Tyr Gly Phe Thr Gly
            580                 585                 590

Ala Gly Lys Gly Ile Leu Pro Cys Val Pro Ile Ala Ser Thr Thr Thr
        595                 600                 605

Ser Lys Gly Arg Ser Met Ile Glu Glu Thr Lys Asn Tyr Val Glu Lys
    610                 615                 620

Asn Phe Pro Gly Ala Lys Val Arg Tyr Gly Asp Thr Asp Ser Val Met
625                 630                 635                 640

Val Glu Phe Asp Val Gly Asp Arg Lys Gly Glu Glu Ala Ile Ala Tyr
                645                 650                 655

Ser Trp Glu Val Gly Glu Arg Ala Ala Glu Glu Cys Ser Ala Leu Phe
            660                 665                 670

Lys Lys Pro Asn Asn Leu Glu Leu Glu Lys Val Tyr Trp Pro Tyr Phe
        675                 680                 685

Leu Tyr Ser Lys Lys Arg Tyr Ala Ala Lys Leu Trp Thr Lys Gly Lys
    690                 695                 700

Asp Gly Lys Met His Met Asp Tyr Ile Asp Ile Lys Gly Leu Gln Val
705                 710                 715                 720

Val Arg Arg Asp Asn Thr Pro His Val Arg Glu Val Cys Lys Glu Leu
                725                 730                 735

Leu Asp Val Ile Leu Thr Ser Ser Asp Pro Gly Pro Lys Glu Leu
            740                 745                 750

Ala Lys Glu Arg Ala Ile Glu Leu Leu Ser Gly Asp Val Pro Asn Asp
        755                 760                 765

Lys Leu Ile Leu Ser Gln Gly Leu Ser Asp Thr Tyr Lys Val Gly Gly
    770                 775                 780

Lys Asn Val Ser Val Thr Ser Ala Asp Ser Val Asn Ile Asn Gln Ser
785                 790                 795                 800

His Val Gln Val Val Thr Lys Met Arg Gln Arg Lys Pro Gly Ser Glu
                805                 810                 815

Pro Gln Ser Gly Asp Arg Val Pro Tyr Leu Leu Thr Lys Thr Gln Asp
            820                 825                 830

Pro Lys Ala Lys Ala Tyr Glu Lys Ala Glu Asp Pro Lys Tyr Val Glu
        835                 840                 845

Glu His Gly Val Pro Val Asp Tyr His Tyr Tyr Phe Leu Asn Lys Phe
    850                 855                 860

Leu Asn Pro Val Cys Asp Leu Leu Asp Pro Leu Tyr Glu Asn Val Lys
865                 870                 875                 880

Glu Asp Ile Phe Gly Glu Ile Ile Asn Ala His Lys Pro Val Lys Pro
                885                 890                 895

Pro Lys Leu Pro Ser Leu Ser Gly Met Lys Lys Asp Asp Leu Ile Ala
            900                 905                 910

Glu Cys Gln Arg Leu Gly Leu Glu Glu Thr Gly Thr Leu Ala Ile Leu
        915                 920                 925

Arg Ala Arg Leu Lys Asp Ala Arg His Gly Ser Val Glu Asp Leu Phe
    930                 935                 940

Lys Asn Tyr Glu Leu Thr Gln Ser Lys Asp Glu Ser Ser
945                 950                 955
```

<210> SEQ ID NO 26
<211> LENGTH: 1046
<212> TYPE: PRT
<213> ORGANISM: Ectocarpus siliculosus virus 1

<400> SEQUENCE: 26

Met Glu Leu Tyr Leu His Asp Ile Arg Asp Asn Ser Gly Ser Phe Gln
1               5                   10                  15

Asn Pro Thr Met Gln Leu Phe Ala Met Glu Glu Asp Gly Thr Asn Val
            20                  25                  30

Phe Val Ser Val Lys Asn Phe Lys Thr Tyr Leu Tyr Val Gly Phe Asp
        35                  40                  45

Leu Asp Ile Ser Glu Asp Ser Val Arg Ser Asn Tyr Leu Glu Lys Phe
    50                  55                  60

Lys Gln Glu Lys Trp Glu Arg Asn Val Tyr Lys Met Ser Val Val Lys
65                  70                  75                  80

Arg Lys Arg Leu Ile Gly Phe Ser Asn Gly Asp Leu Phe Pro Tyr Ile
                85                  90                  95

Leu Met Glu Phe Thr Gly Thr Ile Ser Phe Tyr Ile Val Arg Lys His
            100                 105                 110

Leu His Glu Leu Cys Gly Glu Arg Asp Pro Gly Pro Asn Thr Phe Val
        115                 120                 125

Asp Leu Asn Lys Tyr Pro Gly Met Cys Val Tyr Glu Ser Lys Ser Val
    130                 135                 140

Asp Ser Ile Leu Lys Phe Phe His Ala Ser Gly Val Arg Pro Ser Ser
145                 150                 155                 160

Tyr Phe Arg Met Glu Asn Tyr Val Arg Val Ala Asp Lys Ala Arg Lys
                165                 170                 175

Thr His Cys Ala Lys Glu Phe Ile Val Asp Phe Val Asn Val Arg Pro
            180                 185                 190

Val Gly Glu Glu Val Val Asp Arg Lys Pro Pro Met Thr Ile Cys
        195                 200                 205

Ser Tyr Asp Leu Glu Thr Ser Gly Leu Asn Thr Asn Glu Asp Tyr Ile
    210                 215                 220

Phe Gln Ala Ser Met Ile Phe Ser Arg Leu Gly Asp Pro Cys Pro Asp
225                 230                 235                 240

Ser Glu Gly Ser Ala Thr Gly His Ala Val Asp Ser Tyr Thr Asp Gly
                245                 250                 255

Val Val Ile Cys Val Gly Asp Thr Glu Ser Val Asp Gly Thr Pro Leu
            260                 265                 270

Leu Ile Val Glu Asn Glu Leu Gln Leu Leu Asp Lys Phe Arg Glu Ile
        275                 280                 285

Leu Val Glu Arg Gly Cys Asn Ile Leu Cys Gly Tyr Asn Thr Phe Lys
    290                 295                 300

Phe Asp Ser Ala Phe Leu Tyr Lys Arg Ala Glu Arg Tyr Gly Phe Asp
305                 310                 315                 320

Gly Phe Lys Lys Leu Ser Phe Ile Lys Asp Leu Ala Cys Asp Leu Glu
                325                 330                 335

Val Lys Thr Leu Gln Ser Ala Ala Leu Gly Lys Asn Glu Leu Lys Gln
            340                 345                 350

Ile Ile Ile Pro Gly Arg Val Glu Ile Asp Leu Phe Met Val Met Arg
        355                 360                 365

Arg Ser Gln Lys Leu Ser Ser Tyr Lys Leu Asn Ala Val Cys Asp Lys
    370                 375                 380

```
Phe Phe Gly Gly Lys Lys Asp Asp Val Thr Tyr Ala Asp Ile Leu Gln
385                 390                 395                 400

Ala Cys Thr Ser Lys Asp Pro Lys Lys Leu Gly Val Ile Ala Lys Tyr
            405                 410                 415

Cys Tyr Gln Asp Ser Gly Leu Val Leu Lys Leu Leu Asp Lys Ile Lys
        420                 425                 430

Glu Val Tyr Asp Ala Thr Glu Met Ala Lys Leu Cys Thr Val Pro Leu
    435                 440                 445

Thr Tyr Ile Val Gly Arg Gly Gln Gln Ile Lys Cys Met Ser Leu Ile
450                 455                 460

Leu Asn Arg Ile His Gly Glu Tyr Val Cys Asn Tyr Ala Ala Ala Lys
465                 470                 475                 480

Lys Lys Met Ala Ala Asp Gly Lys Gln Val Leu Asn Glu Gly Tyr Lys
            485                 490                 495

Gly Ala Ser Val Ile Asp Ala Lys Lys Gly Phe Tyr Glu Lys Asp Pro
        500                 505                 510

Ile Val Thr Met Asp Phe Ala Ser Leu Tyr Pro Ser Ile Met Arg Leu
    515                 520                 525

Lys Gln Leu Cys Tyr Thr Thr Ile Val Arg Asp Val Lys Tyr Arg Gly
530                 535                 540

Ile Glu Gly Val Asn Tyr Glu Asp His Gln Ile Ser Asp Gly Val Ser
545                 550                 555                 560

Val Thr Phe Ala His Arg Pro Gly Ser Arg Ser Ile Leu Cys Glu Leu
            565                 570                 575

Glu Glu Met Leu Gly Glu Glu Arg Lys Ala Thr Lys Lys Leu Met Lys
        580                 585                 590

Ser Glu Lys Asp Pro Phe Ala Tyr Ser Leu Leu Asp Ser Lys Gln Lys
    595                 600                 605

Ala Gln Lys Val Thr Met Asn Ser Ile Tyr Gly Phe Thr Gly Thr Val
610                 615                 620

Asn Asn Gly Met Leu Pro Leu Val Glu Ile Ala Ala Ala Val Thr Ser
625                 630                 635                 640

Thr Gly Arg Asp Met Ile Lys Arg Thr Lys Glu Tyr Ala Glu Lys Glu
            645                 650                 655

His Gly Cys Asn Val Ile Tyr Gly Asp Thr Asp Ser Val Met Val Ile
        660                 665                 670

Phe Pro Glu His Arg Asn Ile Glu Asn Leu Gly Asp Lys Met Arg Tyr
    675                 680                 685

Cys Phe Asp Met Gly Thr Lys Val Ser Lys Glu Ile Ser Glu Met Phe
690                 695                 700

Gly His Pro Ile Leu Leu Glu Phe Glu Asn Ile Tyr Phe Lys Tyr Leu
705                 710                 715                 720

Leu Val Ser Lys Lys Arg Tyr Ala Gly Leu Ser Trp Glu Thr Val Glu
            725                 730                 735

Gly Pro Pro Thr Met Thr Met Lys Gly Leu Val Thr Val Arg Arg Asp
        740                 745                 750

Asn Ala Pro Phe Val Gly Arg Cys Ala Ser Glu Ala Ile His Met Leu
    755                 760                 765

Met Asp Val Asp Val Thr Asp Gly Arg Gly Ala Val Lys Lys His Leu
770                 775                 780

Thr Glu Thr Leu Leu Arg Leu Glu Arg Gly Gln Ile Ser Ile Glu Asp
785                 790                 795                 800

Leu Thr Ile Arg Lys Glu Leu Lys Gln Trp Val Tyr Lys Thr Pro Ser
```

```
                    805                 810                 815
Pro His Ala Thr Leu Ala Leu Lys Ile Leu Glu Arg Thr Lys Glu Gln
                820                 825                 830

Ala Val Phe Arg Glu Phe Ile Lys Pro Ala Tyr Glu Thr Ile Gly Gly
            835                 840                 845

Tyr Asp Ser Leu Leu Ser Ser Val Trp Thr Lys Met Thr Asn Leu
    850                 855                 860

Lys Ser Tyr Leu Ser Val Arg Ala Lys Arg Glu Ile Ala Met Ser Asp
865                 870                 875                 880

Met Val Glu Ser Ile Arg Gly Asp Thr Thr Ser Pro Phe Lys Ala Glu
                885                 890                 895

Ala Tyr Ala Val Val Ala Leu Arg Gln Leu Tyr Asp Asp Val His Ser
            900                 905                 910

Val Leu Val Gly Glu Ser Phe Ala Arg Val Val Gly Leu Val Met Ala
        915                 920                 925

Gly Ile Gly Asp Val His Lys Leu Gly Glu Arg Tyr Met Ala Phe Val
    930                 935                 940

Arg Tyr Asn Ile Val Asp Trp Asp Pro Thr Leu Gly Glu Arg Ile
945                 950                 955                 960

Pro Tyr Val Ile Thr Thr Gly Lys Gly Asp Ile Ser Ser Arg Ala Glu
                965                 970                 975

Asp Pro Arg Met Val Asn Val Gly Arg Cys Arg Pro Ala Phe Leu Tyr
            980                 985                 990

Tyr Ile Asp His Gln Leu Arg Asn Pro Met Val Asp Leu Leu Gln His
        995                 1000                1005

Val Ile Glu Ser Pro Ser Ser Leu Phe Val Glu Ser Gln Arg Arg
    1010                1015                1020

Met Ser Asn Leu Asn His Gly Arg Lys Glu Ile Thr Thr Phe Phe
    1025                1030                1035

Lys Lys Arg Lys Val Thr Glu Gly
    1040                1045

<210> SEQ ID NO 27
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asn His Leu Val His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
            35                  40                  45

Val Trp Ala Tyr Gly Tyr Met Asn Ile Glu Asp His Ser Glu Tyr Lys
        50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110
```

-continued

Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Tyr Ala Tyr Ile Lys
            180                 185                 190

Asn Asp Ile Gln Ile Ile Ala Glu Ala Leu Leu Ile Gln Phe Lys Gln
            195                 200                 205

Gly Leu Asp Arg Met Thr Ala Gly Ser Asp Ser Leu Lys Gly Phe Lys
            210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
            275                 280                 285

Pro Tyr Gly Glu Pro Ile Val Phe Glu Gly Lys Tyr Val Trp Asp Glu
            290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Gly Glu Ile Ala Asp Leu Trp
            340                 345                 350

Leu Ser Asn Val Asp Leu Glu Leu Met Lys Glu His Tyr Asp Leu Tyr
            355                 360                 365

Asn Val Glu Tyr Ile Ser Gly Leu Lys Phe Lys Ala Thr Thr Gly Leu
370                 375                 380

Phe Lys Asp Phe Ile Asp Lys Trp Thr Tyr Ile Lys Thr Thr Ser Glu
385                 390                 395                 400

Gly Ala Ile Lys Ala Leu Ala Lys Leu Met Leu Asn Ser Leu Tyr Gly
                405                 410                 415

Lys Phe Ala Ser Asn Pro Asp Val Thr Gly Lys Val Pro Tyr Leu Lys
            420                 425                 430

Glu Asn Gly Ala Leu Gly Phe Arg Leu Gly Glu Glu Thr Lys Asp
            435                 440                 445

Pro Val Tyr Thr Pro Met Gly Val Phe Ile Thr Ala Trp Ala Arg Tyr
            450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
            500                 505                 510

Thr Phe Lys Arg Ala Lys Tyr Leu Arg Gln Lys Thr Tyr Ile Gln Asp
            515                 520                 525

Ile Tyr Met Lys Glu Val Asp Gly Lys Leu Val Glu Gly Ser Pro Asp

```
                530                 535                 540
Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
                580                 585                 590

Val Asp Asp Thr Phe Thr Ile Lys
                595                 600

<210> SEQ ID NO 28
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asn His Leu Val His His His His Ile Glu Gly Arg His
1               5                   10                  15

Met Glu Leu Gly Thr Leu Glu Gly Ser Met Lys His Met Pro Arg Lys
                20                  25                  30

Met Tyr Ser Cys Ala Phe Glu Thr Thr Thr Lys Val Glu Asp Cys Arg
                35                  40                  45

Val Trp Ala Tyr Gly Tyr Met Asn Ile Glu Asp His Ser Glu Tyr Lys
            50                  55                  60

Ile Gly Asn Ser Leu Asp Glu Phe Met Ala Trp Val Leu Lys Val Gln
65                  70                  75                  80

Ala Asp Leu Tyr Phe His Asn Leu Lys Phe Ala Gly Ala Phe Ile Ile
                85                  90                  95

Asn Trp Leu Glu Arg Asn Gly Phe Lys Trp Ser Ala Asp Gly Leu Pro
            100                 105                 110

Asn Thr Tyr Asn Thr Ile Ile Ser Arg Met Gly Gln Trp Tyr Met Ile
            115                 120                 125

Asp Ile Cys Leu Gly Tyr Lys Gly Lys Arg Lys Ile His Thr Val Ile
        130                 135                 140

Tyr Asp Ser Leu Lys Lys Leu Pro Phe Pro Val Lys Lys Ile Ala Lys
145                 150                 155                 160

Asp Phe Lys Leu Thr Val Leu Lys Gly Asp Ile Asp Tyr His Lys Glu
                165                 170                 175

Arg Pro Val Gly Tyr Lys Ile Thr Pro Glu Glu Tyr Ala Tyr Ile Lys
            180                 185                 190

Asn Asp Ile Gln Ile Ile Ala Glu Ala Leu Leu Ile Gln Phe Lys Gln
        195                 200                 205

Gly Leu Asp Arg Met Thr Ala Gly Ser Asp Ser Leu Lys Gly Phe Lys
    210                 215                 220

Asp Ile Ile Thr Thr Lys Lys Phe Lys Lys Val Phe Pro Thr Leu Ser
225                 230                 235                 240

Leu Gly Leu Asp Lys Glu Val Arg Tyr Ala Tyr Arg Gly Gly Phe Thr
                245                 250                 255

Trp Leu Asn Asp Arg Phe Lys Glu Lys Glu Ile Gly Glu Gly Met Val
            260                 265                 270

Phe Asp Val Asn Ser Leu Tyr Pro Ala Gln Met Tyr Ser Arg Leu Leu
        275                 280                 285
```

```
Pro Tyr Gly Glu Pro Ile Val Phe Glu Gly Lys Tyr Val Trp Asp Glu
    290                 295                 300

Asp Tyr Pro Leu His Ile Gln His Ile Arg Cys Glu Phe Glu Leu Lys
305                 310                 315                 320

Glu Gly Tyr Ile Pro Thr Ile Gln Ile Lys Arg Ser Arg Phe Tyr Lys
                325                 330                 335

Gly Asn Glu Tyr Leu Lys Ser Ser Gly Glu Ile Ala Asp Leu Trp
                340                 345                 350

Leu Ser Asn Val Asp Leu Glu Leu Met Lys Glu His Tyr Asp Leu Tyr
        355                 360                 365

Asn Val Glu Tyr Ile Ser Gly Leu Lys Phe Lys Ala Thr Thr Gly Leu
    370                 375                 380

Phe Lys Asp Phe Ile Asp Lys Trp Thr Tyr Ile Lys Thr Thr Ser Glu
385                 390                 395                 400

Gly Ala Ile Lys Gln Leu Ala Lys Leu Met Leu Asn Gly Leu Tyr Gly
                405                 410                 415

Lys Phe Ala Ser Asn Pro Asp Val Thr Gly Lys Val Pro Tyr Leu Lys
                420                 425                 430

Glu Asn Gly Ala Leu Gly Phe Arg Leu Gly Glu Glu Thr Lys Asp
    435                 440                 445

Pro Val Tyr Thr Pro Met Gly Val Phe Ile Thr Ala Trp Ala Arg Tyr
    450                 455                 460

Thr Thr Ile Thr Ala Ala Gln Ala Cys Tyr Asp Arg Ile Ile Tyr Cys
465                 470                 475                 480

Asp Thr Asp Ser Ile His Leu Thr Gly Thr Glu Ile Pro Asp Val Ile
                485                 490                 495

Lys Asp Ile Val Asp Pro Lys Lys Leu Gly Tyr Trp Ala His Glu Ser
                500                 505                 510

Thr Phe Lys Arg Ala Lys Tyr Leu Arg Gln Lys Thr Tyr Ile Gln Asp
            515                 520                 525

Ile Tyr Met Lys Glu Val Asp Gly Lys Leu Val Glu Gly Ser Pro Asp
    530                 535                 540

Asp Tyr Thr Asp Ile Lys Phe Ser Val Lys Cys Ala Gly Met Thr Asp
545                 550                 555                 560

Lys Ile Lys Lys Glu Val Thr Phe Glu Asn Phe Lys Val Gly Phe Ser
                565                 570                 575

Arg Lys Met Lys Pro Lys Pro Val Gln Val Pro Gly Gly Val Val Leu
            580                 585                 590

Val Asp Asp Thr Phe Thr Ile Lys
        595                 600

<210> SEQ ID NO 29
<211> LENGTH: 912
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met His His His His His Lys His Met Lys Glu Phe Tyr Leu Thr
1               5                   10                  15

Val Glu Gln Ile Gly Asp Ser Ile Phe Glu Arg Tyr Ile Asp Ser Asn
            20                  25                  30

Gly Arg Glu Arg Thr Arg Glu Val Glu Tyr Lys Pro Ser Leu Phe Ala
        35                  40                  45
```

His Cys Pro Glu Ser Gln Ala Thr Lys Tyr Phe Asp Ile Tyr Gly Lys
 50                  55                  60

Pro Cys Thr Arg Lys Leu Phe Ala Asn Met Arg Asp Ala Ser Gln Trp
 65                  70                  75                  80

Ile Lys Arg Met Glu Asp Ile Gly Leu Glu Ala Leu Gly Met Asp Asp
                 85                  90                  95

Phe Lys Leu Ala Tyr Leu Ser Asp Thr Tyr Asn Tyr Glu Ile Lys Tyr
                100                 105                 110

Asp His Thr Lys Ile Arg Val Ala Asn Phe Asp Ile Glu Val Thr Ser
                115                 120                 125

Pro Asp Gly Phe Pro Glu Pro Ser Gln Ala Lys His Pro Ile Asp Ala
130                 135                 140

Ile Thr His Tyr Asp Ser Ile Asp Asp Arg Phe Tyr Val Phe Asp Leu
145                 150                 155                 160

Leu Asn Ser Pro Tyr Gly Asn Val Glu Glu Trp Ser Ile Glu Ile Ala
                165                 170                 175

Ala Lys Leu Gln Glu Gln Gly Gly Asp Glu Val Pro Ser Glu Ile Ile
                180                 185                 190

Asp Lys Ile Ile Tyr Met Pro Phe Asp Asn Glu Lys Glu Leu Leu Met
                195                 200                 205

Glu Tyr Leu Asn Phe Trp Gln Gln Lys Thr Pro Val Ile Leu Thr Gly
210                 215                 220

Trp Asn Val Glu Ser Phe Asp Ile Pro Tyr Val Tyr Asn Arg Ile Lys
225                 230                 235                 240

Asn Ile Phe Gly Glu Ser Thr Ala Lys Arg Leu Ser Pro His Arg Lys
                245                 250                 255

Thr Arg Val Lys Val Ile Glu Asn Met Tyr Gly Ser Arg Glu Ile Ile
                260                 265                 270

Thr Leu Phe Gly Ile Ser Val Leu Asp Tyr Ile Asp Leu Tyr Lys Lys
                275                 280                 285

Phe Ser Phe Thr Asn Gln Pro Ser Tyr Ser Leu Asp Tyr Ile Ser Glu
290                 295                 300

Phe Glu Leu Asn Val Gly Lys Leu Lys Tyr Asp Gly Pro Ile Ser Lys
305                 310                 315                 320

Leu Arg Glu Ser Asn His Gln Arg Tyr Ile Ser Tyr Asn Ile Ile Asp
                325                 330                 335

Val Tyr Arg Val Leu Gln Ile Asp Ala Lys Arg Gln Phe Ile Asn Leu
                340                 345                 350

Ser Leu Asp Met Gly Tyr Tyr Ala Lys Ile Gln Ile Gln Ser Val Phe
                355                 360                 365

Ser Pro Ile Lys Thr Trp Asp Ala Ile Ile Phe Asn Ser Leu Lys Glu
                370                 375                 380

Gln Asn Lys Val Ile Pro Gln Gly Arg Ser His Pro Val Gln Pro Tyr
385                 390                 395                 400

Pro Gly Ala Phe Val Lys Glu Pro Ile Pro Asn Arg Tyr Lys Tyr Val
                405                 410                 415

Met Ser Phe Asp Leu Thr Ser Leu Tyr Pro Ser Ile Ile Arg Gln Val
                420                 425                 430

Asn Ile Ser Pro Glu Thr Ile Ala Gly Thr Phe Lys Val Ala Pro Leu
                435                 440                 445

His Asp Tyr Ile Asn Ala Val Ala Glu Arg Pro Ser Asp Val Tyr Ser
450                 455                 460

```
Cys Ser Pro Asn Gly Met Met Tyr Tyr Lys Asp Arg Asp Gly Val Val
465                 470                 475                 480

Pro Thr Glu Ile Thr Lys Val Phe Asn Gln Arg Lys Glu His Lys Gly
            485                 490                 495

Tyr Met Leu Ala Ala Gln Arg Asn Gly Glu Ile Ile Lys Glu Ala Leu
        500                 505                 510

His Asn Pro Asn Leu Ser Val Asp Glu Pro Leu Asp Val Asp Tyr Arg
    515                 520                 525

Phe Asp Phe Ser Asp Glu Ile Lys Glu Lys Ile Lys Lys Leu Ser Ala
530                 535                 540

Lys Ser Leu Asn Glu Met Leu Phe Arg Ala Gln Arg Thr Glu Val Ala
545                 550                 555                 560

Gly Met Thr Ala Gln Ile Asn Arg Lys Leu Leu Ile Asn Ser Leu Tyr
                565                 570                 575

Gly Ala Leu Gly Asn Val Trp Phe Arg Tyr Tyr Asp Leu Arg Asn Ala
            580                 585                 590

Thr Ala Ile Thr Thr Phe Gly Gln Met Ala Leu Gln Trp Ile Glu Arg
        595                 600                 605

Lys Val Asn Glu Tyr Leu Asn Glu Val Cys Gly Thr Glu Gly Glu Ala
    610                 615                 620

Phe Val Leu Tyr Gly Asp Thr Asp Ser Ile Tyr Val Ser Ala Asp Lys
625                 630                 635                 640

Ile Ile Asp Lys Val Gly Glu Ser Lys Phe Arg Asp Thr Asn His Trp
                645                 650                 655

Val Asp Phe Leu Asp Lys Phe Ala Arg Glu Arg Met Glu Pro Ala Ile
            660                 665                 670

Asp Arg Gly Phe Arg Glu Met Cys Glu Tyr Met Asn Asn Lys Gln His
        675                 680                 685

Leu Met Phe Met Asp Arg Glu Ala Ile Ala Gly Pro Pro Leu Gly Ser
    690                 695                 700

Lys Gly Ile Gly Gly Phe Trp Thr Gly Lys Lys Arg Tyr Ala Leu Asn
705                 710                 715                 720

Val Trp Asp Met Glu Gly Thr Arg Tyr Ala Glu Pro Lys Leu Lys Ile
                725                 730                 735

Met Gly Leu Glu Thr Gln Lys Ser Ser Thr Pro Lys Ala Val Gln Lys
            740                 745                 750

Ala Leu Lys Glu Cys Ile Arg Arg Met Leu Gln Glu Gly Glu Glu Ser
        755                 760                 765

Leu Gln Glu Tyr Phe Lys Glu Phe Glu Lys Glu Phe Arg Gln Leu Asn
    770                 775                 780

Tyr Ile Ser Ile Ala Ser Val Ser Ser Ala Asn Asn Ile Ala Lys Tyr
785                 790                 795                 800

Asp Val Gly Gly Phe Pro Gly Pro Lys Cys Pro Phe His Ile Arg Gly
                805                 810                 815

Ile Leu Thr Tyr Asn Arg Ala Ile Lys Gly Asn Ile Asp Ala Pro Gln
            820                 825                 830

Val Val Glu Gly Glu Lys Val Tyr Val Leu Pro Leu Arg Glu Gly Asn
        835                 840                 845

Pro Phe Gly Asp Lys Cys Ile Ala Trp Pro Ser Gly Thr Glu Ile Thr
    850                 855                 860

Asp Leu Ile Lys Asp Asp Val Leu His Trp Met Asp Tyr Thr Val Leu
865                 870                 875                 880

Leu Glu Lys Thr Phe Ile Lys Pro Leu Glu Gly Phe Thr Ser Ala Ala
```

```
                    885                 890                 895
Lys Leu Asp Tyr Glu Lys Lys Ala Ser Leu Phe Asp Met Phe Asp Phe
            900                 905                 910

<210> SEQ ID NO 30
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met His His His His His Lys His Met Ala Arg Ser Val Tyr Val
1               5                   10                  15

Cys Asp Phe Glu Thr Thr Thr Asp Pro Glu Asp Cys Arg Leu Trp Ala
            20                  25                  30

Trp Gly Trp Met Asp Ile Tyr Asn Thr Asp Lys Trp Ser Tyr Gly Glu
        35                  40                  45

Asp Ile Asp Ser Phe Met Glu Trp Ala Leu Asn Ser Asn Ser Asp Ile
    50                  55                  60

Tyr Phe His Asn Leu Lys Phe Asp Gly Ser Phe Ile Leu Pro Trp Trp
65                  70                  75                  80

Leu Arg Asn Gly Tyr Val His Thr Glu Glu Asp Arg Thr Asn Thr Pro
                85                  90                  95

Lys Glu Phe Thr Thr Thr Ile Ser Gly Met Gly Gln Trp Tyr Ala Val
            100                 105                 110

Asp Val Cys Ile Asn Thr Arg Gly Lys Asn Lys Asn His Val Val Phe
        115                 120                 125

Tyr Asp Ser Leu Lys Lys Leu Pro Phe Lys Val Glu Gln Ile Ala Lys
    130                 135                 140

Gly Phe Gly Leu Pro Val Leu Lys Gly Asp Ile Asp Tyr Lys Lys Tyr
145                 150                 155                 160

Arg Pro Val Gly Tyr Val Met Asp Asp Asn Glu Ile Glu Tyr Leu Lys
                165                 170                 175

His Asp Leu Leu Ile Val Ala Leu Ala Leu Arg Ser Met Phe Asp Asn
            180                 185                 190

Asp Phe Thr Ser Met Thr Val Gly Ser Asp Ala Leu Asn Thr Tyr Lys
        195                 200                 205

Glu Met Leu Gly Val Lys Gln Trp Glu Lys Tyr Phe Pro Val Leu Ser
    210                 215                 220

Leu Lys Val Asn Ser Glu Ile Arg Lys Ala Tyr Lys Gly Gly Phe Thr
225                 230                 235                 240

Trp Val Asn Pro Lys Tyr Gln Gly Glu Thr Val Tyr Gly Gly Met Val
                245                 250                 255

Phe Asp Val Asn Ser Met Tyr Pro Ala Met Met Lys Asn Lys Leu Leu
            260                 265                 270

Pro Tyr Gly Glu Pro Val Met Phe Lys Gly Glu Tyr Lys Lys Asn Val
        275                 280                 285

Glu Tyr Pro Leu Tyr Ile Gln Gln Val Arg Cys Phe Phe Glu Leu Lys
    290                 295                 300

Lys Asp Lys Ile Pro Cys Ile Gln Ile Lys Gly Asn Ala Arg Phe Gly
305                 310                 315                 320

Gln Asn Glu Tyr Leu Ser Thr Ser Gly Asp Glu Tyr Val Asp Leu Tyr
                325                 330                 335
```

Val Thr Asn Val Asp Trp Glu Leu Ile Lys Lys His Tyr Asp Ile Phe
              340                 345                 350

Glu Glu Glu Phe Ile Gly Gly Phe Met Phe Lys Gly Phe Ile Gly Phe
          355                 360                 365

Phe Asp Glu Tyr Ile Asp Arg Phe Met Glu Ile Lys Asn Ser Pro Asp
      370                 375                 380

Ser Ser Ala Glu Gln Ser Leu Gln Ala Lys Leu Met Leu Asn Ser Leu
385                 390                 395                 400

Tyr Gly Lys Phe Ala Thr Asn Pro Asp Ile Thr Gly Lys Val Pro Tyr
              405                 410                 415

Leu Asp Glu Asn Gly Val Leu Lys Phe Arg Lys Gly Glu Leu Lys Glu
          420                 425                 430

Arg Asp Pro Val Tyr Thr Pro Met Gly Cys Phe Ile Thr Ala Tyr Ala
      435                 440                 445

Arg Glu Asn Ile Leu Ser Asn Ala Gln Lys Leu Tyr Pro Arg Phe Ile
450                 455                 460

Tyr Ala Asp Thr Asp Ser Ile His Val Glu Gly Leu Gly Glu Val Asp
465                 470                 475                 480

Ala Ile Lys Asp Val Ile Asp Pro Lys Lys Leu Gly Tyr Trp Asp His
              485                 490                 495

Glu Ala Thr Phe Gln Arg Ala Arg Tyr Val Arg Gln Lys Thr Tyr Phe
          500                 505                 510

Ile Glu Thr Thr Trp Lys Glu Asn Asp Lys Gly Lys Leu Val Val Cys
      515                 520                 525

Glu Pro Gln Asp Ala Thr Lys Val Lys Pro Lys Ile Ala Cys Ala Gly
530                 535                 540

Met Ser Asp Ala Ile Lys Glu Arg Ile Arg Phe Asn Glu Phe Lys Ile
545                 550                 555                 560

Gly Tyr Ser Thr His Gly Ser Leu Lys Pro Lys Asn Val Leu Gly Gly
              565                 570                 575

Val Val Leu Met Asp Tyr Pro Phe Ala Ile Lys
          580                 585

<210> SEQ ID NO 31
<211> LENGTH: 581
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met His His His His His Lys His Met Pro Arg Lys Met Phe Ser
1               5                   10                  15

Cys Asp Phe Glu Thr Thr Thr Lys Leu Asp Asp Cys Arg Val Trp Ala
              20                  25                  30

Tyr Gly Tyr Met Glu Ile Gly Asn Leu Asp Asn Tyr Lys Ile Gly Asn
          35                  40                  45

Ser Leu Asp Glu Phe Met Gln Trp Val Met Glu Ile Gln Ala Asp Leu
50                  55                  60

Tyr Phe His Asn Leu Lys Phe Asp Gly Ala Phe Ile Val Asn Trp Leu
65                  70                  75                  80

Glu His His Gly Phe Lys Trp Ser Asn Glu Gly Leu Pro Asn Thr Tyr
              85                  90                  95

Asn Thr Ile Ile Ser Lys Met Gly Gln Trp Tyr Met Ile Asp Ile Cys
          100                 105                 110

```
Phe Gly Tyr Lys Gly Lys Arg Lys Leu His Thr Val Ile Tyr Asp Ser
            115                 120                 125

Leu Lys Lys Leu Pro Phe Pro Val Lys Ile Ala Lys Asp Phe Gln
130                 135                 140

Leu Pro Leu Leu Lys Gly Asp Ile Asp Tyr His Ala Glu Arg Pro Val
145                 150                 155                 160

Gly His Glu Ile Thr Pro Glu Glu Tyr Glu Tyr Ile Lys Asn Asp Ile
                165                 170                 175

Glu Ile Ile Ala Arg Ala Leu Asp Ile Gln Phe Lys Gln Gly Leu Asp
                180                 185                 190

Arg Met Thr Ala Gly Ser Asp Ser Leu Lys Gly Phe Lys Asp Ile Leu
            195                 200                 205

Ser Thr Lys Lys Phe Asn Lys Val Phe Pro Lys Leu Ser Leu Pro Met
        210                 215                 220

Asp Lys Glu Ile Arg Arg Ala Tyr Arg Gly Gly Phe Thr Trp Leu Asn
225                 230                 235                 240

Asp Lys Tyr Lys Glu Lys Gly Ile Glu Gly Met Val Phe Asp Val
                    245                 250                 255

Asn Ser Leu Tyr Pro Ser Gln Met Tyr Ser Arg Pro Leu Pro Tyr Gly
            260                 265                 270

Ala Pro Ile Val Phe Gln Gly Lys Tyr Glu Lys Asp Glu Gln Tyr Pro
            275                 280                 285

Leu Tyr Ile Gln Arg Ile Arg Phe Glu Phe Glu Leu Lys Glu Gly Tyr
        290                 295                 300

Ile Pro Thr Ile Gln Ile Lys Lys Asn Pro Phe Phe Lys Gly Asn Glu
305                 310                 315                 320

Tyr Leu Lys Asn Ser Gly Ala Glu Pro Val Glu Leu Tyr Leu Thr Asn
                    325                 330                 335

Val Asp Leu Glu Leu Ile Gln Glu His Tyr Glu Met Tyr Asn Val Glu
            340                 345                 350

Tyr Ile Asp Gly Phe Lys Phe Arg Glu Lys Thr Gly Leu Phe Lys Glu
        355                 360                 365

Phe Ile Asp Lys Trp Thr Tyr Val Lys Thr His Glu Lys Gly Ala Lys
370                 375                 380

Lys Gln Leu Ala Lys Leu Met Phe Asp Ser Leu Tyr Gly Lys Phe Ala
385                 390                 395                 400

Ser Asn Pro Asp Val Thr Gly Lys Val Pro Tyr Leu Lys Glu Asp Gly
                405                 410                 415

Ser Leu Gly Phe Arg Val Gly Asp Glu Tyr Lys Asp Pro Val Tyr
            420                 425                 430

Thr Pro Met Gly Val Phe Ile Thr Ala Trp Ala Arg Phe Thr Thr Ile
            435                 440                 445

Thr Ala Ala Gln Ala Cys Tyr Asp Arg Ile Ile Tyr Cys Asp Thr Asp
        450                 455                 460

Ser Ile His Leu Thr Gly Thr Glu Val Pro Glu Ile Ile Lys Asp Ile
465                 470                 475                 480

Val Asp Pro Lys Lys Leu Gly Tyr Trp Ala His Glu Ser Thr Phe Lys
                485                 490                 495

Arg Ala Lys Tyr Leu Arg Gln Lys Thr Tyr Ile Gln Asp Ile Tyr Ala
                500                 505                 510

Lys Glu Val Asp Gly Lys Leu Ile Glu Cys Ser Pro Asp Glu Ala Thr
            515                 520                 525
```

```
Thr Thr Lys Phe Ser Val Lys Cys Ala Gly Met Thr Asp Thr Ile Lys
    530                 535                 540

Lys Lys Val Thr Phe Asp Asn Phe Arg Val Gly Phe Ser Ser Thr Gly
545                 550                 555                 560

Lys Pro Lys Pro Val Gln Val Asn Gly Gly Val Val Leu Val Asp Ser
                565                 570                 575

Val Phe Thr Ile Lys
            580

<210> SEQ ID NO 32
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300
```

-continued

```
Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Phe Asp
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 33
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
```

-continued

```
                85                  90                  95
Trp Tyr Met Ile Asp Ile Cys Phe Gly Tyr Lys Gly Lys Arg Lys Leu
            100                 105                 110

His Thr Val Ile Tyr Asp Ser Leu Lys Lys Pro Phe Pro Val Lys
            115                 120                 125

Lys Ile Ala Lys Asp Phe Gln Leu Pro Leu Leu Lys Gly Asp Ile Asp
            130                 135                 140

Tyr His Ala Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Arg Ala Tyr Arg
            210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
            290                 295                 300

Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
            355                 360                 365

Thr His Glu Lys Gly Ala Lys Lys Gln Leu Ala Lys Leu Met Leu Asn
            370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
            405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
            450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510
```

```
Cys Ser Pro Asp Glu Ala Thr Thr Thr Lys Phe Ser Val Lys Cys Ala
        515                 520                 525

Gly Met Thr Asp Thr Ile Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 34
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Pro Arg Lys Met Phe Ser Cys Asp Phe Glu Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
                35                  40                  45

Met Glu Ile Gln Ala Asp Leu Tyr Phe His Asn Leu Lys Phe Asp Gly
            50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
145                 150                 155                 160

Glu Tyr Ile Lys Asn Ala Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Arg Ala Tyr Arg
210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
```

```
                    290                 295                 300
Pro Phe Phe Lys Gly Asn Glu Tyr Leu Lys Asn Ser Gly Ala Glu Pro
305                 310                 315                 320

Val Glu Leu Tyr Leu Thr Asn Val Asp Leu Glu Leu Ile Gln Glu His
                325                 330                 335

Tyr Glu Met Tyr Asn Val Glu Tyr Ile Asp Gly Phe Lys Phe Arg Glu
            340                 345                 350

Lys Thr Gly Leu Phe Lys Glu Phe Ile Asp Lys Trp Thr Tyr Val Lys
        355                 360                 365

Thr His Glu Lys Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Ala Lys Glu Val Asp Gly Lys Leu Ile Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 35
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asn Leu Lys Phe Asp Gly
        50                  55                  60

Ala Phe Ile Val Asn Trp Leu Glu Gln His Gly Phe Lys Trp Ser Asn
65                  70                  75                  80
```

```
Glu Gly Leu Pro Asn Thr Tyr Asn Thr Ile Ile Ser Lys Met Gly Gln
                 85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
            130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
            195                 200                 205

Pro Lys Leu Ser Leu Pro Met Asp Lys Glu Ile Arg Lys Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
            340                 345                 350

Lys Thr Gly Leu Phe Lys Asp Phe Ile Asp Lys Trp Thr Tyr Val Lys
            355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
```

```
                500                 505                 510
Cys Ser Pro Asp Glu Thr Thr Thr Lys Phe Ser Val Lys Cys Ala
        515                 520                 525

Gly Met Thr Asp Thr Ile Lys Lys Lys Val Thr Phe Asp Asn Phe Ala
        530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 36
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Arg Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285
```

-continued

```
Phe Glu Leu Lys Glu Gly Tyr Ile Pro Thr Ile Gln Ile Lys Lys Asn
            290                 295                 300
Pro Phe Lys Gly Asn Glu Tyr Leu Lys Asn Ser Gly Val Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
            340                 345                 350
Lys Thr Gly Leu Phe Lys Asp Phe Ile Asp Lys Trp Thr Tyr Val Lys
        355                 360                 365
Thr His Glu Glu Gly Ala Lys Lys Gln Leu Ala Lys Leu Met Leu Asn
    370                 375                 380
Ser Leu Tyr Gly Lys Phe Ala Ser Asn Pro Asp Val Thr Gly Lys Val
385                 390                 395                 400
Pro Tyr Leu Lys Asp Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
        435                 440                 445
Ile Ile Tyr Cys Asp Thr Asp Ser Ile His Leu Thr Gly Thr Glu Val
    450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Val Lys Glu Val Asp Gly Lys Leu Lys Glu
            500                 505                 510
Cys Ser Pro Asp Glu Ala Thr Thr Thr Lys Phe Ser Val Lys Cys Ala
        515                 520                 525
Gly Met Thr Asp Thr Ile Lys Lys Lys Val Thr Phe Asp Asn Phe Ala
    530                 535                 540
Val Gly Phe Ser Ser Met Gly Lys Pro Lys Pro Val Gln Val Asn Gly
545                 550                 555                 560
Gly Val Val Leu Val Asp Ser Val Phe Thr Ile Lys
                565                 570

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Asn Leu Tyr Phe Gln
1               5

<210> SEQ ID NO 38
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

```
Met Asn His Lys Val His His His His His Ile Glu Gly Arg Glu
1               5                   10                  15

Asn Leu Tyr Phe Gln Cys Met Glu Leu Gly Thr Leu Gly Ser Met
            20                  25                  30

Lys His Met Pro Arg Lys Met Tyr Ser Cys Ala Phe Glu Thr Thr Thr
            35                  40                  45

Lys Val Glu Asp Cys Arg Val Trp Ala Tyr Gly Tyr Met Asn Ile Glu
        50                  55                  60

Asp His Ser Glu Tyr Lys Ile Gly Asn Ser Leu Asp Glu Phe Met Ala
65                      70                  75                  80

Trp Val Leu Lys Val Gln Ala Asp Leu Tyr Phe His Asn Leu Lys Phe
                85                  90                  95

Ala Gly Ala Phe Ile Ile Asn Trp Leu Glu Arg Asn Gly Phe Lys Trp
            100                 105                 110

Ser Ala Asp Gly Leu Pro Asn Thr Tyr Asn Thr Ile Ile Ser Arg Met
            115                 120                 125

Gly Gln Trp Tyr Met Ile Asp Ile Cys Leu Gly Tyr Lys Gly Lys Arg
            130                 135                 140

Lys Ile His Thr Val Ile Tyr Asp Ser Leu Lys Lys Leu Pro Phe Pro
145                 150                 155                 160

Val Lys Lys Ile Ala Lys Asp Phe Lys Leu Thr Val Leu Lys Gly Asp
                165                 170                 175

Ile Asp Tyr His Lys Glu Arg Pro Val Gly Tyr Lys Ile Thr Pro Glu
            180                 185                 190

Glu Tyr Ala Tyr Ile Lys Asn Asp Ile Gln Ile Ala Glu Ala Leu
            195                 200                 205

Leu Ile Gln Phe Lys Gln Gly Leu Asp Arg Met Thr Ala Gly Ser Asp
210                 215                 220

Ser Leu Lys Gly Phe Lys Asp Ile Ile Thr Thr Lys Lys Phe Lys Lys
225                 230                 235                 240

Val Phe Pro Thr Leu Ser Leu Gly Leu Asp Lys Glu Val Arg Tyr Ala
            245                 250                 255

Tyr Arg Gly Gly Phe Thr Trp Leu Asn Asp Arg Phe Lys Glu Lys Glu
            260                 265                 270

Ile Gly Glu Gly Met Val Phe Asp Val Asn Ser Leu Tyr Pro Ala Gln
            275                 280                 285

Met Tyr Ser Arg Leu Leu Pro Tyr Gly Glu Pro Ile Val Phe Glu Gly
            290                 295                 300

Lys Tyr Val Trp Asp Glu Asp Tyr Pro Leu His Ile Gln His Ile Arg
305                 310                 315                 320

Cys Glu Phe Glu Leu Lys Glu Gly Tyr Ile Pro Thr Ile Gln Ile Lys
            325                 330                 335

Arg Ser Arg Phe Tyr Lys Gly Asn Glu Tyr Leu Lys Ser Ser Gly Gly
            340                 345                 350

Glu Ile Ala Asp Leu Trp Leu Ser Asn Val Asp Leu Glu Leu Met Lys
            355                 360                 365

Glu His Tyr Asp Leu Tyr Asn Val Glu Tyr Ile Ser Gly Leu Lys Phe
            370                 375                 380

Lys Ala Thr Thr Gly Leu Phe Lys Asp Phe Ile Asp Lys Trp Thr Tyr
385                 390                 395                 400

Ile Lys Thr Thr Ser Glu Gly Ala Ile Lys Gln Leu Ala Lys Leu Met
                405                 410                 415

Leu Asn Ser Leu Tyr Gly Lys Phe Ala Ser Asn Pro Asp Val Thr Gly
```

```
                420                 425                 430
Lys Val Pro Tyr Leu Lys Glu Asn Gly Ala Leu Gly Phe Arg Leu Gly
            435                 440                 445

Glu Glu Glu Thr Lys Asp Pro Val Tyr Thr Pro Met Gly Val Phe Ile
            450                 455                 460

Thr Ala Trp Ala Arg Tyr Thr Thr Ile Thr Ala Ala Gln Ala Cys Tyr
465                 470                 475                 480

Asp Arg Ile Ile Tyr Cys Asp Thr Asp Ser Ile His Leu Thr Gly Thr
                485                 490                 495

Glu Ile Pro Asp Val Ile Lys Asp Ile Val Asp Pro Lys Lys Leu Gly
            500                 505                 510

Tyr Trp Ala His Glu Ser Thr Phe Lys Arg Ala Lys Tyr Leu Arg Gln
            515                 520                 525

Lys Thr Tyr Ile Gln Asp Ile Tyr Met Lys Glu Val Asp Gly Lys Leu
            530                 535                 540

Val Glu Gly Ser Pro Asp Asp Tyr Thr Asp Ile Lys Phe Ser Val Lys
545                 550                 555                 560

Cys Ala Gly Met Thr Asp Lys Ile Lys Lys Glu Val Thr Phe Glu Asn
                565                 570                 575

Phe Lys Val Gly Phe Ser Arg Lys Met Lys Pro Lys Pro Val Gln Val
            580                 585                 590

Pro Gly Gly Val Val Leu Val Asp Asp Thr Phe Thr Ile Lys
            595                 600                 605

<210> SEQ ID NO 39
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His His His His His Leu Leu Gly Gly Gly Gly Glu Asn Leu
1               5                  10                  15

Tyr Phe Gln Cys Gly Gly Gly Ser Ala Ala Gly Ser Ala Ala
                20                  25                  30

Arg Lys Met Phe Ser Cys Asp Phe Glu Thr Thr Thr Lys Leu Asp Asp
            35                  40                  45

Cys Arg Val Trp Ala Tyr Gly Tyr Met Glu Ile Gly Asn Leu Asp Asn
50              55                  60

Tyr Lys Ile Gly Asn Ser Leu Asp Glu Phe Met Gln Trp Val Met Glu
65                  70                  75                  80

Ile Gln Ala Asp Leu Tyr Phe His Asn Leu Lys Phe Asp Gly Ala Phe
                85                  90                  95

Ile Val Asn Trp Leu Glu His His Gly Phe Lys Trp Ser Asn Glu Gly
            100                 105                 110

Leu Pro Asn Thr Tyr Asn Thr Ile Ile Ser Lys Met Gly Gln Trp Tyr
            115                 120                 125

Met Ile Asp Ile Cys Phe Gly Tyr Lys Gly Lys Arg Lys Leu His Thr
            130                 135                 140

Val Ile Tyr Asp Ser Leu Lys Lys Leu Pro Phe Pro Val Lys Lys Ile
145                 150                 155                 160

Ala Lys Asp Phe Gln Leu Pro Leu Leu Lys Gly Asp Ile Asp Tyr His
                165                 170                 175
```

-continued

```
Ala Glu Arg Pro Val Gly His Glu Ile Thr Pro Glu Glu Tyr Glu Tyr
            180                 185                 190

Ile Lys Asn Ala Ile Glu Ile Ile Ala Arg Ala Leu Asp Ile Gln Phe
        195                 200                 205

Lys Gln Gly Leu Asp Arg Met Thr Ala Gly Ser Asp Ser Leu Lys Gly
    210                 215                 220

Phe Lys Asp Ile Leu Ser Thr Lys Lys Phe Asn Lys Val Phe Pro Lys
225                 230                 235                 240

Leu Ser Leu Pro Met Asp Lys Glu Ile Arg Arg Ala Tyr Arg Gly Gly
                245                 250                 255

Phe Thr Trp Leu Asn Asp Lys Tyr Lys Glu Lys Glu Ile Gly Glu Gly
            260                 265                 270

Met Val Phe Asp Val Asn Ser Leu Tyr Pro Ser Gln Met Tyr Ser Arg
        275                 280                 285

Pro Leu Pro Tyr Gly Ala Pro Ile Val Phe Gln Gly Lys Tyr Glu Lys
    290                 295                 300

Asp Glu Gln Tyr Pro Leu Tyr Ile Gln Arg Ile Arg Phe Glu Phe Glu
305                 310                 315                 320

Leu Lys Glu Gly Tyr Ile Pro Thr Ile Gln Ile Lys Lys Asn Pro Phe
                325                 330                 335

Phe Lys Gly Asn Glu Tyr Leu Lys Asn Ser Gly Ala Glu Pro Val Glu
            340                 345                 350

Leu Tyr Leu Thr Asn Val Asp Leu Glu Leu Ile Gln Glu His Tyr Glu
        355                 360                 365

Met Tyr Asn Val Glu Tyr Ile Asp Gly Phe Lys Phe Arg Glu Lys Thr
    370                 375                 380

Gly Leu Phe Lys Glu Phe Ile Asp Lys Trp Thr Tyr Val Lys Thr His
385                 390                 395                 400

Glu Lys Gly Ala Lys Lys Gln Leu Ala Lys Leu Met Leu Asn Ser Leu
                405                 410                 415

Tyr Gly Lys Phe Ala Ser Asn Pro Asp Val Thr Gly Lys Val Pro Tyr
            420                 425                 430

Leu Lys Glu Asp Gly Ser Leu Gly Phe Arg Val Gly Asp Glu Glu Tyr
        435                 440                 445

Lys Asp Pro Val Tyr Thr Pro Met Gly Val Phe Ile Thr Ala Trp Ala
    450                 455                 460

Arg Phe Thr Thr Ile Thr Ala Ala Gln Ala Cys Tyr Asp Arg Ile Ile
465                 470                 475                 480

Tyr Cys Asp Thr Asp Ser Ile His Leu Thr Gly Thr Glu Val Pro Glu
                485                 490                 495

Ile Ile Lys Asp Ile Val Asp Pro Lys Lys Leu Gly Tyr Trp Ala His
            500                 505                 510

Glu Ser Thr Phe Lys Arg Ala Lys Tyr Leu Arg Gln Lys Thr Tyr Ile
        515                 520                 525

Gln Asp Ile Tyr Ala Lys Glu Val Asp Gly Lys Leu Ile Glu Cys Ser
    530                 535                 540

Pro Asp Glu Ala Thr Thr Thr Lys Phe Ser Val Lys Cys Ala Gly Met
545                 550                 555                 560

Thr Asp Thr Ile Lys Lys Lys Val Thr Phe Asp Asn Phe Arg Val Gly
                565                 570                 575

Phe Ser Ser Thr Gly Lys Pro Lys Pro Val Gln Val Asn Gly Gly Val
            580                 585                 590

Val Leu Val Asp Ser Val Phe Thr
```

595            600

<210> SEQ ID NO 40
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ser His His His His His Ser Met Ser Gly Leu Asn Asp Ile
1               5                   10                  15

Phe Glu Ala Gln Lys Ile Glu Trp His Glu Gly Ala Pro Gly Ala Arg
            20                  25                  30

Gly Ser Lys His Met Pro Arg Lys Met Phe Ser Cys Asp Phe Glu Thr
        35                  40                  45

Thr Thr Lys Leu Asp Asp Cys Arg Val Trp Ala Tyr Gly Tyr Met Glu
    50                  55                  60

Ile Gly Asn Leu Asp Asn Tyr Lys Ile Gly Asn Ser Leu Asp Glu Phe
65                  70                  75                  80

Met Gln Trp Val Met Glu Ile Gln Ala Asp Leu Tyr Phe His Asn Leu
                85                  90                  95

Lys Phe Asp Gly Ala Phe Ile Val Asn Trp Leu Glu His His Gly Phe
            100                 105                 110

Lys Trp Ser Asn Glu Gly Leu Pro Asn Thr Tyr Asn Thr Ile Ile Ser
        115                 120                 125

Lys Met Gly Gln Trp Tyr Met Ile Asp Ile Cys Phe Gly Tyr Lys Gly
    130                 135                 140

Lys Arg Lys Leu His Thr Val Ile Tyr Asp Ser Leu Lys Lys Leu Pro
145                 150                 155                 160

Phe Pro Val Lys Lys Ile Ala Lys Asp Phe Gln Leu Pro Leu Leu Lys
                165                 170                 175

Gly Asp Ile Asp Tyr His Ala Glu Arg Pro Val Gly His Glu Ile Thr
            180                 185                 190

Pro Glu Glu Tyr Glu Tyr Ile Lys Asn Ala Ile Glu Ile Ala Arg
        195                 200                 205

Ala Leu Asp Ile Gln Phe Lys Gln Gly Leu Asp Arg Met Thr Ala Gly
    210                 215                 220

Ser Asp Ser Leu Lys Gly Phe Lys Asp Ile Leu Ser Thr Lys Lys Phe
225                 230                 235                 240

Asn Lys Val Phe Pro Lys Leu Ser Leu Pro Met Asp Lys Glu Ile Arg
                245                 250                 255

Arg Ala Tyr Arg Gly Gly Phe Thr Trp Leu Asn Asp Lys Tyr Lys Glu
            260                 265                 270

Lys Glu Ile Gly Glu Gly Met Val Phe Asp Val Asn Ser Leu Tyr Pro
        275                 280                 285

Ser Gln Met Tyr Ser Arg Pro Leu Pro Tyr Gly Ala Pro Ile Val Phe
    290                 295                 300

Gln Gly Lys Tyr Glu Lys Asp Glu Gln Tyr Pro Leu Tyr Ile Gln Arg
305                 310                 315                 320

Ile Arg Phe Glu Phe Glu Leu Lys Glu Gly Tyr Ile Pro Thr Ile Gln
                325                 330                 335

Ile Lys Lys Asn Pro Phe Phe Lys Gly Asn Glu Tyr Leu Lys Asn Ser
            340                 345                 350

Gly Ala Glu Pro Val Glu Leu Tyr Leu Thr Asn Val Asp Leu Glu Leu
        355                 360                 365

Ile Gln Glu His Tyr Glu Met Tyr Asn Val Glu Tyr Ile Asp Gly Phe
370                 375                 380

Lys Phe Arg Glu Lys Thr Gly Leu Phe Lys Glu Phe Ile Asp Lys Trp
385                 390                 395                 400

Thr Tyr Val Lys Thr Arg Glu Lys Gly Ala Lys Gln Leu Ala Lys
                405                 410                 415

Leu Met Leu Asn Ser Leu Tyr Gly Lys Phe Ala Ser Asn Pro Asp Val
                420                 425                 430

Thr Gly Lys Val Pro Tyr Leu Lys Glu Asp Gly Ser Leu Gly Phe Arg
                435                 440                 445

Val Gly Asp Glu Glu Tyr Lys Asp Pro Val Tyr Thr Pro Met Gly Val
        450                 455                 460

Phe Ile Thr Ala Trp Ala Arg Phe Thr Thr Ile Thr Ala Ala Gln Ala
465                 470                 475                 480

Cys Tyr Asp Arg Ile Ile Tyr Cys Asp Thr Asp Ser Ile His Leu Thr
                485                 490                 495

Gly Thr Glu Val Pro Glu Ile Ile Lys Asp Ile Val Asp Pro Lys Lys
        500                 505                 510

Leu Gly Tyr Trp Ala His Glu Ser Thr Phe Lys Arg Ala Lys Tyr Leu
        515                 520                 525

Arg Gln Lys Thr Tyr Ile Gln Asp Ile Tyr Ala Lys Glu Val Asp Gly
                530                 535                 540

Lys Leu Ile Glu Cys Ser Pro Asp Glu Ala Thr Thr Thr Lys Phe Ser
545                 550                 555                 560

Val Lys Cys Ala Gly Met Thr Asp Thr Ile Lys Lys Val Thr Phe
                565                 570                 575

Asp Asn Phe Arg Val Gly Phe Ser Ser Thr Gly Lys Pro Lys Pro Val
                580                 585                 590

Gln Val Asn Gly Gly Val Val Leu Val Asp Ser Val Phe Thr Ile Lys
                595                 600                 605

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tttttccccg cgtaactctt taccccgaca cggaggttct atca                44

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgatagaacc tccgtgtc                                              18

<210> SEQ ID NO 43
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43
tttttttgca ggtgacaggt ttttcctgtc acctgc                                36

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgttaaccgc ccgctccttt gcaac                                            25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gttgcaaagg agcgggcg                                                    18

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cagtaacgga gttggttgga cggctgcgag gc                                    32

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctcgcagc cgtccaacca actcc                                            25

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttttgcggg tgacaggttt ttcctgtcac cc                                    32

<210> SEQ ID NO 49
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
ttatctttgt gggtgacagg tttttcctgt caccc                                35

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tttttttgcc cccagggtga caggtttttc ctgtcaccc                            39

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttatctttgt gggtgacagg tttttcctgt caccc                                35

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 tttttttagtc tgggtgacag gtt                                            23

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tttttgaggg tgacaggttt ttcctgtcac cc                                   32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tttttgcggg tgacaggttt ttcctgtcac cc                                   32

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 55
ttatctttgt gggtgacagg tttttcctgt cacc        34

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggtactaagc ggccgcatg        19

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
taaagccccc ccatgcggcc gcttagtacc        30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
taaagttttt tcatgcggcc gcttagtacc        30

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggtactaagc ggccgcatg        19

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aaaaaaacat gcggccgctt agtacc        26

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgatagaacc tccgtgt                                                17

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggtactaagc ggccgcatg                                              19

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ttttacccat gcggccgctt agtacc                                      26

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggtactaagc ggccgc                                                 16

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ttttacccat gcggccgctt agtacc                                      26

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggtactaagc ggccgcatg                                              19

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 67
tggacccatg cggccgctta gtacc                                           25

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggtactaagc ggccgcatg                                                  19

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tggacccatg cggccgctta gtacc                                           25

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtactaagc ggccgcatg                                                  19

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tggacccccc catgcggccg cttagtacc                                       29

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggtactaagc ggccgcatg                                                  19

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```

```
tggacccccc catgcggccg cttagtacc                                      29
```

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(8)
<223> OTHER INFORMATION: This sequence may encompass 2-8 "His" residues
<220> FEATURE:
<223> OTHER INFORMATION: See specification as filed for detailed
      description of substitutions and preferred embodiments

<400> SEQUENCE: 74

His His His His His His His His
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Arg Arg Ala Ser Leu Gly
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Lys Pro Gln Gln Phe
1               5

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(12)
<223> OTHER INFORMATION: This sequence may encompass 4-12 "His" residues
<220> FEATURE:
<223> OTHER INFORMATION: See specification as filed for detailed
      description of substitutions and preferred embodiments

<400> SEQUENCE: 77

His His His His His His His His His His His His
1               5                   10

<210> SEQ ID NO 78
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 78

His His His His His His
1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: misc_feature
<222> LOCATION: (1)..(12)
<223> OTHER INFORMATION: This sequence may encompass 3-12 "His" residues
<220> FEATURE:
<223> OTHER INFORMATION: See specification as filed for detailed
      description of substitutions and preferred embodiments

<400> SEQUENCE: 79

His His His His His His His His His His His His
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      polycysteine tag
<220> FEATURE:
<221> NAME/KEY: misc_feature
<222> LOCATION: (1)..(12)
<223> OTHER INFORMATION: This sequence may encompass 6-12 "Cys" residues
<220> FEATURE:
<223> OTHER INFORMATION: See specification as filed for detailed
      description of substitutions and preferred embodiments

<400> SEQUENCE: 80

Cys Cys Cys Cys Cys Cys Cys Cys Cys Cys Cys Cys
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      polylysine tag
<220> FEATURE:
<221> NAME/KEY: misc_feature
<222> LOCATION: (1)..(12)
<223> OTHER INFORMATION: This sequence may encompass 6-12 "Lys" residues
<220> FEATURE:
<223> OTHER INFORMATION: See specification as filed for detailed
      description of substitutions and preferred embodiments

<400> SEQUENCE: 81

Lys Lys Lys Lys Lys Lys Lys Lys Lys Lys Lys Lys
1               5                   10

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 82

Leu Arg Arg Ala Ser Leu
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Ile Glu Thr
1

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggccagtgaa ttcgagctcg gtacccgg                                        28

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttcctgtcac cc                                                         12

<210> SEQ ID NO 86
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggaacacgga ggttctatca tcgtcatcgt catcgtcatc g                         41

<210> SEQ ID NO 87
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttatctttgt gggtgacagg ttttcctgt caccc                                 35

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic

```
        10xHis tag

<400> SEQUENCE: 88

His His His His His His His His His His
1               5                   10

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 89

His His His His His
1               5

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90 cccccgaaa t                                                           11

<210> SEQ ID NO 91
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91 tttttgaaa t                                                           11
```